(12) United States Patent
Jorand-Lebrun et al.

(10) Patent No.: US 10,059,701 B2
(45) Date of Patent: Aug. 28, 2018

(54) HETEROARYL COMPOUNDS AS IRAK INHIBITORS AND USES THEREOF

(71) Applicant: Merck Patent GmbH, Darmstadt (DE)

(72) Inventors: Catherine Jorand-Lebrun, Arlington, MA (US); Ruoxi Lan, Waltham, MA (US); Austin Chen, San Marcos, CA (US); Ryan C. Clark, San Diego, CA (US)

(73) Assignee: Merck Patent GmbH, Darmstadt (DE)

( * ) Notice: Subject to any disclaimer, the term of this patent is extended or adjusted under 35 U.S.C. 154(b) by 5 days.

(21) Appl. No.: 15/267,565

(22) Filed: Sep. 16, 2016

(65) Prior Publication Data

US 2017/0081317 A1 Mar. 23, 2017

Related U.S. Application Data

(60) Provisional application No. 62/220,307, filed on Sep. 18, 2015.

(51) Int. Cl.

| | | |
|---|---|---|
| A01N 43/00 | (2006.01) |
| A61K 31/397 | (2006.01) |
| C07D 413/14 | (2006.01) |
| C07D 401/04 | (2006.01) |
| C07D 403/04 | (2006.01) |
| C07D 413/04 | (2006.01) |
| C07D 417/04 | (2006.01) |
| C07D 471/08 | (2006.01) |
| C07D 487/08 | (2006.01) |
| C07D 498/08 | (2006.01) |
| C07D 491/08 | (2006.01) |
| A61K 31/4184 | (2006.01) |

(52) U.S. Cl.
CPC ........ *C07D 413/14* (2013.01); *A61K 31/4184* (2013.01); *C07D 401/04* (2013.01); *C07D 403/04* (2013.01); *C07D 413/04* (2013.01); *C07D 417/04* (2013.01); *C07D 471/08* (2013.01); *C07D 487/08* (2013.01); *C07D 491/08* (2013.01); *C07D 498/08* (2013.01)

(58) Field of Classification Search
None
See application file for complete search history.

(56) References Cited

FOREIGN PATENT DOCUMENTS

| WO | 2003030902 A1 | 4/2003 |
|---|---|---|
| WO | 2005079791 A1 | 9/2005 |
| WO | 2008042282 A2 | 4/2008 |
| WO | 2010126743 A1 | 11/2010 |
| WO | 2010126745 A1 | 11/2010 |
| WO | 2010126922 A1 | 11/2010 |
| WO | 2012018668 A1 | 2/2012 |
| WO | 2013074518 A1 | 5/2013 |

OTHER PUBLICATIONS

STN registry database compound 509094-21-7 (Entered STN May 2, 2003).*
Ito et al. (Cancer Science, 2003, 94(1), 3-8).*
STN registry database compound 509094-23-9 (Entered STN May 2, 2003).*
Cohen, Current Opinion in Cell Biology 21, 317-324 (2009).
Ringwood and Li, Cytokine 42, 1-7 (2008).
Cao et al., Science 271(5252): 1128-31 (1996).
Muzio et al., Science 278(5343): 1612-5 (1997).
Wesche et al. J. Biol. Chem. 274(27): 19403-10 (1999).
Li et al. Proc. Natl. Acad. Sci. USA 99(8):5567-5572 (2002).
Buckley et al. Bioorg Med Chem Lett. 18(12):3656-60 (2008).
Periodic Table of the Elements, CAS version, Handbook of Chemistry and Physics, 75th Ed.
Organic Chemistry, Thomas Sorrell, University Science Books, Sausalito (1999).
"March's Advanced Organic Chemistry", 5th Ed., Ed.: Smith, M.B. and March, J., John Wiley & Sons, New York: (2001).
S. M. Berge et al., J. Pharmaceutical Sciences, 66, 1-19 (1977).
Hanzlik et al., J. Org. Chem. 55, 3992-3997 (1990).
Reider et al., J. Org. Chem. 52, 3326-3334 (1987).
Foster, Adv. Drug Res. 14, 1-40 (1985).
Gillette et al., Biochemistry 33(10) 2927-2937 (1994).
Jarman et al., Carcinogenesis 16(4), 683-688 (1993).
Philip J. Kocienski, "Protecting Groups", Georg Thieme Verlag Stuttgart, New York, (1994).
Theodora W. Greene and Peter G. M. Wuts, "Protective Groups in Organic Synthesis", Wiley Interscience, 3rd Edition (1999).

* cited by examiner

*Primary Examiner* — Daniel M Podgorski
(74) *Attorney, Agent, or Firm* — Dwight D. Kim; EMD Serono Research and Development Institute

(57) ABSTRACT

The present invention relates to compounds of Formula I and pharmaceutically acceptable compositions thereof, useful as IRAK inhibitors.

11 Claims, No Drawings

HETEROARYL COMPOUNDS AS IRAK INHIBITORS AND USES THEREOF

RELATED APPLICATIONS

The present application claims the benefit of U.S. provisional application 62/220,307, filed on Sep. 18, 2015, the contents of which are incorporated herein in its entirety by reference.

TECHNICAL FIELD OF THE INVENTION

The present invention provides for compounds of Formula (I) as IRAK inhibitors and their use in the treatment of cancer, and other diseases related to IRAK overexpression, including rheumatoid arthritis, systemic lupus erythematosus or lupus nephritis.

BACKGROUND OF THE INVENTION

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1 (IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAK1 (Muzio et al., 1997. Science 278 (5343): 1612-5). IRAK3 (also called IRAKM) was identified using a murine EST sequence encoding a polypeptide with significant homology to IRAK1 to screen a human phytohemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem Lett. 18(12):3656-60). IRAK1 is essential for the TLR7-mediated and TLR9-mediated activation of IRF7 and the production of interferon-alpha (IFN-α) suggesting that IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

In one aspect, the invention provides compounds of Formula (I):

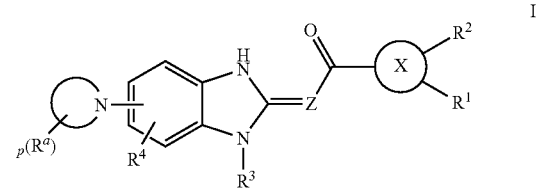

and pharmaceutically acceptable derivatives, solvates, salts, hydrates and stereoisomers thereof, wherein Ring X, Z, R, $R^1$, $R^2$, $R^3$, $R^4$, $R^a$, and p, is as defined below and described in the embodiments.

In another aspect, the invention provides compounds of Formula (I) which are suitable for the treatment and/or prevention of disorders related to IRAK. In another aspect, the invention provides compounds which are able to modulate, especially inhibit the activity or function of IRAK in disease states in mammals, especially in humans.

According to another aspect of the invention are provided methods for the treatment and/or prevention of disorders selected from auto-immune, inflammatory disorders, cardiovascular diseases, neurodegenerative disorders, bacterial and viral infections, allergy, asthma, pancreatitis, multiorgan failure, kidney diseases, platelet aggregation, cancer, transplantation, sperm motility, erythrocyte deficiency, graft rejection, lung injuries, respiratory diseases and ischemic conditions.

According to another aspect, the present invention provides compounds of Formula (I) which are selective for IRAK-4 and/or IRAK-1.

According to another aspect, the present invention provides compounds of Formula (I) which are selective for IRAK-4 and IRAK-1.

DETAILED DESCRIPTION OF CERTAIN EMBODIMENTS

1. General Description of Compounds of the Invention

In certain aspects, the present invention provides for inhibitors of IRAK. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

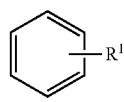

refers to at least

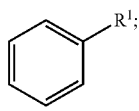

and

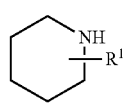

refers to at least

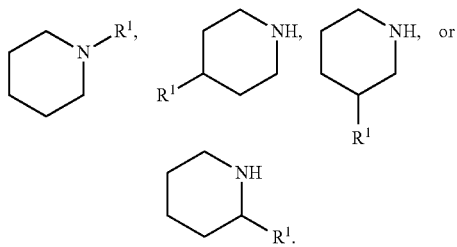

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°); —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-carbocyclyl, —C(O)-aryl, —C(O)-heteroaryl, —C(O)-heterocyclyl, —CONH$_2$, —CONH-alkyl, —CONH-alkenyl, —CONH-alkynyl, —CONH-carbocyclyl, —CONH-aryl, —CONH-heteroaryl, —CONH-heterocyclyl, —OCO$_2$-alkyl, —OCO$_2$-alkenyl, —OCO$_2$-alkynyl, —OCO$_2$-carbocyclyl, —OCO$_2$-aryl, —OCO$_2$-heteroaryl, —OCO$_2$-heterocyclyl, —OCONH$_2$, —OCONH-alkyl, —OCONH-alkenyl, —OCONH-alkynyl, —OCONH-carbocyclyl, —OCONH-aryl, —OCONH-heteroaryl, —OCONH-heterocyclyl, —NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —NHCO$_2$-alkyl, —NHCO$_2$-alkenyl, —NHCO$_2$-alkynyl, —NHCO$_2$-carbocyclyl, —NHCO$_2$-aryl, —NHCO$_2$-heteroaryl, —NHCO$_2$-heterocyclyl, —NHC(O)NH$_2$, —NHC(O)NH-alkyl, —NHC(O)NH-alkenyl, —NHC(O)NH-alkenyl, —NHC(O)NH-carbocyclyl, —NHC(O)NH-aryl, —NHC(O)NH-heteroaryl, —NHC(O)NH-heterocyclyl, NHC(S)NH$_2$, —NHC(S)NH-alkyl, —NHC(S)NH-alkenyl, —NHC(S)NH-alkynyl, —NHC(S)NH-carbocyclyl, —NHC(S)NH-aryl, —NHC(S)NH-heteroaryl, —NHC(S)NH-heterocyclyl, —NHC(NH)NH$_2$, —NHC(NH)NH-alkyl, —NHC(NH)NH-alkenyl, —NHC(NH)NH-alkenyl, —NHC(NH)NH-carbocyclyl, —NHC(NH)NH-aryl, —NHC(NH)NH-heteroaryl, —NHC(NH)NH-heterocyclyl, —NHC(NH)-alkyl, —NHC(NH)-alkenyl, —NHC(NH)-alkenyl, —NHC(NH)-carbocyclyl, —NHC(NH)-aryl, —NHC(NH)-heteroaryl, —NHC(NH)-heterocyclyl, —C(NH)NH-alkyl, —C(NH)NH-alkenyl, —C(NH)NH-alkynyl, —C(NH)NH-carbocyclyl, —C(NH)NH-aryl, —C(NH)NH-heteroaryl, —C(NH)NH-heterocyclyl, —S(O)-alkyl, —S(O)-alkenyl, —S(O)-alkynyl, —S(O)-carbocyclyl, —S(O)-aryl, —S(O)-heteroaryl, —S(O)-heterocyclyl, —SO$_2$NH$_2$, —SO$_2$NH-alkyl, —SO$_2$NH-alkenyl, —SO$_2$NH-alkynyl, —SO$_2$NH-carbocyclyl, —SO$_2$NH-aryl, —SO$_2$NH-heteroaryl, —SO$_2$NH-heterocyclyl, —NHSO$_2$-alkyl, —NHSO$_2$-alkenyl, —NHSO$_2$-alkynyl, —NHSO$_2$-carbocyclyl, —NHSO$_2$-aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. For example, the invention contemplates tautomers of the following formulae, so long as valency and/or other chemical requirements are satisfied:

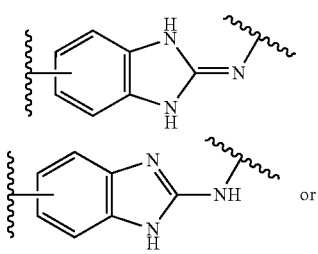

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3$H or $^{14}$C, has been incorporated, is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in IRAK activity between a sample comprising a compound of the present invention, or composition thereof, and IRAK, and an equivalent sample comprising IRAK, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

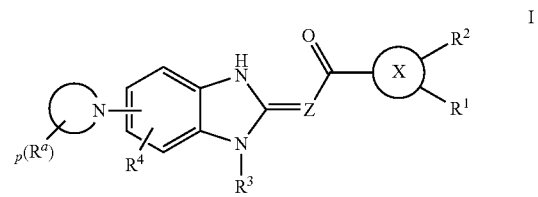

or a pharmaceutically acceptable salt thereof, wherein:

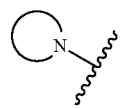

is a 3-7 membered nitrogen-containing heterocyclic or heteroaryl ring having 0-2 additional heteroatoms independently selected from nitrogen, oxygen, or sulfur;

each $R^a$ is independently —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

Ring X is a $C_{3-10}$ aryl; a 5-6 membered monocyclic heteroaryl ring having 1-4 heteroatoms independently selected from nitrogen, oxygen, or sulfur; a fused $C_{3-10}$ aryl, a fused 5-10 membered saturated or partially unsaturated carbocyclic ring, a fused 5-10 membered heterocyclic ring having 1-4 heteroatoms independently selected from nitrogen, oxygen, or sulfur, or a fused 5-10 membered monocyclic heteroaryl ring having 1-4 heteroatoms independently selected from nitrogen, oxygen, or sulfur; each of which is optionally substituted;

$R^1$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^2$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^3$ is —R or -haloalkyl;

$R^4$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

Z is N or CR;

each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

and p is 0, 1, 2, 3, 4, or 5;

wherein when Ring X is phenyl, Z is N, $R^1$ is

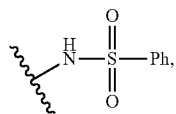

$R^2$ is H, $R^3$ is n-propyl, and $R^4$ is H, then

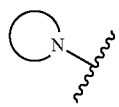

is not

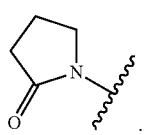

In certain embodiments,

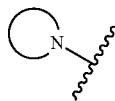

is pyrrolidine, oxazolidine, imidazolidine, dihydrotriazole, piperidine, tetrahydropyrimidine, morpholine, oxazinane, piperazine, thiomorpholine, thiazinane dioxide, pyridine, pyridazine, oxazepane, diazepane, diazabicyclo[3.1.1]heptane, diazabicyclo[3.2.1]octane, diazabicyclo[3.2.2]nonane, or oxaazabicyclo[3.2.1]octane.

In certain embodiments,

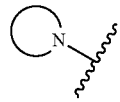

is pyrrolidinone, oxazolidinone, imidazolidinone, dihydrotriazolone, piperidinone, tetrahydropyrimidinone, morpholinone, oxazinanone, piperazinone, thiomorpholinone, thiazinane dioxide, pyridinone, pyridazinone, oxazepanone, diazepanone, diazabicyclo[3.1.1]heptanone, diazabicyclo[3.2.1]octanone, diazabicyclo[3.2.2]nonanone, or oxaazabicyclo[3.2.1]octanone.

In certain embodiments,

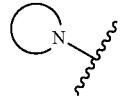 [SMILES: *N]

is

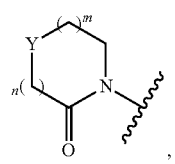

wherein Y is O, S, SO$_2$, SO, NR, or C(R)$_2$; m is 0, 1, 2, or 3; and n is 0, 1, 2, or 3.

In certain embodiments, Y is O, NR, or C(R)$_2$. In certain embodiments, Y is O. In certain embodiments, Y is NR. In certain embodiments, Y is NH. In certain embodiments, Y is C(R)$_2$. In certain embodiments, Y is CH$_2$.

In certain embodiments, ring

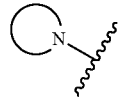 [SMILES: *N]

is selected from:

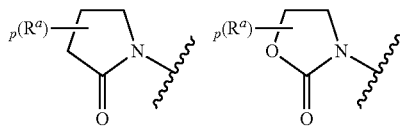

-continued
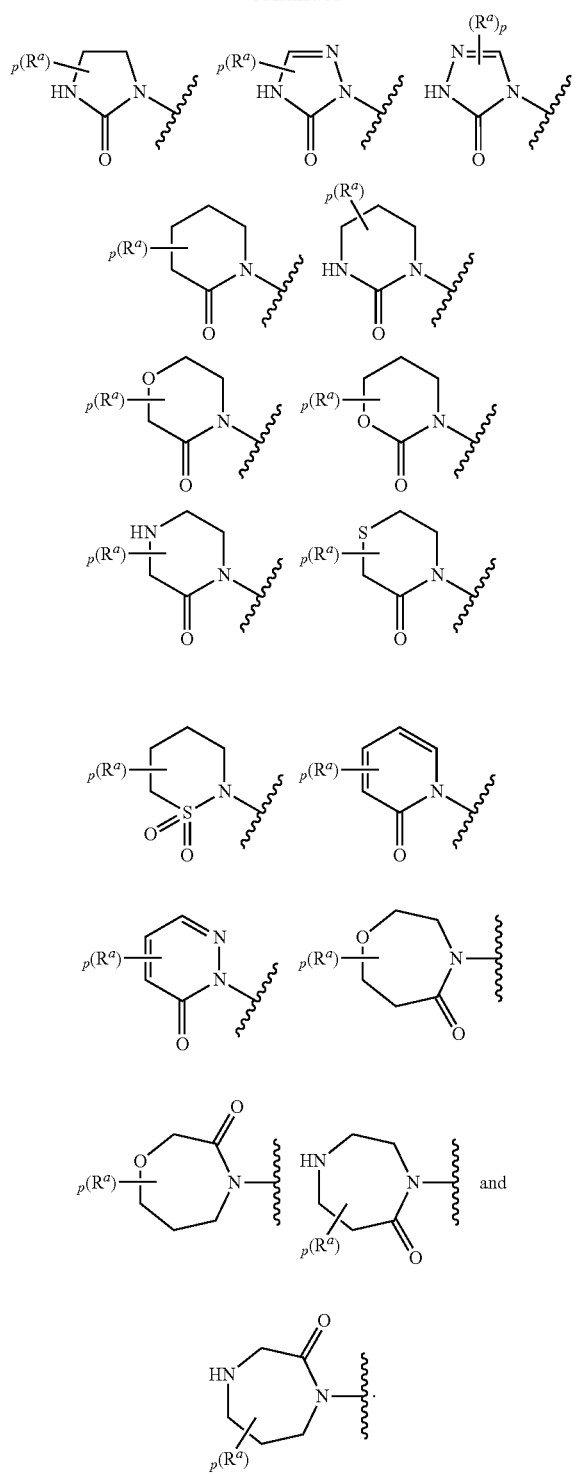
In certain embodiments, ring
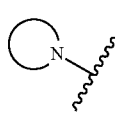 [SMILES: *N]
is selected from:
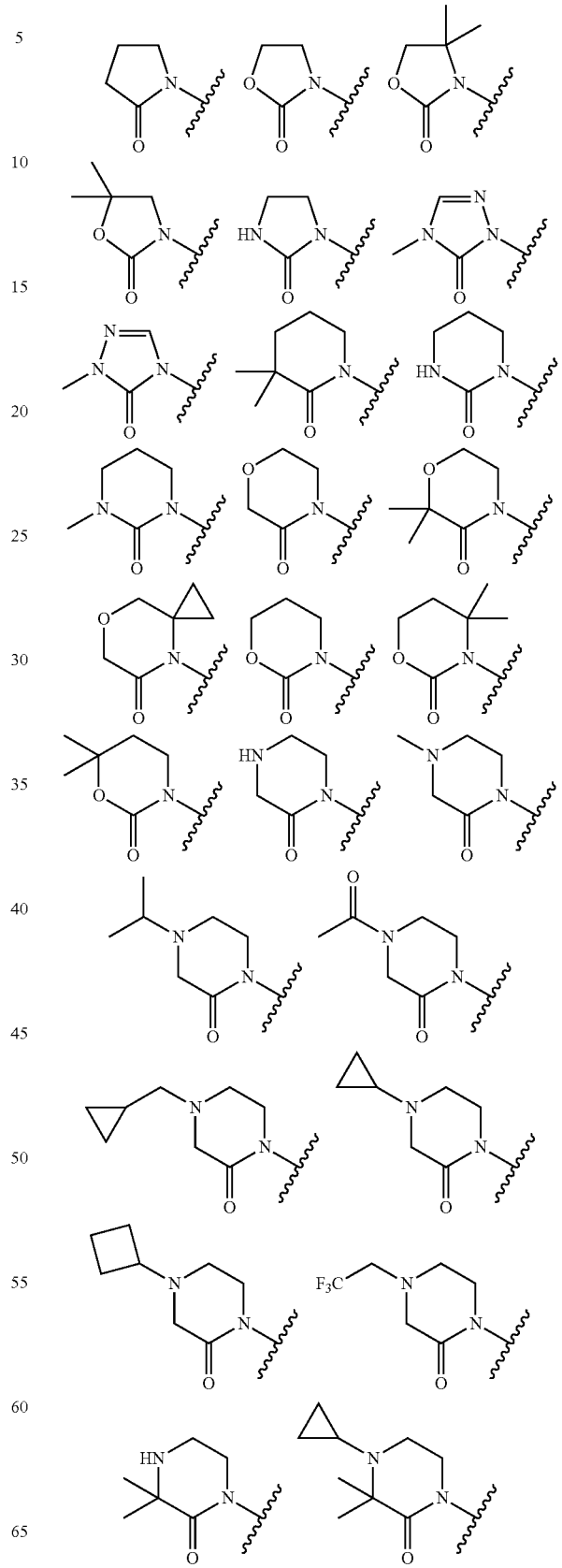

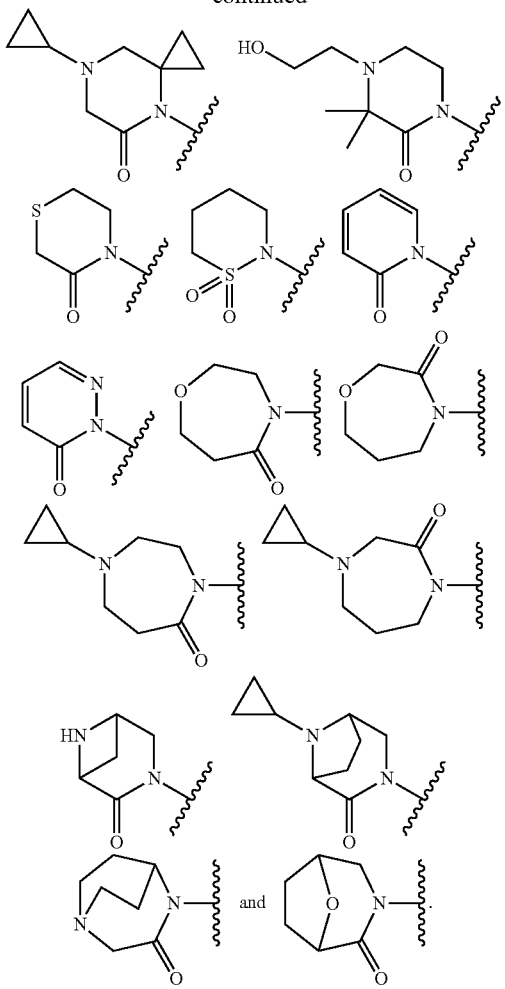

In certain embodiments, Ring X is an optionally substituted $C_{3-10}$ aryl. In certain embodiments, Ring X is an optionally substituted 5-6 membered monocyclic heteroaryl ring having 1-4 heteroatoms independently selected from nitrogen, oxygen, or sulfur. In certain embodiments, Ring X is an optionally substituted fused $C_{3-10}$ aryl. In certain embodiments, Ring X is an optionally substituted fused 5-10 membered saturated or partially unsaturated carbocyclic ring. In certain embodiments, Ring X is an optionally substituted fused 5-10 membered heterocylic ring having 1-4 heteroatoms independently selected from nitrogen, oxygen, or sulfur. In certain embodiments, Ring X is an optionally substituted fused 5-10 membered monocyclic heteroaryl ring having 1-4 heteroatoms independently selected from nitrogen, oxygen, or sulfur.

In certain embodiments, Ring X is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, Ring X is an optionally substituted $C_{3-10}$ aryl; an optionally substituted 5-6 membered monocyclic heteroaryl ring having 1-4 heteroatoms independently selected from nitrogen, oxygen, or sulfur; an optionally substituted fused $C_{3-10}$ aryl; or an optionally substituted fused 5-10 membered monocyclic heteroaryl ring having 1-4 heteroatoms independently selected from nitrogen, oxygen, or sulfur.

In certain embodiments, Ring X is phenyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isoindazolyl, isoindolinyl, isoindolyl, isoquinolinyl, isothiazolyl, isoxazolyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, tetrazole, triazinyl, 1,2,3-triazolyl, 1,2,4-triazolyl, 1,2,5-triazolyl, or 1,3,4-triazolyl; each of which is optionally substituted.

In certain embodiments, Ring X is phenyl, benzimidazolyl, benzofuranyl, benzothiofuranyl, benzothiophenyl, 1H-indazolyl, isobenzofuranyl, isoxazolyl, pyrazinyl, pyrazolyl, pyridinyl, pyridyl, or tetrazole; each of which is optionally substituted.

In certain embodiments, Ring X is selected from:

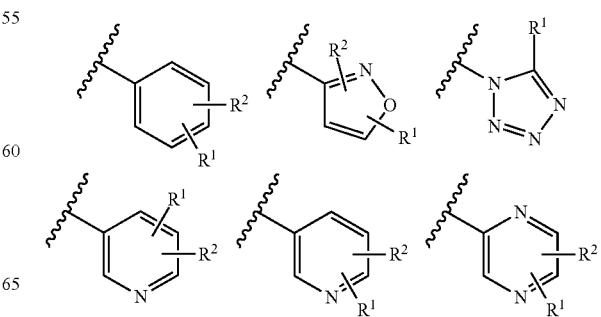

-continued
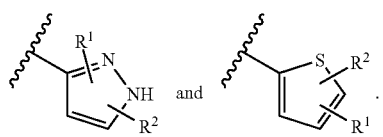
In certain embodiments, Ring X is selected from:
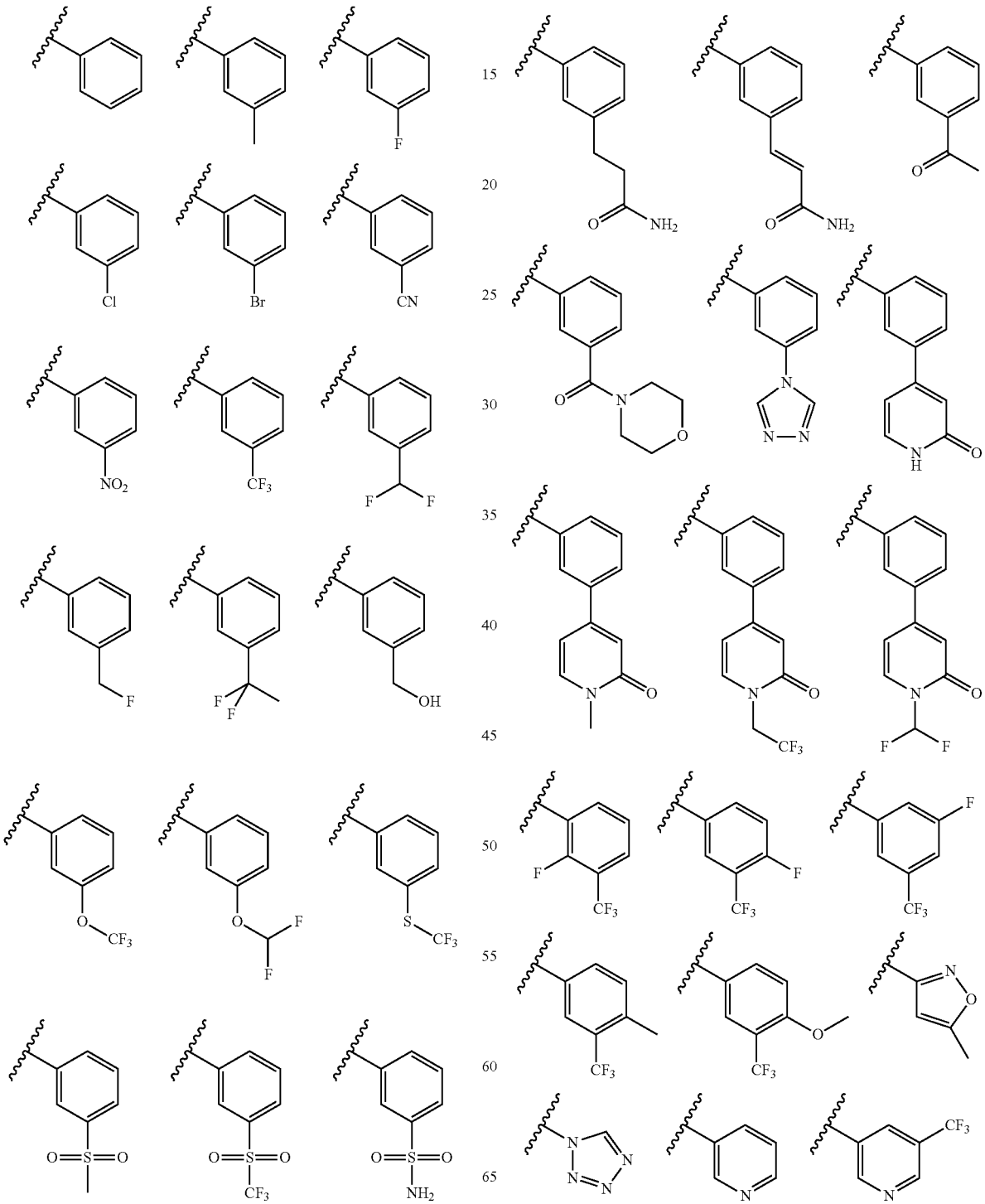
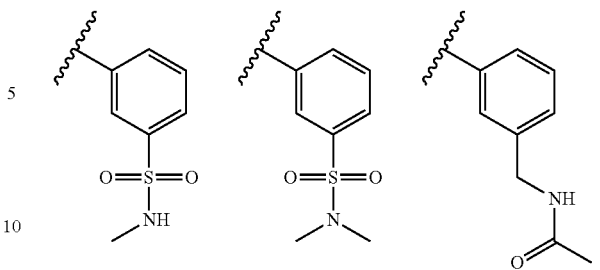

-continued

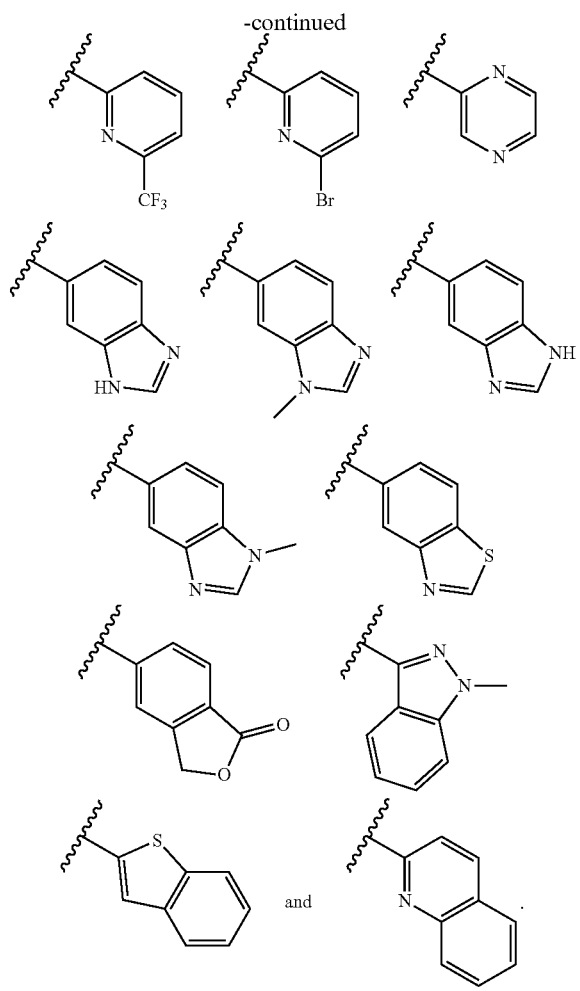

In certain embodiments, R³ is —R.

In certain embodiments, R³ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R³ is $C_{1-6}$ aliphatic, a 3-8 membered saturated or partially unsaturated carbocyclic ring, or a 3-7 membered heterocylic ring having 1-4 heteroatoms independently selected from nitrogen, oxygen, or sulfur; each of which is optionally substituted.

In certain embodiments, R³ is methyl, ethyl, propyl, i-propyl, n-butyl, s-butyl, t-butyl, a straight chain or branched pentyl, a straight chain or branched hexyl, cyclopropyl, cyclobutyl, cyclopentyl, cyclohexyl, cycloheptyl, piperazinyl, piperidinyl, pyrrolidinyl, pyrrolidinone, tetrahydrothiophene dioxide, or tetrahydrothiopyran dioxide; each of which is optionally substituted.

In certain embodiments, R³ is selected from:

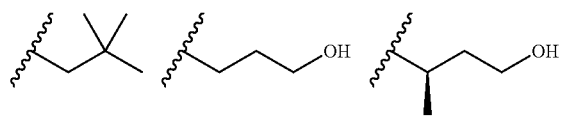

-continued

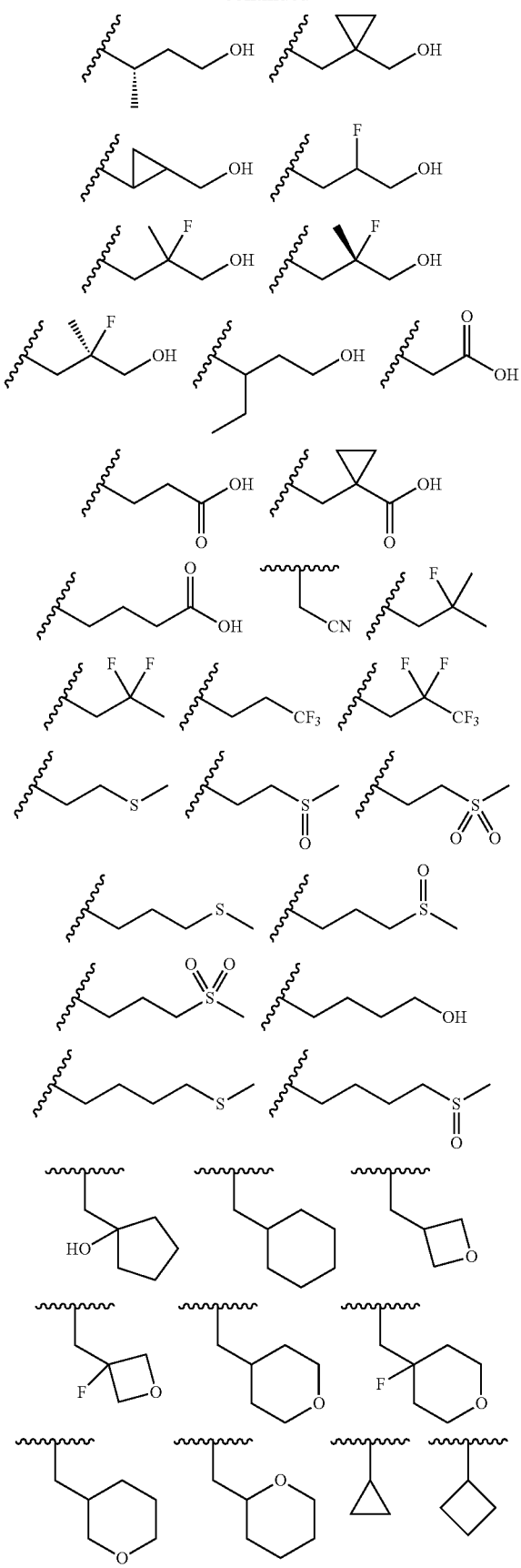

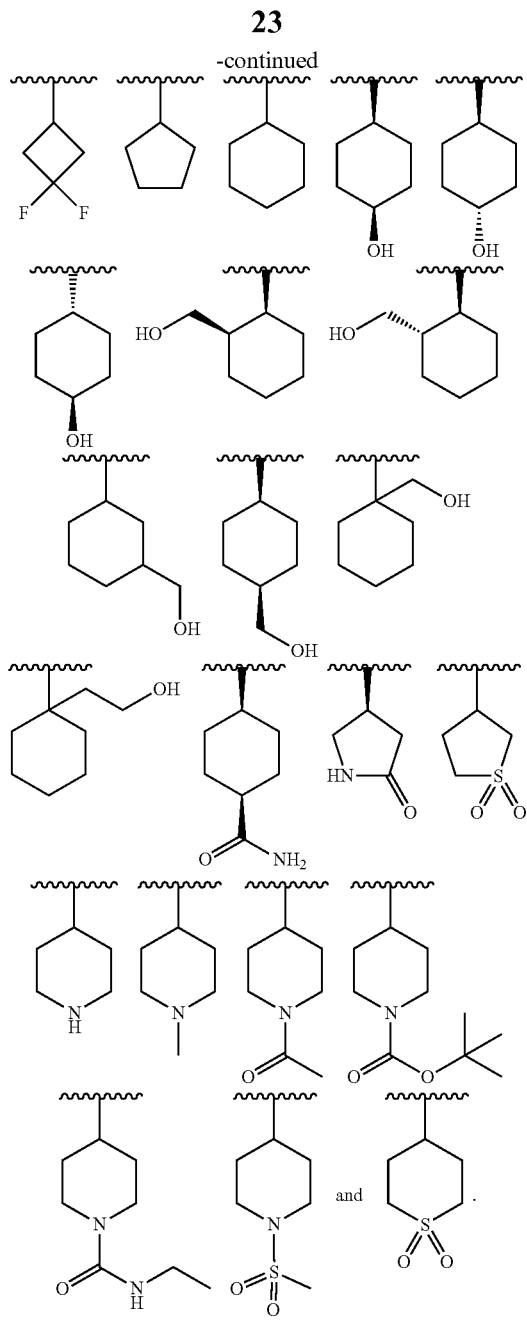

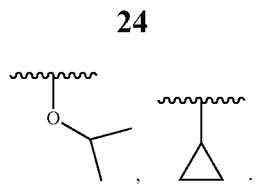

In certain embodiments, Z is N.

In certain embodiments, Z is CR. In certain embodiments, Z is CH.

In certain embodiments, each of Ring X, Z, R, $R^1$, $R^2$, $R^3$, $R^4$, $R^a$, and p, is as defined above and described in embodiments, classes and subclasses above and herein, singly or in combination.

In certain embodiments, the present invention provides a compound of formula I-a,

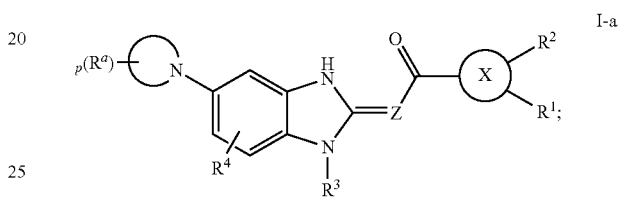

I-a or a pharmaceutically acceptable salt thereof, wherein each of Ring X, Z, $R^1$, $R^2$, $R^3$, $R^4$, $R^a$, and p, is as defined above and described in embodiments, classes and subclasses above and herein, singly or in combination.

In certain embodiments, the present invention provides a compound of formula I-b,

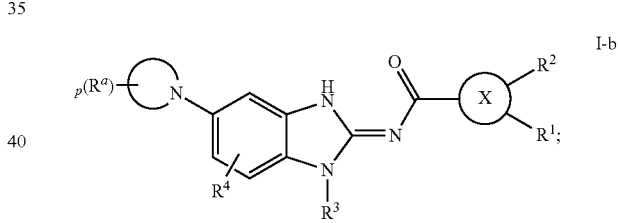

I-b or a pharmaceutically acceptable salt thereof, wherein each of Ring X, $R^1$, $R^2$, $R^3$, $R^4$, $R^a$, and p, is as defined above and described in embodiments, classes and subclasses above and herein, singly or in combination.

In certain embodiments, the present invention provides a compound of formula I-c,

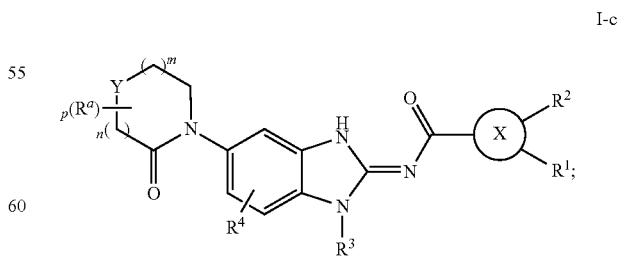

I-c or a pharmaceutically acceptable salt thereof, wherein each of Ring X, $R^1$, $R^2$, $R^3$, $R^4$, $R^a$, Y, n, m, and p, is as defined above and described in embodiments, classes and subclasses above and herein, singly or in combination.

In certain embodiments, $R^3$ is

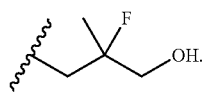

In certain embodiments, $R^4$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$.

In certain embodiments, $R^4$ is —R, —CN, halogen, or —OR.

In certain embodiments, $R^4$ is —H, —F, —Cl, —Br, —$CH_3$, —$OCH_3$, —$OCD_3$, —$OCHF_2$, —CN, In certain embodiments, the present invention provides a compound of formula I-d,

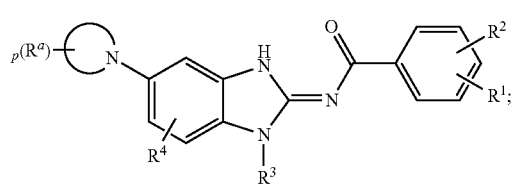

I-d or a pharmaceutically acceptable salt thereof, wherein each of $R^1$, $R^2$, $R^3$, $R^4$, $R^a$, and p, is as defined above and described in embodiments, classes and subclasses above and herein, singly or in combination.

In certain embodiments, the present invention provides a compound of formula I-e,

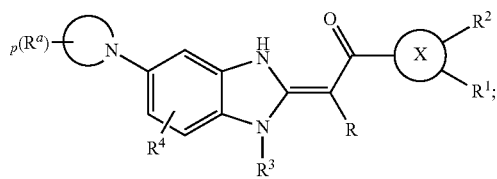

I-e or a pharmaceutically acceptable salt thereof, wherein each of Ring X, $R^1$, $R^2$, $R^3$, $R^4$, $R^a$, and p, is as defined above and described in embodiments, classes and subclasses above and herein, singly or in combination.

In certain embodiments, the present invention provides a compound of formula I-f,

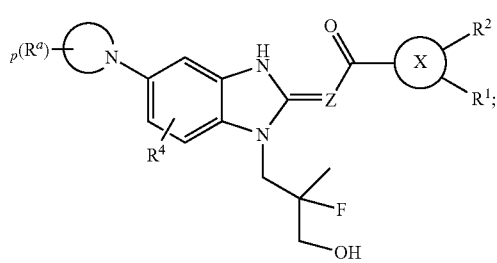

I-f or a pharmaceutically acceptable salt thereof, wherein each of Ring X, $R^1$, $R^2$, $R^4$, $R^a$, and p, is as defined above and described in embodiments, classes and subclasses above and herein, singly or in combination.

In certain embodiments, the invention provides a compound selected from Table 1:

TABLE 1

| | |
|---|---|
| 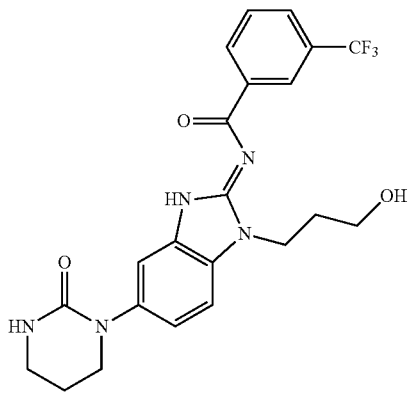 [SMILES: O=C(/N=c1\[nH]c2cc(N3CCCNC3=O)ccc2n1CCCO)c1cccc(C(F)(F)F)c1] | 1 |
| 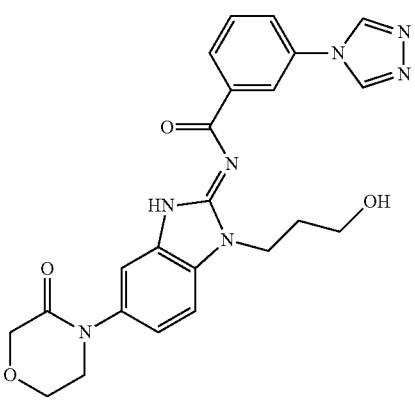 [SMILES: O=C(/N=c1\[nH]c2cc(N3CCOCC3=O)ccc2n1CCCO)c1cccc(-n2cnnc2)c1] | 2 |
| 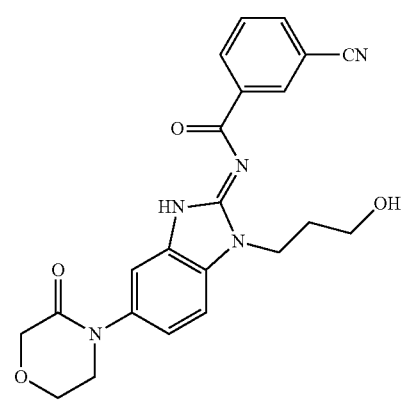 [SMILES: N#Cc1cccc(C(=O)/N=c2\[nH]c3cc(N4CCOCC4=O)ccc3n2CCCO)c1] | 3 |
| 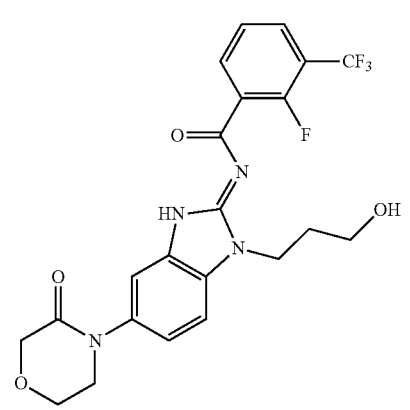 [SMILES: O=C(/N=c1\[nH]c2cc(N3CCOCC3=O)ccc2n1CCCO)c1cccc(C(F)(F)F)c1F] | 4 |

TABLE 1-continued
| | |
|---|---|
| 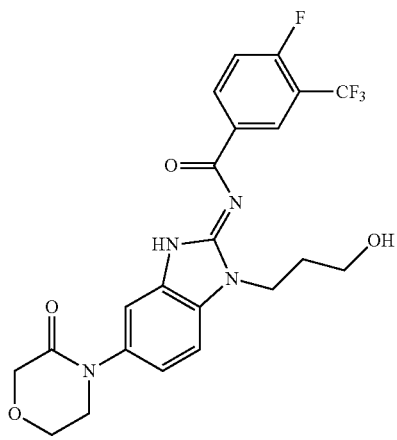 [SMILES: O=C(/N=c1\[nH]c2cc(N3CCOCC3=O)ccc2n1CCCO)c1ccc(F)c(C(F)(F)F)c1] | 5 |
| 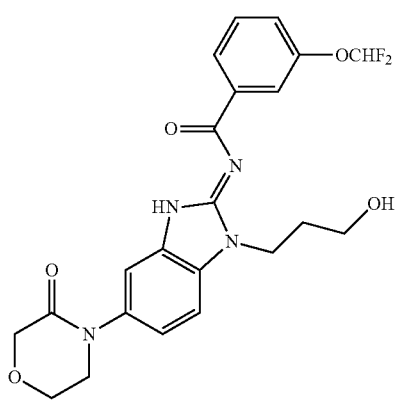 [SMILES: O=C(/N=c1\[nH]c2cc(N3CCOCC3=O)ccc2n1CCCO)c1cccc(OC(F)F)c1] | 6 |
| 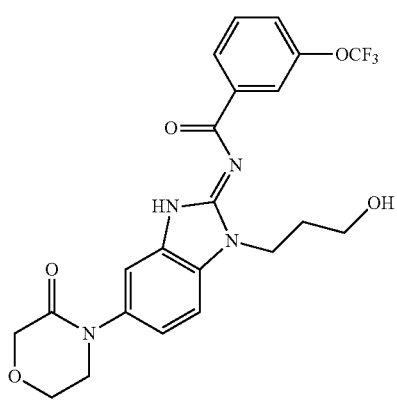 [SMILES: O=C(/N=c1\[nH]c2cc(N3CCOCC3=O)ccc2n1CCCO)c1cccc(OC(F)(F)F)c1] | 7 |
| 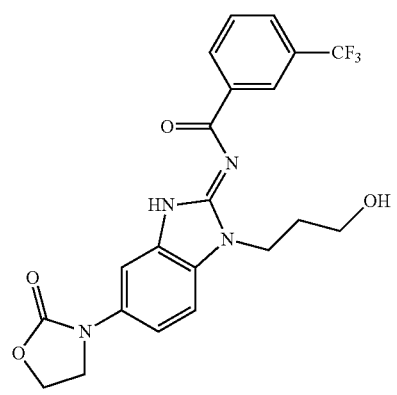 [SMILES: O=C(/N=c1\[nH]c2cc(N3CCOC3=O)ccc2n1CCCO)c1cccc(C(F)(F)F)c1] | 8 |
TABLE 1-continued
| | |
|---|---|
| 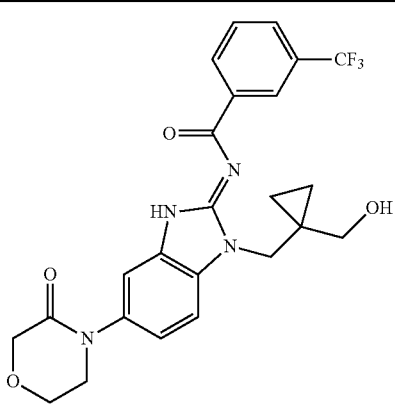 | 9 |
| 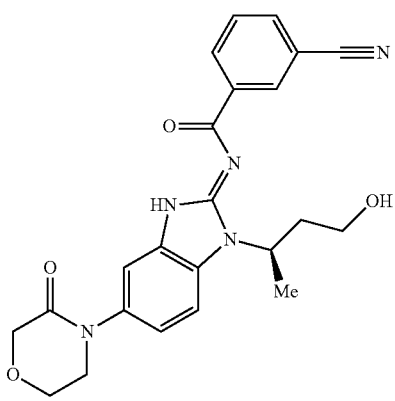 [SMILES: C[C@H](CCO)n1/c(=N/C(=O)c2cccc(C#N)c2)[nH]c2cc(N3CCOCC3=O)ccc21] | 10 |
| 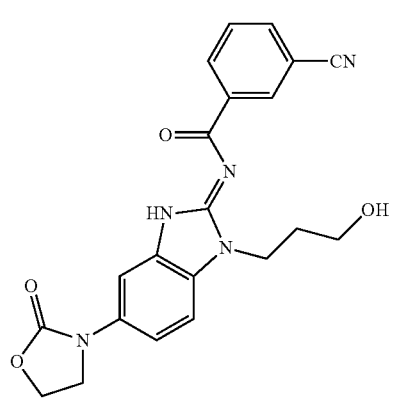 [SMILES: N#Cc1cccc(C(=O)/N=c2\[nH]c3cc(N4CCOC4=O)ccc3n2CCCO)c1] | 11 |
| 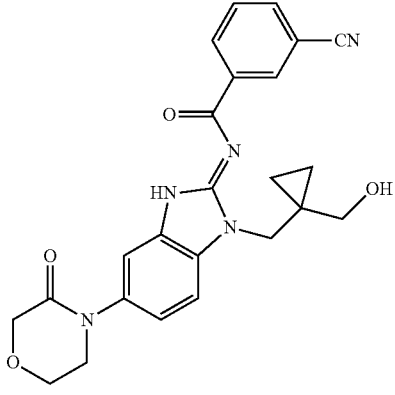 [SMILES: N#Cc1cccc(C(=O)/N=c2\[nH]c3cc(N4CCOCC4=O)ccc3n2CC2(CO)CC2)c1] | 12 |

TABLE 1-continued
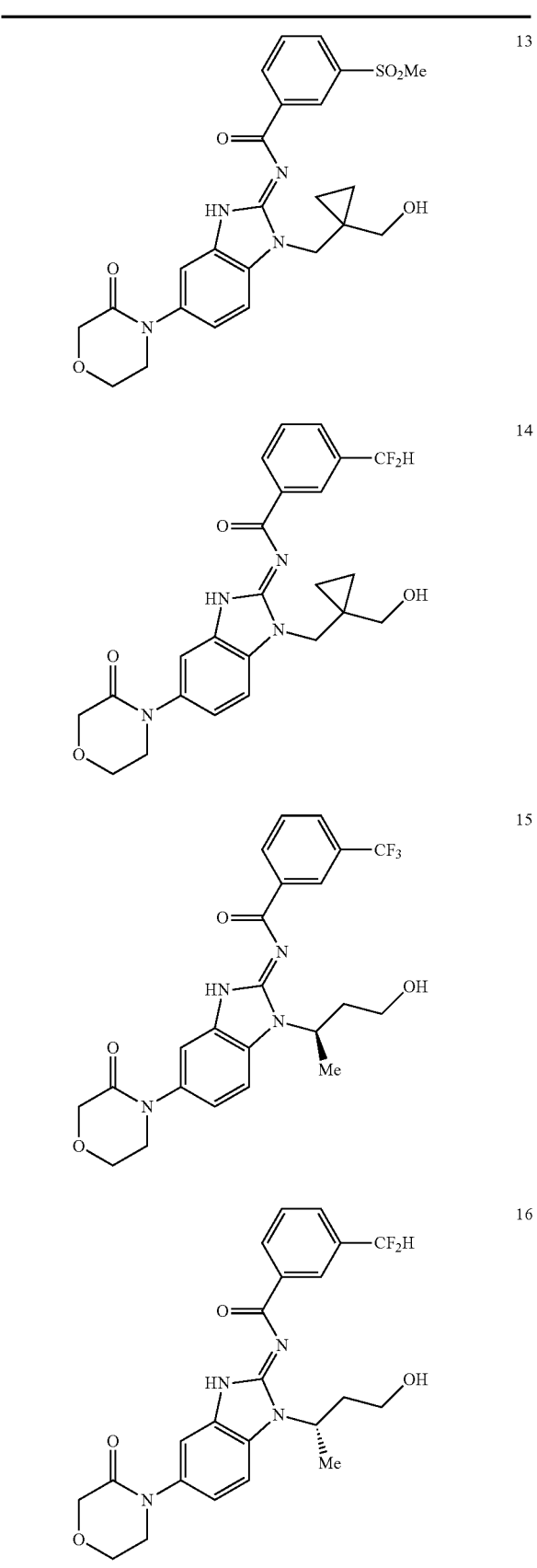
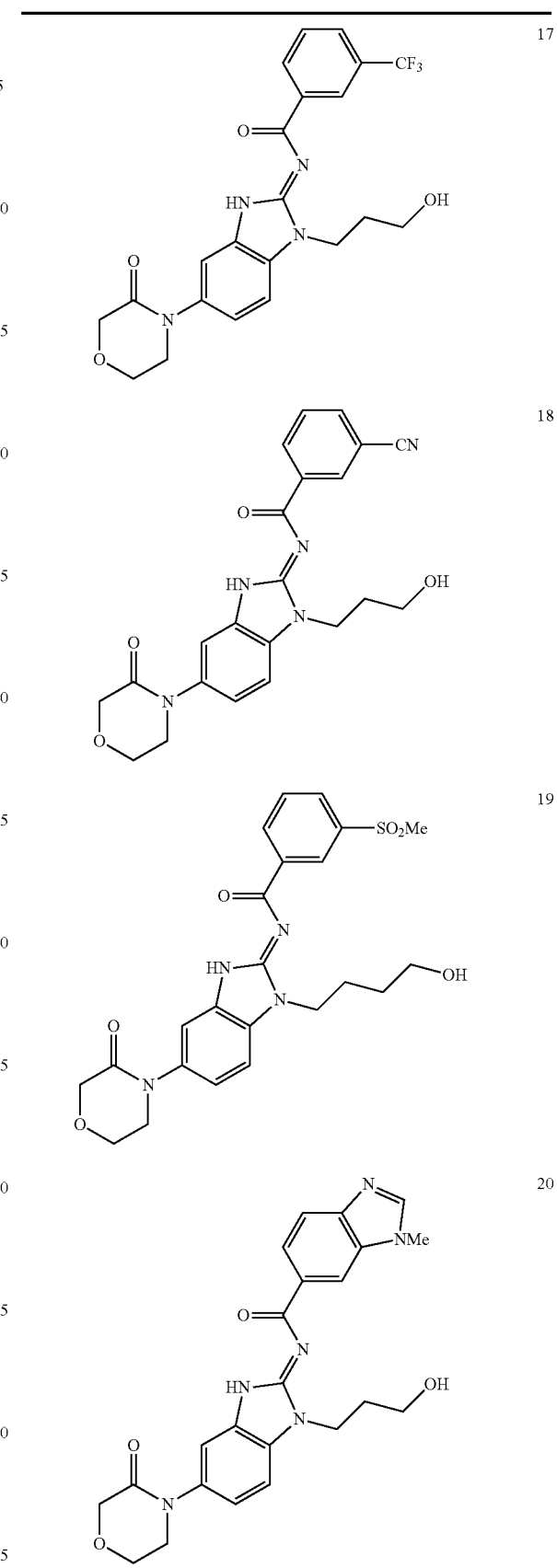

TABLE 1-continued
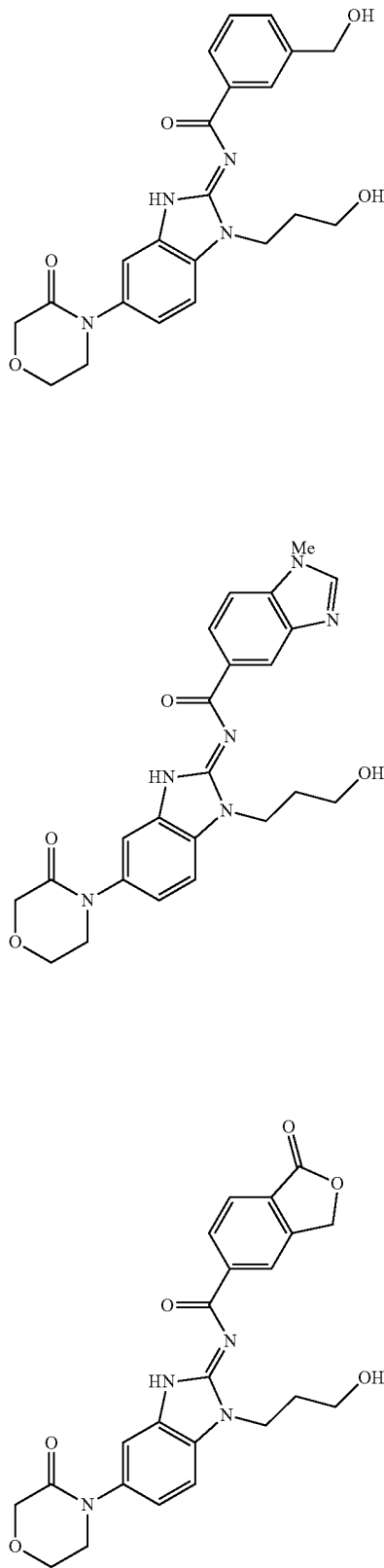
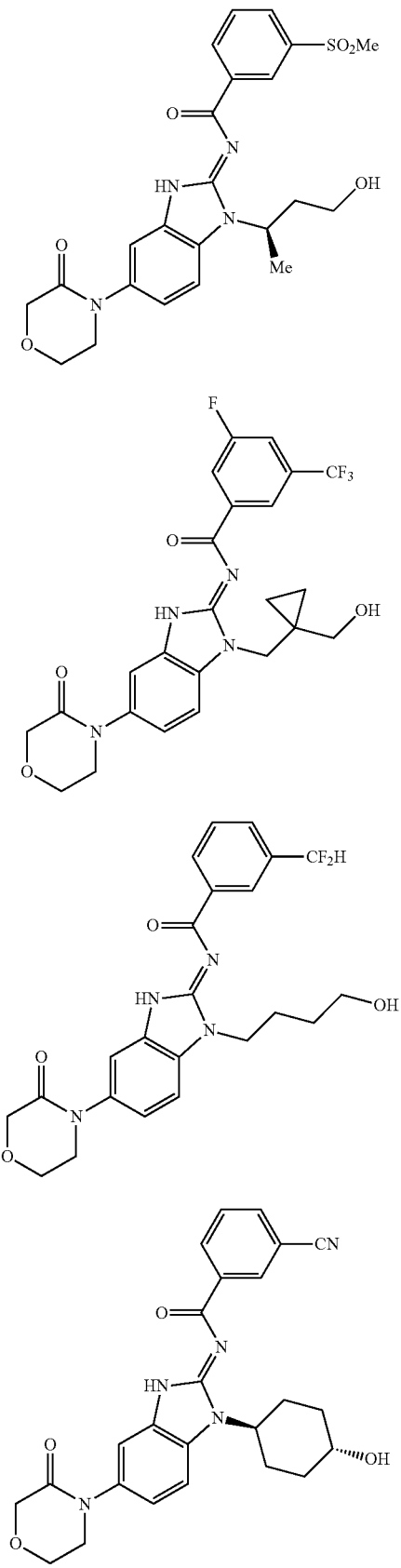

TABLE 1-continued
| | |
|---|---|
| 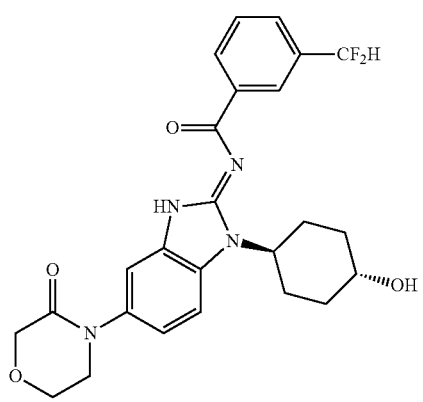 28 | 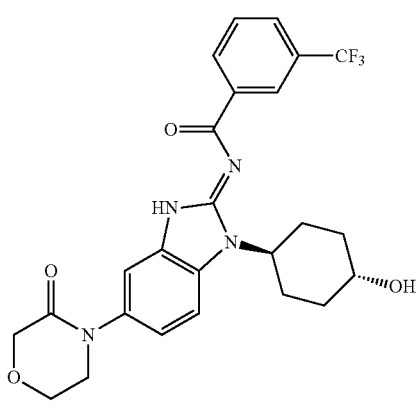 32 |
| 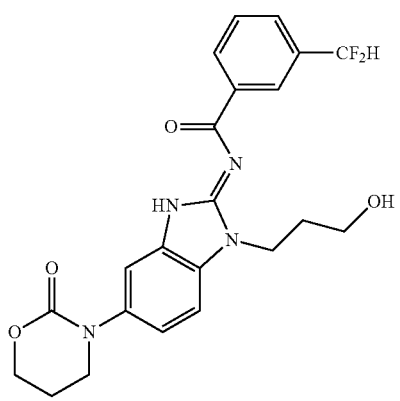 [SMILES: O=C(/N=c1\[nH]c2cc(N3CCCOC3=O)ccc2n1CCCO)c1cccc(C(F)F)c1] 29 | 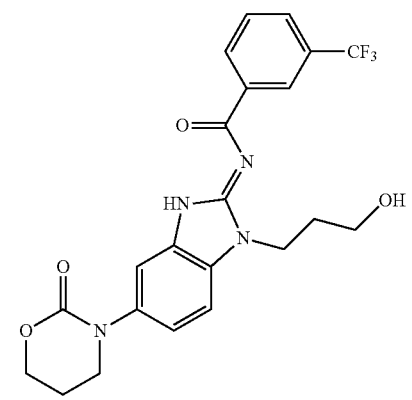 33 |
| 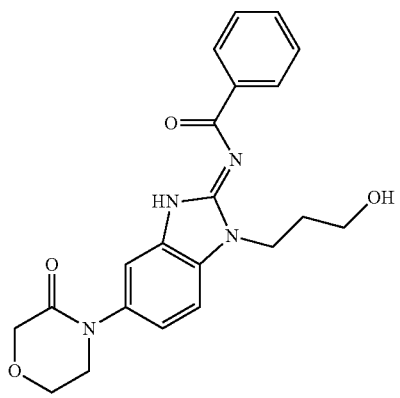 [SMILES: O=C(/N=c1\[nH]c2cc(N3CCOCC3=O)ccc2n1CCCO)c1ccccc1] 30 | 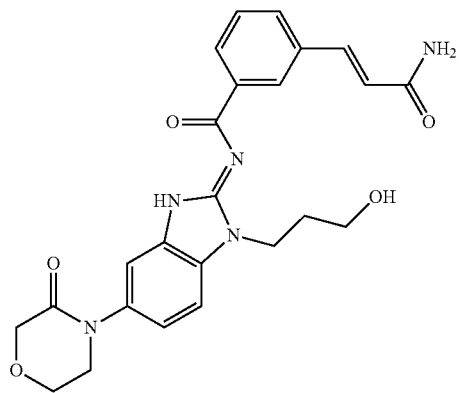 34 |
| 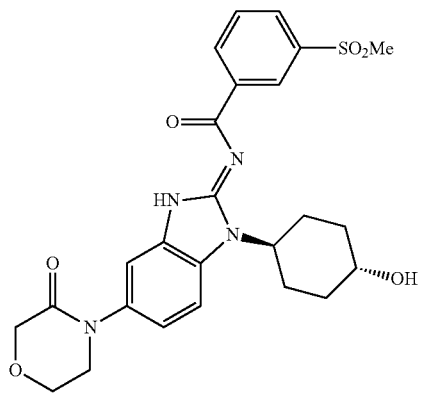 [SMILES: CS(=O)(=O)c1cccc(C(=O)/N=c2\[nH]c3cc(N4CCOCC4=O)ccc3n2[C@H]2CC[C@H](O)CC2)c1] 31 | 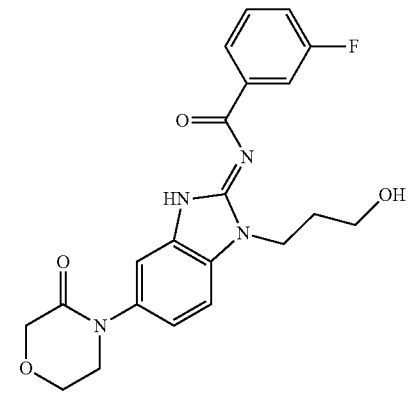 [SMILES: O=C(/N=c1\[nH]c2cc(N3CCOCC3=O)ccc2n1CCCO)c1cccc(F)c1] 35 |

TABLE 1-continued
36
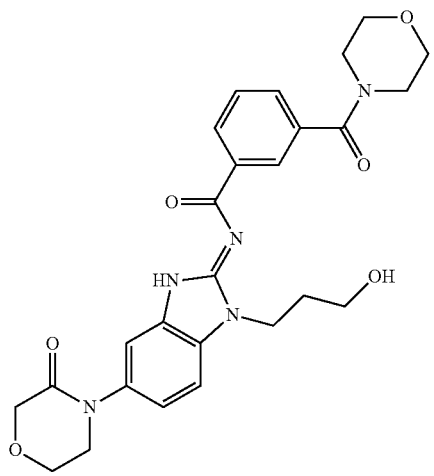 [SMILES: O=C(/N=c1\[nH]c2cc(N3CCOCC3=O)ccc2n1CCCO)c1cccc(C(=O)N2CCOCC2)c1]
37
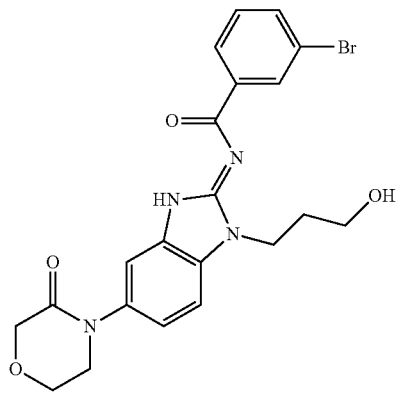 [SMILES: O=C(/N=c1\[nH]c2cc(N3CCOCC3=O)ccc2n1CCCO)c1cccc(Br)c1]
38
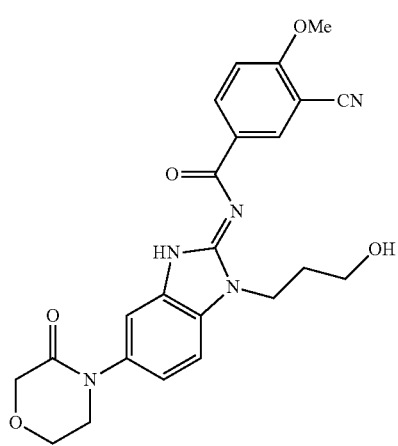 [SMILES: COc1ccc(C(=O)/N=c2\[nH]c3cc(N4CCOCC4=O)ccc3n2CCCO)cc1C#N]
TABLE 1-continued
39
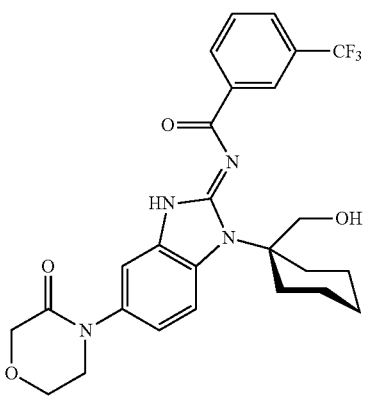
40
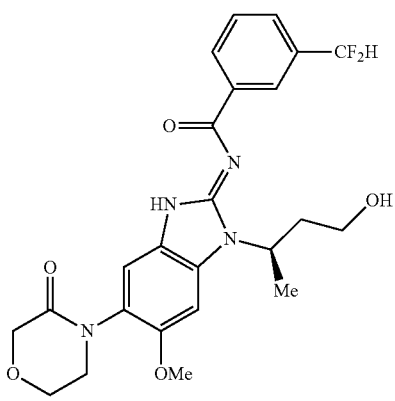 [SMILES: COc1cc2c(cc1N1CCOCC1=O)[nH]/c(=N\C(=O)c1cccc(C(F)F)c1)n2[C@H](C)CCO]
41
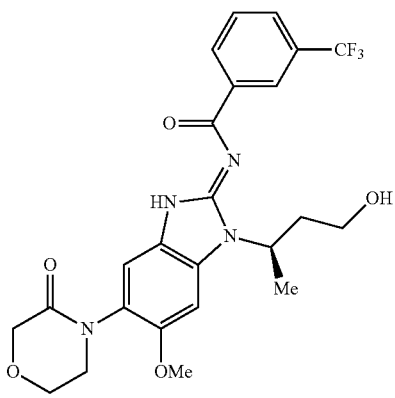
42
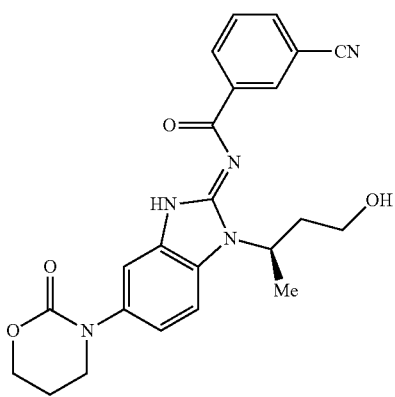 [SMILES: C[C@H](CCO)n1/c(=N/C(=O)c2cccc(C#N)c2)[nH]c2cc(N3CCCOC3=O)ccc21]

TABLE 1-continued
43 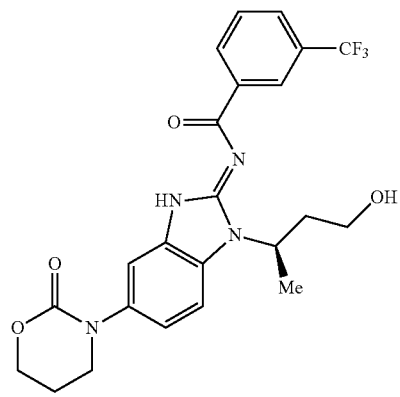
44 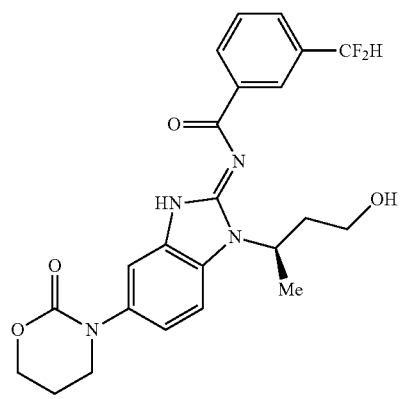 [SMILES: C[C@H](CCO)n1/c(=N/C(=O)c2cccc(C(F)F)c2)[nH]c2cc(N3CCCOC3=O)ccc21]
45 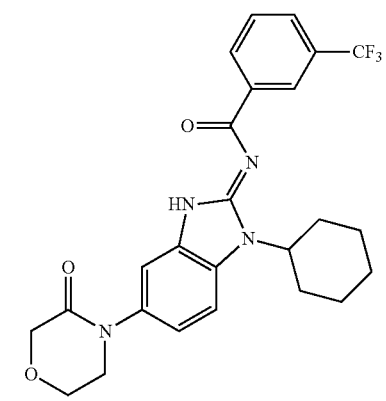 [SMILES: O=C(/N=c1\[nH]c2cc(N3CCOCC3=O)ccc2n1C1CCCCC1)c1cccc(C(F)(F)F)c1]
46 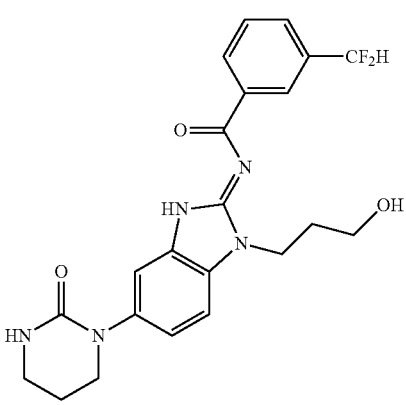 [SMILES: O=C(/N=c1\[nH]c2cc(N3CCCNC3=O)ccc2n1CCCO)c1cccc(C(F)F)c1]
TABLE 1-continued
47 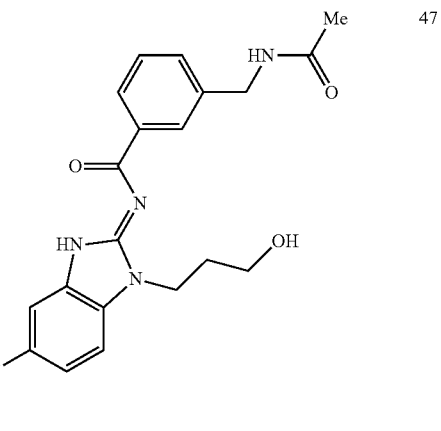
48 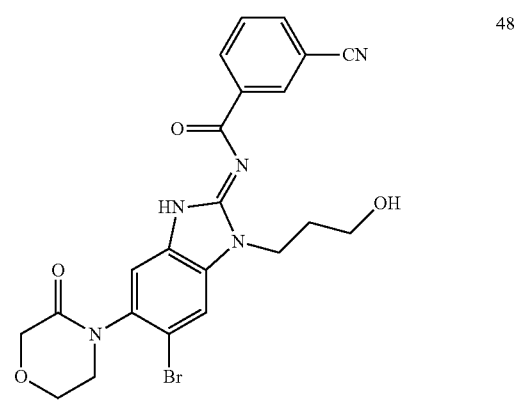
49 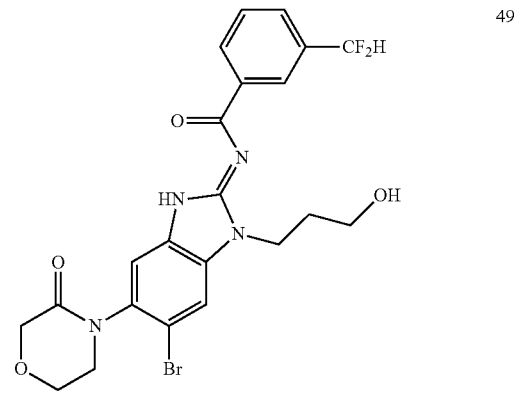
50 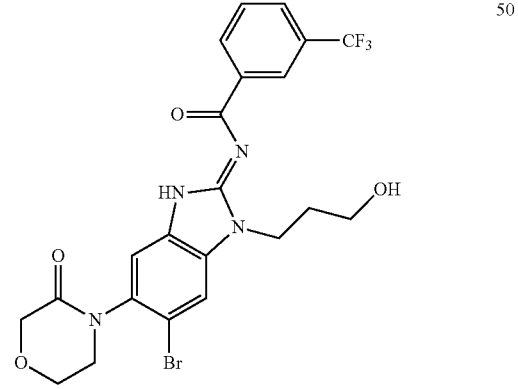

TABLE 1-continued
| 51 | 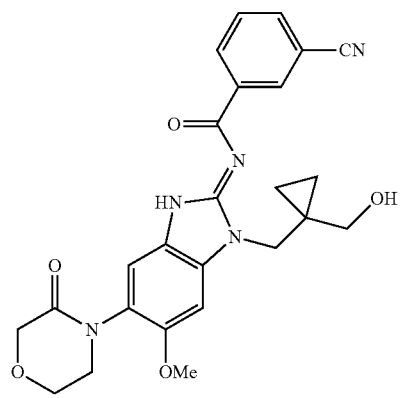 [SMILES: COc1cc2c(cc1N1CCOCC1=O)[nH]/c(=N\C(=O)c1cccc(C#N)c1)n2CC1(CO)CC1] |
| 52 | 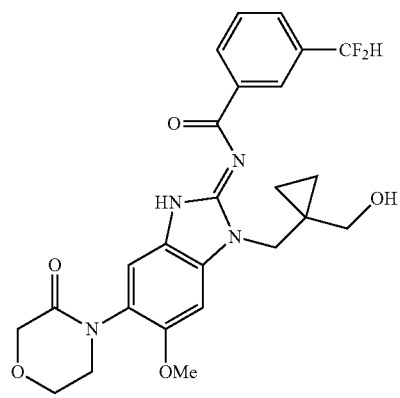 [SMILES: COc1cc2c(cc1N1CCOCC1=O)[nH]/c(=N\C(=O)c1cccc(C(F)F)c1)n2CC1(CO)CC1] |
| 53 | 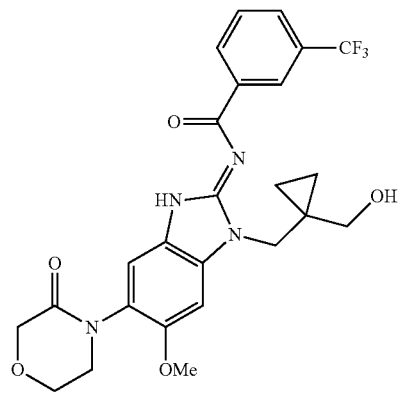 |
| 54 | |
TABLE 1-continued
| 55 | 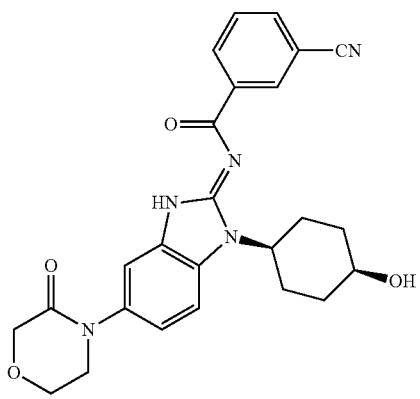 [SMILES: N#Cc1cccc(C(=O)/N=c2\[nH]c3cc(N4CCOCC4=O)ccc3n2[C@H]2CC[C@@H](O)CC2)c1] |
| 56 | 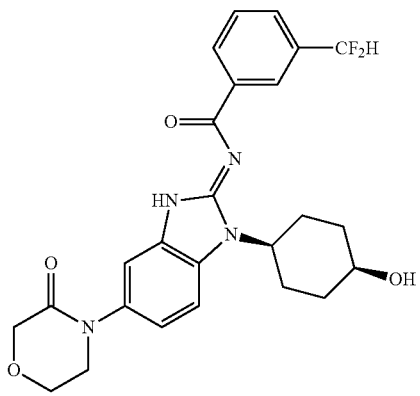 [SMILES: O=C(/N=c1\[nH]c2cc(N3CCOCC3=O)ccc2n1[C@H]1CC[C@@H](O)CC1)c1cccc(C(F)F)c1] |
| 57 | 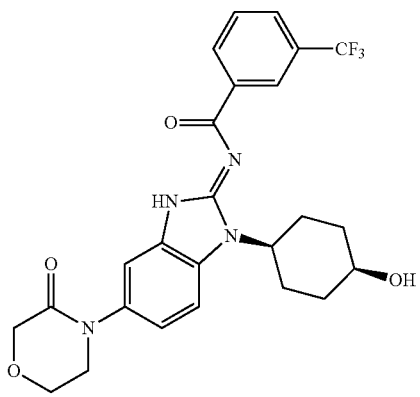 |
| 58 | 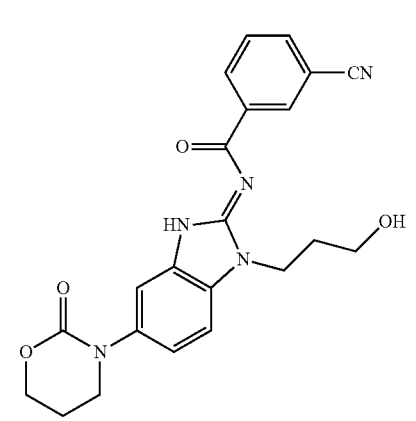 [SMILES: N#Cc1cccc(C(=O)/N=c2\[nH]c3cc(N4CCCOC4=O)ccc3n2CCCO)c1] |

TABLE 1-continued
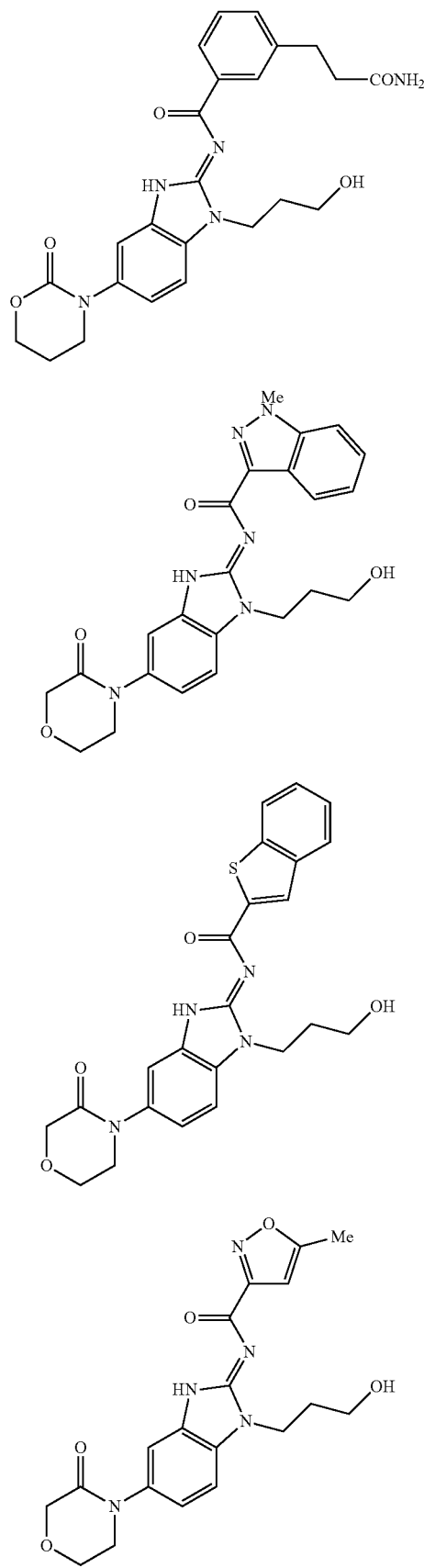
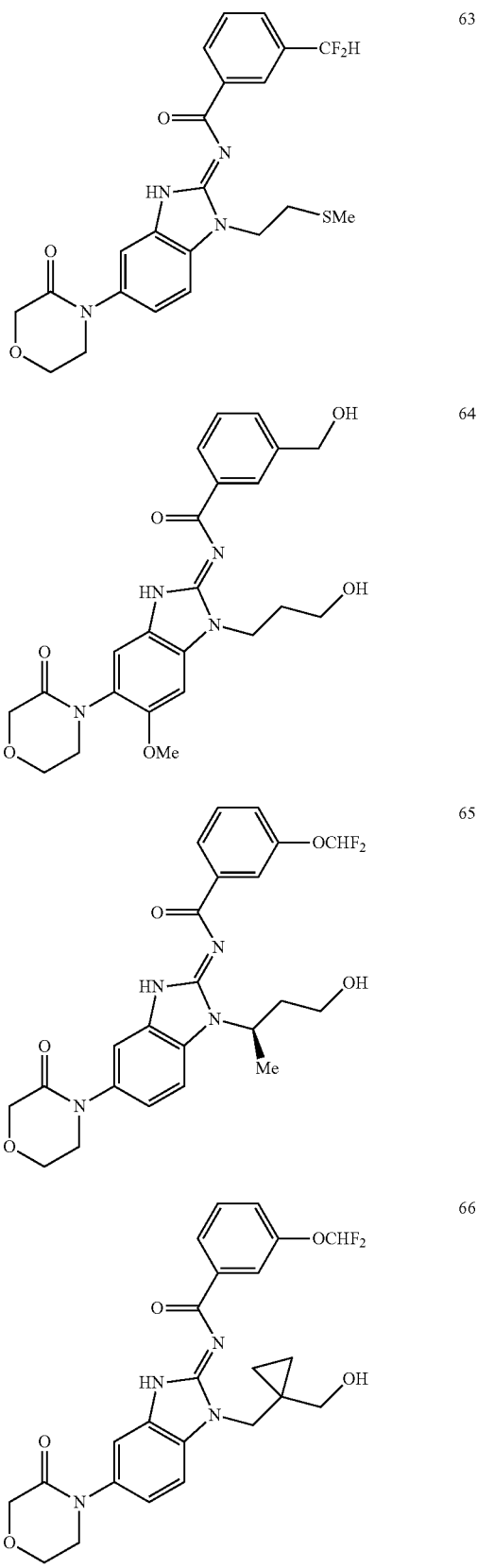

TABLE 1-continued
67 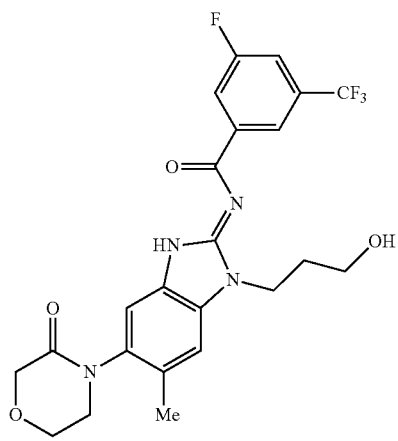 [SMILES: Cc1cc2c(cc1N1CCOCC1=O)[nH]/c(=N\C(=O)c1cc(F)cc(C(F)(F)F)c1)n2CCCO]
68 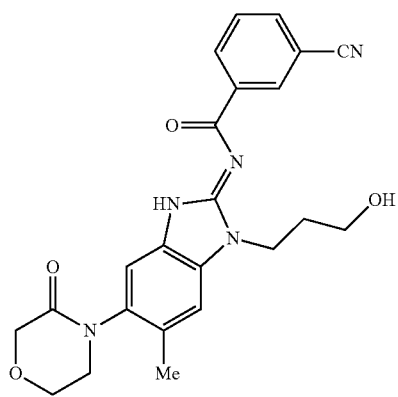
69 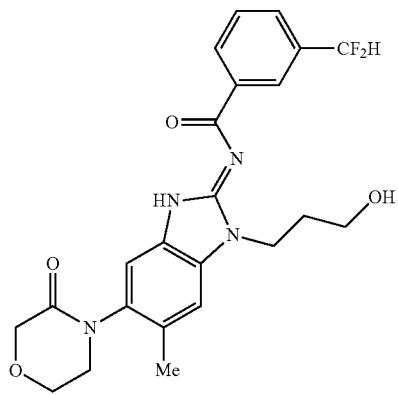
70 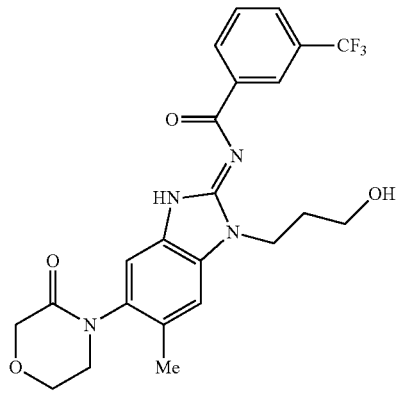 [SMILES: Cc1cc2c(cc1N1CCOCC1=O)[nH]/c(=N\C(=O)c1cccc(C(F)(F)F)c1)n2CCCO]
TABLE 1-continued
71 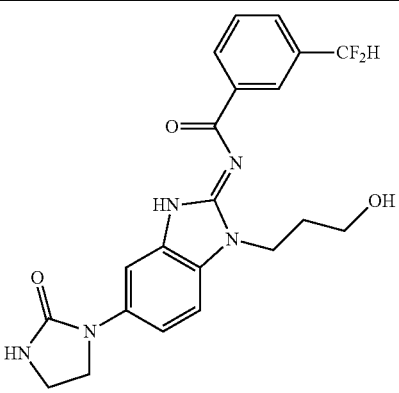
72 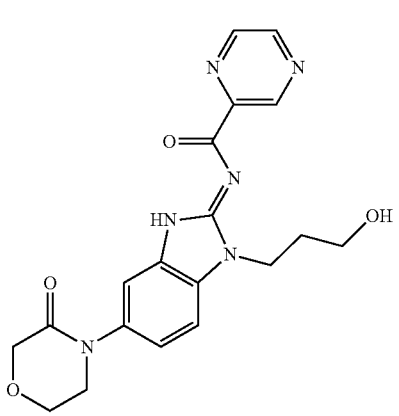 [SMILES: O=C(/N=c1\[nH]c2cc(N3CCOCC3=O)ccc2n1CCCO)c1cnccn1]
73 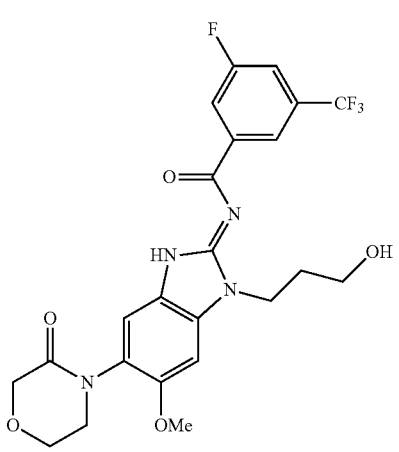 [SMILES: COc1cc2c(cc1N1CCOCC1=O)[nH]/c(=N\C(=O)c1cc(F)cc(C(F)(F)F)c1)n2CCCO]
74 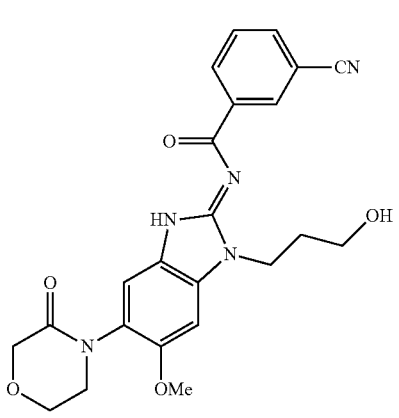 [SMILES: COc1cc2c(cc1N1CCOCC1=O)[nH]/c(=N\C(=O)c1cccc(C#N)c1)n2CCCO]

TABLE 1-continued
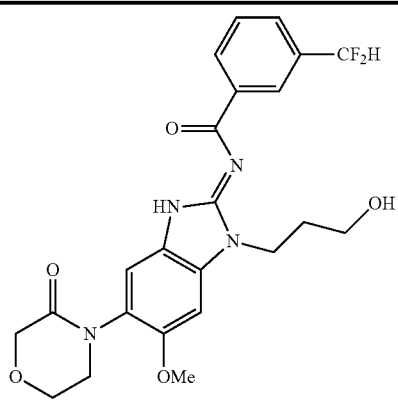 75
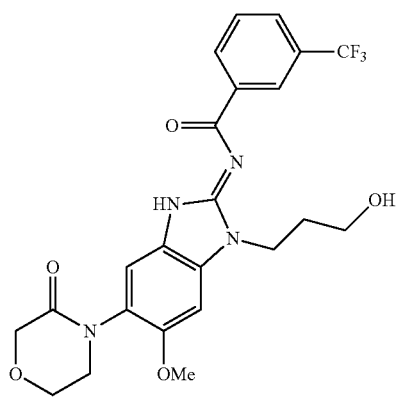 [SMILES: COc1cc2c(cc1N1CCOCC1=O)[nH]/c(=N\C(=O)c1cccc(C(F)(F)F)c1)n2CCCO] 76
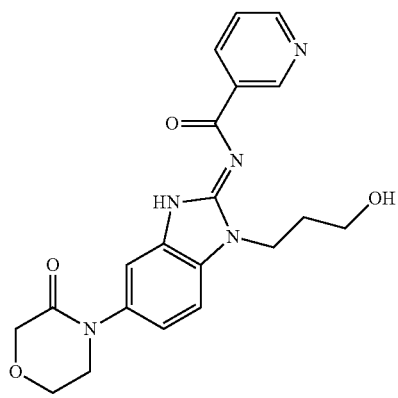 [SMILES: O=C(/N=c1\[nH]c2cc(N3CCOCC3=O)ccc2n1CCCO)c1cccnc1] 77
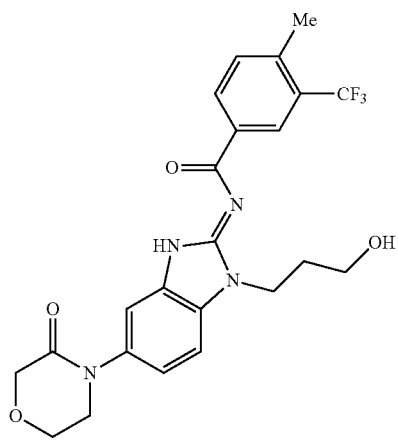 [SMILES: Cc1ccc(C(=O)/N=c2\[nH]c3cc(N4CCOCC4=O)ccc3n2CCCO)cc1C(F)(F)F] 78
TABLE 1-continued
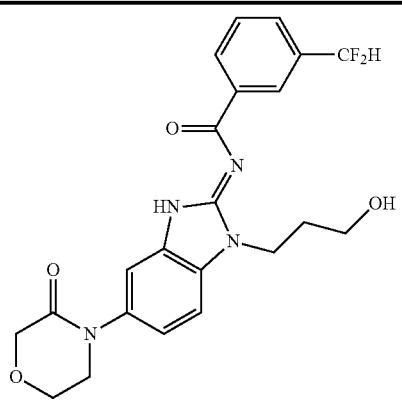 79
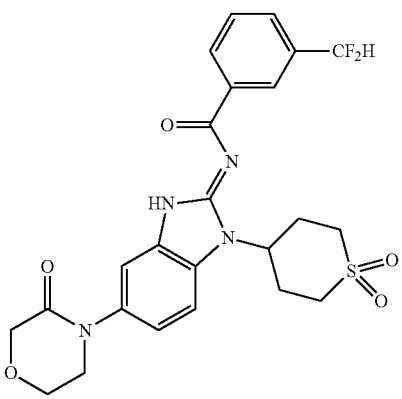 [SMILES: O=C(/N=c1\[nH]c2cc(N3CCOCC3=O)ccc2n1C1CCS(=O)(=O)CC1)c1cccc(C(F)F)c1] 80
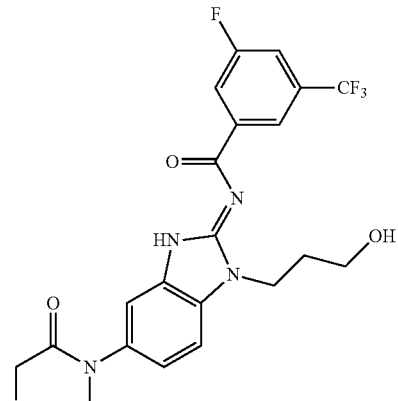 81
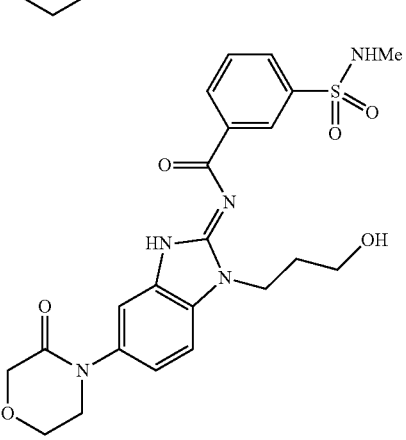 82

TABLE 1-continued
| | |
|---|---|
| 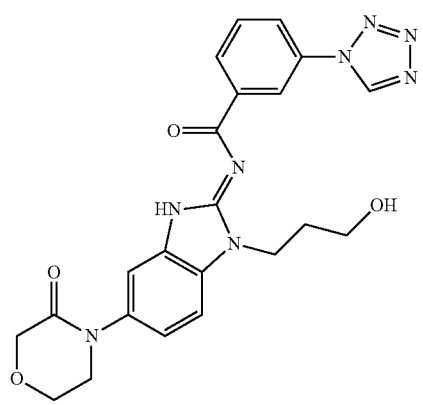 [SMILES: O=C(/N=c1\[nH]c2cc(N3CCOCC3=O)ccc2n1CCCO)c1cccc(-n2cnnn2)c1] 83 | 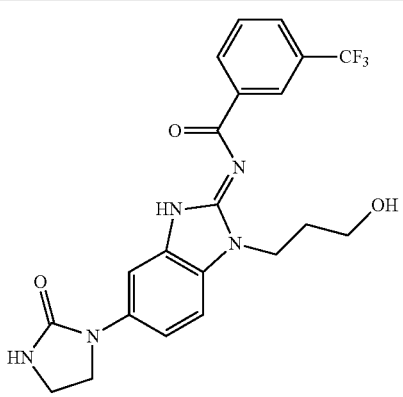 87 |
| 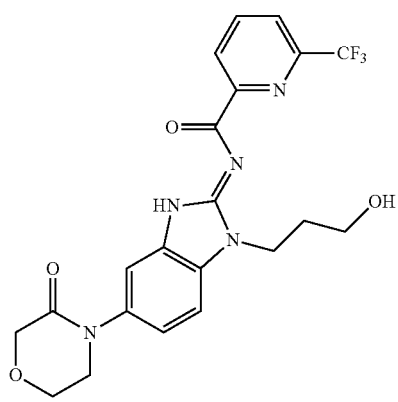 [SMILES: O=C(/N=c1\[nH]c2cc(N3CCOCC3=O)ccc2n1CCCO)c1cccc(C(F)(F)F)n1] 84 | 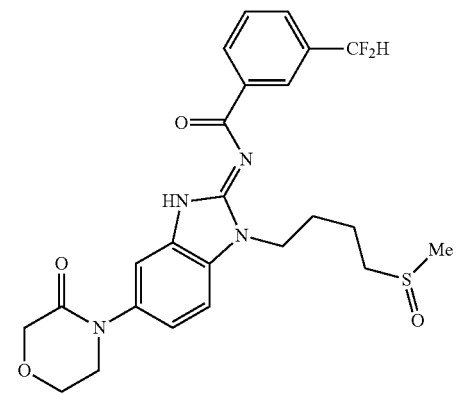 88 |
| 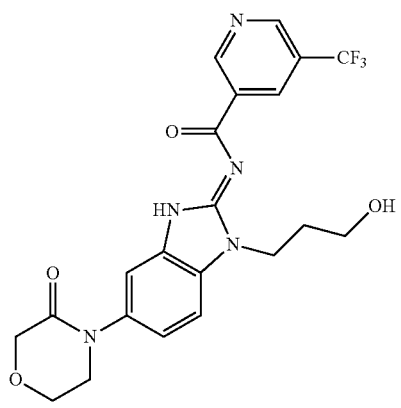 [SMILES: O=C(/N=c1\[nH]c2cc(N3CCOCC3=O)ccc2n1CCCO)c1cncc(C(F)(F)F)c1] 85 | 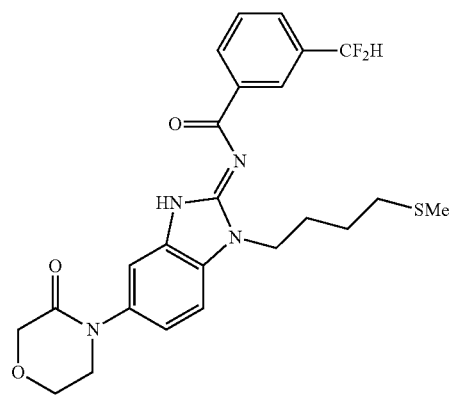 89 |
| 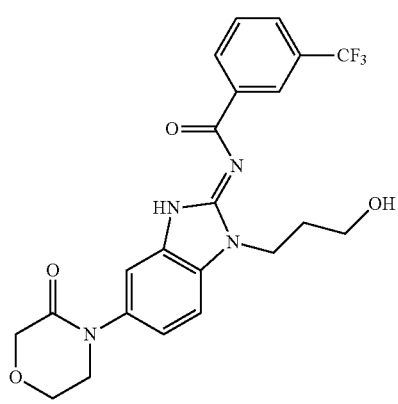 86 | 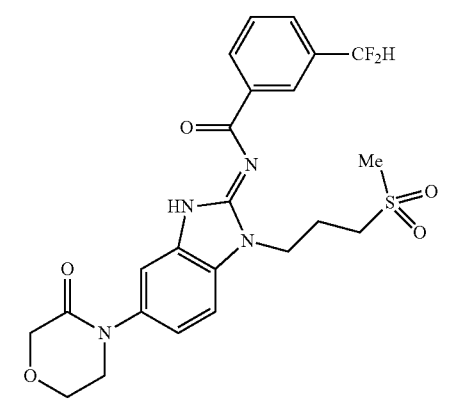 [SMILES: CS(=O)(=O)CCCn1/c(=N/C(=O)c2cccc(C(F)F)c2)[nH]c2cc(N3CCOCC3=O)ccc21] 90 |

TABLE 1-continued
| | |
|---|---|
| 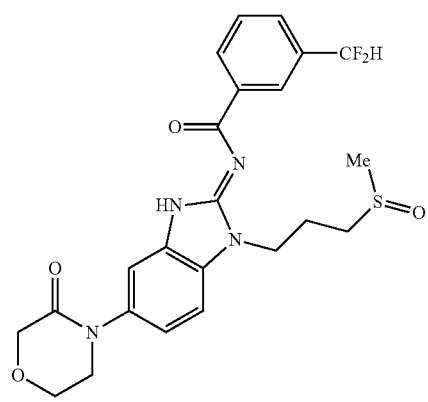 [SMILES: CS(=O)CCCn1/c(=N/C(=O)c2cccc(C(F)F)c2)[nH]c2cc(N3CCOCC3=O)ccc21] 91 | 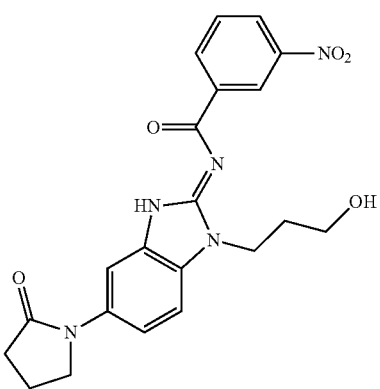 95 |
| 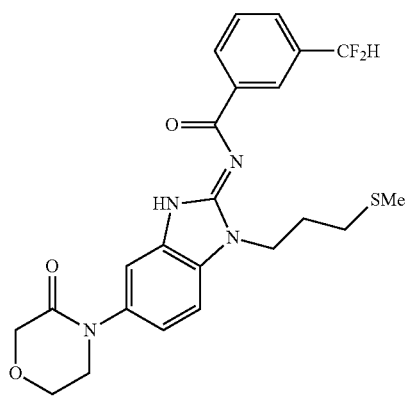 [SMILES: CSCCCn1/c(=N/C(=O)c2cccc(C(F)F)c2)[nH]c2cc(N3CCOCC3=O)ccc21] 92 | 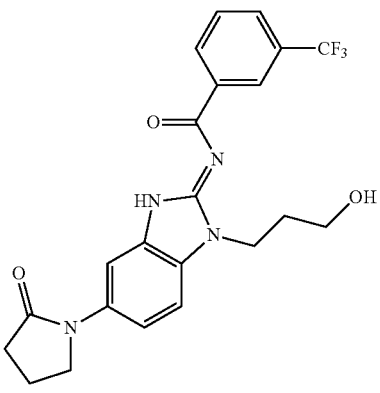 96 |
| 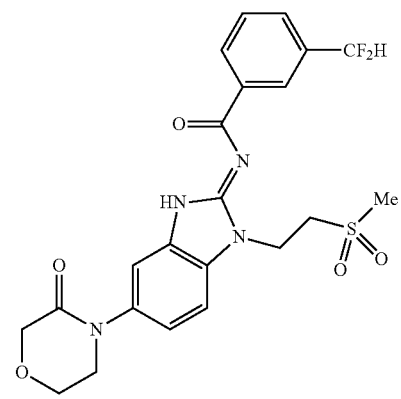 [SMILES: CS(=O)(=O)CCn1/c(=N/C(=O)c2cccc(C(F)F)c2)[nH]c2cc(N3CCOCC3=O)ccc21] 93 | 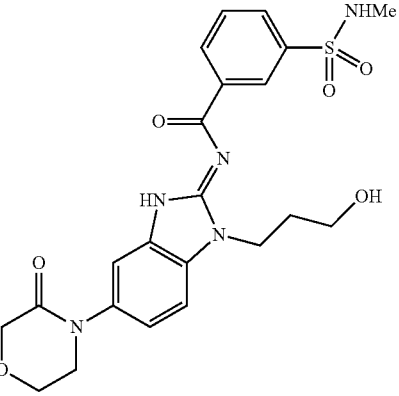 97 |
| 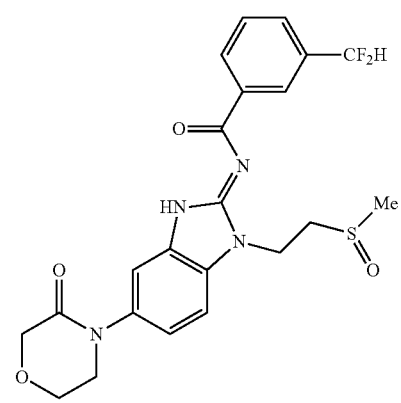 [SMILES: CS(=O)CCn1/c(=N/C(=O)c2cccc(C(F)F)c2)[nH]c2cc(N3CCOCC3=O)ccc21] 94 | 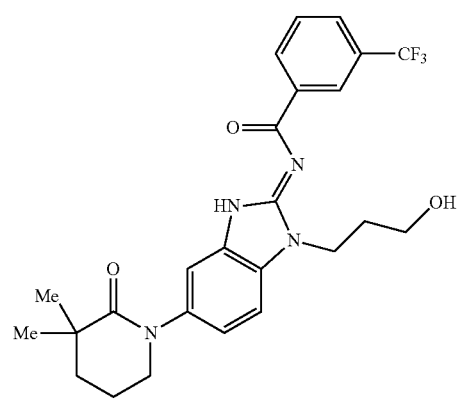 [SMILES: CC1(C)CCCN(c2ccc3c(c2)[nH]/c(=N\C(=O)c2cccc(C(F)(F)F)c2)n3CCCO)C1=O] 98 |

TABLE 1-continued
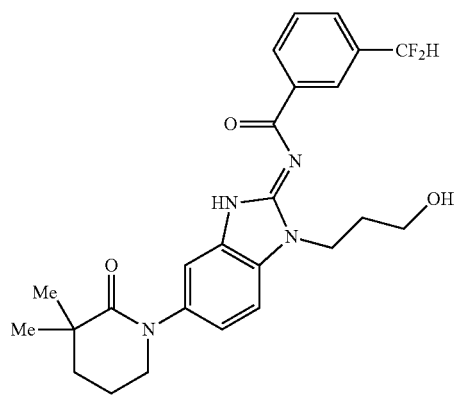 [SMILES: CC1(C)CCCN(c2ccc3c(c2)[nH]/c(=N\C(=O)c2cccc(C(F)F)c2)n3CCCO)C1=O] 99
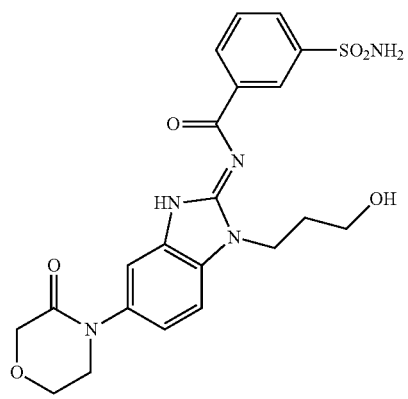 [SMILES: NS(=O)(=O)c1cccc(C(=O)/N=c2\[nH]c3cc(N4CCOCC4=O)ccc3n2CCCO)c1] 100
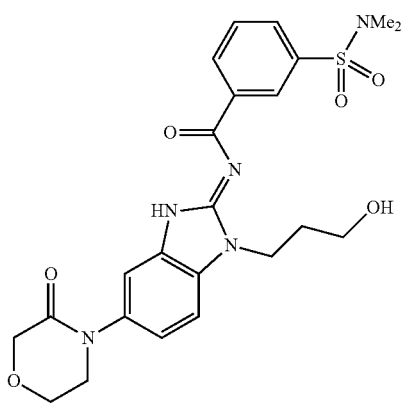 [SMILES: CN(C)S(=O)(=O)c1cccc(C(=O)/N=c2\[nH]c3cc(N4CCOCC4=O)ccc3n2CCCO)c1] 101
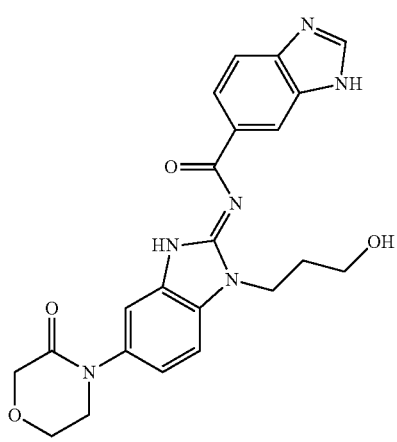 [SMILES: O=C(/N=c1\[nH]c2cc(N3CCOCC3=O)ccc2n1CCCO)c1ccc2nc[nH]c2c1] 102
TABLE 1-continued
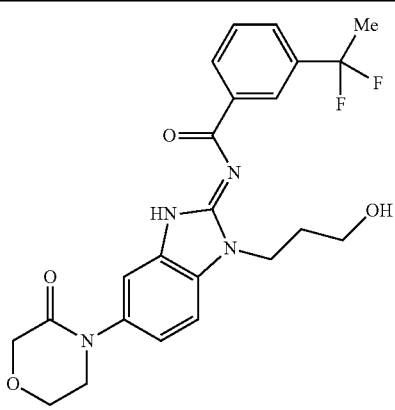 103
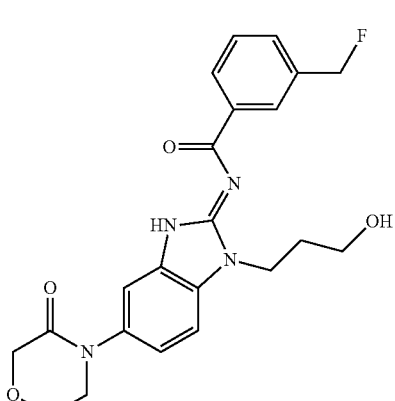 104
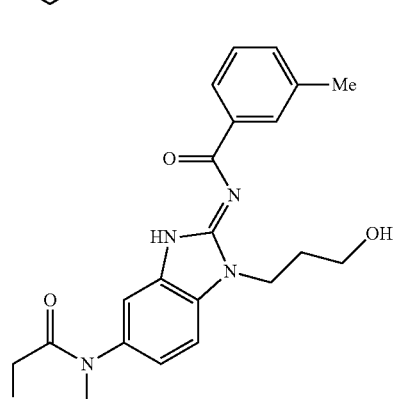 105
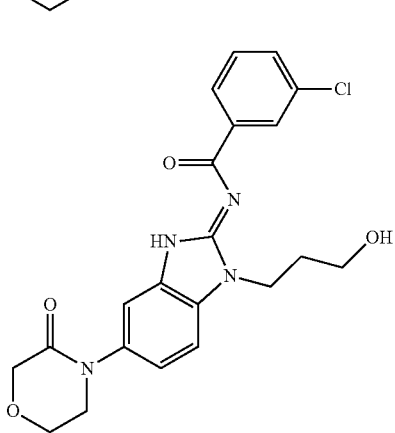 106

TABLE 1-continued
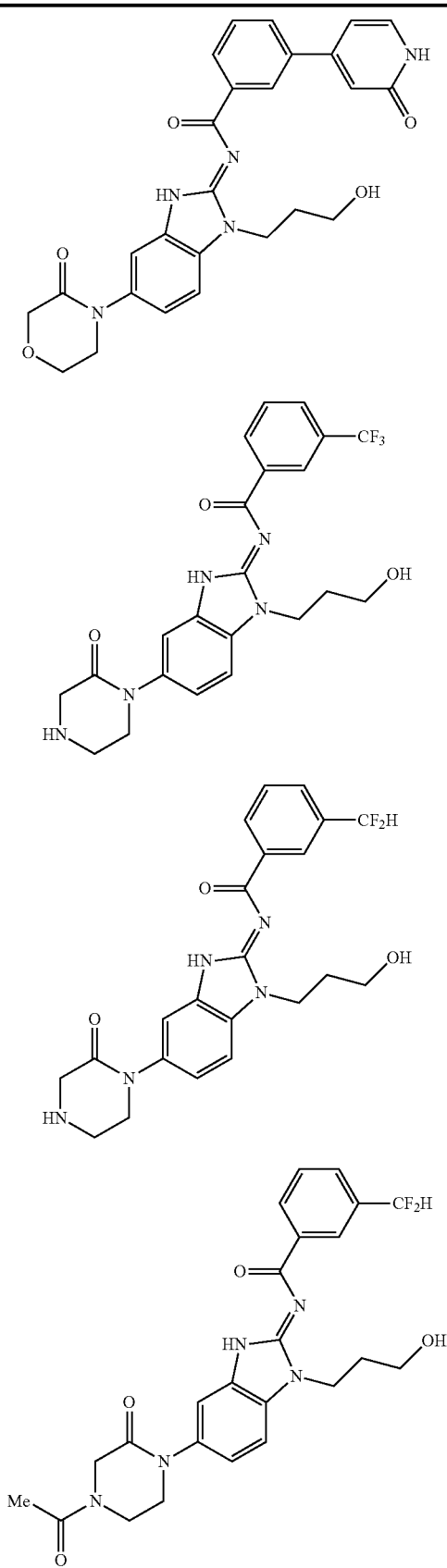
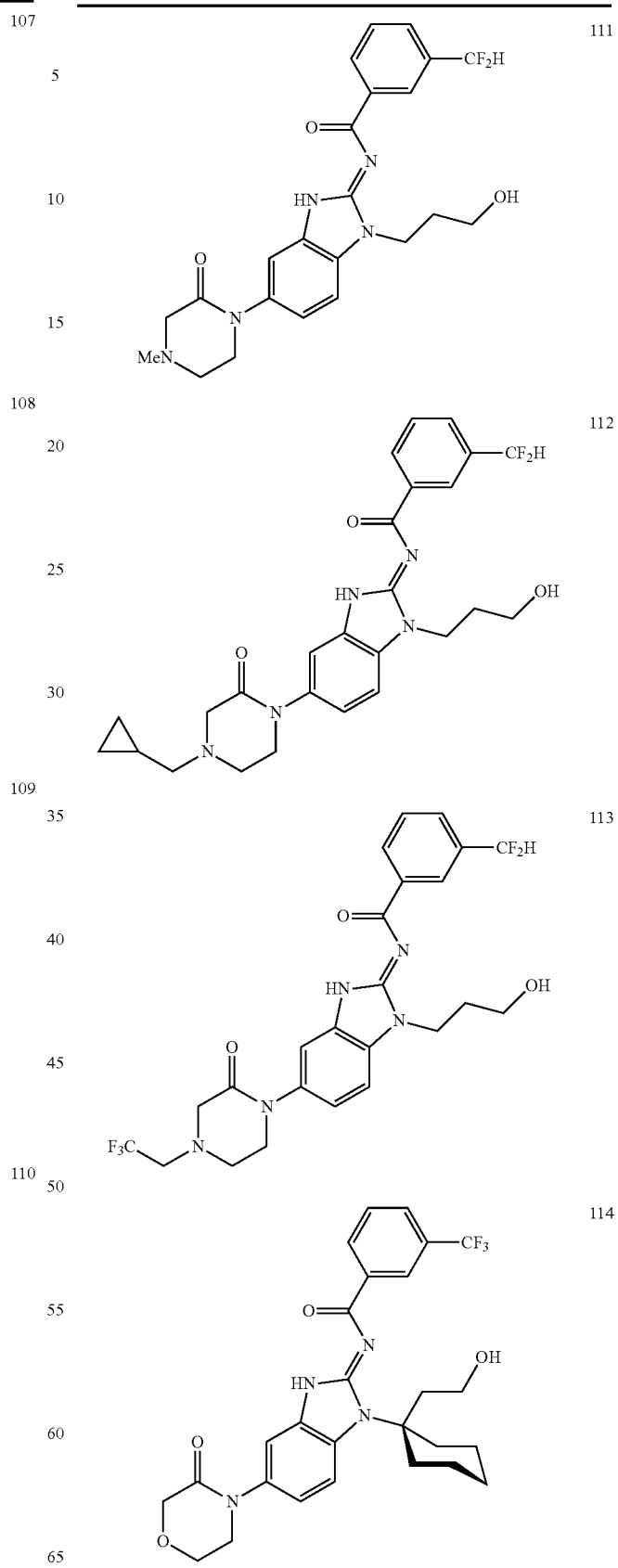

TABLE 1-continued
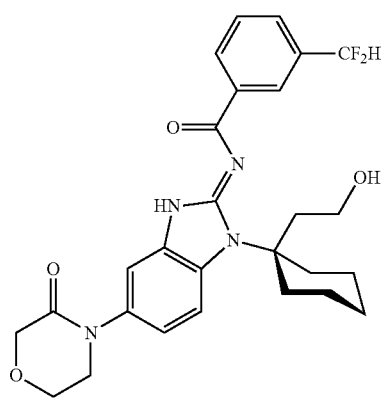 115
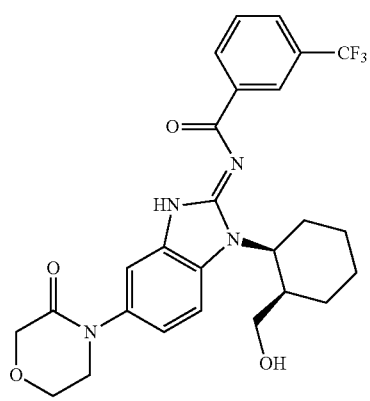 [SMILES: O=C(/N=c1\[nH]c2cc(N3CCOCC3=O)ccc2n1[C@H]1CCCC[C@H]1CO)c1cccc(C(F)(F)F)c1] 116
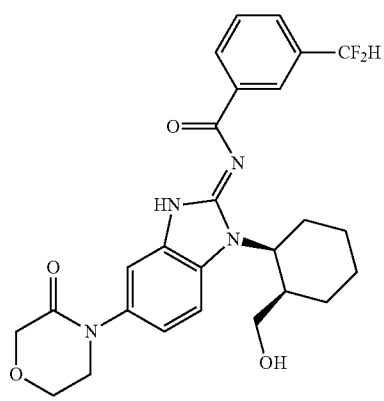 [SMILES: O=C(/N=c1\[nH]c2cc(N3CCOCC3=O)ccc2n1[C@H]1CCCC[C@H]1CO)c1cccc(C(F)F)c1] 117
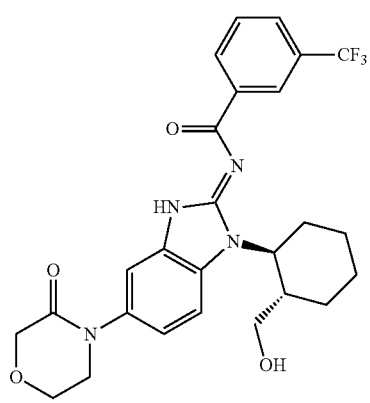 [SMILES: O=C(/N=c1\[nH]c2cc(N3CCOCC3=O)ccc2n1[C@H]1CCCC[C@@H]1CO)c1cccc(C(F)(F)F)c1] 118
TABLE 1-continued
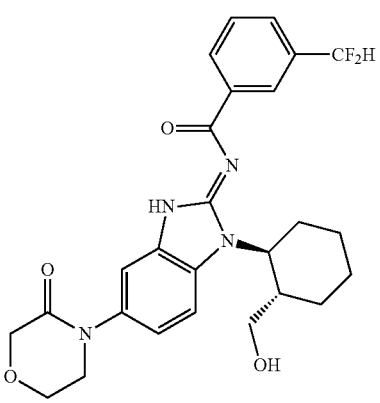 [SMILES: O=C(/N=c1\[nH]c2cc(N3CCOCC3=O)ccc2n1[C@H]1CCCC[C@@H]1CO)c1cccc(C(F)F)c1] 119
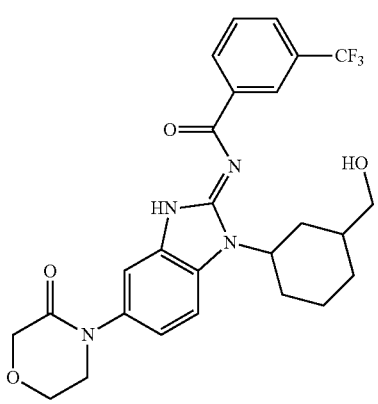 [SMILES: O=C(/N=c1\[nH]c2cc(N3CCOCC3=O)ccc2n1C1CCCC(CO)C1)c1cccc(C(F)(F)F)c1] 120
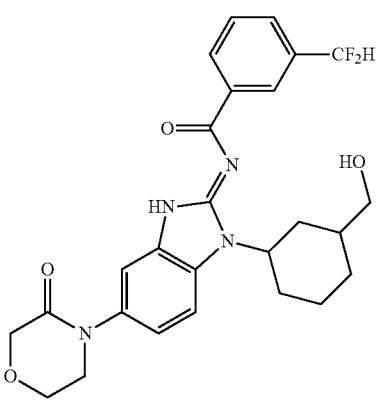 [SMILES: O=C(/N=c1\[nH]c2cc(N3CCOCC3=O)ccc2n1C1CCCC(CO)C1)c1cccc(C(F)F)c1] 121
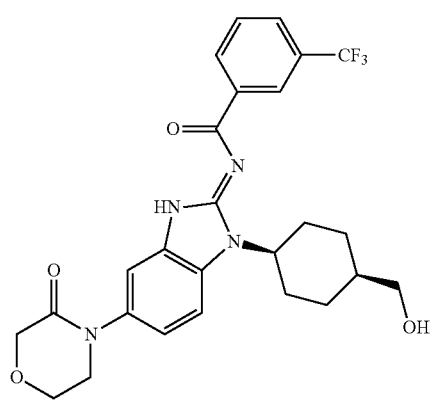 [SMILES: O=C(/N=c1\[nH]c2cc(N3CCOCC3=O)ccc2n1[C@H]1CC[C@@H](CO)CC1)c1cccc(C(F)(F)F)c1] 122

TABLE 1-continued
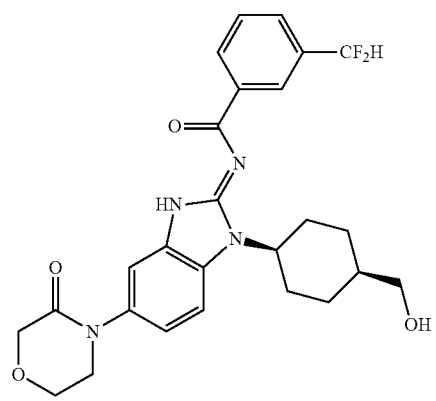 [SMILES: O=C(/N=c1\[nH]c2cc(N3CCOCC3=O)ccc2n1[C@H]1CC[C@@H](CO)CC1)c1cccc(C(F)F)c1]
123
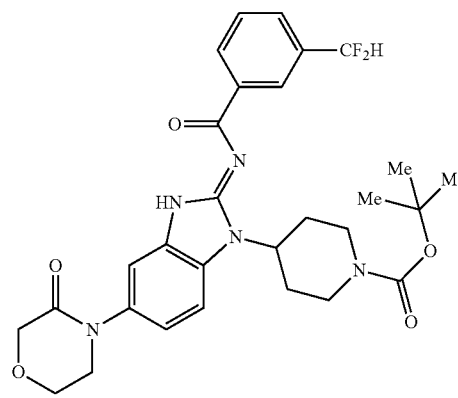
127
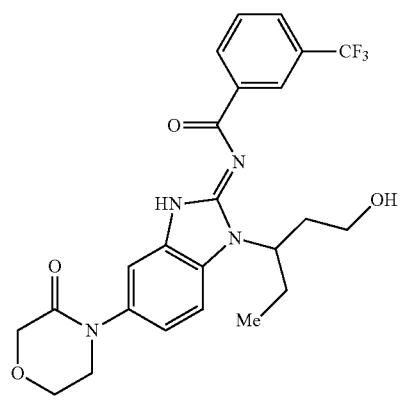 [SMILES: CCC(CCO)n1/c(=N/C(=O)c2cccc(C(F)(F)F)c2)[nH]c2cc(N3CCOCC3=O)ccc21]
124
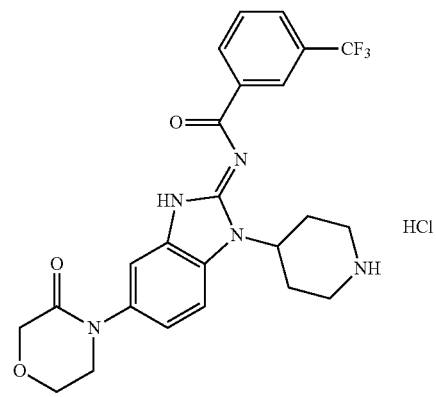
128
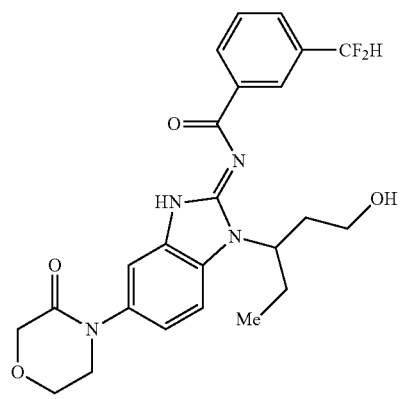 [SMILES: CCC(CCO)n1/c(=N/C(=O)c2cccc(C(F)F)c2)[nH]c2cc(N3CCOCC3=O)ccc21]
125
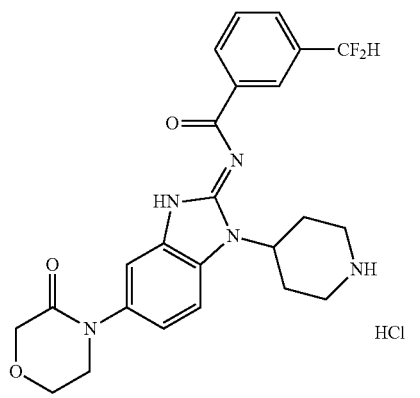
129
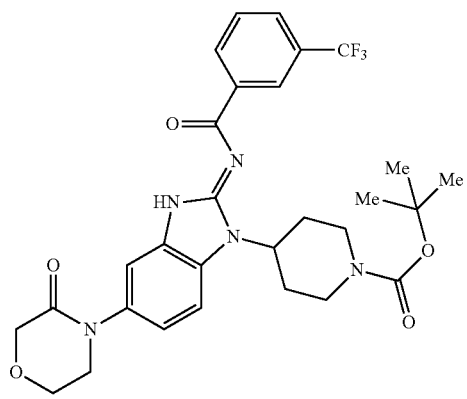 [SMILES: CC(C)(C)OC(=O)N1CCC(n2/c(=N/C(=O)c3cccc(C(F)(F)F)c3)[nH]c3cc(N4CCOCC4=O)ccc32)CC1]
126
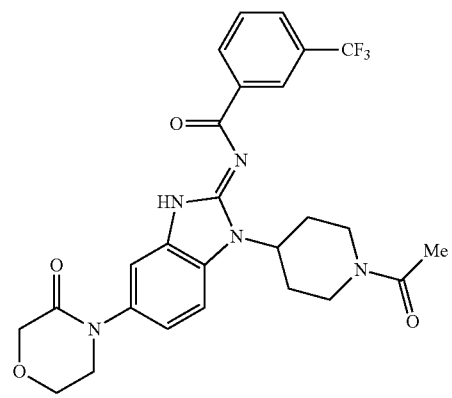 [SMILES: CC(=O)N1CCC(n2/c(=N/C(=O)c3cccc(C(F)(F)F)c3)[nH]c3cc(N4CCOCC4=O)ccc32)CC1]
130

TABLE 1-continued
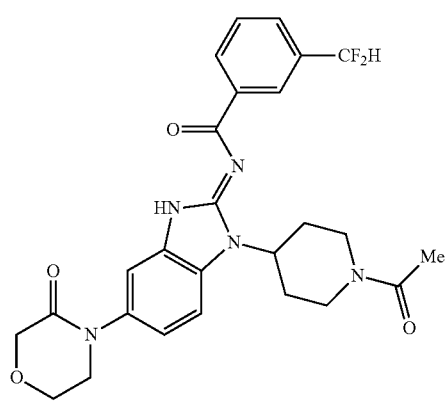 [SMILES: CC(=O)N1CCC(n2/c(=N/C(=O)c3cccc(C(F)F)c3)[nH]c3cc(N4CCOCC4=O)ccc32)CC1]
131
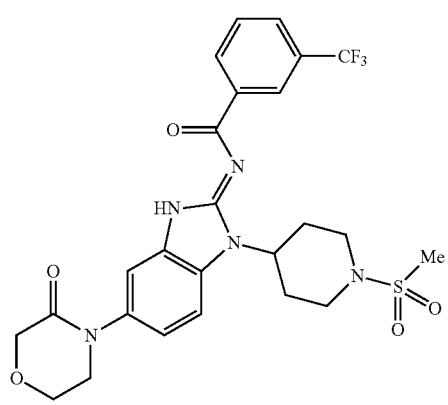 [SMILES: CS(=O)(=O)N1CCC(n2/c(=N/C(=O)c3cccc(C(F)(F)F)c3)[nH]c3cc(N4CCOCC4=O)ccc32)CC1]
132
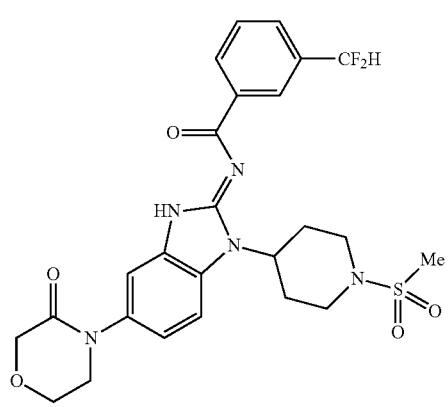 [SMILES: CS(=O)(=O)N1CCC(n2/c(=N/C(=O)c3cccc(C(F)F)c3)[nH]c3cc(N4CCOCC4=O)ccc32)CC1]
133
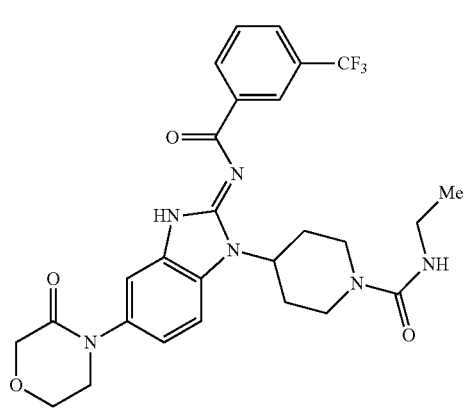 [SMILES: CCNC(=O)N1CCC(n2/c(=N/C(=O)c3cccc(C(F)(F)F)c3)[nH]c3cc(N4CCOCC4=O)ccc32)CC1]
134
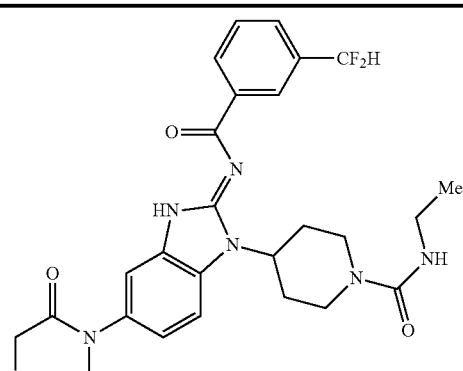
135
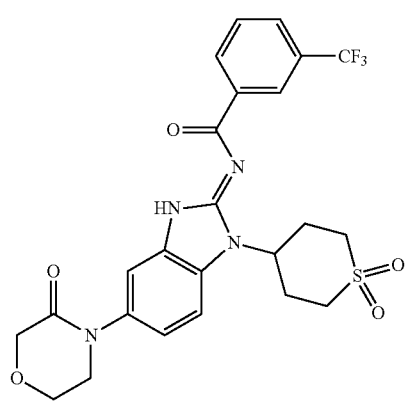 [SMILES: O=C(/N=c1\[nH]c2cc(N3CCOCC3=O)ccc2n1C1CCS(=O)(=O)CC1)c1cccc(C(F)(F)F)c1]
136
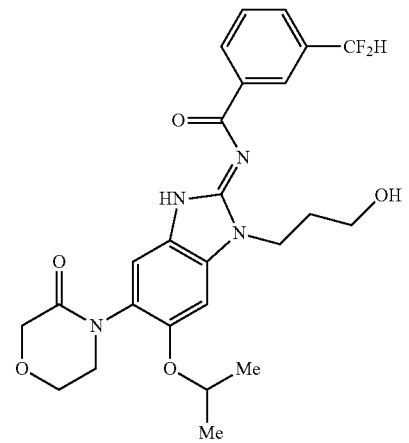 [SMILES: CC(C)Oc1cc2c(cc1N1CCOCC1=O)[nH]/c(=N\C(=O)c1cccc(C(F)F)c1)n2CCCO]
137
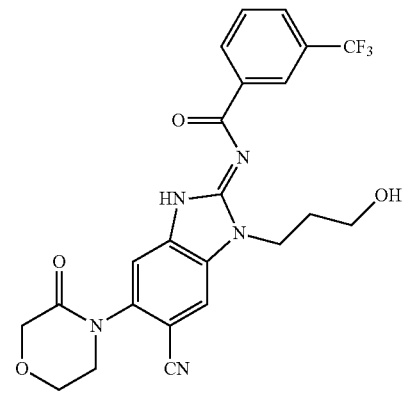
138

TABLE 1-continued
| | |
|---|---|
| 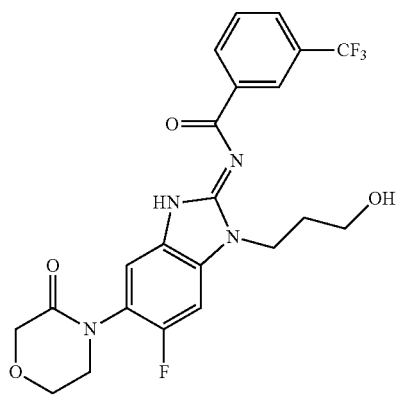 [SMILES: O=C(/N=c1\[nH]c2cc(N3CCOCC3=O)c(F)cc2n1CCCO)c1cccc(C(F)(F)F)c1] 139 | 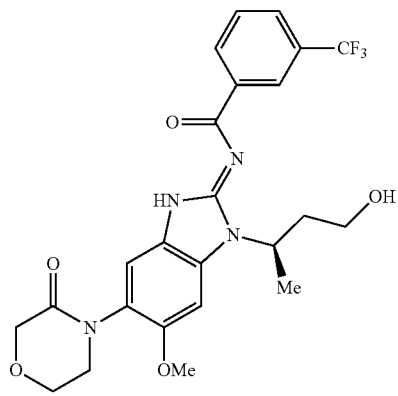 143 |
| 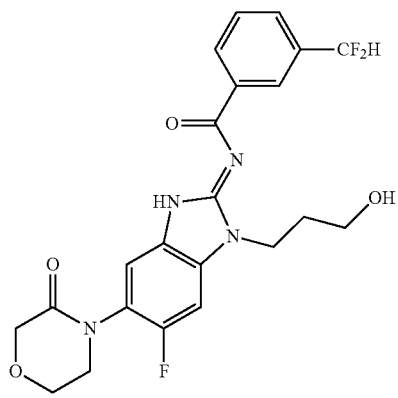 [SMILES: O=C(/N=c1\[nH]c2cc(N3CCOCC3=O)c(F)cc2n1CCCO)c1cccc(C(F)F)c1] 140 | 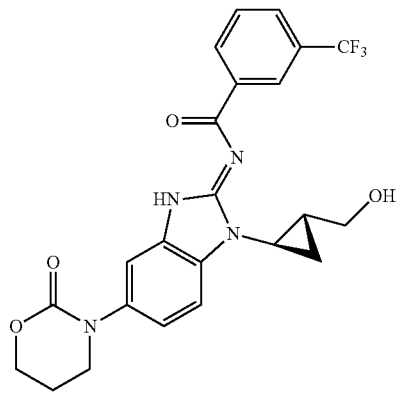 144 |
| 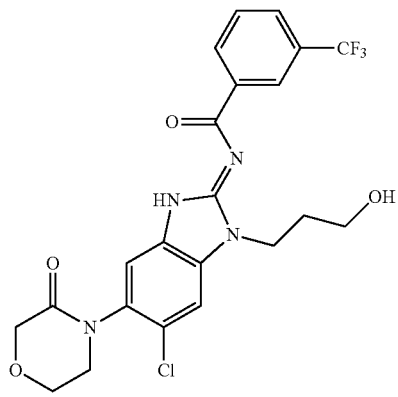 [SMILES: O=C(/N=c1\[nH]c2cc(N3CCOCC3=O)c(Cl)cc2n1CCCO)c1cccc(C(F)(F)F)c1] 141 | 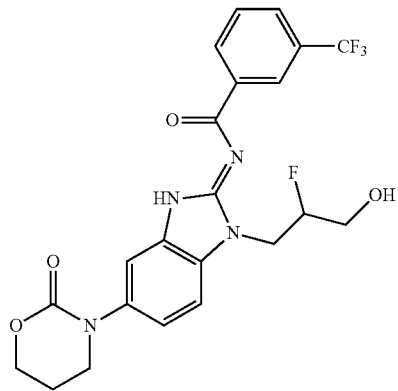 145 |
| 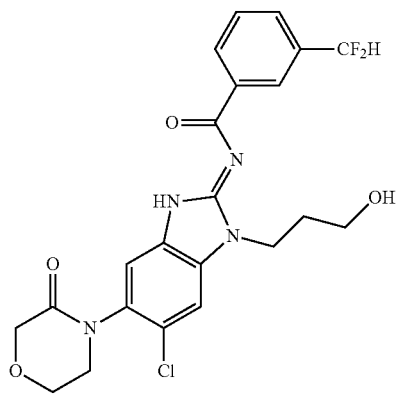 [SMILES: O=C(/N=c1\[nH]c2cc(N3CCOCC3=O)c(Cl)cc2n1CCCO)c1cccc(C(F)F)c1] 142 | 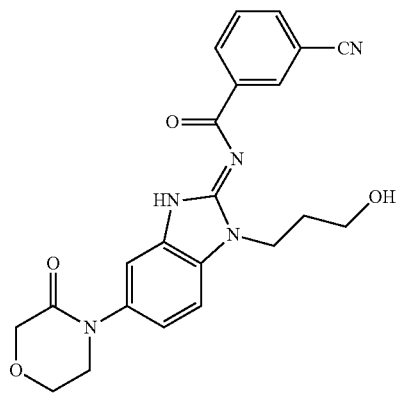 146 |

TABLE 1-continued
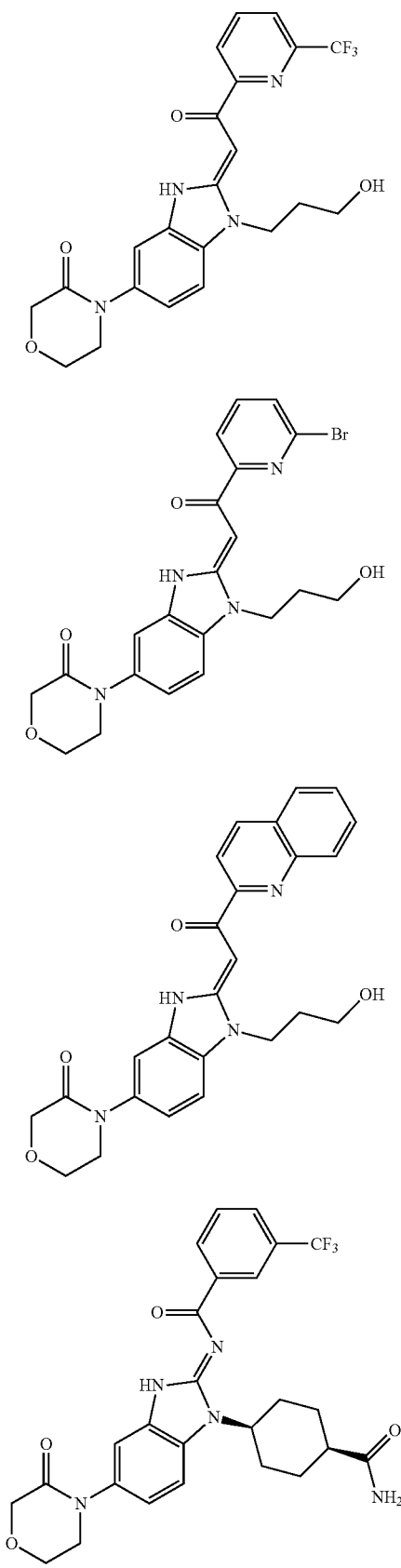
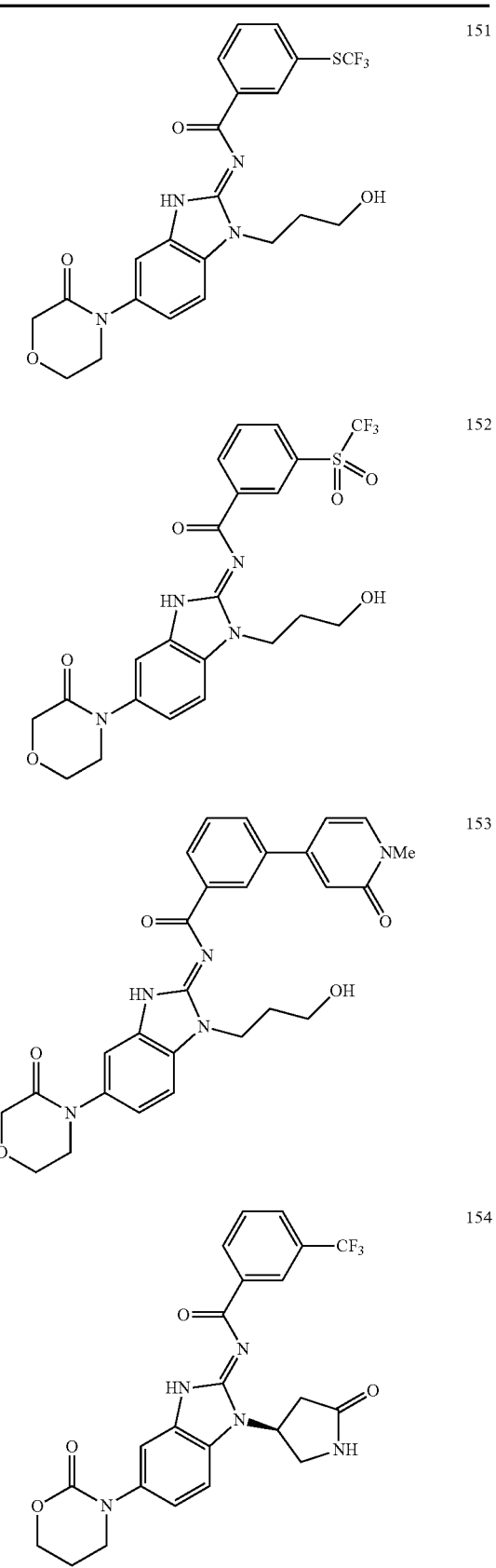

TABLE 1-continued
| | |
|---|---|
| 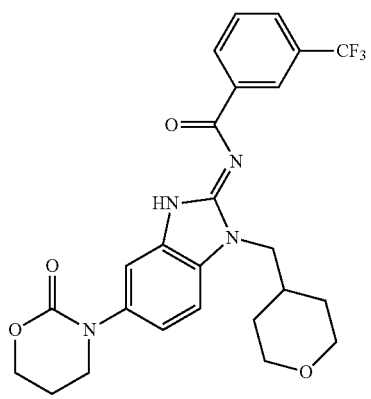 [SMILES: O=C(/N=c1\[nH]c2cc(N3CCCOC3=O)ccc2n1CC1CCOCC1)c1cccc(C(F)(F)F)c1] 155 | 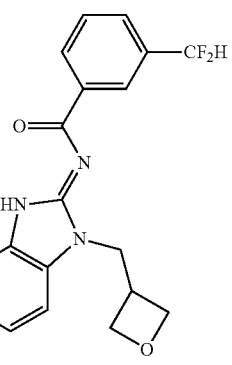 159 |
| 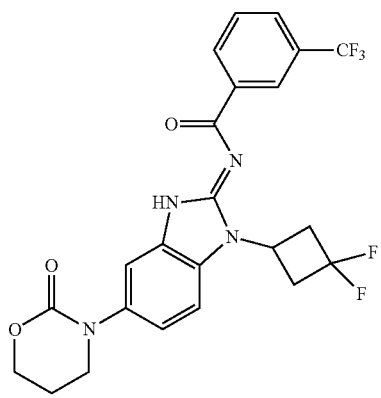 [SMILES: O=C(/N=c1\[nH]c2cc(N3CCCOC3=O)ccc2n1C1CC(F)(F)C1)c1cccc(C(F)(F)F)c1] 156 | 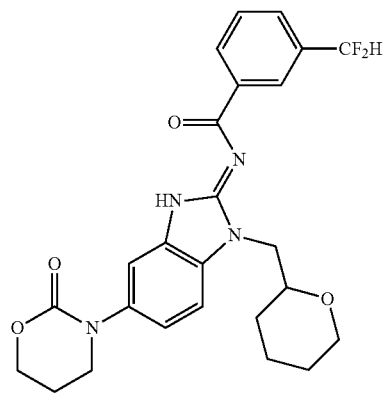 160 |
| 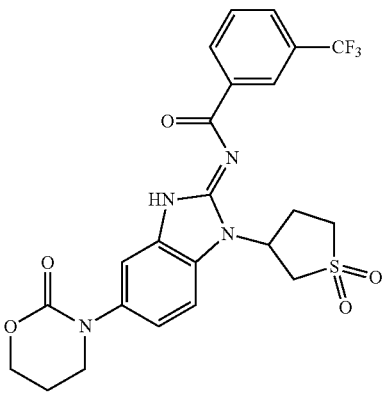 [SMILES: O=C(/N=c1\[nH]c2cc(N3CCCOC3=O)ccc2n1C1CCS(=O)(=O)C1)c1cccc(C(F)(F)F)c1] 157 | 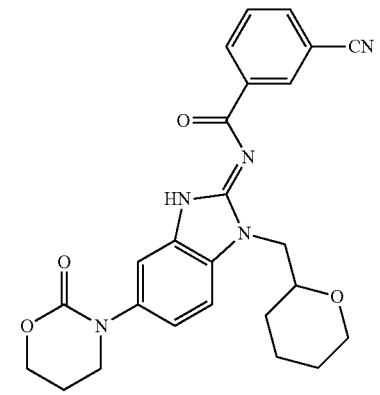 161 |
| 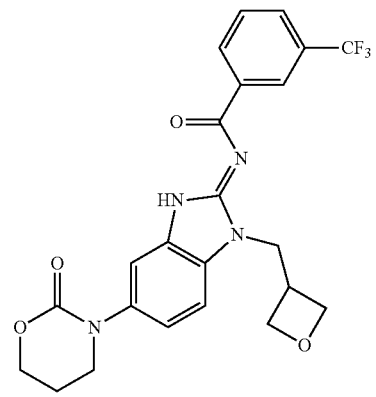 [SMILES: O=C(/N=c1\[nH]c2cc(N3CCCOC3=O)ccc2n1CC1COC1)c1cccc(C(F)(F)F)c1] 158 | 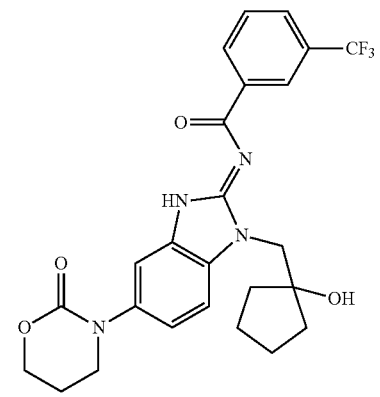 [SMILES: O=C(/N=c1\[nH]c2cc(N3CCCOC3=O)ccc2n1CC1(O)CCCC1)c1cccc(C(F)(F)F)c1] 162 |

TABLE 1-continued
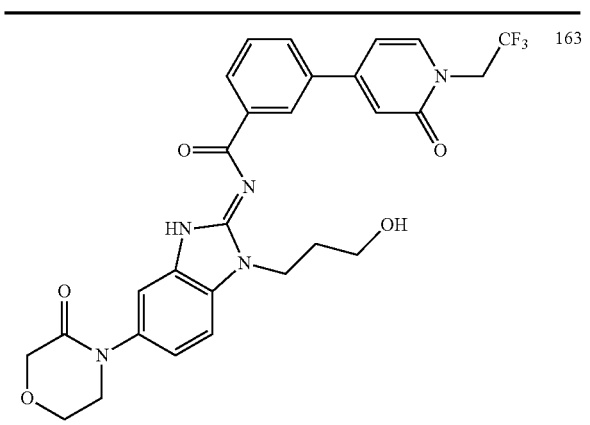
163
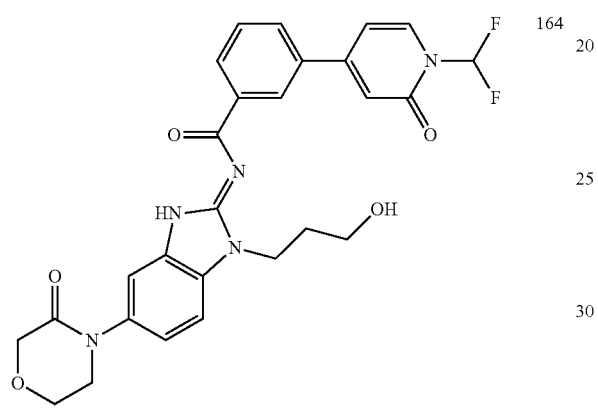
164
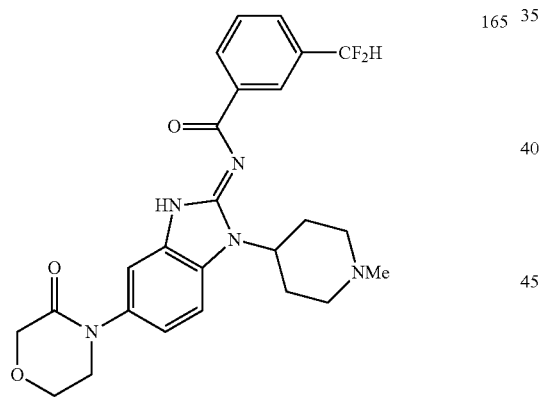
165
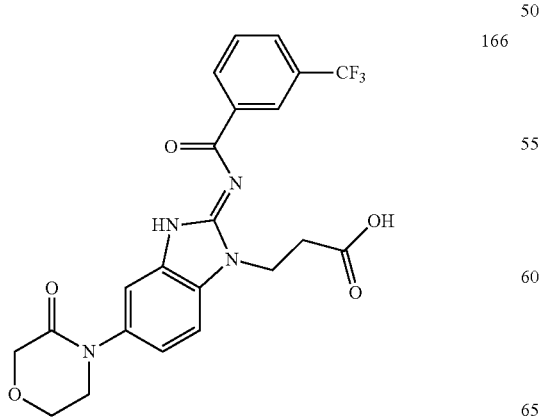
166
TABLE 1-continued
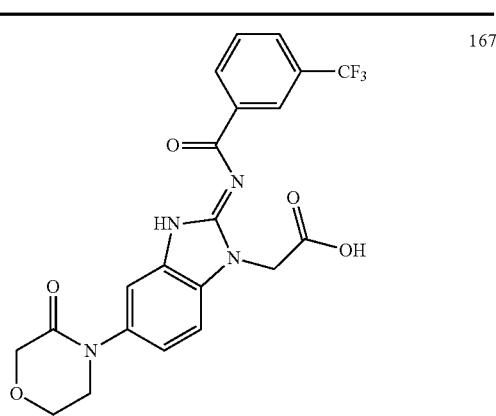
167
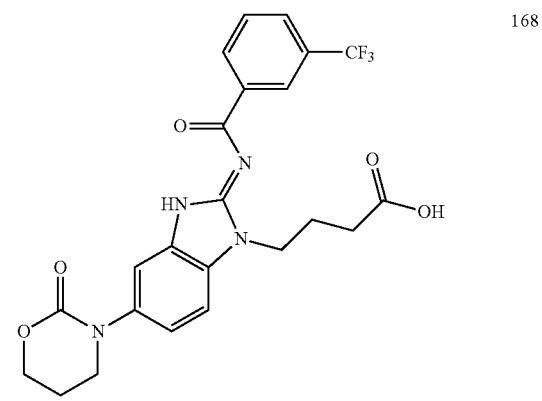
168
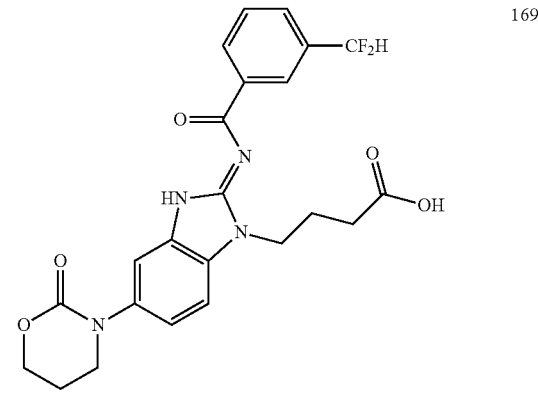
169
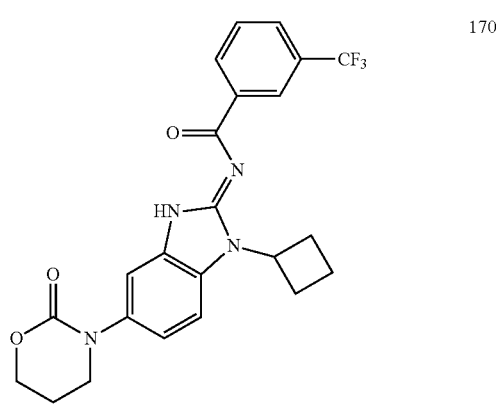
170

TABLE 1-continued
171 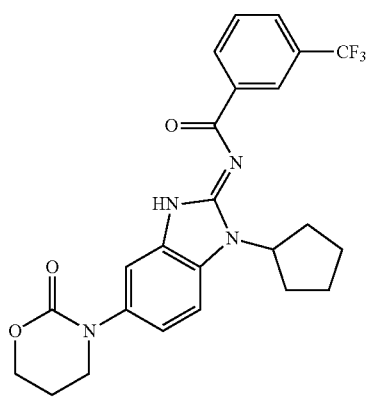 [SMILES: O=C(/N=c1\[nH]c2cc(N3CCCOC3=O)ccc2n1C1CCCC1)c1cccc(C(F)(F)F)c1]
172 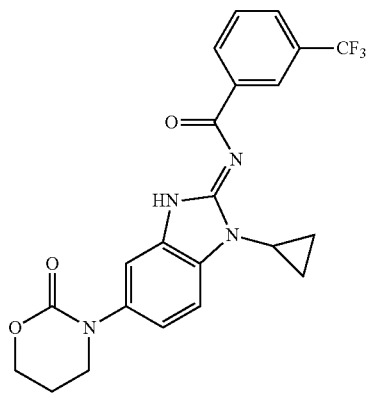 [SMILES: O=C(/N=c1\[nH]c2cc(N3CCCOC3=O)ccc2n1C1CC1)c1cccc(C(F)(F)F)c1]
173 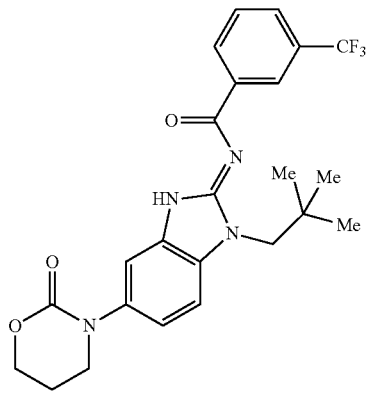 [SMILES: CC(C)(C)Cn1/c(=N/C(=O)c2cccc(C(F)(F)F)c2)[nH]c2cc(N3CCCOC3=O)ccc21]
174 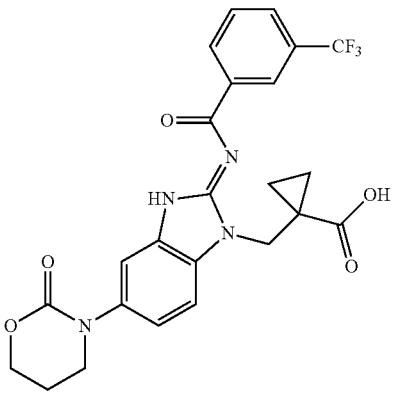 [SMILES: O=C(/N=c1\[nH]c2cc(N3CCCOC3=O)ccc2n1CC1(C(=O)O)CC1)c1cccc(C(F)(F)F)c1]
175 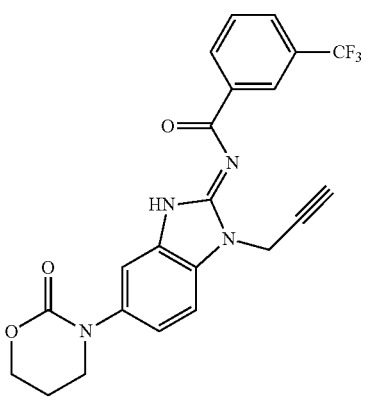 [SMILES: C#CCn1/c(=N/C(=O)c2cccc(C(F)(F)F)c2)[nH]c2cc(N3CCCOC3=O)ccc21]
176 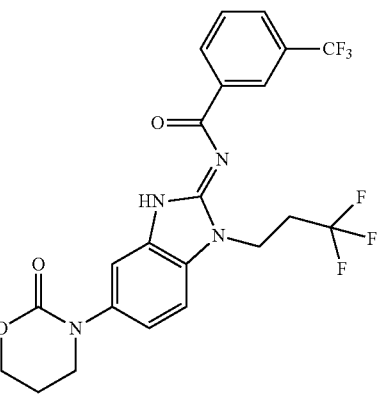
177 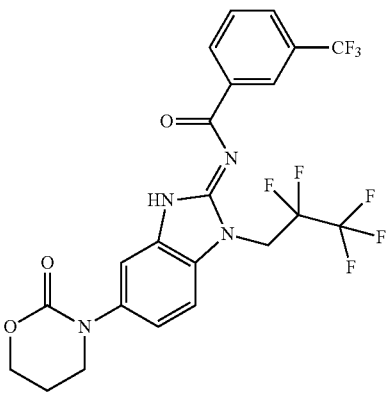 [SMILES: O=C(/N=c1\[nH]c2cc(N3CCCOC3=O)ccc2n1CC(F)(F)C(F)(F)F)c1cccc(C(F)(F)F)c1]
178 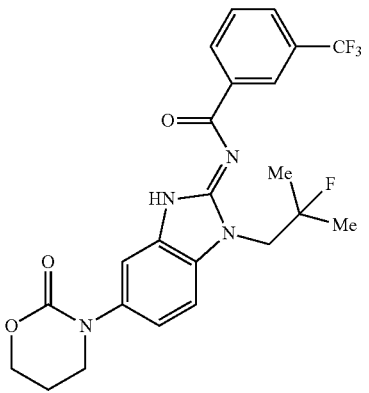 [SMILES: CC(C)(F)Cn1/c(=N/C(=O)c2cccc(C(F)(F)F)c2)[nH]c2cc(N3CCCOC3=O)ccc21]

TABLE 1-continued
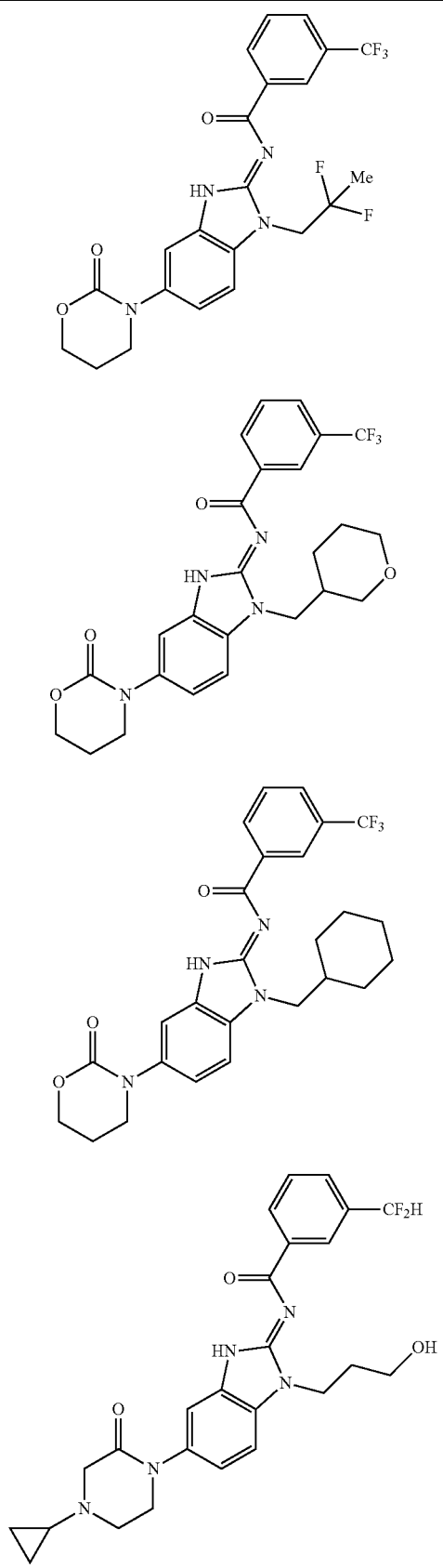
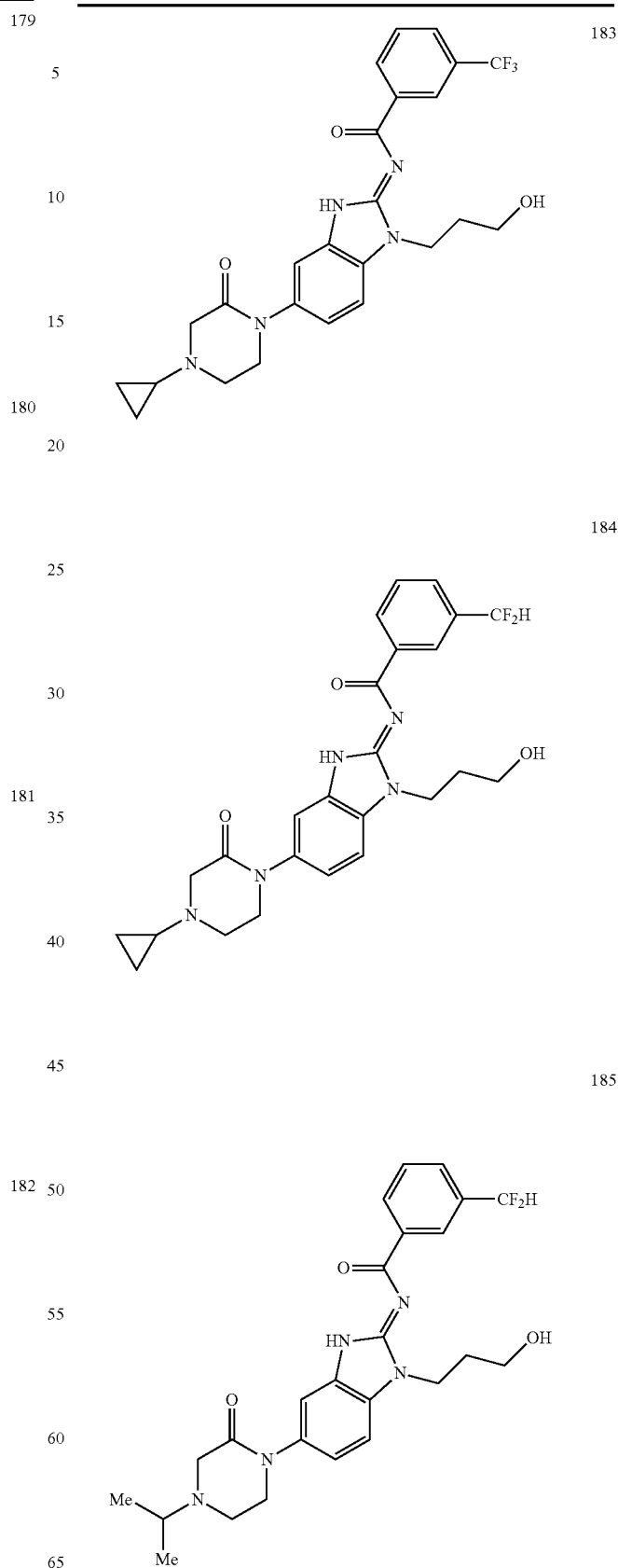

TABLE 1-continued
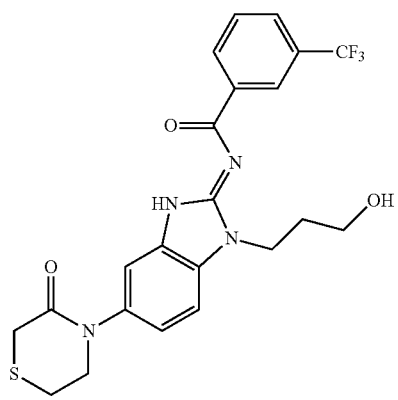 [SMILES: O=C(/N=c1\[nH]c2cc(N3CCSCC3=O)ccc2n1CCCO)c1cccc(C(F)(F)F)c1] 186
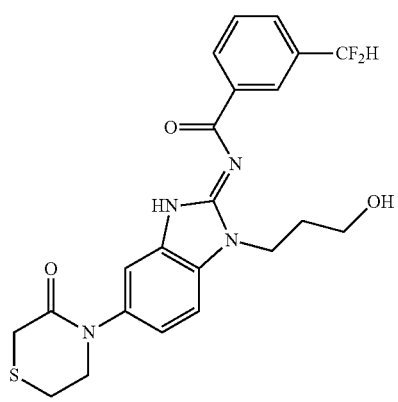 [SMILES: O=C(/N=c1\[nH]c2cc(N3CCSCC3=O)ccc2n1CCCO)c1cccc(C(F)F)c1] 187
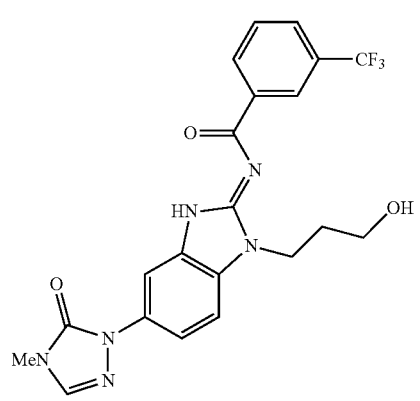 [SMILES: Cn1cnn(-c2ccc3c(c2)[nH]/c(=N\C(=O)c2cccc(C(F)(F)F)c2)n3CCCO)c1=O] 188
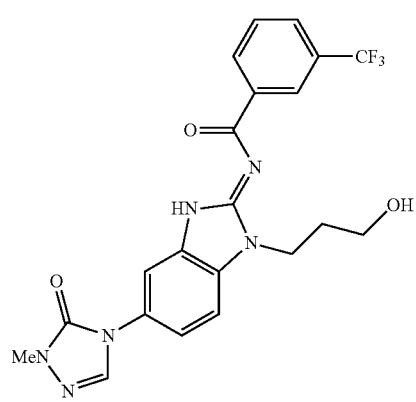 [SMILES: Cn1ncn(-c2ccc3c(c2)[nH]/c(=N\C(=O)c2cccc(C(F)(F)F)c2)n3CCCO)c1=O] 189
TABLE 1-continued
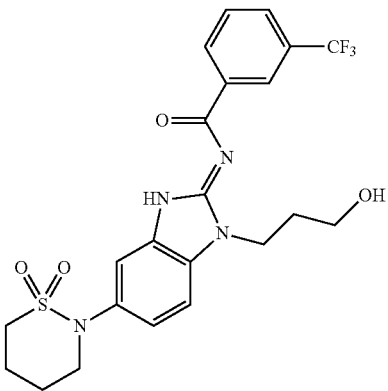 [SMILES: O=C(/N=c1\[nH]c2cc(N3CCCCS3(=O)=O)ccc2n1CCCO)c1cccc(C(F)(F)F)c1] 190
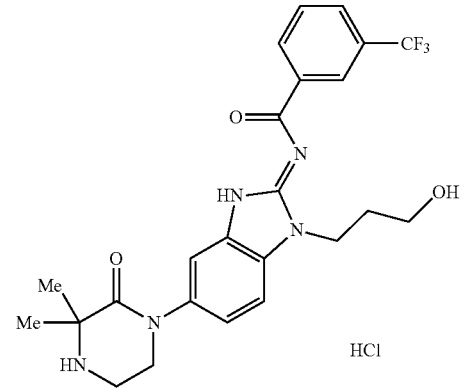 [SMILES: CC1(C)NCCN(c2ccc3c(c2)[nH]/c(=N\C(=O)c2cccc(C(F)(F)F)c2)n3CCCO)C1=O ; Cl] 191
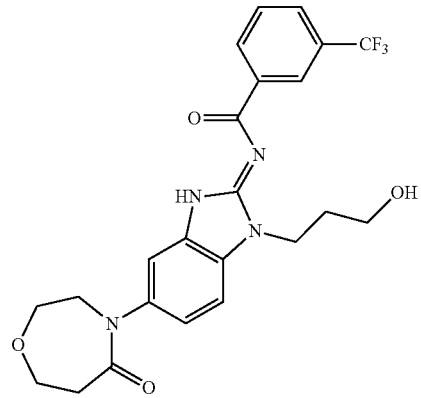 [SMILES: O=C(/N=c1\[nH]c2cc(N3CCOCCC3=O)ccc2n1CCCO)c1cccc(C(F)(F)F)c1] 192
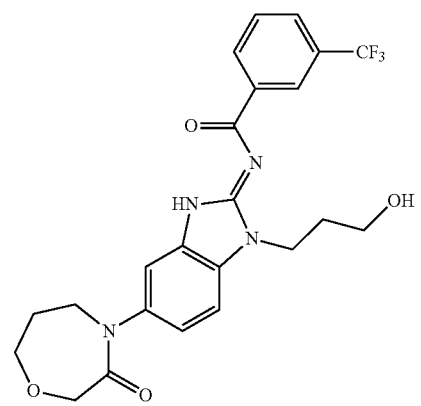 [SMILES: O=C(/N=c1\[nH]c2cc(N3CCCOCC3=O)ccc2n1CCCO)c1cccc(C(F)(F)F)c1] 193

TABLE 1-continued
194 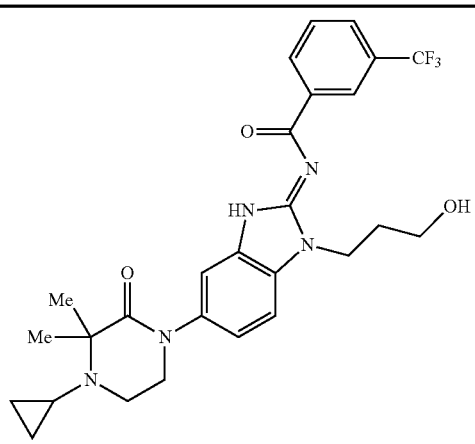
195 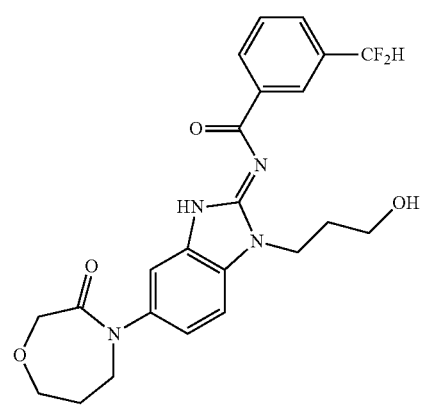 [SMILES: O=C(/N=c1\[nH]c2cc(N3CCCOCC3=O)ccc2n1CCCO)c1cccc(C(F)F)c1]
196 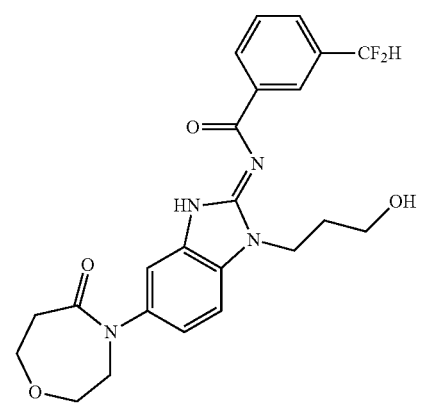 [SMILES: O=C(/N=c1\[nH]c2cc(N3CCOCCC3=O)ccc2n1CCCO)c1cccc(C(F)F)c1]
197 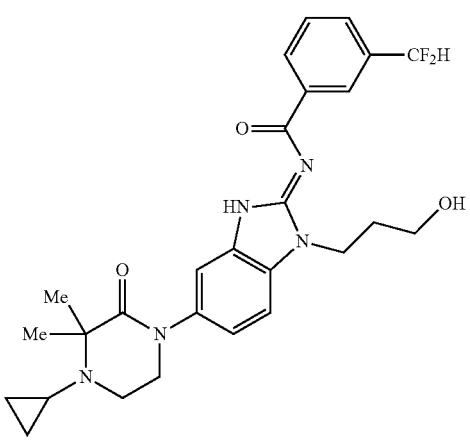 [SMILES: CC1(C)C(=O)N(c2ccc3c(c2)[nH]/c(=N\C(=O)c2cccc(C(F)F)c2)n3CCCO)CCN1C1CC1]
TABLE 1-continued
198 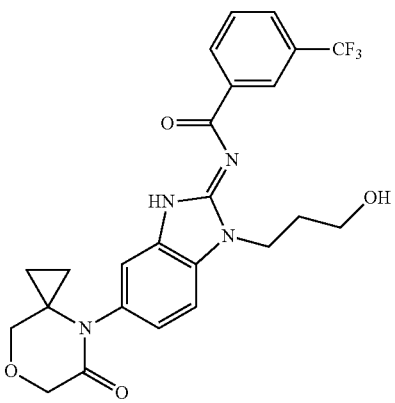 [SMILES: O=C(/N=c1\[nH]c2cc(N3C(=O)COCC34CC4)ccc2n1CCCO)c1cccc(C(F)(F)F)c1]
199
200
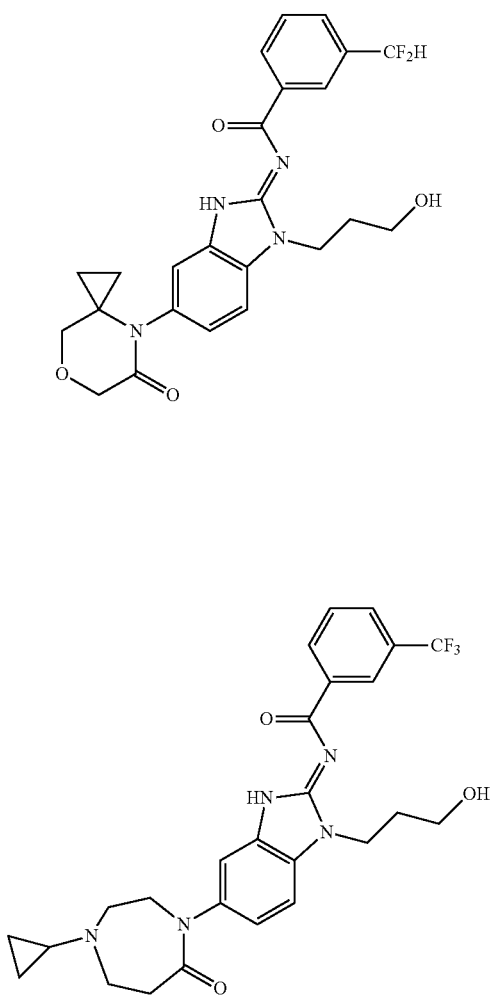

TABLE 1-continued
201
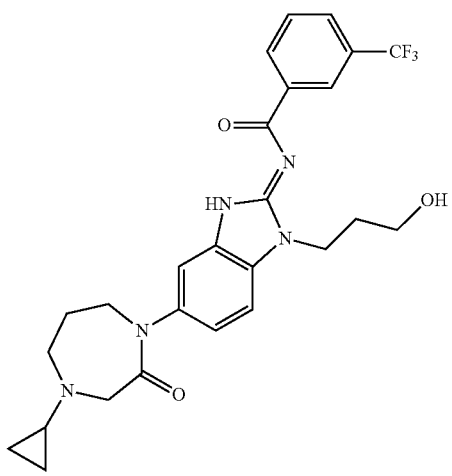 [SMILES: O=C(/N=c1\[nH]c2cc(N3CCCN(C4CC4)CC3=O)ccc2n1CCCO)c1cccc(C(F)(F)F)c1]
202
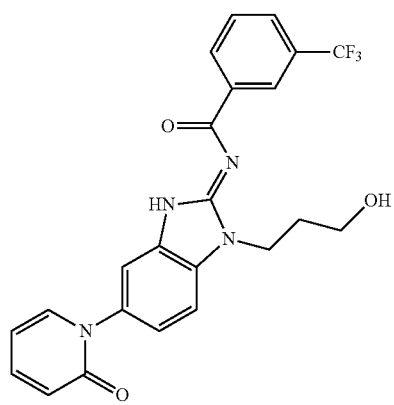 [SMILES: O=C(/N=c1\[nH]c2cc(-n3ccccc3=O)ccc2n1CCCO)c1cccc(C(F)(F)F)c1]
203
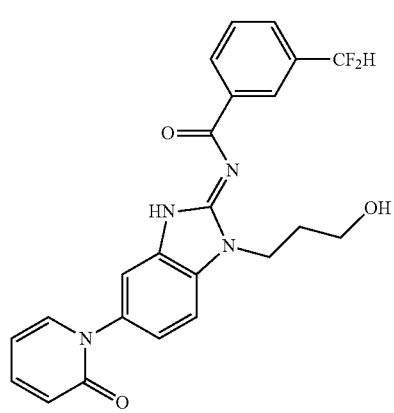 [SMILES: O=C(/N=c1\[nH]c2cc(-n3ccccc3=O)ccc2n1CCCO)c1cccc(C(F)F)c1]
TABLE 1-continued
204
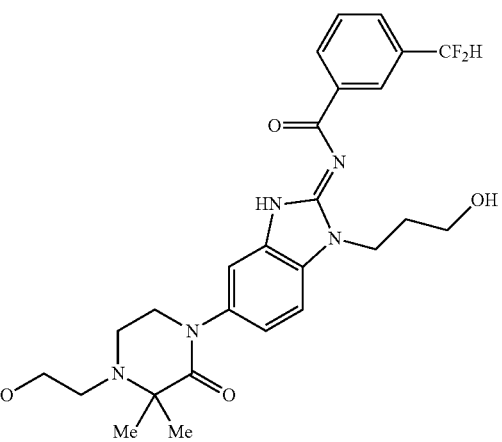
205
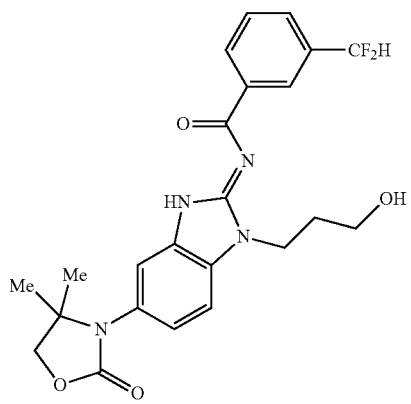 [SMILES: CC1(C)COC(=O)N1c1ccc2c(c1)[nH]/c(=N\C(=O)c1cccc(C(F)F)c1)n2CCCO]
206
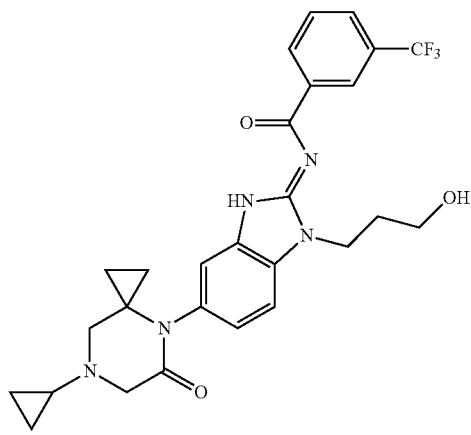 [SMILES: O=C(/N=c1\[nH]c2cc(N3C(=O)CN(C4CC4)CC34CC4)ccc2n1CCCO)c1cccc(C(F)(F)F)c1]

TABLE 1-continued
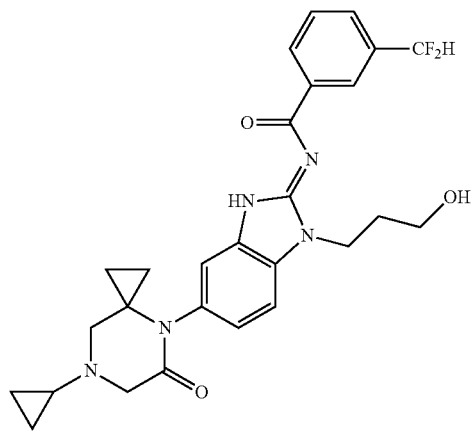 [SMILES: O=C(/N=c1\[nH]c2cc(N3C(=O)CN(C4CC4)CC34CC4)ccc2n1CCCO)c1cccc(C(F)F)c1]
207
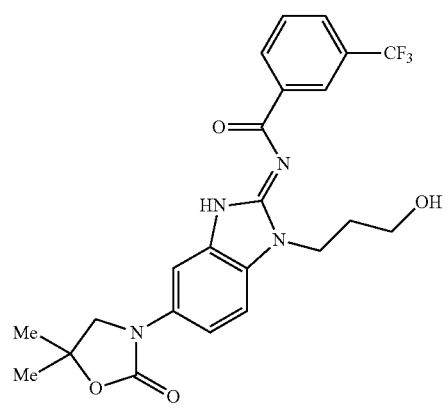 [SMILES: CC1(C)CN(c2ccc3c(c2)[nH]/c(=N\C(=O)c2cccc(C(F)(F)F)c2)n3CCCO)C(=O)O1]
208
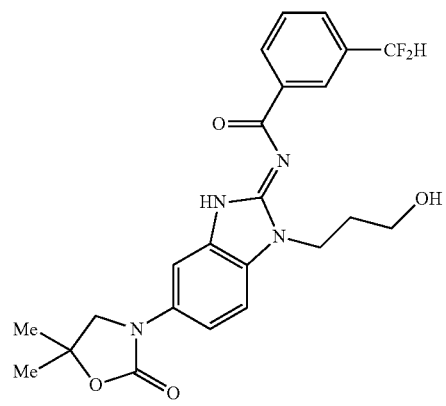 [SMILES: CC1(C)CN(c2ccc3c(c2)[nH]/c(=N\C(=O)c2cccc(C(F)F)c2)n3CCCO)C(=O)O1]
209
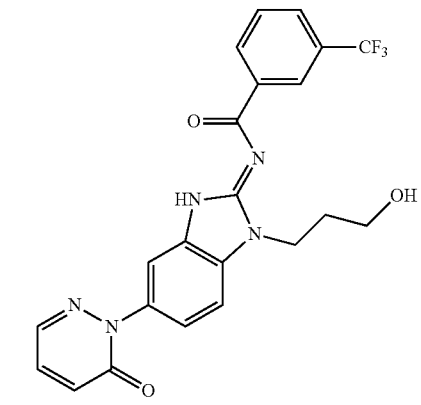 [SMILES: O=C(/N=c1\[nH]c2cc(-n3ncccc3=O)ccc2n1CCCO)c1cccc(C(F)(F)F)c1]
210
TABLE 1-continued
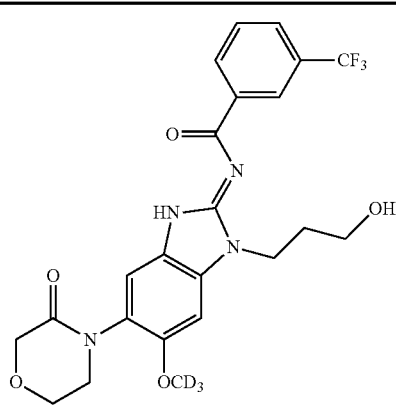
211
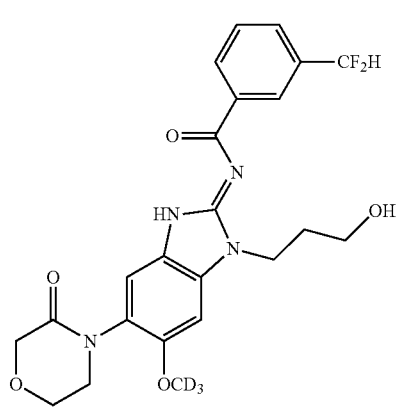
212
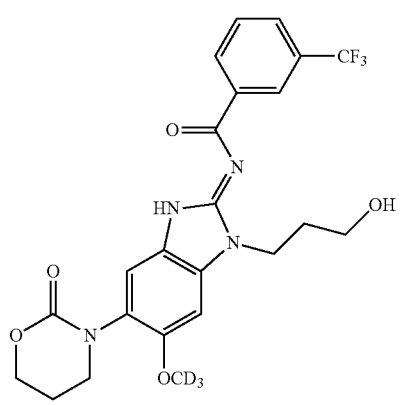
213
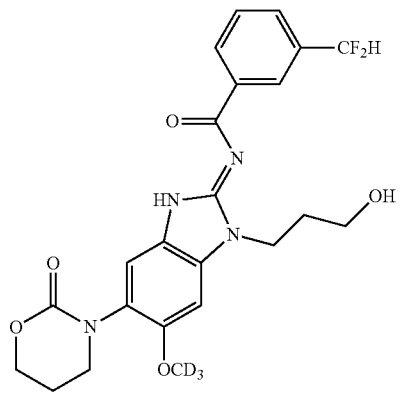
214

TABLE 1-continued
215 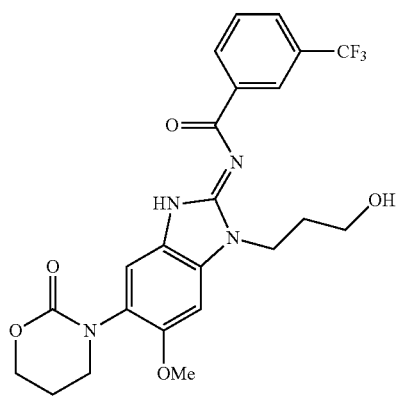 [SMILES: COc1cc2c(cc1N1CCCOC1=O)[nH]/c(=N\C(=O)c1cccc(C(F)(F)F)c1)n2CCCO]
216 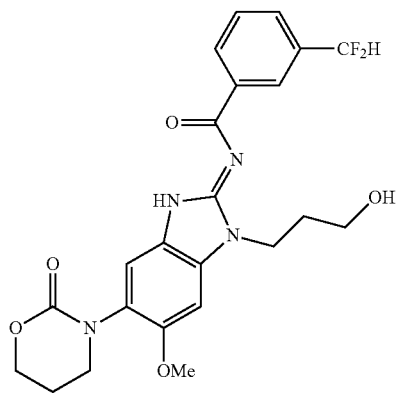
217 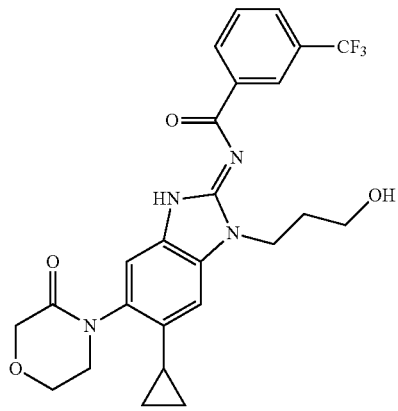 [SMILES: O=C(/N=c1\[nH]c2cc(N3CCOCC3=O)c(C3CC3)cc2n1CCCO)c1cccc(C(F)(F)F)c1]
218 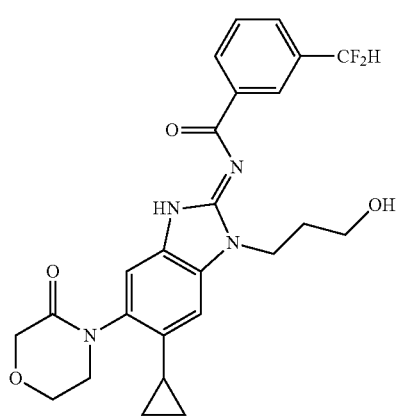 [SMILES: O=C(/N=c1\[nH]c2cc(N3CCOCC3=O)c(C3CC3)cc2n1CCCO)c1cccc(C(F)F)c1]
TABLE 1-continued
219 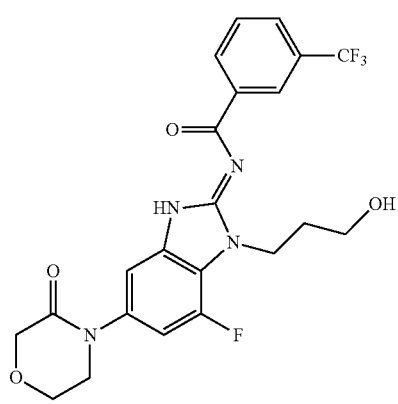 [SMILES: O=C(/N=c1\[nH]c2cc(N3CCOCC3=O)cc(F)c2n1CCCO)c1cccc(C(F)(F)F)c1]
220 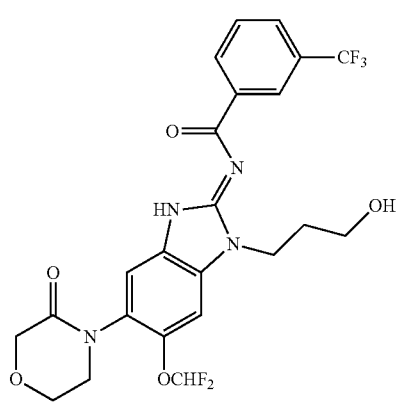 [SMILES: O=C(/N=c1\[nH]c2cc(N3CCOCC3=O)c(OC(F)F)cc2n1CCCO)c1cccc(C(F)(F)F)c1]
221 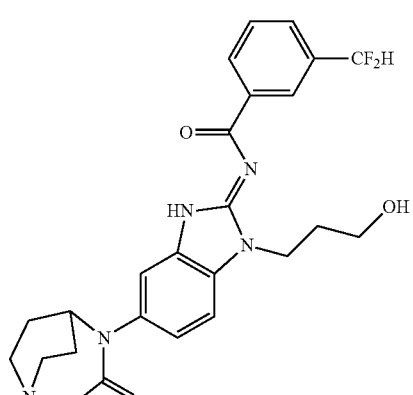
222 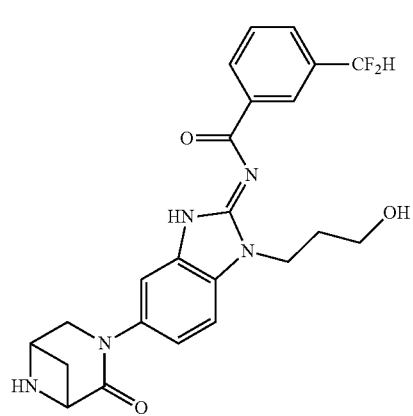 [SMILES: O=C(/N=c1\[nH]c2cc(N3CC4CC(N4)C3=O)ccc2n1CCCO)c1cccc(C(F)F)c1]

TABLE 1-continued
223
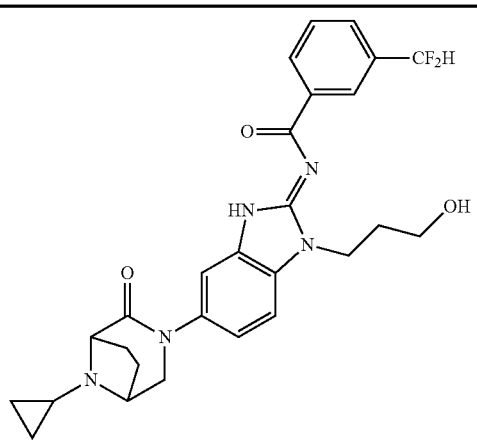
224
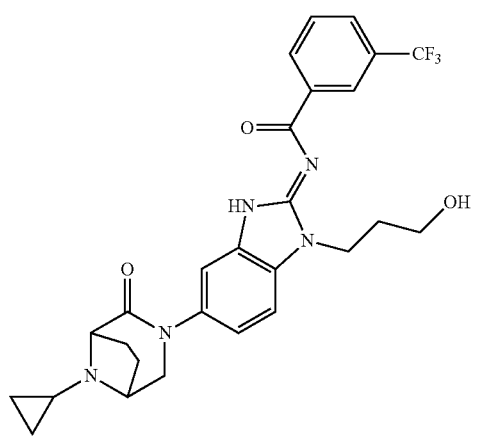 [SMILES: O=C(/N=c1\[nH]c2cc(N3CC4CCC(C3=O)N4C3CC3)ccc2n1CCCO)c1cccc(C(F)(F)F)c1]
225
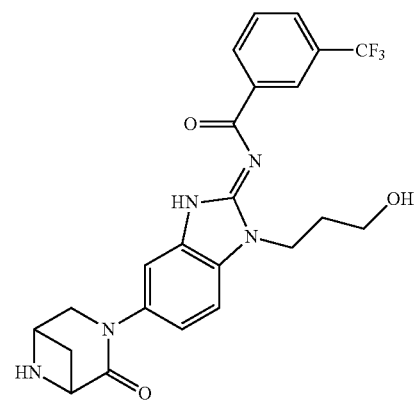 [SMILES: O=C(/N=c1\[nH]c2cc(N3CC4CC(N4)C3=O)ccc2n1CCCO)c1cccc(C(F)(F)F)c1]
226
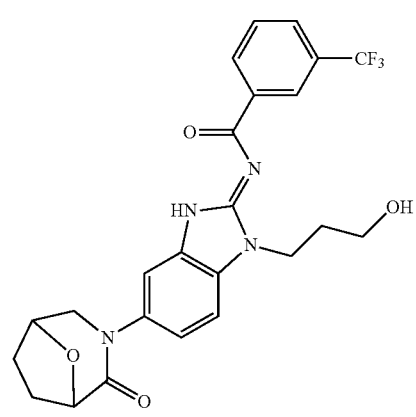 [SMILES: O=C(/N=c1\[nH]c2cc(N3CC4CCC(O4)C3=O)ccc2n1CCCO)c1cccc(C(F)(F)F)c1]
TABLE 1-continued
227
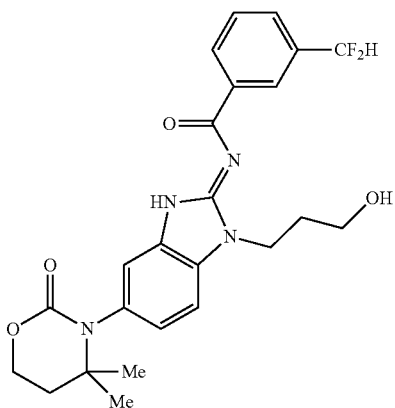 [SMILES: CC1(C)CCOC(=O)N1c1ccc2c(c1)[nH]/c(=N\C(=O)c1cccc(C(F)F)c1)n2CCCO]
228
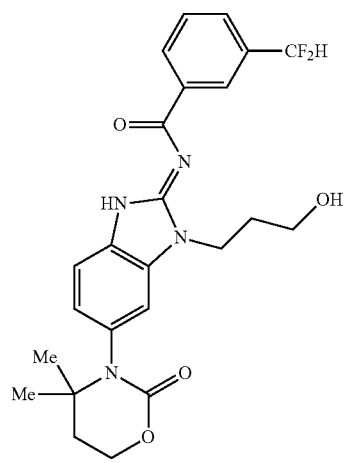
229
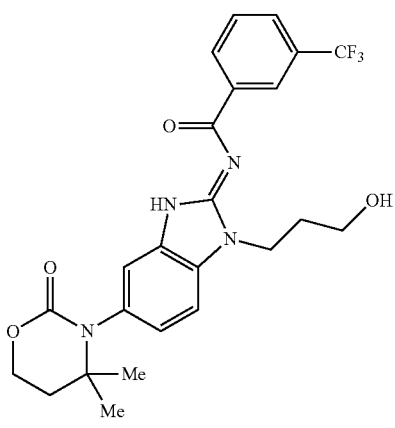 [SMILES: CC1(C)CCOC(=O)N1c1ccc2c(c1)[nH]/c(=N\C(=O)c1cccc(C(F)(F)F)c1)n2CCCO]

TABLE 1-continued
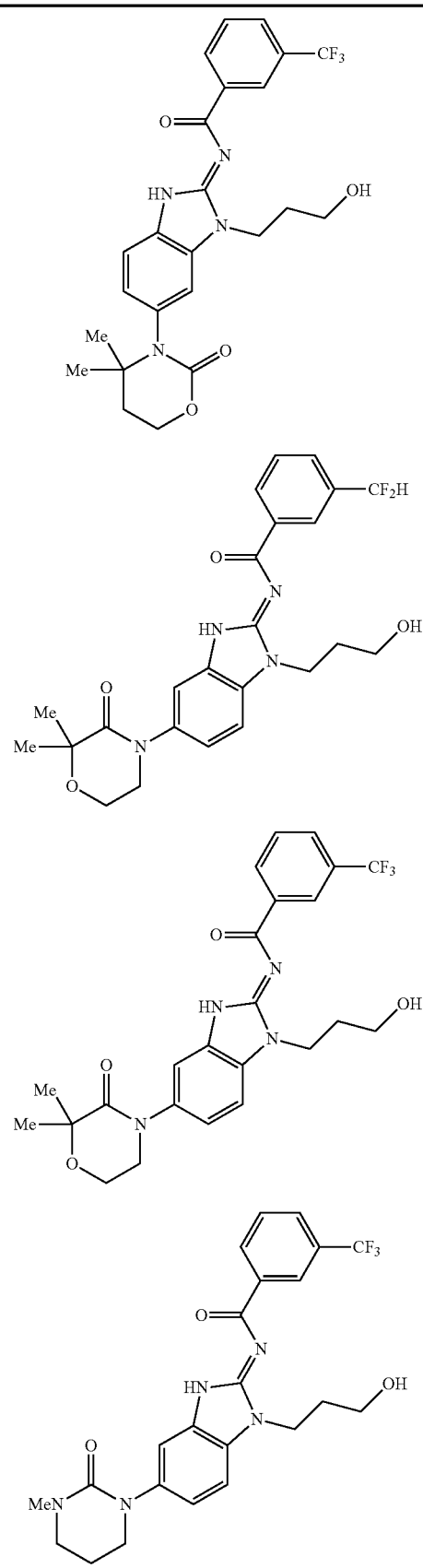
230
231
232
233
TABLE 1-continued
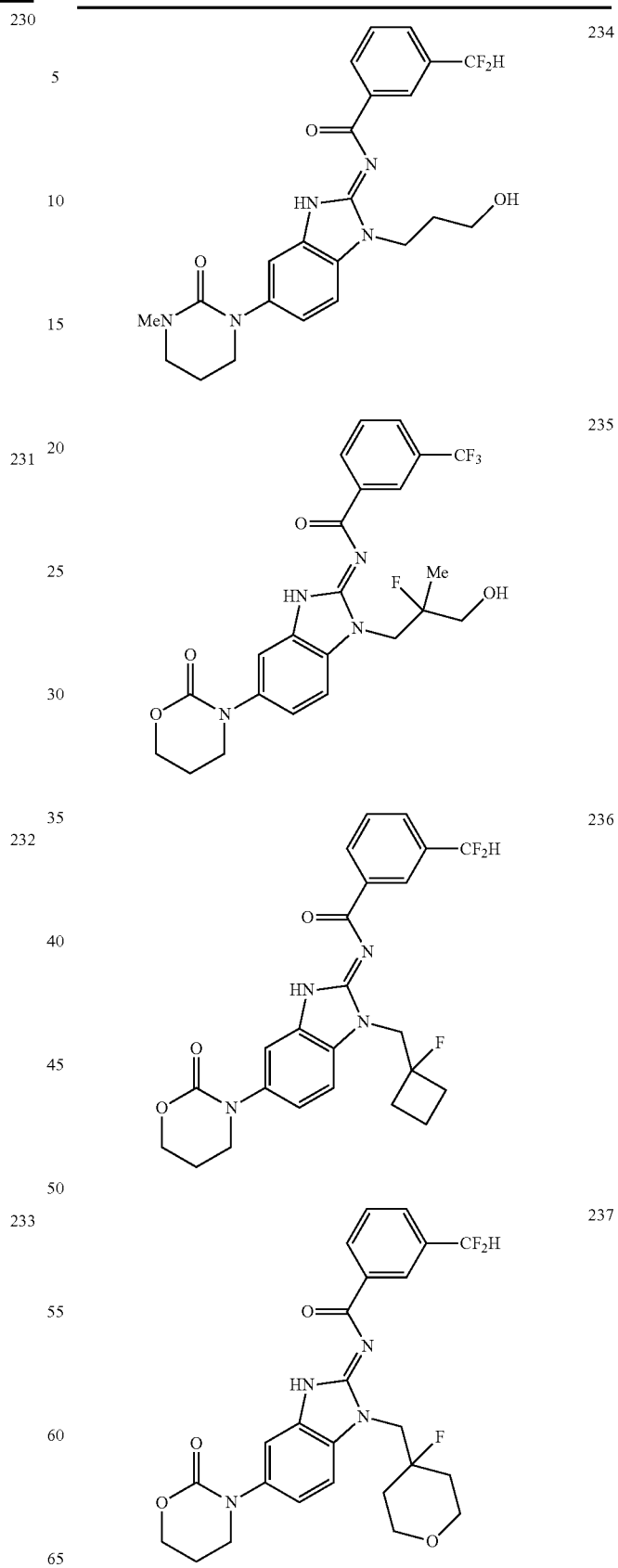
234
235
236
237

TABLE 1-continued

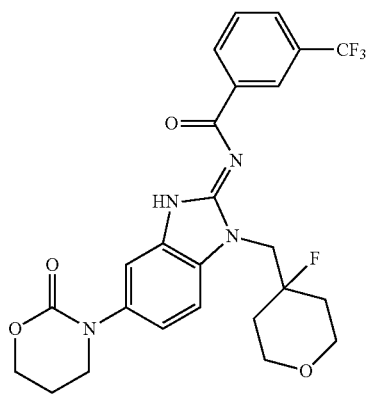
238

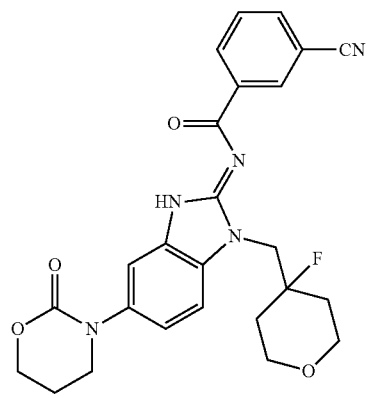 [SMILES: N#Cc1cccc(C(=O)/N=c2\[nH]c3cc(N4CCCOC4=O)ccc3n2CC2(F)CCOCC2)c1]
239

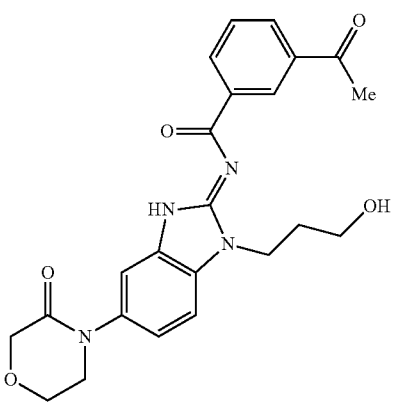 [SMILES: CC(=O)c1cccc(C(=O)/N=c2\[nH]c3cc(N4CCOCC4=O)ccc3n2CCCO)c1]
240

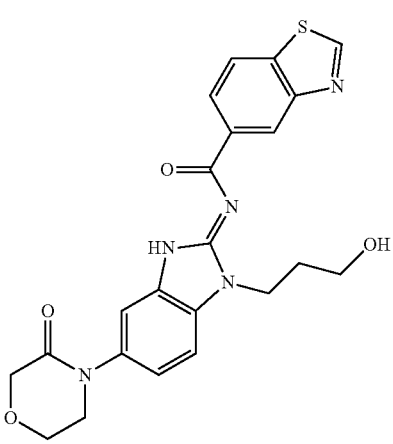 [SMILES: O=C(/N=c1\[nH]c2cc(N3CCOCC3=O)ccc2n1CCCO)c1ccc2scnc2c1]
241

TABLE 1-continued

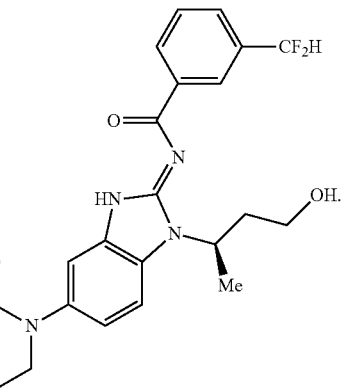
242

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit IRAK, or a mutant thereof, in a biological sample or in a patient. In certain embodiments, the amount of compound in compositions of this invention is such that is effective to measurably inhibit IRAK, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from an IRAK related disorder, comprising administering to said subject an effective amount of a compound of formula I and related formulae.

The present invention preferably relates to a method, wherein the IRAK associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality.

The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

The present invention furthermore relates to a method wherein the immunoregulatory abnormality is bone marrow or organ transplant rejection or graft-versus-host disease.

The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

In certain embodiments, disorders associated with IRAK are selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

In certain embodiments, the cancer is selected from carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

In certain embodiments, the cancer is brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. In some embodiments, the cancer is metastatic cancer. In some embodiments, the cancer is colorectal cancer. In some embodiments, the cancer is colon cancer.

In various embodiments, compounds of formula (I), and related formulae exhibit a IC50 for the binding to IRAK of less than about 5 µM, preferably less than about 1 µM and even more preferably less than about 0.100 µM.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit IRAK activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing IRAK-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of IRAK activity if expedient.

The invention also relates to the use of compounds according to formula (I) and/or physiologically acceptable salts thereof for the prophylactic or therapeutic treatment and/or monitoring of diseases that are caused, mediated and/or propagated by IRAK activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by IRAK activity. In certain embodiments, the invention provides the use of a compound according to formula I or physiologically acceptable salts thereof, for the production of a medicament for the prophylactic or therapeutic treatment of an IRAK-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with IRAK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with IRAK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1] Prop. INN (Proposed International Nonproprietary Name); [2] Rec. INN (Recommended International Nonproprietary Names); [3] USAN (United States Adopted Name); [4] no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight poletyhylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting IRAK activity in a biological sample comprising the step of contacting said biological sample with a compound of this invention, or a composition comprising said compound.

According to another embodiment, the invention relates to a method of inhibiting IRAK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of IRAK, including the evaluation of the many factors thought to influence, and be influenced by, the production of IRAK and the interaction of IRAK. The present compounds are also useful in the development of other compounds that interact with IRAK since the present compounds provide important structure-activity relationship (SAR) information that facilitate that development. Compounds of the present invention that bind to IRAK can be used as reagents for detecting IRAK in living cells, fixed cells, in biological fluids, in tissue homogenates, in purified, natural biological materials, etc. For example, by labeling such compounds, one can identify cells expressing IRAK. In addition, based on their ability to bind IRAK, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing IRAK inside permeabilized cells. The compounds of the invention can also be utilized as commercial research reagents for various medical research and diagnostic uses. Such uses can include but are not limited to: use as a calibration standard for quantifying the activities of candidate IRAK inhibitors in a variety of functional assays; use as blocking reagents in random compound screening, i.e. in looking for new families of IRAK ligands, the compounds can be used to block recovery of the presently claimed IRAK compounds; use in the co-crystallization with IRAK enzyme, i.e. the compounds of the present invention will allow formation of crystals of the compound bound to IRAK, enabling the determination of enzyme/compound structure by x-ray crystallography; other research and diagnostic applications, wherein IRAK is preferably activated or such activation is conveniently calibrated against a known quantity of an IRAK inhibitor, etc.; use in assays as probes for determining the expression of IRAK in cells; and developing assays for detecting compounds which bind to the same site as the IRAK binding ligands.

The compounds of the invention can be applied either themselves and/or in combination with physical measurements for diagnostics of treatment effectiveness. Pharmaceutical compositions containing said compounds and the use of said compounds to treat IRAK-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of IRAK, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade).

All reactions were conducted at room temperature unless otherwise noted. All compounds of the present invention were synthesiszed by processes developed by the inventors. $^1$H-NMR spectra were acquired on a Bruker Fourier-300 MHz instrument. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), qt (quintuplet) or br (broad).

Mass spectra were obtained on Shimadzu LC-MS-2020 Series mass spectrometers, using Electrospray Ionization (ESI). Column: Luna C18, 5 μm, 2.0×50 mm; Solvent A: water+0.1% formic acid; Solvent B: MeCN+0.1% formic acid; Flow: 0.7 ml/min; Gradient: 0 min: 5% B, 5 min: 100% B, 6.5 min: 100% B, 6.51 min: 5% B, 7 min 5% B.

Compound numbers utilized in the Examples below correspond to compound numbers set forth supra.

The following abbreviations refer to the abbreviations used below:

Ac (acetyl), BINAP (2,2'-bis(disphenylphosphino)-1,1'-binaphthalene), dba (dibenzylidene acetone), Bu (Butyl), $^t$Bu (tert-Butyl), DCE (dichloroethane), DCM (Dichloromethane), δ (chemical shift), DIEA (di-isopropyl ethylamine), DMA (dimethyl acetamide), DMSO (Dimethyl Sulfoxide), DMF (N,N-Dimethylformamide), Dppf (1,1'-bis(diphenyl phosphine ferrocene)), EtOAc (Ethyl acetate), EtOH (Ethanol), eq (equivalent), g (gram), $^c$Hex (Cyclohexane), HATU (N-[(Dimethylamino)(3H-[1,2,3]triazolo[4,5-b]pyridin-3-yloxy)methylene]-N-methylmethanaminiumhexafluoro phosphate), HPLC (High Performance Liquid Chromatography), h (hour), LDA (lithium diisopropyl amine), LiHMDS (lithium bis(trimethylsilyl)amide), MHz (Megahertz), MeOH (Methanol), min (minute), mL (milliliter), mmol (millimole), mM (millimolar), MS (Mass Spectrometry), NMR (Nuclear Magnetic Resonance), O/N (overnight), PBS (Phosphate Buffered Saline), RT (room temperature), TEA (Triethyl amine), TFA (Trifluoroacetic acid), THF (Tetrahydrofuran), TLC (Thin Layer Chromatography).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme trichloride and 1,2-dimethylhydrazine, and the like. From the resulting bis-aniline VII, condensation with agents such as cyanogen bromide, and the like, furnished the requisite amino benzimidazole VIII. Finally, its coupling with an appropriately functionalized acid (IX, Scheme 1) completed the synthetic sequence.

Compound numbers, formulae numbers, and Markush groups, provided in the Schemes and Scheme descriptions are unique to the Schemes and do not necessarily correspond to the formulae of the compounds of the invention.

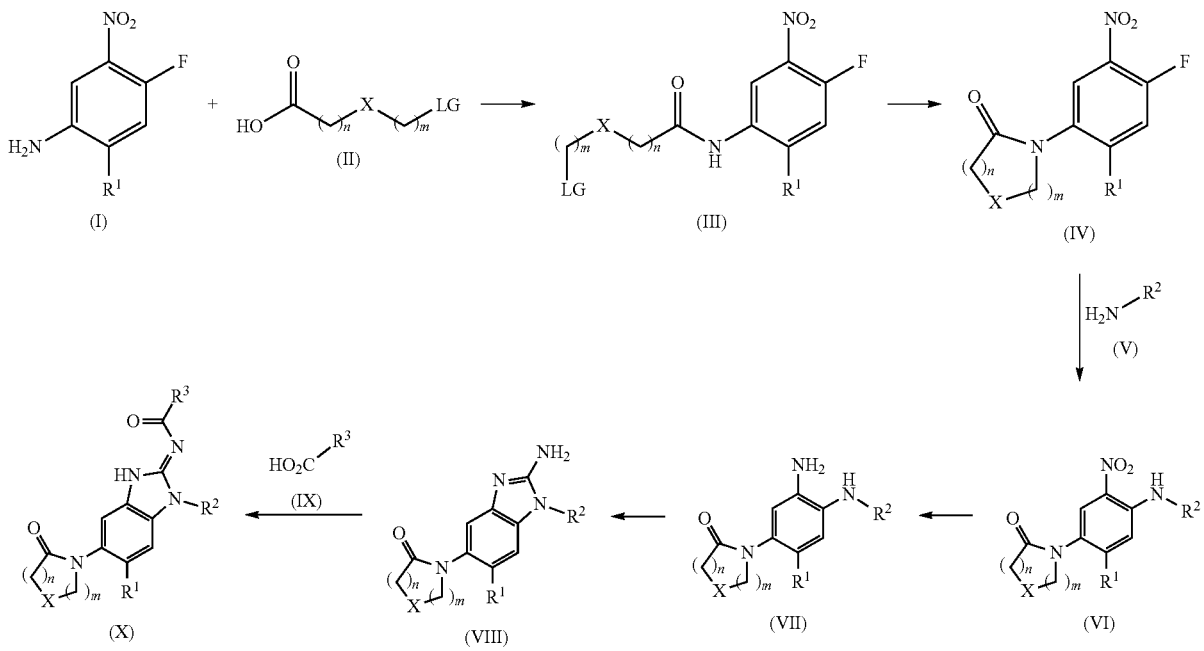

Verlag Stuttgart, New York, 1994 and, Theodora W. Greene 3rd and Peter G. M. Wuts in "Protective Groups in Organic Synthesis", Wiley Interscience, Edition 1999.

General Synthetic Scheme for Exemplary Compounds

The compounds exemplified herein (X, Scheme 1) were conveniently accessed, for example, from the corresponding aniline (I, Scheme 1) via its initial condensation with an appropriately functionalized acid (II, Scheme 1), or the like, followed by ring closure. The condensation with the acid was, for example, carried out in the presence of an appropriate coupling reagent such as HATU, CDI, or the like, and an appropriate base such as triethylamine, ethyl-diisopropylamine, or the like. Alternatively, the acid was pre-activated via its conversion into the corresponding acid chloride using an agent such as thionyl chloride, oxalyl chloride, or the like. The subsequent ring closure was affected, for example, by heating the intermediate amide III with an appropriate base such as cesium carbonate, sodium hydride, or the like. The resulting aryl fluoride IV was then be converted into its corresponding nitro aniline VI by, for example, heating IV with an appropriately functionalized amine (V, scheme 1) in the presence of an appropriate base, such as cesium carbonate, potassium carbonate, or the like. Subsequent nitro reduction was readily carried out on VI under known reducing conditions such as, but not limited to, palladium black and hydrogen gas, zinc powder and acetic acid, iron(III)

Alternatively, accessing the requisite amino benzimidazole core from the corresponding iodide (XI, Scheme 2) was realized via a copper- or palladium-mediated coupling reaction with an appropriately functionalized lactam, carbamate, urea, or the like (XII, Scheme 2), as the coupling partner. Subsequent site selective nitration of the resulting aryl fluoride XIII was then be carried out, using either nitric acid or other suitable sources of $NO_2^+$, to furnish the same intermediate IV seen in Scheme 1.

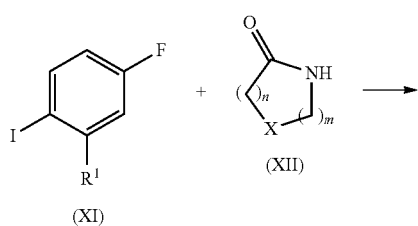

-continued

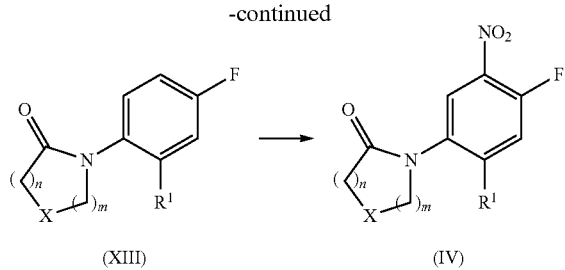

(XIII) → (IV)

In a similar vein, in instances where both aniline I in Scheme 1 and iodide XI in Scheme 2 are not readily available, the same intermediate IV was also be accessed via nitration of aryl fluoride XIII that is itself prepared instead from the more readily available aniline XIV, using the sequence described previously in Scheme 1.

Scheme 3

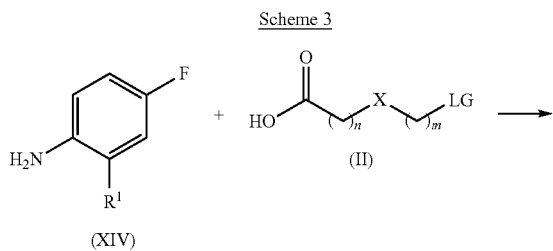

(XIV) + (II)

-continued

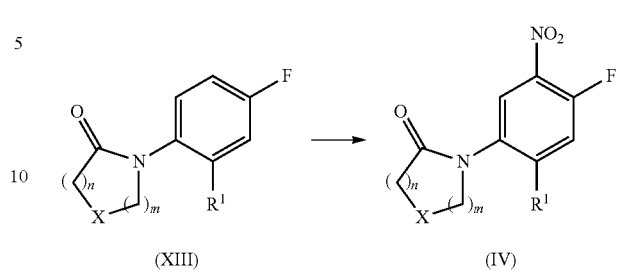

(XIII) → (IV)

It may also be practical or advantageous to postpone the cyclization event to a point later in the synthesis. For such endeavors, aniline I was protected as, but not limited to, its tert-butyl carbamate (XV, Scheme 4). Then, using the sequence described previous in Scheme 1, XV was readily transformed into carbamate XIX. The unmasking of the free aniline XX via, for example, the treatment of XIX with strong protic acids such as HCl, TFA, or the like, provided the suitable stage for subsequent elaboration events.

Scheme 4

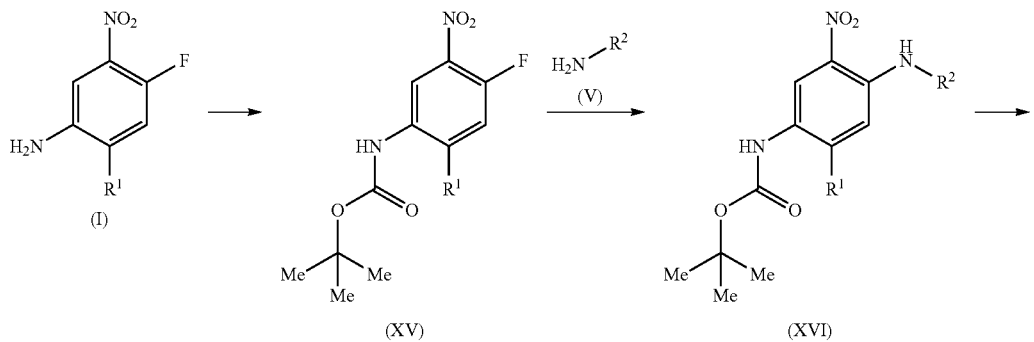

(I) → (XV) → (XVI)

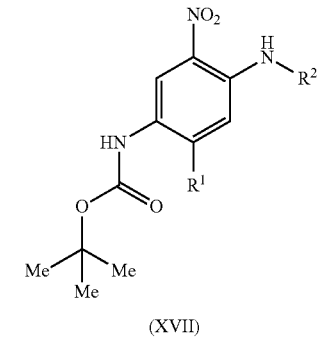

(XVII)

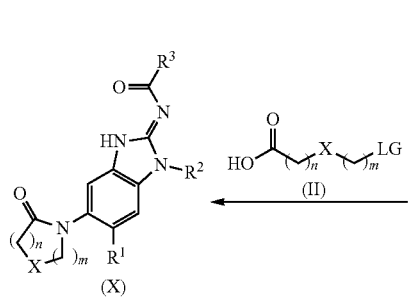
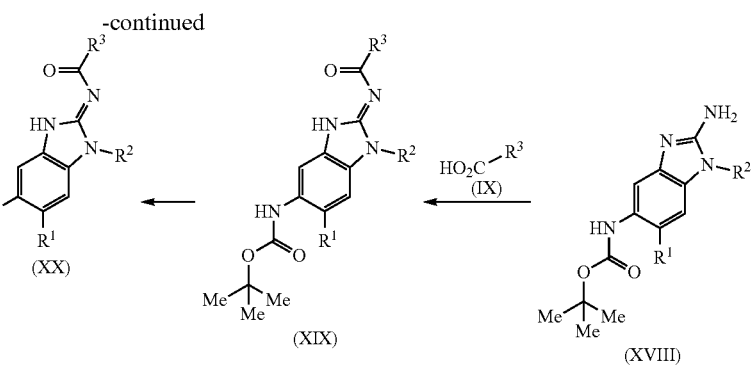

Depending on the identity of $R^1$, $R^2$, $R^3$ or X, further transformation of the various functional groups present in X were also be readily achieved. In instances where X=NH (Scheme 5), its elaboration into amide XXI (via, for example, acylation with $R^4$—C(=O)Cl), into amine XXII (via, for example, reductive amination with $R^4$—CHO), into amine XXIII (via, for example, metal-catalyzed arylation or base-mediated alkylation with $R^4$—I), into sulfonamide XXIV (via, for example, sulfonylation with $R^4$—S(=O)$_2$Cl), or into urea XXV (via, for example, condensation with $R^4$—N=C=O), were carried out using standard procedures known to those skilled in the art. In instances where X=S (Scheme 6), its derivatization into sulfoxide XXVI or sulfone XXVII was realized using controlled amounts of oxidants such as mCPBA, oxone, or the like. In fact, manipulations of similar functional groups found in $R^1$, $R^2$ and/or $R^3$ using some of, but not limited to, the chemical transformations described above (i.e. acylation, sulfonylation, oxidation, reduction, alkylation, arylation, or the like), were envisioned.

Scheme 5

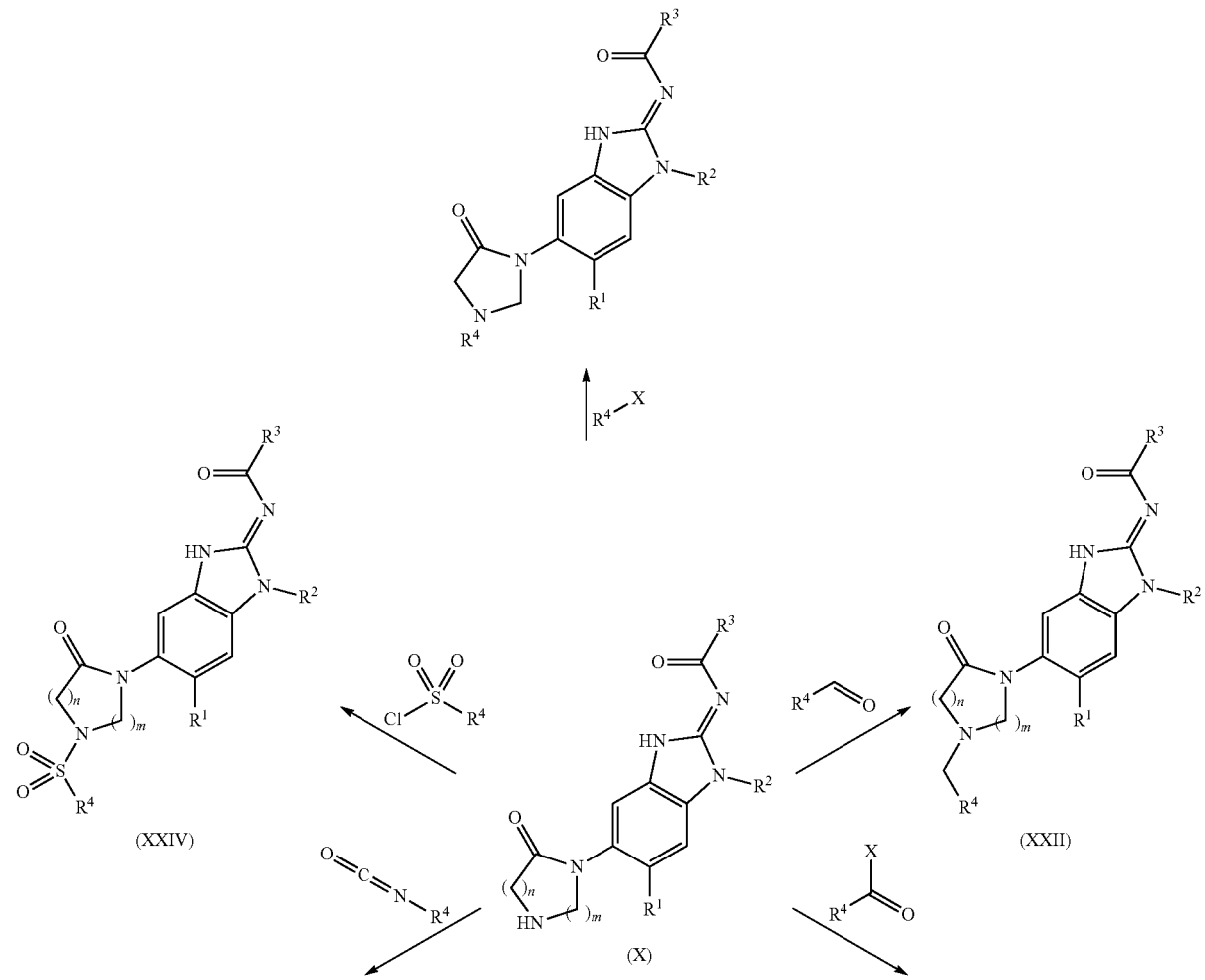

-continued

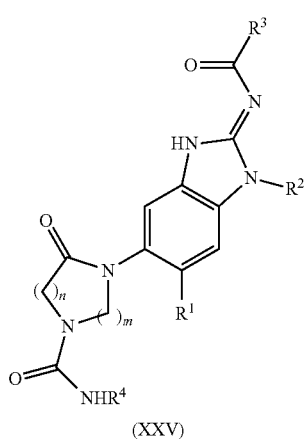

(XXV)

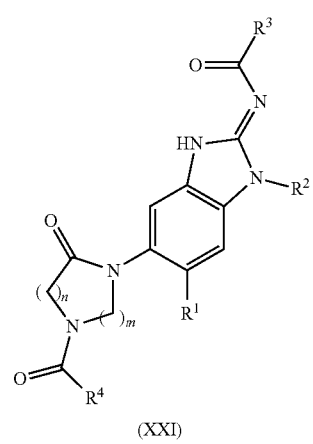

(XXI)

Scheme 6

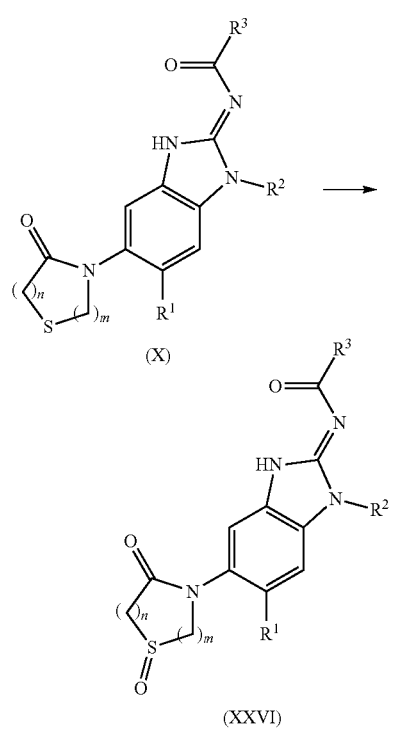

In examples where R[1] is a halogen (XXVIII, Scheme 7) and/or R[3] is a halogenated arene or heteroarene (XXIX, Scheme 7), metal-catalyzed cross-couplings such as Suzuki reaction, Stille reaction, Negishi reaction, Buchwald-Hartwig reaction, Heck reaction, carbonylative coupling, cyanation, or the like, were employed to facilitate further structural diversification (Scheme 7). Depending on the catalyst and coupling condition used, it may be beneficial to first protect the free benzimidazole NH as, for example, the SEM group.

Scheme 7

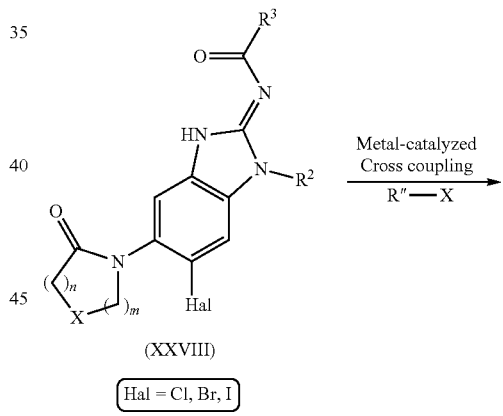

(XXVIII)

Hal = Cl, Br, I

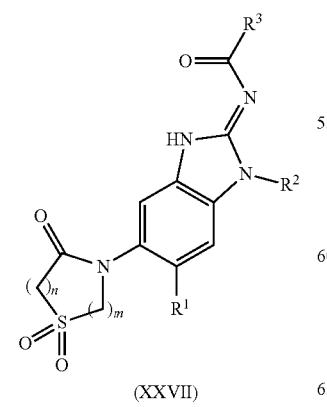

(XXVII)

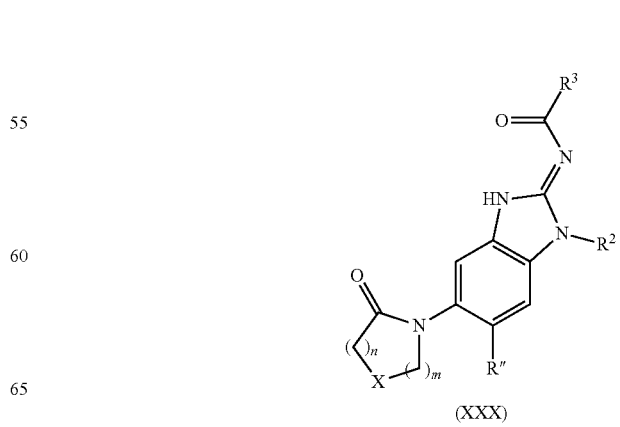

(XXX)

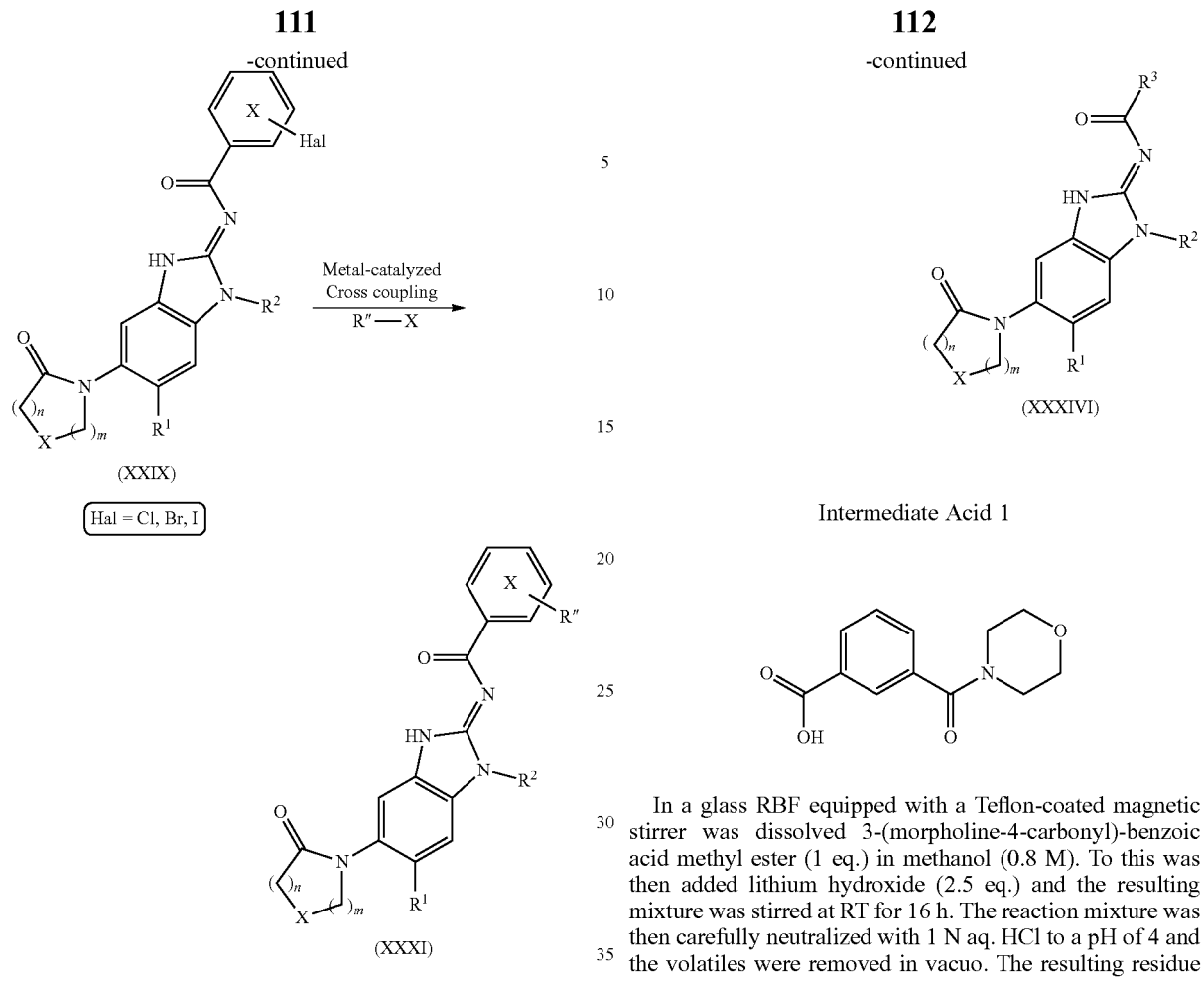

In examples featuring a benzo imidazole core (XXXIV, Scheme 8), the requisite scaffold can be conveniently accessed by, for example, the condensation of bis-aniline VIII with bis-sulfide XXXIII. The latter reactant can itself be prepared from readily available ketone XXXII in the presence of a suitable base, such as potassium tert-butoxide, sodium hydride or the like, carbon disulfide and iodomethane. Further transformation of the appropriate functionalities present in $R^1$, $R^2$ and $R^3$ of XXXIV, similar to those previously described, can also be applied here to enable additional structural diversification.

Scheme 8

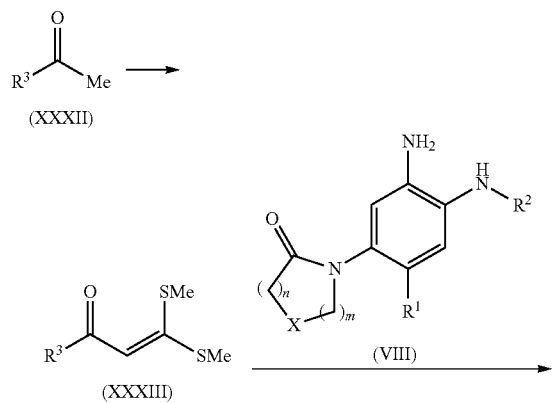

Intermediate Acid 1

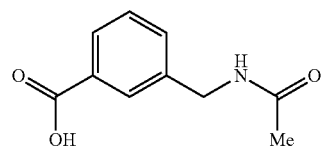 [SMILES: CC(=O)NCc1cccc(C(=O)O)c1]

In a glass RBF equipped with a Teflon-coated magnetic stirrer was dissolved 3-(morpholine-4-carbonyl)-benzoic acid methyl ester (1 eq.) in methanol (0.8 M). To this was then added lithium hydroxide (2.5 eq.) and the resulting mixture was stirred at RT for 16 h. The reaction mixture was then carefully neutralized with 1 N aq. HCl to a pH of 4 and the volatiles were removed in vacuo. The resulting residue was subjected to column chromatography ($SiO_2$, gradient elution, 9:1 (v/v) Hex:EtOAc+5% MeOH→EtOAc+5% MeOH) to furnish the desired product as a white solid (93% yield).

Intermediate Acid 2

In a glass RBF equipped with a Teflon-coated magnetic stirrer was dissolved 3-aminomethyl-benzoic acid methyl ester hydrochloride (1 eq.) in dichloromethane (0.13 M). To this was then added sequentially triethylamine (3 eq.) and acetic anhydride (2 eq.). The reaction mixture was then stirred at RT for 16 h. The volatiles were then removed in vacuo and the resulting residue was taken up in methanol (0.13 M). To this was then added lithium hydroxide (5 eq.) and the resulting mixture was stirred at RT for 16 h. The reaction mixture was then carefully neutralized with 1 N aq. HCl to a pH of 4 and the volatiles were removed in vacuo. The resulting residue was subjected to column chromatography ($SiO_2$, gradient elution, 9:1 (v/v) Hex:EtOAc+5% MeOH→EtOAc+5% MeOH) to furnish the desired product as a white solid (85% yield).

Intermediate Acid 3

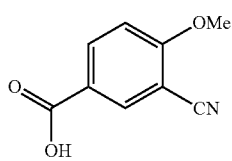 [SMILES: COc1ccc(C(=O)O)cc1C#N]

Prepared in an analogous fashion to Intermediate acid 1, but using 3-cyano-4-fluorobenzoic acid methyl ester (1 eq.) in place of 3-(morpholine-4-carbonyl)-benzoic acid methyl ester (71% yield).

Intermediate Acid 4

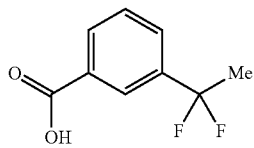 [SMILES: CC(F)(F)c1cccc(C(=O)O)c1]

In a plastic reaction vessel equipped with a Teflon-coated magnetic stirrer was charged DEOXO-FLUOR® (6 eq., 2.7 M solution in toluene). To this was then added sequentially 3-acetyl-benzoic acid methyl ester (1 eq.) and ethanol (1 eq.), and the resulting mixture was heated at 85° C. for 3 days. The reaction mixture was then cooled to RT, diluted with EtOAc and washed with brine. The organic extract was then dried over $MgSO_4$, filtered and the filtrate concentrated in vacuo. Purification of the residue thus obtained by way of column chromatography ($SiO_2$, gradient elution, Hex→9:1 (v/v) Hex:EtOAc) afforded the intermediate ester as a colorless oil. This was then immediately taken up in methanol (0.1 M), added lithium hydroxide (1 eq.) and then stirred at RT for 16 h. The resulting reaction mixture was carefully neutralized with HCl (4 M in dioxane) and the volatiles were removed in vacuo. The resulting residue was subjected to column chromatography ($SiO_2$, gradient elution, 9:1 (v/v) Hex:EtOAc→EtOAc) to furnish the desired product as a white solid (68% yield).

Intermediate Acid 5

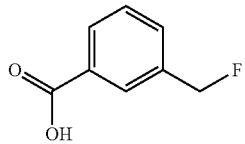 [SMILES: O=C(O)c1cccc(CF)c1]

Prepared in an analogous fashion to Intermediate acid 4, but using 3-hydroxymethyl-benzoic acid methyl ester (1 eq.) in place of 3-acetyl-benzoic acid methyl ester and DAST (1.5 eq.) in place of DEOXO-FLUOR®. Furthermore, the reaction took place at −78° C. over 1 h instead of 85° C. over 3 days (14% yield).

Intermediate Acid 6

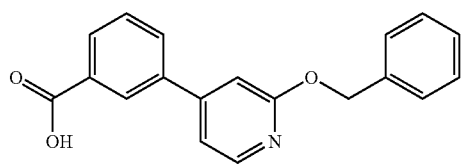 [SMILES: O=C(O)c1cccc(-c2ccnc(OCc3ccccc3)c2)c1]

In a sealable glass reaction vessel equipped with a Teflon-coated screw cap was dissolved 3-bromo-benzoic acid ethyl ester (1 eq.), (2-benzyloxy-4-pyridyl)boronic acid (1.1 eq.), sodium carbonate (3 eq.) and tetrakis(triphenylphosphine)palladium(0) (0.1 eq.) in a 9:1 (v/v) dioxane: water solution (0.2 M). The resulting mixture was deoxygenated via sub-surface purging with nitrogen for 30 min. The vessel was then tightly sealed and heated at 100° C. for 18 h. The resulting black mixture was then directly subjected to column chromatography ($SiO_2$, gradient elution, 9:1 (v/v)→1:1 (v/v) Hex:EtOAc) to furnish the intermediate ester as a colorless oil. This coupled product was then taken up in methanol (0.15 M), added lithium hydroxide (2.5 eq.) and the resulting mixture was stirred at 50° C. for 1 h. The reaction mixture was then carefully neutralized with 1 N aq. HCl to a pH of 4 and the volatiles were removed in vacuo. The resulting residue was subjected to column chromatography ($SiO_2$, gradient elution, $CH_2Cl_2$→4:1 (v/v) $CH_2Cl_2$:MeOH) to furnish the desired product as a white solid (47% yield).

Intermediate Acid 7

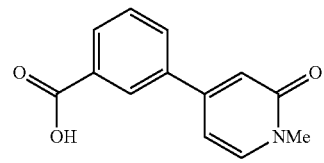 [SMILES: Cn1ccc(-c2cccc(C(=O)O)c2)cc1=O]

Prepared in an analogous fashion to Intermediate acid 6, but using 1-methyl-4-(4,4,5,5,-tetramethyl-1,3,2-dioxaborolan-2-yl)pyridine-2(1H)-one (1 eq.) in place of (2-benzyloxy-4-pyridyl)boronic acid (12% yield).

Intermediate Acid 8

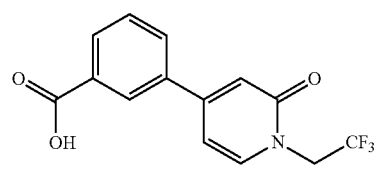 [SMILES: O=C(O)c1cccc(-c2ccn(CC(F)(F)F)c(=O)c2)c1]

Step 1: ethyl 3-(2-oxo-1,2-dihydropyridin-4-yl)benzoate

In a sealable glass reaction vessel equipped with a Teflon-coated screw cap was dissolved 3-bromo-benzoic acid ethyl ester (1 eq.), (2-benzyloxy-4-pyridyl)boronic acid (1 eq.), sodium carbonate (2 eq.) and Pd(dppf)Cl$_2$ (0.03 eq.) in a 9:1

(v/v) dioxane: water solution (0.1 M). The resulting mixture was deoxygenated via sub-surface purging with nitrogen for 30 min. The vessel was then tightly sealed and heated at 100° C. for 18 h. The resulting black mixture was then directly subjected to column chromatography (SiO$_2$, gradient elution, 9:1 (v/v)→1:1 (v/v) Hex:EtOAc) to furnish the intermediate ester as a colorless oil. This coupled product was then taken up in methanol (0.15 M), added palladium (0.1 eq., dry, 10% w/w over carbon) and the resulting suspension was evacuated and back-filled with nitrogen (3×) and then hydrogen (3×). The reaction suspension was then stirred under a balloon-maintained hydrogen atmosphere at RT for 4 h. The reaction was quenched with dichloromethane and the resulting suspension was filtered through a pad of dichloromethane-wetted celite. The filtrate thus obtained was then concentrated in vacuo to afford the desired product as a white solid (67% yield).

Step 2: 3-(2-oxo-1-(2,2,2-trifluoroethyl)-1,2-dihydropyridin-4-yl)benzoic acid

In a sealable glass reaction vessel equipped with a Teflon-coated screw cap was suspended ethyl 3-(2-oxo-1,2-dihydropyridin-4-yl)benzoate (1 eq.) from the previous step, cesium carbonate (1 eq.) and 1,1,1-trifluoro-2-iodoethane (1.1 eq.) in DMF (0.15 M). The vessel was then tightly sealed and heated at 80° C. for 18 h. The resulting mixture was then directly subjected to column chromatography (SiO$_2$, gradient elution, 9:1 (v/v) Hex:EtOAc→EtOAc) to furnish the intermediate ester as a colorless oil. This alkylated product was then taken up in methanol (0.15 M), added lithium hydroxide (2.5 eq.) and the resulting mixture was stirred at 50° C. for 16 h. The reaction mixture was then carefully neutralized with 1 N aq. HCl to a pH of 4 and the volatiles were removed in vacuo. The resulting residue was subjected to column chromatography (SiO$_2$, gradient elution, CH$_2$Cl$_2$→4:1 (v/v) CH$_2$Cl$_2$:MeOH) to furnish the desired product as a white solid (24% yield).

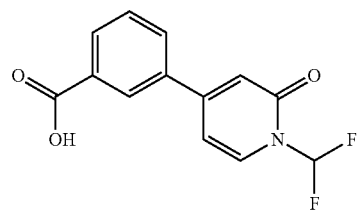 [SMILES: O=C(O)c1cccc(-c2ccn(C(F)F)c(=O)c2)c1]

Intermediate Acid 9

Step 1: ethyl 3-(2-chloropyridin-4-yl)benzoate

In a glass RBF equipped with a Teflon-coated magnetic stirrer was dissolved ethyl 3-(2-oxo-1,2-dihydropyridin-4-yl)benzoate (1 eq., Intermediate acid 8, Step 1) in phosphorus oxychloride (26 eq.). The resulting mixture was then heated at 80° C. for 16 h. The reaction mixture was slowly poured into crushed ice and then carefully neutralized with sat. aq. NaHCO$_3$. The aqueous suspension thus obtained was extracted with EtOAc. The combined organic extracts were then dried over MgSO$_4$, filtered and the filtrate concentrated in vacuo. Further purification by way of column chromatography (SiO$_2$, gradient elution, 9:1 (v/v)→1:1 (v/v) Hex: EtOAc) furnished the desired product as a white solid (91% yield).

Step 2: 3-(1-(difluoromethyl)-2-oxo-1,2-dihydropyridin-4-yl)benzoic acid

In a sealable glass reaction vessel equipped with a Teflon-coated screw cap was suspended ethyl 3-(2-chloropyridin-4-yl)benzoate (1 eq.) from the previous step, sodium bicarbonate (3 eq.) and 2-(fluorosulfonyl)difluoroacetic acid (3 eq.) in acetonitrile (0.5 M). The vessel was then tightly sealed and heated at 80° C. for 16 h. The resulting mixture was then directly subjected to column chromatography (SiO$_2$, gradient elution, 9:1 (v/v) Hex:EtOAc→EtOAc) to furnish the intermediate ester as a colorless oil. This alkylated product was then taken up in methanol (0.15 M), added lithium hydroxide (2.5 eq.) and the resulting mixture was stirred at 50° C. for 16 h. The reaction mixture was then carefully neutralized with 1 N aq. HCl to a pH of 4 and the volatiles were removed in vacuo. The resulting residue was subjected to column chromatography (SiO$_2$, gradient elution, CH$_2$Cl$_2$→4:1 (v/v) CH$_2$Cl$_2$: MeOH) to furnish the desired product as a white solid (35% yield).

Intermediate Acid 10

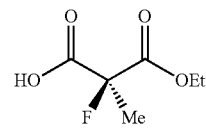 [SMILES: CCOC(=O)[C@@](C)(F)C(=O)O]

Step 1: diethyl 2-fluoro-2-methylmalonate

To a THF (0.5 M) solution of diethyl methylmalonate (1 eq.) was added sodium hydride (1.4 eq., 60% (w/w) dispersion in paraffin oil) in four equal portions, three to five minutes apart. The reaction was maintained at 0° C. for 15 min, before it was allowed to warm to RT over 30 min. After another 30 min of stirring at RT, the mixture was re-cooled to 0° C. and then added N-fluorobenzenesulfonamide (1.1 eq.) in four equal portions. Stirring was continued at 0° C. for 30 min and then at RT for 4 h, at which time it was determined to be >95% complete by $^1$H NMR. The reaction was then diluted with hexanes and vacuum filtered. The filter cake was washed further with hexanes and the product-containing filtrate was concentrated. More hexanes was added to induce further precipitation of unwanted-by-products and the suspension was filtered again. The filtrate thus obtained was then concentrated in vacuo to furnish a biphasic oil. The upper layer was determined to be paraffin oil and was discarded. The lower layer was the desired product (82% yield).

Step 2:
(S)-3-ethoxy-2-fluoro-2-methyl-3-oxopropanoic acid

Diethyl 2-fluoro-2-methylmalonate (1 eq.) from the previous step was taken up in an aqueous pH 7.3 phosphate buffer (0.14 M, prepared by dissolving 7.3 g of NaHPO$_4$ and 2.1 g of KH$_2$PO$_4$ per L of water). Lipase from *Candida Rugosa* (70 mg per mmol of substrate, 847 U/mg, Sigma Cat# L1754) was then added and the resulting heterogeneous mixture was vigorously stirred at RT for 18 h. Depending on scale, occasional addition of 1 N NaOH was necessary to maintain the pH of the reaction mixture at ~7.3 to ensure optimal activity. The reaction mixture was then added celite, stirred at RT for 1 h and filtered. The filtrate was extracted with EtOAc, dried over MgSO$_4$, and filtered. Concentration of the filtrate in vacuo furnished the desired product as a white, crystalline solid (71% yield, 93% enantiomeric excess).

Intermediate Acid 11

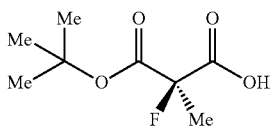

Step 1: (R)-1-tert-butyl 3-ethyl 2-fluoro-2-methylmalonate

Intermediate acid 10 (1 eq.) was dissolved in thionyl chloride (2.3 M) at RT. To this was then added a few drops of neat DMF and the resulting mixture was heated at 75° C. for 2 h. The volatiles were then removed in vacuo and the intermediate acid chloride was taken up in dichloromethane (0.12 M). At 0° C., N,N-diisopropylethylamine (3 eq.) and tert-butanol (1.5 eq.) were then added sequentially to the above dichloromethane solution, and the resulting reaction mixture was allowed to warm slowly to RT over 16 h. The reaction was then carefully quenched with the addition of 1 N aq. HCl and extracted with dichloromethane. The combined organic extracts were washed further with sat. aq. NaHCO$_3$, water and brine, dried over MgSO$_4$ and filtered. Concentration of the filtrate in vacuo furnished the desired product as a colorless oil (65% yield).

Step 2: (R)-3-(tert-butoxy)-2-fluoro-2-methyl-3-oxopropanoic acid

To a THF solution (0.16 M) of (R)-1-tert-butyl 3-ethyl 2-fluoro-2-methylmalonate (1 eq.) from the previous step was added 1 N aq. NaOH (2 eq.). The resulting biphasic mixture was vigorously stirred at RT for 2 h. The reaction was then carefully quenched with the addition of 1 N aq. HCl (until pH of ~4) and extracted with EtOAc. The combined organic extracts were washed further with water and brine, dried over MgSO$_4$ and filtered. Concentration of the filtrate in vacuo furnished the desired product as a white solid (52% yield).

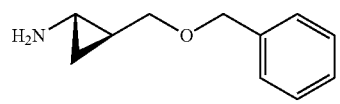 [SMILES: N[C@H]1C[C@@H]1COCc1ccccc1]

Intermediate Amine 1

Step 1: rac-(1S,2S)-2-benzyloxymethyl-cyclopropanecarboxylic acid ethyl ester

In a glass RBF equipped with a Teflon-coated magnetic stirrer was suspended sodium hydride (2.1 eq., 60% dispersion in paraffin oil) in toluene (0.68 M). To this was then added neat (diethoxy-phosphoryl)-acetic acid ethyl ester (2 eq.) drop-wise over a period of 10 min, leading to the vigorous evolution of hydrogen gas. The resulting suspension was stirred at RT for another 10 min before 2-benzyloxymethyl-oxirane (1 eq.) was added. Finally, a reflux condenser was attached and the reaction mixture was heated at reflux for 14 h. The reaction solution was then cooled to RT, diluted with tBuOMe and washed sequentially with sat. aq. NH$_4$Cl, water and brine. The organic layer thus obtained was then dried over MgSO$_4$, filtered and the filtrate concentrated in vacuo. Further purification by way of column chromatography (SiO$_2$, gradient elution, 9:1 (v/v) Hex:EtOAc→3:7 (v/v) Hex:EtOAc) furnished the desired product as a colorless oil (52% yield).

Step 2: rac-(1S,2S)-2-benzyloxymethyl-cyclopropanecarboxylic acid

In a glass RBF equipped with a Teflon-coated magnetic stirrer was dissolved rac-(1S,2S)-2-benzyloxymethyl-cyclopropanecarboxylic acid ethyl ester (1 eq.) from the previous step in ethanol (0.1 M). To this was then added sodium hydroxide (2 eq., 1 N solution in water) and the resulting mixture was allowed to stir at RT for 16 h. The volatiles were then removed in vacuo and the resulting residue was taken up in water. The pH of the aqueous solution was then carefully acidified to ~4 with 10 N aq. HCl and the resulting suspension was extracted with EtOAc. The combined organic extracts were then washed with brine, dried over MgSO$_4$ and filtered. Concentration of the filtrate thus obtained in vacuo furnished the desired product as a white solid (93% yield).

Step 3: rac-((1S,2S)-2-benzyloxymethyl-cyclopropyl)-carbamic acid tert-butyl ester In a glass RBF equipped with a Teflon-coated magnetic stirrer and a reflux condenser was combined rac-(1S,2S)-2-benzyloxymethyl-cyclopropanecarboxylic acid (1 eq.) from the previous step and triethylamine (1.2 eq.) in tert-butanol (0.1 M). To this was then added neat phosphorazidic acid diphenyl ester (1.1 eq.) drop-wise over a period of 10 min and the resulting mixture was heated at reflux for 48 h. The now golden yellow solution was cooled to RT, diluted with tBuOMe and washed with water. The organic extract was then dried over MgSO$_4$, filtered and the filtrate concentrated in vacuo. Further purification by way of column chromatography (SiO$_2$, gradient elution, 9:1 (v/v) Hex:EtOAc→1:1 (v/v) Hex:EtOAc) furnished the desired product as a colorless oil (18% yield).

Step 4: rac-(1S,2S)-2-benzyloxymethyl-cyclopropylamine

In a glass RBF equipped with a Teflon-coated magnetic stirrer was dissolved rac-((1S,2S)-2-benzyloxymethyl-cyclopropyl)-carbamic acid tert-butyl ester (1 eq.) from the previous step in dichloromethane (0.1 M). To this was then added HCl (20 eq., 4 M solution in dioxane) and the resulting solution was stirred at RT for 48 h. The volatiles were then removed in vacuo and the resulting residue was partitioned between 5:1 (v/v) hexanes: tBuOMe and water. The aqueous layer was separated and washed further with hexanes. The pH of the aqueous layer was then adjusted to ~10 with the addition of 1 N aq. NaOH. The resulting emulsion was then extracted with dichloromethane. The combined dichloromethane extracts were then washed further with brine, dried over K$_2$CO$_3$ and filtered. Concentration of the filtrate thus obtained in vacuo furnished the desired product as a pale yellow oil (63% yield).

Intermediate Amine 2

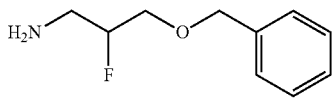

Step 1: 1-azido-3-benzyloxy-propan-2-ol

In a glass RBF equipped with a Teflon-coated magnetic stirrer and a reflux condenser was dissolved 2-benzyloxymethyl-oxirane (1 eq.) in a 3:1 (v/v) solution (0.08 M) of methanol and water. To this was then added sodium azide (2 eq.) and ammonium chloride (1.5 eq.), and the resulting mixture was heated at reflux for 14 h. The reaction solution was cooled to RT and diluted with tBuOMe. The organic layer was separated, washed further with sat. aq. NH$_4$Cl, dried over MgSO$_4$, and filtered. Concentration of the filtrate in vacuo delivered the crude product as a pale yellow oil. Further purification by way of column chromatography (SiO$_2$, gradient elution, 9:1 (v/v) Hex:EtOAc→3:7 (v/v) Hex:EtOAc) furnished the desired product as a colorless oil (71% yield).

Step 2: (3-azido-2-fluoro-propoxymethyl)-benzene

In a Nalgene bottle equipped with a Teflon-coated magnetic stirrer was dissolved 1-azido-3-benzyloxy-propan-2-ol (1 eq.) from the previous step in dichloromethane (0.02 M). To this was then added at −78° C. DAST (2 eq.) drop-wise over a period of 1 min and the resulting solution was allowed to stir at −78° C. for 3 h. The crude reaction mixture was then diluted with dichloromethane and quenched with 10% aq. NaHCO$_3$. The organic layer was separated, washed further with water and brine, dried over MgSO$_4$, and filtered. Concentration of the filtrate in vacuo delivered the crude product as a pale yellow oil. Further purification by way of column chromatography (SiO$_2$, gradient elution, Hex→1:1 (v/v) Hex:EtOAc) furnished the desired product as a colorless oil (35% yield).

Step 3: 3-benzyloxy-2-fluoro-propylamine

In a glass RBF equipped with a Teflon-coated magnetic stirrer was dissolved (3-azido-2-fluoro-propoxymethyl)-benzene (1 eq.) from the previous step in THF (0.15 M). To this was then added triphenylphosphine (1.5 eq.) and water (10 eq.), and the resulting solution was stirred at RT for 16 h. The volatiles were then removed in vacuo. The resulting residue was taken up in ether and extracted with 10% aq. HCl. The combined aqueous extracts were then rendered basic with 1 N aq. NaOH and extracted with dichloromethane. The combined organic extracts were then dried over K$_2$CO$_3$ and filtered. Concentration of the filtrate thus obtained in vacuo furnished the desired product as a colorless oil (89% yield).

Intermediate Amine 3

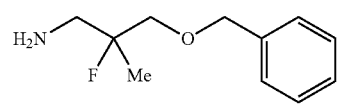 [SMILES: CC(F)(CN)COCc1ccccc1]

Step 1: (((2-methylallyl)oxy)methyl)benzene

In a glass RBF equipped with a Teflon-coated magnetic stirrer and a reflux condenser was combined NaOH (1.4 eq., 14 N aqueous solution), benzyl alcohol (1 eq.) and tetrabutylammonium bromide (0.02 eq.) in toluene (2.5 M). The resulting biphasic solution was then vigorously stirred at RT for 30 min before 3-chloro-2-methylprop-1-ene (1 eq.) was added neat and drop-wise over a period of 10 min. Following the completion of addition, the resulting mixture was heated at 75° C. for 12 h. The organic layer was then separated, washed further with water and brine, dried over MgSO$_4$, and filtered. Concentration of the filtrate in vacuo delivered the crude product as a pale yellow oil. Further purification by way of column chromatography (SiO$_2$, gradient elution, Hex→1:1 (v/v) Hex:EtOAc) furnished the desired product as a colorless oil (46% yield).

Step 2: 2-((benzyloxy)methyl)-2-methyloxirane

In a glass RBF equipped with a Teflon-coated magnetic stirrer was suspended (((2-methylallyl)oxy)methyl)benzene (1 eq.) from the previous step and sodium bicarbonate (1.5 eq.) in dichloromethane (0.18 M). To this was then added at 0° C. mCPBA (1.2 eq.) portion-wise over a period of 30 min, while taking care to keep the internal reaction temperature below 5° C. The resulting suspension was then allowed to warm slowly to RT over a period 2 h. The now gel-like suspension was diluted with ether and washed sequentially with 10% aq. Na$_2$S$_2$O$_3$, 1 N aq. NaOH, water and brine. The organic extract was then dried over Na$_2$SO$_4$ and filtered. Concentration of the filtrate in vacuo furnished the product as a colorless oil (93% yield)

Step 3: 1-azido-3-(benzyloxy)-2-methylpropan-2-ol

In a glass RBF equipped with a Teflon-coated magnetic stirrer and a reflux condenser was dissolved 2-((benzyloxy)methyl)-2-methyloxirane (1 eq.) from the previous step in DMF (0.5 M). To this was then added sodium azide (2 eq.) and ammonium chloride (1.5 eq.), and the resulting mixture was heated at reflux for 14 h. The reaction solution was cooled to RT and diluted with tBuOMe. The organic layer was separated, washed further with water and brine, dried over MgSO$_4$, and filtered. Concentration of the filtrate in vacuo delivered the crude product as a pale yellow oil. Further purification by way of column chromatography (SiO$_2$, gradient elution, 9:1 (v/v) Hex:EtOAc→3:7 (v/v) Hex:EtOAc) furnished the desired product as a colorless oil (93% yield).

Step 4: ((3-azido-2-fluoro-2-methylpropoxy)methyl)benzene

In a Nalgene bottle equipped with a Teflon-coated magnetic stirrer was dissolved 1-azido-3-(benzyloxy)-2-methylpropan-2-ol (1 eq.) from the previous step in dichloromethane (0.13 M). To this was then added at −78° C. DAST (2 eq.) drop-wise over a period of 1 min and the resulting solution was allowed to stir at −78° C. for 3 h. The crude reaction mixture was then diluted with dichloromethane and quenched with 10% aq. NaHCO$_3$. The organic layer was separated, washed further with water and brine, dried over MgSO$_4$, and filtered. Concentration of the filtrate in vacuo delivered the crude product as a pale yellow oil. Further purification by way of column chromatography (SiO$_2$, gradient elution, Hex→1:1 (v/v) Hex:EtOAc) furnished the desired product as a colorless oil (98% yield).

Step 5:
3-(benzyloxy)-2-fluoro-2-methylpropan-1-amine

In a glass RBF equipped with a Teflon-coated magnetic stirrer was dissolved ((3-azido-2-fluoro-2-methylpropoxy)methyl)benzene (1 eq.) from the previous step in THF (0.25 M). To this was then added triphenylphosphine (1.5 eq.) and water (10 eq.), and the resulting solution was stirred at RT for 16 h. The volatiles were then removed in vacuo. The resulting residue was taken up in ether and extracted with 10% aq. HCl. The combined aqueous extracts were then rendered basic with 1 N aq. NaOH and extracted with dichloromethane. The combined organic extracts were then dried over K$_2$CO$_3$ and filtered. Concentration of the filtrate thus obtained in vacuo furnished the desired product as a colorless oil (96% yield).

Intermediate Amine 4

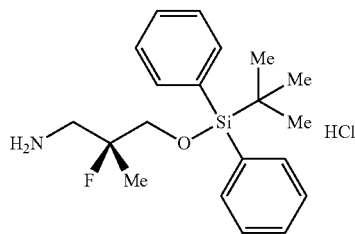 [SMILES: CC(C)(C)[Si](OC[C@@](C)(F)CN)(c1ccccc1)c1ccccc1 ; Cl]

Step 1: (5)-ethyl 2-fluoro-3-((4-methoxybenzyl)amino)-2-methyl-3-oxopropanoate

Intermediate acid 10 (1 eq.), 4-methoxybenzyl amine hydrochloride (1.1 eq.) and N,N-diisopropylethylamine (3.5 eq.) were combined in dichloromethane (0.15 M). To this was then added HATU (1.05 eq.) and the resulting mixture was stirred at RT for 18 h. The reaction was then quenched with the addition of 1 N aq. HCl and extracted with dichloromethane. The combined organic extracts were washed further with water, 10% aq. NaHCO$_3$ and brine, dried over MgSO$_4$, filtered and the filtrate concentrated in vacuo. Further purification of the crude product thus obtained by way of column chromatography (SiO$_2$, gradient elution, Hex→7:3 (v/v) Hex:EtOAc) furnished the desired product as a golden yellow oil (70% yield).

Step 2: (R)-2-fluoro-3-hydroxy-N-(4-methoxybenzyl)-2-methylpropanamide

To a methanol (0.23 M) solution of (S)-ethyl 2-fluoro-3-((4-methoxybenzyl)amino)-2-methyl-3-oxopropanoate (1 eq.) from the previous step was added at 0° C. calcium iodide (1 eq.) and sodium borohydride (2 eq.). Following an initial vigorous evolution of gas, the cooling bath was removed and the reaction mixture was allowed to stir at RT for 4 h. The reaction was then quenched with the addition of 10% aq. HCl and extracted with EtOAc. The combined organic extracts were washed further with water, 1 N aq. NaOH and brine, dried over MgSO$_4$, filtered and the filtrate concentrated in vacuo. Recrystallization of the crude product thus obtained from dichloromethane, ether and hexanes furnished the desired product as a white crystalline solid (86% yield).

Step 3: (R)-2-fluoro-N-(4-methoxybenzyl)-2-methyl-3-((triisopropylsilyl)oxy)-propanamide To a dichloromethane (0.31 M) solution of (R)-2-fluoro-3-hydroxy-N-(4-methoxybenzyl)-2-methylpropanamide (1 eq.) from the previous step was added at 0° C. 2,6-lutidine (1.5 eq.) and then triisopropylsilyl trifluoromethanesulfonate (1.2 eq.). The resulting solution was allowed to stir at 0° C. for 10 min and then at RT for 30 min. The reaction was then carefully quenched with the addition of 0.1 N aq. HCl and extracted with dichloromethane. The combined organic extracts were washed further with water and brine, dried over MgSO$_4$ and filtered. Concentration of the filtrate in vacuo furnished the desired product as a colorless oil (71% yield).

Step 4: (5)-2-fluoro-N-(4-methoxybenzyl)-2-methyl-3-((triisopropylsilyl)oxy)propan-1-amine To a THF (0.25 M) solution of (R)-2-fluoro-N-(4-methoxybenzyl)-2-methyl-3-((triisopropylsilyl)oxy)-propanamide (1 eq.) from the previous step was added at RT borane (6 eq., 1 M solution in THF) drop-wise over a period of 30 min. Following the completion of addition, a reflux condenser was attached and the reaction mixture was heated at reflux for 18 h. With the reaction deemed complete, the reaction was quenched slowly and carefully at 0° C. with the drop-wise addition of methanol. The volatiles were then removed in vacuo and the resulting residue was co-evaporated with toluene (3×). The crude product thus obtained was used as is immediately in the next step.

Step 5: (5)-tert-butyl (2-fluoro-2-methyl-3-((triisopropylsilyl)oxy)propyl)(4-methoxybenzyl)carbamate To a dichloromethane (0.29 M) solution of (S)-2-fluoro-N-(4-methoxybenzyl)-2-methyl-3-((triisopropylsilyl)oxy) propan-1-amine (1 eq.) from the previous step was added N,N-diisopropylethylamine (3 eq.) and then di-tert-butyl dicarbonate (1.5 eq.). The resulting solution was allowed to stir at RT for 5 h. The reaction was then carefully quenched with the addition of 1 N aq. HCl and extracted with dichloromethane. The combined organic extracts were washed further with water and brine, dried over MgSO$_4$ and filtered. Concentration of the filtrate in vacuo furnished the desired product as a colorless oil (62% yield over two steps).

Step 6: (S)-tert-butyl (2-fluoro-3-hydroxy-2-methylpropyl)carbamate

To a 3:1 (v/v) acetonitrile:water solution (0.1 M) of ((S)-tert-butyl (2-fluoro-2-methyl-3-((triisopropylsilyl)-oxy)propyl)(4-methoxybenzyl)carbamate (1 eq.) from the previous step was added ammonium cerium nitrate (2 eq.) and the resulting mixture was stirred at RT for 18 h. The reaction solution was then diluted with water and extracted with EtOAc. The combined organic extracts were washed further with water and brine, dried over MgSO$_4$, filtered and the filtrate concentrated in vacuo. Further purification of the crude product thus obtained by way of column chromatography (SiO$_2$, gradient elution, Hex→EtOAc) furnished the desired product as a white crystalline solid (70% yield).

Step 7: (S)-tert-butyl (3-((tert-butyldiphenylsilyl)oxy)-2-fluoro-2-methylpropyl)carbamate To a dichloromethane (0.1 M) solution of (S)-tert-butyl (2-fluoro-3-hydroxy-2-methylpropyl)carbamate (1 eq.) from the previous step was added sequentially N,N-diisopropylethylamine (2.5 eq.), DMAP (0.05 eq.) and tert-butyldiphenylchlorosilane (1.3 eq.). The resulting solution was allowed to stir at RT for 72 h. The reaction was then carefully quenched with the addition of 1 N aq. HCl and extracted with dichloromethane. The combined organic extracts were washed further with water and brine, dried over MgSO$_4$, filtered and the filtrate concentrated in vacuo. Further purification of the crude product thus obtained by way of column chromatography (SiO$_2$, gradient elution, Hex→1:1 (v/v) Hex:EtOAc) furnished the desired product as a colorless oil (88% yield).

Step 8: (5)-3-((tert-butyldiphenylsilyl)oxy)-2-fluoro-2-methylpropan-1-amine hydrochloride To a dichloromethane (0.1 M) solution of (5)-tert-butyl (3-((tert-butyldiphenylsilyl)oxy)-2-fluoro-2-methylpropyl) carbamate (1 eq.) from the previous step was added HCl (5 eq., 4 M solution in 1,4-dioxane) and the resulting solution was stirred at RT for 2 h. The volatiles were then removed in vacuo and the resulting residue was re-crystallized from ether and hexanes. The title compound was isolated as a white crystalline solid (86% yield).

Intermediate Amine 5

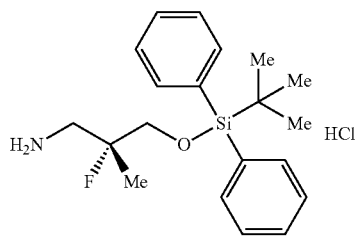 [SMILES: CC(C)(C)[Si](OC[C@](C)(F)CN)(c1ccccc1)c1ccccc1 ; Cl]

Prepared in an analogous fashion to Intermediate amine 4, but using Intermediate acid 11 (1 eq.) in place of Intermediate acid 10 in step 1.

Intermediate Aniline 1

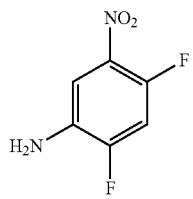

In a glass RBF equipped with a Teflon-coated magnetic stirrer was dissolved 2,4-difluoro-phenylamine (1 eq.) in concentrated sulfuric acid (2.4 M). The resulting solution was cooled in an ice-brine bath and then added fuming nitric acid (0.8 eq.) drop-wise over a period of 20 min. After 1 h of stirring at 0° C., the reaction mixture was poured over ice and carefully adjusted to a pH of ~8 with sat. aq. NaHCO$_3$. The resulting suspension was stirred at RT for 15 min and the solid thus obtained was harvested via filtration. The filter cake thus obtained was washed with copious amount of water and then dried under reduced pressure for 18 h to furnish the desired product as a dark, orange solid (45% yield).

Intermediate Aniline 2

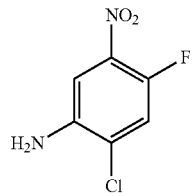

Prepared in an analogous fashion to Intermediate aniline 1, but using 2-chloro-4-fluoro-phenylamine (1 eq.) in place of 2,4-difluoro-phenylamine. Furthermore, the crude product needed to be purified further via reverse-phase column chromatography (C$_{18}$, gradient elution, 9:1 (v/v) H$_2$O: MeCN+0.1% formic acid→MeCN+0.1% formic acid) to furnish the title compound as a blood red solid (27% yield).

Intermediate Aniline 3

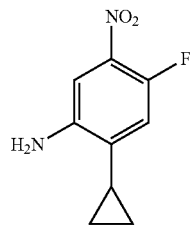

In a glass reaction vessel equipped with a Teflon-coated screw cap was suspended 2-bromo-4-fluoro-5-nitro-phenylamine (1 eq.), potassium cyclopropyltrifluoroborate (2 eq.), palladium(II) acetate (0.15 eq.), tricyclohexylphosphine (0.3 eq.) and cesium carbonate (6 eq.) in a 3:1 (v/v) toluene: water solution (0.1 M). The resulting suspension was deoxygenated via sub-surface purging with nitrogen for 10 min. The vessel was then tightly sealed and heated at 120° C. for 18 h. The now black suspension was then cooled to RT and diluted with EtOAc. The aqueous layer was separated and back-extracted with EtOAc. The combined organic extracts were then washed further with water and brine, dried over Na$_2$SO$_4$, filtered and the filtrate concentrated in vacuo. Purification of the crude product thus obtained by way of column chromatography (SiO$_2$, gradient elution, 9:1 (v/v) Hex:EtOAc→EtOAc) furnished the title compound as a red semi-solid (74% yield).

125
Intermediate Aniline 4

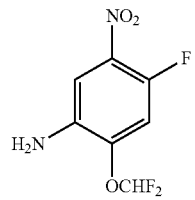

Step 1: 2-difluoromethoxy-4-fluoro-1-nitro-benzene

In a glass reaction vessel equipped with a Teflon-coated screw cap was suspended 5-fluoro-2-nitro-phenol (1 eq.) and sodium carbonate (1.2 eq.) in DMF (0.5 M). To this was then added sodium 2-chloro-2,2-difluoroacetate (2 eq.) and the resulting suspension was then heated at 100° C. for 4.5 h. The reaction mixture was then allowed to cool to RT and carefully quenched with 4 N aq. HCl. The resulting solution was stirred at RT for 2 h, diluted further with water and extracted with dichloromethane. The combined organic extracts were washed further with 1 N aq. NaOH, water and brine, dried over $Na_2SO_4$, filtered and the filtrate concentrated in vacuo. Purification of the crude product thus obtained by way of column chromatography ($SiO_2$, gradient elution, 9:1 (v/v) Hex:EtOAc→1:1 (v/v) Hex:EtOAc) furnished the title compound as a yellow oil (82% yield).

Step 2: 2-difluoromethoxy-4-fluoro-phenylamine

In a Parr shaker flask was suspended 2-difluoromethoxy-4-fluoro-1-nitro-benzene (1 eq.) from the previous step and palladium black (0.14 eq, dry, 10% w/w over carbon) in ethanol (0.15 M). The vessel was then repeatedly evacuated and back-filled with nitrogen (3×) and then hydrogen (3×). The resulting suspension was shaken under 50 psi of hydrogen for 1 h. The reaction was then quenched with $CH_2Cl_2$ and filtered through a bed of $CH_2Cl_2$-wetted celite. The insoluble bed was washed further with MeOH and $CH_2Cl_2$. Concentration of the filtrate thus obtained in vacuo furnished the desired product as a purple oil (92% yield).

Step 3: 2-difluoromethoxy-4-fluoro-5-nitro-phenylamine

In a glass RBF equipped with a Teflon-coated magnetic stirrer was dissolved 2-difluoromethoxy-4-fluoro-phenylamine (1 eq.) from the previous step in concentrated sulfuric acid (1.1 M) at 0° C. While keeping the internal temperature below 5° C., potassium nitrate (1 eq.) was added portion-wise over a period of 30 min. After another 4 h of stirring at 0° C., the reaction mixture was poured over ice and carefully adjusted to a pH of ~8 with potassium carbonate. The resulting suspension was stirred at RT for 15 min and the solid thus obtained was harvested via filtration. The filter cake thus obtained was washed with copious amount of water and then dried under reduced pressure for 18 h to furnish the desired product as a yellow solid (77% yield).

126
Intermediate 1-OTIPS

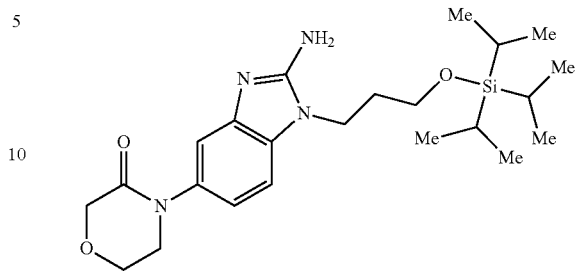

Step 1: 4-(4-fluorophenyl)-morpholin-3-one

In a glass reaction vessel equipped with a Teflon-coated screw cap was combined morpholin-3-one (1 eq.), 1-fluoro-4-iodo-benzene (1.5 eq.), L-proline (0.2 eq.), copper (I) iodide (0.1 eq.) and potassium carbonate (2.5 eq.) in DMSO (0.2 M). The reaction suspension was then sub-surface purged with nitrogen for 15 min before the reaction vessel was tightly sealed and heated at 100° C. for 16 h. The resulting brown reaction suspension was diluted with tBuOMe and washed sequentially with water, 1 N aq. NaOH, 10% aq. HCl, water and brine. The organic extract was then dried over $MgSO_4$, filtered and the filtrate concentrated in vacuo to furnish a brown semi-solid. Recrystallization from hot hexanes furnished the desired product as a tan solid (21% yield).

Step 2: 4-(4-fluoro-3-nitrophenyl)-morpholin-3-one

In a glass RBF equipped with a Teflon-coated magnetic stirrer was dissolved 4-(4-fluorophenyl)-morpholin-3-one (1 eq.) from the previous step in concentrated sulfuric acid (0.33 M). The resulting solution was cooled in an ice-water bath and then added drop-wise fuming nitric acid (2 eq.). The resulting mixture was stirred at 0° C. for 15 min, quenched with ice and then extracted with EtOAc. The combined organic extracts were then washed further with 10% aq. $NaHCO_3$, 10% aq. $NH_4Cl$, water and brine. The organic extract was dried over $Na_2SO_4$, filtered and the filtrate concentrated in vacuo to furnish the desired product, slightly contaminated with its inseparable 2-nitro regioisomer. This was used as is without further purification.

Step 3: 4-(4-(3-hydroxy-propylamino)-3-nitrophenyl)-morpholin-3-one

In a glass RBF equipped with a Teflon-coated magnetic stirrer was dissolved 4-(4-fluoro-3-nitrophenyl)-morpholin-3-one (1 eq.) from the previous step in ethanol (0.14 M). To this was then added 3-amino-propan-1-ol (3 eq.) and triethylamine (4 eq.). The resulting solution was heated at 80° C. for 8 h. The volatiles were then removed in vacuo and the resulting residue was directly subjected to column chromatography ($SiO_2$, gradient elution, 1:1 (v/v) Hex:EtOAc→EtOAc→10:1 (v/v) EtOAc:MeOH) to furnish the desired product as a red oil that solidified upon standing (28% yield over two steps).

Step 4: 4-(3-amino-4-(3-hydroxy-propylamino)-phenyl)-morpholin-3-one

In a Parr shaker flask was suspended 4-(4-(3-hydroxy-propylamino)-3-nitrophenyl)-morpholin-3-one (1 eq.) from the previous step and palladium black (0.24 eq., dry, 10% w/w over carbon) in ethanol (0.025 M). The vessel was then repeatedly evacuated and back-filled with nitrogen (3×) and then hydrogen (3×). The resulting suspension was shaken under 50 psi of hydrogen for 1 h. The reaction was then quenched with $CH_2Cl_2$ and filtered through a bed of $CH_2Cl_2$-wetted celite. The insoluble bed was washed further with MeOH and $CH_2Cl_2$. Concentration of the filtrate thus obtained in vacuo furnished the desired product as a brown solid.

Step 5: 4-(3-amino-4-(3-triisopropylsilanyloxy-propylamino)-phenyl)-morpholin-3-one In a glass RBF equipped with a Teflon-coated magnetic stirrer was dissolved 4-(3-amino-4-(3-hydroxy-propylamino)-phenyl)-morpholin-3-one (1 eq.) from the previous step in DMF (0.11 M). To this was then added chloro-triisopropyl-silane (6 eq.), imidazole (6 eq.) and a few crystals of DMAP. The resulting solution was stirred at RT for 18 h. The crude reaction mixture was diluted with EtOAc and washed sequentially with water, 10% aq. $NaHCO_3$, water and brine. The organic extract was then dried over $Na_2SO_4$, filtered and the filtrate concentrated in vacuo. Further purification by way of column chromatography ($SiO_2$, gradient elution, 1:1 (v/v) Hex:EtOAc→EtOAc) furnished the desired product as a white solid (61% yield over two steps).

Step 6: 4-(2-amino-1-(3-triisopropylsilanyloxy-propyl)-1H-benzoimidazol-5-yl)-morpholin-3-one In a glass RBF equipped with a Teflon-coated magnetic stirrer was added cyanogen bromide (1.5 eq., 5 M solution in acetonitrile) to water (0.14 M). To this was then added a methanol (0.07 M) solution of 4-(3-amino-4-(3-triisopropyl-silanyloxy-propylamino)-phenyl)-morpholin-3-one (1 eq.) from the previous step drop-wise over a period of 10 min. The resulting mixture was allowed to stir at RT for 12 h. The crude reaction mixture was diluted with EtOAc and washed sequentially with 10% aq. $NaHCO_3$, water and brine. The organic extract was then dried over $Na_2SO_4$ and filtered. Concentration of the filtrate thus obtained in vacuo furnished the desired product as an off-white solid (72% yield).

Intermediate 1-OH

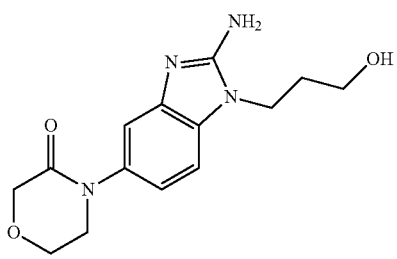 [SMILES: Nc1nc2cc(N3CCOCC3=O)ccc2n1CCCO]

Prepared in an analogous fashion to Intermediate 1-OTIPS, but Step 5 was omitted.

Intermediate 1-OAc

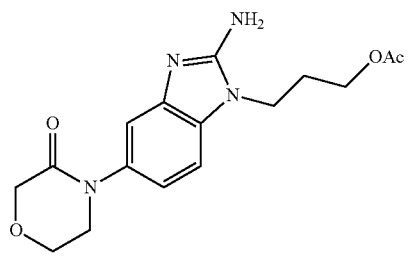

Prepared in an analogous fashion to Intermediate 1-OTIPS, but using acetic anhydride (3 eq.) in place of chloro-triisopropyl-silane, cesium carbonate (2 eq.) in place of imidazole, and acetonitrile (0.44 M) in place of DMF in Step 5.

Intermediate 2-$CF_3$

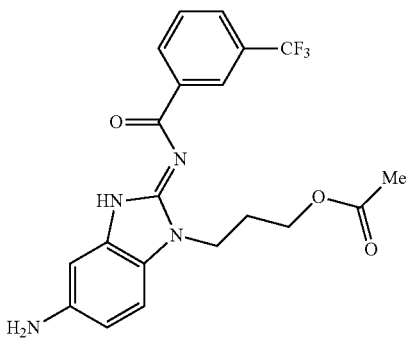

Step 1: (4-fluoro-3-nitro-phenyl)-carbamic acid tert-butyl ester

In a glass RBF equipped with a Teflon-coated magnetic stirrer was dissolved 4-fluoro-3-nitro-phenylamine (1 eq.) in DMF (0.5 M). To this was then added $BOC_2O$ (1.1 eq.) and DMAP (0.05 eq.), and the resulting solution was allowed to stir at RT for 23 h. The reaction was quenched with the addition of saturated aq. $NaHCO_3$ and then extracted with EtOAc. The combined organic extracts were washed further with 10% aq. HCl, water and brine, dried over $MgSO_4$, filtered and the filtrate concentrated in vacuo. Purification of the crude product thus obtained by way of column chromatography ($SiO_2$, gradient elution, 10:1 (v/v) Hex:EtOAc→EtOAc) furnished the desired product, after a further recrystallization from ether, as a white, crystalline solid (29% yield).

Step 2: (4-(3-hydroxy-propylamino)-3-nitro-phenyl) carbamic acid tert-butyl ester In a glass RBF equipped with a Teflon-coated magnetic stirrer was dissolved (4-fluoro-3-nitro-phenyl)-carbamic acid tert-butyl ester (1 eq.) from the previous step in DMF (0.5 M). To this was then added 3-amino-propan-1-ol (2 eq.) and potassium carbonate (3 eq.). The resulting solution was heated at 70° C. for 23 h. The crude reaction mixture was then diluted with EtOAc and washed sequentially with water and brine. The organic extract was then dried over MgSO$_4$ and filtered. Concentration of the filtrate in vacuo afforded the desired product as a red oil that solidified upon standing.

Step 3: 3-((4-((tert-butoxycarbonyl)amino)-2-nitrophenyl)amino)propyl acetate

In a glass RBF equipped with a Teflon-coated magnetic stirrer was dissolved (4-(3-hydroxy-propylamino)-3-nitrophenyl)carbamic acid tert-butyl ester (1 eq.) from the previous step in pyridine (0.3 M). To this was then added acetic anhydride (1.1 eq.) drop-wise and neat over 10 min. After 3 h of stirring at RT, the volatiles were removed in vacuo and the resulting residue was partitioned between EtOAc and sat. aq. NH$_4$Cl. The aqueous layer was separated and back-extracted with EtOAc. The combined organic extracts were then dried over MgSO$_4$, filtered and the filtrate concentrated in vacuo. Purification of the crude product thus obtained by way of column chromatography (SiO$_2$, gradient elution, 8:1 (v/v) Hex:EtOAc→EtOAc) furnished the desired product (82% yield over two steps).

Step 4: 3-((2-amino-4-((tert-butoxycarbonyl)amino)phenyl)amino)propyl acetate

In a Parr shaker flask was suspended 3-((4-((tert-butoxycarbonyl)amino)-2-nitrophenyl)amino)propyl acetate (1 eq.) from the previous step and palladium black (0.05 eq, dry, 10% w/w over carbon) in methanol (0.1 M). The vessel was then repeatedly evacuated and back-filled with nitrogen (3×) and then hydrogen (3×). The resulting suspension was shaken under 50 psi of hydrogen for 2 h. The reaction was then quenched with CH$_2$Cl$_2$ and filtered through a bed of CH$_2$Cl$_2$-wetted celite. The insoluble bed was washed further with MeOH and CH$_2$Cl$_2$. Concentration of the filtrate thus obtained in vacuo furnished the desired product as a brown solid.

Step 5: 3-(2-amino-5-((tert-butoxycarbonyl)amino)-1H-benzo[d]imidazol-1-yl)propyl acetate In a glass RBF equipped with a Teflon-coated magnetic stirrer was added cyanogen bromide (2 eq., 5 M solution in acetonitrile) slowly to ethanol (0.5 M) over a period of 10 min. To this was then added an ethanol (0.25 M) solution of 3-((2-amino-4-((tert-butoxycarbonyl)amino)phenyl)amino)propyl acetate (1 eq.) from the previous step drop-wise over a period of 10 min. The resulting mixture was allowed to stir at RT for 1.5 h. The crude reaction mixture was diluted with EtOAc and washed sequentially with 10% aq. NaHCO$_3$, water and brine. The organic extract was then dried over Na$_2$SO$_4$ and filtered. Concentration of the filtrate thus obtained in vacuo furnished the desired product as an off-white solid.

Step 6: (E)-3-(5-((tert-butoxycarbonyl)amino)-2-((3-(trifluoromethyl)benzoyl)imino)-2,3-dihydro-M-benzo[d]imidazol-1-yl)propyl acetate In a glass RBF equipped with a Teflon-coated magnetic stirrer was dissolved 3-(2-amino-5-((tert-butoxycarbonyl)amino)-1H-benzo[d]imidazole-1-yl)propyl acetate (1 eq.) from the previous step, 3-trifluoromethyl-benzoic acid (1 eq.) and HATU (1.2 eq.) in DMF (0.1 M). To this was then added ethyl-diisopropyl-amine (2.5 eq.) and the resulting yellow solution was allowed to stir at RT for 14 h. The crude reaction mixture was diluted with EtOAc and washed sequentially with water, 10% aq. HCl, water and brine. The organic extract was then dried over MgSO$_4$, filtered and the filtrate concentrated in vacuo. Further purification by way of column chromatography (SiO$_2$, gradient elution, 9:1 (v/v) Hex:EtOAc→EtOAc) furnished the desired product as an off-white solid (82% yield over three steps).

Step 7: (E)-3-((5-amino)-2-((3-(trifluoromethyl)benzoyl)imino)-2,3-dihydro-M-benzo[d]imidazol-1-yl)propyl acetate In a glass RBF equipped with a Teflon-coated magnetic stirrer was dissolved (E)-3-(5-((tert-butoxycarbonyl)amino)-2-((3-(trifluoromethyl)benzoyl)imino)-2,3-dihydro-1H-benzo[d]imidazol-1-yl)propyl acetate (1 eq.) from the previous step in dichloromethane (0.1 M). To this was then added trifluoroacetic acid (30 eq.) and the resulting solution was allowed to stir at RT for 14 h. The volatiles were then removed in vacuo and the resulting residue was taken up in EtOAc. The organic extract was then washed with sat. aq. NaHCO$_3$, water and brine, dried over MgSO$_4$, and filtered. Concentration of the filtrate thus obtained in vacuo furnished the desired product as an off-white solid (82% yield).

Intermediate 2-CF$_2$H

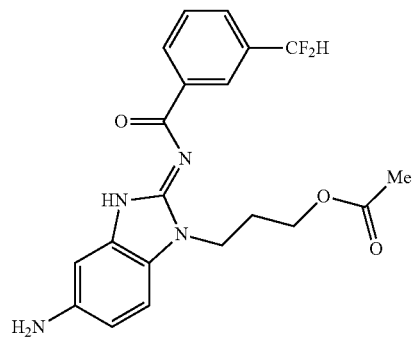 [SMILES: CC(=O)OCCCn1/c(=N/C(=O)c2cccc(C(F)F)c2)[nH]c2cc(N)ccc21]

Prepared in an analogous fashion to Intermediate 2-CF$_3$, but using 3-(difluoromethyl)-benzoic acid (1 eq.) in place of 3-trifluoromethyl-benzoic acid in step 6.

Intermediate 2-CN

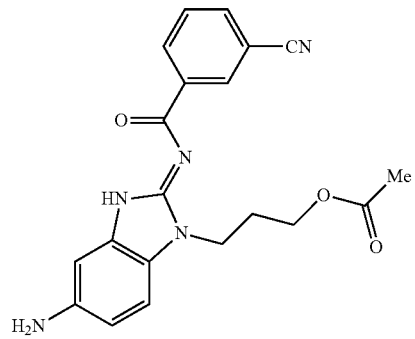

Prepared in an analogous fashion to Intermediate 2-CF₃, but using 3-cyano-benzoic acid (1 eq.) in place of 3-trifluoromethyl-benzoic acid in step 6.

Intermediate 3-CF₃

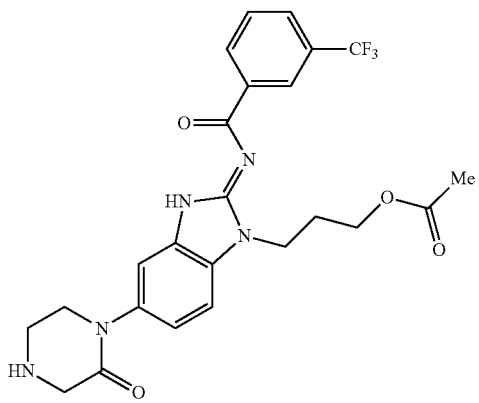 [SMILES: CC(=O)OCCCn1/c(=N/C(=O)c2cccc(C(F)(F)F)c2)[nH]c2cc(N3CCNCC3=O)ccc21]

Step 1: tert-butyl (2-chloroethyl)(2-((4-fluoro-3-nitrophenyl)amino)-2-oxoethyl)carbamate In a glass RBF equipped with a Teflon-coated magnetic stirrer was combined 2-((tert-butoxycarbonyl)(2-chloroethyl)amino)acetic acid (1.7 eq.), and HATU (1.2 eq.) in DMF (0.2 M). After 15 min of stirring at RT, 4-fluoro-3-nitro-phenylamine (1 eq.) was added, followed by ethyldiisopropyl-amine (3 eq.). The resulting yellow solution was allowed to stir at RT for 6 h. The crude reaction mixture was diluted with EtOAc and washed sequentially with water, 10% aq. HCl, 10% aq. NaHCO₃, water and brine. The organic extract was then dried over Na₂SO₄, filtered and the filtrate concentrated in vacuo. Further purification by way of column chromatography (SiO₂, gradient elution, 9:1 (v/v) Hex:EtOAc→EtOAc) furnished the desired product (51% yield).

Step 2: tert-butyl 4-(4-fluoro-3-nitrophenyl)-3-oxopiperazine-1-carboxylate

In a glass RBF equipped with a Teflon-coated magnetic stirrer was dissolved tert-butyl (2-chloroethyl)(2-((4-fluoro-3-nitrophenyl)amino)-2-oxoethyl)carbamate (1 eq.) from the previous step in MeCN (0.1 M). To this was then added cesium carbonate (2 eq.) and the resulting suspension was allowed to stir at RT for 3 h. The volatiles were then removed in vacuo. The resulting reside was taken up in EtOAc and washed sequentially with water and brine, dried over MgSO₄, filtered and the filtrate concentrated in vacuo. Purification of the crude product thus obtained by way of column chromatography (SiO₂, gradient elution, 10:1 (v/v) Hex:EtOAc→EtOAc) furnished the desired product (72% yield).

Step 3: tert-butyl 4-(4-((3-hydroxypropyl)amino)-3-nitrophenyl)-3-oxopiperazine-1-carboxylate In a glass RBF equipped with a Teflon-coated magnetic stirrer was dissolved tert-butyl 4-(4-fluoro-3-nitrophenyl)-3-oxopiperazine-1-carboxylate (1 eq.) from the previous step in DMF (0.3 M). To this was then added 3-aminopropan-1-ol (1.2 eq.) and potassium carbonate (3 eq.). The resulting solution was heated at 70° C. for 4 h. The crude reaction mixture was then diluted with EtOAc and washed sequentially with water and brine. The organic extract was then dried over MgSO₄, filtered and the filtrate concentrated in vacuo. Purification of the crude product thus obtained by way of column chromatography (SiO₂, gradient elution, 10:1 (v/v) Hex:EtOAc→EtOAc) furnished the desired product (67% yield).

Step 4: tert-butyl 4-(4-((3-acetoxypropyl)amino)-3-nitrophenyl)-3-oxopiperazine-1-carboxylate In a glass RBF equipped with a Teflon-coated magnetic stirrer was dissolved tert-butyl 4-(4-((3-hydroxypropyl)amino)-3-nitrophenyl)-3-oxopiperazine-1-carboxylate (1 eq.) from the previous step in pyridine (0.15 M). To this was then added acetic anhydride (1.8 eq.) drop-wise and neat over 10 min. After 18 h, the volatiles were then removed in vacuo and the resulting residue was partitioned between EtOAc and sat. aq. NaHCO₃. The aqueous layer was separated and back-extracted with EtOAc. The combined organic extracts were then dried over MgSO₄ and filtered. Concentration of the filtrate in vacuo furnished the desired product.

Step 5: tert-butyl 4-(4-((3-acetoxypropyl)amino)-3-aminophenyl)-3-oxopiperazine-1-carboxylate In a Parr shaker flask was suspended tert-butyl 4-(4-((3-acetoxypropyl)amino)-3-nitrophenyl)-3-oxopiperazine-1-carboxylate (1 eq.) from the previous step and palladium black (0.1 eq., dry, 10% w/w over carbon) in a 3:1 (v/v) methanol:EtOAc solution (0.1 M). The vessel was then repeatedly evacuated and back-filled with nitrogen (3×) and then hydrogen (3×). The resulting suspension was shaken under 50 psi of hydrogen for 2 h. The reaction was then quenched with CH₂Cl₂ and filtered through a bed of CH₂Cl₂-wetted celite. The insoluble bed was washed further with MeOH and CH₂Cl₂. Concentration of the filtrate thus obtained in vacuo furnished the desired product as a brown solid.

Step 6: tert-butyl 4-(1-(3-acetoxypropyl)-2-amino-1H-benzo[d]imidazol-5-yl)-3-oxopiperazine-1-carboxylate In a glass RBF equipped with a Teflon-coated magnetic stirrer was added cyanogen bromide (2 eq., 5 M solution in acetonitrile) slowly to ethanol (0.1 M) over a period of 10 min. To this was then added drop-wise an ethanol (0.1 M) solution of tert-butyl 4-(4-((3-acetoxypropyl)amino)-3-aminophenyl)-3-oxopiperazine-1-carboxylate (1 eq.) from the previous step over a period of 10 min. The resulting mixture was allowed to stir at RT for 16 h. The crude reaction mixture was diluted with EtOAc and washed sequentially with 10% aq. NaHCO₃, water and brine. The organic extract was then dried over Na₂SO₄ and filtered. Concentration of the filtrate thus obtained in vacuo furnished the desired product as an off-white solid.

Step 7: (E)-tert-butyl 4-(1-(3-acetoxypropyl)-2-((3-(trifluoromethyl)benzoyl)imino)-2,3-dihydro-1H-benzo[d]imidazol-5-yl)-3-oxopiperazine-1-carboxylate In a glass RBF equipped with a Teflon-coated magnetic stirrer was dissolved tert-butyl 4-(1-(3-acetoxypropyl)-2-amino-1H-benzo[d]imidazol-5-yl)-3-oxopiperazine-1-carboxylate (1 eq.) from the previous step, 3-trifluoromethyl-benzoic acid (1 eq.) and HATU (1.2 eq.) in DMF (0.1 M). To this was then added ethyl-diisopropyl-amine (3 eq.) and the resulting yellow solution was allowed to stir at RT for 2 h. The crude reaction mixture was diluted with EtOAc and washed sequentially with water, 10% aq. HCl, water and brine. The organic extract was then dried over $Na_2SO_4$, filtered and the filtrate concentrated in vacuo. Further purification by way of column chromatography ($SiO_2$, gradient elution, 9:1 (v/v) Hex:EtOAc→EtOAc) furnished the desired product as an off-white solid (80% yield over four steps).

Step 8: (E)-3-(5-(2-oxopiperazin-1-yl)-2-((3-(trifluoromethyl)benzoyl)imino)-2,3-dihydro-1H-benzo[d]imidazol-1-yl)propyl acetate In a glass RBF equipped with a Teflon-coated magnetic stirrer was dissolved (E)-tert-butyl 4-(1-(3-acetoxypropyl)-2-((3-(trifluoromethyl)benzoyl)imino)-2,3-dihydro-1H-benzo[d]imidazol-5-yl)-3-oxopiperazine-1-carboxylate (1 eq.) from the previous step in dichloromethane (0.1 M). To this was then added trifluoroacetic acid (25 eq.) and the resulting solution was allowed to stir at RT for 14 h. The volatiles were then removed in vacuo and the resulting residue was taken up in EtOAc. The organic extract was then washed with sat. aq. $NaHCO_3$, water and brine, dried over $MgSO_4$, and filtered. Concentration of the filtrate thus obtained in vacuo furnished the desired product as an off-white solid (93% yield).

Intermediate 3-CF₂H

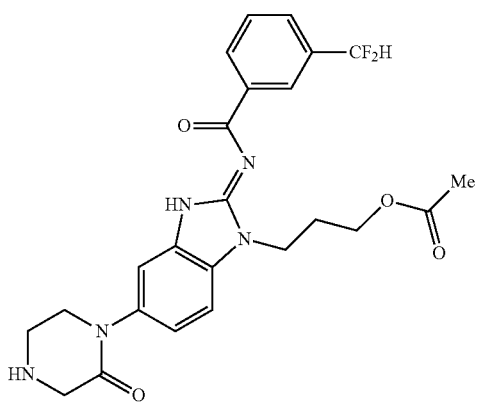 [SMILES: CC(=O)OCCCn1/c(=N/C(=O)c2cccc(C(F)F)c2)[nH]c2cc(N3CCNCC3=O)ccc21]

Prepared in an analogous fashion to Intermediate 3-CF₃, but using 3-(difluoromethyl)-benzoic acid (1 eq.) in place of 3-trifluoromethyl-benzoic acid in step 7.

Intermediate 4-CF₃

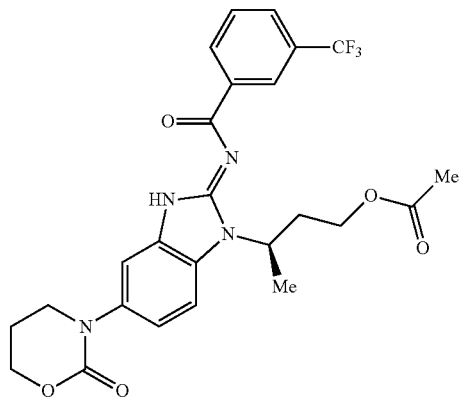

Step 1: 3-chloropropyl (4-fluoro-3-nitrophenyl)carbamate

In a glass RBF equipped with a Teflon-coated magnetic stirrer was dissolved 4-fluoro-3-nitro-phenylamine (1 eq.) in chloroform (0.25 M). To this was then added, at 0° C., sequentially pyridine (2 eq.) and 3-chloropropyl carbonochloridate (1.5 eq.). The resulting suspension was allowed to warm slowly to RT over 16 h. The crude reaction mixture was diluted with dichloromethane and washed sequentially with water, sat. aq. $NH_4Cl$ and brine. The organic extract was then dried over $Na_2SO_4$ and filtered. Concentration of the filtrate thus obtained in vacuo furnished the desired product.

Step 2: 3-(4-fluoro-3-nitrophenyl)-1,3-oxazinan-2-one

In a glass RBF equipped with a Teflon-coated magnetic stirrer was dissolved 3-chloropropyl (4-fluoro-3-nitrophenyl)carbamate (1 eq.) from the previous step in acetonitrile (0.1 M). To this was then added cesium carbonate (2 eq.) and the resulting suspension was allowed to stir at RT for 1 h. The volatiles were then removed in vacuo. The resulting reside was taken up in EtOAc and washed sequentially with water and brine, dried over $MgSO_4$ and filtered. Concentration of the filtrate thus obtained in vacuo furnished the desired product.

Step 3: (R)-3-(4-((4-hydroxybutan-2-yl)amino)-3-nitrophenyl)-1,3-oxazinan-2-one In a glass RBF equipped with a Teflon-coated magnetic stirrer was dissolved 3-(4-fluoro-3-nitrophenyl)-1,3-oxazinan-2-one (1 eq.) from the previous step in DMF (0.3 M). To this was then added (R)-3-amino-butan-1-ol (1.1 eq.) and potassium carbonate (3 eq.). The resulting solution was heated at 70° C. for 2 h. The crude reaction mixture was then diluted with EtOAc and washed sequentially with water and brine. The organic extract was then dried over $MgSO_4$ and filtered. Concentration of the filtrate thus obtained in vacuo furnished the desired product.

Step 4: (R)-3-((2-nitro-4-(2-oxo-1,3-oxazinan-3-yl)phenyl)amino)butyl acetate In a glass RBF equipped with a Teflon-coated magnetic stirrer was dissolved (R)-3-(4-((4-hydroxybutan-2-yl)

amino)-3-nitrophenyl)-1,3-oxazinan-2-one (1 eq.) from the previous step in pyridine (0.15 M). To this was then added acetic anhydride (1.5 eq.) drop-wise and neat over 10 min. After 4 h, the volatiles were then removed in vacuo and the resulting residue was partitioned between EtOAc and sat. aq. NH$_4$Cl. The aqueous layer was separated and back-extracted with EtOAc. The combined organic extracts were then dried over MgSO$_4$ and filtered. Concentration of the filtrate in vacuo furnished the desired product.

Step 5: (R)-3-((2-amino-4-(2-oxo-1,3-oxazinan-3-yl)phenyl)amino)butyl acetate

In a Parr shaker flask was suspended (R)-3-((2-nitro-4-(2-oxo-1,3-oxazinan-3-yl)phenyl)amino)butyl acetate (1 eq.) from the previous step and palladium black (0.1 eq., dry, 10% w/w over carbon) in methanol (0.1 M). The vessel was then repeatedly evacuated and back-filled with nitrogen (3×) and then hydrogen (3×). The resulting suspension was shaken under 50 psi of hydrogen for 30 min. The reaction was then quenched with CH$_2$Cl$_2$ and filtered through a bed of CH$_2$Cl$_2$-wetted celite. The insoluble bed was washed further with MeOH and CH$_2$Cl$_2$. Concentration of the filtrate thus obtained in vacuo furnished the desired product as a brown solid.

Step 6: (R)-3-(2-amino-5-(2-oxo-1,3-oxazinan-3-yl)-1H-benzo[d]imidazol-1-yl)butyl acetate In a glass RBF equipped with a Teflon-coated magnetic stirrer was added cyanogen bromide (2 eq., 5 M solution in acetonitrile) slowly to ethanol (0.1 M) over a period of 10 min. To this was then added drop-wise an ethanol (0.1 M) solution of (R)-3-((2-amino-4-(2-oxo-1,3-oxazinan-3-yl)phenyl)amino)butyl acetate (1 eq.) from the previous step over a period of 10 min. The resulting mixture was allowed to stir at RT for 48 h. The crude reaction mixture was diluted with EtOAc and washed sequentially with 10% aq. NaHCO$_3$, water and brine. The organic extract was then dried over Na$_2$SO$_4$, filtered and the filtrate concentrated in vacuo. Purification of the crude product thus obtained by way of reverse phase column chromatography (C18, gradient elution, 10:1 (v/v) H$_2$O:MeCN+0.1% TFA→MeCN+ 0.1% TFA) furnished, after neutralizing with 10% aq. NaHCO$_3$ and extraction with dichloromethane, the desired product (49% yield over six steps).

Step 7: (R,E)-3-(5-(2-oxo-1,3-oxazinan-3-yl)-2-((3-(trifluoromethyl)benzoyl)imino)-2,3-dihydro-1H-benzo[d]imidazol-1-yl)butyl acetate In a glass RBF equipped with a Teflon-coated magnetic stirrer was dissolved (R)-3-(2-amino-5-(2-oxo-1,3-oxazinan-3-yl)-1H-benzo[d]imidazol-1-yl)butyl acetate (1 eq.) from the previous step, 3-trifluoromethyl-benzoic acid (1 eq.) and HATU (1.2 eq.) in DMF (0.15 M). To this was then added ethyl-diisopropyl-amine (3 eq.) and the resulting yellow solution was allowed to stir at RT for 2 h. The crude reaction mixture was diluted with EtOAc and washed sequentially with water, 10% aq. HCl, water and brine. The organic extract was then dried over Na$_2$SO$_4$, filtered and the filtrate concentrated in vacuo. Further purification by way of column chromatography (SiO$_2$, gradient elution, 9:1 (v/v) Hex:EtOAc→EtOAc) furnished the desired product as an off-white solid (43% yield).

Intermediate 4-CF$_2$H

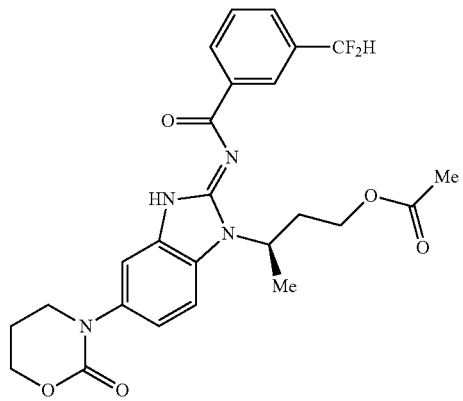 [SMILES: CC(=O)OCC[C@@H](C)n1/c(=N/C(=O)c2cccc(C(F)F)c2)[nH]c2cc(N3CCCOC3=O)ccc21]

Prepared in an analogous fashion to Intermediate 4-CF$_3$, but using 3-(difluoromethyl)-benzoic acid (1 eq.) in place of 3-trifluoromethyl-benzoic acid in step 7.

Intermediate 4-CN

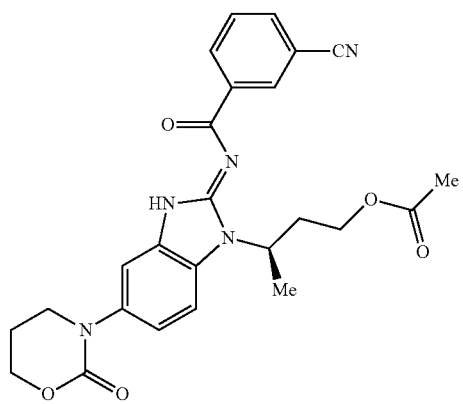 [SMILES: CC(=O)OCC[C@@H](C)n1/c(=N/C(=O)c2cccc(C#N)c2)[nH]c2cc(N3CCCOC3=O)ccc21]

Prepared in an analogous fashion to Intermediate 4-CF$_3$, but using 3-cyano-benzoic acid (1 eq.) in place of 3-trifluoromethyl-benzoic acid in step 7.

Intermediate 5

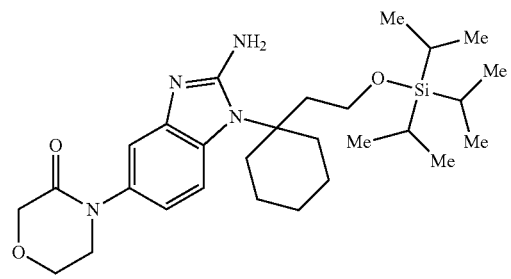 [SMILES: CC(C)[Si](OCCC1(n2c(N)nc3cc(N4CCOCC4=O)ccc32)CCCCC1)(C(C)C)C(C)C]

Prepared in an analogous fashion to Intermediate 1-OTIPS, but using 2-(1-amino-cyclohexyl)-ethanol (1 eq.) in place of 3-amino-propan-1-ol in step 3.

Intermediate 6

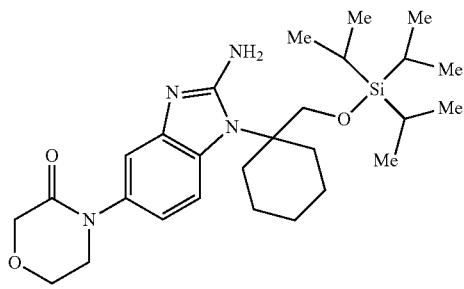 [SMILES: CC(C)[Si](OCC1(n2c(N)nc3cc(N4CCOCC4=O)ccc32)CCCCC1)(C(C)C)C(C)C]

Prepared in an analogous fashion to Intermediate 1-OTIPS, but using (1-amino-cyclohexyl)-methanol (1 eq.) in place of 3-amino-propan-1-ol in step 3.

Intermediate 7

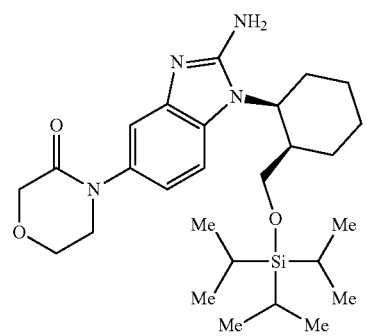 [SMILES: CC(C)[Si](OC[C@@H]1CCCC[C@@H]1n1c(N)nc2cc(N3CCOCC3=O)ccc21)(C(C)C)C(C)C]

Prepared in an analogous fashion to Intermediate 1-OTIPS, but using cis-(2-amino-cyclohexyl)-methanol (1 eq.) in place of 3-amino-propan-1-ol in step 3.

Intermediate 8

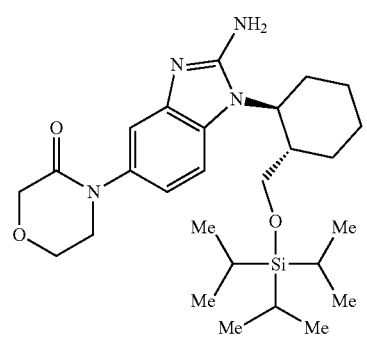 [SMILES: CC(C)[Si](OC[C@H]1CCCC[C@@H]1n1c(N)nc2cc(N3CCOCC3=O)ccc21)(C(C)C)C(C)C]

Prepared in an analogous fashion to Intermediate 1-OTIPS, but using trans-(2-amino-cyclohexyl)-methanol (1 eq.) in place of 3-amino-propan-1-ol in step 3.

Intermediate 9

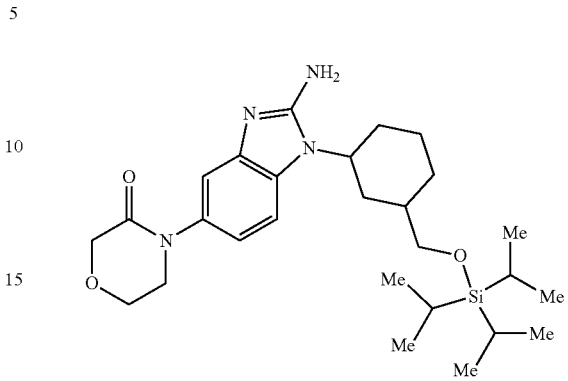

Prepared in an analogous fashion to Intermediate 1-OTIPS, but using (3-amino-cyclohexyl)-methanol (1 eq.) in place of 3-amino-propan-1-ol in step 3.

Intermediate 10

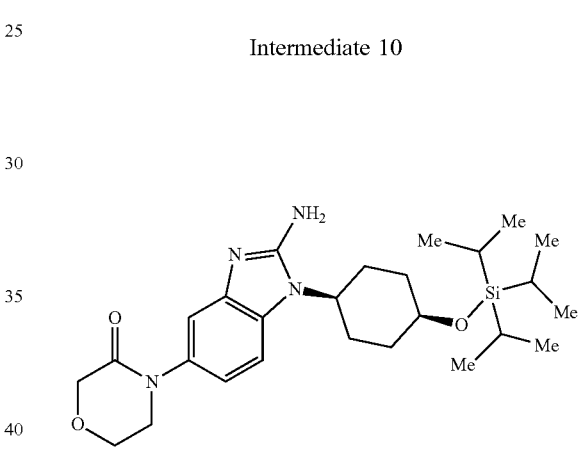

Prepared in an analogous fashion to Intermediate 1-OTIPS, but using cis-4-amino-cyclohexanol (1 eq.) in place of 3-amino-propan-1-ol in step 3.

Intermediate 11

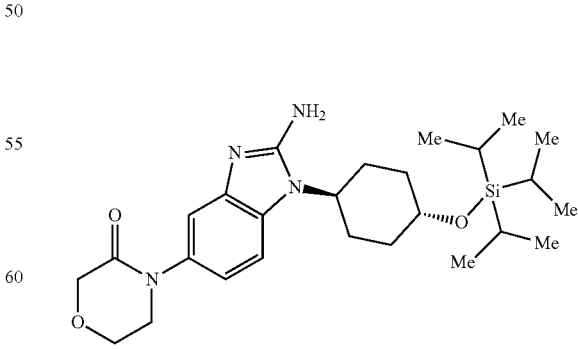

Prepared in an analogous fashion to Intermediate 1-OTIPS, but using trans-4-amino-cyclohexanol (1 eq.) in place of 3-amino-propan-1-ol in step 3.

Intermediate 12

Intermediate 15

Prepared in an analogous fashion to Intermediate 1-OTIPS, but using cis-(4-amino-cyclohexyl)-methanol (1 eq.) in place of 3-amino-propan-1-ol in step 3.

Intermediate 13

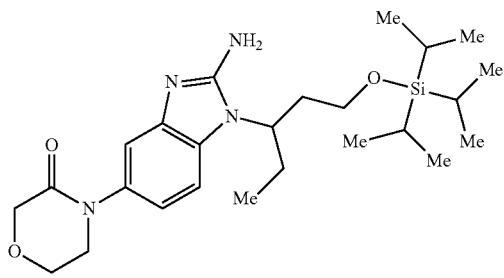

Prepared in an analogous fashion to Intermediate 1-OTIPS, but using rac-3-amino-pentan-1-ol (1 eq.) in place of 3-amino-propan-1-ol in step 3.

Intermediate 16

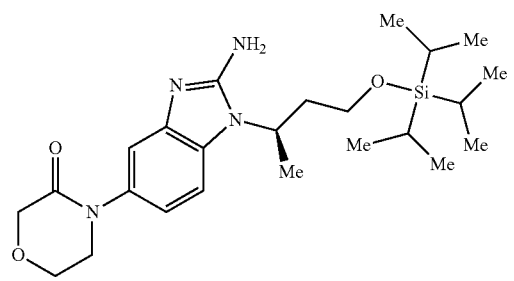 [SMILES: CC(C)[Si](OCC[C@@H](C)n1c(N)nc2cc(N3CCOCC3=O)ccc21)(C(C)C)C(C)C]

Prepared in an analogous fashion to Intermediate 1-OTIPS, but using (R)-3-amino-butan-1-ol (1 eq.) in place of 3-amino-propan-1-ol in step 3.

Intermediate 14

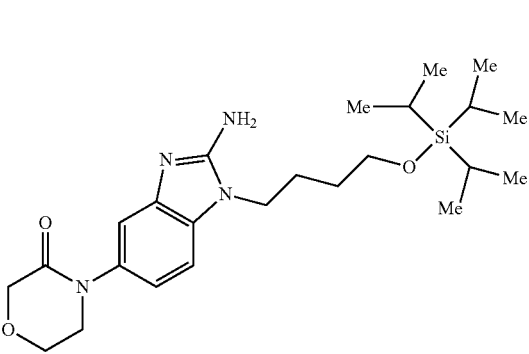

Prepared in an analogous fashion to Intermediate 1-OTIPS, but using 4-amino-butan-1-ol (1 eq.) in place of 3-amino-propan-1-ol in step 3.

Intermediate 17

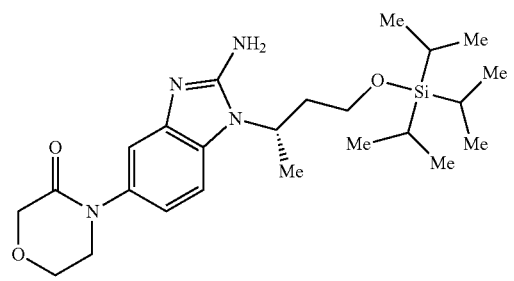 [SMILES: CC(C)[Si](OCC[C@H](C)n1c(N)nc2cc(N3CCOCC3=O)ccc21)(C(C)C)C(C)C]

Prepared in an analogous fashion to Intermediate 1-OTIPS, but using (S)-3-amino-butan-1-ol (1 eq.) in place of 3-amino-propan-1-ol in step 3.

Prepared in an analogous fashion to Intermediate 1-OTIPS, but using cyclohexylamine (1 eq.) in place of 3-amino-propan-1-ol in step 3, and step 5 was omitted.

Intermediate 18

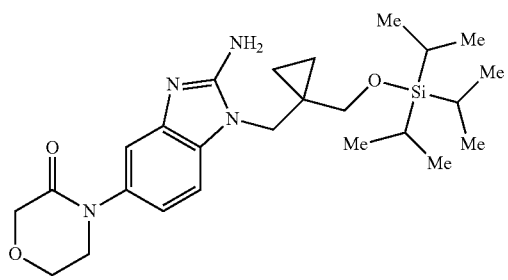 [SMILES: CC(C)[Si](OCC1(Cn2c(N)nc3cc(N4CCOCC4=O)ccc32)CC1)(C(C)C)C(C)C]

Prepared in an analogous fashion to Intermediate 1-OTIPS, but using (1-(aminomethyl)cyclopropyl)methanol (1 eq.) in place of 3-amino-propan-1-ol in step 3.

Intermediate 19

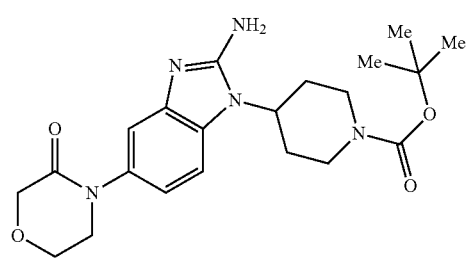 [SMILES: CC(C)(C)OC(=O)N1CCC(n2c(N)nc3cc(N4CCOCC4=O)ccc32)CC1]

Prepared in an analogous fashion to Intermediate 1-OTIPS, but using 4-amino-piperidin-1-carboxylic acid tert-butyl ester (1 eq.) in place of 3-amino-propan-1-ol in step 3, and step 5 was omitted.

Intermediate 20

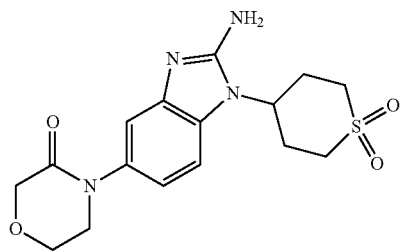 [SMILES: Nc1nc2cc(N3CCOCC3=O)ccc2n1C1CCS(=O)(=O)CC1]

Prepared in an analogous fashion to Intermediate 1-OTIPS, but using 4-aminotetrahydro-2H-thiopyran 1,1-dioxide (1 eq.) in place of 3-amino-propan-1-ol in step 3, and step 5 was omitted.

Intermediate 21

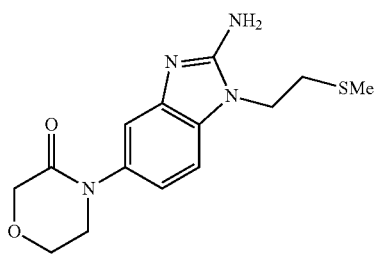 [SMILES: CSCCn1c(N)nc2cc(N3CCOCC3=O)ccc21]

Prepared in an analogous fashion to Intermediate 1-OTIPS, but using 2-methylsulfanyl-ethylamine (1.2 eq.) in place of 3-amino-propan-1-ol in step 3, and step 5 was omitted.

Intermediate 22

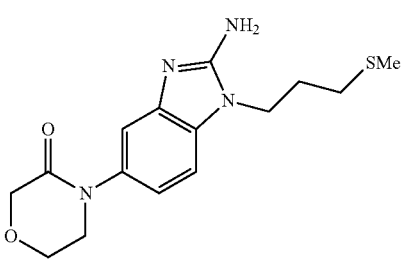 [SMILES: CSCCCn1c(N)nc2cc(N3CCOCC3=O)ccc21]

Prepared in an analogous fashion to Intermediate 1-OTIPS, but using 3-methylsulfanyl-propylamine (1.2 eq.) in place of 3-amino-propan-1-ol in step 3, and step 5 was omitted.

Intermediate 23

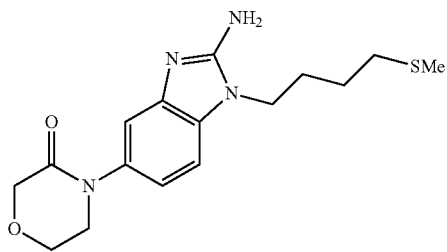 [SMILES: CSCCCCn1c(N)nc2cc(N3CCOCC3=O)ccc21]

Prepared in an analogous fashion to Intermediate 1-OTIPS, but using 4-methylsulfanyl-butylamine (1.2 eq.) in place of 3-amino-propan-1-ol in step 3, and step 5 was omitted.

Intermediate 24

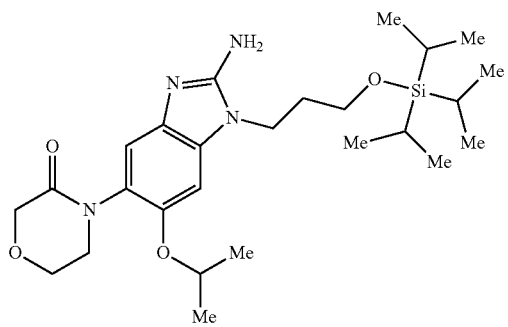 [SMILES: CC(C)Oc1cc2c(cc1N1CCOCC1=O)nc(N)n2CCCO[Si](C(C)C)(C(C)C)C(C)C]

Step 1: 2-(2-chloro-ethoxy)-N-(4-fluoro-2-methoxy-5-nitro-phenyl)acetamide

In a glass RBF equipped with a Teflon-coated magnetic stirrer was dissolved 4-fluoro-2-methoxy-5-nitro-phenylamine (1 eq.) in DMF (0.32 M). To this was then added sequentially HATU (1.2 eq.), DMAP (0.1 eq.), (2-chloro-ethoxy)-acetic acid (1.1 eq.) and finally ethyl-diisopropylamine (3 eq.). When the reaction was deemed to be complete by LCMS (14 h), the reaction mixture was diluted with EtOAc and washed sequentially with 10% aq. HCl, sat. aq. NaHCO$_3$, water and brine. The organic extract was then dried over MgSO$_4$ and filtered. Concentration of the filtrate thus obtained in vacuo furnished the desired product as a tan solid (99% yield).

Step 2: 4-(4-fluoro-2-methoxy-5-nitro-phenyl)-morpholin-3-one

In a glass RBF equipped with a Teflon-coated magnetic stirrer was dissolved 2-(2-chloro-ethoxy)-N-(4-fluoro-2-methoxy-5-nitro-phenyl)acetamide (1 eq.) from the previous step in acetonitrile (0.17 M). To this solution was then added cesium carbonate (2 eq.) in one rapid portion and the resulting suspension was allowed to stir at RT for 48 h. The reaction was quenched with the addition of water and EtOAc. The organic layer was separated, washed further with water and brine, and dried over Na$_2$SO$_4$. Filtration and concentration of the filtrate thus obtained in vacuo furnished the desired product as a brown solid (88% yield).

Step 3: 4-(4-fluoro-2-hydroxy-5-nitro-phenyl)-morpholin-3-one

In a glass RBF equipped with a Teflon-coated magnetic stirrer was dissolved 4-(4-fluoro-2-methoxy-5-nitro-phenyl)-morpholin-3-one (1 eq.) from the previous step in dichloromethane (0.12 M). To this was then added boron tribromide (1.2 eq., 1 M solution in dichloromethane) at 0° C. and the resulting mixture was allowed to slowly warm to RT over 16 h. The reaction was quenched with the careful addition of water and the resulting suspension was filtered to afford the desired product as a grey solid. The filtrate was basified with the addition of sat. aq. NaHCO$_3$ and the organic layer was discarded. The basified aqueous layer was subsequently acidified to a pH of ~1 with the careful addition of 10% aq. HCl and then extracted with EtOAc. The combined EtOAc extracts were washed further with water and brine, dried over Na$_2$SO$_4$, and filtered. Concentration of the filtrate in vacuo afforded another batch of the desired product, also as a grey solid (83% total yield).

Step 4: 4-(4-fluoro-2-isopropoxy-5-nitro-phenyl)-morpholin-3-one

In a glass RBF equipped with a Teflon-coated magnetic stirrer was dissolved 4-(4-fluoro-2-hydroxy-5-nitro-phenyl)-morpholin-3-one (1 eq.) from the previous step in DMF (0.8 M). To this was then added potassium carbonate (1 eq.) and 2-bromo-propane (1.15 eq.) and the resulting mixture was heated at 60° C. for 16 h. The reaction was quenched with water and extracted with dichloromethane. The combined organic extracts were washed further with water and brine, dried over MgSO$_4$, filtered and the filtrate concentrated in vacuo. Further purification by way of column chromatography (SiO$_2$, gradient elution, 1:1 (v/v) Hex:EtOAc→3:7 (v/v) Hex:EtOAc) furnish the desired product as an orange oil that solidified upon standing (58% yield).

Step 5: 4-(4-(3-hydroxy-propylamino)-2-isopropoxy-5-nitro-phenyl)-morpholin-3-one In a glass RBF equipped with a Teflon-coated magnetic stirrer was dissolved 4-(4-fluoro-2-isopropoxy-5-nitro-phenyl)-morpholin-3-one (1 eq.) from the previous step in DMSO (0.2 M). To this solution was then added 3-amino-propan-1-ol (1 eq.) and potassium carbonate (1.2 eq.). The resulting mixture was heated at 70° C. for 16 h. The reaction was quenched with water and extracted with EtOAc. The combined organic extracts were washed further with water and brine, dried over MgSO$_4$ and filtered. Concentration of the filtrate thus obtained in vacuo furnished the desired product as an orange solid (90% yield).

Step 6: 4-(5-amino-4-(3-hydroxy-propylamino)-2-isopropoxy-phenyl)-morpholin-3-one In a Parr shaker flask was suspended 4-(4-(3-hydroxypropylamino)-2-isopropoxy-5-nitrophenyl)-morpholin-3-one (1 eq.) from the previous step and palladium black (0.3 eq., dry, 10% w/w over carbon) in ethanol (0.025 M). The vessel was then repeatedly evacuated and back-filled with nitrogen (3×) and then hydrogen (3×). The resulting suspension was shaken under 50 psi of hydrogen for 18 h. The reaction was then quenched with CH$_2$Cl$_2$ and filtered through a bed of CH$_2$Cl$_2$-wetted celite. The insoluble bed was washed further with MeOH and CH$_2$Cl$_2$. Concentration of the filtrate thus obtained in vacuo furnished the desired product as a purple solid (88% yield).

Step 7: 4-(5-amino-2-isopropoxy-4-(3-triisopropylsilanyloxy-propylamino)-phenyl)-morpholin-3-one In a glass RBF equipped with a Teflon-coated magnetic stirrer was dissolved 4-(5-amino-4-(3-hydroxy-propylamino)-2-isopropoxy-phenyl)-morpholin-3-one (1 eq.) from the previous step in DMF (0.26 M). To this was then added chloro-triisopropyl-silane (2.1 eq.), imidazole (4.5 eq.) and a few crystals of DMAP. The resulting solution was stirred at RT for 18 h. The crude reaction mixture was diluted with EtOAc and washed sequentially with water and brine. The organic extract was then dried over MgSO$_4$, filtered and the filtrate concentrated in vacuo. Further purification by way of column chromatography (SiO$_2$, gradient elution, Hex 4 EtOAc) furnished the desired product as an off-white solid (18% yield).

Step 8: 4-(2-amino-6-isopropoxy-1-(3-triisopropyl-silanyloxy-propyl)-1H-benzoimidazol-5-yl)-morpholin-3-one In a glass RBF equipped with a Teflon-coated magnetic stirrer was dissolved 4-(5-amino-2-isopropoxy-4-(3-triisopropylsilanyloxy-propylamino)-phenyl)-morpholin-3-one (1 eq.) from the previous step in ethanol (0.14 M). To this was then added cyanogen bromide (2 eq., 5 M solution in THF) drop-wise over a period of 10 min. The resulting mixture was allowed to stir at RT for 18 h. The crude reaction mixture was diluted with EtOAc and washed sequentially with water and brine. The organic extract was then dried over Na$_2$SO$_4$ and filtered. Concentration of the filtrate thus obtained in vacuo furnished the desired product as a tan solid (32% yield)

Intermediate 25

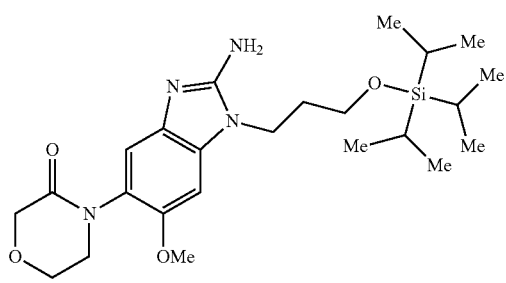 [SMILES: COc1cc2c(cc1N1CCOCC1=O)nc(N)n2CCCO[Si](C(C)C)(C(C)C)C(C)C]

Prepared in an analogous fashion to Intermediate 24, but omitting both step 3 and step 4.

Intermediate 26

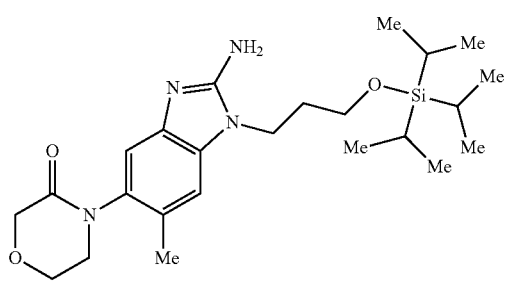

Prepared in an analogous fashion to Intermediate 24, but using 4-fluoro-2-methyl-5-nitro-phenylamine (1 eq.) in place of 4-fluoro-2-methoxy-5-nitro-phenylamine in step 1, and omitting both step 3 and step 4.

Intermediate 27

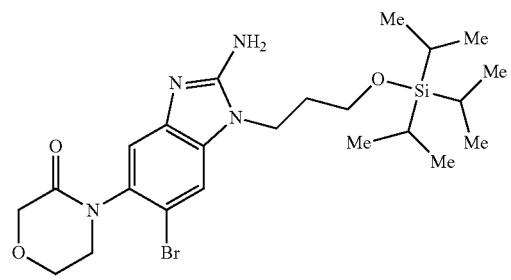 [SMILES: CC(C)[Si](OCCCn1c(N)nc2cc(N3CCOCC3=O)c(Br)cc21)(C(C)C)C(C)C]

Step 1: N-(2-bromo-4-fluoro-5-nitro-phenyl)-2-(2-chloro-ethoxy)-acetamide

In a glass RBF equipped with a Teflon-coated magnetic stirrer was dissolved (2-chloro-ethoxy)-acetic acid (1 eq.) in dichlormethane (0.67 M). To this was then added sequentially pyridine (2.5 eq.) and thionyl chloride (1.5 eq.), the latter of which was added drop-wise over 10 min. The resulting orange solution was stirred at RT under nitrogen for 30 min before 2-bromo-4-fluoro-5-nitro-phenylamine (1 eq.) was added drop-wise as a solution in dichloromethane (0.67 M). Finally, triethylamine (3.5 eq.) and DMAP (0.1 eq.) were added and the resulting mixture was allowed to stir at RT for 18 h. The reaction was quenched with the addition of water and extracted with EtOAc. The combined organic extracts were then washed further with water and brine, dried over MgSO$_4$, filtered and the filtrate concentrated in vacuo. Further purification by way of column chromatography (SiO$_2$, gradient elution, 9:1 (v/v) Hex:EtOAc→EtOAc) furnish the desired product as an orange oil that solidified upon standing (51% yield).

Step 2: 4-(2-bromo-4-fluoro-5-nitro-phenyl)-morpholin-3-one

In a glass RBF equipped with a Teflon-coated magnetic stirrer was dissolved N-(2-bromo-4-fluoro-5-nitro-phenyl)-2-(2-chloro-ethoxy)-acetamide (1 eq.) from the previous step in acetonitrile (0.16 M). To this solution was then added cesium carbonate (2 eq.) in one rapid portion and the resulting suspension was allowed to stir at RT for 48 h. The reaction was quenched with the addition of water and EtOAc. The organic layer was separated, washed further with water and brine, and dried over Na$_2$SO$_4$. Filtration and concentration of the filtrate thus obtained in vacuo furnished the desired product as a brown solid (78% yield).

Step 3: 4-(2-bromo-4-(3-hydroxy-propylamino)-5-nitro-phenyl)-morpholin-3-one In a glass RBF equipped with a Teflon-coated magnetic stirrer was dissolved 4-(2-bromo-4-fluoro-5-nitro-phenyl)-morpholin-3-one (1 eq.) from the previous step in DMF (0.2 M). To this solution was then added 3-amino-propan-1-ol (2 eq.) and potassium carbonate (2 eq.). The resulting mixture was heated at 70° C. for 16 h. The reaction was quenched with water and extracted with EtOAc. The combined organic extracts were washed further with water and brine, dried over MgSO$_4$ and filtered. Concentration of the filtrate thus obtained in vacuo furnished the desired product as a yellow solid (58% yield).

Step 4: 4-(5-amino-2-bromo-4-(3-hydroxy-propylamino)-phenyl)-morpholin-3-one In a glass RBF equipped with a Teflon-coated magnetic stirrer was dissolved 4-(2-bromo-4-(3-hydroxy-propylamino)-5-nitro-phenyl)-morpholin-3-one (1 eq.) from the previous step in methanol (0.15 M) and acetic acid (6 eq.). To this solution was then added freshly activate zinc powder (6 eq.) in three separate portions over a period of 30 min at RT. Following the completion of addition, the resulting suspension was allowed to stir at RT for another 30 min. The reaction suspension was then diluted with CH$_2$Cl$_2$ and filtered through a bed of CH$_2$Cl$_2$-wetted celite. The insoluble bed was washed further with MeOH and CH$_2$Cl$_2$. Concentration of the filtrate thus obtained in vacuo furnished the desired product as a grey solid (88% yield).

Step 5: 4-(5-amino-2-bromo-4-(3-triisopropylsilanyloxy-propylamino)-phenyl)-morpholin-3-one In a glass RBF equipped with a Teflon-coated magnetic stirrer was dissolved 4-(5-amino-2-bromo-4-(3-hydroxy-propylamino)-phenyl)-morpholin-3-one (1 eq.) from the previous step in DMF (0.29 M). To this was then added chloro-triisopropyl-silane (1.2 eq.), imidazole (2 eq.) and a few crystals of DMAP. The resulting solution was stirred at RT for 18 h. The crude reaction mixture was diluted with EtOAc and washed sequentially with water and brine. The organic extract was then dried over MgSO$_4$, filtered and the filtrate concentrated in vacuo. Further purification by way of column chromatography (SiO$_2$, gradient elution, Hex 4 EtOAc) furnished the desired product as a brown solid (37% yield).

Step 6: 4-(2-amino-6-bromo-1-(3-((triisopropylsilyl)oxy)propyl)-1H-benzo[d]imidazol-5-yl)morpholin-3-one In a glass RBF equipped with a Teflon-coated magnetic stirrer was dissolved 4-(5-amino-2-bromo-4-(3-triisopropyl-silanyloxy-propylamino)-phenyl)-morpholin-3-one (1 eq.) from the previous step in ethanol (0.15 M). To this was then added cyanogen bromide (2 eq., 5 M solution in THF) drop-wise over a period of 10 min. The resulting mixture was allowed to stir at RT for 18 h. The crude reaction mixture was diluted with EtOAc and washed sequentially with water and brine. The organic extract was then dried over Na$_2$SO$_4$ and filtered. Concentration of the filtrate thus obtained in vacuo furnished the desired product as a tan solid (98% yield)

Intermediate 28

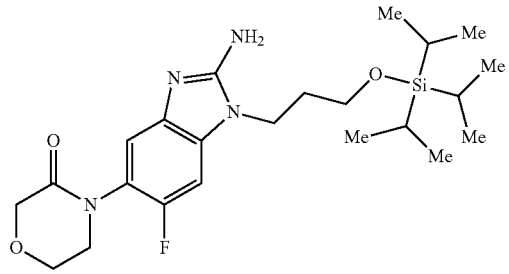 [SMILES: CC(C)[Si](OCCCn1c(N)nc2cc(N3CCOCC3=O)c(F)cc21)(C(C)C)C(C)C]

Prepared in an analogous fashion to Intermediate 24, but using Intermediate aniline 1 (1 eq.) in place of 4-fluoro-2-methoxy-5-nitro-phenylamine in step 1, and omitting both step 3 and step 4.

Intermediate 29

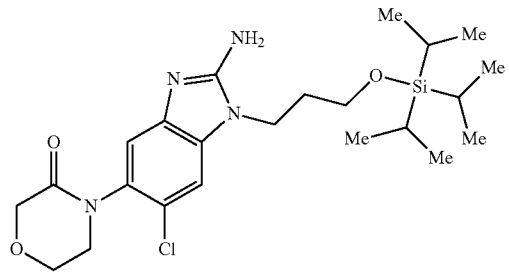 [SMILES: CC(C)[Si](OCCCn1c(N)nc2cc(N3CCOCC3=O)c(Cl)cc21)(C(C)C)C(C)C]

Prepared in an analogous fashion to Intermediate 27, but using Intermediate aniline 2 (1 eq.) in place of 2-bromo-4-fluoro-5-nitro-phenylamine in step 1.

Intermediate 30

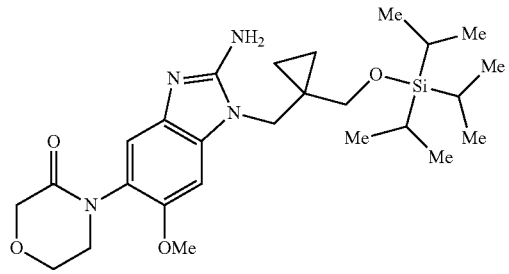 [SMILES: COc1cc2c(cc1N1CCOCC1=O)nc(N)n2CC1(CO[Si](C(C)C)(C(C)C)C(C)C)CC1]

Prepared in an analogous fashion to Intermediate 24, but omitting both step 3 and step 4, and using (1-(aminomethyl)cyclopropyl)methanol (2 eq.) in place of 3-amino-propan-1-ol in step 5.

Intermediate 31

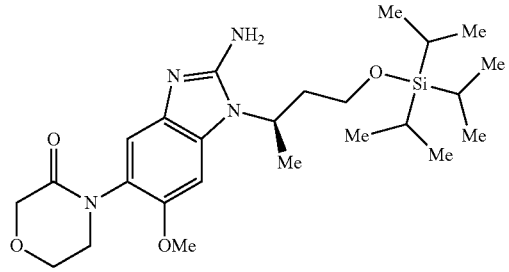 [SMILES: COc1cc2c(cc1N1CCOCC1=O)nc(N)n2[C@H](C)CCO[Si](C(C)C)(C(C)C)C(C)C]

Prepared in an analogous fashion to Intermediate 24, but omitting both step 3 and step 4, and using (R)-3-amino-butan-1-ol (2 eq.) in place of 3-amino-propan-1-ol in step 5.

Intermediate 32-CF₃

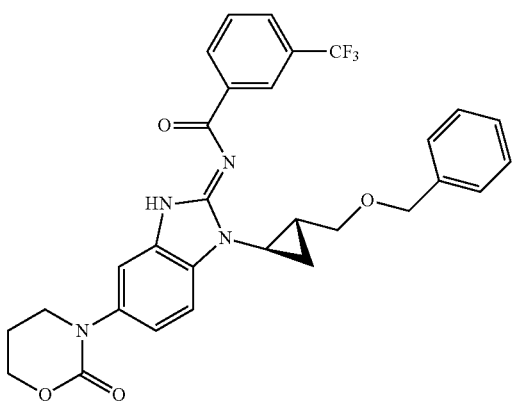 [SMILES: O=C(/N=c1\[nH]c2cc(N3CCCOC3=O)ccc2n1[C@@H]1C[C@H]1COCc1ccccc1)c1cccc(C(F)(F)F)c1]

Prepared in an analogous fashion to Intermediate 4-CF₃, but using Intermediate amine 1 (1.3 eq.) in place of (R)-3-amino-butan-1-ol in step 3, and omitting step 4.

Intermediate 33-CF₃

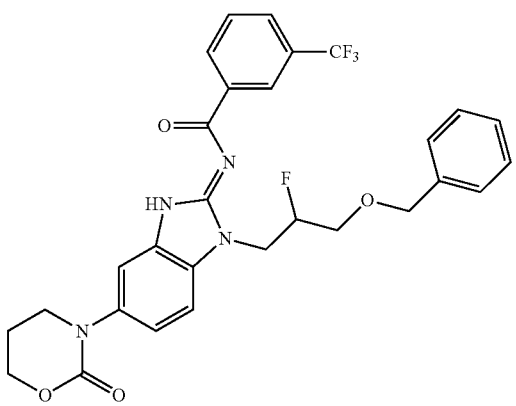 [SMILES: O=C(/N=c1\[nH]c2cc(N3CCCOC3=O)ccc2n1CC(F)COCc1ccccc1)c1cccc(C(F)(F)F)c1]

Prepared in an analogous fashion to Intermediate 4-CF₃, but using Intermediate amine 2 (1.3 eq.) in place of (R)-3-amino-butan-1-ol in step 3, and omitting step 4.

Intermediate 34

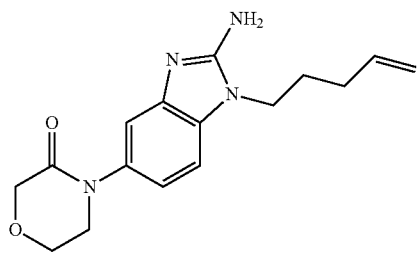 [SMILES: C=CCCCn1c(N)nc2cc(N3CCOCC3=O)ccc21]

Prepared in an analogous fashion to Intermediate 27, but using 4-fluoro-3-nitroaniline (1 eq.) in place of 2-bromo-4-fluoro-5-nitro-phenylamine in step 1, pent-4-enylamine (1.5 eq.) in place of 3-amino-propan-1-ol in step 3, and omitting step 5.

Intermediate 35

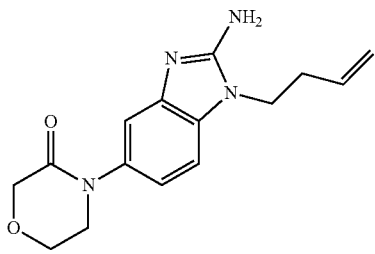 [SMILES: C=CCCn1c(N)nc2cc(N3CCOCC3=O)ccc21]

Prepared in an analogous fashion to Intermediate 27, but using 4-fluoro-3-nitroaniline (1 eq.) in place of 2-bromo-4-fluoro-5-nitro-phenylamine in step 1, but-3-enylamine (1.5 eq.) in place of 3-amino-propan-1-ol in step 3, and omitting step 5.

Intermediate 36

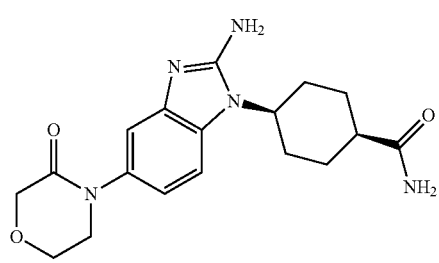 [SMILES: Nc1nc2cc(N3CCOCC3=O)ccc2n1[C@H]1CC[C@@H](C(N)=O)CC1]

Prepared in an analogous fashion to Intermediate 1-OTIPS, but using cis-4-amino-cyclohexanecarboxylic acid amide (1 eq.) in place of 3-amino-propan-1-ol in step 3, and step 5 was omitted.

Intermediate 37

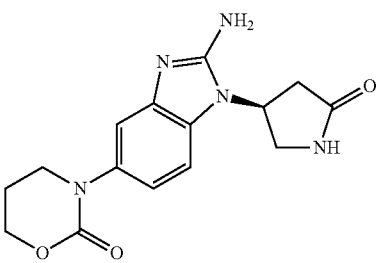 [SMILES: Nc1nc2cc(N3CCCOC3=O)ccc2n1[C@@H]1CNC(=O)C1]

Prepared in an analogous fashion to Intermediate 4-CF₃, but using (S)-4-amino-pyrrolidine-2-one hydrochloride (1.1 eq.) in place of (R)-3-amino-butan-1-ol in step 3, and omitting both step 4 and step 7.

151

Intermediate 38

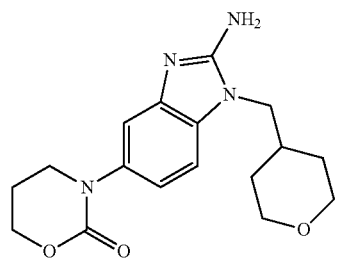 [SMILES: Nc1nc2cc(N3CCCOC3=O)ccc2n1CC1CCOCC1]

Prepared in an analogous fashion to Intermediate 4-CF₃, but using (tetrahydro-2H-pyran-4-yl)methanamine hydrochloride (1.1 eq.) in place of (R)-3-amino-butan-1-ol in step 3, and omitting both step 4 and step 7.

Intermediate 39

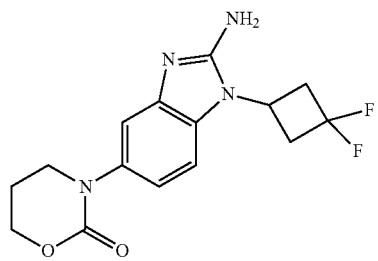 [SMILES: Nc1nc2cc(N3CCCOC3=O)ccc2n1C1CC(F)(F)C1]

Prepared in an analogous fashion to Intermediate 4-CF₃, but using 3,3-difluoro-cyclobutylamine hydrochloride (1.1 eq.) in place of (R)-3-amino-butan-1-ol in step 3, and omitting both step 4 and step 7.

Intermediate 40

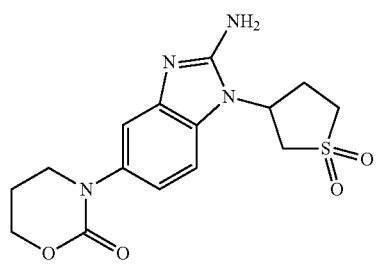 [SMILES: Nc1nc2cc(N3CCCOC3=O)ccc2n1C1CCS(=O)(=O)C1]

Prepared in an analogous fashion to Intermediate 4-CF₃, but using rac-3-aminotetrahydrothiophene 1,1-dioxide hydrochloride (1.1 eq.) in place of (R)-3-amino-butan-1-ol in step 3, and omitting both step 4 and step 7.

152

Intermediate 41

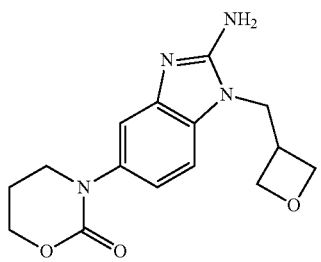 [SMILES: Nc1nc2cc(N3CCCOC3=O)ccc2n1CC1COC1]

Prepared in an analogous fashion to Intermediate 4-CF₃, but using oxetan-3-ylmethanamine (1.1 eq.) in place of (R)-3-amino-butan-1-ol in step 3, and omitting both step 4 and step 7.

Intermediate 42

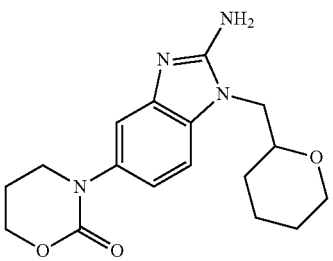 [SMILES: Nc1nc2cc(N3CCCOC3=O)ccc2n1CC1CCCCO1]

Prepared in an analogous fashion to Intermediate 4-CF₃, but using (tetrahydro-2H-pyran-2-yl)methanamine (1.1 eq.) in place of (R)-3-amino-butan-1-ol in step 3, and omitting both step 4 and step 7.

Intermediate 43

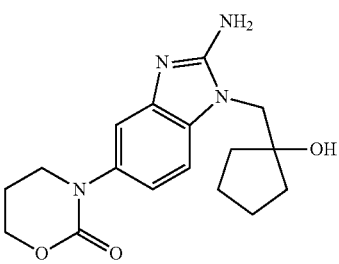 [SMILES: Nc1nc2cc(N3CCCOC3=O)ccc2n1CC1(O)CCCC1]

Prepared in an analogous fashion to Intermediate 4-CF₃, but using 1-(aminomethyl)cyclopentanol hydrochloride (1.1 eq.) in place of (R)-3-amino-butan-1-ol in step 3, and omitting both step 4 and step 7.

Intermediate 44

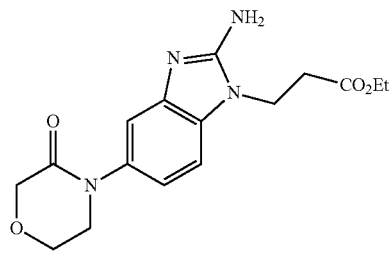 [SMILES: CCOC(=O)CCn1c(N)nc2cc(N3CCOCC3=O)ccc21]

Prepared in an analogous fashion to Intermediate 1-OTIPS, but using ethyl 3-aminopropanoate (1.2 eq.) in place of 3-amino-propan-1-ol in step 3, and step 5 was omitted.

Intermediate 45

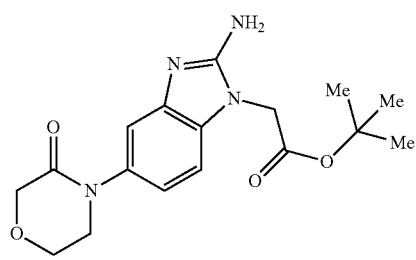 [SMILES: CC(C)(C)OC(=O)Cn1c(N)nc2cc(N3CCOCC3=O)ccc21]

Prepared in an analogous fashion to Intermediate 1-OTIPS, but using tert-butyl 2-aminoacetate (1.2 eq.) in place of 3-amino-propan-1-ol in step 3, and step 5 was omitted.

Intermediate 46

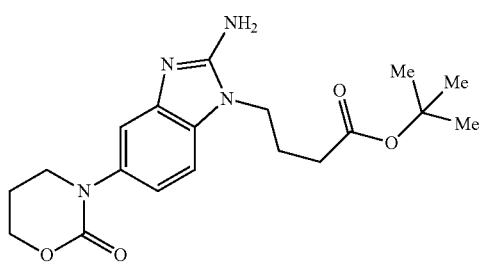 [SMILES: CC(C)(C)OC(=O)CCCn1c(N)nc2cc(N3CCCOC3=O)ccc21]

Prepared in an analogous fashion to Intermediate 4-CF$_3$, but using tert-butyl 4-aminobutanoate (1.1 eq.) in place of (R)-3-amino-butan-1-ol in step 3, and omitting both step 4 and step 7.

Intermediate 47

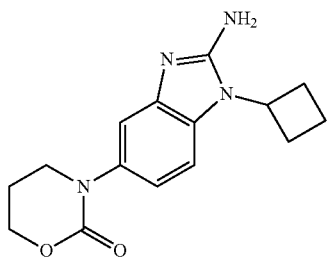 [SMILES: Nc1nc2cc(N3CCCOC3=O)ccc2n1C1CCC1]

Prepared in an analogous fashion to Intermediate 4-CF$_3$, but using cyclobutylamine (1.1 eq.) in place of (R)-3-amino-butan-1-ol in step 3, and omitting both step 4 and step 7.

Intermediate 48

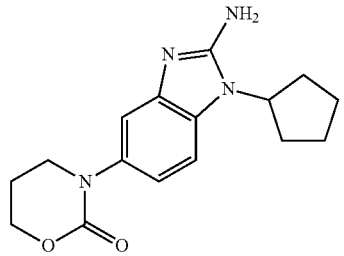 [SMILES: Nc1nc2cc(N3CCCOC3=O)ccc2n1C1CCCC1]

Prepared in an analogous fashion to Intermediate 4-CF$_3$, but using cyclopentylamine (1.1 eq.) in place of (R)-3-amino-butan-1-ol in step 3, and omitting both step 4 and step 7.

Intermediate 49

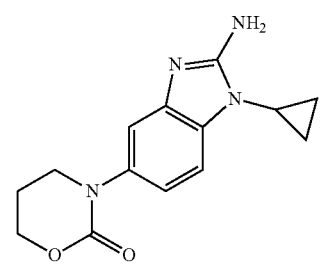 [SMILES: Nc1nc2cc(N3CCCOC3=O)ccc2n1C1CC1]

Prepared in an analogous fashion to Intermediate 4-CF$_3$, but using cyclopropylamine (1.1 eq.) in place of (R)-3-amino-butan-1-ol in step 3, and omitting both step 4 and step 7.

Intermediate 50

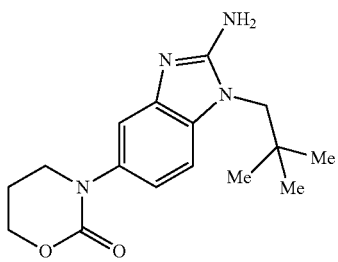 [SMILES: CC(C)(C)Cn1c(N)nc2cc(N3CCCOC3=O)ccc21]

Prepared in an analogous fashion to Intermediate 4-CF$_3$, but using 2,2-dimethylpropan-1-amine (1.1 eq.) in place of (R)-3-amino-butan-1-ol in step 3, and omitting both step 4 and step 7.

Intermediate 51

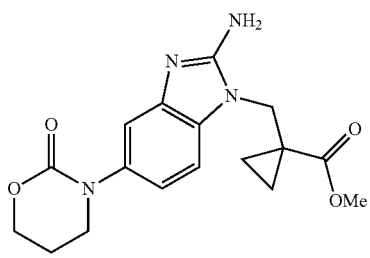 [SMILES: COC(=O)C1(Cn2c(N)nc3cc(N4CCCOC4=O)ccc32)CC1]

Prepared in an analogous fashion to Intermediate 4-CF$_3$, but using methyl 1-(aminomethyl)cyclopropanecarboxylate (1.1 eq.) in place of (R)-3-amino-butan-1-ol in step 3, and omitting both step 4 and step 7.

Intermediate 52

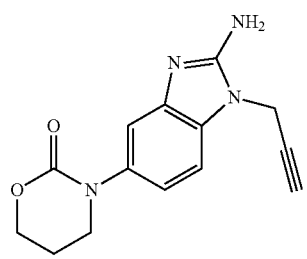 [SMILES: C#CCn1c(N)nc2cc(N3CCCOC3=O)ccc21]

Prepared in an analogous fashion to Intermediate 4-CF$_3$, but using prop-2-yn-1-amine (1.1 eq.) in place of (R)-3-amino-butan-1-ol in step 3, and omitting both step 4 and step 7.

Intermediate 53

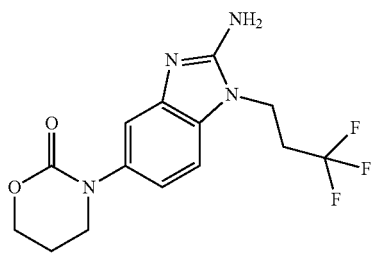 [SMILES: Nc1nc2cc(N3CCCOC3=O)ccc2n1CCC(F)(F)F]

Prepared in an analogous fashion to Intermediate 4-CF$_3$, but using 3,3,3-trifluoropropan-1-amine (1.1 eq.) in place of (R)-3-amino-butan-1-ol in step 3, and omitting both step 4 and step 7.

Intermediate 54

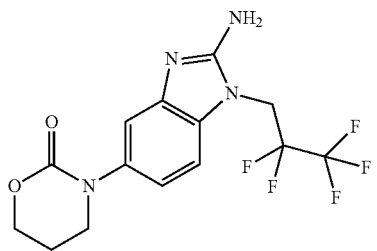 [SMILES: Nc1nc2cc(N3CCCOC3=O)ccc2n1CC(F)(F)C(F)(F)F]

Prepared in an analogous fashion to Intermediate 4-CF$_3$, but using 2,2,3,3,3-pentafluoropropan-1-amine (1.1 eq.) in place of (R)-3-amino-butan-1-ol in step 3, and omitting both step 4 and step 7.

Intermediate 55

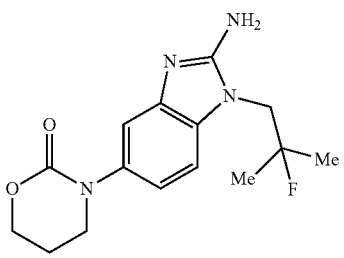 [SMILES: CC(C)(F)Cn1c(N)nc2cc(N3CCCOC3=O)ccc21]

Prepared in an analogous fashion to Intermediate 4-CF$_3$, but using 2-fluoro-2-methylpropan-1-amine (1.1 eq.) in place of (R)-3-amino-butan-1-ol in step 3, and omitting both step 4 and step 7.

Intermediate 56

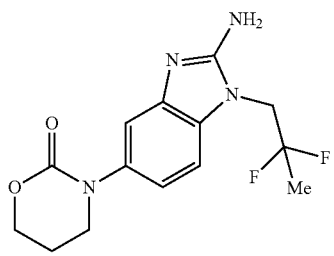 [SMILES: CC(F)(F)Cn1c(N)nc2cc(N3CCCOC3=O)ccc21]

Prepared in an analogous fashion to Intermediate 4-CF$_3$, but using 2,2-difluoropropan-1-amine (1.1 eq.) in place of (R)-3-amino-butan-1-ol in step 3, and omitting both step 4 and step 7.

Intermediate 57

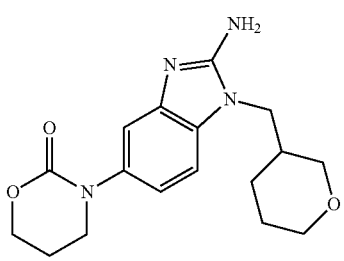 [SMILES: Nc1nc2cc(N3CCCOC3=O)ccc2n1CC1CCCOC1]

Prepared in an analogous fashion to Intermediate 4-CF$_3$, but using (tetrahydro-2H-pyran-3-yl)methanamine (1.1 eq.) in place of (R)-3-amino-butan-1-ol in step 3, and omitting both step 4 and step 7.

Intermediate 58

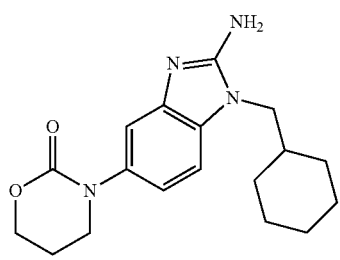 [SMILES: Nc1nc2cc(N3CCCOC3=O)ccc2n1CC1CCCCC1]

Prepared in an analogous fashion to Intermediate 4-CF$_3$, but using cyclohexylmethanamine (1.1 eq.) in place of (R)-3-amino-butan-1-ol in step 3, and omitting both step 4 and step 7.

Intermediate 59-CF$_3$

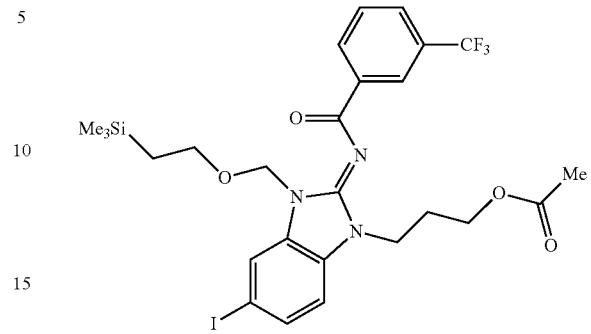

Step 1: 3-(4-iodo-2-nitro-phenylamino)-propan-1-ol

In a glass RBF equipped with a Teflon-coated magnetic stirrer was dissolved 1-fluoro-4-iodo-2-nitro-benzene (1 eq.) in DMF (0.3 M). To this was then added 3-amino-propan-1-ol (1.2 eq.) and potassium carbonate (3 eq.). The resulting solution was heated at 65° C. for 18 h. The crude reaction mixture was then diluted with EtOAc and washed sequentially with water and brine. The organic extract was then dried over MgSO$_4$, filtered and the filtrate concentrated in vacuo. Purification of the crude product thus obtained by way of column chromatography (SiO$_2$, gradient elution, 8:1 (v/v) Hex:EtOAc→EtOAc) furnished the desired product (79% yield).

Step 2: 3-((4-iodo-2-nitrophenyl)amino)propyl acetate

In a glass RBF equipped with a Teflon-coated magnetic stirrer was dissolved 3-(4-iodo-2-nitro-phenylamino)-propan-1-ol (1 eq.) from the previous step in pyridine (0.1 M). To this was then added acetic anhydride (1.8 eq.) drop-wise and neat over 10 min. After 18 h of stirring at RT, the volatiles were removed in vacuo and the resulting residue was partitioned between EtOAc and sat. aq. NH$_4$Cl. The aqueous layer was separated and back-extracted with EtOAc. The combined organic extracts were then dried over MgSO$_4$, filtered and the filtrate concentrated in vacuo. Purification of the crude product thus obtained by way of column chromatography (SiO$_2$, gradient elution, 8:1 (v/v) Hex:EtOAc→EtOAc) furnished the desired product (91% yield).

Step 3: 3-((2-amino-4-iodophenyl)amino)propyl acetate

In a glass RBF equipped with a Teflon-coated magnetic stirrer was suspended iron trichloride (0.25 eq.), activated charcoal (100 mg per mmol of substrate), and 3-((4-iodo-2-nitrophenyl)amino)propyl acetate (1 eq.) from the previous step in methanol (0.15 M). To this was then added N,N-dimethyl hydrazine (5 eq.) drop-wise and neat over a period of 10 min. The resulting suspension was then heated at 65° C. for 4 h. The insolubles were removed via filtration through a bed of MeOH-wetted celite and the filtrate thus obtained was then concentrated in vacuo. The resulting residue was taken up in EtOAc, washed sequentially with water and brine, dried over MgSO$_4$, filtered and the filtrate concentrated in vacuo. Purification of the crude product thus obtained by way of column chromatography (SiO₂, gradient elution, 1:1 (v/v) Hex:EtOAc→EtOAc) furnished the desired product (89% yield).

Step 4: 3-(2-amino-5-iodo-M-benzo[d]imidazol-1-yl)propyl acetate

In a glass RBF equipped with a Teflon-coated magnetic stirrer was added cyanogen bromide (2 eq., 5 M solution in acetonitrile) slowly to ethanol (0.5 M) over a period of 10 min. To this solution was then added an ethanol (0.25 M) solution of 3-((2-amino-4-iodophenyl)amino)propyl acetate (1 eq.) from the previous step dropwise over a period of 10 min. The resulting mixture was allowed to stir at RT for 3 h. The volatiles were then removed in vacuo and the resulting residue was taken up in EtOAc and washed sequentially with 10% aq. NaHCO₃, water and brine. The organic extract thus obtained was then dried over Na₂SO₄, filtered and the filtrate concentrated in vacuo. Purification of the crude product thus obtained by way of column chromatography (SiO₂, gradient elution, 1:1 (v/v) Hex:EtOAc→EtOAc→10:1 (v/v) EtOAc:MeOH) furnished the desired product (81% yield).

Step 5: (E)-3-(5-iodo-2-((3-(trifluoromethyl)benzoyl)imino)-2,3-dihydro-M-benzo[d]imidazol-1-yl)propyl acetate In a glass RBF equipped with a Teflon-coated magnetic stirrer was dissolved 3-(2-amino-5-iodo-1H-benzo[d]imidazol-1-yl)propyl acetate (1 eq.) from the previous step, 3-trifluoromethyl-benzoic acid (1 eq.) and HATU (1.2 eq.) in DMF (0.1 M). To this was then added ethyl-diisopropylamine (2.5 eq.) and the resulting yellow solution was allowed to stir at RT for 14 h. The crude reaction mixture was diluted with EtOAc and washed sequentially with water, 10% aq. HCl, water and brine. The organic extract was then dried over MgSO₄, filtered and the filtrate concentrated in vacuo. Further purification by way of column chromatography (SiO₂, gradient elution, 9:1 (v/v) Hex:EtOAc→EtOAc) furnished the desired product as an off-white solid (77% yield).

Step 6: (Z)-3-(5-iodo-2-((3-(trifluoromethyl)benzoyl)imino)-3-((2-(trimethylsilyl)ethoxy)methyl)-2,3-dihydro-1H-benzo[d]imidazol-1-yl)propyl acetate In a glass RBF equipped with a Teflon-coated magnetic stirrer was suspended sodium hydride (1.6 eq., 60% (w/w) dispersion in paraffin oil) in DMF (0.09 M). To this was then added, at 0° C., (E)-3-(5-iodo-2-((3-(trifluoromethyl)benzoyl)imino)-2,3-dihydro-1H-benzo[d]imidazol-1-yl)propyl acetate (1 eq.) from the previous step. The resulting suspension was then stirred at 0° C. for 30 min before (2-(chloromethoxy)ethyl)trimethylsilane (2 eq.) was added drop-wise and neat over a period of 5 min. After another 1 h of stirring at 0° C., the reaction then quenched with the addition of water and extracted with EtOAc. The combined organic extracts were washed further with water and brine, dried over MgSO₄, filtered and the filtrate concentrated in vacuo. Further purification by way of column chromatography (SiO₂, gradient elution, 9:1 (v/v) Hex:Acteone→Acetone) furnished the desired product as a viscous oil (78% yield).

Intermediate 59-CF₂H

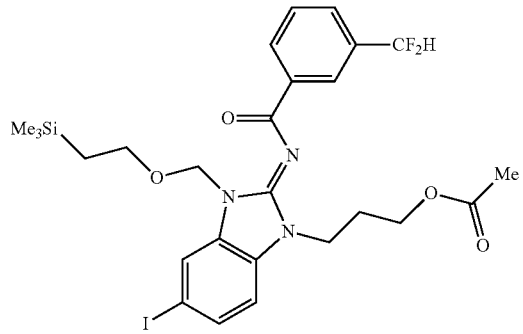 [SMILES: CC(=O)OCCCn1/c(=N/C(=O)c2cccc(C(F)F)c2)n(COCC[Si](C)(C)C)c2cc(I)ccc21]

Prepared in an analogous fashion to Intermediate 59-CF₃, but using 3-(difluoromethyl)-benzoic acid (1 eq.) in place of 3-trifluoromethyl-benzoic acid in step 5.

Intermediate 60

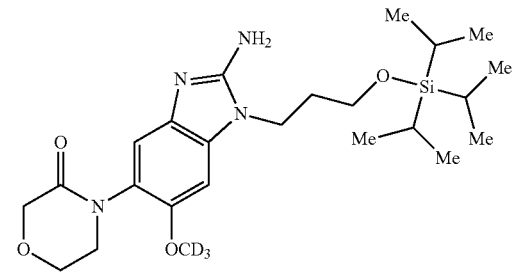

Prepared in an analogous fashion to Intermediate 24, but using CD₃I (1 eq.) in place of 2-bromo-propane in step 4.

Intermediate 61

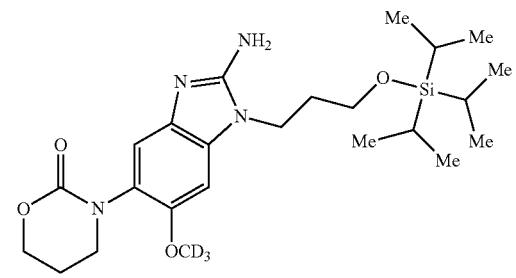

Prepared in an analogous fashion to Intermediate 24, but using 3-chloropropyl carbonochloridate (1.1 eq.), pyridine (1.6 eq.) and DCM (0.5 M) in place of (2-chloro-ethoxy)-acetic acid, HATU, ethyl diisopropylamine and DMF in step 1. Furthermore, CD₃I (1 eq.) was used in place of 2-bromo-propane in step 4.

Intermediate 62

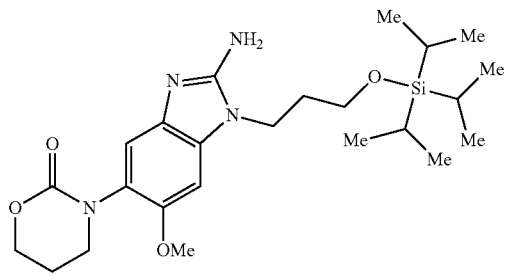

Prepared in an analogous fashion to Intermediate 24, but using 3-chloropropyl carbonochloridate (1.1 eq.), pyridine (1.6 eq.) and DCM (0.5 M) in place of (2-chloro-ethoxy)-acetic acid, HATU, ethyl diisopropylamine and DMF in step 1. Furthermore, both step 3 and step 4 were omitted.

Intermediate 63

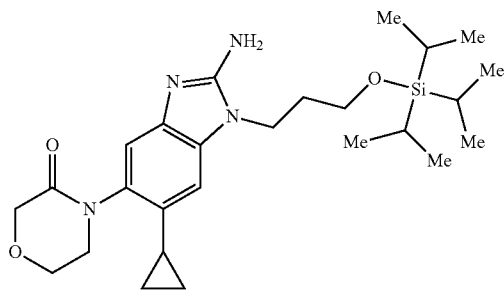 [SMILES: CC(C)[Si](OCCCn1c(N)nc2cc(N3CCOCC3=O)c(C3CC3)cc21)(C(C)C)C(C)C]

Prepared in an analogous fashion to Intermediate 24, but using Intermediate aniline 3 (1 eq.) in place of 4-fluoro-2-methoxy-5-nitro-phenylamine in step 1, and omitting both step 3 and step 4.

Intermediate 64-CF$_3$

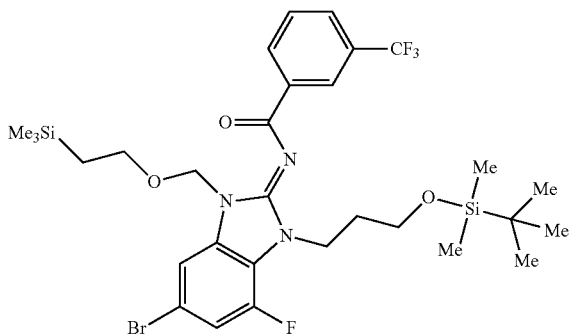 [SMILES: CC(C)(C)[Si](C)(C)OCCCn1/c(=N/C(=O)c2cccc(C(F)(F)F)c2)n(COCC[Si](C)(C)C)c2cc(Br)cc(F)c21]

Step 1: 5-bromo-7-fluoro-1H-benzo[d]imidazol-2-amine

In a glass RBF equipped with a Teflon-coated magnetic stirrer was dissolved 5-bromo-3-fluoro-benzene-1,2-diamine (1 eq.) in ethanol (0.5 M). To this was then added cyanogen bromide (2 eq., 5 M solution in acetonitrile, 2 eq.) drop-wise over a period of 10 min. The resulting mixture was allowed to stir at RT for 3 h before the desired product was precipitated out of the solution with the careful addition of dichloromethane and ether. The crude product thus obtained was used without further purification.

Step 2: N-(5-bromo-7-fluoro-1H-benzo[d]imidazol-2-yl)-3-(trifluoromethyl)benzamide In a glass RBF equipped with a Teflon-coated magnetic stirrer was dissolved 5-bromo-7-fluoro-1H-benzo[d]imidazol-2-amine (1 eq.) from the previous step, 3-trifluoromethyl-benzoic acid (1.1 eq.), 1-hydroxy-7-azabenzotriazole (1.5 eq.), and EDCI (1.9 eq.) in DMF (0.48 M). To this was then added N-methylmorpholine (4 eq.) and the resulting yellow solution was allowed to stir at RT for 14 h. The crude reaction mixture was diluted with EtOAc and washed sequentially with water, 10% aq. HCl, water and brine. The organic extract was then dried over MgSO$_4$, filtered and the filtrate concentrated in vacuo. Further purification by way of column chromatography (SiO$_2$, gradient elution, 9:1 (v/v) Hex:EtOAc→EtOAc) furnished the desired product as an off-white solid (26% yield over two steps).

Step 3: (E)-N-(5-bromo-1-(3-((tert-butyldimethylsilyl)oxy)propyl)-7-fluoro-1H-benzo[d]imidazole-2(3H)-ylidene)-3-(trifluoromethyl)benzamide In a glass RBF equipped with a Teflon-coated magnetic stirrer was suspended N-(5-bromo-7-fluoro-1H-benzo[d]imidazole-2-yl)-3-(trifluoromethyl)benzamide (1 eq.) from the previous step and potassium carbonate (2 eq.) in a 5:1 (v/v) solution (0.24 M) of DMF and acetone. To this was then added tert-butyl (3-iodopropoxy)dimethylsilane (1 eq.) drop-wise and neat over 10 min. After 18 h of stirring at RT, the volatiles were removed in vacuo and the resulting residue was directly subjected to purification by way of column chromatography (SiO$_2$, gradient elution, 8:1 (v/v) Hex:EtOAc→EtOAc) to furnish the desired product (94% yield).

Step 4: (Z)—N-(6-bromo-3-(3-((tert-butyldimethylsilyl)oxy)propyl)-4-fluoro-1-((2-(trimethylsilyl)ethoxy)methyl)-1H-benzo[d]imidazole-2(3H)-ylidene)-3-(trifluoromethyl)benzamide In a glass RBF equipped with a Teflon-coated magnetic stirrer was suspended sodium hydride (1.6 eq., 60% (w/w) dispersion in paraffin oil) in DMF (0.18 M). To this was then added, at 0° C., (E)-N-(5-bromo-1-(3-((tert-butyldimethylsilyl)oxy)propyl)-7-fluoro-1H-benzo[d]imidazole-2(3H)-ylidene)-3-(trifluoromethyl)benzamide (1 eq.) from the previous step. The resulting suspension was then stirred at 0° C. for 10 min before (2-(chloromethoxy)ethyl)trimethylsilane (2 eq.) was added drop-wise and neat over a period of 5 min. After another 1 h of stirring at 0° C., the reaction was then carefully quenched with the addition of water and extracted with EtOAc. The combined organic extracts were washed further with water and brine, dried over MgSO$_4$, filtered and the filtrate concentrated in vacuo. Further purification by way of column chromatography (SiO$_2$, gradient elution, 9:1 (v/v) Hex:Acteone→Acetone) furnished the desired product as a colorless oil (49% yield).

Intermediate 65

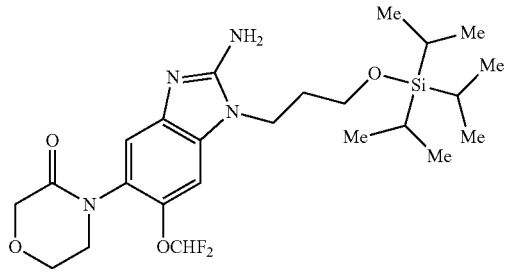 [SMILES: CC(C)[Si](OCCCn1c(N)nc2cc(N3CCOCC3=O)c(OC(F)F)cc21)(C(C)C)C(C)C]

Prepared in an analogous fashion to Intermediate 24, but using Intermediate aniline 4 (1 eq.) in place of 4-fluoro-2-methoxy-5-nitro-phenylamine in step 1, and omitting both step 3 and step 4.

Intermediate 66

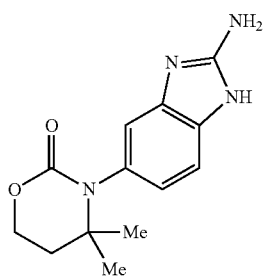 [SMILES: CC1(C)CCOC(=O)N1c1ccc2[nH]c(N)nc2c1]

Step 1: 3-((3,4-dinitrophenyl)amino)-3-methylbutan-1-ol

In a glass RBF equipped with a Teflon-coated magnetic stirrer was combined 4-fluoro-1,2-dinitrobenzene (1 eq.), 3-amino-3-methylbutan-1-ol (1 eq.) and ethyl diisopropyl amine (1.5 eq.) in DMSO (0.5 M). The resulting mixture was then heated at 100° C. for 24 h. The reaction mixture was then diluted with water and extracted with EtOAc. The combined organic extracts were washed further with water and brine, dried over $MgSO_4$, filtered and the filtrate concentrated in vacuo. Further purification of the crude product thus obtained by way of column chromatography ($SiO_2$, gradient elution, 9:1 (v/v) Hex:EtOAc→EtOAc) furnished the desired product (22% yield).

Step 2: 3-((3,4-dinitrophenyl)amino)-3-methylbutyl 1H-imidazole-1-carboxylate In a glass RBF equipped with a Teflon-coated magnetic stirrer was dissolved 3-((3,4-dinitrophenyl)amino)-3-methylbutan-1-ol (1 eq.) from the previous step and CDI (3 eq.) in DMF (0.25 M). The resulting solution was allowed to stir at RT for 14 h. The crude reaction mixture was then diluted with EtOAc and washed sequentially with water and brine. The organic extract was then dried over $MgSO_4$, filtered and the filtrate concentrated in vacuo. The crude product thus obtained was used as is without further purification.

Step 3: 1-((3-((3,4-dinitrophenyl)amino)-3-methylbutoxy)carbonyl)-3-methyl-1H-imidazole-3-ium triflate In a glass RBF equipped with a Teflon-coated magnetic stirrer was suspended 3-((3,4-dinitrophenyl)amino)-3-methylbutyl 1H-imidazole-1-carboxylate (1 eq.) from the previous step in dichloromethane (0.25 M). At 0° C., methyl trifluoromethanesulfonate (1 eq.) was then added neat and drop-wise over a period of 5 min. The resulting solution was then allowed to warm slowly to RT over 14 h. Removal of the volatiles in vacuo furnished the crude product that was used immediately in the next step.

Step 4: 3-(3,4-dinitrophenyl)-4,4-dimethyl-1,3-oxazinan-2-one

In a glass RBF equipped with a Teflon-coated magnetic stirrer was suspended sodium hydride (1.2 eq., 60% (w/w) dispersion in paraffin oil) in THF (0.11 M). To this was then added, at 0° C., 1-((3-((3,4-dinitrophenyl)amino)-3-methylbutoxy)carbonyl)-3-methyl-1H-imidazole-3-ium triflate (1 eq.) from the previous step. The resulting suspension was then stirred at 0° C. for 3 h before the reaction was quenched with the addition of 10% aq. $NH_4Cl$ and EtOAc. The crude solid product thus obtained was isolated via filtration and washed further with water and EtOAc. Further purification by trituration in ether and EtOAc afforded the desired product as a red solid (74% yield over 3 steps).

Step 5: 3-(3,4-diaminophenyl)-4,4-dimethyl-1,3-oxazinan-2-one

In a Parr shaker flask was suspended 3-(3,4-dinitrophenyl)-4,4-dimethyl-1,3-oxazinan-2-one (1 eq.) from the previous step and palladium black (0.3 eq., dry, 10% w/w over carbon) in methanol (0.1 M). The vessel was then repeatedly evacuated and back-filled with nitrogen (3×) and then hydrogen (3×). The resulting suspension was shaken under 50 psi of hydrogen for 18 h. The reaction was then quenched with $CH_2Cl_2$ and filtered through a bed of $CH_2Cl_2$-wetted celite. The insoluble bed was washed further with MeOH and $CH_2Cl_2$. Concentration of the filtrate thus obtained in vacuo furnished the desired product as a dark red oil.

Step 6: 3-(2-amino-1H-benzo[d]imidazol-6-yl)-4,4-dimethyl-1,3-oxazinan-2-one In a glass RBF equipped with a Teflon-coated magnetic stirrer was dissolved 3-(3,4-diaminophenyl)-4,4-dimethyl-1,3-oxazinan-2-one (1 eq.) from the previous step in ethanol (0.2 M). To this was then added cyanogen bromide (2 eq., 5 M solution in THF) drop-wise over a period of 10 min. The resulting mixture was allowed to stir at RT for 18 h. The volatiles were then removed in vacuo. The resulting residue was taken up in water and washed sequentially with EtOAc and dichloromethane. Finally, the aqueous layer rendered basic with the addition $NaHCO_3$ and then extracted with n-BuOH. The n-BuOH extracts were then combined and concentrated in vacuo to furnish the desired product as a white solid (68% yield over two steps).

Intermediate 67

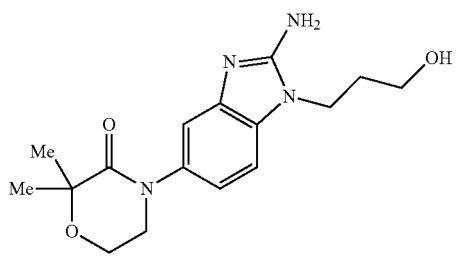 [SMILES: CC1(C)OCCN(c2ccc3c(c2)nc(N)n3CCCO)C1=O]

Step 1: 4-(4-fluorophenyl)-morpholin-3-one

In a glass reaction vessel equipped with a Teflon-coated screw cap was combined morpholin-3-one (1 eq.), 1-fluoro-4-iodo-benzene (1.5 eq.), L-proline (0.2 eq.), copper (I) iodide (0.1 eq.) and potassium carbonate (2.5 eq.) in DMSO (0.2 M). The reaction suspension was then sub-surface purged with nitrogen for 15 min before the reaction vessel was tightly sealed and heated at 100° C. for 16 h. The resulting brown reaction suspension was diluted with tBuOMe and washed sequentially with water, 1 N aq. NaOH, 10% aq. HCl, water and brine. The organic extract was then dried over $MgSO_4$, filtered and the filtrate concentrated in vacuo to furnish a brown semi-solid. Recrystallization from hot hexanes furnished the desired product as a tan solid (21% yield).

Step 2: 4-(4-fluorophenyl)-2-methylmorpholin-3-one

In a glass reaction vessel equipped with a Teflon-coated magnetic stirrer was dissolved 4-(4-fluorophenyl)-morpholin-3-one (1 eq.) from the previous step in THF (0.24 M). At −78° C., LHMDS (1.2 eq., 1.0 M solution in THF) was added drop-wise over a period of 5 min. The resulting orange-red solution was stirred at −78° C. for a further 15 min before iodomethane (1.3 eq.) was added neat and drop-wise over a period of 10 min. The resulting yellow solution was allowed to warm slowly to RT over 16 h. The volatiles were then removed in vacuo and the resulting residue was partitioned between 10% (w/v) aq. $NH_4Cl$ and EtOAc. The organic layer was separated, washed further with water and brine, dried over $MgSO_4$, filtered and the filtrate concentrated in vacuo. Purification of the crude product thus obtained by way of column chromatography ($SiO_2$, gradient elution, 95:5 (v/v) Hex:EtOAc→2:3 (v/v) Hex:EtOAc) furnished the desired product as an oil that solidified upon standing (78% yield).

Step 3: 4-(4-fluorophenyl)-2,2-dimethylmorpholin-3-one

In a glass reaction vessel equipped with a Teflon-coated magnetic stirrer was dissolved 4-(4-fluorophenyl)-2-methylmorpholin-3-one (1 eq.) from the previous step in THF (0.2 M). At −78° C., LHMDS (1.2 eq., 1.0 M solution in THF) was added drop-wise over a period of 5 min. The resulting orange-red solution was stirred at −78° C. for a further 15 min before iodomethane (2.5 eq.) was added neat and drop-wise over a period of 10 min. The resulting yellow solution was allowed to warm slowly to RT over 16 h. The volatiles were then removed in vacuo and the resulting residue was partitioned between 10% aq. $NH_4Cl$ and EtOAc. The organic layer was separated, washed further with water and brine, dried over $MgSO_4$, filtered and the filtrate concentrated in vacuo. Purification of the crude product thus obtained by way of column chromatography ($SiO_2$, gradient elution, 95:5 (v/v) Hex:EtOAc→2:3 (v/v) Hex:EtOAc) furnished the desired product as an oil that solidified upon standing (35% yield).

Step 4: 4-(4-fluoro-3-nitrophenyl)-2,2-dimethylmorpholin-3-one

In a glass RBF equipped with a Teflon-coated magnetic stirrer was dissolved 4-(4-fluorophenyl)-2,2-dimethylmorpholin-3-one (1 eq.) from the previous step in concentrated sulfuric acid (29 eq.). The resulting solution was cooled in an ice-water bath and then added drop-wise fuming nitric acid (2 eq.). The resulting mixture was stirred at 0° C. for 1 h, quenched with ice and then extracted with EtOAc. The combined organic extracts were then washed further with 10% aq. $NaHCO_3$, 10% aq. $NH_4Cl$, water and brine. The organic extract was dried over $Na_2SO_4$, filtered and the filtrate concentrated in vacuo to furnish the desired product, slightly contaminated with its inseparable 2-nitro regioisomer. This was used as is without further purification.

Step 5: 3-((4-(2,2-dimethyl-3-oxomorpholino)-2-nitrophenyl)amino)propyl acetate In a glass RBF equipped with a Teflon-coated magnetic stirrer was dissolved 4-(4-fluoro-3-nitrophenyl)-2,2-dimethylmorpholin-3-one (1 eq.) from the previous step in acetonitrile (0.1 M). To this was then added 3-aminopropyl acetate (1.2 eq.) and sodium carbonate (3 eq.). The resulting suspension was heated at 70° C. for 4 days. The volatiles were then removed in vacuo and the resulting residue was directly subjected to column chromatography ($SiO_2$, gradient elution, 1:1 (v/v) Hex:EtOAc→EtOAc) to furnish the desired product as a red oil that solidified upon standing (10% yield over two steps).

Step 6: 3-((2-amino-4-(2,2-dimethyl-3-oxomorpholino)phenyl)amino)propyl acetate In a Parr shaker flask was suspended 3-((4-(2,2-dimethyl-3-oxomorpholino)-2-nitrophenyl)amino)propyl acetate (1 eq.) from the previous step and palladium black (0.24 eq., dry, 10% w/w over carbon) in methanol (0.12 M). The vessel was then repeatedly evacuated and back-filled with nitrogen (3×) and then hydrogen (3×). The resulting suspension was shaken under 50 psi of hydrogen for 2 h. The reaction was then quenched with $CH_2Cl_2$ and filtered through a bed of $CH_2Cl_2$-wetted celite. The insoluble bed was washed further with MeOH and $CH_2Cl_2$. Concentration of the filtrate thus obtained in vacuo furnished the desired product as a brown solid.

Step 7: 4-(2-amino-1-(3-hydroxypropyl)-1H-benzo[d]imidazol-5-yl)-2,2-dimethylmorpholin-3-one In a glass RBF equipped with a Teflon-coated magnetic stirrer was dissolved 3-((2-amino-4-(2,2-dimethyl-3-oxomorpholino)phenyl)amino)propyl acetate (1 eq.) from the previous step in ethanol (0.11 M). To this was then added cyanogen bromide (1.5 eq., 5 M solution in acetonitrile) drop-wise over a period of 10 min. The resulting mixture was allowed to stir at RT for 12 h. The crude reaction mixture was diluted with EtOAc and washed sequentially with 10% aq. NaHCO$_3$, water and brine. The organic extract was then dried over Na$_2$SO$_4$ and filtered. Concentration of the filtrate thus obtained in vacuo furnished the desired product as an off-white solid (42% yield).

Intermediate 68-CF$_3$

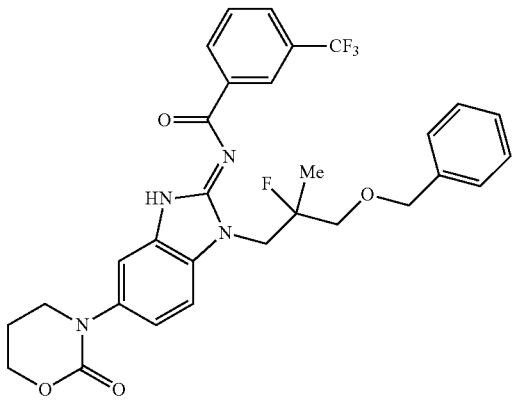 [SMILES: CC(F)(COCc1ccccc1)Cn1/c(=N/C(=O)c2cccc(C(F)(F)F)c2)[nH]c2cc(N3CCCOC3=O)ccc21]

Prepared in an analogous fashion to Intermediate 4-CF$_3$, but using Intermediate amine 3 (1.3 eq.) in place of (R)-3-amino-butan-1-ol in step 3, and omitting step 4.

Intermediate 69

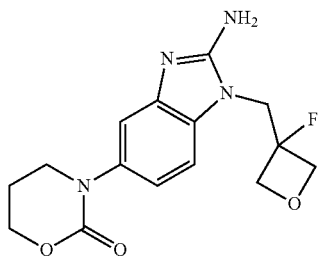 [SMILES: Nc1nc2cc(N3CCCOC3=O)ccc2n1CC1(F)COC1]

Prepared in an analogous fashion to Intermediate 4-CF$_3$, but using (3-fluorooxetan-3-yl)methanamine (1.1 eq.) in place of (R)-3-amino-butan-1-ol in step 3, and omitting both step 4 and step 7.

Intermediate 70

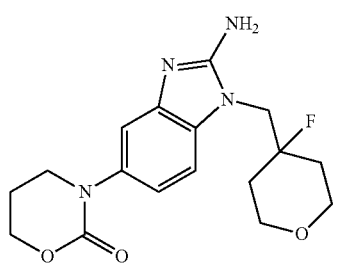 [SMILES: Nc1nc2cc(N3CCCOC3=O)ccc2n1CC1(F)CCOCC1]

Prepared in an analogous fashion to Intermediate 4-CF$_3$, but using (4-fluorotetrahydro-2H-pyran-4-yl)methanamine (1.1 eq.) in place of (R)-3-amino-butan-1-ol in step 3, and omitting both step 4 and step 7.

Example 1: (E)-N-(1-(3-hydroxypropyl)-5-(3-oxo-morpholino)-1H-benzo[d]imidazol-2(3H)-ylidene)-3-(trifluoromethyl)benzamide (86)

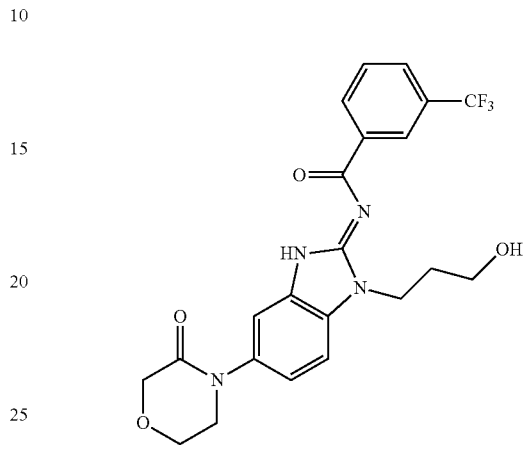

Step 1: N-(5-(3-oxo-morpholin-4-yl)-1-(3-triisopropylsilanyloxy-propyl)-1H-benzoimidazol-2-yl)-3-trifluoromethyl-benzamide In a glass RBF equipped with a Teflon-coated magnetic stirrer was dissolved Intermediate 1-OTIPS (1 eq.), 3-trifluoromethyl-benzoic acid (1.1 eq.) and HATU (1.2 eq.) in DMF (0.1 M). To this was then added ethyl-diisopropylamine (2.5 eq.) and the resulting yellow solution was allowed to stir at RT for 14 h. The crude reaction mixture was diluted with EtOAc and washed sequentially with water, 10% aq. NaHCO$_3$, 10% aq. NH$_4$Cl, water and brine. The organic extract was then dried over Na$_2$SO$_4$, filtered and the filtrate concentrated in vacuo. Further purification by way of column chromatography (SiO$_2$, gradient elution, 1:1 (v/v) Hex:EtOAc→EtOAc) furnished the desired product as a pink solid (52% yield).

Step 2: (E)-N-(1-(3-hydroxypropyl)-5-(3-oxomorpholino)-1H-benzo[d]imidazol-2(3H)-ylidene)-3-(trifluoromethyl)benzamide In a glass RBF equipped with a Teflon-coated magnetic stirrer was dissolved N-(5-(3-oxo-morpholin-4-yl)-1-(3-triisopropylsilanyloxy-propyl)-1H-benzoimidazol-2-yl)-3-trifluoromethyl-benzamide (1 eq.) from the previous step in THF (0.1 M). To this was then added tetrabutylammonium fluoride (3.5 eq., 1 M solution in THF) drop-wise over a period of 1 min. The resulting mixture was allowed to stir at RT for 3 h. The crude reaction mixture was diluted with EtOAc and washed sequentially with 10% aq. NaHCO$_3$, water and brine. The organic extract was then dried over Na$_2$SO$_4$, filtered and the filtrate concentrated in vacuo. Trituration of the crude product thus obtained in ether and hexanes afforded the title product as a white solid (42% yield). ESI$^+$: M+1: 463. $^1$H NMR (300 MHz, CDCl$_3$) δ 12.63 (s, 1H), 8.63-8.53 (m, 2H), 8.01 (s, 1H), 7.85 (d, J=7.7 Hz, 1H), 7.70 (t, J=7.7 Hz, 1H), 7.63-7.49 (m, 2H), 4.68-

4.62 (m, 1H), 4.51-4.40 (m, 2H), 4.33 (s, 2H), 4.03-3.93 (m, 2H), 3.68-3.58 (m, 2H), 3.49-3.43 (m, 2H), 2.03-1.92 (m, 2H).

Example 2: (E)-3-(difluoromethoxy)-N-(1-(3-hydroxypropyl)-5-(3-oxomorpholino)-1H-benzo[d]imidazol-2(3H)-ylidene)benzamide (6)

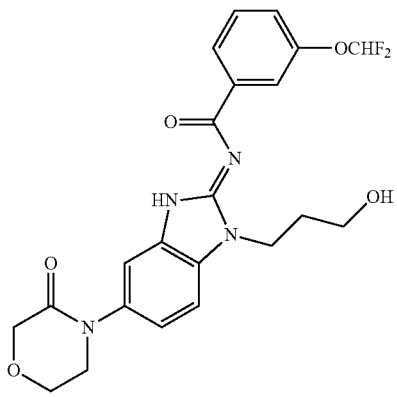

Prepared in an analogous fashion to Example 1, but using 3-difluoromethoxy-benzoic acid (1 eq.) in place of 3-trifluoromethyl-benzoic acid in Step 1. ESI⁺: M+1: 461. ¹H NMR (300 MHz, CDCl₃) δ 12.66 (s, 1H), 8.17-8.07 (m, 1H), 8.04-7.96 (m, 1H), 7.46 (t, J=7.9 Hz, 1H), 7.37-7.18 (m, 4H), 6.60 (t, J=73.8 Hz, 1H), 4.67-4.60 (m, 1H), 4.51-4.38 (m, 2H), 4.34 (s, 2H), 4.06-3.96 (m, 2H), 3.73-3.63 (m, 2H), 3.52-3.43 (m, 2H), 2.03 (dd, J=10.8, 4.6 Hz, 2H).

Example 3: (E)-N-(1-(3-hydroxypropyl)-5-(3-oxomorpholino)-1H-benzo[d]imidazol-2(3H)-ylidene)-3-sulfamoylbenzamide (100)

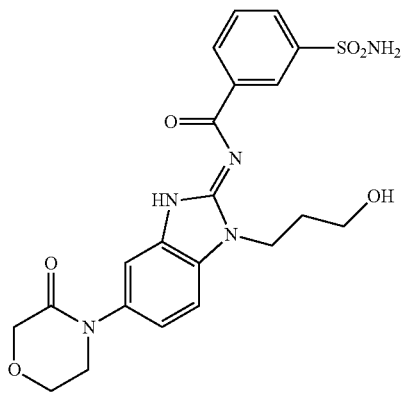 [SMILES: NS(=O)(=O)c1cccc(C(=O)/N=c2\[nH]c3cc(N4CCOCC4=O)ccc3n2CCCO)c1]

Prepared in an analogous fashion to Example 1, but using 3-sulfamoyl-benzoic acid (1 eq.) in place of 3-trifluoromethyl-benzoic acid in Step 1. ESI⁺: M+1: 474. ¹H NMR (300 MHz, DMSO-d₆) δ 12.86 (s, 1H), 8.69-8.62 (m, 1H), 8.50-8.41 (m, 1H), 8.01-7.91 (m, 1H), 7.68 (t, J=7.8 Hz, 1H), 7.57 (d, J=8.6 Hz, 1H), 7.53-7.45 (m, 3H), 7.27 (dd, J=8.6, 2.0 Hz, 1H), 4.72-4.65 (m, 1H), 4.34 (t, J=6.9 Hz, 2H), 4.23 (s, 2H), 4.05-3.95 (m, 2H), 3.79-3.69 (m, 2H), 3.48 (s, 2H), 2.02-1.91 (m, 2H).

Example 4: (E)-3-fluoro-N-(1-(3-hydroxypropyl)-5-(3-oxomorpholino)-1H-benzo[d]imidazol-2(3H)-ylidene)-5-(trifluoromethyl)benzamide (81)

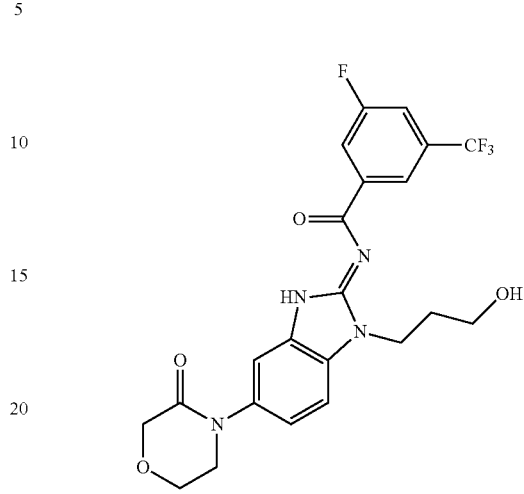

Prepared in an analogous fashion to Example 1, but using 3-fluoro-5-trifluoromethyl-benzoic acid (1 eq.) in place of 3-trifluoromethyl-benzoic acid in Step 1. ESI⁺: M+1: 481. ¹H NMR (300 MHz, CDCl₃) δ 12.45 (s, 1H), 8.31 (s, 1H), 8.11 (d, J=9.2 Hz, 1H), 7.45 (d, J=7.8 Hz, 1H), 7.42-7.35 (m, 2H), 7.35-7.27 (m, 1H), 4.51-4.45 (m, 2H), 4.39 (s, 2H), 4.13-3.97 (m, 3H), 3.84-3.78 (m, 2H), 3.54-3.47 (m, 2H), 3.16 (s, 1H), 2.09-2.01 (m, 2H).

Example 5: (E)-2-fluoro-N-(1-(3-hydroxypropyl)-5-(3-oxomorpholino)-1H-benzo[d]imidazol-2(3H)-ylidene)-3-(trifluoromethyl)benzamide (4)

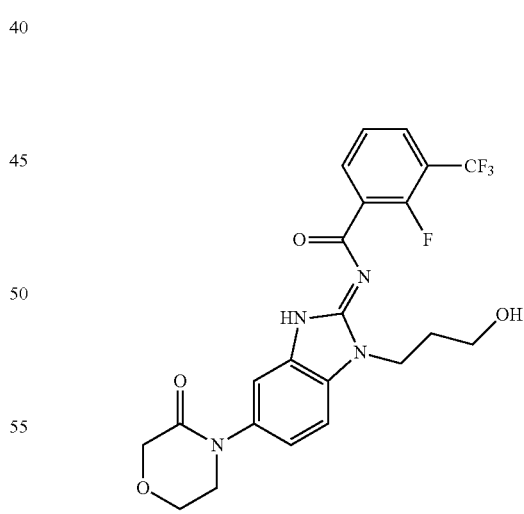

Prepared in an analogous fashion to Example 1, but using 2-fluoro-3-trifluoromethyl-benzoic acid (1 eq.) in place of 3-trifluoromethyl-benzoic acid in Step 1. ESI⁺: M+1: 481. ¹H NMR (300 MHz, CDCl₃) δ 12.44 (s, 1H), 8.28-8.17 (m, 1H), 7.74-7.63 (m, 1H), 7.38-7.20 (m, 4H), 4.55-4.48 (m, 1H), 4.44-4.26 (m, 4H), 4.07-3.93 (m, 2H), 3.80-3.66 (m, 2H), 3.49-3.38 (m, 2H), 2.01-1.86 (m, 2H).

Example 6: (E)-4-fluoro-N-(1-(3-hydroxypropyl)-5-(3-oxomorpholino)-1H-benzo[d]imidazol-2(3H)-ylidene)-3-(trifluoromethyl)benzamide (5)

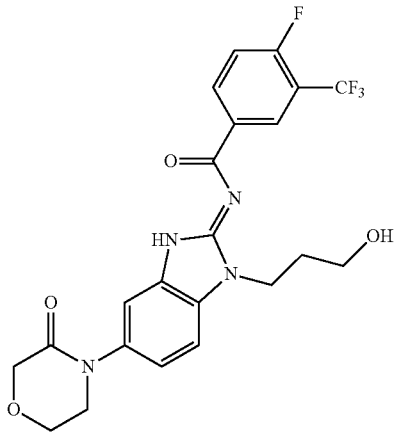

Prepared in an analogous fashion to Example 1, but using 4-fluoro-5-trifluoromethyl-benzoic acid (1 eq.) in place of 3-trifluoromethyl-benzoic acid in Step 1. ESI$^+$: M+1: 481. $^1$H NMR (300 MHz, acetone-d$_6$) δ12.51 (s, 1H), 8.66-8.55 (m, 2H), 7.67 (s, 1H), 7.56 (d, J=8.6 Hz, 1H), 7.46 (t, J=9.7 Hz, 1H), 7.32 (d, J=8.5 Hz, 1H), 4.46 (t, J=6.7 Hz, 2H), 4.19 (s, 2H), 4.09-3.99 (m, 3H), 3.86-3.79 (m, 1H), 3.88-3.78 (m, 1H), 3.65-3.53 (m, 2H), 2.14-2.04 (m, 2H).

Example 7: (E)-N-(1-(3-hydroxypropyl)-5-(3-oxomorpholino)-1H-benzo[d]imidazol-2(3H)-ylidene)-3-(trifluoromethoxy)benzamide (7)

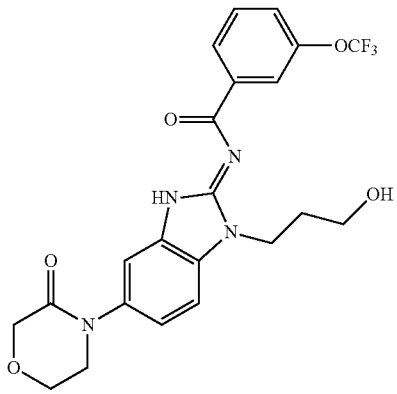

Prepared in an analogous fashion to Example 1, but using 3-trifluoromethoxy-benzoic acid (1 eq.) in place of 3-trifluoromethyl-benzoic acid in Step 1. ESI$^+$: M+1: 479. $^1$H NMR (300 MHz, acetone-d$_6$) δ12.52 (s, 1H), 8.28 (d, J=7.7 Hz, 1H), 8.16 (s, 1H), 7.69-7.61 (m, 1H), 7.61-7.49 (m, 2H), 7.48-7.39 (m, 1H), 7.36-7.25 (m, 1H), 4.51-4.40 (m, 2H), 4.19 (s, 2H), 4.11-4.05 (m, 1H), 4.07-3.99 (m, 2H), 3.87-3.77 (m, 2H), 3.63-3.51 (m, 2H), 2.11-1.97 (m, 2H).

Example 8: (E)-3-(difluoromethyl)-N-(1-(3-hydroxypropyl)-5-(3-oxomorpholino)-1H-benzo[d]imidazol-2(3H)-ylidene)benzamide (79)

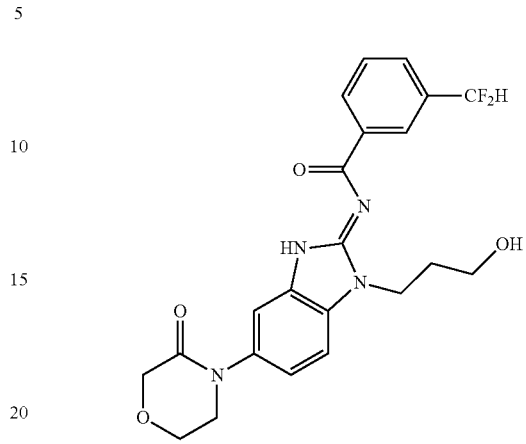

Prepared in an analogous fashion to Example 1, but using 3-difluoromethyl-benzoic acid (1 eq.) in place of 3-trifluoromethyl-benzoic acid in Step 1. ESI$^+$: M+1: 445. $^1$H NMR (300 MHz, CDCl$_3$) δ 12.73 (s, 1H), 8.43-8.35 (m, 2H), 7.73-7.63 (m, 1H), 7.62-7.50 (m, 1H), 7.38-7.20 (m, 3H), 6.73 (t, J=56.4 Hz, 1H), 4.68-4.62 (m, 1H), 4.51-4.40 (m, 2H), 4.33 (s, 2H), 4.03-3.93 (m, 2H), 3.68-3.58 (m, 2H), 3.49-3.43 (m, 2H), 2.03-1.92 (m, 2H).

Example 9: (E)-N-(1-(3-hydroxypropyl)-5-(3-oxomorpholino)-1H-benzo[d]imidazol-2(3H)-ylidene)-4-methyl-3-(trifluoromethyl)benzamide (78)

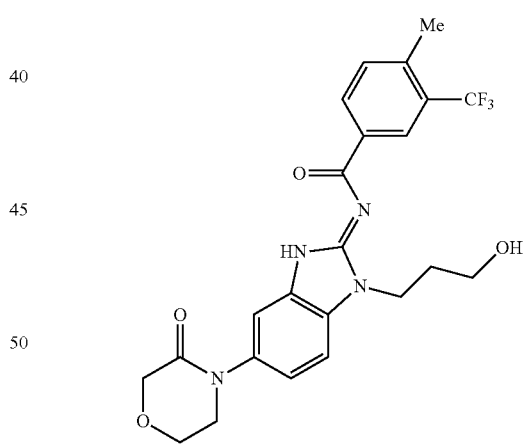

In a glass RBF equipped with a Teflon-coated magnetic stirrer was dissolved 4-methyl-3-trifluoromethyl-benzoic acid (1 eq.), HBTU (1.1 eq.) and ethyl-diisopropyl-amine (3 eq.) in acetonitrile (0.12 M). To this was then added Intermediate 1-OH (1 eq.) as a solution (0.12 M) in 9:1 (v/v) DMF:MeCN and the resulting yellow solution was allowed to stir at RT for 1 h. The crude reaction mixture was directly subjected to purification by way of column chromatography (SiO$_2$, gradient elution, CH$_2$Cl$_2$→9:1 (v/v) CH$_2$Cl$_2$:MeOH). The product thus obtained can then be triturated in methanol and ether to furnish the title compound as a white solid (22% yield). ESI$^+$: M+1: 477. $^1$H NMR (300 MHz, DMSO-d$_6$) δ

12.85 (s, 1H), 8.50 (s, 1H), 8.38 (d, J=7.9 Hz, 1H), 7.62-7.46 (m, 3H), 7.27 (dd, J=8.5, 2.0 Hz, 1H), 4.68 (t, J=5.1 Hz, 1H), 4.33 (t, J=6.8 Hz, 2H), 4.23 (s, 2H), 4.00 (dd, J=6.1, 4.0 Hz, 2H), 3.74 (t, J=5.1 Hz, 2H), 3.48 (q, J=5.9 Hz, 2H), 2.53 (s, 3H), 1.96 (t, J=6.5 Hz, 2H).

Example 10: (E)-N-(1-(3-hydroxypropyl)-5-(3-oxo-morpholino)-1H-benzo[d]imidazol-2(3H)-ylidene)nicotinamide (77)

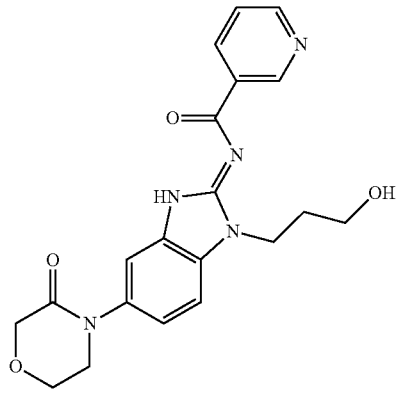

Prepared in an analogous fashion to Example 9, but using nicotinic acid (1 eq.) in place of 4-methyl-3-trifluoromethyl-benzoic acid and triethylamine (3 eq.) in place of ethyl-diisopropyl-amine (8% yield). ESI+: M+1: 396. ¹H NMR (300 MHz, CDCl₃) δ 12.88 (s, 1H), 9.39 (dd, J=2.1, 0.9 Hz, 1H), 8.70 (dd, J=4.8, 1.8 Hz, 1H), 8.50 (dt, J=8.0, 1.9 Hz, 1H), 7.63-7.46 (m, 3H), 7.28 (dd, J=8.6, 2.0 Hz, 1H), 4.70 (t, J=5.1 Hz, 1H), 4.35 (t, J=6.9 Hz, 2H), 4.23 (s, 2H), 4.01 (dd, J=6.0, 4.0 Hz, 2H), 3.74 (t, J=5.0 Hz, 2H), 3.55-3.36 (m, 2H), 2.02-1.91 (m, 1H).

Example 11: (E)-3-(N,N-dimethylsulfamoyl)-N-(1-(3-hydroxypropyl)-5-(3-oxomorpholino)-1H-benzo[d]imidazol-2(3H)-ylidene)benzamide (101)

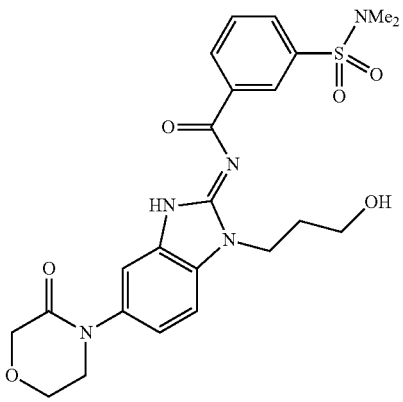 [SMILES: CN(C)S(=O)(=O)c1cccc(C(=O)/N=c2\[nH]c3cc(N4CCOCC4=O)ccc3n2CCCO)c1]

Prepared in an analogous fashion to Example 9, but using 3-dimethylsulfamoyl-benzoic acid (1.2 eq.) in place of 4-methyl-3-trifluoromethyl-benzoic acid and TBTU (1.2 eq.) in place of HBTU (25% yield). ESI+: M+1: 502. ¹H NMR (300 MHz, DMSO-d₆) δ 8.59-8.50 (m, 2H), 7.95-7.85 (m, 1H), 7.77 (t, J=7.9 Hz, 1H), 7.63-7.47 (m, 2H), 7.28 (dd, J=8.6, 2.0 Hz, 1H), 4.34 (t, J=6.8 Hz, 2H), 4.23 (s, 2H), 4.06-3.96 (m, 2H), 3.75 (t, J=5.1 Hz, 2H), 3.48 (t, J=6.2 Hz, 2H), 2.65 (s, 6H), 1.97 (t, J=6.5 Hz, 2H).

Example 12: (E)-3-(hydroxymethyl)-N-(1-(3-hydroxypropyl)-5-(3-oxomorpholino)-1H-benzo[d]imidazol-2(3H)-ylidene)benzamide (21)

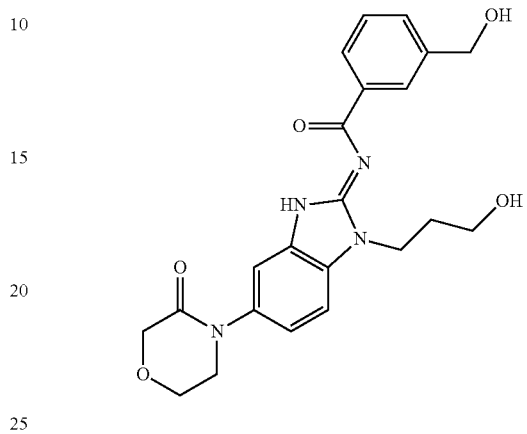

In a glass RBF equipped with a Teflon-coated magnetic stirrer was dissolved 3-hydroxymethyl-benzoic acid (1.2 eq.), HATU (1.2 eq.) and triethylamine (3 eq.) in acetonitrile (0.18 M). To this was then added Intermediate 1-OAc (1 eq.) as a solution (0.12 M) in acetonitrile and the resulting yellow solution was allowed to stir at RT for 16 h. The crude reaction mixture was directly subjected to purification by way of column chromatography (SiO₂, gradient elution, CH₂Cl₂→9:1 (v/v) CH₂Cl₂: MeOH). The coupling product thus obtained was then taken up in methanol (0.05 M) and added potassium carbonate (2 eq.). The resulting mixture was allowed to stir at RT for 2 h. The crude de-protected product thus obtained was then subjected to column chromatography (SiO₂, gradient elution, CH₂Cl₂→8:1 (v/v) CH₂Cl₂:MeOH) to furnish the title compound as a white solid (27% yield). ESI+: M+1: 425. ¹H NMR (300 MHz, DMSO-d₆) δ 12.80 (s, 1H), 8.21-8.08 (m, 2H), 7.59-7.36 (m, 4H), 7.25 (d, J=8.5 Hz, 1H), 5.29 (s, 1H), 4.71 (s, 1H), 4.57 (d, J=4.6 Hz, 2H), 4.32 (t, J=6.7 Hz, 2H), 4.23 (s, 2H), 4.00 (dd, J=6.1, 4.0 Hz, 2H), 3.74 (t, J=5.1 Hz, 2H), 3.47 (s, 3H), 1.96 (t, J=6.6 Hz, 2H).

Example 13: (E)-N-(1-(3-hydroxypropyl)-5-(3-oxomorpholino)-1H-benzo[d]imidazol-2(3H)-ylidene)-1-methyl-1H-benzo[d]imidazole-6-carboxamide (20)

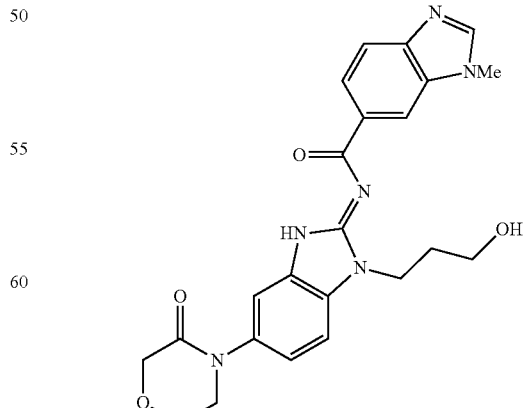

Prepared in an analogous fashion to Example 12, but using 3-methyl-3H-benzoimidazole-5-carboxylic acid (1.2 eq.) in place of 3-hydroxymethyl-benzoic acid and PyBOP (1.2 eq.) in place of HBTU (67% yield). ESI+: M+1: 449. $^1$H NMR (300 MHz, DMSO-$d_6$) δ 12.80 (s, 1H), 8.49-8.42 (m, 1H), 8.32 (s, 1H), 7.69 (d, J=8.4 Hz, 1H), 7.60-7.45 (m, 2H), 7.25 (dd, J=8.5, 2.0 Hz, 1H), 4.74 (s, 1H), 4.37 (s, 2H), 4.23 (s, 2H), 4.01 (dd, J=6.1, 4.0 Hz, 2H), 3.93 (s, 3H), 3.75 (dd, J=6.0, 4.1 Hz, 2H), 3.52 (d, J=5.2 Hz, 2H), 2.05-1.94 (m, 2H).

Example 14: (E)-N-(1-(3-hydroxypropyl)-5-(3-oxo-morpholino)-1H-benzo[d]imidazol-2(3H)-ylidene)-1-methyl-1H-benzo[d]imidazole-5-carboxamide (22)

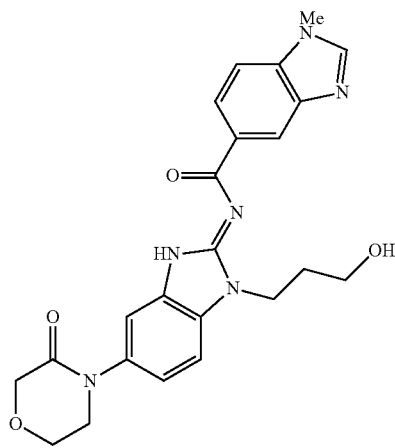 [SMILES: Cn1cnc2cc(C(=O)/N=c3\[nH]c4cc(N5CCOCC5=O)ccc4n3CCCO)ccc21]

Prepared in an analogous fashion to Example 12, but using 1-methyl-3H-benzoimidazole-5-carboxylic acid (1.2 eq.) in place of 3-hydroxymethyl-benzoic acid and PyBOP (1.2 eq.) in place of HBTU (86% yield). ESI+: M+1: 449. $^1$H NMR (300 MHz, DMSO-$d_6$) δ 12.83 (s, 1H), 8.57 (s, 1H), 8.26 (d, J=22.8 Hz, 2H), 7.67-7.44 (m, 3H), 7.25 (dd, J=8.5, 2.0 Hz, 1H), 4.74 (s, 1H), 4.36 (s, 2H), 4.23 (s, 2H), 4.01 (dd, J=6.1, 4.0 Hz, 2H), 3.89 (s, 3H), 3.79-3.69 (m, 2H), 3.50 (s, 2H), 2.00 (t, J=6.5 Hz, 2H).

Example 15: (E)-N-(1-(3-hydroxypropyl)-5-(3-oxo-morpholino)-1H-benzo[d]imidazol-2(3H)-ylidene)-1-oxo-1,3-dihydroisobenzofuran-5-carboxamide (23)

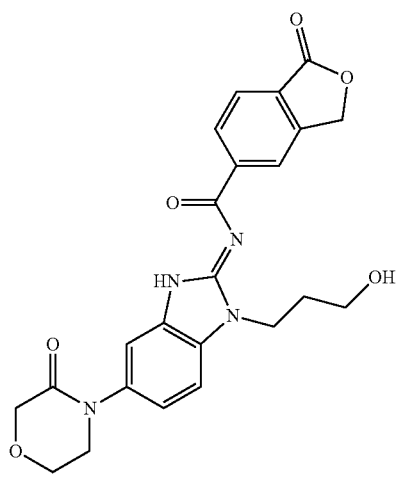 [SMILES: O=C(/N=c1\[nH]c2cc(N3CCOCC3=O)ccc2n1CCCO)c1ccc2c(c1)COC2=O]

Prepared in an analogous fashion to Example 12, but using 1-oxo-1,3-dihydroisobenzofuran-5-carboxylic acid (1.2 eq.) in place of 3-hydroxymethyl-benzoic acid and PyBOP (1.2 eq.) in place of HBTU (54% yield). ESI+: M+1: 451. $^1$H NMR (300 MHz, DMSO-$d_6$) δ 12.95 (s, 1H), 8.53-8.41 (m, 2H), 8.00-7.90 (m, 1H), 7.65-7.49 (m, 2H), 7.30 (dd, J=8.5, 2.0 Hz, 1H), 5.53 (s, 2H), 4.70 (t, J=5.1 Hz, 1H), 4.37 (t, J=6.8 Hz, 2H), 4.24 (s, 2H), 4.07-3.97 (m, 2H), 3.76 (t, J=5.0 Hz, 2H), 3.50 (q, J=6.0 Hz, 2H), 1.98 (q, J=6.7 Hz, 2H).

Example 16: (E)-N-(1-(3-hydroxypropyl)-5-(3-oxo-morpholino)-1H-benzo[d]imidazol-2(3H)-ylidene)-1-methyl-1H-indazole-3-carboxamide (60)

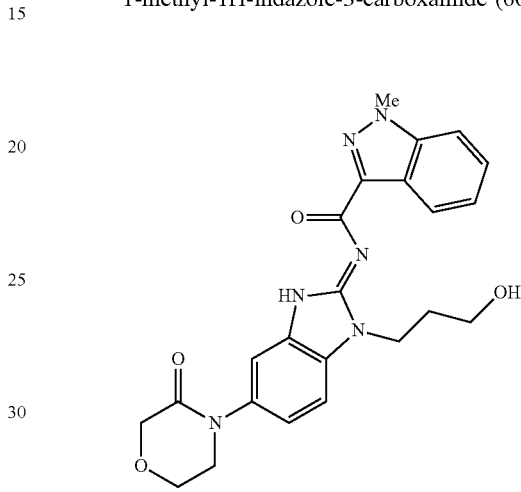

Prepared in an analogous fashion to Example 12, but using 1-methyl-1H-indazole-3-carboxylic acid (1 eq.) in place of 3-hydroxymethyl-benzoic acid and PyBOP (1.2 eq.) in place of HBTU (64% yield). ESI+: M+1: 449. $^1$H NMR (300 MHz, DMSO-$d_6$) δ 8.49 (d, J=8.1 Hz, 1H), 7.74 (d, J=8.4 Hz, 1H), 7.66-7.41 (m, 3H), 7.31 (ddt, J=9.5, 8.5, 1.5 Hz, 2H), 4.39 (t, J=6.7 Hz, 2H), 4.24 (s, 2H), 4.01 (dd, J=6.1, 4.0 Hz, 2H), 3.76 (dd, J=6.0, 4.0 Hz, 2H), 3.49 (t, J=5.9 Hz, 2H), 3.17 (s, 1H), 2.03-1.92 (m, 2H).

Example 17: (E)-3-bromo-N-(1-(3-hydroxypropyl)-5-(3-oxomorpholino)-1H-benzo[d]imidazol-2(3H)-ylidene)benzamide (37)

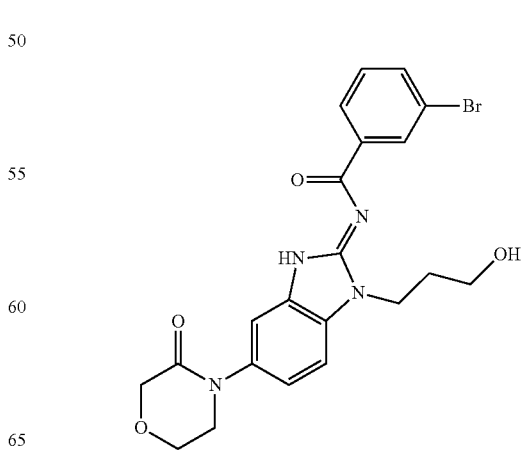

Step 1: 3-(2-(3-bromobenzamido)-5-(3-oxomorpholino)-1H-benzo[d]imidazol-1-yl)propyl acetate In a glass RBF equipped with a Teflon-coated magnetic stirrer was dissolved Intermediate 1-OAc (1 eq.) in DMF (0.4 M). To this was then added triethylamine (3 eq.) and 3-bromo-benzoyl chloride (1.2 eq.). The resulting mixture was stirred at RT for 4 h. The crude reaction mixture was directly subjected to purification by way of column chromatography (SiO$_2$, gradient elution, Hex 4 EtOAc) to furnish the desired product as a beige powder (46% yield).

Step 2: (E)-3-bromo-N-(1-(3-hydroxypropyl)-5-(3-oxomorpholino)-1H-benzo[d]imidazol-2(3H)-ylidene)benzamide In a glass RBF equipped with a Teflon-coated magnetic stirrer was dissolved 3-(2-(3-bromobenzamido)-5-(3-oxomorpholino)-1H-benzo[d]imidazol-1-yl)propyl acetate (1 eq.) from the previous step in methanol (0.05 M). To this was then added potassium carbonate (2 eq.) and the resulting mixture was allowed to stir at RT for 2 h. The crude de-protected product thus obtained was then subjected to column chromatography (SiO$_2$, gradient elution, CH$_2$Cl$_2$→8:1 (v/v) CH$_2$Cl$_2$: MeOH) to furnish the title compound as a white solid (27% yield). ESI$^+$: M+1: 475. $^1$H NMR (300 MHz, DMSO-d$_6$) δ 12.87 (s, 1H), 8.34 (t, J=1.8 Hz, 1H), 8.24 (dt, J=7.7, 1.3 Hz, 1H), 7.73 (ddd, J=7.9, 2.2, 1.1 Hz, 1H), 7.62-7.40 (m, 3H), 7.27 (dd, J=8.5, 2.0 Hz, 1H), 4.33 (t, J=6.8 Hz, 2H), 4.23 (s, 2H), 4.00 (dd, J=6.0, 4.0 Hz, 2H), 3.74 (dd, J=6.0, 4.0 Hz, 2H), 3.48 (t, J=6.1 Hz, 2H), 3.36 (s, 7H), 1.96 (t, J=6.5 Hz, 2H).

Example 18: (E)-3-((E)-3-amino-3-oxoprop-1-en-1-yl)-N-(1-(3-hydroxypropyl)-5-(3-oxomorpholino)-1H-benzo[d]imidazol-2(3H)-ylidene)benzamide (34)

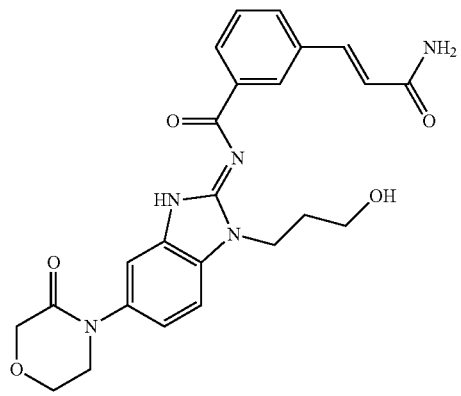 [SMILES: NC(=O)/C=C/c1cccc(C(=O)/N=c2\[nH]c3cc(N4CCOCC4=O)ccc3n2CCCO)c1]

In a sealable glass reaction vessel equipped with a Teflon-coated screw cap was dissolved 3-(2-(3-bromobenzamido)-5-(3-oxomorpholino)-1H-benzo[d]imidazol-1-yl)propyl acetate (1 eq., Example 17, Step 1), acrylamide (10 eq.), L-lactic acid (8 eq.), and triethylamine (8 eq.) in DMF (0.05 M). The resulting solution was sub-surface purged with nitrogen for 10 min before tri-o-tolylphosphane (0.1 eq.) and palladium(II) acetate (0.1 eq.) were added in one rapid portion. The vessel was then tightly sealed and heated at 110° C. for 16 h. The crude reaction mixture thus obtained was directly subjected to purification by way of column chromatography (SiO$_2$, gradient elution, EtOAc+3% NEt$_3$→9:1 (v/v) EtOAc:MeOH+3% NEt$_3$). The coupling product thus obtained was then taken up in methanol (0.05 M) and added potassium carbonate (2 eq.). The resulting mixture was allowed to stir at RT for 2 h. The crude de-protected product thus obtained was then subjected to column chromatography (SiO$_2$, gradient elution, EtOAc+3% NEt$_3$→8:1 (v/v) EtOAc:MeOH+3% NEt$_3$) to furnish the title compound as a white solid (78% yield). ESI$^+$: M+1: 464. $^1$H NMR (300 MHz, DMSO-d$_6$) δ 8.40 (s, 2H), 8.23 (dt, J=7.7, 1.4 Hz, 3H), 7.79-7.58 (m, 6H), 7.64-7.48 (m, 9H), 7.49 (s, 2H), 7.29 (dd, J=8.5, 2.0 Hz, 3H), 7.20 (s, 3H), 6.72 (d, J=15.9 Hz, 3H), 4.38 (t, J=6.8 Hz, 6H), 4.24 (s, 6H), 4.01 (dd, J=6.1, 4.1 Hz, 6H), 3.76 (s, 1H), 3.50 (t, J=6.1 Hz, 6H), 1.99 (q, J=6.6 Hz, 6H).

Example 19: (E)-N-(1-(3-hydroxypropyl)-5-(3-oxomorpholino)-1H-benzo[d]imidazol-2(3H)-ylidene)benzamide (30)

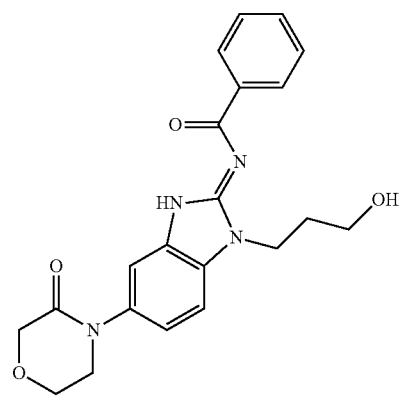

Prepared in an analogous fashion to Example 12, but using benzoic acid (1 eq.) in place of 3-hydroxymethyl-benzoic acid and PyBOP (1.1 eq.) in place of HBTU (24% yield). ESI$^+$: M+1: 395. $^1$H NMR (300 MHz, DMSO-d$_6$) δ 12.84 (s, 1H), 8.29-8.20 (m, 2H), 7.60-7.41 (m, 5H), 7.26 (dd, J=8.5, 2.1 Hz, 1H), 4.33 (t, J=6.6 Hz, 2H), 4.00 (dd, J=6.1, 3.9 Hz, 2H), 3.74 (t, J=5.0 Hz, 2H), 3.48 (t, J=6.1 Hz, 2H), 1.96 (t, J=6.6 Hz, 2H).

Example 20: (E)-N-(1-(3-hydroxypropyl)-5-(3-oxomorpholino)-1H-benzo[d]imidazol-2(3H)-ylidene)-3-(morpholine-4-carbonyl)benzamide (36)

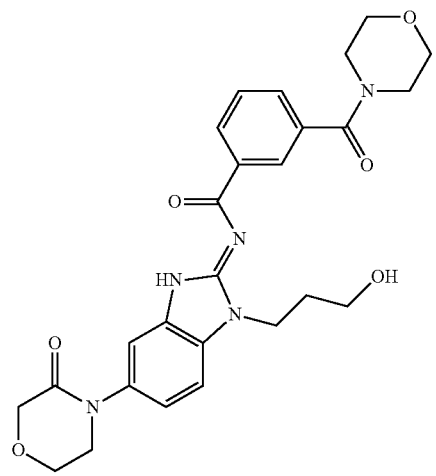 [SMILES: O=C(/N=c1\[nH]c2cc(N3CCOCC3=O)ccc2n1CCCO)c1cccc(C(=O)N2CCOCC2)c1]

Prepared in an analogous fashion to Example 12, but using Intermediate acid 1 (1 eq.) in place of 3-hydroxymethyl-benzoic acid and PyBOP (1.1 eq.) in place of HBTU (29% yield). ESI+: M+1: 508. ¹H NMR (300 MHz, DMSO-d₆) δ 12.87 (s, 1H), 8.37-8.28 (m, 1H), 8.28-8.20 (s, 1H), 7.62-7.52 (m, 3H), 7.52-7.45 (d, 1H), 7.27 (dd, J=8.5, 2.0 Hz, 1H), 4.70 (s, 1H), 4.34 (t, J=6.7 Hz, 2H), 4.23 (s, 2H), 4.00 (dd, J=6.0, 4.0 Hz, 2H), 3.74 (dd, J=6.0, 4.1 Hz, 2H), 3.66 (s, 4H), 3.48 (t, J=6.1 Hz, 2H), 3.35 (s, 4H), 1.96 (t, J=6.5 Hz, 2H).

Example 21: (E)-3-(acetamidomethyl)-N-(1-(3-hydroxypropyl)-5-(3-oxomorpholino)-1H-benzo[d]imidazol-2(3H)-ylidene)benzamide (47)

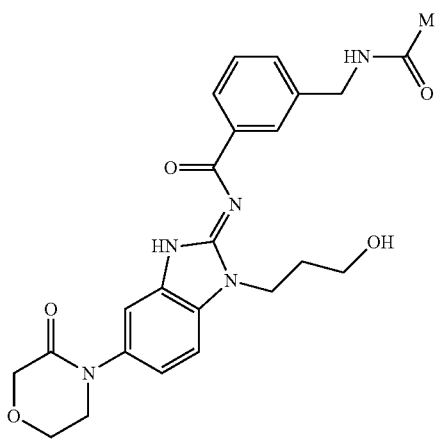

Prepared in an analogous fashion to Example 12, but using Intermediate acid 2 (1 eq.) in place of 3-hydroxymethyl-benzoic acid and PyBOP (1.1 eq.) in place of HBTU (32% yield). ESI+: M+1: 466. ¹H NMR (300 MHz, DMSO-d₆) δ 12.81 (s, 1H), 8.45 (t, J=5.9 Hz, 1H), 8.13 (s, 2H), 7.55 (d, J=9.0 Hz, 1H), 7.48 (d, J=3.0 Hz, 1H), 7.41 (m, 2H), 7.26 (dd, J=8.5, 2.0 Hz, 1H), 4.70 (t, J=5.2 Hz, 1H), 4.33 (m, 4H), 4.23 (s, 2H), 4.01 (t, J=5.1 Hz, 2H), 3.74 (t, J=5.1 Hz, 2H), 3.48 (q, J=5.9 Hz, 2H), 1.96 (t, J=6.7 Hz, 2H), 1.90 (s, 3H).

Example 22: (E)-3-fluoro-N-(1-(3-hydroxypropyl)-5-(3-oxomorpholino)-1H-benzo[d]imidazol-2(3H)-ylidene)benzamide (35)

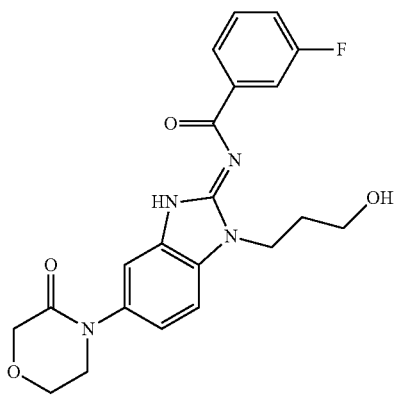

Prepared in an analogous fashion to Example 12, but using 3-fluoro-benzoic acid (1 eq.) in place of 3-hydroxymethyl-benzoic acid and PyBOP (1.1 eq.) in place of HBTU (48% yield). ESI+: M+1: 413. ¹H NMR (300 MHz, DMSO-d₆) δ 8.08 (dt, J=7.7, 1.2 Hz, 1H), 8.00-7.89 (m, 1H), 7.62-7.45 (m, 3H), 7.44-7.31 (m, 1H), 7.27 (dd, J=8.5, 2.0 Hz, 1H), 4.69 (t, J=5.1 Hz, 1H), 4.34 (t, J=6.8 Hz, 2H), 4.23 (s, 2H), 4.00 (dd, J=6.1, 4.0 Hz, 2H), 3.74 (t, J=5.1 Hz, 2H), 3.48 (q, J=6.0 Hz, 2H), 1.97 (q, J=6.4 Hz, 2H).

Example 23: (E)-3-cyano-N-(1-(3-hydroxypropyl)-5-(3-oxomorpholino)-1H-benzo[d]imidazol-2(3H)-ylidene)-4-methoxybenzamide (38)

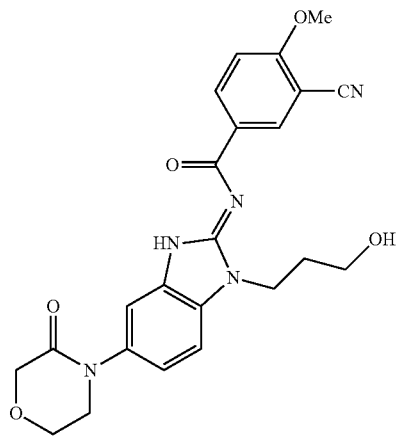 [SMILES: COc1ccc(C(=O)/N=c2\[nH]c3cc(N4CCOCC4=O)ccc3n2CCCO)cc1C#N]

Prepared in an analogous fashion to Example 12, but using Intermediate acid 3 (1.1 eq.) in place of 3-hydroxymethyl-benzoic acid and PyBOP (1.1 eq.) in place of HBTU (32% yield). ESI+: M+1: 450. ¹H NMR (300 MHz, DMSO-d₆) δ 12.82 (s, 1H), 8.49 (d, J=8.7 Hz, 2H), 7.61-7.44 (m, 2H), 7.40-7.21 (m, 2H), 4.69 (t, J=5.1 Hz, 1H), 4.34 (t, J=6.8 Hz, 2H), 4.23 (s, 2H), 3.74 (t, J=5.0 Hz, 2H), 3.48 (q, J=5.9 Hz, 2H), 3.35 (s, 4H), 1.95 (t, J=6.5 Hz, 2H).

Example 24: (E)-N-(1-(3-hydroxypropyl)-5-(3-oxomorpholino)-1H-benzo[d]imidazol-2(3H)-ylidene)-1H-benzo[d]imidazole-6-carboxamide (102)

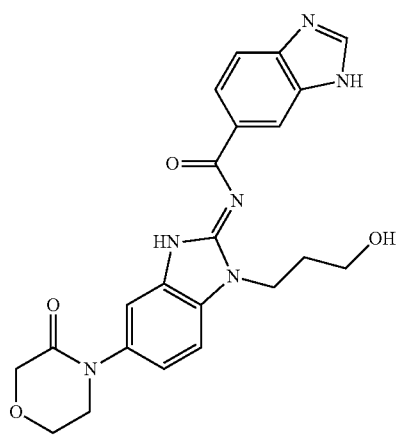

Prepared in an analogous fashion to Example 12, but using benzoimidazole-1,5-dicarboxylic acid 1-tert-butyl ester (1.1 eq.) in place of 3-hydroxymethyl-benzoic acid and PyBOP (1.1 eq.) in place of HBTU (47% yield). ESI+: M+1: 435. ¹H NMR (300 MHz, DMSO-d₆) δ 12.82 (s, 1H), 12.64 (s, 1H), 8.51 (s, 1H), 8.33 (s, 1H), 8.18 (d, J=8.6 Hz, 1H), 7.62 (s, 1H), 7.59-7.43 (m, 2H), 7.24 (dd, J=8.5, 2.0 Hz, 1H), 4.73 (t, J=5.2 Hz, 1H), 4.35 (t, J=6.7 Hz, 2H), 4.23 (s, 2H), 4.06-3.96 (m, 2H), 3.74 (t, J=5.1 Hz, 2H), 3.50 (d, J=5.3 Hz, 1H), 2.56 (d, J=8.2 Hz, 1H), 2.00 (dd, J=7.4, 5.5 Hz, 2H).

Example 25: (E)-3-(1,1-difluoroethyl)-N-(1-(3-hydroxypropyl)-5-(3-oxomorpholino)-1H-benzo[d]imidazol-2(3H)-ylidene)benzamide (103)

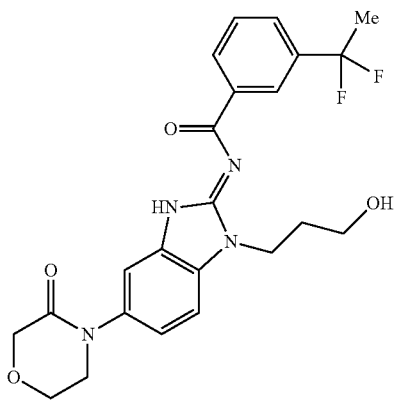

Prepared in an analogous fashion to Example 12, but using Intermediate acid 4 (1.1 eq.) in place of 3-hydroxymethyl-benzoic acid and PyBOP (1.1 eq.) in place of HBTU (35% yield). ESI+: M+1: 459. ¹H NMR (300 MHz, DMSO-d₆) δ 12.85 (s, 1H), 8.43-8.31 (m, 2H), 7.72 (d, J=7.8 Hz, 1H), 7.66-7.46 (m, 2H), 7.27 (dd, J=8.5, 2.0 Hz, 1H), 4.69 (t, J=5.1 Hz, 1H), 4.34 (t, J=6.9 Hz, 2H), 4.23 (s, 2H), 4.07-3.96 (m, 2H), 3.74 (t, J=5.0 Hz, 2H), 3.48 (q, J=5.9 Hz, 2H), 2.09-1.95 (m, 5H).

Example 26: (E)-3-(fluoromethyl)-N-(1-(3-hydroxypropyl)-5-(3-oxomorpholino)-1H-benzo[d]imidazol-2(3H)-ylidene)benzamide (104)

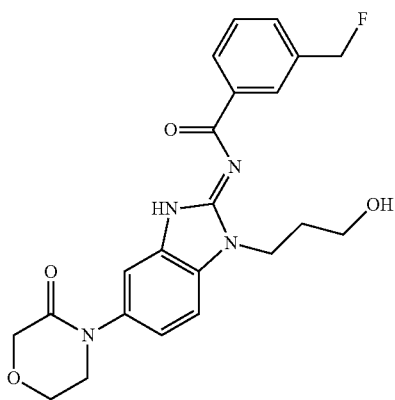

Prepared in an analogous fashion to Example 12, but using Intermediate acid 5 (1.1 eq.) in place of 3-hydroxymethyl-benzoic acid and PyBOP (1.1 eq.) in place of HBTU (22% yield). ESI+: M+1: 427. ¹H NMR (300 MHz, DMSO-d₆) δ 12.84 (s, 1H), 8.27 (dt, J=5.6, 1.8 Hz, 2H), 7.62-7.45 (m, 4H), 7.26 (dd, J=8.5, 2.0 Hz, 1H), 5.60 (s, 1H), 5.44 (s, 1H), 4.69 (t, J=5.1 Hz, 1H), 4.34 (t, J=6.8 Hz, 2H), 4.23 (s, 2H), 4.00 (dd, J=6.1, 4.0 Hz, 2H), 3.74 (dd, J=5.9, 4.2 Hz, 2H), 3.48 (q, J=5.9 Hz, 2H), 2.02-1.91 (m, 2H).

Example 27: (E)-N-(1-(3-hydroxypropyl)-5-(3-oxomorpholino)-1H-benzo[d]imidazol-2(3H)-ylidene)-3-methylbenzamide (105)

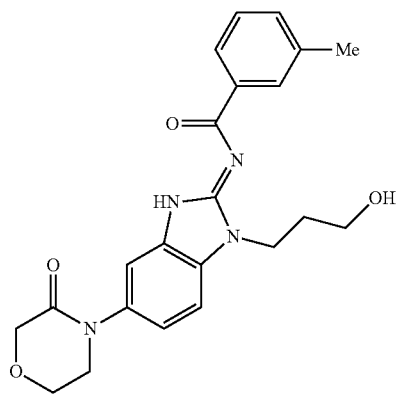

Prepared in an analogous fashion to Example 12, but using 3-methyl-benzoic acid (1.1 eq.) in place of 3-hydroxymethyl-benzoic acid and PyBOP (1.1 eq.) in place of HBTU (15% yield). ESI+: M+1: 409. ¹H NMR (300 MHz, DMSO-d₆) δ 12.81 (s, 1H), 8.05 (dd, J=5.7, 2.0 Hz, 2H), 7.59-7.44 (m, 2H), 7.42-7.30 (m, 2H), 7.25 (dd, J=8.5, 2.0 Hz, 1H), 4.71 (t, J=5.2 Hz, 1H), 4.32 (t, J=6.8 Hz, 2H), 4.23 (s, 2H), 4.05-3.95 (m, 2H), 3.74 (dd, J=6.0, 4.1 Hz, 2H), 3.48 (q, J=6.0 Hz, 2H), 2.39 (s, 3H), 2.02-1.91 (m, 2H).

Example 28: (E)-3-chloro-N-(1-(3-hydroxypropyl)-5-(3-oxomorpholino)-1H-benzo[d]imidazol-2(3H)-ylidene)benzamide (106)

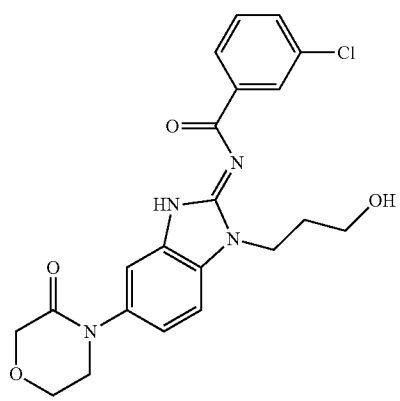

Prepared in an analogous fashion to Example 12, but using 3-chloro-benzoic acid (1.1 eq.) in place of 3-hydroxymethyl-benzoic acid and PyBOP (1.1 eq.) in place of HBTU (39% yield). ESI+: M+1: 429. ¹H NMR (300 MHz, DMSO-d₆) δ 12.87 (s, 1H), 8.24-8.15 (m, 2H), 7.65-7.45 (m, 4H), 7.27 (dd, J=8.6, 2.0 Hz, 1H), 4.70 (t, J=5.1 Hz, 1H), 4.34 (t, J=6.8 Hz, 2H), 4.23 (s, 2H), 4.05-3.95 (m, 2H), 3.74 (t, J=5.0 Hz, 2H), 3.54-3.34 (m, 3H), 1.96 (t, J=6.4 Hz, 2H).

Example 29: (E)-N-(1-(3-hydroxypropyl)-5-(3-oxo-morpholino)-1H-benzo[d]imidazol-2(3H)-ylidene)-3-(2-oxo-1,2-dihydropyridin-4-yl)benzamide (107)

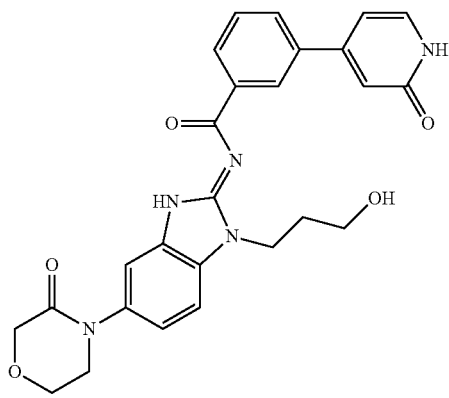 [SMILES: O=C(/N=c1\[nH]c2cc(N3CCOCC3=O)ccc2n1CCCO)c1cccc(-c2cc[nH]c(=O)c2)c1]

Prepared in an analogous fashion to Example 12, but using Intermediate acid 6 (1.1 eq.) in place of 3-hydroxymethyl-benzoic acid and PyBOP (1.1 eq.) in place of HBTU (18% yield). ESI+: M+1: 488. ¹H NMR (300 MHz, DMSO-d6) δ 12.87 (s, 1H), 11.70 (s, 1H), 8.50 (s, 1H), 8.32 (d, J=7.8 Hz, 1H), 7.86 (d, J=7.8 Hz, 1H), 7.66-7.46 (m, 4H), 7.27 (dd, J=8.5, 2.0 Hz, 1H), 6.66-6.53 (m, 2H), 4.73 (t, J=5.1 Hz, 1H), 4.35 (d, J=6.9 Hz, 2H), 4.23 (s, 2H), 4.01 (t, J=5.1 Hz, 2H), 3.75 (s, 2H), 3.74 (d, J=10.2 Hz, 1H), 3.49 (d, J=5.6 Hz, 2H), 1.97 (t, J=5.4 Hz, 2H).

Example 30: (E)-N-(1-(3-hydroxypropyl)-5-(3-oxo-morpholino)-1H-benzo[d]imidazol-2(3H)-ylidene)-3-(N-methylsulfamoyl)benzamide (97)

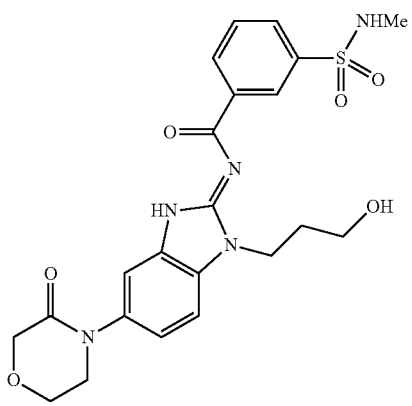 [SMILES: CNS(=O)(=O)c1cccc(C(=O)/N=c2\[nH]c3cc(N4CCOCC4=O)ccc3n2CCCO)c1]

Prepared in an analogous fashion to Example 1, but using 3-methylsulfamoyl-benzoic acid (1 eq.) in place of 3-trifluoromethyl-benzoic acid in Step 1. ESI+: M+1: 488. ¹H NMR (300 MHz, DMSO-d6) δ 12.88 (s, 1H), 8.60 (t, J=1.7 Hz, 1H), 8.55-8.46 (m, 1H), 7.96-7.86 (m, 1H), 7.72 (t, J=7.7 Hz, 1H), 7.65-7.48 (m, 3H), 7.28 (dd, J=8.5, 2.0 Hz, 1H), 4.68 (t, J=5.1 Hz, 1H), 4.35 (t, J=6.8 Hz, 2H), 4.23 (s, 2H), 4.06-3.96 (m, 2H), 3.80-3.70 (m, 2H), 3.48 (q, J=6.0 Hz, 2H), 2.45 (d, J=5.0 Hz, 3H), 1.97 (p, J=6.7 Hz, 2H).

Example 31: (E)-N-(1-(3-hydroxypropyl)-5-(3-oxo-morpholino)-1H-benzo[d]imidazol-2(3H)-ylidene)-3-(methylsulfonyl)benzamide (82)

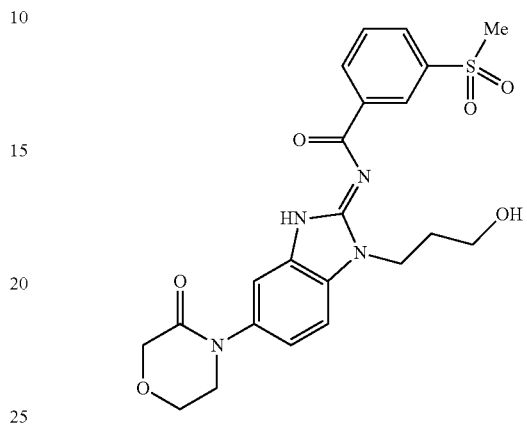

Prepared in an analogous fashion to Example 1, but using 3-methanesulfonyl-benzoic acid (1 eq.) in place of 3-trifluoromethyl-benzoic acid in Step 1. ESI+: M+1: 473. ¹H NMR (300 MHz, DMSO-d6) δ 12.90 (s, 1H), 8.69 (s, 1H), 8.57 (d, J=7.7 Hz, 1H), 8.09 (d, J=7.7 Hz, 1H), 7.78 (t, J=7.9 Hz, 1H), 7.64-7.49 (m, 2H), 7.29 (d, J=8.5 Hz, 1H), 4.41-4.30 (m, 2H), 4.23 (s, 2H), 4.07-3.94 (m, 2H), 3.80-3.71 (m, 2H), 3.28 (s, 3H), 2.03-1.92 (m, 2H).

Example 32: (E)-N-(1-(3-hydroxypropyl)-5-(3-oxo-morpholino)-1H-benzo[d]imidazol-2(3H)-ylidene)-3-(1H-tetrazol-1-yl)benzamide (83)

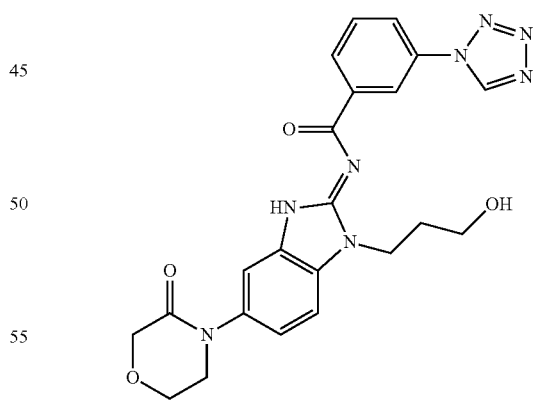

Prepared in an analogous fashion to Example 1, but using 3-tetrazol-1-yl-benzoic acid (1 eq.) in place of 3-trifluoromethyl-benzoic acid in Step 1. ESI+: M+1: 463. ¹H NMR (300 MHz, DMSO-d6) δ 12.95 (s, 1H), 10.21 (s, 1H), 8.68 (s, 1H), 8.42 (d, J=7.8 Hz, 1H), 8.08 (d, J=8.0 Hz, 1H), 7.78 (t, J=7.9 Hz, 1H), 7.65-7.49 (m, 2H), 7.30 (d, J=8.5 Hz, 1H), 4.37 (d, J=7.9 Hz, 2H), 4.24 (s, 2H), 3.80-3.70 (m, 2H), 3.55-3.44 (m, 2H), 2.01-1.95 (m, 2H).

Example 33: (E)-3-cyano-N-(1-(3-hydroxypropyl)-5-(3-oxomorpholino)-1H-benzo[d]imidazol-2(3H)-ylidene)benzamide (3)

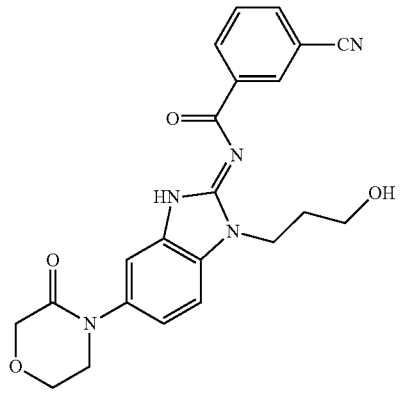

Prepared in an analogous fashion to Example 1, but using 3-cyano-benzoic acid (1 eq.) in place of 3-trifluoromethyl-benzoic acid in Step 1. ESI+: M+1: 420. $^1$H NMR (300 MHz, DMSO-d$_6$) δ 12.91 (s, 1H), 8.61-8.48 (m, 2H), 8.01 (dt, J=7.8, 1.4 Hz, 1H), 7.77-7.65 (m, 1H), 7.59 (d, J=8.6 Hz, 1H), 7.51 (d, J=1.9 Hz, 1H), 7.28 (dd, J=8.5, 2.0 Hz, 1H), 4.69 (t, J=5.1 Hz, 1H), 4.36 (t, J=6.8 Hz, 2H), 4.23 (s, 2H), 4.06-3.96 (m, 2H), 3.79-3.69 (m, 2H), 3.48 (q, J=5.9 Hz, 2H), 1.97 (p, J=6.5 Hz, 2H).

Example 34: (E)-N-(1-(3-hydroxypropyl)-5-(3-oxomorpholino)-1H-benzo[d]imidazol-2(3H)-ylidene)-3-(4H-1,2,4-triazol-4-yl)benzamide (2)

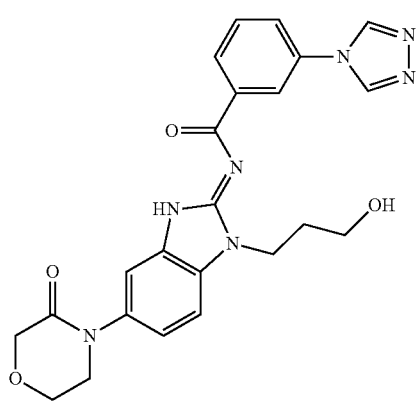 [SMILES: O=C(/N=c1\[nH]c2cc(N3CCOCC3=O)ccc2n1CCCO)c1cccc(-n2cnnc2)c1]

Prepared in an analogous fashion to Example 1, but using 3-(1,2,4)triazol-4-yl-benzoic acid (1 eq.) in place of 3-trifluoromethyl-benzoic acid in Step 1. ESI+: M+1: 462. $^1$H NMR (300 MHz, DMSO-d$_6$) δ 12.87 (s, 1H), 9.21 (s, 2H), 8.48-8.40 (m, 1H), 8.29 (d, J=7.7 Hz, 1H), 7.90-7.81 (m, 1H), 7.68 (t, J=7.9 Hz, 1H), 7.59 (d, J=8.6 Hz, 1H), 7.51 (d, J=2.0 Hz, 1H), 7.28 (dd, J=8.5, 2.0 Hz, 1H), 4.75 (t, J=4.4 Hz, 1H), 4.38 (t, J=6.7 Hz, 2H), 4.23 (s, 2H), 4.06-3.96 (m, 2H), 3.80-3.70 (m, 2H), 3.54-3.45 (m, 2H), 2.02-1.91 (m, 2H).

Example 35: (E)-N-(1-(3-hydroxypropyl)-5-(3-oxomorpholino)-1H-benzo[d]imidazol-2(3H)-ylidene)-6-(trifluoromethyl)picolinamide (84)

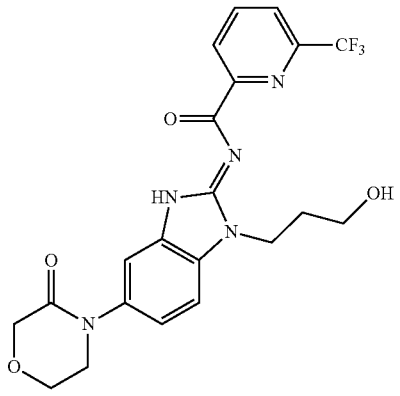

Prepared in an analogous fashion to Example 1, but using 6-trifluoromethyl-pyridine-2-carboxylic acid (1 eq.) in place of 3-trifluoromethyl-benzoic acid in Step 1. ESI+: M+1: 464. $^1$H NMR (300 MHz, DMSO-d$_6$) δ 12.92 (s, 1H), 8.57 (d, J=7.7 Hz, 1H), 8.24 (t, J=7.7 Hz, 1H), 8.03 (d, J=7.7 Hz, 1H), 7.66-7.52 (m, 2H), 7.30 (dd, J=8.5, 2.0 Hz, 1H), 4.87-4.80 (m, 1H), 4.38-4.32 (m, 2H), 4.23 (s, 2H), 4.06-3.96 (m, 2H), 3.81-3.70 (m, 2H), 3.47-3.38 (m, 2H), 1.98-1.87 (m, 2H).

Example 36: (E)-N-(1-(3-hydroxypropyl)-5-(3-oxomorpholino)-1H-benzo[d]imidazol-2(3H)-ylidene)-5-(trifluoromethyl)nicotinamide (85)

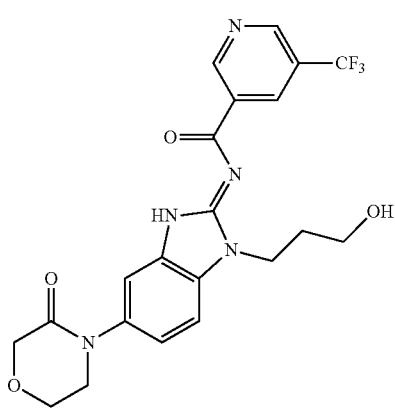 [SMILES: O=C(/N=c1\[nH]c2cc(N3CCOCC3=O)ccc2n1CCCO)c1cncc(C(F)(F)F)c1]

Prepared in an analogous fashion to Example 1, but using 5-trifluoromethyl-nicotinic acid (1 eq.) in place of 3-trifluoromethyl-benzoic acid in Step 1. ESI+: M+1: 464. $^1$H NMR (300 MHz, DMSO-d$_6$) δ 12.94 (s, 1H), 9.65 (d, J=1.8 Hz, 1H), 9.18-9.10 (m, 1H), 8.78-8.71 (m, 1H), 7.62 (d, J=8.6 Hz, 1H), 7.53 (d, J=2.0 Hz, 1H), 7.31 (dd, J=8.6, 2.0 Hz, 1H), 4.69 (t, J=5.0 Hz, 1H), 4.38 (t, J=6.9 Hz, 2H), 4.23 (s, 2H), 4.06-3.96 (m, 2H), 3.80-3.70 (m, 2H), 3.49 (q, J=5.8 Hz, 2H), 2.02-1.91 (m, 2H).

Example 37: (E)-N-(1-(3-hydroxypropyl)-5-(2-oxooxazolidin-3-yl)-1H-benzo[d]imidazol-2(3H)-ylidene)-3-(trifluoromethyl)benzamide (8)

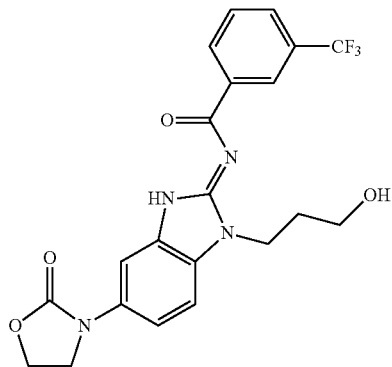

In a sealable glass reaction vessel equipped with a Teflon-coated screw cap was dissolved Intermediate 2-CF$_3$ (1 eq) in dichloroethane (0.15 M). To this was then added sequentially 2-chloroethyl carbonochloridate (1 eq.) and pyridine (1.6 eq.). The resulting solution was allowed to first stir at RT for 14 h and then at 50° C. for 24 h. Finally, potassium carbonate (6 eq.) and methanol (300 eq.) were added to the reaction mixture and the reaction suspension was allowed to stir at RT for another 24 h. The insoluble were removed via vacuum filtration and the filtrate was directly subjected to purification by way of column chromatography (SiO$_2$, gradient elution, EtOAc→8:1 (v/v) EtOAc:MeOH) to furnish the title compound as a white solid (45% yield). ESI$^+$: M+1: 449. $^1$H NMR (300 MHz, acetone-d$_6$) δ12.63 (s, 1H), 8.63-8.53 (m, 2H), 8.01 (s, 1H), 7.85 (d, J=7.7 Hz, 1H), 7.70 (t, J=7.7 Hz, 1H), 7.63-7.49 (m, 2H), 4.59-4.43 (m, 4H), 4.21 (dd, J=9.0, 6.8 Hz, 2H), 3.60 (t, J=5.9 Hz, 2H), 2.17-2.01 (m, 2H).

Example 38: (E)-3-cyano-N-(1-(3-hydroxypropyl)-5-(2-oxooxazolidin-3-yl)-1H-benzo[d]imidazol-2(3H)-ylidene)benzamide (11)

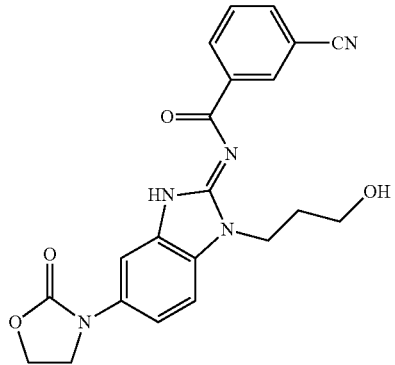 [SMILES: N#Cc1cccc(C(=O)/N=c2\[nH]c3cc(N4CCOC4=O)ccc3n2CCCO)c1]

Prepared in an analogous fashion to Example 37, but using Intermediate 2-CN (1 eq.) in place of intermediate 2-CF$_3$. ESI$^+$: M+1: 406. $^1$H NMR (300 MHz, DMSO-d$_6$) δ 12.80 (s, 1H), 8.57-8.52 (m, 1H), 8.52-8.47 (m, 1H), 8.02-7.90 (m, 1H), 7.83 (d, J=2.1 Hz, 1H), 7.68 (t, J=7.8 Hz, 1H), 7.54 (d, J=8.8 Hz, 1H), 7.41 (dd, J=8.8, 2.2 Hz, 1H), 4.76-4.62 (m, 1H), 4.49-4.39 (m, 2H), 4.32 (t, J=6.8 Hz, 2H), 4.13-3.93 (m, 2H), 3.51-3.40 (m, 2H), 2.00-1.86 (m, 2H).

Example 39: (E)-N-(1-(3-hydroxypropyl)-5-(2-oxo-1,3-oxazinan-3-yl)-1H-benzo[d]imidazol-2(3H)-ylidene)-3-(trifluoromethyl)benzamide (33)

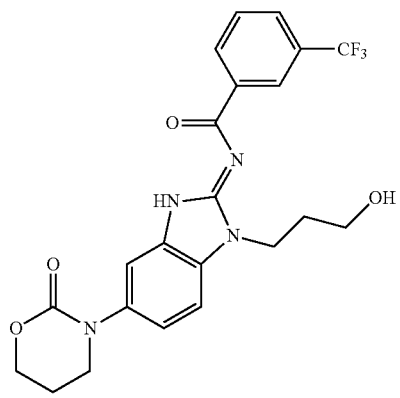

Prepared in an analogous fashion to Example 37, but using 3-chloropropyl carbonochloridate (1 eq.) in place of 2-chloroethyl carbonochloridate. ESI$^+$: M+1: 463. $^1$H NMR (300 MHz, CDCl$_3$) δ 12.53 (s, 1H), 8.55-8.39 (m, 2H), 7.76 (d, J=7.7 Hz, 1H), 7.59 (t, J=7.8 Hz, 1H), 7.38-7.23 (m, 4H), 4.47 (q, J=5.3, 4.5 Hz, 5H), 3.73 (t, J=6.1 Hz, 2H), 3.48 (s, 2H), 2.24 (p, J=5.9 Hz, 2H), 2.04 (s, 2H).

Example 40: (E)-3-(difluoromethyl)-N-(1-(3-hydroxypropyl)-5-(2-oxo-1,3-oxazinan-3-yl)-1H-benzo[d]imidazol-2(3H)-ylidene)benzamide (29)

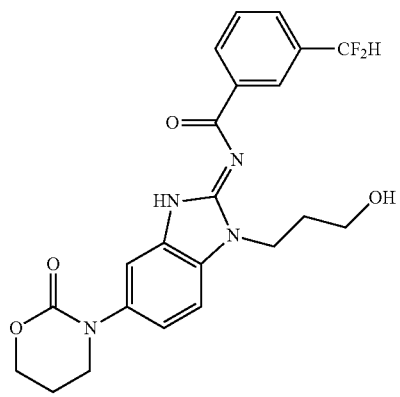 [SMILES: O=C(/N=c1\[nH]c2cc(N3CCCOC3=O)ccc2n1CCCO)c1cccc(C(F)F)c1]

Prepared in an analogous fashion to Example 37, but using Intermediate 2-CF$_2$H (1 eq.) in place of Intermediate 2-CF$_3$, and 3-chloropropyl carbonochloridate (1 eq.) in place of 2-chloroethyl carbonochloridate. ESI$^+$: M+1: 445. $^1$H NMR (300 MHz, CDCl$_3$) δ 12.56 (s, 1H), 8.41-8.32 (m, 2H), 7.67 (d, J=7.7 Hz, 1H), 7.56 (t, J=7.8 Hz, 1H), 7.38-7.28 (m, 3H), 6.73 (t, J=56.3 Hz, 1H), 4.63-4.56 (m, 1H), 4.51-4.40 (m, 4H), 3.75-3.66 (m, 2H), 3.50-3.44 (m, 2H), 2.27-2.18 (m, 2H), 2.08-2.01 (m, 2H).

Example 41: (E)-3-cyano-N-(1-(3-hydroxypropyl)-5-(2-oxo-1,3-oxazinan-3-yl)-1H-benzo[d]imidazol-2(3H)-ylidene)benzamide (58)

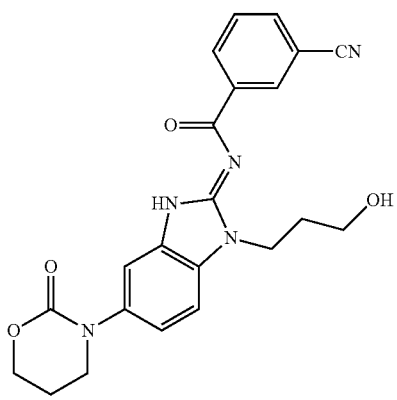

Prepared in an analogous fashion to Example 37, but using Intermediate 2-CN (1 eq.) in place of Intermediate 2-CF$_3$, and 3-chloropropyl carbonochloridate (1 eq.) in place of 2-chloroethyl carbonochloridate. ESI$^+$: M+1: 420. $^1$H NMR (300 MHz, DMSO-d$_6$) δ 12.87 (s, 1H), 8.58-8.46 (m, 2H), 7.98 (d, J=7.6 Hz, 1H), 7.69 (t, J=7.7 Hz, 1H), 7.53 (d, J=8.6 Hz, 1H), 7.45 (s, 1H), 7.24 (d, J=8.6 Hz, 1H), 4.70-4.63 (m, 1H), 4.37-4.31 (m, 4H), 3.67-3.60 (m, 2H), 3.51-3.41 (m, 2H), 2.10 (s, 2H), 1.93 (s, 2H).

Example 42: (E)-N-(1-(3-hydroxypropyl)-5-(2-oxo-tetrahydropyrimidin-1(2H)-yl)-1H-benzo[d]imidazol-2(3H)-ylidene)-3-(trifluoromethyl)benzamide (1)

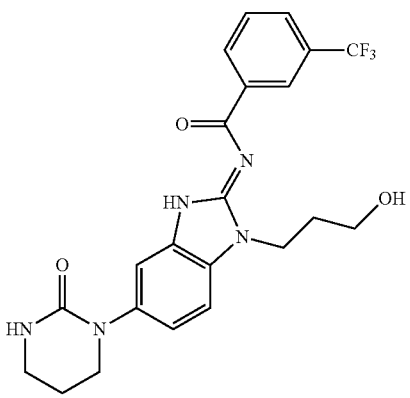 [SMILES: O=C(/N=c1\[nH]c2cc(N3CCCNC3=O)ccc2n1CCCO)c1cccc(C(F)(F)F)c1]

In a sealable glass reaction vessel equipped with a Teflon-coated screw cap was dissolved Intermediate 2-CF$_3$ (1 eq.) in dichloroethane (0.1 M). To this was then added 1-chloro-3-isocyanato-propane (1.1 eq.) and the resulting mixture was heated at 50° C. for 24 h. The volatiles were then removed in vacuo and the resulting residue was taken up in THF (0.1 M). To this was then added potassium tert-butoxide (5 eq.) and the resulting mixture was stirred at RT for 48 h. The reaction was then quenched with the addition of sat. aq. NH$_4$Cl and extracted with EtOAc. The combined organic extracts were dried over MgSO$_4$, filtered and the filtrate concentrated in vacuo. Purification by way of high pressure liquid chromatography (C$_{18}$, gradient elution, 3:7 (v/v) H$_2$O:MeCN+0.1% TFA→2:3 (v/v) H$_2$O:MeCN+0.1% TFA) furnished the title compound as a white solid (35% yield). ESI$^+$: M+1: 462. $^1$H NMR (300 MHz, DMSO-d$_6$) δ 12.79 (s, 1H), 8.57-8.48 (m, 2H), 7.90 (d, J=7.8 Hz, 1H), 7.73 (t, J=7.7 Hz, 1H), 7.52-7.40 (m, 2H), 7.18 (dd, J=8.5, 2.0 Hz, 1H), 6.64-6.58 (m, 1H), 4.69 (t, J=5.1 Hz, 1H), 4.33 (t, J=6.8 Hz, 2H), 3.63 (t, J=5.7 Hz, 2H), 3.48 (q, J=5.9 Hz, 2H), 3.30-3.22 (m, 2H), 2.01-1.91 (m, 4H).

Example 43: (E)-3-(difluoromethyl)-N-(1-(3-hydroxypropyl)-5-(2-oxotetrahydropyrimidin-1(2H)-yl)-1H-benzo[d]imidazol-2(3H)-ylidene)benzamide (46)

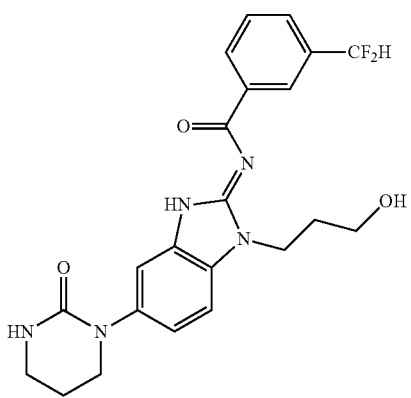 [SMILES: O=C(/N=c1\[nH]c2cc(N3CCCNC3=O)ccc2n1CCCO)c1cccc(C(F)F)c1]

Prepared in an analogous fashion to Example 42, but using Intermediate 2-CF$_2$H (1 eq.) in place of intermediate 2-CF$_3$. ESI$^+$: M+1: 444. $^1$H NMR (300 MHz, DMSO-d$_6$) δ 12.74 (s, 1H), 8.41-8.34 (m, 2H), 7.75-7.66 (m, 1H), 7.66-7.56 (m, 1H), 7.49-7.36 (m, 2H), 7.35-6.90 (m, 2H), 6.57 (s, 1H), 4.70-4.63 (m, 1H), 4.33-4.27 (m, 2H), 3.63-3.57 (m, 2H), 3.48-3.42 (m, 2H), 3.26-3.20 (m, 2H), 1.98-1.91 (m, 4H).

Example 44: (E)-N-(1-(3-hydroxypropyl)-5-(2-oxopiperazin-1-yl)-1H-benzo[d]imidazol-2(3H)-ylidene)-3-(trifluoromethyl)benzamide (108)

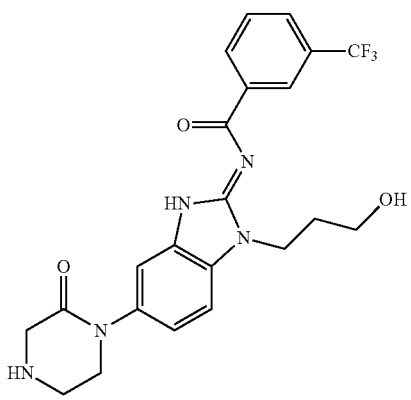

In a glass RBF equipped with a Teflon-coated magnetic stirrer was dissolved Intermediate 3-CF$_3$ (1 eq.) in methanol (0.025 M). To this was then added potassium carbonate (3 eq.) and the resulting suspension was stirred at RT for 16 h. The volatiles were then removed in vacuo and the resulting residue was partitioned between water and dichloromethane. The aqueous layer was separated and back-extracted with dichloromethane. The combined organic extracts were washed further with water and brine, dried over MgSO$_4$ and filtered. Concentration of the in vacuo furnished the title compound as an off-white foam (80% yield). ESI$^+$: M+1: 462. $^1$H NMR (300 MHz, CDCl$_3$) δ 12.57 (s, 1H), 8.54-8.38 (m, 2H), 7.75 (d, J=7.9 Hz, 1H), 7.58 (t, J=7.9 Hz, 1H), 7.40-7.23 (m, 3H), 4.52-4.42 (m, 2H), 3.77-3.63 (m, 4H), 3.53-3.42 (m, 2H), 3.29-3.19 (m, 2H), 2.07-1.97 (m, 3H), 1.94-1.68 (m, 1H).

Example 45: (E)-3-(difluoromethyl)-N-(1-(3-hydroxypropyl)-5-(2-oxopiperazin-1-yl)-1H-benzo[d]imidazol-2(3H)-ylidene)benzamide (109)

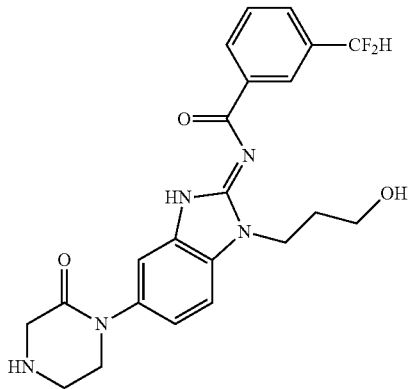 [SMILES: O=C(/N=c1\[nH]c2cc(N3CCNCC3=O)ccc2n1CCCO)c1cccc(C(F)F)c1]

Prepared in an analogous fashion to Example 44, but using Intermediate 3-CF$_2$H (1 eq.) in place of Intermediate 3-CF$_3$. ESI$^+$: M+1: 444. $^1$H NMR (300 MHz, CDCl$_3$) δ 12.81 (s, 1H), 8.47-8.39 (m, 2H), 7.71 (d, J=7.7 Hz, 1H), 7.66-7.54 (m, 1H), 7.38-7.27 (m, 3H), 6.77 (t, J=56.4 Hz, 1H), 4.54-4.43 (m, 2H), 3.71 (s, 2H), 3.64-3.44 (m, 4H), 3.25-3.15 (m, 2H), 2.11-1.99 (m, 2H).

Example 46: (E)-N-(5-(4-acetyl-2-oxopiperazin-1-yl)-(1-(3-hydroxypropyl)-1H-benzo[d]imidazol-2(3H)-ylidene))-3-(difluoromethyl)benzamide (110)

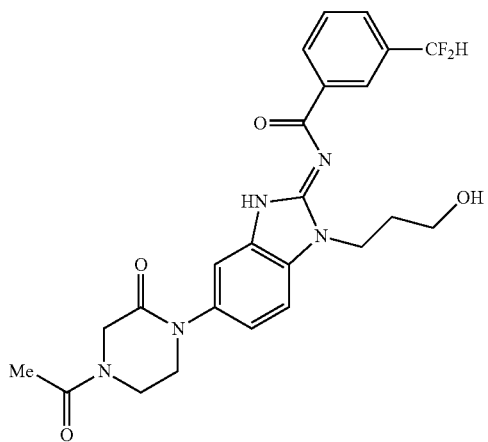 [SMILES: CC(=O)N1CCN(c2ccc3c(c2)[nH]/c(=N\C(=O)c2cccc(C(F)F)c2)n3CCCO)C(=O)C1]

Step 1: (E)-3-(5-(4-acetyl-2-oxopiperazin-1-yl)-2-((3-(difluoromethyl)benzoyl)imino)-2,3-dihydro-1H-benzo[d]imidazol-1-yl)propyl acetate In a glass RBF equipped with a Teflon-coated magnetic stirrer was dissolved Intermediate 3-CF$_2$H (1 eq.) in pyridine (0.03 M). To this was then added acetic anhydride (2 eq.) and the resulting solution was stirred at RT for 16 h. The volatiles were then removed in vacuo and the resulting residue was partitioned between 10% aq. NaHCO$_3$ and EtOAc. The aqueous layer was separated and back-extracted with EtOAc. The combined organic extracts were washed further with water and brine, dried over Na$_2$SO$_4$, filtered and the filtrate concentrated in vacuo. Purification by way of column chromatography (SiO$_2$, gradient elution, 2:1 (v/v) Hex:EtOAc→EtOAc) furnished the desired product compound as a viscous oil (99% yield).

Step 2: (E)-N-(5-(4-acetyl-2-oxopiperazin-1-yl)-(1-(3-hydroxypropyl)-1H-benzo[d]imidazol-2(3H)-ylidene))-3-(difluoromethyl)benzamide In a glass RBF equipped with a Teflon-coated magnetic stirrer was dissolved (E)-3-(5-(4-acetyl-2-oxopiperazin-1-yl)-2-((3-(difluoromethyl)benzoyl)imino)-2,3-dihydro-1H-benzo[d]imidazol-1-yl)propyl acetate (1 eq.) from the previous step in methanol (0.02 M). To this was then added potassium carbonate (3 eq.) and the resulting suspension was stirred at RT for 4 h. The volatiles were then removed in vacuo and the resulting residue was partitioned between water and dichloromethane. The aqueous layer was separated and back-extracted with dichloromethane. The combined organic extracts were washed further with water and brine, dried over Na$_2$SO$_4$, filtered and the filtrate concentrated in vacuo. Purification by way of column chromatography (SiO$_2$, gradient elution, EtOAc→4:1 (v/v) EtOAc:MeOH) furnished the desired product compound as a white solid (87% yield). ESI$^+$: M+1: 486. $^1$H NMR (300 MHz, CDCl$_3$) δ 12.60 (s, 1H), 8.40-8.34 (m, 2H), 7.72-7.63 (m, 1H), 7.62-7.51 (m, 1H), 7.38-7.18 (m, 3H), 6.73 (t, J=56.4 Hz, 1H), 4.61-4.54 (m, 1H), 4.54-4.29 (m, 4H), 4.05-3.69 (m, 4H), 3.51-3.45 (m, 2H), 2.19 (s, 3H), 2.07-2.01 (m, 2H).

Example 47: (E)-3-(difluoromethyl)-N-(1-(3-hydroxypropyl)-5-(4-methyl-2-oxopiperazin-1-yl)-1H-benzo[d]imidazol-2(3H)-ylidene)benzamide (111)

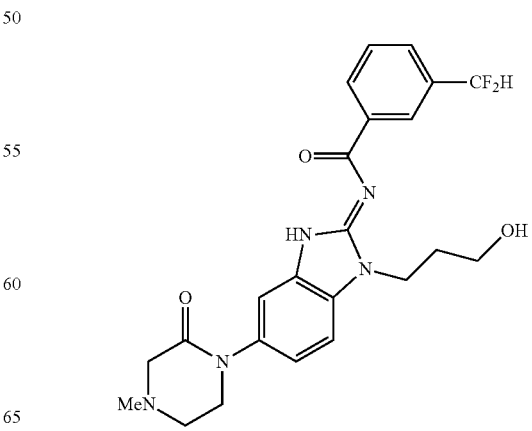

Step 1: (E)-3-(2-((3-(difluoromethyl)benzoyl)imino)-5-(4-methyl-2-oxopiperazin-1-yl)-2,3-dihydro-1H-benzo[d]imidazol-1-yl)propyl acetate In a glass RBF equipped with a Teflon-coated magnetic stirrer was dissolved Intermediate 3-CF$_2$H (1 eq.) in methanol (0.08 M). To this was then added formaldehyde (5.5 eq., 37% aqueous solution) and glacial acetic acid (4 eq.), and the resulting solution was stirred at RT for 30 min. Finally, sodium cyanoborohydride (2 eq.) was added in one rapid portion and the resulting mixture was allowed to stir at RT for another 1.5 h. The volatiles were removed in vacuo and the resulting residue was partitioned between 10% aq. NaHCO$_3$ and EtOAc. The aqueous layer was separated and back-extracted with EtOAc. The combined organic extracts were washed further with water and brine, dried over Na$_2$SO$_4$, filtered and the filtrate concentrated in vacuo. Purification by way of column chromatography (SiO$_2$, gradient elution, 2:1 (v/v) Hex:EtOAc→EtOAc) furnished the desired product compound as a viscous oil (99% yield).

Step 2: (E)-3-(difluoromethyl)-N-(1-(3-hydroxypropyl)-5-(4-methyl-2-oxopiperazin-1-yl)-1H-benzo[d]imidazol-2(3H)-ylidene)benzamide In a glass RBF equipped with a Teflon-coated magnetic stirrer was dissolved (E)-3-(2-((3-(difluoromethyl)benzoyl)imino)-5-(4-methyl-2-oxopiperazin-1-yl)-2,3-dihydro-1H-benzo[d]imidazol-1-yl)propyl acetate (1 eq.) from the previous step in methanol (0.04 M). To this was then added potassium carbonate (3 eq.) and the resulting suspension was stirred at RT for 16 h. The volatiles were then removed in vacuo and the resulting residue was partitioned between water and dichloromethane. The aqueous layer was separated and back-extracted with dichloromethane. The combined organic extracts were washed further with water and brine, dried over Na$_2$SO$_4$, filtered and the filtrate concentrated in vacuo. Purification by way of column chromatography (SiO$_2$, gradient elution, EtOAc→4:1 (v/v) EtOAc: MeOH) furnished the desired product compound as a white solid (84% yield). ESI$^+$: M+1: 458. $^1$H NMR (300 MHz, CDCl$_3$) δ 12.52 (s, 1H), 8.39-8.33 (m, 2H), 7.72-7.63 (m, 1H), 7.62-7.52 (m, 1H), 7.39-7.22 (m, 3H), 6.73 (t, J=56.3 Hz, 1H), 4.69-4.60 (m, 1H), 4.51-4.45 (m, 2H), 3.77-3.71 (m, 2H), 3.51-3.44 (m, 2H), 3.31 (s, 2H), 2.86-2.80 (m, 2H), 2.43 (s, 3H), 2.07-2.00 (m, 2H).

Example 48: (E)-N-(5-(4-(cyclopropylmethyl)-2-oxopiperazin-1-yl)-1-(3-hydroxypropyl)-1H-benzo[d]imidazol-2(3H)-ylidene)-3-(difluoromethyl)benzamide (112)

Prepared in an analogous fashion to Example 47, but using cyclopropanecarbaldehyde (1 eq.) in place of formaldehyde in step 1. ESI$^+$: M+1: 498. $^1$H NMR (300 MHz, CDCl$_3$) δ 12.53 (s, 1H), 8.39-8.33 (m, 2H), 7.72-7.63 (m, 1H), 7.62-7.50 (m, 1H), 7.39-7.29 (m, 2H), 7.31-7.22 (m, 1H), 6.73 (t, J=56.4 Hz, 1H), 4.70-4.64 (m, 1H), 4.51-4.44 (m, 2H), 3.78-3.71 (m, 2H), 3.48-3.41 (m, 4H), 2.96-2.89 (m, 2H), 2.45-2.36 (m, 2H), 2.06-2.00 (m, 2H), 0.95-0.88 (m, 1H), 0.65-0.56 (m, 2H), 0.23-0.15 (m, 2H).

Example 49: (E)-3-(difluoromethyl)-N-(1-(3-hydroxypropyl)-5-(2-oxo-4-(2,2,2-trifluoroethyl)piperazin-1-yl)-1H-benzo[d]imidazol-2(3H)-ylidene)benzamide (113)

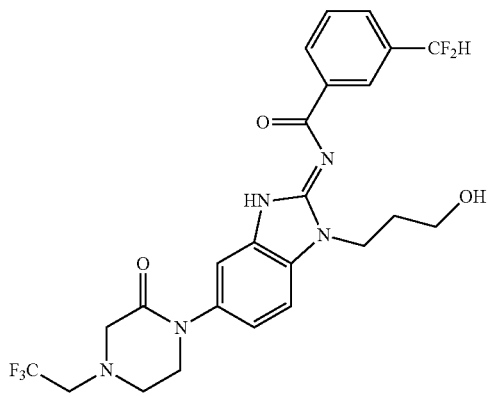 [SMILES: O=C(/N=c1\[nH]c2cc(N3CCN(CC(F)(F)F)CC3=O)ccc2n1CCCO)c1cccc(C(F)F)c1]

Prepared in an analogous fashion to Example 47, but using 1-ethoxy-2,2,2-trifluoro-ethanol (2 eq.) in place of formaldehyde, and trifluoroacetic acid (0.1 M) in place of methanol in step 1. ESI$^+$: M+1: 526. $^1$H NMR (300 MHz, CDCl$_3$) δ 12.70 (s, 1H), 8.44-8.36 (m, 2H), 7.74-7.65 (m, 1H), 7.64-7.53 (m, 1H), 7.39-7.22 (m, 3H), 6.75 (t, J=56.4 Hz, 1H), 4.72-4.65 (m, 1H), 4.56-4.39 (m, 2H), 3.70-3.56 (m, 4H), 3.51-3.45 (m, 2H), 3.23-3.02 (m, 4H), 2.07-2.01 (m, 2H).

Example 50: (R,E)-N-(1-(4-hydroxybutan-2-yl)-5-(2-oxo-1,3-oxazinan-3-yl)-1H-benzo[d]imidazol-2(3H)-ylidene)-3-(trifluoromethyl)benzamide (43)

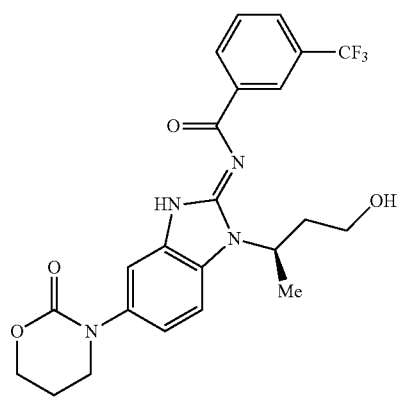

In a glass RBF equipped with a Teflon-coated magnetic stirrer was dissolved Intermediate 4-CF$_3$ (1 eq.) in methanol (0.02 M). To this was then added potassium carbonate (3 eq.) and the resulting suspension was stirred at RT for 16 h. The volatiles were then removed in vacuo and the resulting residue was partitioned between water and dichloromethane. The aqueous layer was separated and back-extracted with dichloromethane. The combined organic extracts were washed further with water and brine, dried over Na$_2$SO$_4$, filtered and the filtrate concentrated in vacuo. Purification by way of column chromatography (SiO$_2$, gradient elution, EtOAc→4:1 (v/v) EtOAc:MeOH) furnished the desired product compound as a white solid (79% yield). ESI$^+$: M+1: 477. $^1$H NMR (300 MHz, DMSO-d$_6$) δ 12.90 (s, 1H), 8.52-8.42 (m, 2H), 7.88 (m, 1H), 7.62 (d, J=8.6 Hz, 1H), 7.48 (s, 1H), 7.21 (d, J=8.7 Hz, 1H), 5.24-5.17 (m, 1H), 4.57-4.50 (m, 1H), 4.39-4.30 (m, 2H), 3.68-3.61 (m, 2H), 2.53-2.46 (m, 1H), 2.40-2.33 (m, 1H), 1.61 (d, J=6.8 Hz, 3H).

Example 51: (R,E)-3-(difluoromethyl)-N-(1-(4-hydroxybutan-2-yl)-5-(2-oxo-1,3-oxazinan-3-yl)-1H-benzo[d]imidazol-2(3H)-ylidene)benzamide (44)

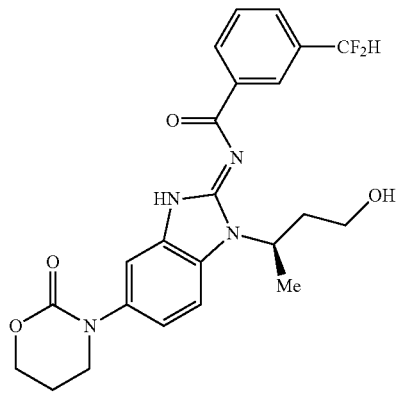

Prepared in an analogous fashion to Example 50, but using Intermediate 4-CF$_2$H (1 eq.) in place of Intermediate 4-CF$_3$. ESI$^+$: M+1: 459. $^1$H NMR (300 MHz, CDCl$_3$) δ 12.67 (s, 1H), 8.42-8.35 (m, 2H), 7.72-7.63 (m, 1H), 7.62-7.53 (m, 1H), 7.49-7.39 (m, 1H), 7.35-7.23 (m, 2H), 6.74 (t, J=56.3 Hz, 1H), 4.48-4.41 (m, 2H), 3.85-3.79 (m, 1H), 3.72-3.65 (m, 2H), 3.62-3.55 (m, 1H), 3.22-3.15 (m, 1H), 2.25-2.19 (m, 2H), 2.18-2.12 (m, 2H), 1.78 (d, J=7.1 Hz, 3H).

Example 52: (R,E)-3-cyano-N-(1-(4-hydroxybutan-2-yl)-5-(2-oxo-1,3-oxazinan-3-yl)-1H-benzo[d]imidazol-2(3H)-ylidene)benzamide (42)

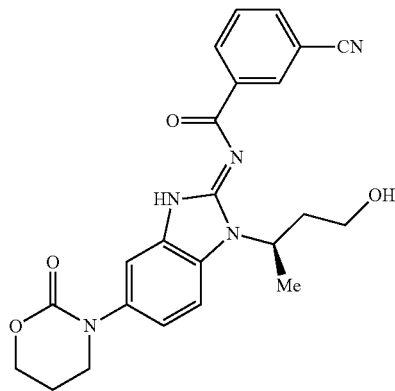

Prepared in an analogous fashion to Example 50, but using Intermediate 4-CN (1 eq.) in place of Intermediate 4-CF$_3$. ESI$^+$: M+1: 434. $^1$H NMR (300 MHz, DMSO-d$_6$) δ 12.91 (s, 1H), 8.53-8.43 (m, 2H), 7.99 (d, J=7.5 Hz, 1H), 7.76-7.58 (m, 2H), 7.47 (s, 1H), 7.21 (d, J=8.6 Hz, 1H), 5.28-5.21 (m, 1H), 4.57-4.51 (m, 1H), 4.38-4.32 (m, 2H), 3.67-3.61 (m, 2H), 2.36-2.29 (m, 1H), 2.10 (s, 4H), 1.60 (d, J=6.8 Hz, 3H).

Example 53: (E)-N-(1-(1-(2-hydroxyethyl)cyclohexyl)-5-(3-oxomorpholino)-1H-benzo[d]imidazol-2(3H)-ylidene)-3-(trifluoromethyl)benzamide (114)

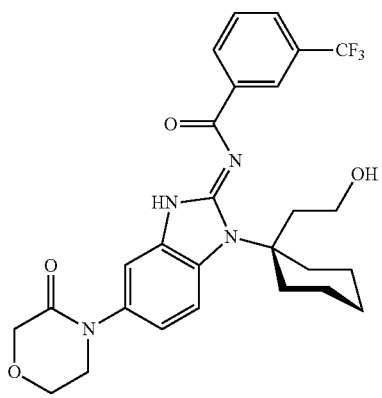

Prepared in an analogous fashion to Example 1, but using Intermediate 5 (1 eq.) in place of Intermediate 1-OTIPS in step 1. ESI$^+$: M+1: 531. $^1$H NMR (300 MHz, CDCl$_3$) δ 13.37 (s, 1H), 8.50 (s, 1H), 8.38 (d, J=7.8 Hz, 1H), 7.72 (dd, J=13.9, 8.4 Hz, 2H), 7.58 (t, J=7.8 Hz, 1H), 7.34-7.20 (m, 2H), 7.14 (dt, J=8.9, 2.1 Hz, 1H), 4.36 (d, J=1.9 Hz, 2H), 4.11-4.01 (m, 2H), 3.77 (dd, J=6.1, 4.0 Hz, 2H), 3.60 (s, 2H), 3.36 (d, J=12.9 Hz, 2H), 2.47 (t, J=6.5 Hz, 2H), 2.07 (d, J=13.4 Hz, 2H), 1.91 (s, br, 1H), 1.71 (s, br, 2H), 1.63 (s, br, 2H), 1.26 (d, J=3.1 Hz, 2H), 1.07-0.80 (m, 2H).

Example 54: (E)-3-(difluoromethyl)-N-(1-(1-(2-hydroxyethyl)cyclohexyl)-5-(3-oxomorpholino)-1H-benzo[d]imidazol-2(3H)-ylidene)benzamide (115)

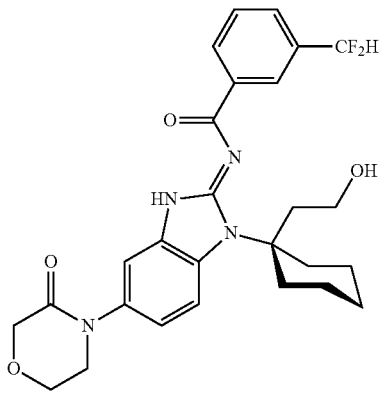

Prepared in an analogous fashion to Example 1, but using Intermediate 5 (1 eq.) in place of intermediate 1-OTIPS, and 3-difluoromethyl-benzoic acid (1 eq.) in place of 3-trifluoromethyl-benzoic acid in step 1. ESI+: M+1: 513. ¹H NMR (300 MHz, CDCl₃) δ 13.42 (s, 1H), 8.39-8.27 (m, 2H), 7.74-7.61 (m, 2H), 7.55 (t, J=7.6 Hz, 1H), 7.30 (d, J=2.2 Hz, 1H), 7.14 (dd, J=9.0, 2.2 Hz, 1H), 6.73 (t, J=56.4 Hz, 1H), 4.37 (s, 2H), 4.12-4.01 (m, 2H), 3.77 (dd, J=5.9, 4.2 Hz, 2H), 3.64-3.57 (m, 2H), 3.44-3.33 (m, 2H), 2.47 (t, J=6.5 Hz, 2H), 2.15-1.88 (m, 1H), 1.79-1.60 (m, 4H), 1.57-1.47 (m, 4H).

Example 55: (E)-N-(1-(1-(hydroxymethyl)cyclohexyl)-5-(3-oxomorpholino)-1H-benzo[d]imidazol-2(3H)-ylidene)-3-(trifluoromethyl)benzamide (39)

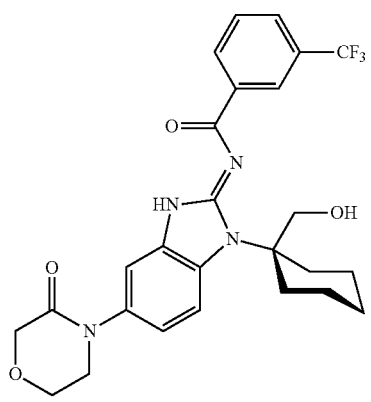

Prepared in an analogous fashion to Example 1, but using Intermediate 6 (1 eq.) in place of intermediate 1-OTIPS in step 1. ESI+: M+1: 517. ¹H NMR (300 MHz, CDCl₃) δ 13.54 (s, 1H), 8.15-7.98 (m, 2H), 7.78 (d, J=8.9 Hz, 1H), 7.50 (t, J=7.9 Hz, 1H), 7.36 (q, J=4.1, 3.4 Hz, 2H), 7.24 (dd, J=8.9, 2.1 Hz, 1H), 6.03 (t, J=7.8 Hz, 1H), 4.46 (d, J=7.5 Hz, 2H), 4.38 (s, 2H), 4.08 (t, J=5.0 Hz, 2H), 3.80 (t, J=5.1 Hz, 2H), 2.59 (s, 1H), 2.14 (d, J=13.8 Hz, 2H), 1.84 (d, J=11.6 Hz, 3H), 1.67 (d, J=18.8 Hz, 4H), 1.26 (d, J=3.1 Hz, 2H), 1.01-0.80 (m, 2H).

Example 56: rac-(E)-N-(1-((1S,2R)-2-(hydroxymethyl)cyclohexyl)-5-(3-oxomorpholino)-1H-benzo[d]imidazol-2(3H)-ylidene)-3-(trifluoromethyl)benzamide (116)

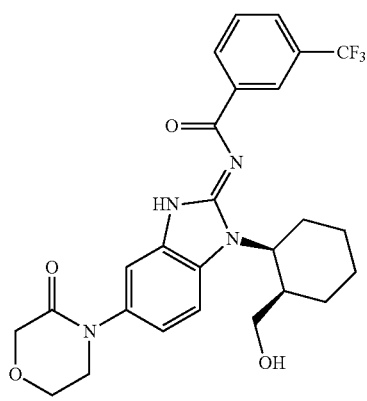 [SMILES: O=C(/N=c1\[nH]c2cc(N3CCOCC3=O)ccc2n1[C@H]1CCCC[C@H]1CO)c1cccc(C(F)(F)F)c1]

Prepared in an analogous fashion to Example 1, but using Intermediate 7 (1 eq.) in place of Intermediate 1-OTIPS in step 1. ESI+: M+1: 517. ¹H NMR (300 MHz, CDCl₃) δ 12.75 (s, 1H), 8.55 (s, 1H), 8.41 (d, J=7.8 Hz, 1H), 7.76 (d, J=7.7 Hz, 1H), 7.60 (t, J=7.8 Hz, 1H), 7.43 (d, J=8.7 Hz, 1H), 7.22 (dd, J=8.7, 2.0 Hz, 1H), 4.85 (d, J=12.7 Hz, 1H), 4.37 (s, 2H), 4.11-4.01 (m, 2H), 3.89-3.72 (m, 4H), 3.04 (d, J=13.1 Hz, 1H), 2.72 (s, 1H), 2.41 (s, 1H), 2.13 (d, J=9.5 Hz, 2H), 1.96 (d, J=12.2 Hz, 1H), 1.71 (s, 3H), 1.61 (s, 3H), 1.26 (d, J=3.4 Hz, 2H), 1.01-0.80 (m, 2H).

Example 57: rac-(E)-3-(difluoromethyl)-N-(1-((1S,2R)-2-(hydroxymethyl)cyclohexyl)-5-(3-oxomorpholino)-1H-benzo[d]imidazol-2(3H)-ylidene)benzamide (117)

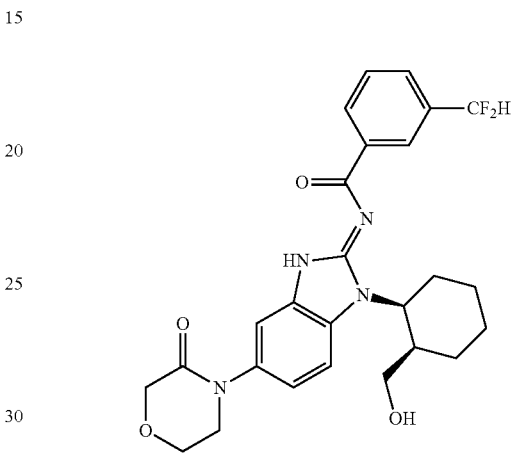

Prepared in an analogous fashion to Example 1, but using Intermediate 7 (1 eq.) in place of Intermediate 1-OTIPS, and 3-difluoromethyl-benzoic acid (1 eq.) in place of 3-trifluoromethyl-benzoic acid in step 1. ESI+: M+1: 499. ¹H NMR (300 MHz, CDCl₃) δ 12.82 (s, 1H), 8.44-8.31 (m, 2H), 7.67 (d, J=7.6 Hz, 1H), 7.57 (t, J=7.7 Hz, 1H), 7.41 (d, J=8.7 Hz, 1H), 7.33-7.17 (m, 4H), 4.83 (d, J=13.2 Hz, 1H), 4.37 (s, 2H), 4.05 (t, J=5.0 Hz, 2H), 3.85 (s, 2H), 3.76 (d, J=5.5 Hz, 1H), 3.07 (d, J=13.5 Hz, 1H), 2.40 (s, 1H), 2.13 (d, J=10.5 Hz, 2H), 1.95 (d, J=12.9 Hz, 1H), 1.75-0.80 (m, 4H).

Example 58: rac-(E)-N-(1-((1S,2S)-2-(hydroxymethyl)cyclohexyl)-5-(3-oxomorpholino)-1H-benzo[d]imidazol-2(3H)-ylidene)-3-(trifluoromethyl)benzamide (118)

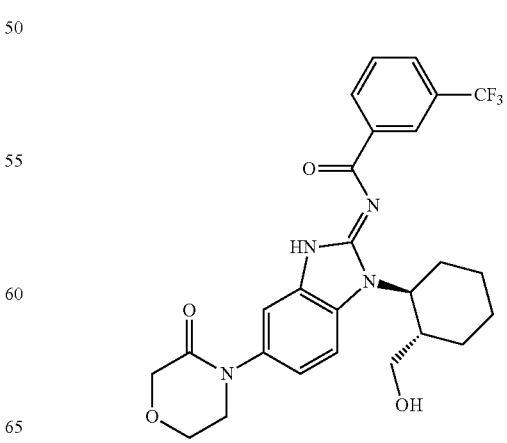

Prepared in an analogous fashion to Example 1, but using Intermediate 8 (1 eq.) in place of Intermediate 1-OTIPS in step 1. ESI+: M+1: 517. ¹H NMR (300 MHz, CDCl₃) δ 12.68 (s, 1H), 8.55-8.40 (m, 2H), 7.76 (d, J=7.7 Hz, 1H), 7.66-7.49 (m, 2H), 7.36 (s, 1H), 7.26 (s, 2H), 4.99 (s, 1H), 4.37 (s, 2H), 4.11-4.01 (m, 2H), 3.82-3.72 (m, 2H), 3.29 (s, 2H), 2.39 (d, J=13.7 Hz, 1H), 1.27 (s, 2H), 1.26 (d, J=2.7 Hz, 2H), 1.01-0.80 (m, 4H).

Example 59: rac-(E)-3-(difluoromethyl)-N-(1-((1S, 2S)-2-(hydroxymethyl)cyclohexyl)-5-(3-oxomorpholino)-1H-benzo[d]imidazol-2(3H)-ylidene)benzamide (119)

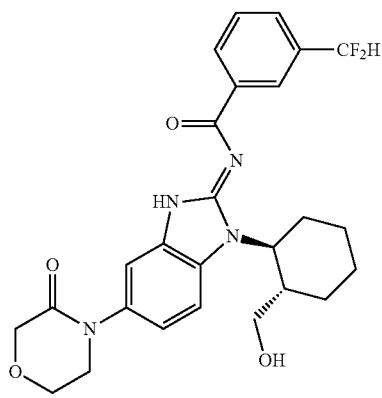 [SMILES: O=C(/N=c1\[nH]c2cc(N3CCOCC3=O)ccc2n1[C@H]1CCCC[C@@H]1CO)c1cccc(C(F)F)c1]

Prepared in an analogous fashion to Example 1, but using Intermediate 8 (1 eq.) in place of Intermediate 1-OTIPS, and 3-difluoromethyl-benzoic acid (1 eq.) in place of 3-trifluoromethyl-benzoic acid in step 1. ESI+: M+1: 499. ¹H NMR (300 MHz, CDCl₃) δ 12.72 (s, 1H), 8.38 (d, J=6.6 Hz, 2H), 7.73-7.49 (m, 3H), 7.34 (s, 1H), 7.30-7.17 (m, 3H), 6.74 (t, J=56.4 Hz, 1H), 4.99 (s, 1H), 4.37 (s, 2H), 4.05 (dd, J=5.9, 4.1 Hz, 2H), 3.91 (s, 1H), 3.80-3.70 (m, 2H), 3.29 (s, 2H), 2.39 (d, J=13.1 Hz, 1H), 2.04 (s, 3H), 2.02-1.86 (m, 4H), 1.61-0.80 (m, 6H).

Example 60: (E)-N-(1-(3-(hydroxymethyl)cyclohexyl)-5-(3-oxomorpholino)-1H-benzo[d]imidazol-2(3H)-ylidene)-3-(trifluoromethyl)benzamide (120)

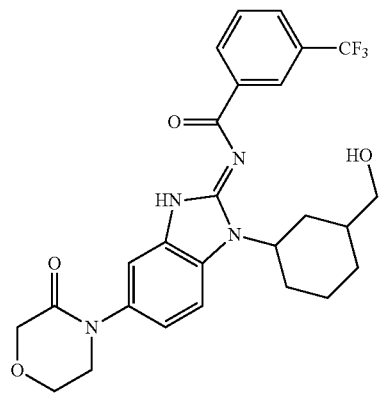 [SMILES: O=C(/N=c1\[nH]c2cc(N3CCOCC3=O)ccc2n1C1CCCC(CO)C1)c1cccc(C(F)(F)F)c1]

Prepared in an analogous fashion to Example 1, but using Intermediate 9 (1 eq.) in place of Intermediate 1-OTIPS in step 1. ESI+: M+1: 517. ¹H NMR (300 MHz, CDCl₃) δ 12.63 (s, 1H), 8.61 (s, 1H), 8.48 (d, J=7.8 Hz, 1H), 7.75 (d, J=7.7 Hz, 1H), 7.59 (t, J=7.7 Hz, 1H), 7.46 (d, J=8.6 Hz, 1H), 7.30 (d, J=2.0 Hz, 1H), 7.21 (dd, J=8.6, 2.0 Hz, 1H), 4.86 (s, 1H), 4.37 (s, 2H), 4.11-4.01 (m, 2H), 3.76 (dd, J=6.0, 4.1 Hz, 2H), 3.70-3.51 (m, 2H), 2.34 (d, J=13.2 Hz, 1H), 2.11-1.83 (m, 4H), 1.26-0.80 (m, 4H).

Example 61: (E)-3-(difluoromethyl)-N-(1-(3-(hydroxymethyl)cyclohexyl)-5-(3-oxomorpholino)-1H-benzo[d]imidazol-2(3H)-ylidene)benzamide (121)

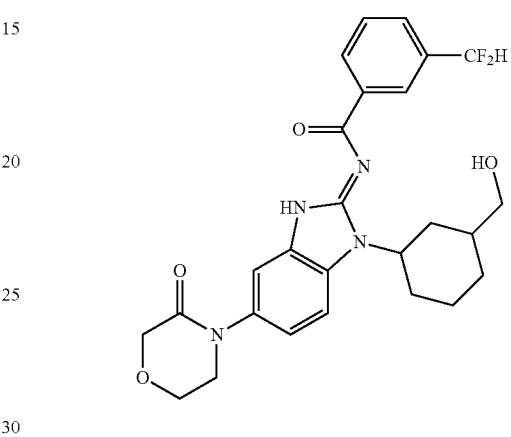

Prepared in an analogous fashion to Example 1, but using Intermediate 9 (1 eq.) in place of Intermediate 1-OTIPS, and 3-difluoromethyl-benzoic acid (1 eq.) in place of 3-trifluoromethyl-benzoic acid in step 1. ESI+: M+1: 499. ¹H NMR (300 MHz, CDCl₃) δ 12.66 (s, 1H), 8.55-8.38 (m, 2H), 7.66 (d, J=7.7 Hz, 1H), 7.56 (t, J=7.7 Hz, 1H), 7.46 (d, J=8.6 Hz, 1H), 7.28 (d, J=1.9 Hz, 1H), 7.20 (dd, J=8.6, 2.0 Hz, 1H), 6.75 (t, J=56.4 Hz, 1H), 4.88 (s, 1H), 4.37 (s, 2H), 4.10-4.00 (m, 2H), 3.80-3.70 (m, 2H), 3.61 (t, J=5.9 Hz, 2H), 2.32 (d, J=14.1 Hz, 1H), 2.07 (s, 2H), 1.62-0.80 (m, 6H).

Example 62: cis-(E)-N-(1-(4-hydroxycyclohexyl)-5-(3-oxomorpholino)-1H-benzo[d]imidazol-2(3H)-ylidene)-3-(trifluoromethyl)benzamide (57)

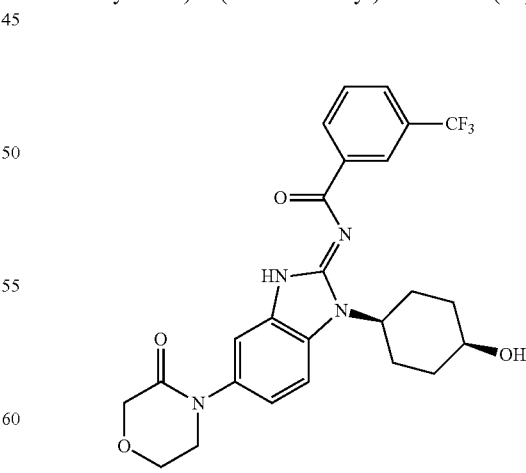

Prepared in an analogous fashion to Example 1, but using Intermediate 10 (1 eq.) in place of Intermediate 1-OTIPS in step 1. ESI+: M+1: 503. ¹H NMR (300 MHz, CDCl₃) δ 12.63 (s, 1H), 8.63 (s, 1H), 8.52 (d, J=7.7 Hz, 1H), 7.75 (d, J=7.7 Hz, 1H), 7.58 (dd, J=8.3, 5.4 Hz, 2H), 7.30 (d, J=1.9 Hz, 1H), 7.20 (dd, J=8.6, 2.0 Hz, 1H), 4.91 (s, 1H), 4.38 (s, 2H), 4.26 (s, 1H), 4.11-4.01 (m, 2H), 3.82-3.72 (m, 2H), 2.85-2.70 (m, 2H), 2.06 (d, J=13.8 Hz, 2H), 1.82 (d, J=14.4 Hz, 2H), 1.73-1.61 (m, 4H).

Example 63: cis-(E)-3-(difluoromethyl)-N-(1-(4-hydroxycyclohexyl)-5-(3-oxomorpholino)-1H-benzo[d]imidazol-2(3H)-ylidene)benzamide (56)

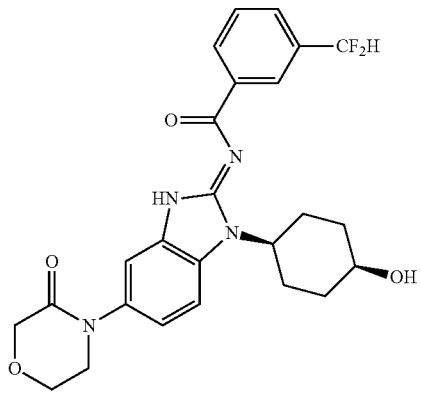

Prepared in an analogous fashion to Example 1, but using Intermediate 10 (1 eq.) in place of Intermediate 1-OTIPS, and 3-difluoromethyl-benzoic acid (1 eq.) in place of 3-trifluoromethyl-benzoic acid in step 1. ESI+: M+1: 485. $^1$H NMR (300 MHz, CDCl$_3$) δ 8.55-8.41 (m, 2H), 7.67 (d, J=7.7 Hz, 1H), 7.57 (d, J=8.2 Hz, 2H), 7.30 (d, J=2.0 Hz, 1H), 7.19 (dd, J=8.6, 2.0 Hz, 1H), 6.75 (t, J=56.4 Hz, 1H), 4.89 (s, 1H), 4.38 (s, 2H), 4.26 (s, 1H), 4.06 (dd, J=6.0, 4.0 Hz, 2H), 3.76 (t, J=5.1 Hz, 2H), 2.86 (d, J=11.5 Hz, 1H), 2.78 (d, J=13.2 Hz, 1H), 2.05 (d, J=13.9 Hz, 2H), 1.26 (d, J=3.2 Hz, 1H), 1.01-0.80 (m, 1H).

Example 64: cis-(E)-3-cyano-N-(1-(4-hydroxycyclohexyl)-5-(3-oxomorpholino)-1H-benzo[d]imidazol-2(3H)-ylidene)benzamide (55)

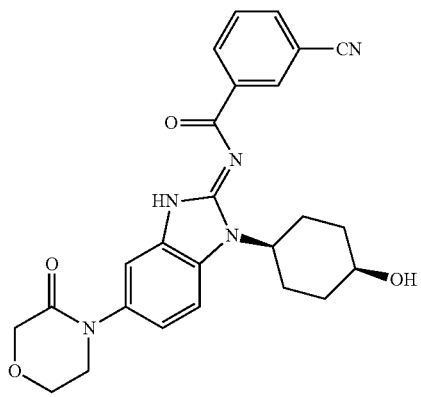

Prepared in an analogous fashion to Example 1, but using Intermediate 10 (1 eq.) in place of Intermediate 1-OTIPS, and 3-cyano-benzoic acid (1 eq.) in place of 3-trifluoromethyl-benzoic acid in step 1. ESI+: M+1: 460. $^1$H NMR (300 MHz, CDCl$_3$) δ 8.73 (s, 1H), 8.52 (dt, J=7.9, 1.4 Hz, 1H), 7.77 (dt, J=7.6, 1.4 Hz, 1H), 7.68-7.51 (m, 2H), 7.34 (d, J=1.9 Hz, 1H), 7.21 (dd, J=8.6, 2.0 Hz, 1H), 4.89 (s, 1H), 4.39 (s, 2H), 4.28 (s, 1H), 4.08 (dd, J=5.9, 4.2 Hz, 2H), 3.85-3.75 (m, 2H), 2.93-2.78 (m, 2H), 2.07 (d, J=14.0 Hz, 2H), 1.73 (d, J=14.1 Hz, 4H), 1.25 (m, 1H).

Example 65: cis-(E)-N-(1-(4-hydroxycyclohexyl)-5-(3-oxomorpholino)-1H-benzo[d]imidazol-2(3H)-ylidene)-3-(methylsulfonyl)benzamide (54)

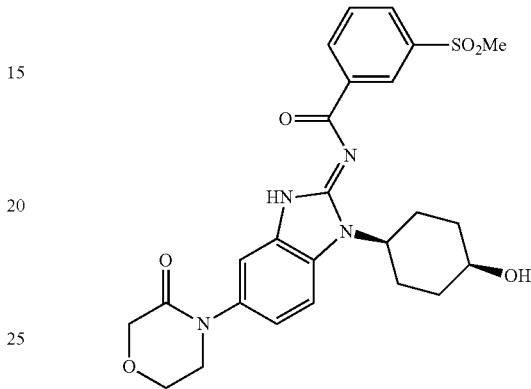

Prepared in an analogous fashion to Example 1, but using Intermediate 10 (1 eq.) in place of Intermediate 1-OTIPS, and 3-methylsulfonyl-benzoic acid (1 eq.) in place of 3-trifluoromethyl-benzoic acid in step 1. ESI+: M+1: 513. $^1$H NMR (300 MHz, CDCl$_3$) δ 9.02 (s, 1H), 8.57 (dt, J=7.8, 1.4 Hz, 1H), 8.07 (ddd, J=7.8, 2.0, 1.2 Hz, 1H), 7.74-7.44 (m, 3H), 7.41-7.18 (m, 2H), 4.38 (s, 2H), 4.22 (s, 1H), 4.14-4.04 (m, 2H), 3.86-3.76 (m, 2H), 3.42 (s, 1H), 3.48-3.37 (m, 1H), 3.17 (s, 3H), 3.02 (d, J=13.1 Hz, 2H), 2.85 (s, 1H), 2.60 (s, 2H), 2.06 (d, J=13.7 Hz, 2H), 1.83-1.80 (m, 4H).

Example 66: trans-(E)-N-(1-(4-hydroxycyclohexyl)-5-(3-oxomorpholino)-1H-benzo[d]imidazol-2(3H)-ylidene)-3-(trifluoromethyl)benzamide (32)

Prepared in an analogous fashion to Example 1, but using Intermediate 11 (1 eq.) in place of Intermediate 1-OTIPS in step 1. ESI+: M+1: 503. $^1$H NMR (300 MHz, CDCl$_3$) δ 12.95 (s, 1H), 8.54-8.45 (m, 2H), 7.92 (d, J=8.0 Hz, 1H), 7.76 (dt, J=8.0, 3.6 Hz, 2H), 7.53 (d, J=2.0 Hz, 1H), 7.25 (dd, J=8.6, 2.1 Hz, 1H), 4.79 (d, J=4.2 Hz, 1H), 4.23 (s, 2H), 4.01 (dd, J=6.0, 4.1 Hz, 2H), 3.79-3.66 (m, 2H), 2.55 (s, 1H), 2.03 (d, J=12.3 Hz, 2H), 1.82 (d, J=12.4 Hz, 2H), 1.46 (q, J=12.3 Hz, 2H).

Example 67: trans-(E)-3-(difluoromethyl)-N-(1-(4-hydroxycyclohexyl)-5-(3-oxomorpholino)-1H-benzo[d]imidazol-2(3H)-ylidene)benzamide (28)

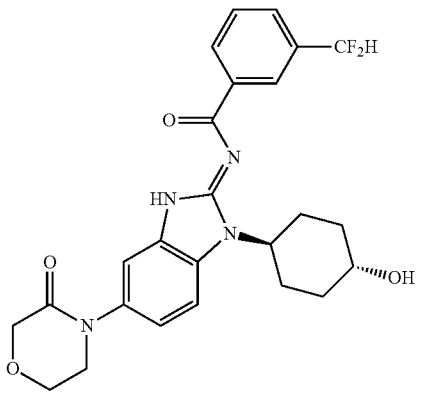

Prepared in an analogous fashion to Example 1, but using Intermediate 11 (1 eq.) in place of Intermediate 1-OTIPS, and 3-difluoromethyl-benzoic acid (1 eq.) in place of 3-trifluoromethyl-benzoic acid in step 1. ESI+: M+1: 485. $^1$H NMR (300 MHz, DMSO-$d_6$) δ 12.93 (s, 1H), 8.38 (d, J=8.5 Hz, 2H), 7.88-7.60 (m, 3H), 7.52 (d, J=2.0 Hz, 1H), 7.29-7.15 (m, 2H), 4.78 (d, J=4.2 Hz, 2H), 4.01 (dd, J=6.1, 4.0 Hz, 2H), 3.79-3.69 (m, 2H), 3.35 (s, 2H), 2.56 (d, J=11.9 Hz, 1H), 2.03 (d, J=12.0 Hz, 2H), 1.81 (d, J=12.0 Hz, 2H), 1.48 (q, J=12.1 Hz, 2H).

Example 68: trans-(E)-3-cyano-N-(1-(4-hydroxycyclohexyl)-5-(3-oxomorpholino)-1H-benzo[d]imidazol-2(3H)-ylidene)benzamide (27)

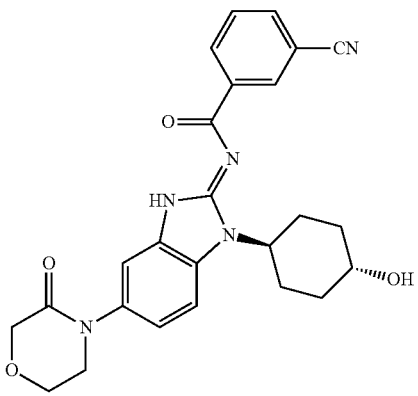

Prepared in an analogous fashion to Example 1, but using Intermediate 11 (1 eq.) in place of Intermediate 1-OTIPS, and 3-cyano-benzoic acid (1 eq.) in place of 3-trifluoromethyl-benzoic acid in step 1. ESI+: M+1: 460. $^1$H NMR (300 MHz, CDCl$_3$) δ 12.97 (s, 1H), 8.57-8.46 (m, 2H), 8.02 (dt, J=7.7, 1.4 Hz, 1H), 7.82-7.68 (m, 2H), 7.53 (d, J=2.0 Hz, 1H), 7.25 (dd, J=8.7, 2.1 Hz, 1H), 4.87-4.74 (m, 2H), 4.23 (s, 2H), 4.01 (dd, J=6.1, 4.0 Hz, 2H), 3.74 (dd, J=6.0, 4.1 Hz, 2H), 2.46 (s, 2H), 2.03 (d, J=11.8 Hz, 2H), 1.81 (d, J=11.5 Hz, 2H), 1.50 (q, J=11.9 Hz, 2H).

Example 69: trans-(E)-N-(1-(4-hydroxycyclohexyl)-5-(3-oxomorpholino)-1H-benzo[d]imidazol-2(3H)-ylidene)-3-(methylsulfonyl)benzamide (31)

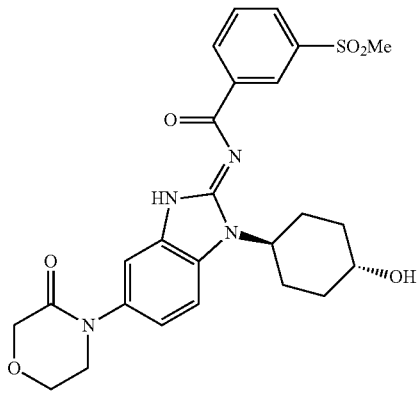 [SMILES: CS(=O)(=O)c1cccc(C(=O)/N=c2\[nH]c3cc(N4CCOCC4=O)ccc3n2[C@H]2CC[C@H](O)CC2)c1]

Prepared in an analogous fashion to Example 1, but using Intermediate 11 (1 eq.) in place of Intermediate 1-OTIPS, and 3-methylsulfonyl-benzoic acid (1 eq.) in place of 3-trifluoromethyl-benzoic acid in step 1. ESI+: M+1: 513. $^1$H NMR (300 MHz, CDCl$_3$) δ 12.95 (s, 1H), 8.71 (t, J=1.7 Hz, 1H), 8.53 (dt, J=7.8, 1.3 Hz, 1H), 8.10 (ddd, J=7.8, 2.0, 1.2 Hz, 1H), 7.86-7.72 (m, 2H), 7.53 (d, J=2.0 Hz, 1H), 7.25 (dd, J=8.7, 2.1 Hz, 1H), 4.84-4.73 (m, 2H), 4.23 (s, 2H), 4.01 (dd, J=6.1, 4.0 Hz, 2H), 3.81-3.70 (m, 3H), 3.29 (s, 3H), 2.56 (d, J=12.4 Hz, 1H), 2.03 (d, J=11.8 Hz, 2H), 1.81 (d, J=11.9 Hz, 2H), 1.46 (q, J=11.9 Hz, 2H).

Example 70: cis-(E)-N-(1-(4-(hydroxymethyl)cyclohexyl)-5-(3-oxomorpholino)-1H-benzo[d]imidazol-2(3H)-ylidene)-3-(trifluoromethyl)benzamide (122)

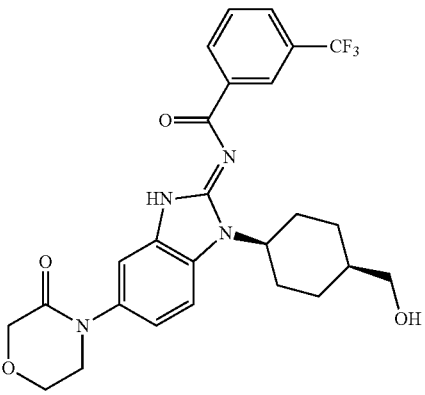 [SMILES: O=C(/N=c1\[nH]c2cc(N3CCOCC3=O)ccc2n1[C@H]1CC[C@@H](CO)CC1)c1cccc(C(F)(F)F)c1]

Prepared in an analogous fashion to Example 1, but using Intermediate 12 (1 eq.) in place of Intermediate 1-OTIPS in step 1. ESI+: M+1: 517. $^1$H NMR (300 MHz, CDCl$_3$) δ 12.74 (s, 1H), 8.60 (s, 1H), 8.49 (d, J=7.7 Hz, 1H), 7.76 (d, J=7.8 Hz, 1H), 7.60 (t, J=7.8 Hz, 1H), 7.40 (d, J=8.6 Hz, 1H), 7.33-7.15 (m, 2H), 4.71 (s, 1H), 4.37 (s, 2H), 4.10-4.00 (m, 2H), 3.94 (d, J=7.4 Hz, 2H), 3.80-3.70 (m, 2H), 2.67-2.45 (m, 2H), 2.07 (d, J=11.7 Hz, 3H), 1.76 (d, J=12.0 Hz, 2H), 1.01-0.80 (m, 2H).

Example 71: cis-(E)-3-(difluoromethyl)-N-(1-(4-(hydroxymethyl)cyclohexyl)-5-(3-oxomorpholino)-1H-benzo[d]imidazol-2(3H)-ylidene)benzamide (123)

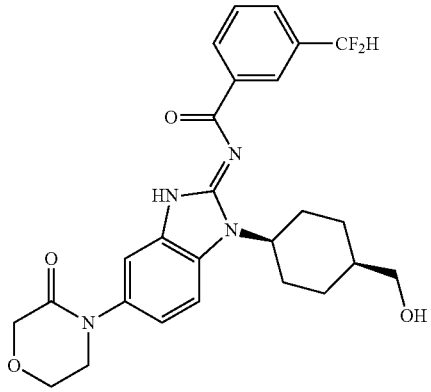 [SMILES: O=C(/N=c1\[nH]c2cc(N3CCOCC3=O)ccc2n1[C@H]1CC[C@@H](CO)CC1)c1cccc(C(F)F)c1]

Prepared in an analogous fashion to Example 1, but using Intermediate 12 (1 eq.) in place of Intermediate 1-OTIPS, and 3-difluoromethyl-benzoic acid (1 eq.) in place of 3-trifluoromethyl-benzoic acid in step 1. ESI+: M+1: 499. ¹H NMR (300 MHz, CDCl₃) δ 12.73 (s, 1H), 8.52-8.36 (m, 2H), 7.70-7.51 (m, 2H), 7.40 (d, J=8.6 Hz, 1H), 7.30 (d, J=1.9 Hz, 1H), 7.21 (dd, J=8.6, 2.0 Hz, 1H), 6.83 (t, J=56.2 Hz, 1H), 4.69 (d, J=12.7 Hz, 1H), 4.38 (s, 2H), 4.12-4.02 (m, 2H), 3.97 (d, J=7.0 Hz, 2H), 3.83-3.73 (m, 2H), 2.61 (q, J=12.8 Hz, 2H), 2.12-2.04 (m, 3H), 1.97-1.85 (m, 2H), 1.58 (s, 1H), 1.26 (s, 1H).

Example 72: (R,E)-N-(1-(4-hydroxybutan-2-yl)-5-(3-oxomorpholino)-1H-benzo[d]imidazol-2(3H)-ylidene)-3-(trifluoromethyl)benzamide (15)

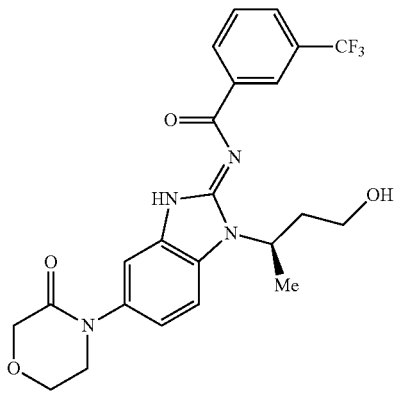

Prepared in an analogous fashion to Example 1, but using Intermediate 13 (1 eq.) in place of Intermediate 1-OTIPS in step 1. ESI+: M+1: 477. ¹H NMR (300 MHz, CDCl₃) δ 12.73 (s, 1H), 8.72-8.42 (m, 2H), 7.77 (d, J=7.6 Hz, 1H), 7.59 (t, J=7.8 Hz, 1H), 7.47 (d, J=8.6 Hz, 1H), 7.43-7.18 (m, 3H), 5.49-5.40 (m, 1H), 4.36 (s, 2H), 4.03 (dd, J=6.0, 4.2 Hz, 2H), 3.73 (dd, J=6.1, 4.1 Hz, 2H), 3.60 (dt, J=12.0, 4.0 Hz, 1H), 3.29-3.11 (m, 1H), 2.22-2.12 (m, 1H), 1.79 (d, J=7.2 Hz, 3H), 1.77-1.53 (m, 1H), 1.08-0.79 (m, 1H).

Example 73: (R,E)-3-(difluoromethyl)-N-(1-(4-hydroxybutan-2-yl)-5-(3-oxomorpholino)-1H-benzo[d]imidazol-2(3H)-ylidene)benzamide (242

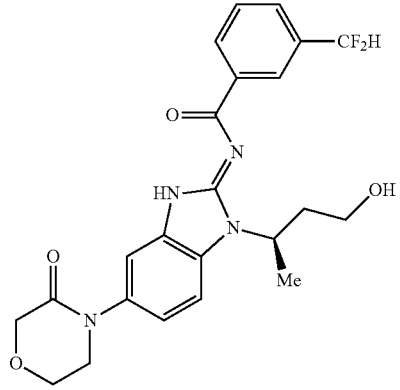

Prepared in an analogous fashion to Example 1, but using Intermediate 13 (1 eq.) in place of Intermediate 1-OTIPS, and 3-difluoromethyl-benzoic acid (1 eq.) in place of 3-trifluoromethyl-benzoic acid in step 1. ESI+: M+1: 459. ¹H NMR (300 MHz, CDCl₃) δ 12.81 (s, 1H), 8.41 (dd, J=4.3, 2.6 Hz, 2H), 7.69 (d, J=7.7 Hz, 1H), 7.57 (t, J=7.9 Hz, 1H), 7.46 (d, J=8.6 Hz, 1H), 7.34-7.17 (m, 2H), 6.74 (t, J=56.3 Hz, 1H), 5.46 (d, J=7.5 Hz, 1H), 4.34 (s, 2H), 4.00 (dd, J=6.0, 4.2 Hz, 2H), 3.68 (d, J=4.0 Hz, 2H), 3.70-3.53 (m, 1H), 3.21-3.18 (m, 1H), 2.15 (d, J=6.6 Hz, 1H), 1.77 (d, J=7.1 Hz, 3H), 1.26 (d, J=2.6 Hz, 1H), 1.01-0.80 (m, 1H).

Example 74: (S,E)-3-(difluoromethyl)-N-(1-(4-hydroxybutan-2-yl)-5-(3-oxomorpholino)-1H-benzo[d]imidazol-2(3H)-ylidene)benzamide (16)

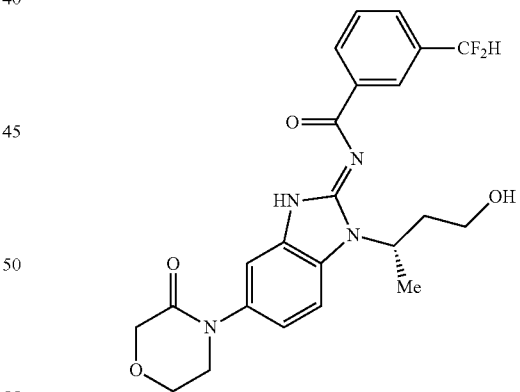

Prepared in an analogous fashion to Example 1, but using Intermediate 14 (1 eq.) in place of Intermediate 1-OTIPS, and 3-difluoromethyl-benzoic acid (1 eq.) in place of 3-trifluoromethyl-benzoic acid in step 1. ESI+: M+1: 459. ¹H NMR (300 MHz, CDCl₃) δ 12.81 (s, 1H), 8.41 (dd, J=4.3, 2.6 Hz, 2H), 7.69 (d, J=7.7 Hz, 1H), 7.57 (t, J=7.9 Hz, 1H), 7.46 (d, J=8.6 Hz, 1H), 7.34-7.17 (m, 2H), 6.74 (t, J=56.3 Hz, 1H), 5.46 (d, J=7.5 Hz, 1H), 4.34 (s, 2H), 4.00 (dd, J=6.0, 4.2 Hz, 2H), 3.68 (d, J=4.0 Hz, 2H), 3.70-3.53 (m, 1H), 3.21-3.18 (m, 1H), 2.15 (d, J=6.6 Hz, 1H), 1.77 (d, J=7.1 Hz, 3H), 1.26 (d, J=2.6 Hz, 1H), 1.01-0.80 (m, 1H).

Example 75: (R,E)-3-cyano-N-(1-(4-hydroxybutan-2-yl)-5-(3-oxomorpholino)-1H-benzo[d]imidazol-2(3H)-ylidene)benzamide (10)

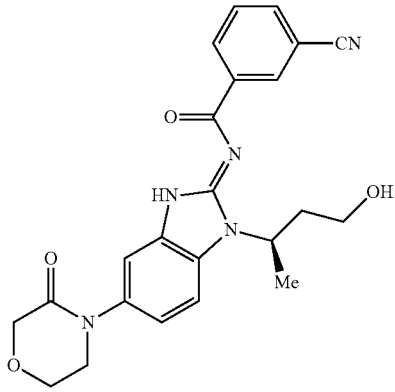

Prepared in an analogous fashion to Example 1, but using Intermediate 13 (1 eq.) in place of Intermediate 1-OTIPS, and 3-cyano-benzoic acid (1 eq.) in place of 3-trifluoromethyl-benzoic acid in step 1. ESI$^+$: M+1: 434. $^1$H NMR (300 MHz, CDCl$_3$) δ 12.63 (s, 1H), 8.66-8.43 (m, 2H), 7.78 (dt, J=7.7, 1.4 Hz, 1H), 7.63-7.44 (m, 2H), 7.38 (d, J=1.9 Hz, 1H), 4.38 (s, 2H), 4.13-4.03 (m, 2H), 3.85-3.75 (m, 2H), 3.61 (dt, J=12.0, 4.1 Hz, 1H), 3.30-3.14 (m, 1H), 2.19 (dt, J=9.4, 4.9 Hz, 1H), 1.79 (d, J=7.1 Hz, 3H), 1.61 (d, J=7.6 Hz, 1H), 1.46-1.42 (m, 1H), 1.26 (d, J=3.1 Hz, 1H), 1.02 (d, J=7.2 Hz, 1H).

Example 76: (R,E)-N-(1-(4-hydroxybutan-2-yl)-5-(3-oxomorpholino)-1H-benzo[d]imidazol-2(3H)-ylidene)-3-(methylsulfonyl)benzamide (24)

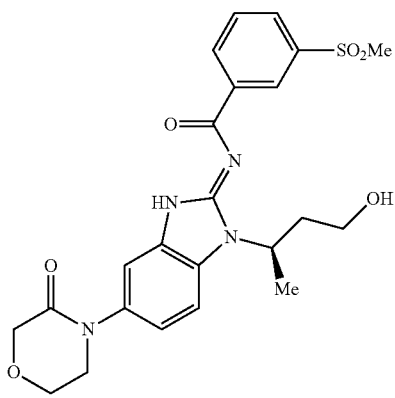

Prepared in an analogous fashion to Example 1, but using Intermediate 13 (1 eq.) in place of Intermediate 1-OTIPS, and 3-methylsulfonyl-benzoic acid (1 eq.) in place of 3-trifluoromethyl-benzoic acid in step 1. ESI$^+$: M+1: 487. $^1$H NMR (300 MHz, CDCl$_3$) δ 8.82 (t, J=1.8 Hz, 1H), 8.54 (dt, J=7.8, 1.4 Hz, 1H), 8.08 (ddd, J=7.8, 2.0, 1.2 Hz, 1H), 7.70 (t, J=7.8 Hz, 1H), 7.52 (d, J=8.7 Hz, 1H), 7.43 (d, J=1.9 Hz, 1H), 7.35 (s, 1H), 7.29-7.19 (m, 1H), 5.33 (s, 1H), 4.38 (s, 2H), 4.15-4.05 (m, 2H), 3.87-3.77 (m, 2H), 3.61 (m, 2H), 3.42-3.25 (m, 1H), 3.15 (s, 3H), 2.17-2.05 (m, 2H), 1.78 (d, J=7.1 Hz, 3H).

Example 77: (R,E)-3-(difluoromethoxy)-N-(1-(4-hydroxybutan-2-yl)-5-(3-oxomorpholino)-1H-benzo[d]imidazol-2(3H)-ylidene)benzamide (65)

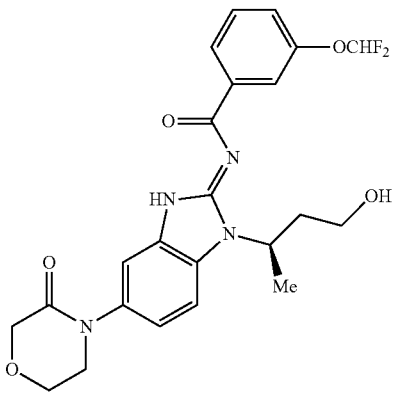

Prepared in an analogous fashion to Example 1, but using Intermediate 13 (1 eq.) in place of Intermediate 1-OTIPS, and 3-difluoromethoxy-benzoic acid (1 eq.) in place of 3-trifluoromethyl-benzoic acid in step 1. ESI$^+$: M+1: 475. $^1$H NMR (300 MHz, DMSO-d$_6$) δ 12.90 (s, 1H), 8.09 (d, J=7.8 Hz, 1H), 7.94 (s, 1H), 7.65 (d, J=8.7 Hz, 1H), 7.62-7.47 (m, 2H), 7.34-7.03 (m, 2H), 4.55 (t, J=4.9 Hz, 1H), 4.23 (s, 2H), 4.00 (dd, J=6.1, 4.0 Hz, 2H), 3.76-3.73 (m, 2H), 3.35-3.25 (s, 3H), 2.40-2.37 (m, 1H), 2.09 (dt, J=13.6, 6.5 Hz, 1H), 1.63 (d, J=6.9 Hz, 3H).

Example 78: rac-(E)-N-(1-(1-hydroxypentan-3-yl)-5-(3-oxomorpholino)-1H-benzo[d]imidazol-2(3H)-ylidene)-3-(trifluoromethyl)benzamide (124)

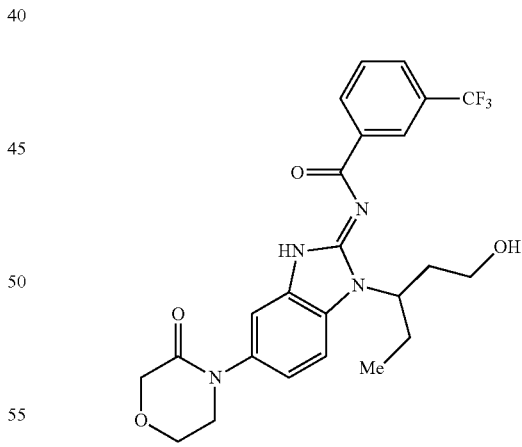

Prepared in an analogous fashion to Example 1, but using Intermediate 15 (1 eq.) in place of Intermediate 1-OTIPS in step 1. ESI$^+$: M+1: 491. $^1$H NMR (300 MHz, CDCl$_3$) δ 12.65 (s, 1H), 8.55-8.40 (m, 2H), 7.76 (d, J=7.9 Hz, 1H), 7.59 (t, J=7.8 Hz, 1H), 7.46 (d, J=8.7 Hz, 1H), 7.37 (s, 1H), 7.30-7.18 (m, 2H), 5.23 (s, 1H), 4.38 (s, 2H), 4.09-4.05 (m, 2H), 3.81-3.77 (m, 2H), 3.62-3.58 (m, 1H), 3.21 (s, 1H), 2.15-1.99 (m, 2H), 1.26 (d, J=3.1 Hz, 2H), 1.01-0.80 (m, 3H).

Example 79: rac-(E)-3-(difluoromethyl)-N-(1-(1-hydroxypentan-3-yl)-5-(3-oxomorpholino)-1H-benzo[d]imidazol-2(3H)-ylidene)benzamide (125)

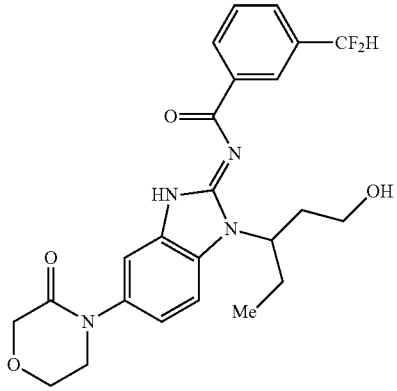

Prepared in an analogous fashion to Example 1, but using Intermediate 15 (1 eq.) in place of Intermediate 1-OTIPS, and 3-difluoromethyl-benzoic acid (1 eq.) in place of 3-trifluoromethyl-benzoic acid in step 1. ESI$^+$: M+1: 473. $^1$H NMR (300 MHz, CDCl$_3$) δ 12.68 (s, 1H), 8.39 (d, J=6.4 Hz, 2H), 7.68 (d, J=7.7 Hz, 1H), 7.56 (t, J=7.9 Hz, 1H), 7.45 (d, J=8.7 Hz, 1H), 7.36 (d, J=1.9 Hz, 1H), 7.23 (dd, J=8.6, 2.0 Hz, 1H), 6.72 (t, J=56.3 Hz, 1H), 5.24 (s, 1H), 4.38 (s, 2H), 4.06 (dd, J=5.9, 4.1 Hz, 2H), 3.83-3.73 (m, 2H), 3.59 (s, 1H), 3.18-3.14 (m, 2H), 2.12-2.01 (m, 2H), 1.07-0.80 (m, 5H).

Example 80: (E)-N-(1-(4-hydroxybutyl)-5-(3-oxomorpholino)-1H-benzo[d]imidazol-2(3H)-ylidene)-3-(trifluoromethyl)benzamide (17)

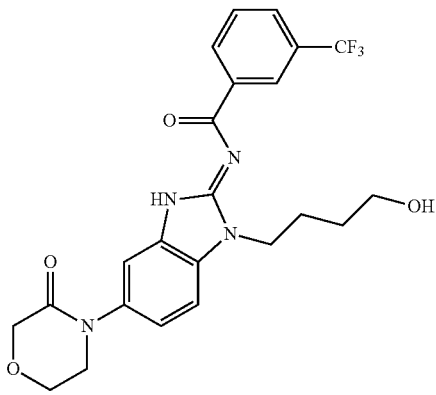

Prepared in an analogous fashion to Example 1, but using Intermediate 16 (1 eq.) in place of Intermediate 1-OTIPS in step 1. ESI$^+$: M+1: 477. $^1$H NMR (300 MHz, CDCl$_3$) δ 12.48 (s, 1H), 8.61 (s, 1H), 8.50 (d, J=7.7 Hz, 1H), 7.75 (d, J=7.7 Hz, 1H), 7.58 (t, J=7.8 Hz, 1H), 7.38-7.26 (m, 2H), 7.24 (dd, J=8.5, 2.0 Hz, 1H), 4.39-4.35 (m, 4H), 4.10-4.00 (m, 2H), 3.81-3.68 (m, 4H), 2.02 (p, J=7.1 Hz, 2H), 1.63 (s, 2H).

Example 81: (E)-3-(difluoromethyl)-N-(1-(4-hydroxybutyl)-5-(3-oxomorpholino)-1H-benzo[d]imidazol-2(3H)-ylidene)benzamide (26)

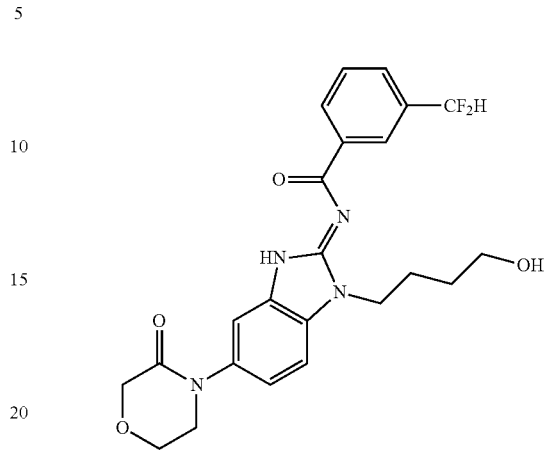

Prepared in an analogous fashion to Example 1, but using Intermediate 16 (1 eq.) in place of Intermediate 1-OTIPS, and 3-difluoromethyl-benzoic acid (1 eq.) in place of 3-trifluoromethyl-benzoic acid in step 1. ESI$^+$: M+1: 459. $^1$H NMR (300 MHz, CDCl$_3$) δ 8.49-8.37 (m, 2H), 7.71-7.62 (m, 1H), 7.56 (t, J=7.7 Hz, 1H), 7.38-7.16 (m, 3H), 6.75 (t, J=56.4 Hz, 1H), 4.37-4.34 (m, 4H), 4.09-3.99 (m, 2H), 3.81-3.62 (m, 4H), 2.07-1.93 (m, 2H), 1.64 (dq, J=9.0, 6.4 Hz, 2H).

Example 82: (E)-3-cyano-N-(1-(4-hydroxybutyl)-5-(3-oxomorpholino)-1H-benzo[d]imidazol-2(3H)-ylidene)benzamide (18)

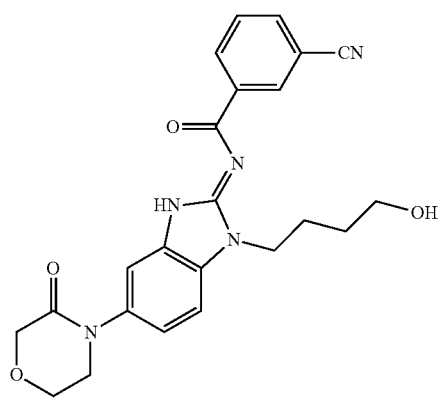

Prepared in an analogous fashion to Example 1, but using Intermediate 16 (1 eq.) in place of Intermediate 1-OTIPS, and 3-cyano-benzoic acid (1 eq.) in place of 3-trifluoromethyl-benzoic acid in step 1. ESI$^+$: M+1: 434. $^1$H NMR (300 MHz, CDCl$_3$) δ 12.40 (s, 1H), 8.65 (t, J=1.6 Hz, 1H), 8.51 (dt, J=7.9, 1.4 Hz, 1H), 7.82-7.72 (m, 1H), 7.57 (t, J=7.8 Hz, 1H), 7.40-7.21 (m, 3H), 4.38-4.34 (m, 4H), 4.10-3.98 (m, 2H), 3.86-3.71 (m, 4H), 2.03 (p, J=7.3 Hz, 2H), 1.67 (p, J=7.6, 7.0 Hz, 2H).

Example 83: (E)-N-(1-(4-hydroxybutyl)-5-(3-oxomorpholino)-1H-benzo[d]imidazol-2(3H)-ylidene)-3-(methylsulfonyl)benzamide (19)

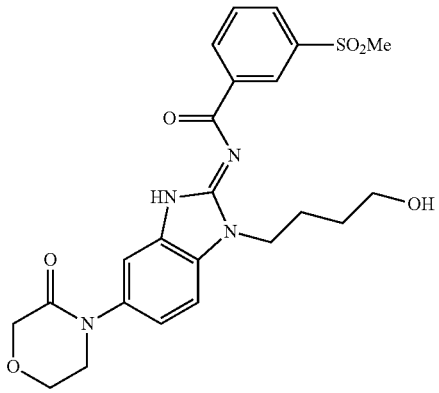

Prepared in an analogous fashion to Example 1, but using Intermediate 16 (1 eq.) in place of Intermediate 1-OTIPS, and 3-methylsulfonyl-benzoic acid (1 eq.) in place of 3-trifluoromethyl-benzoic acid in step 1. ESI$^+$: M+1: 487. $^1$H NMR (300 MHz, DMSO-d$_6$) δ 12.90 (s, 1H), 8.70 (t, J=1.8 Hz, 1H), 8.57 (dt, J=7.8, 1.4 Hz, 1H), 8.09 (ddd, J=7.8, 2.0, 1.2 Hz, 1H), 7.78 (t, J=7.8 Hz, 1H), 7.61 (d, J=8.6 Hz, 1H), 7.52 (d, J=2.0 Hz, 1H), 7.28 (dd, J=8.5, 2.0 Hz, 1H), 4.44 (t, J=5.2 Hz, 1H), 4.33 (t, J=6.9 Hz, 2H), 4.23 (s, 2H), 4.01 (dd, J=6.1, 4.0 Hz, 2H), 3.75 (t, J=5.1 Hz, 2H), 3.44 (q, J=6.1 Hz, 2H), 3.28 (s, 3H), 1.87 (t, J=7.7 Hz, 2H), 1.49 (t, J=7.6 Hz, 2H).

Example 84: (E)-N-(1-cyclohexyl-5-(3-oxomorpholino)-1H-benzo[d]imidazol-2(3H)-ylidene)-3-(trifluoromethyl)benzamide (45)

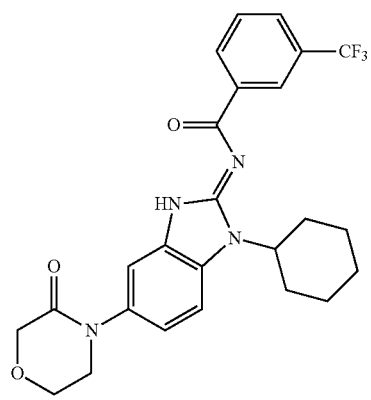 [SMILES: O=C(/N=c1\[nH]c2cc(N3CCOCC3=O)ccc2n1C1CCCCC1)c1cccc(C(F)(F)F)c1]

Prepared in an analogous fashion to Example 9, but using Intermediate 17 (1 eq.) in place of Intermediate 1-OH, 3-trifluoromethyl-benzoic acid (1 eq.) in place of 4-methyl-3-trifluoromethyl-benzoic acid, and HATU (1.5 eq.) in place of HBTU. ESI$^+$: M+1: 487. $^1$H NMR (300 MHz, CDCl$_3$) δ 12.64 (s, 1H), 8.62 (s, 1H), 8.50 (d, J=7.8 Hz, 1H), 7.75 (d, J=7.7 Hz, 1H), 7.60-7.50 (m, 2H), 7.33-7.16 (m, 2H), 4.84-4.80 (m, 1H), 4.37 (s, 2H), 4.11-4.01 (m, 2H), 3.82-3.72 (m, 2H), 2.34 (dq, J=12.6, 12.0 Hz, 2H), 1.99-1.34 (m, 8H).

Example 85: (E)-N-(1-((1-(hydroxymethyl)cyclopropyl)methyl)-5-(3-oxomorpholino)-1H-benzo[d]imidazol-2(3H)-ylidene)-3-(trifluoromethyl)benzamide (9)

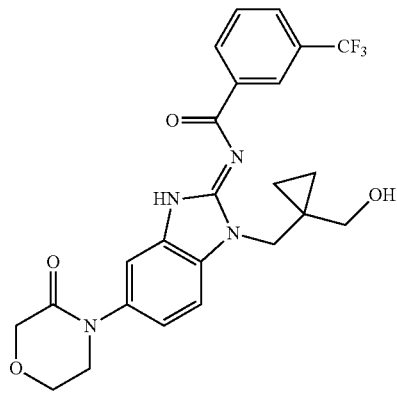

Prepared in an analogous fashion to Example 1, but using Intermediate 18 (1 eq.) in place of Intermediate 1-OTIPS in step 1. ESI$^+$: M+1: 489. $^1$H NMR (300 MHz, CDCl$_3$) δ 12.68 (s, 1H), 8.54-8.36 (m, 2H), 7.77 (d, J=7.8 Hz, 1H), 7.60 (t, J=7.8 Hz, 1H), 7.40-7.23 (m, 3H), 4.96 (s, 1H), 4.38 (s, 2H), 4.30 (s, 2H), 4.12-4.02 (m, 2H), 3.82-3.72 (m, 2H), 3.22 (s, 2H), 0.85-0.81 (m, 2H), 0.66-0.63 (m, 2H).

Example 86: (E)-3-(difluoromethyl)-N-(1-((1-(hydroxymethyl)cyclopropyl)methyl)-5-(3-oxomorpholino)-1H-benzo[d]imidazol-2(3H)-ylidene)benzamide (14)

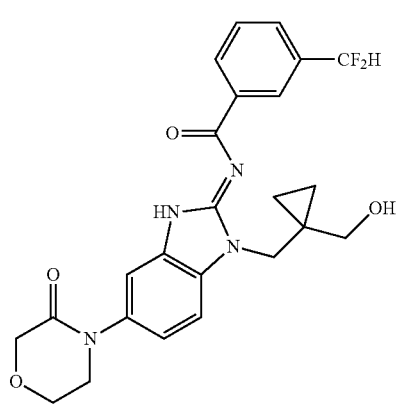

Prepared in an analogous fashion to Example 1, but using Intermediate 18 (1 eq.) in place of Intermediate 1-OTIPS, and 3-difluoromethyl-benzoic acid (1 eq.) in place of 3-trifluoromethyl-benzoic acid in step 1. ESI$^+$: M+1: 471. $^1$H NMR (300 MHz, CDCl$_3$) δ 12.72 (s, 1H), 8.43-8.33 (m, 2H), 7.69 (d, J=7.7 Hz, 1H), 7.58 (t, J=8.0 Hz, 1H), 7.39-7.21 (m, 3H), 6.74 (t, J=56.3 Hz, 1H), 5.15 (s, 1H), 4.37 (s, 2H), 4.30 (s, 2H), 4.11-4.01 (m, 2H), 3.81-3.71 (m, 2H), 3.23 (s, 2H), 0.92-0.70 (m, 2H), 0.67-0.64 (m, 2H).

Example 87: (E)-3-cyano-N-(1-((1-(hydroxymethyl)cyclopropyl)methyl)-5-(3-oxomorpholino)-1H-benzo[d]imidazol-2(3H)-ylidene)benzamide (12)

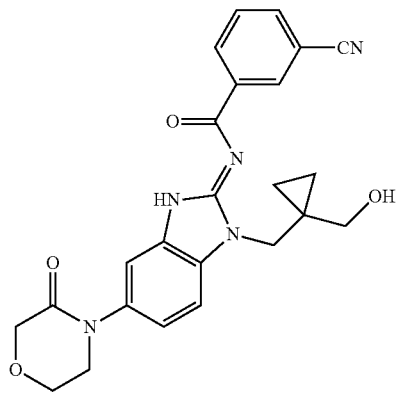

Prepared in an analogous fashion to Example 1, but using Intermediate 18 (1 eq.) in place of Intermediate 1-OTIPS, and 3-cyano-benzoic acid (1 eq.) in place of 3-trifluoromethyl-benzoic acid in step 1. ESI+: M+1: 446. $^1$H NMR (300 MHz, DMSO-$d_6$) δ 13.03 (s, 1H), 8.60-8.46 (m, 2H), 8.01 (dt, J=7.7, 1.5 Hz, 1H), 7.78-7.64 (m, 2H), 7.52 (d, J=2.0 Hz, 1H), 7.29 (dd, J=8.6, 2.0 Hz, 1H), 4.90 (s, 1H), 4.34 (s, 2H), 4.24 (s, 2H), 4.01 (dd, J=6.1, 4.0 Hz, 2H), 3.75 (dd, J=6.0, 4.0 Hz, 2H), 3.27 (s, 2H), 0.99-0.82 (m, 2H), 0.58-0.43 (m, 2H).

Example 88: (E)-N-(1-((1-(hydroxymethyl)cyclopropyl)methyl)-5-(3-oxomorpholino)-1H-benzo[d]imidazol-2(3H)-ylidene)-3-(methylsulfonyl)benzamide (13)

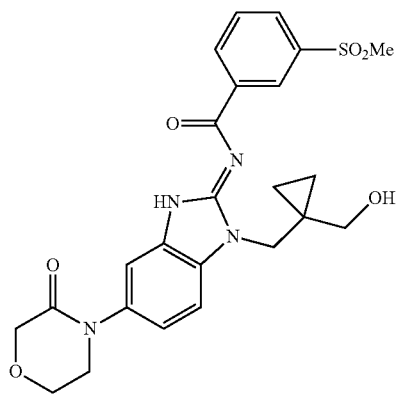

Prepared in an analogous fashion to Example 1, but using Intermediate 18 (1 eq.) in place of Intermediate 1-OTIPS, and 3-methylsulfonyl-benzoic acid (1 eq.) in place of 3-trifluoromethyl-benzoic acid in step 1. ESI+: M+1: 499. $^1$H NMR (300 MHz, CDCl$_3$) δ 8.80 (t, J=1.7 Hz, 1H), 8.51 (dt, J=7.9, 1.3 Hz, 1H), 8.09 (ddd, J=7.8, 1.9, 1.1 Hz, 1H), 7.70 (t, J=7.8 Hz, 1H), 7.48-7.38 (m, 2H), 7.35-7.13 (m, 1H), 4.37 (s, 2H), 4.30 (s, 2H), 4.15-4.05 (m, 2H), 3.87-3.77 (m, 2H), 3.25 (s, 2H), 3.15 (s, 3H), 0.95-0.80 (m, 2H), 0.66-0.62 (s, 2H).

Example 89: (E)-3-(difluoromethoxy)-N-(1-((1-(hydroxymethyl)cyclopropyl)methyl)-5-(3-oxomorpholino)-1H-benzo[d]imidazol-2(3H)-ylidene)benzamide (66)

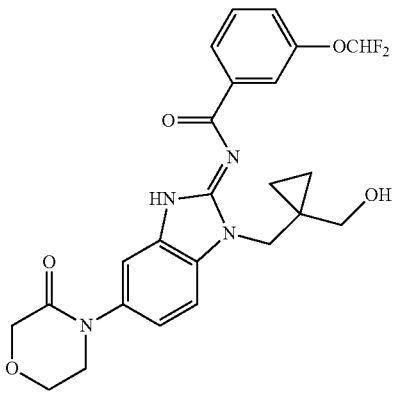

Prepared in an analogous fashion to Example 1, but using Intermediate 18 (1 eq.) in place of Intermediate 1-OTIPS, and 3-difluoromethoxy-benzoic acid (1 eq.) in place of 3-trifluoromethyl-benzoic acid in step 1. ESI+: M+1: 487. $^1$H NMR (300 MHz, DMSO-$d_6$) δ 12.94 (s, 1H), 8.08 (dt, J=7.8, 1.2 Hz, 1H), 7.96 (t, J=1.9 Hz, 1H), 7.68 (d, J=8.6 Hz, 1H), 7.61-7.46 (m, 2H), 7.40-7.07 (m, 3H), 4.93 (t, J=5.6 Hz, 1H), 4.34 (s, 2H), 4.24 (s, 2H), 4.01 (d, J=6.1, 4.0 Hz, 2H), 3.75 (dd, J=6.1, 4.0 Hz, 2H), 3.23 (d, J=5.6 Hz, 2H), 0.93-0.83 (m, 2H), 0.52-0.42 (m, 2H).

Example 90: (E)-3-fluoro-N-(1-((1-(hydroxymethyl)cyclopropyl)methyl)-5-(3-oxomorpholino)-1H-benzo[d]imidazol-2(3H)-ylidene)-5-(trifluoromethyl)benzamide (25)

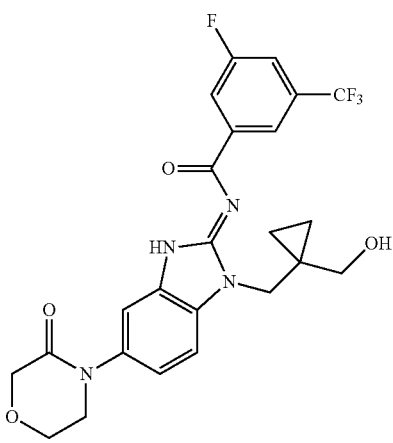 [SMILES: O=C(/N=c1\[nH]c2cc(N3CCOCC3=O)ccc2n1CC1(CO)CC1)c1cc(F)cc(C(F)(F)F)c1]

Prepared in an analogous fashion to Example 1, but using Intermediate 18 (1 eq.) in place of Intermediate 1-OTIPS, and 3-fluoro-5-trifluoromethyl-benzoic acid (1 eq.) in place of 3-trifluoromethyl-benzoic acid in step 1. ESI+: M+1: 507. $^1$H NMR (300 MHz, CDCl$_3$) δ 12.57 (s, 1H), 8.31 (s, 1H), 8.11 (d, J=9.0 Hz, 1H), 7.51-7.35 (m, 3H), 7.30-7.26 (m, 1H), 4.45 (t, J=7.0 Hz, 1H), 4.39 (s, 2H), 4.31 (s, 2H), 4.14-4.04 (m, 2H), 3.82 (dd, J=5.9, 4.2 Hz, 2H), 3.24 (d, J=7.0 Hz, 2H), 0.87-0.84 (m, 2H), 0.67-0.63 (m, 2H).

Example 91: (E)-tert-butyl 4-(5-(3-oxomorpholino)-2-((3-(trifluoromethyl)benzoyl)imino)-2,3-dihydro-1H-benzo[d]imidazole-1-yl)piperidine-1-carboxylate (126)

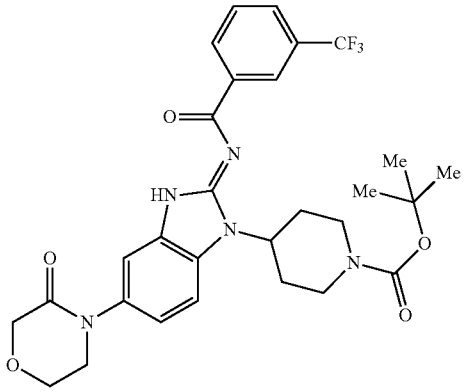 [SMILES: CC(C)(C)OC(=O)N1CCC(n2/c(=N/C(=O)c3cccc(C(F)(F)F)c3)[nH]c3cc(N4CCOCC4=O)ccc32)CC1]

In a glass RBF equipped with a Teflon-coated magnetic stirrer was dissolved 3-trifluoromethyl-benzoic acid (1.1 eq.), HATU (1.1 eq.) and Intermediate 19 (1 eq.) in DMF (0.35 M). To the resulting solution was then added ethyl-diisopropyl-amine (2 eq.) and the resulting mixture was stirred at RT for 18 h. The crude reaction mixture was then diluted with EtOAc and washed sequentially with water and brine. The organic extract was then dried over MgSO$_4$, filtered and the filtrate concentrated in vacuo. Purification of the crude product thus obtained by way of column chromatography (SiO$_2$, gradient elution, 4:1 (v/v) Hex: EtOAc→EtOAc) furnished the title compound as a white solid (88% yield). ESI$^+$: M+1: 588. $^1$H NMR (300 MHz, CDCl$_3$) δ 12.67 (s, 1H), 8.58 (s, 1H), 8.49 (d, J=7.8 Hz, 1H), 7.76 (d, J=7.8 Hz, 1H), 7.58 (t, J=7.7 Hz, 1H), 7.45 (d, J=8.7 Hz, 1H), 7.32 (d, J=1.9 Hz, 1H), 7.21 (dd, J=8.6, 2.0 Hz, 1H), 5.05 (t, J=12.4 Hz, 1H), 4.37 (s, 2H), 4.11-4.00 (m, 2H), 3.81-3.71 (m, 2H), 2.99-2.95 (s, 2H), 2.49-2.46 (m, 2H), 1.96-1.92 (m, 2H), 1.64-1.60 (m, 2H), 1.53 (s, 9H).

Example 92: (E)-tert-butyl 4-(2-((3-(difluoromethyl)benzoyl)imino)-5-(3-oxomorpholino)-2,3-dihydro-1H-benzo[d]imidazole-1-yl)piperidine-1-carboxylate (127)

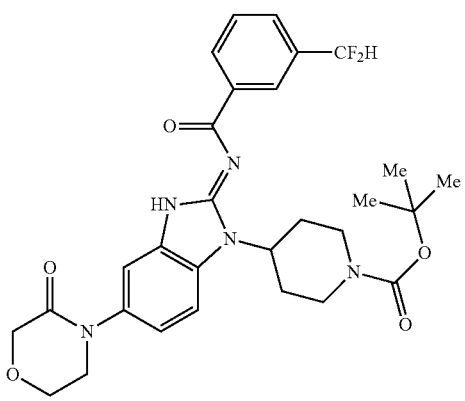 [SMILES: CC(C)(C)OC(=O)N1CCC(n2/c(=N/C(=O)c3cccc(C(F)F)c3)[nH]c3cc(N4CCOCC4=O)ccc32)CC1]

Prepared in an analogous fashion to Example 91, but using 3-difluoromethyl-benzoic acid (1.1 eq.) in place of 3-trifluoromethyl-benzoic acid. ESI$^+$: M+1: 570. $^1$H NMR (300 MHz, CDCl$_3$) δ 12.73 (s, 1H), 8.43 (d, J=7.5 Hz, 2H), 7.68 (d, J=7.6 Hz, 1H), 7.56 (t, J=7.7 Hz, 1H), 7.43 (d, J=8.7 Hz, 1H), 7.32-7.15 (m, 2H), 6.74 (t, J=56.3 Hz, 1H), 5.06 (t, J=12.5 Hz, 1H), 4.36 (s, 2H), 4.04 (dd, J=6.1, 4.0 Hz, 2H), 3.73 (t, J=5.0 Hz, 2H), 2.97-2.93 (m, 2H), 2.52-2.42 (m, 2H), 1.95-1.91 (m, 2H), 1.63-1.61 (m, 2H), 1.53 (s, 9H).

Example 93: (E)-N-(5-(3-oxomorpholino)-1-(piperidin-4-yl)-1H-benzo[d]imidazole-2(3H)-ylidene)-3-(trifluoromethyl)benzamide hydrochloride (128)

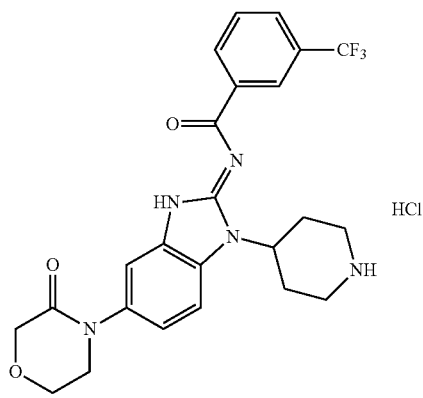 [SMILES: O=C(/N=c1\[nH]c2cc(N3CCOCC3=O)ccc2n1C1CCNCC1)c1cccc(C(F)(F)F)c1 ; Cl]

In a glass RBF equipped with a Teflon-coated magnetic stirrer was dissolved Example 91 (1 eq.) in dichloromethane (0.1 M). To the resulting solution was then added HCl (5 eq., 4 M solution in dioxane) and the resulting mixture was stirred at RT for 2 h. The volatiles were then removed in vacuo to furnish the title compound as a white solid (88% yield). ESI$^+$: M+1: 488. $^1$H NMR (300 MHz, CDCl$_3$) δ 9.60 (s, 1H), 8.73 (d, J=7.9 Hz, 1H), 8.43 (s, 1H), 8.04 (d, J=8.7 Hz, 1H), 7.93 (d, J=7.8 Hz, 1H), 7.76 (t, J=7.8 Hz, 1H), 7.58 (d, J=2.0 Hz, 1H), 7.31 (dd, J=8.7, 2.0 Hz, 1H), 5.26 (s, 1H), 4.24 (s, 2H), 4.01 (t, J=5.1 Hz, 2H), 3.76 (t, J=5.0 Hz, 2H), 3.25-3.21 (m, 2H), 2.90-2.86 (m, 2H), 2.04-2.00 (m, 2H), 2.04-2.02 (m, 2H).

Example 94: (E)-3-(difluoromethyl)-N-(5-(3-oxo-morpholino)-1-(piperidin-4-yl)-1H-benzo[d]imidazole-2(3H)-ylidene)benzamide hydrochloride (129)

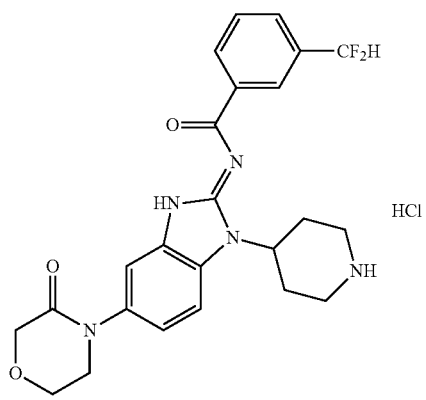 [SMILES: O=C(/N=c1\[nH]c2cc(N3CCOCC3=O)ccc2n1C1CCNCC1)c1cccc(C(F)F)c1 ; Cl]

Prepared in an analogous fashion to Example 93, but using Example 92 (1 eq.) in place of Example 91. ESI⁺: M+1: 470. ¹H NMR (300 MHz, CDCl₃) δ 9.48-9.45 (m, 1H), 9.24-9.20 (m, 1H), 8.55 (d, J=7.8 Hz, 1H), 8.38 (s, 1H), 7.98 (d, J=8.7 Hz, 1H), 7.77 (d, J=7.6 Hz, 1H), 7.72-7.53 (m, 2H), 7.36-7.05 (m, 2H), 5.35 (s, br, 2H), 5.23 (s, br, 1H), 4.24 (s, 2H), 4.06-3.96 (m, 2H), 3.76 (t, J=5.1 Hz, 2H), 3.57-3.47 (m, 2H), 3.30-3.17 (m, 2H), 2.89-2.81 (m, 2H), 2.02 (d, J=12.9 Hz, 2H).

Example 95: (E)-N-(1-(1-acetylpiperidin-4-yl)-5-(3-oxomorpholino)-1H-benzo[d]imidazole-2(3H)-ylidene)-3-(trifluoromethyl)benzamide (130)

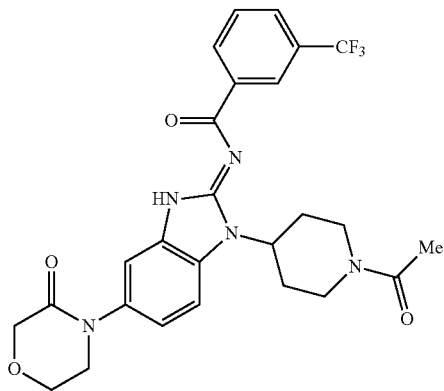 [SMILES: CC(=O)N1CCC(n2/c(=N/C(=O)c3cccc(C(F)(F)F)c3)[nH]c3cc(N4CCOCC4=O)ccc32)CC1]

In a glass RBF equipped with a Teflon-coated magnetic stirrer was dissolved Example 93 (1 eq.) and ethyl-diisopropyl-amine (3 eq.) in dichloromethane (0.1 M). To the resulting solution was then added acetyl chloride (1.1 eq.) drop-wise and the resulting mixture was stirred at RT for 1 h. The volatiles were removed in vacuo and the resulting residue was partitioned between EtOAc and water. The aqueous layer was separated and back-extracted with EtOAc. The combined organic extracts were washed further with water and brine, dried over MgSO₄, filtered and the filtrate concentrated in vacuo. Purification of the crude product thus obtained by way of reverse phase column chromatography (C₁₈, gradient elution, 10:1 (v/v) H₂O:MeCN+0.1% formic acid 4 MeCN+0.1% formic acid) furnished the title compound as a white solid (71% yield). ESI⁺: M+1: 530. ¹H NMR (300 MHz, CDCl₃) δ 12.66 (s, 1H), 8.57 (s, 1H), 8.47 (d, J=7.8 Hz, 1H), 7.76 (d, J=7.7 Hz, 1H), 7.59 (t, J=7.7 Hz, 1H), 7.41 (d, J=8.7 Hz, 1H), 7.35-7.16 (m, 1H), 5.16-4.95 (m, 2H), 4.36 (s, 2H), 4.15-4.00 (m, 2H), 3.75 (dd, J=6.0, 4.1 Hz, 2H), 3.34 (t, J=13.1 Hz, 1H), 2.78 (t, J=12.8 Hz, 1H), 2.52 (dd, J=16.5, 8.0 Hz, 2H), 2.23 (s, 3H), 2.03 (d, J=10.3 Hz, 2H).

Example 96: (E)-N-(1-(1-acetylpiperidin-4-yl)-5-(3-oxomorpholino)-1H-benzo[d]imidazole-2(3H)-ylidene)-3-(difluoromethyl)benzamide (131)

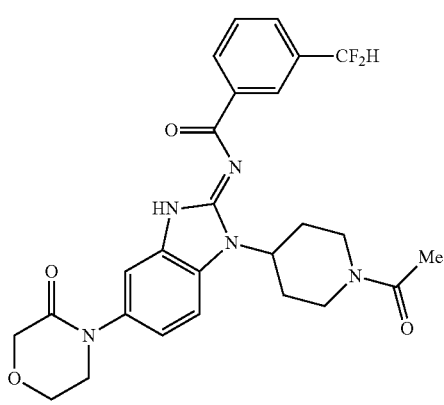 [SMILES: CC(=O)N1CCC(n2/c(=N/C(=O)c3cccc(C(F)F)c3)[nH]c3cc(N4CCOCC4=O)ccc32)CC1]

Prepared in an analogous fashion to Example 95, but using Example 94 (1 eq.) in place of Example 93. ESI⁺: M+1: 512. ¹H NMR (300 MHz, CDCl₃) δ 12.64 (s, 1H), 8.40 (d, J=9.5 Hz, 2H), 7.68 (d, J=7.8 Hz, 1H), 7.56 (t, J=7.6 Hz, 1H), 7.45-7.29 (m, 2H), 7.21 (d, J=8.6 Hz, 1H), 6.76 (t, J=56.4 Hz, 1H), 5.13-4.91 (m, 2H), 4.37 (s, 2H), 4.10-4.00 (m, 2H), 3.78-3.74 (m, 2H), 3.34 (t, J=13.1 Hz, 1H), 2.78 (t, J=12.8 Hz, 1H), 2.59-2.56 (m, 2H), 2.23 (s, 3H), 2.03-2.01 (m, 2H).

Example 97: (E)-N-(1-(1-(methylsulfonyl)piperidin-4-yl)-5-(3-oxomorpholino)-1H-benzo[d]imidazole-2(3H)-ylidene)-3-(trifluoromethyl)benzamide (132)

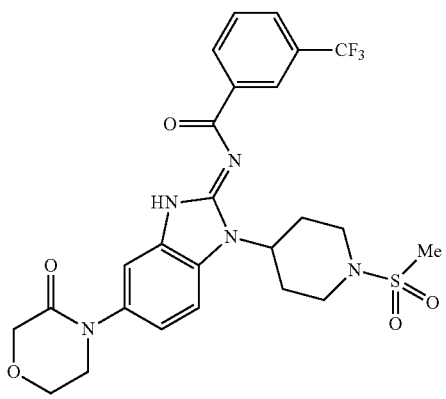 [SMILES: CS(=O)(=O)N1CCC(n2/c(=N/C(=O)c3cccc(C(F)(F)F)c3)[nH]c3cc(N4CCOCC4=O)ccc32)CC1]

Prepared in an analogous fashion to Example 95, but using methanesulfonyl chloride (1.2 eq.) in place of acetyl chloride. ESI⁺: M+1: 566. ¹H NMR (300 MHz, CDCl₃) δ 12.66 (s, 1H), 8.57 (s, 1H), 8.48 (d, J=7.7 Hz, 1H), 7.77 (d, J=7.7 Hz, 1H), 7.56 (t, J=7.7 Hz, 1H), 7.40 (d, J=8.7 Hz, 1H), 7.30-7.18 (m, 2H), 5.16-4.95 (m, 1H), 4.36 (s, 2H), 4.17-4.00 (m, 4H), 3.81-3.71 (m, 2H), 3.06-2.95 (m, 2H), 2.94 (s, 3H), 2.76-2.63 (m, 2H), 2.09-2.04 (m, 2H).

Example 98: (E)-3-(difluoromethyl)-N-(1-(1-(methylsulfonyl)piperidin-4-yl)-5-(3-oxomorpholino)-1H-benzo[d]imidazole-2(3H)-ylidene)benzamide (133)

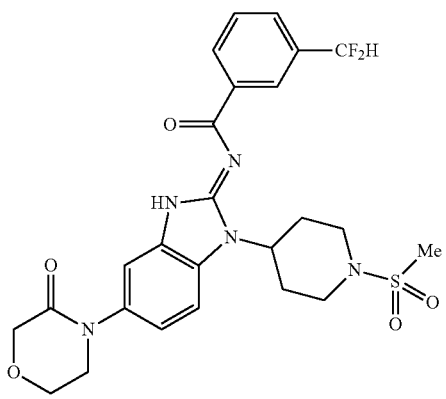

Prepared in an analogous fashion to Example 95, but using Example 94 (1 eq.) in place of Example 93, and methanesulfonyl chloride (1.2 eq.) in place of acetyl chloride. ESI⁺: M+1: 548. ¹H NMR (300 MHz, CDCl₃) δ 12.67

(s, 1H), 8.42 (d, J=11.5 Hz, 2H), 7.67 (d, J=7.7 Hz, 1H), 7.59-7.48 (m, 2H), 7.33 (d, J=2.0 Hz, 1H), 7.22 (dd, J=8.6, 2.0 Hz, 1H), 6.76 (t, J=56.4 Hz, 1H), 5.06 (dd, J=14.6, 10.3 Hz, 1H), 4.36 (s, 2H), 4.13-4.04 (m, 4H), 3.76 (t, J=5.0 Hz, 2H), 3.06-2.94 (m, 2H), 2.94 (s, 3H), 2.81-2.63 (m, 2H), 2.08-2.04 (m, 2H).

Example 99: (E)-N-ethyl-4-(5-(3-oxomorpholino)-2-((3-(trifluoromethyl)benzoyl)imino)-2,3-dihydro-1H-benzo[d]imidazol-1-yl)piperidine-1-carboxamide (134)

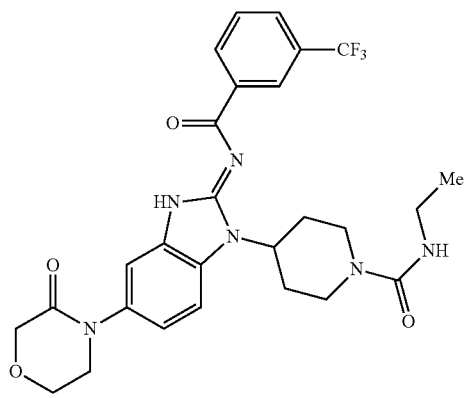 [SMILES: CCNC(=O)N1CCC(n2/c(=N/C(=O)c3cccc(C(F)(F)F)c3)[nH]c3cc(N4CCOCC4=O)ccc32)CC1]

Prepared in an analogous fashion to Example 95, but using isocyanato-ethane (1.2 eq.) in place of acetyl chloride. ESI+: M+1: 559. $^1$H NMR (300 MHz, CDCl$_3$) δ 12.63 (s, 1H), 8.57 (s, 1H), 8.48 (d, J=7.7 Hz, 1H), 7.76 (d, J=7.6 Hz, 1H), 7.59 (t, J=7.7 Hz, 1H), 7.43 (d, J=8.7 Hz, 1H), 7.35-7.15 (m, 2H), 5.15-5.00 (m, 1H), 4.57 (t, J=5.4 Hz, 1H), 4.36 (s, 2H), 4.24 (d, J=13.5 Hz, 2H), 4.10-4.00 (m, 2H), 3.80-3.70 (m, 2H), 3.43-3.28 (m, 2H), 3.04 (t, J=12.4 Hz, 2H), 2.60-2.42 (m, 2H), 1.96 (d, J=11.0 Hz, 2H), 1.27-1.18 (m, 5H).

Example 100: (E)-4-(2-((3-(difluoromethyl)benzoyl)imino)-5-(3-oxomorpholino)-2,3-dihydro-1H-benzo[d]imidazol-1-yl)-N-ethylpiperidine-1-carboxamide (135)

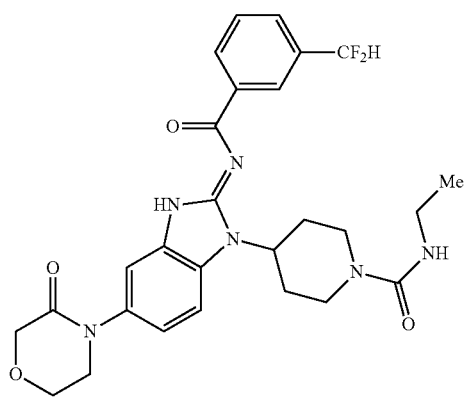

Prepared in an analogous fashion to Example 95, but using Example 94 (1 eq.) in place of Example 93, and isocyanato-ethane (1.2 eq.) in place of acetyl chloride. ESI+: M+1: 541. $^1$H NMR (300 MHz, CDCl$_3$) δ 12.69 (s, 1H), 8.42-8.40 (m, 2H), 7.68 (d, J=7.6 Hz, 1H), 7.56 (t, J=7.6 Hz, 1H), 7.42 (d, J=8.6 Hz, 1H), 7.32-7.14 (m, 2H), 6.75 (t, J=56.4 Hz, 1H), 5.05 (s, br, 1H), 4.57 (t, J=5.4 Hz, 1H), 4.35 (s, 2H), 4.23 (d, J=13.4 Hz, 2H), 4.03 (dd, J=5.9, 4.1 Hz, 2H), 3.73 (dd, J=5.9, 4.2 Hz, 2H), 3.43-3.28 (m, 2H), 3.04 (t, J=12.5 Hz, 2H), 2.63-2.45 (m, 2H), 1.95-1.92 (m, 2H), 1.27-1.12 (m, 5H).

Example 101: (E)-N-(1-(1,1-dioxidotetrahydro-2H-thiopyran-4-yl)-5-(3-oxomorpholino)-1H-benzo[d]imidazol-2(3H)-ylidene)-3-(trifluoromethyl)benzamide (136)

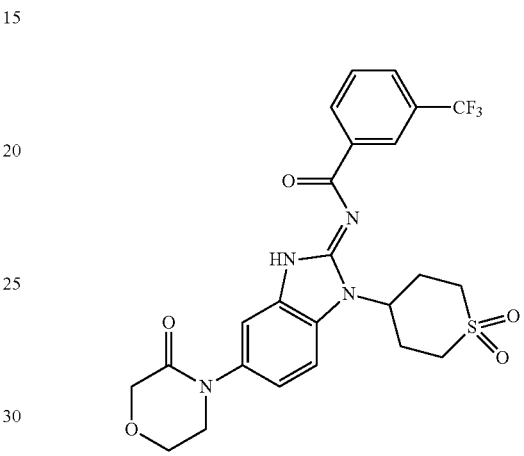

Prepared in an analogous fashion to Example 9, but using Intermediate 20 (1 eq.) in place of Intermediate 1-OH, 3-trifluoromethyl-benzoic acid (1.1 eq.) in place of 4-methyl-3-trifluoromethyl-benzoic acid, and PyBOP (1.1 eq.) in place of HBTU. ESI+: M+1: 537. $^1$H NMR (300 MHz, DMSO-d$_6$) δ 13.01 (s, 1H), 8.68 (d, J=7.7 Hz, 1H), 8.49 (s, 1H), 7.91 (d, J=7.7 Hz, 1H), 7.71 (t, J=7.8 Hz, 1H), 7.64-7.50 (m, 2H), 7.34 (dd, J=8.6, 2.0 Hz, 1H), 5.09 (s, 1H), 4.23 (s, 2H), 4.01 (dd, J=6.1, 4.0 Hz, 2H), 3.74 (t, J=5.0 Hz, 2H), 3.52 (d, J=13.4 Hz, 2H), 3.28 (d, J=13.3 Hz, 4H), 2.18 (d, J=12.3 Hz, 2H).

Example 102: (E)-3-(difluoromethyl)-N-(1-(2-(methylthio)ethyl)-5-(3-oxomorpholino)-1H-benzo[d]imidazol-2(3H)-ylidene)benzamide (63)

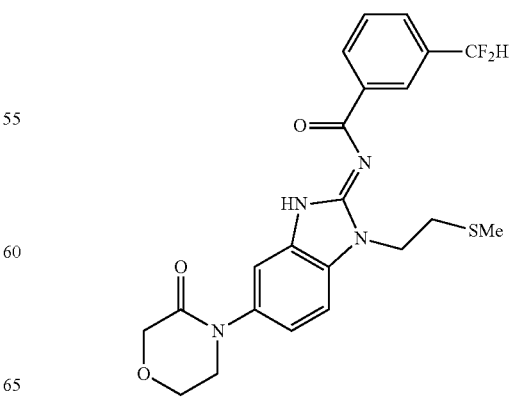

In a glass RBF equipped with a Teflon-coated magnetic stirrer was dissolved 3-difluoromethyl-benzoic acid (1.2 eq.), HATU (1.1 eq.) and Intermediate 21 (1 eq.) in DMF (0.2 M). The resulting solution was heated to 50° C. before ethyl-diisopropyl-amine (3.2 eq.) was added. When the reaction was deemed to be complete, the crude reaction mixture was directly subjected to high pressure liquid chromatography ($C_{18}$, gradient elution, 9:1 (v/v)→1:9 (v/v) $H_2O$:MeCN+0.1% TFA) to furnish the title compound as a white solid (95% yield). ESI$^+$: M+1: 461. $^1$H NMR (300 MHz, DMSO-$d_6$) δ 12.85 (s, 1H), 8.45-8.34 (m, 2H), 7.76-7.57 (m, 3H), 7.51 (d, J=2.0 Hz, 1H), 7.26 (dd, J=8.5, 2.0 Hz, 1H), 7.15 (t, 1H), 4.50 (t, J=6.9 Hz, 2H), 4.23 (s, 2H), 4.01 (t, J=6.1, 4.1 Hz, 2H), 3.75 (t, J=6.1, 4.1 Hz, 2H), 2.99 (t, J=6.9 Hz, 2H), 2.19 (s, 3H).

Example 103: (E)-3-(difluoromethyl)-N-(1-(3-(methylthio)propyl)-5-(3-oxomorpholino)-1H-benzo[d]imidazol-2(3H)-ylidene)benzamide (92)

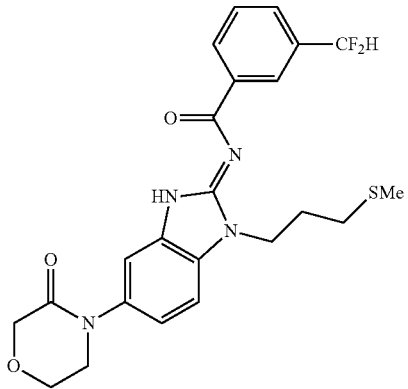 [SMILES: CSCCCn1/c(=N/C(=O)c2cccc(C(F)F)c2)[nH]c2cc(N3CCOCC3=O)ccc21]

Prepared in an analogous fashion to Example 102, but using Intermediate 22 (1 eq.) in place of Intermediate 21. ESI$^+$: M+1: 475. $^1$H NMR (300 MHz, DMSO-$d_6$) δ 12.87 (s, 1H), 8.48-8.38 (m, 2H), 7.77-7.55 (m, 3H), 7.50 (d, J=2.0 Hz, 1H), 7.28 (dd, J=8.5, 2.0 Hz, 1H), 7.15 (t, 1H), 4.39 (t, J=6.9 Hz, 2H), 4.23 (s, 2H), 4.01 (t, J=6.1, 4.0 Hz, 2H), 3.74 (t, J=6.0, 4.1 Hz, 2H), 2.58 (t, J=7.0 Hz, 2H), 2.17-2.05 (m, 2H), 2.06 (s, 3H).

Example 104: (E)-3-(difluoromethyl)-N-(1-(4-(methylthio)butyl)-5-(3-oxomorpholino)-1H-benzo[d]imidazol-2(3H)-ylidene)benzamide (89)

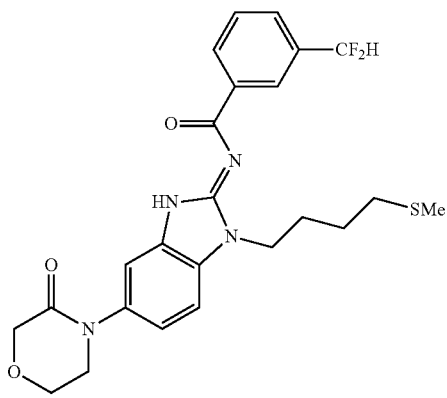 [SMILES: CSCCCCn1/c(=N/C(=O)c2cccc(C(F)F)c2)[nH]c2cc(N3CCOCC3=O)ccc21]

Prepared in an analogous fashion to Example 102, but using Intermediate 23 (1 eq.) in place of Intermediate 21. ESI$^+$: M+1: 489. $^1$H NMR (300 MHz, DMSO-$d_6$) δ 12.87 (s, 1H), 8.47-8.37 (m, 2H), 7.77-7.54 (m, 3H), 7.50 (d, J=2.0 Hz, 1H), 7.27 (dd, J=8.4, 2.0 Hz, 1H), 7.15 (t, 1H), 4.40 (t, J=6.7 Hz, 2H), 4.23 (s, 2H), 4.01 (t, J=6.1, 4.0 Hz, 2H), 3.76 (t, J=6.0, 4.0 Hz, 2H), 2.55 (t, J=7.0 Hz, 2H), 2.17-2.00 (m, 7H).

Example 105: (E)-3-(difluoromethyl)-N-(1-(2-(methylsulfinyl)ethyl)-5-(3-oxomorpholino)-1H-benzo[d]imidazol-2(3H)-ylidene)benzamide (94)

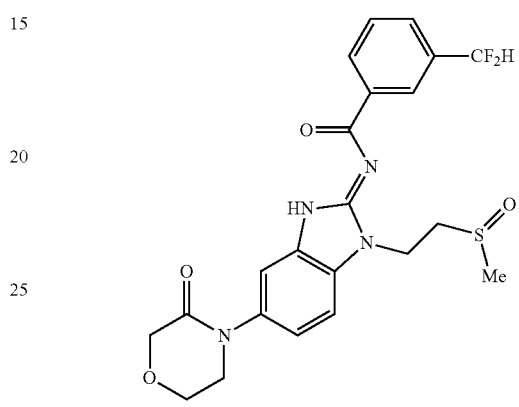

In a glass RBF equipped with a Teflon-coated magnetic stirrer was dissolved Example 102 (1 eq.) in methanol (0.2 M). To this mixture was then added at 0° C. oxone (2.4 eq., 0.8 M aqueous solution) drop-wise over a period of 5 min. The resulting solution was then allowed to warm slowly to RT over 16 h. The crude reaction mixture was directly subjected to high pressure liquid chromatography ($C_{18}$, gradient elution, 9:1 (v/v) $H_2O$:MeCN+0.1% TFA→1:9 (v/v) $H_2O$:MeCN+0.1% TFA) to furnish the title compound as a white solid (7% yield). ESI$^+$: M+1: 477. $^1$H NMR (300 MHz, $CD_3OD$) δ 8.41-8.31 (m, 2H), 7.63-7.33 (m, 4H), 7.19 (d, J=8.5 Hz, 1H), 6.75 (t, J=56.2 Hz, 1H), 4.66 (t, J=6.3 Hz, 2H), 4.21 (s, 2H), 4.01-3.91 (m, 2H), 3.75-3.65 (m, 2H), 3.46-3.31 (m, 2H), 2.60 (s, 3H).

Example 106: (E)-3-(difluoromethyl)-N-(1-(2-(methylsulfonyl)ethyl)-5-(3-oxomorpholino)-1H-benzo[d]imidazol-2(3H)-ylidene)benzamide (93)

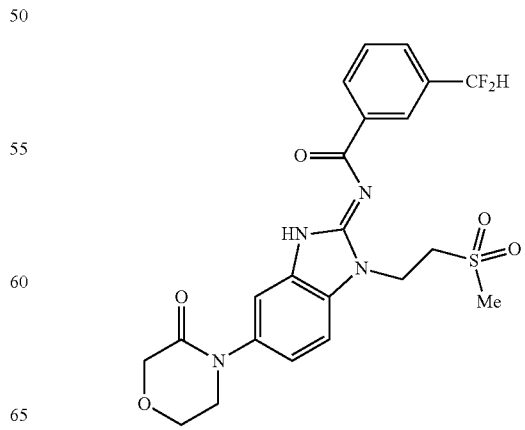

Prepared in an analogous fashion to Example 105, but using instead 12 eq. of oxone. ESI+: M+1: 493. ¹H NMR (300 MHz, DMSO-d6) δ 12.89 (s, 1H), 8.46-8.39 (m, 1H), 7.79-7.58 (m, 3H), 7.50 (d, J=2.0 Hz, 1H), 7.36-6.92 (m, 2H), 4.73 (t, J=6.7 Hz, 2H), 4.23 (s, 2H), 4.06-3.96 (m, 2H), 3.76 (dq, J=6.0, 4.7 Hz, 4H), 3.14 (s, 3H).

Example 107: (E)-3-(difluoromethyl)-N-(1-(3-(methylsulfinyl)propyl)-5-(3-oxomorpholino)-1H-benzo[d]imidazol-2(3H)-ylidene)benzamide (91) and Example 108: (E)-3-(difluoromethyl)-N-(1-(3-(methylsulfonyl)propyl)-5-(3-oxomorpholino)-1H-benzo[d]imidazol-2(3H)-ylidene)benzamide (90)

Example 107

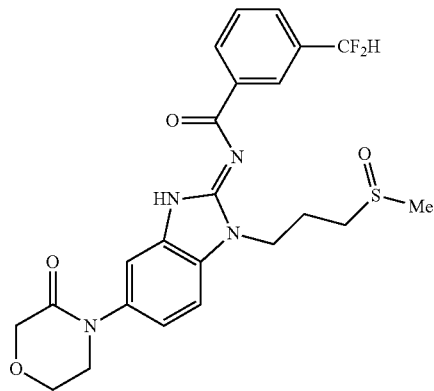

Example 108

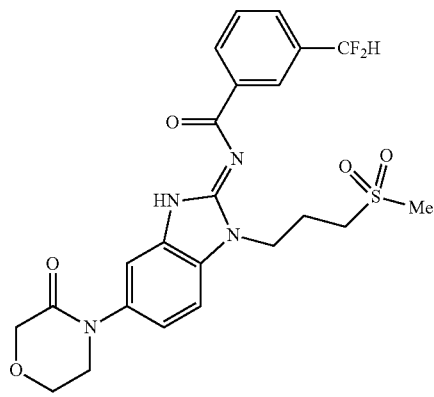

In a glass RBF equipped with a Teflon-coated magnetic stirrer was dissolved Example 103 (1 eq.) in dichloromethane (0.2 M). To this mixture was then added mCPBA (1.5 eq.) in one rapid portion. The resulting solution was then stirred at RT for 1 h. The crude reaction mixture thus obtained was directly subjected to high pressure liquid chromatography (C18, gradient elution, 9:1 (v/v) H2O:MeCN+0.1% TFA→1:9 (v/v) H2O:MeCN+0.1% TFA) to furnish both Example 107 (39% yield) and Example 108 (29% yield) as white solid. Example 107: ESI+: M+1: 491. ¹H NMR (300 MHz, DMSO-d6) δ 12.88 (s, 1H), 8.48-8.38 (m, 2H), 7.78-7.58 (m, 3H), 7.51 (d, J=1.9 Hz, 1H), 7.38-6.95 (m, 2H), 4.44 (t, J=6.8 Hz, 2H), 4.23 (s, 2H), 4.04-3.96 (m, 2H), 3.80-3.70 (m, 2H), 2.99-2.72 (m, 2H), 2.49 (s, 3H), 2.29-2.17 (m, 2H). Example 108: ESI+: M+1: 507. ¹H NMR (300 MHz, DMSO-d6) δ 12.88 (s, 1H), 8.50-8.39 (m, 2H), 7.78-7.57 (m, 3H), 7.51 (d, J=1.9 Hz, 1H), 7.38-6.92 (m, 2H), 4.44 (t, J=6.7 Hz, 2H), 4.23 (s, 2H), 4.07-3.96 (m, 2H), 3.75 (t, J=5.0 Hz, 2H), 3.29 (dd, J=9.0, 6.6 Hz, 2H), 2.98 (s, 3H), 2.27-2.15 (m, 2H).

Example 109: (E)-3-(difluoromethyl)-N-(1-(2-(methylsulfonyl)ethyl)-5-(3-oxomorpholino)-1H-benzo[d]imidazol-2(3H)-ylidene)benzamide (88)

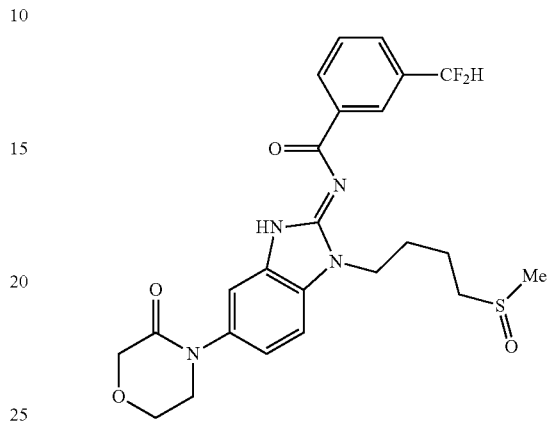

Prepared in an analogous fashion to Example 105, but using Example 104 (1 eq.) in place of Example 102. ESI+: M+1: 505. ¹H NMR (300 MHz, DMSO-d6) δ 12.88 (s, 1H), 8.44-8.38 (m, 2H), 7.78-7.58 (m, 3H), 7.51 (d, J=2.0 Hz, 1H), 7.38-6.96 (m, 2H), 4.36 (t, J=6.7 Hz, 2H), 4.23 (s, 2H), 4.06-3.96 (m, 2H), 3.75 (t, J=5.1 Hz, 2H), 2.96-2.71 (m, 2H), 2.45 (s, 3H), 1.98 (s, 2H), 1.76-1.72 (q, J=7.6 Hz, 2H).

Example 110: (E)-3-(difluoromethyl)-N-(1-(3-hydroxypropyl)-6-isopropoxy-5-(3-oxomorpholino)-1H-benzo[d]imidazol-2(3H)-ylidene)benzamide (137)

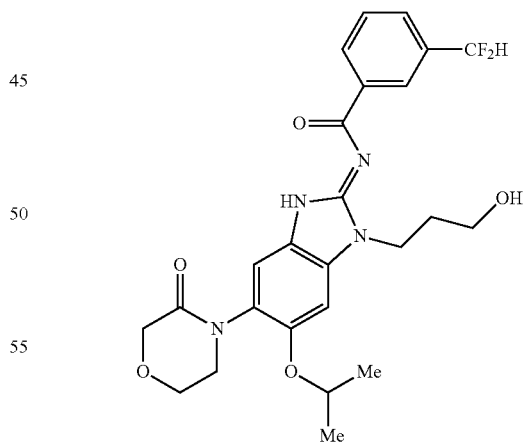

Prepared in an analogous fashion to Example 1, but using Intermediate 24 (1 eq.) in place of Intermediate 1-OTIPS, and 3-difluoromethyl-benzoic acid (1 eq.) in place of 3-trifluoromethyl-benzoic acid in step 1. ESI+: M+1: 503. ¹H NMR (300 MHz, CD3OD) δ 8.47-8.35 (m, 2H), 7.68 (d, J=7.7 Hz, 1H), 7.57 (t, J=7.7 Hz, 1H), 7.39 (s, 1H), 7.30 (s, 1H), 6.85 (t, J=56.3 Hz, 1H), 4.75 (p, J=6.0 Hz, 1H), 4.45

(t, J=6.7 Hz, 2H), 4.30 (s, 2H), 4.13-3.96 (m, 2H), 3.76-3.66 (m, 2H), 3.62 (t, J=6.0 Hz, 2H), 2.22-2.01 (m, 2H), 1.37 (d, J=6.0 Hz, 6H).

Example 111: (E)-N-(1-(3-hydroxypropyl)-6-methoxy-5-(3-oxomorpholino)-1H-benzo[d]imidazol-2(3H)-ylidene)-3-(trifluoromethyl)benzamide (76)

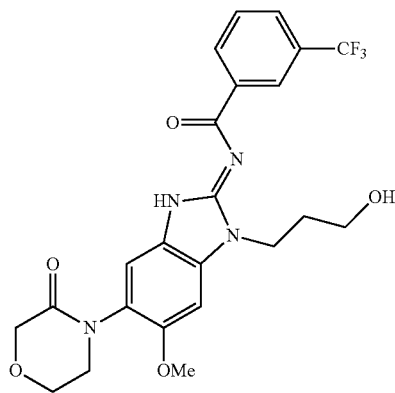 [SMILES: COc1cc2c(cc1N1CCOCC1=O)[nH]/c(=N\C(=O)c1cccc(C(F)(F)F)c1)n2CCCO]

Prepared in an analogous fashion to Example 1, but using Intermediate 25 (1 eq.) in place of Intermediate 1-OTIPS. ESI$^+$: M+1: 494. $^1$H NMR (300 MHz, DMSO-d$_6$) δ 12.80 (s, 1H), 8.57-8.47 (m, 2H), 7.90 (d, J=7.7 Hz, 1H), 7.73 (t, J=7.8 Hz, 1H), 7.39-7.31 (m, 2H), 4.71 (t, J=5.0 Hz, 1H), 4.37 (t, J=6.7 Hz, 2H), 4.21 (s, 2H), 3.98 (t, J=5.1 Hz, 2H), 3.88 (s, 3H), 3.61-3.54 (m, 2H), 3.50 (q, J=5.9 Hz, 2H), 2.04-1.93 (m, 2H).

Example 112: (E)-3-(difluoromethyl)-N-(1-(3-hydroxypropyl)-6-methoxy-5-(3-oxomorpholino)-1H-benzo[d]imidazol-2(3H)-ylidene)benzamide (75)

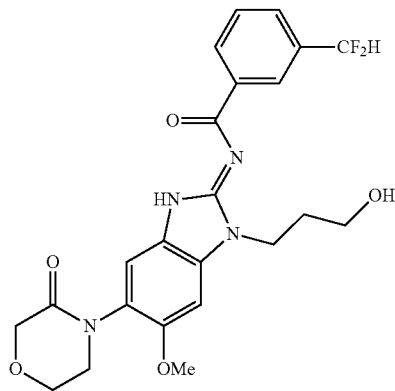

Prepared in an analogous fashion to Example 1, but using Intermediate 25 (1 eq.) in place of Intermediate 1-OTIPS, and 3-difluoromethyl-benzoic acid (1 eq.) in place of 3-trifluoromethyl-benzoic acid in step 1. ESI$^+$: M+1: 475. $^1$H NMR (300 MHz, CD$_3$OD) δ 8.50-8.25 (m, 2H), 7.67 (d, J=7.7 Hz, 1H), 7.57 (t, J=7.7 Hz, 1H), 7.40 (s, 1H), 7.29 (s, 1H), 6.85 (t, J=56.2 Hz, 1H), 4.45 (t, J=6.7 Hz, 2H), 4.31 (s, 2H), 4.05 (t, J=5.1 Hz, 2H), 3.94 (s, 3H), 3.72-3.65 (m, 2H), 3.62 (t, J=6.0 Hz, 2H), 2.18-2.03 (m, 2H).

Example 113: (E)-3-cyano-N-(1-(3-hydroxypropyl)-6-methoxy-5-(3-oxomorpholino)-1H-benzo[d]imidazol-2(3H)-ylidene)benzamide (74)

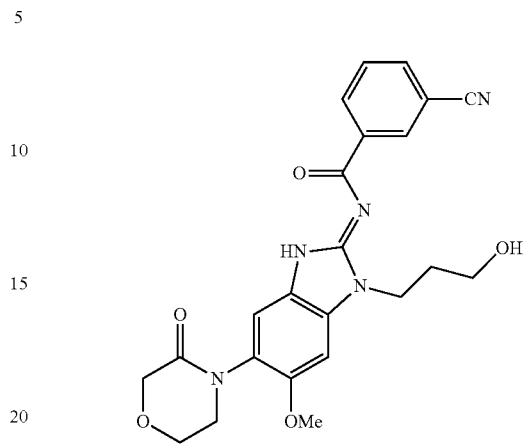

Prepared in an analogous fashion to Example 1, but using Intermediate 25 (1 eq.) in place of Intermediate 1-OTIPS, and 3-cyano-benzoic acid (1 eq.) in place of 3-trifluoromethyl-benzoic acid in step 1. ESI$^+$: M+1: 450. $^1$H NMR (300 MHz, DMSO-d$_6$) δ 12.81 (s, 1H), 8.60-8.47 (m, 2H), 8.00 (d, J=7.7 Hz, 1H), 7.71 (t, J=7.8 Hz, 1H), 7.39-7.31 (m, 2H), 4.72 (s, 1H), 4.53-4.29 (m, 2H), 4.21 (s, 2H), 4.01-3.94 (m, 2H), 3.88 (s, 3H), 3.60-3.45 (m, 4H), 2.04-1.93 (m, 2H).

Example 114: (E)-3-fluoro-N-(1-(3-hydroxypropyl)-6-methoxy-5-(3-oxomorpholino)-1H-benzo[d]imidazol-2(3H)-ylidene)-5-(trifluoromethyl)benzamide (73)

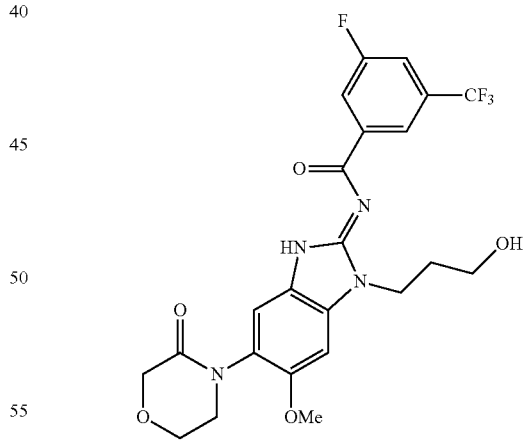

Prepared in an analogous fashion to Example 1, but using Intermediate 25 (1 eq.) in place of Intermediate 1-OTIPS, and 3-fluoro-5-trifluoromethyl-benzoic acid (1 eq.) in place of 3-trifluoromethyl-benzoic acid in step 1. ESI$^+$: M+1: 512. $^1$H NMR (300 MHz, DMSO-d$_6$) δ 12.83 (s, 1H), 8.34 (s, 1H), 8.25 (d, J=8.4 Hz, 1H), 7.88 (d, J=8.7 Hz, 1H), 7.41-7.32 (m, 2H), 4.71 (t, J=5.0 Hz, 1H), 4.38 (t, J=6.7 Hz, 2H), 4.21 (s, 2H), 3.98 (t, J=5.1 Hz, 2H), 3.88 (s, 3H), 3.60-3.43 (m, 4H), 2.05-1.92 (m, 2H).

Example 115: (E)-3-(hydroxymethyl)-N-(1-(3-hydroxypropyl)-6-methoxy-5-(3-oxomorpholino)-1H-benzo[d]imidazol-2(3H)-ylidene)benzamide (64)

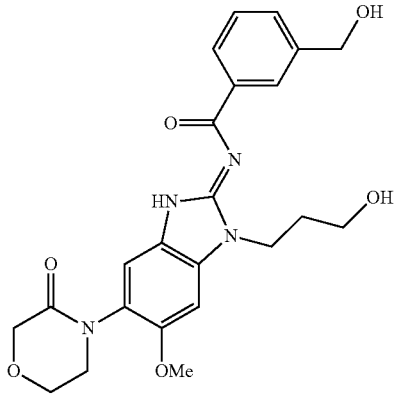 [SMILES: COc1cc2c(cc1N1CCOCC1=O)[nH]/c(=N\C(=O)c1cccc(CO)c1)n2CCCO]

Prepared in an analogous fashion to Example 1, but using Intermediate 25 (1 eq.) in place of Intermediate 1-OTIPS, and 3-hydroxymethyl-benzoic acid (1 eq.) in place of 3-trifluoromethyl-benzoic acid in step 1. ESI$^+$: M+1: 455. $^1$H NMR (300 MHz, DMSO-d$_6$) δ 12.72 (s, 1H), 8.21-8.08 (m, 2H), 7.51-7.36 (m, 2H), 7.32 (s, 2H), 5.28 (t, J=5.8 Hz, 1H), 4.74 (s, 1H), 4.57 (d, J=5.7 Hz, 2H), 4.21 (s, 2H), 3.97 (t, J=5.0 Hz, 2H), 3.87 (s, 3H), 3.60-3.53 (m, 2H), 3.53-3.44 (m, 2H), 2.03-1.96 (m, 2H).

Example 116: (E)-N-(1-(3-hydroxypropyl)-6-methyl-5-(3-oxomorpholino)-1H-benzo[d]imidazol-2(3H)-ylidene)-3-(trifluoromethyl)benzamide (70)

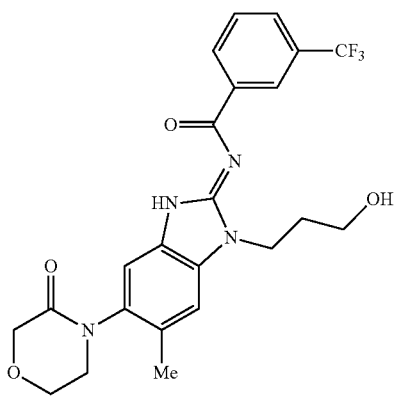 [SMILES: Cc1cc2c(cc1N1CCOCC1=O)[nH]/c(=N\C(=O)c1cccc(C(F)(F)F)c1)n2CCCO]

Prepared in an analogous fashion to Example 1, but using Intermediate 26 (1 eq.) in place of Intermediate 1-OTIPS. ESI$^+$: M+1: 477. $^1$H NMR (300 MHz, DMSO-d$_6$) δ 12.83 (s, 1H), 8.57-8.47 (m, 2H), 7.90 (d, J=7.8 Hz, 1H), 7.74 (t, J=7.7 Hz, 1H), 7.50 (s, 1H), 7.35 (s, 1H), 4.69 (t, J=5.0 Hz, 1H), 4.33 (t, J=7.0 Hz, 2H), 4.24 (d, J=1.6 Hz, 2H), 4.10-3.92 (m, 2H), 3.74-3.60 (m, 1H), 3.58-3.42 (m, 3H), 2.25 (s, 3H), 1.98 (p, J=6.4 Hz, 2H).

Example 117: (E)-3-(difluoromethyl)-N-(1-(3-hydroxypropyl)-6-methyl-5-(3-oxomorpholino)-1H-benzo[d]imidazol-2(3H)-ylidene)benzamide (69)

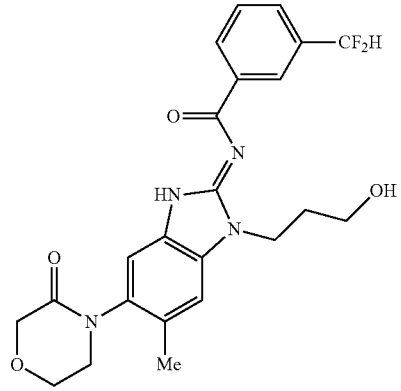

Prepared in an analogous fashion to Example 1, but using Intermediate 26 (1 eq.) in place of Intermediate 1-OTIPS, and 3-difluoromethyl-benzoic acid (1 eq.) in place of 3-trifluoromethyl-benzoic acid in step 1. ESI$^+$: M+1: 459. $^1$H NMR (300 MHz, DMSO-d$_6$) δ 12.81 (s, 1H), 8.45-8.36 (m, 2H), 7.73 (d, J=7.6 Hz, 1H), 7.63 (t, J=7.9 Hz, 1H), 7.49 (s, 1H), 7.41-6.89 (m, 2H), 4.69 (t, J=5.1 Hz, 1H), 4.32 (t, J=6.9 Hz, 2H), 4.24 (d, J=1.6 Hz, 2H), 4.10-3.90 (m, 2H), 3.73-3.60 (m, 1H), 3.55-3.45 (m, 2H), 2.25 (s, 3H), 1.97 (p, J=6.5 Hz, 2H).

Example 118: (E)-3-cyano-N-(1-(3-hydroxypropyl)-6-methyl-5-(3-oxomorpholino)-1H-benzo[d]imidazol-2(3H)-ylidene)benzamide (68)

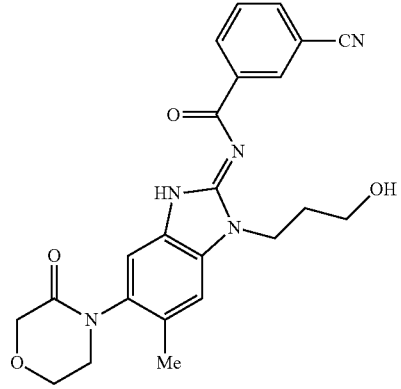

Prepared in an analogous fashion to Example 1, but using Intermediate 26 (1 eq.) in place of Intermediate 1-OTIPS, and 3-cyano-benzoic acid (1 eq.) in place of 3-trifluoromethyl-benzoic acid in step 1. ESI$^+$: M+1: 434. $^1$H NMR (300 MHz, DMSO-d$_6$) δ 12.85 (s, 1H), 8.60-8.48 (m, 2H), 8.00 (dt, J=7.7, 1.5 Hz, 1H), 7.71 (t, J=7.8 Hz, 1H), 7.50 (s, 1H), 7.34 (s, 1H), 4.69 (t, J=5.1 Hz, 1H), 4.34 (t, J=6.9 Hz, 2H), 4.24 (d, J=1.6 Hz, 2H), 4.12-3.87 (m, 2H), 3.73-3.62 (m, 1H), 3.55-3.45 (m, 3H), 2.25 (s, 3H), 2.03-1.91 (m, 2H).

Example 119: (E)-3-fluoro-N-(1-(3-hydroxypropyl)-6-methyl-5-(3-oxomorpholino)-1H-benzo[d]imidazol-2(3H)-ylidene)-5-(trifluoromethyl)benzamide (67)

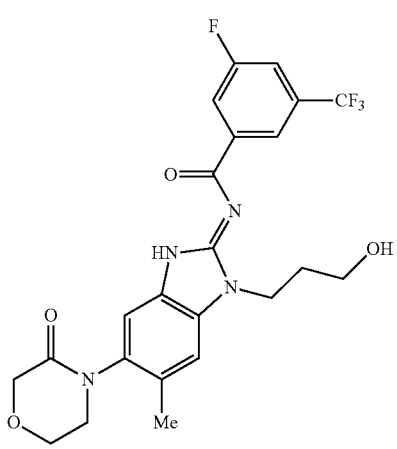

Prepared in an analogous fashion to Example 1, but using Intermediate 26 (1 eq.) in place of Intermediate 1-OTIPS, and 3-fluoro-5-trifluoromethyl-benzoic acid (1 eq.) in place of 3-trifluoromethyl-benzoic acid in step 1. ESI$^+$: M+1: 495. $^1$H NMR (300 MHz, DMSO-d$_6$) δ 12.86 (s, 1H), 8.34 (s, 1H), 8.25 (d, J=8.6 Hz, 1H), 7.88 (d, J=8.4 Hz, 1H), 7.52 (s, 1H), 7.36 (s, 1H), 4.68 (t, J=5.0 Hz, 1H), 4.34 (t, J=6.9 Hz, 2H), 4.24 (d, J=1.6 Hz, 2H), 4.10-3.92 (m, 2H), 3.75-3.62 (m, 1H), 3.55-3.43 (m, 3H), 2.25 (s, 3H), 1.96 (p, J=6.5 Hz, 2H).

Example 120: (E)-N-(6-bromo-1-(3-hydroxypropyl)-5-(3-oxomorpholino)-1H-benzo[d]imidazol-2(3H)-ylidene)-3-(trifluoromethyl)benzamide (50)

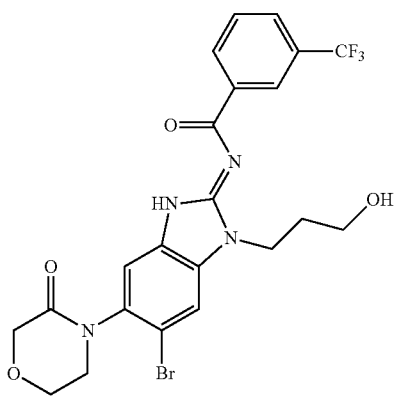

Prepared in an analogous fashion to Example 1, but using Intermediate 27 (1 eq.) in place of Intermediate 1-OTIPS. ESI$^+$: M+1: 541. $^1$H NMR (300 MHz, DMSO-d$_6$) δ 12.99 (s, 1H), 8.57-8.47 (m, 2H), 8.00 (s, 1H), 7.92 (d, J=7.9 Hz, 1H), 7.75 (t, J=7.7 Hz, 1H), 7.51 (s, 1H), 4.71-4.64 (m, 1H), 4.34 (t, J=7.2 Hz, 2H), 4.25 (d, J=3.1 Hz, 2H), 4.13-3.92 (m, 2H), 3.63 (p, J=6.7, 6.0 Hz, 2H), 3.48 (t, J=6.4 Hz, 2H), 2.01-1.88 (m, 2H).

Example 121: (E)-N-(6-cyano-1-(3-hydroxypropyl)-5-(3-oxomorpholino)-1H-benzo[d]imidazol-2(3H)-ylidene)-3-(trifluoromethyl)benzamide (138)

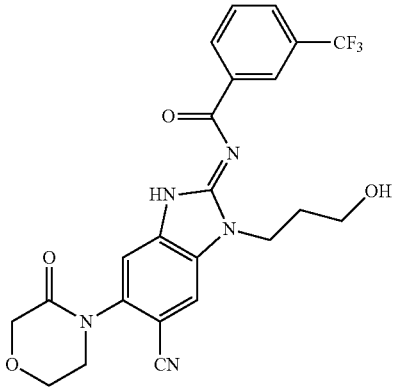

In a sealable glass reaction vessel equipped with a Teflon-coated screw cap was combined Example 120 (1 eq.) and copper(I) cyanide (60 eq.) in NMP (0.015 M). The resulting suspension was then sub-surface purged with nitrogen for 2 min before the vessel was tightly sealed and heated at 180° C. for 4 h. The reaction mixture was cooled to RT and diluted with methanol. The insoluble copper waste was removed via filtration and the filtrate thus obtained was concentrated in vacuo. Further purification using high-pressure liquid chromatography (C18, gradient elution, 4:1 (v/v) H$_2$O:MeCN+0.1% TFA 4 MeCN+0.1% TFA) furnished the title compound as a white solid (24% yield). ESI$^+$: M+1: 488. $^1$H NMR (300 MHz, CD$_3$OD) δ 8.59-8.52 (m, 2H), 8.07 (s, 1H), 7.83 (d, J=8.0 Hz, 1H), 7.71-7.58 (m, 2H), 4.47 (t, J=6.7 Hz, 2H), 4.37 (s, 2H), 4.12 (t, J=5.0 Hz, 2H), 3.85 (t, J=5.2 Hz, 2H), 3.64 (t, J=5.9 Hz, 2H), 2.17-2.08 (m, 2H).

Example 122: (E)-N-(6-bromo-1-(3-hydroxypropyl)-5-(3-oxomorpholino)-1H-benzo[d]imidazol-2(3H)-ylidene)-3-(difluoromethyl)benzamide (49)

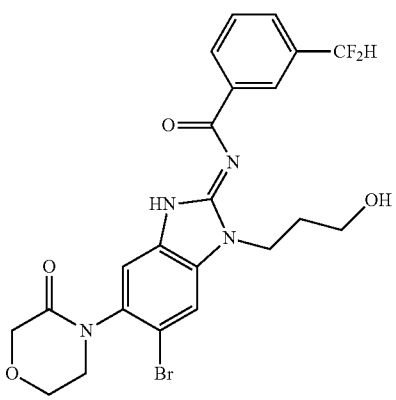

Prepared in an analogous fashion to Example 1, but using Intermediate 27 (1 eq.) in place of Intermediate 1-OTIPS, and 3-difluoromethyl-benzoic acid (1 eq.) in place of 3-trifluoromethyl-benzoic acid in step 1. ESI$^+$: M+1: 525. $^1$H NMR (300 MHz, DMSO-d$_6$) δ 12.96 (s, 1H), 8.46-8.36 (m, 2H), 7.98 (s, 1H), 7.74 (d, J=7.7 Hz, 1H), 7.64 (t, J=7.8 Hz, 1H), 7.50 (s, 1H), 7.16 (t, J=55.9 Hz, 1H), 4.68 (s, 1H), 4.33 (t, J=6.7 Hz, 2H), 4.25 (d, J=3.1 Hz, 2H), 4.02 (dp, J=22.2, 5.9, 5.3 Hz, 2H), 3.60 (p, J=6.9, 6.4 Hz, 2H), 3.52-3.45 (m, 2H), 1.96 (p, J=6.5 Hz, 2H).

Example 123: (E)-N-(6-bromo-1-(3-hydroxypropyl)-5-(3-oxomorpholino)-1H-benzo[d]imidazol-2(3H)-ylidene)-3-cyanobenzamide (48)

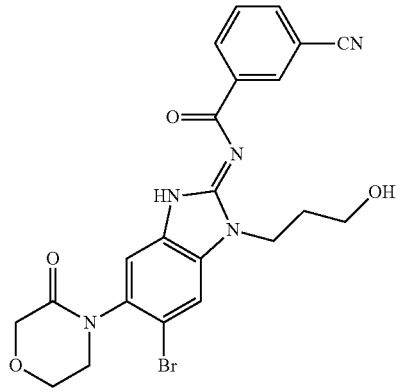

Prepared in an analogous fashion to Example 1, but using Intermediate 27 (1 eq.) in place of Intermediate 1-OTIPS, and 3-cyano-benzoic acid (1 eq.) in place of 3-trifluoromethyl-benzoic acid in step 1. ESI+: M+1: 499. $^1$H NMR (300 MHz, DMSO-d$_6$) δ 13.01 (s, 1H), 8.57 (dt, J=1.7, 1.0 Hz, 1H), 8.53 (dt, J=8.0, 1.4 Hz, 1H), 8.06-7.97 (m, 2H), 7.72 (t, J=7.7 Hz, 1H), 7.50 (s, 1H), 4.68 (s, 1H), 4.35 (t, J=6.8 Hz, 2H), 4.25 (d, J=3.2 Hz, 2H), 4.13-3.92 (m, 2H), 3.61 (h, J=7.1, 6.6 Hz, 2H), 3.49 (s, 2H), 1.95 (t, J=6.4 Hz, 2H).

Example 124: (E)-N-(6-fluoro-1-(3-hydroxypropyl)-5-(3-oxomorpholino)-1H-benzo[d]imidazol-2(3H)-ylidene)-3-(trifluoromethyl)benzamide (139)

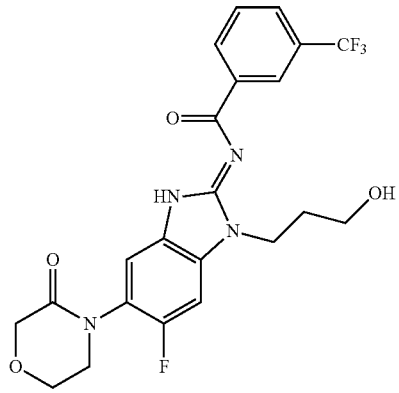

Prepared in an analogous fashion to Example 1, but using Intermediate 28 (1 eq.) in place of Intermediate 1-OTIPS. ESI+: M+1: 481. $^1$H NMR (300 MHz, DMSO-d$_6$) δ 12.94 (s, 1H), 8.57-8.47 (m, 2H), 7.91 (d, J=7.9 Hz, 1H), 7.74 (t, J=7.7 Hz, 1H), 7.69 (d, J=10.1 Hz, 1H), 7.50 (d, J=6.6 Hz, 1H), 4.68 (t, J=5.0 Hz, 1H), 4.33 (t, J=6.8 Hz, 2H), 4.26 (s, 2H), 4.02 (t, J=5.1 Hz, 2H), 3.69-3.65 (m, 2H), 3.48 (t, J=5.8 Hz, 2H), 2.02-1.91 (m, 2H).

Example 125: (E)-3-(difluoromethyl)-N-(6-fluoro-1-(3-hydroxypropyl)-5-(3-oxomorpholino)-1H-benzo[d]imidazol-2(3H)-ylidene)benzamide (140)

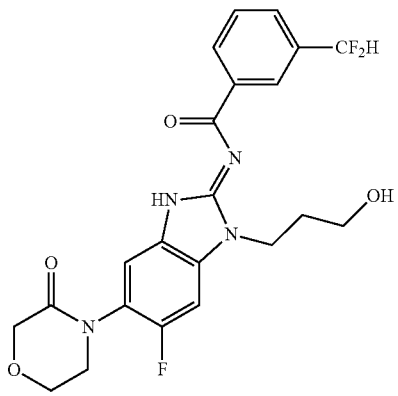

Prepared in an analogous fashion to Example 1, but using Intermediate 28 (1 eq.) in place of Intermediate 1-OTIPS. ESI+: M+1: 463. $^1$H NMR (300 MHz, DMSO-d$_6$) δ 12.91 (s, 1H), 8.46-8.37 (m, 2H), 7.78-7.58 (m, 3H), 7.48 (d, J=6.7 Hz, 1H), 7.16 (t, J=55.9 Hz, 1H), 4.68 (t, J=5.0 Hz, 1H), 4.32 (t, J=6.9 Hz, 2H), 4.26 (s, 2H), 4.02 (t, J=5.1 Hz, 2H), 3.67 (t, J=5.1 Hz, 2H), 3.49 (q, J=5.8 Hz, 2H), 2.07-1.87 (m, 2H).

Example 126: (E)-N-(6-chloro-1-(3-hydroxypropyl)-5-(3-oxomorpholino)-1H-benzo[d]imidazol-2(3H)-ylidene)-3-(trifluoromethyl)benzamide (141)

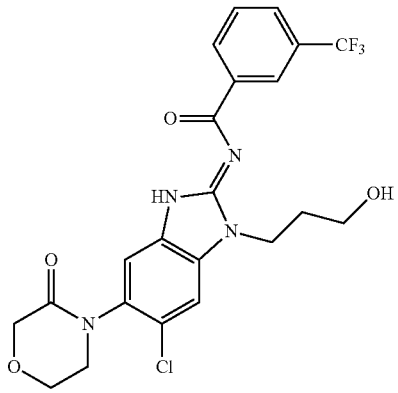

Prepared in an analogous fashion to Example 1, but using Intermediate 29 (1 eq.) in place of Intermediate 1-OTIPS. ESI+: M+1: 497. $^1$H NMR (300 MHz, DMSO-d$_6$) δ 13.00 (s, 1H), 8.52 (s, 2H), 7.92 (d, J=7.9 Hz, 1H), 7.88 (s, 1H), 7.75 (t, J=7.7 Hz, 1H), 7.51 (s, 1H), 4.67 (s, br, 1H), 4.34 (t, J=6.9 Hz, 2H), 4.26 (s, 2H), 4.02 (dq, J=18.3, 7.0, 6.0 Hz, 2H), 3.62 (dt, J=10.9, 5.6 Hz, 2H), 3.49 (q, J=4.6 Hz, 2H), 1.96 (p, J=6.5 Hz, 2H).

Example 127: (E)-N-(6-chloro-1-(3-hydroxypropyl)-5-(3-oxomorpholino)-1H-benzo[d]imidazol-2(3H)-ylidene)-3-(difluoromethyl)benzamide (142)

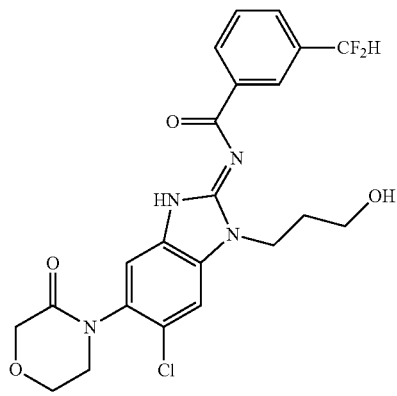

Prepared in an analogous fashion to Example 1, but using Intermediate 29 (1 eq.) in place of Intermediate 1-OTIPS. ESI$^+$: M+1: 479. $^1$H NMR (300 MHz, DMSO-d$_6$) δ 12.97 (s, 1H), 8.48-8.34 (m, 2H), 7.74 (d, J=7.7 Hz, 1H), 7.64 (t, J=7.7 Hz, 1H), 7.50 (s, 1H), 7.16 (t, J=55.9 Hz, 1H), 4.67 (t, J=5.1 Hz, 1H), 4.33 (t, J=6.8 Hz, 2H), 4.26 (s, 2H), 4.02 (tt, J=12.3, 7.1 Hz, 2H), 3.62 (dt, J=10.7, 5.6 Hz, 2H), 3.49 (q, J=5.3 Hz, 2H), 1.97 (p, J=6.5 Hz, 2H).

Example 128: (E)-N-(1-((1-(hydroxymethyl)cyclopropyl)methyl)-6-methoxy-5-(3-oxomorpholino)-1H-benzo[d]imidazol-2(3H)-ylidene)-3-(trifluoromethyl)benzamide (53)

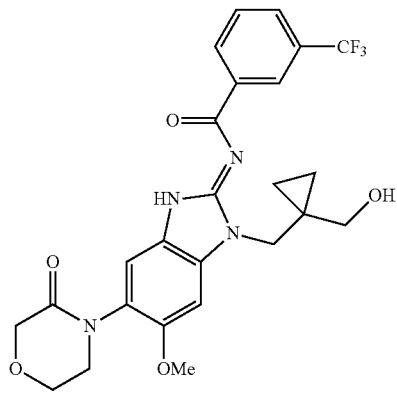

Prepared in an analogous fashion to Example 1, but using Intermediate 30 (1 eq.) in place of Intermediate 1-OTIPS. ESI$^+$: M+1: 519. $^1$H NMR (300 MHz, DMSO-d$_6$) δ 12.87 (s, 1H), 8.53-8.43 (m, 2H), 7.90 (d, J=8.0 Hz, 1H), 7.74 (t, J=7.9 Hz, 1H), 7.51 (s, 1H), 7.35 (s, 1H), 4.99 (s, 1H), 4.33 (s, 2H), 4.22 (s, 2H), 3.98 (t, J=4.9 Hz, 2H), 3.87 (s, 3H), 3.61-3.54 (m, 2H), 3.24 (d, J=4.6 Hz, 2H), 0.96-0.88 (m, 2H), 0.61-0.34 (m, 2H).

Example 129: (E)-3-(difluoromethyl)-N-(1-((1-(hydroxymethyl)cyclopropyl)methyl)-6-methoxy-5-(3-oxomorpholino)-1H-benzo[d]imidazol-2(3H)-ylidene)benzamide (52)

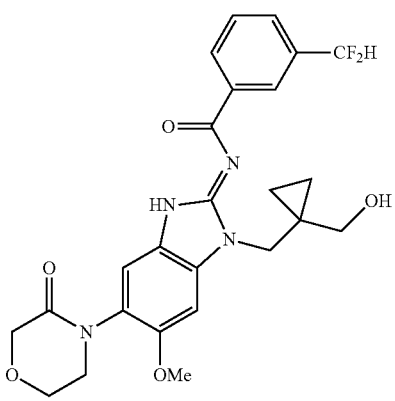 [SMILES: COc1cc2c(cc1N1CCOCC1=O)[nH]/c(=N\C(=O)c1cccc(C(F)F)c1)n2CC1(CO)CC1]

Prepared in an analogous fashion to Example 1, but using Intermediate 30 (1 eq.) in place of Intermediate 1-OTIPS, and 3-difluoromethyl-benzoic acid (1 eq.) in place of 3-trifluoromethyl-benzoic acid in step 1. ESI$^+$: M+1: 501. $^1$H NMR (300 MHz, DMSO-d$_6$) δ 12.84 (s, 1H), 8.41-8.32 (m, 2H), 7.77-7.58 (m, 2H), 7.49 (s, 1H), 7.41-6.89 (m, 2H), 5.02 (s, 1H), 4.32 (s, 2H), 4.22 (s, 2H), 3.98 (t, J=5.0 Hz, 2H), 3.87 (s, 3H), 3.58 (s, 2H), 3.23 (s, 2H), 0.96-0.88 (m, 2H), 0.48 (q, J=4.1 Hz, 1H).

Example 130: (E)-3-cyano-N-(1-((1-(hydroxymethyl)cyclopropyl)methyl)-6-methoxy-5-(3-oxomorpholino)-1H-benzo[d]imidazol-2(3H)-ylidene)benzamide (51)

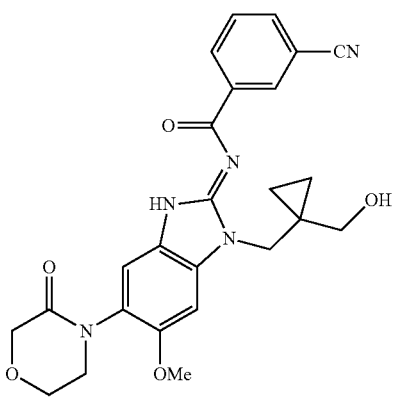 [SMILES: COc1cc2c(cc1N1CCOCC1=O)[nH]/c(=N\C(=O)c1cccc(C#N)c1)n2CC1(CO)CC1]

Prepared in an analogous fashion to Example 1, but using Intermediate 30 (1 eq.) in place of Intermediate 1-OTIPS, and 3-cyano-benzoic acid (1 eq.) in place of 3-trifluoromethyl-benzoic acid in step 1. ESI$^+$: M+1: 476. $^1$H NMR (300 MHz, DMSO-d$_6$) δ 12.88 (s, 1H), 8.54 (t, J=1.7 Hz, 1H), 8.49 (dt, J=7.9, 1.4 Hz, 1H), 8.00 (dt, J=7.7, 1.4 Hz, 1H), 7.71 (t, J=7.7 Hz, 1H), 7.50 (s, 1H), 7.35 (s, 1H), 4.98 (s, 1H), 4.35 (s, 2H), 4.22 (s, br, 2H), 3.98 (t, J=4.9 Hz, 2H), 3.87 (s, 3H), 3.61-3.54 (m, 2H), 3.27-3.19 (m, 2H), 0.95-0.85 (m, 2H), 0.54-0.40 (m, 2H).

Example 131: (R,E)-N-(1-(4-hydroxybutan-2-yl)-6-methoxy-5-(3-oxomorpholino)-1H-benzo[d]imidazol-2(3H)-ylidene)-3-(trifluoromethyl)benzamide (143)

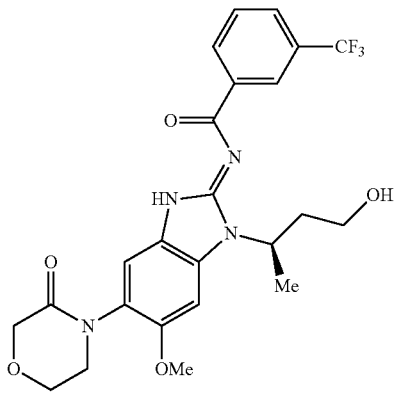 [SMILES: COc1cc2c(cc1N1CCOCC1=O)[nH]/c(=N\C(=O)c1cccc(C(F)(F)F)c1)n2[C@H](C)CCO]

Prepared in an analogous fashion to Example 1, but using Intermediate 31 (1 eq.) in place of Intermediate 1-OTIPS. ESI⁺: M+1: 507. $^1$H NMR (300 MHz, CD$_3$OD) δ 8.50 (s, 1H), 8.47 (d, J=7.9 Hz, 1H), 7.85 (d, J=7.7 Hz, 1H), 7.69 (t, J=7.7 Hz, 1H), 7.49 (s, 1H), 7.31 (s, 1H), 5.39-5.14 (m, 1H), 4.31 (s, 2H), 4.06 (t, J=5.1 Hz, 2H), 3.96 (s, 3H), 3.73-3.66 (m, 2H), 3.65-3.55 (m, 1H), 3.47-3.35 (m, 1H), 2.61-2.55 (m, 1H), 2.31-2.14 (m, 1H), 1.79 (d, J=7.0 Hz, 3H).

Example 132: (R,E)-3-(difluoromethyl)-N-(1-(4-hydroxybutan-2-yl)-6-methoxy-5-(3-oxomorpholino)-1H-benzo[d]imidazol-2(3H)-ylidene)benzamide (40)

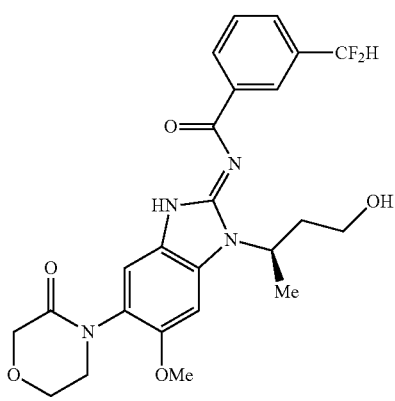

Prepared in an analogous fashion to Example 1, but using Intermediate 31 (1 eq.) in place of Intermediate 1-OTIPS, and 3-difluoromethyl-benzoic acid (1 eq.) in place of 3-trifluoromethyl-benzoic acid in step 1. ESI⁺: M+1: 489. $^1$H NMR (300 MHz, CD$_3$OD) δ 8.36 (s, 1H), 8.33 (d, J=7.7 Hz, 1H), 7.77 (d, J=7.6 Hz, 1H), 7.64 (t, J=7.7 Hz, 1H), 7.53 (s, 1H), 7.34 (s, 1H), 6.88 (t, J=56.1 Hz, 1H), 5.37-5.13 (m, 1H), 4.31 (s, 2H), 4.06 (t, J=5.0 Hz, 2H), 3.97 (s, 3H), 3.72-3.66 (m, 2H), 3.68-3.58 (m, 1H), 3.45-3.35 (m, 1H), 2.59-2.52 (m, 1H), 2.31-2.18 (m, 1H), 1.81 (d, J=7.0 Hz, 3H).

Example 133: rac-(E)-N-(1-((1R,2R)-2-(hydroxymethyl)cyclopropyl)-5-(2-oxo-1,3-oxazinan-3-yl)-1H-benzo[d]imidazol-2(3H)-ylidene)-3-(trifluoromethyl)benzamide (144)

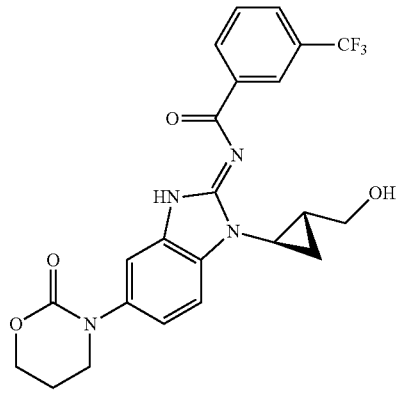 [SMILES: O=C(/N=c1\[nH]c2cc(N3CCCOC3=O)ccc2n1[C@@H]1C[C@H]1CO)c1cccc(C(F)(F)F)c1]

In a Parr shaker flask was dissolved Intermediate 32-CF$_3$ (1 eq.) in a 1:1 (v/v) solution (0.1 M) of MeOH: EtOAc. To this was then added palladium (0.3 eq., dry, 10% w/w over carbon) and the resulting suspension was evacuated and back-filled with nitrogen (3×) and then hydrogen (3×). The reaction suspension was then shaken under 50 psi of hydrogen for 4 h. The reaction was quenched with dichloromethane and the resulting suspension was filtered through a pad of dichloromethane-wetted celite. The filtrate thus obtained was concentrated in vacuo to afford, after extensive trituration with ether/hexanes, the desired product as a white solid (54% yield). ESI⁺: M+1: 475. $^1$H NMR (300 MHz, CD$_3$OD) δ 8.58 (s, 1H), 8.46 (d, J=7.8 Hz, 1H), 7.78 (d, J=7.8 Hz, 1H), 7.71-7.56 (m, 2H), 7.31-7.21 (m, 1H), 4.50 (t, J=5.4 Hz, 2H), 4.07-4.01 (m, 1H), 3.77 (t, J=6.0 Hz, 2H), 3.57 (dd, J=11.5, 7.8 Hz, 1H), 3.44-3.32 (m, 1H), 3.16-3.07 (m, 1H), 2.29 (q, J=5.8 Hz, 2H), 1.99-1.66 (m, 1H), 1.52-1.30 (m, 2H).

Example 134: (E)-N-(1-(2-fluoro-3-hydroxypropyl)-5-(2-oxo-1,3-oxazinan-3-yl)-1H-benzo[d]imidazol-2(3H)-ylidene)-3-(trifluoromethyl)benzamide (145)

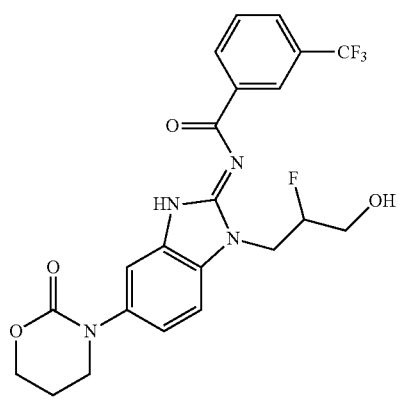 [SMILES: O=C(/N=c1\[nH]c2cc(N3CCCOC3=O)ccc2n1CC(F)CO)c1cccc(C(F)(F)F)c1]

Prepared in an analogous fashion to Example 133, but using Intermediate 33-CF$_3$ (1 eq.) in place of Intermediate 32-CF$_3$. ESI⁺: M+1: 481. $^1$H NMR (300 MHz, DMSO-d$_6$) δ

12.94 (s, 1H), 8.57-8.46 (m, 2H), 7.91 (d, J=7.7 Hz, 1H), 7.74 (t, J=7.7 Hz, 1H), 7.53 (d, J=8.5 Hz, 1H), 7.48 (d, J=2.0 Hz, 1H), 7.27 (dd, J=8.6, 2.0 Hz, 1H), 5.24 (t, J=5.6 Hz, 1H), 5.13-4.85 (m, 1H), 4.64-4.50 (m, 2H), 4.37 (t, J=5.3 Hz, 2H), 3.89-3.54 (m, 4H), 2.14 (m, 2H).

Example 135: (E)-3-(2-(1-(3-hydroxypropyl)-5-(3-oxomorpholino)-1H-benzo[d]imidazol-2(3H)-ylidene)acetyl)benzonitrile (146)

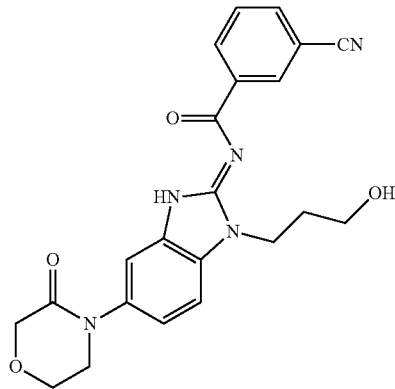

Step 1: (E)-3-(2-(5-(3-oxo-morpholino)-1-(3-((triisopropylsilyl)oxy)propyl)-1H-benzo[d]imidazole-2(3H)-ylidene)acetyl)benzonitrile In a glass RBF equipped with a Teflon-coated magnetic stirrer was combined 4-(3-amino-4-(3-triisopropylsilanyloxy-propylamino)-phenyl)-morpholin-3-one (1 eq., Intermediate 1-OTIPS, Step 5) and Intermediate bis-sulfide 1 (0.75 eq.) in dioxane (0.2 M). A reflux condenser was then attached and the reaction mixture was heated at reflux. After 48 h, another aliquot of Intermediate bis-sulfide 1 (0.75 eq.) was added and the resulting mixture was heated at reflux for another 48 h. The volatiles were then removed in vacuo and the crude product thus obtained was directly subjected to purification by way of column chromatography (SiO$_2$, gradient elution, 1:1 (v/v) Hex:EtOAc→EtOAc). The desired product thus obtained can be further recrystallized from hexanes:ether to furnish a bright yellow solid (29% yield).

Step 2: (E)-3-(2-(1-(3-hydroxypropyl)-5-(3-oxomorpholino)-1H-benzo[d]imidazol-2(3H)-ylidene)acetyl)benzonitrile In a glass RBF equipped with a Teflon-coated magnetic stirrer was dissolved (E)-3-(2-(5-(3-oxo-morpholino)-1-(3-((triisopropylsilyl)oxy)propyl)-1H-benzo[d]imidazole-2(3H)-ylidene)acetyl)benzonitrile (1 eq.) from the previous step in THF (0.1 M). To this was then added tetrabutylammonium fluoride (1.5 eq., 1 M solution in THF) drop-wise over a period of 1 min. The resulting mixture was allowed to stir at RT for 3 h. The crude reaction mixture was diluted with EtOAc and washed sequentially with 10% aq. NaHCO$_3$, water and brine. The organic extract was then dried over Na$_2$SO$_4$, filtered and the filtrate concentrated in vacuo. Trituration of the crude product thus obtained in dichloromethane and ether afforded the title product as a yellow solid (65% yield). ESI$^+$: M+1: 419. $^1$H NMR (300 MHz, CDCl$_3$) δ 8.19 (s, 1H), 8.17-8.10 (m, 1H), 7.74-7.65 (m, 1H), 7.55 (t, J=7.8 Hz, 1H), 7.43 (d, J=1.9 Hz, 1H), 7.37 (d, J=8.5 Hz, 1H), 7.20 (dd, J=8.5, 1.9 Hz, 1H), 6.06 (s, 1H), 4.39 (s, 2H), 4.29 (t, J=6.6 Hz, 2H), 4.08 (dd, J=5.9, 4.2 Hz, 2H), 3.86-3.76 (m, 2H), 3.66 (t, J=5.5 Hz, 2H), 2.12-2.02 (m, 2H).

Example 136: (E)-4-(1-(3-hydroxypropyl)-2-(2-oxo-2-(6-(trifluoromethyl)pyridin-2-yl)ethylidene)-2,3-dihydro-1H-benzo[d]imidazol-5-yl)morpholin-3-one (147)

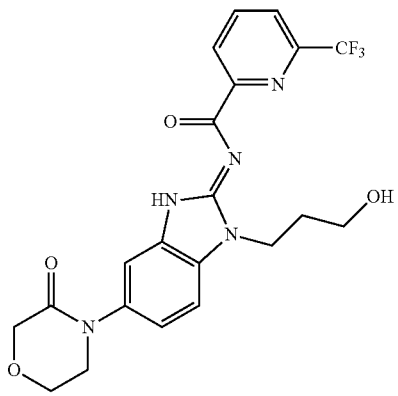

Prepared in an analogous fashion to Example 135, but using Intermediate bis-sulfide 2 (3 eq.) in place of Intermediate bis-sulfide 1 in step 1. ESI$^+$: M+1: 463. $^1$H NMR (300 MHz, CDCl$_3$) δ 8.26 (d, J=7.9 Hz, 1H), 8.00 (t, J=7.8 Hz, 1H), 7.69 (dd, J=7.8, 1.0 Hz, 1H), 7.46 (d, J=1.9 Hz, 1H), 7.40 (d, J=8.5 Hz, 1H), 7.21 (dd, J=8.5, 1.9 Hz, 1H), 6.94 (s, 1H), 4.39-4.35 (m, 4H), 4.13-4.03 (m, 2H), 3.87-3.77 (m, 2H), 3.68 (t, J=5.6 Hz, 2H), 2.17-2.02 (m, 2H).

Example 137: (E)-4-(2-(2-(6-bromopyridin-2-yl)-2-oxoethylidene)-1-(3-hydroxypropyl)-2,3-dihydro-1H-benzo[d]imidazol-5-yl)morpholin-3-one (148)

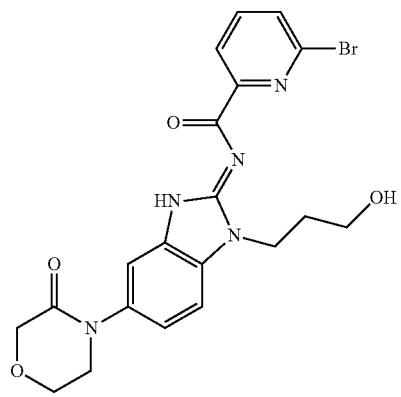

Prepared in an analogous fashion to Example 135, but using Intermediate bis-sulfide 3 (2 eq.) in place of Intermediate bis-sulfide 1 in step 1. ESI$^+$: M+1: 475. $^1$H NMR (300 MHz, CDCl$_3$) δ 8.03 (dd, J=7.6, 0.9 Hz, 1H), 7.67 (t, J=7.8 Hz, 1H), 7.54-7.35 (m, H), 7.21 (dd, J=8.6, 1.9 Hz, 1H), 6.81 (s, 1H), 4.42-4.31 (m, 4H), 4.13-4.03 (m, 2H), 3.87-3.77 (m, 2H), 3.68 (t, J=5.6 Hz, 2H), 2.17-2.02 (m, 2H).

Example 138: (E)-4-(1-(3-hydroxypropyl)-2-(2-oxo-2-(quinolin-2-yl)ethylidene)-2,3-dihydro-1H-benzo[d]imidazol-5-yl)morpholin-3-one (149)

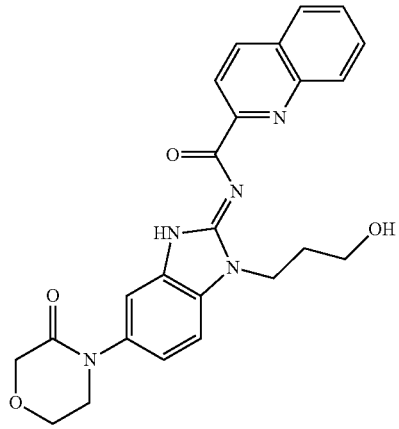

Prepared in an analogous fashion to Example 135, but using Intermediate bis-sulfide 4 (2 eq.) in place of Intermediate bis-sulfide 1 in step 1. ESI+: M+1: 445. $^1$H NMR (300 MHz, CDCl$_3$) δ 8.34-8.12 (m, 3H), 7.86 (d, J=8.2 Hz, 1H), 7.75 (t, J=7.6 Hz, 1H), 7.57 (t, J=7.5 Hz, 1H), 7.47 (s, 1H), 7.40 (d, J=8.6 Hz, 1H), 7.21 (d, J=8.0 Hz, 1H), 7.02 (s, 1H), 4.47-4.33 (m, 4H), 4.08 (t, J=5.1 Hz, 2H), 3.82 (t, J=5.0 Hz, 2H)), 3.70 (t, J=5.5 Hz, 2H), 2.18-2.07 (m, 2H).

Example 139: (E)-N-(1-(3-hydroxypropyl)-5-(3-oxomorpholino)-1H-benzo[d]imidazol-2(3H)-ylidene)pyrazine-2-carboxamide (72)

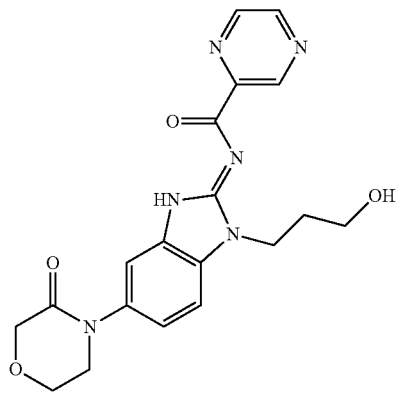 [SMILES: O=C(/N=c1\[nH]c2cc(N3CCOCC3=O)ccc2n1CCCO)c1cnccn1]

Prepared in an analogous fashion to Example 9, but using pyrazine-2-carboxylic acid (1 eq.) in place of 4-methyl-3-trifluoromethyl-benzoic acid and triethylamine (3 eq.) in place of ethyl-diisopropyl-amine (4% yield). ESI+: M+1: 397. $^1$H NMR (300 MHz, DMSO-d$_6$) δ 12.96 (s, 1H), 9.50 (d, J=1.0 Hz, 1H), 8.77 (s, 1H), 7.66-7.50 (m, 2H), 7.30 (dd, J=8.5, 2.0 Hz, 1H), 4.87 (t, J=5.5 Hz, 1H), 4.36 (t, J=6.7 Hz, 2H), 4.23 (s, 2H), 4.01 (t, J=5.0 Hz, 2H), 3.80-3.70 (m, 2H), 3.48-3.42 (m, 2H), 1.96-1.90 (m, 2H).

Example 140: (E)-3-(difluoromethyl)-N-(1-(1,1-dioxidotetrahydro-2H-thiopyran-4-yl)-5-(3-oxomorpholino)-1H-benzo[d]imidazol-2(3H)-ylidene)benzamide (80)

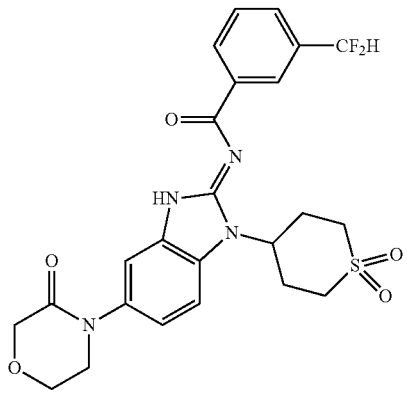 [SMILES: O=C(/N=c1\[nH]c2cc(N3CCOCC3=O)ccc2n1C1CCS(=O)(=O)CC1)c1cccc(C(F)F)c1]

Prepared in an analogous fashion to Example 9, but using Intermediate 20 (1 eq.) in place of Intermediate 1-OH, 3-difluoromethyl-benzoic acid (1.1 eq.) in place of 4-methyl-3-trifluoromethyl-benzoic acid, and PyBOP (1.1 eq.) in place of HBTU (20% yield). ESI+: M+1: 519. $^1$H NMR (300 MHz, DMSO-d$_6$) δ 12.94 (s, 1H), 8.57-8.49 (m, 2H), 7.77-6.92 (m, 6H), 5.11-5.07 (m, 1H), 4.23 (s, 2H), 4.11-3.96 (m, 2H), 3.76-3.69 (m, 2H), 3.52 (d, J=12.9 Hz, 2H), 3.32 (d, J=13.3 Hz, 4H), 2.17 (d, J=12.3 Hz, 2H).

Example 141: (E)-N-(1-((1s,4s)-4-carbamoylcyclohexyl)-5-(3-oxomorpholino)-1H-benzo[d]imidazol-2(3H)-ylidene)-3-(trifluoromethyl)benzamide (150

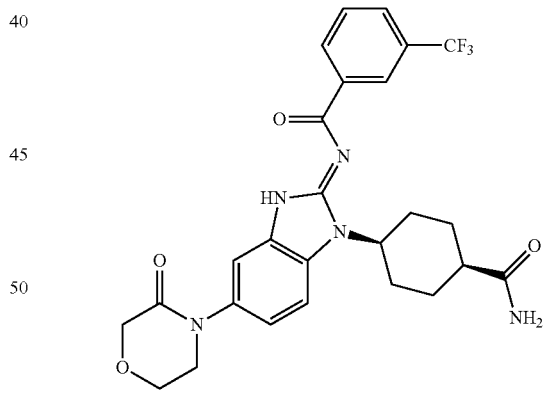

Prepared in an analogous fashion to Example 9, but using Intermediate 36 (1 eq.) in place of Intermediate 1-OH, 3-trifluoromethyl-benzoic acid (1.1 eq.) in place of 4-methyl-3-trifluoromethyl-benzoic acid, and PyBOP (1.1 eq.) in place of HBTU (18% yield). ESI+: M+1: 530. $^1$H NMR (300 MHz, DMSO-d$_6$) δ 12.94 (s, 1H), 8.60 (d, J=7.7 Hz, 1H), 8.42 (s, 1H), 7.91 (d, J=7.8 Hz, 1H), 7.83-7.64 (m, 2H), 7.54 (d, J=2.0 Hz, 1H), 7.33 (s, 1H), 7.26 (dd, J=8.6, 2.1 Hz, 1H), 6.94 (s, 1H), 4.91 (s, 1H), 4.23 (s, 2H), 4.01 (t, J=5.0 Hz, 2H), 3.74 (t, J=5.0 Hz, 2H), 2.71 (d, J=12.4 Hz, 2H), 3.32 (d, J=13.3 Hz, 4H), 2.17 (d, J=13.1 Hz, 2H), 1.68 (d, J=11.0 Hz, 4H).

Example 142: (E)-N-(1-(3-hydroxypropyl)-5-(3-oxomorpholino)-1H-benzo[d]imidazol-2(3H)-ylidene)-3-((trifluoromethyl)thio)benzamide (151)

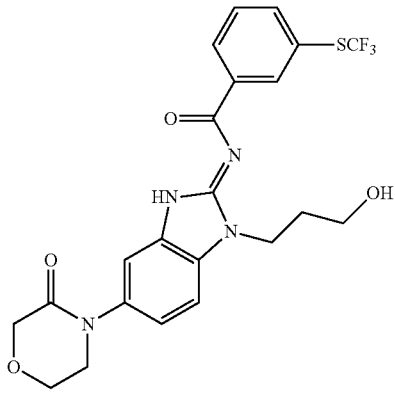

Prepared in an analogous fashion to Example 12, but using 3-trifluoromethylsulfanyl-benzoic acid (1 eq.) in place of 3-hydroxymethyl-benzoic acid and PyBOP (1.2 eq.) in place of HBTU (48% yield). ESI+: M+1: 495. $^1$H NMR (300 MHz, DMSO-$d_6$) δ 12.88 (s, 1H), 8.51-8.43 (m, 2H), 7.88 (d, J=7.8 Hz, 1H), 7.72-7.46 (m, 3H), 7.28 (dd, J=8.5, 2.0 Hz, 1H), 4.67 (t, J=5.1 Hz, 1H), 4.34 (t, J=6.7 Hz, 2H), 4.23 (s, 2H), 4.01 (t, J=5.1 Hz, 2H), 3.74 (t, J=5.1 Hz, 2H), 3.51-3.45 (m, 2H), 1.99-1.94 (m, 2H).

Example 143: (E)-N-(1-(3-hydroxypropyl)-5-(3-oxomorpholino)-1H-benzo[d]imidazol-2(3H)-ylidene)-3-((trifluoromethyl)sulfonyl)benzamide (152)

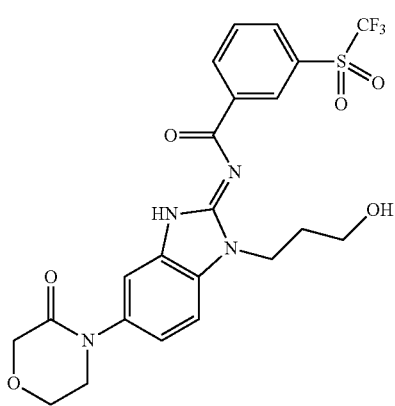 [SMILES: O=C(/N=c1\[nH]c2cc(N3CCOCC3=O)ccc2n1CCCO)c1cccc(S(=O)(=O)C(F)(F)F)c1]

Prepared in an analogous fashion to Example 12, but using 3-((trifluoromethyl)sulfonyl)benzoic acid (1 eq.) in place of 3-hydroxymethyl-benzoic acid and PyBOP (1.2 eq.) in place of HBTU (38% yield). ESI+: M+1: 527. $^1$H NMR (300 MHz, DMSO-$d_6$) δ 12.94 (s, 1H), 8.85-8.83 (m, 2H), 8.31 (d, J=8.1 Hz, 1H), 7.99 (t, J=8.1 Hz, 1H), 7.66-7.49 (m, 2H), 7.30 (dd, J=8.6, 2.0 Hz, 1H), 4.66 (t, J=5.0 Hz, 1H), 4.36 (t, J=6.8 Hz, 2H), 4.24 (s, 2H), 4.01 (t, J=5.0 Hz, 2H), 3.75 (t, J=5.1 Hz, 2H), 3.51-3.32 (m, 2H), 2.00-1.95 (m, 2H).

Example 144: (E)-N-(1-(3-hydroxypropyl)-5-(3-oxomorpholino)-1H-benzo[d]imidazol-2(3H)-ylidene)-3-(1-methyl-2-oxo-1,2-dihydropyridin-4-yl)benzamide (153)

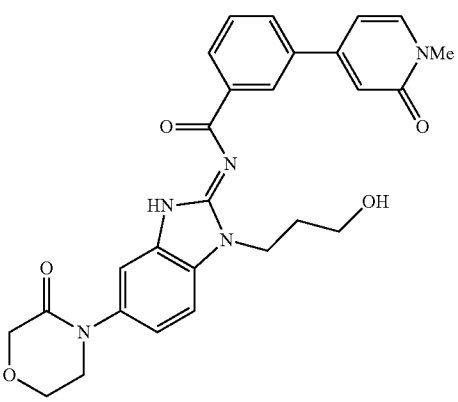 [SMILES: Cn1ccc(-c2cccc(C(=O)/N=c3\[nH]c4cc(N5CCOCC5=O)ccc4n3CCCO)c2)cc1=O]

Prepared in an analogous fashion to Example 12, but using Intermediate acid 7 (1.1 eq.) in place of 3-hydroxymethyl-benzoic acid and PyBOP (1.1 eq.) in place of HBTU (31% yield). ESI+: M+1: 502. $^1$H NMR (300 MHz, DMSO-$d_6$) δ 12.86 (s, 1H), 8.51 (t, J=1.8 Hz, 1H), 8.32 (dt, J=7.8, 1.3 Hz, 1H), 7.92-7.78 (m, 2H), 7.66-7.46 (m, 3H), 7.27 (dd, J=8.5, 2.0 Hz, 1H), 6.74-6.58 (m, 2H), 4.72 (t, J=5.1 Hz, 1H), 4.36 (d, J=6.8 Hz, 2H), 4.23 (s, 2H), 4.01 (dd, J=6.1, 4.0 Hz, 2H), 3.75 (dd, J=6.0, 4.1 Hz, 2H), 3.52-3.48 (m, 2H), 3.35 (s, 3H), 3.17 (d, J=5.0 Hz, 1H), 1.97 (p, J=6.5 Hz, 2H).

Example 145: (S,E)-N-(5-(2-oxo-1,3-oxazinan-3-yl)-1-(5-oxopyrrolidin-3-yl)-1H-benzo[d]imidazol-2(3H)-ylidene)-3-(trifluoromethyl)benzamide (154)

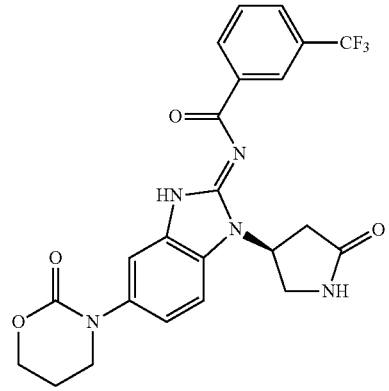 [SMILES: O=C1C[C@H](n2/c(=N/C(=O)c3cccc(C(F)(F)F)c3)[nH]c3cc(N4CCCOC4=O)ccc32)CN1]

Prepared in an analogous fashion to Example 9, but using Intermediate 37 (1 eq.) in place of Intermediate 1-OH, 3-trifluoromethyl-benzoic acid (1.1 eq.) in place of 4-methyl-3-trifluoromethyl-benzoic acid, and PyBOP (1.1 eq.) in place of HBTU (25% yield). ESI+: M+1: 488. $^1$H NMR (300 MHz, DMSO-$d_6$) δ 12.98 (s, 1H), 8.58-8.43 (m, 2H), 8.08 (s, 1H), 7.90 (d, J=7.3 Hz, 1H), 7.71 (t, J=7.7 Hz, 1H), 7.55-7.43 (m, 2H), 7.28 (dd, J=8.6, 2.1 Hz, 1H), 5.87-5.92 (m, 1H), 4.42-4.32 (m, 2H), 3.83 (t, J=9.7 Hz, 1H), 3.75-3.64 (m, 3H), 2.92-2.86 (m, 2H), 2.18-2.08 (m, 2H).

Example 146: (E)-N-(5-(2-oxo-1,3-oxazinan-3-yl)-1-((tetrahydro-2H-pyran-4-yl)methyl)-1H-benzo[d]imidazol-2(3H)-ylidene)-3-(trifluoromethyl)benzamide (155)

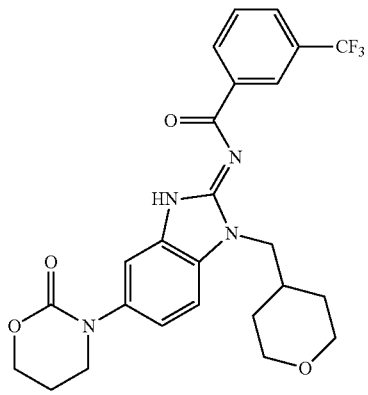 [SMILES: O=C(/N=c1\[nH]c2cc(N3CCCOC3=O)ccc2n1CC1CCOCC1)c1cccc(C(F)(F)F)c1]

Prepared in an analogous fashion to Example 9, but using Intermediate 38 (1 eq.) in place of Intermediate 1-OH, 3-trifluoromethyl-benzoic acid (1.1 eq.) in place of 4-methyl-3-trifluoromethyl-benzoic acid, and PyBOP (1.1 eq.) in place of HBTU (45% yield). ESI+: M+1: 503. $^1$H NMR (300 MHz, DMSO-$d_6$) δ 12.89 (s, 1H), 8.56-8.47 (m, 2H), 7.91 (d, J=7.9 Hz, 1H), 7.75 (t, J=7.9 Hz, 1H), 7.62 (d, J=8.5 Hz, 1H), 7.48 (d, J=2.0 Hz, 1H), 7.26 (dd, J=8.6, 2.0 Hz, 1H), 4.42-4.32 (m, 2H), 4.19 (d, J=7.2 Hz, 2H), 3.84 (d, J=11.4 Hz, 1H), 3.67 (t, J=6.0 Hz, 2H), 3.31-3.13 (m, 2H), 2.28-2.11 (m, 3H), 1.57-1.44 (m, 4H).

Example 147: (E)-N-(1-(3,3-difluorocyclobutyl)-5-(2-oxo-1,3-oxazinan-3-yl)-1H-benzo[d]imidazol-2(3H)-ylidene)-3-(trifluoromethyl)benzamide (156)

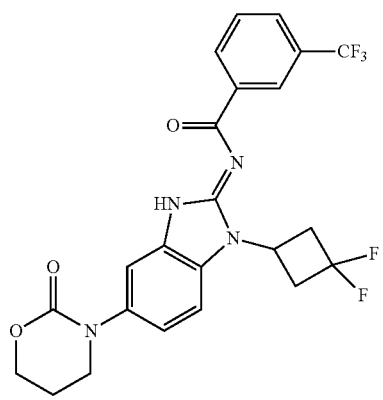 [SMILES: O=C(/N=c1\[nH]c2cc(N3CCCOC3=O)ccc2n1C1CC(F)(F)C1)c1cccc(C(F)(F)F)c1]

Prepared in an analogous fashion to Example 9, but using Intermediate 39 (1 eq.) in place of Intermediate 1-OH, 3-trifluoromethyl-benzoic acid (1.1 eq.) in place of 4-methyl-3-trifluoromethyl-benzoic acid, and PyBOP (1.1 eq.) in place of HBTU (42% yield). ESI+: M+1: 495. $^1$H NMR (300 MHz, DMSO-$d_6$) δ 13.04 (s, 1H), 8.58-8.44 (m, 2H), 7.92 (d, J=7.8 Hz, 1H), 7.77-7.66 (m, 2H), 7.51 (d, J=2.0 Hz, 1H), 7.28 (dd, J=8.6, 2.1 Hz, 1H), 5.26 (td, J=8.5, 4.1 Hz, 1H), 4.42-4.32 (m, 2H), 4.12-3.98 (m, 2H), 3.66 (t, J=6.1 Hz, 2H), 3.22-3.07 (m, 2H), 2.27-2.09 (m, 2H).

Example 148: (E)-N-(1-(1,1-dioxidotetrahydrothiophen-3-yl)-5-(2-oxo-1,3-oxazinan-3-yl)-1H-benzo[d]imidazol-2(3H)-ylidene)-3-(trifluoromethyl)benzamide (157)

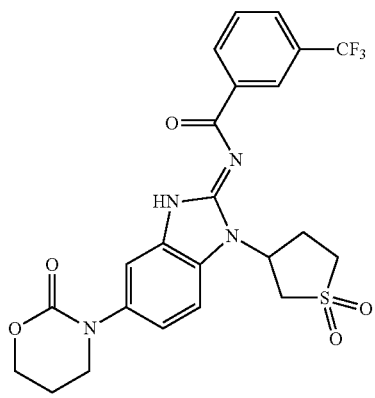 [SMILES: O=C(/N=c1\[nH]c2cc(N3CCCOC3=O)ccc2n1C1CCS(=O)(=O)C1)c1cccc(C(F)(F)F)c1]

Prepared in an analogous fashion to Example 9, but using Intermediate 40 (1 eq.) in place of Intermediate 1-OH, 3-trifluoromethyl-benzoic acid (1.1 eq.) in place of 4-methyl-3-trifluoromethyl-benzoic acid, and PyBOP (1.1 eq.) in place of HBTU (16% yield). ESI+: M+1: 523. $^1$H NMR (300 MHz, DMSO-$d_6$) δ 13.04 (s, 1H), 8.62 (d, J=8.0 Hz, 1H), 8.49 (s, 1H), 7.91 (d, J=7.8 Hz, 1H), 7.74-7.69 (m, 2H), 7.52 (d, J=2.0 Hz, 1H), 7.31 (dd, J=8.7, 2.1 Hz, 1H), 5.89-5.77 (m, 1H), 4.37 (t, J=5.3 Hz, 2H), 4.15-4.01 (m, 1H), 3.77-3.54 (m, 4H), 3.42-3.32 (m, 1H), 2.18-2.08 (m, 2H).

Example 149: (E)-N-(1-(oxetan-3-ylmethyl)-5-(2-oxo-1,3-oxazinan-3-yl)-1H-benzo[d]imidazol-2(3H)-ylidene)-3-(trifluoromethyl)benzamide (158)

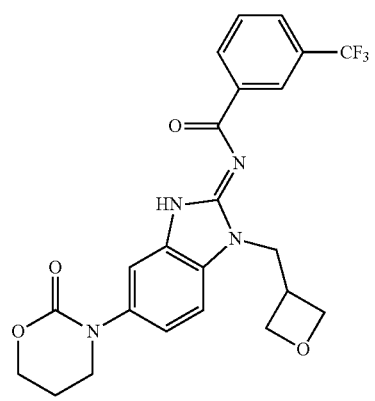 [SMILES: O=C(/N=c1\[nH]c2cc(N3CCCOC3=O)ccc2n1CC1COC1)c1cccc(C(F)(F)F)c1]

Prepared in an analogous fashion to Example 9, but using Intermediate 41 (1 eq.) in place of Intermediate 1-OH, 3-trifluoromethyl-benzoic acid (1.1 eq.) in place of 4-methyl-3-trifluoromethyl-benzoic acid, and PyBOP (1.1 eq.) in place of HBTU (11% yield). ESI+: M+1: 475. $^1$H NMR (300 MHz, DMSO-$d_6$) δ 12.92 (s, 1H), 8.55 (d, J=7.7 Hz, 1H), 8.49 (s, 1H), 7.92 (d, J=7.8 Hz, 1H), 7.76 (t, J=7.8 Hz, 1H), 7.64 (d, J=8.6 Hz, 1H), 7.47 (d, J=2.0 Hz, 1H), 7.27 (dd, J=8.5, 2.0 Hz, 1H), 4.71-4.54 (m, 4H), 4.37 (t, J=5.3 Hz, 2H), 3.66 (t, J=6.0 Hz, 2H), 3.55 (p, J=6.9 Hz, 1H), 3.15-3.02 (m, 1H), 2.12 (p, J=6.9 Hz, 2H), 1.79-1.68 (m, 1H), 1.25 (d, J=5.4 Hz, 1H).

Example 150: (E)-3-(difluoromethyl)-N-(1-(oxetan-3-ylmethyl)-5-(2-oxo-1,3-oxazinan-3-yl)-1H-benzo[d]imidazol-2(3H)-ylidene)benzamide (159)

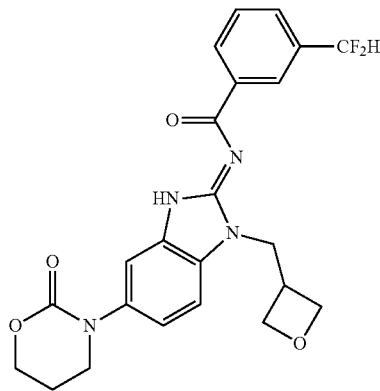 [SMILES: O=C(/N=c1\[nH]c2cc(N3CCCOC3=O)ccc2n1CC1COC1)c1cccc(C(F)F)c1]

Prepared in an analogous fashion to Example 9, but using Intermediate 41 (1 eq.) in place of Intermediate 1-OH, 3-difluoromethyl-benzoic acid (1.1 eq.) in place of 4-methyl-3-trifluoromethyl-benzoic acid, and PyBOP (1.1 eq.) in place of HBTU (15% yield). ESI$^+$: M+1: 457. $^1$H NMR (300 MHz, DMSO-d$_6$) δ 12.89 (s, 1H), 8.48-8.36 (m, 2H), 7.78-7.58 (m, 2H), 7.46 (d, J=2.0 Hz, 1H), 7.26 (dd, J=8.6, 2.0 Hz, 1H), 7.17 (t, J=55.9 Hz, 1H), 4.71-4.54 (m, 4H), 4.42-4.32 (m, 2H), 3.66 (t, J=6.0 Hz, 2H), 3.54 (q, J=7.5 Hz, 1H), 3.18-2.95 (m, 1H), 2.19-2.07 (m, 1H), 1.79-1.68 (m, 1H), 1.31-1.06 (m, 1H).

Example 151: (E)-3-(difluoromethyl)-N-(5-(2-oxo-1,3-oxazinan-3-yl)-1-((tetrahydro-2H-pyran-2-yl)methyl)-1H-benzo[d]imidazol-2(3H)-ylidene)benzamide (160)

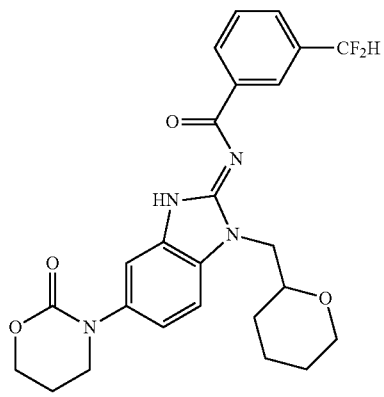 [SMILES: O=C(/N=c1\[nH]c2cc(N3CCCOC3=O)ccc2n1CC1CCCCO1)c1cccc(C(F)F)c1]

Prepared in an analogous fashion to Example 9, but using Intermediate 42 (1 eq.) in place of Intermediate 1-OH, 3-difluoromethyl-benzoic acid (1.1 eq.) in place of 4-methyl-3-trifluoromethyl-benzoic acid, and PyBOP (1.1 eq.) in place of HBTU (86% yield). ESI$^+$: M+1: 485. $^1$H NMR (300 MHz, DMSO-d$_6$) δ 12.87 (s, 1H), 8.38 (d, J=8.2 Hz, 2H), 7.78-7.58 (m, 2H), 7.56-7.41 (m, 2H), 7.37-6.92 (m, 2H), 4.37 (t, J=5.3 Hz, 2H), 4.29 (d, J=5.6 Hz, 2H), 3.83 (d, J=11.0 Hz, 2H), 3.66 (t, J=6.0 Hz, 2H), 3.31 (d, J=6.3 Hz, 2H), 2.17-2.05 (m, 2H), 1.88-1.62 (m, 2H), 1.44-1.26 (m, 2H).

Example 152: (E)-3-cyano-N-(5-(2-oxo-1,3-oxazinan-3-yl)-1-((tetrahydro-2H-pyran-2-yl)methyl)-1H-benzo[d]imidazol-2(3H)-ylidene)benzamide (161)

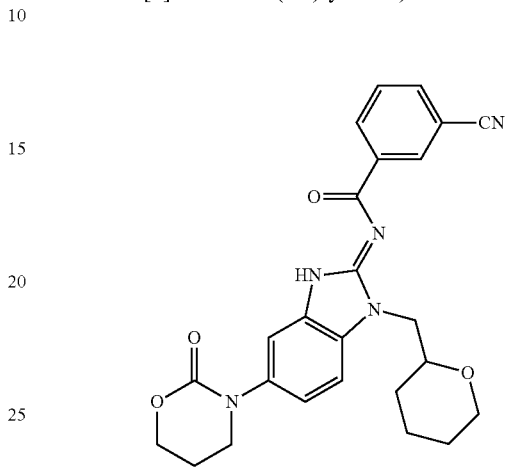

Prepared in an analogous fashion to Example 9, but using Intermediate 42 (1 eq.) in place of Intermediate 1-OH, 3-cyano-benzoic acid (1.1 eq.) in place of 4-methyl-3-trifluoromethyl-benzoic acid, and PyBOP (1.1 eq.) in place of HBTU (17% yield). ESI$^+$: M+1: 460. $^1$H NMR (300 MHz, DMSO-d$_6$) δ 12.91 (s, 1H), 8.57-8.47 (m, 2H), 8.06-7.96 (m, 1H), 7.72 (t, J=7.7 Hz, 1H), 7.53 (d, J=8.6 Hz, 1H), 7.45 (d, J=1.9 Hz, 1H), 7.29-7.19 (m, 1H), 4.42-4.28 (m, 4H), 3.83 (d, J=11.2 Hz, 2H), 3.66 (t, J=6.0 Hz, 2H), 3.31 (d, J=6.3 Hz, 2H), 2.18-2.07 (m, 2H), 1.82-1.67 (m, 2H), 1.44-1.26 (m, 2H).

Example 153: (E)-N-(1-(((1-hydroxycyclopentyl)methyl)-5-(2-oxo-1,3-oxazinan-3-yl)-1H-benzo[d]imidazol-2(3H)-ylidene)-3-(trifluoromethyl)benzamide (162)

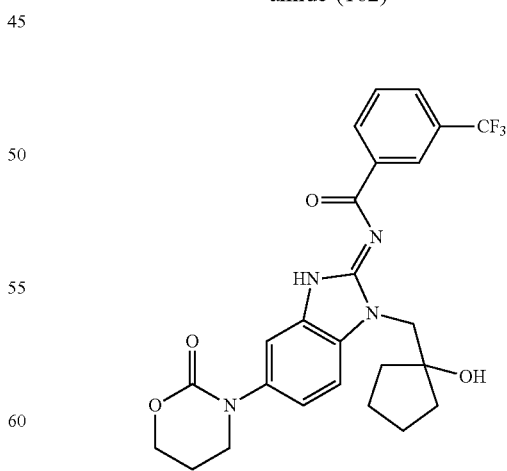

Prepared in an analogous fashion to Example 9, but using Intermediate 43 (1 eq.) in place of Intermediate 1-OH, 3-trifluoromethyl-benzoic acid (1.1 eq.) in place of 4-methyl-3-trifluoromethyl-benzoic acid, and PyBOP (1.1 eq.) in place of HBTU (12% yield). ESI⁺: M+1: 503. ¹H NMR (300 MHz, DMSO-d₆) δ 12.93 (s, 1H), 8.55-8.43 (m, 2H), 7.90 (d, J=7.9 Hz, 1H), 7.74 (t, J=7.7 Hz, 1H), 7.64 (d, J=8.7 Hz, 1H), 7.46 (d, J=2.0 Hz, 1H), 7.23 (dd, J=8.6, 2.1 Hz, 1H), 4.92 (s, 1H), 4.42-4.30 (m, 4H), 3.66 (t, J=6.0 Hz, 2H), 2.18-2.07 (m, 2H), 1.82-1.67 (m, 2H), 1.97-1.47 (m, 8H).

Example 154: (E)-N-(1-(3-hydroxypropyl)-5-(3-oxomorpholino)-1H-benzo[d]imidazol-2(3H)-ylidene)-3-(2-oxo-1-(2,2,2-trifluoroethyl)-1,2-dihydropyridin-4-yl)benzamide (163)

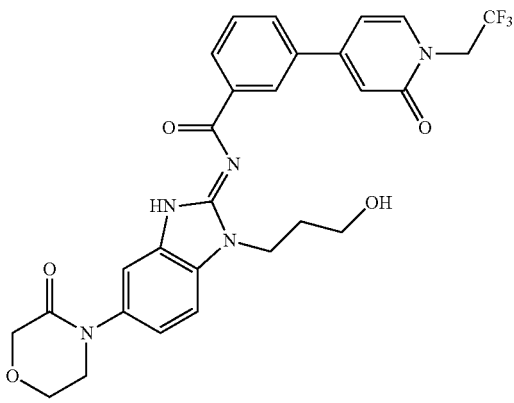 [SMILES: O=C(/N=c1\[nH]c2cc(N3CCOCC3=O)ccc2n1CCCO)c1cccc(-c2ccn(CC(F)(F)F)c(=O)c2)c1]

Prepared in an analogous fashion to Example 12, but using Intermediate acid 8 (1.1 eq.) in place of 3-hydroxymethyl-benzoic acid and PyBOP (1.1 eq.) in place of HBTU (31% yield). ESI⁺: M+1: 570. ¹H NMR (300 MHz, DMSO-d₆) δ 12.86 (s, 1H), 8.53 (s, 1H), 8.35 (d, J=7.7 Hz, 1H), 7.92 (d, J=7.8 Hz, 1H), 7.82 (d, J=7.2 Hz, 1H), 7.68-7.46 (m, 3H), 7.27 (dd, J=8.5, 2.0 Hz, 1H), 6.86-6.73 (m, 2H), 4.93 (q, J=9.3 Hz, 2H), 4.73 (t, J=5.1 Hz, 1H), 4.37 (t, J=6.8 Hz, 2H), 4.23 (s, 2H), 4.07-3.96 (m, 2H), 3.75 (t, J=5.0 Hz, 2H), 3.49 (q, J=5.9 Hz, 2H), 1.98 (p, J=4.1 Hz, 2H).

Example 155: (E)-3-(1-(difluoromethyl)-2-oxo-1,2-dihydropyridin-4-yl)-N-(1-(3-hydroxypropyl)-5-(3-oxomorpholino)-1H-benzo[d]imidazol-2(3H)-ylidene)benzamide (164)

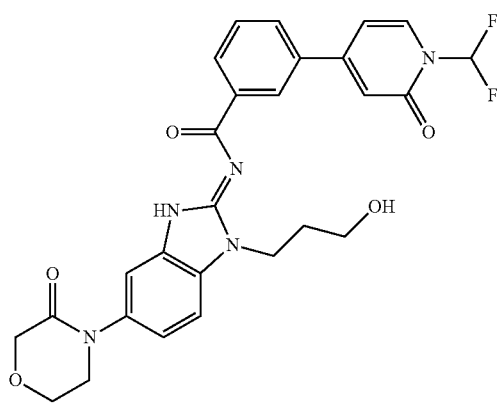 [SMILES: O=C(/N=c1\[nH]c2cc(N3CCOCC3=O)ccc2n1CCCO)c1cccc(-c2ccn(C(F)F)c(=O)c2)c1]

Prepared in an analogous fashion to Example 12, but using Intermediate acid 9 (1.1 eq.) in place of 3-hydroxymethyl-benzoic acid and PyBOP (1.1 eq.) in place of HBTU (63% yield). ESI⁺: M+1: 538. ¹H NMR (300 MHz, DMSO-d₆) δ 12.87 (s, 1H), 8.58 (s, 1H), 8.36 (d, J=7.2 Hz, 1H), 7.95-7.72 (m, 3H), 7.66-7.56 (m, 2H), 7.50 (s, 1H), 7.28 (d, J=8.1 Hz, 1H), 6.87 (d, J=5.0 Hz, 2H), 4.74 (t, J=5.1 Hz, 1H), 4.37 (t, J=6.8 Hz, 2H), 4.23 (s, 2H), 4.02-3.99 (m, 2H), 3.75 (t, J=5.0 Hz, 2H), 3.51-3.44 (m, 2H), 1.99-1.97 (m, 2H).

Example 156: (E)-3-(difluoromethyl)-N-(1-(1-methylpiperidin-4-yl)-5-(3-oxomorpholino)-1H-benzo[d]imidazol-2(3H)-ylidene)benzamide (165)

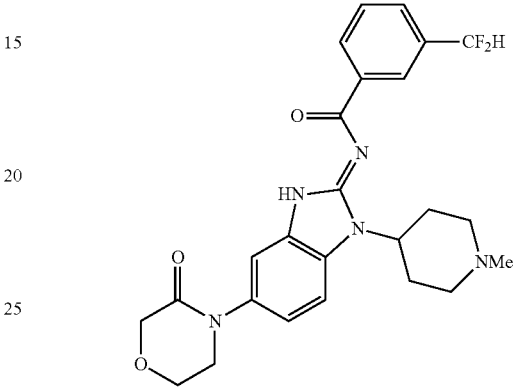

In a glass RBF equipped with a Teflon coated magnetic stirrer was dissolved Example 94 (1 eq.) in MeOH (0.1 M). To this was then added sequentially formaldeyde (5 eq., 37% aqueous solution) and glacial acetic acid (4 eq.), and the resulting solution was allowed to stir at RT for 30 min. Finally, sodium cyanoborohyride (2 eq.) was added. After another 1 hr of stirring at RT, the volatiles were removed in vacuo and the residue thus obtained was directly subjected to reverse phase column chromatography (C₁₈, gradient elution, 10:1 (v/v) H₂O:MeCN+0.1% formic acid 4 MeCN+0.1% formic acid) to furnish the title compound as a white solid (75% yield). ESI⁺: M+1: 484. ¹H NMR (300 MHz, CDCl₃) δ 12.93 (s, 1H), 8.39 (d, J=9.8 Hz, 2H), 7.78-7.60 (m, 3H), 7.53 (d, J=2.0 Hz, 1H), 7.35-6.99 (m, 2H), 4.83-4.89 (m, 1H), 4.23 (s, 2H), 4.00 (dd, J=6.0, 4.0 Hz, 2H), 3.79-3.68 (m, 2H), 2.99 (d, J=11.2 Hz, 2H), 2.66-2.56 (m, 2H), 2.29 (s, 3H), 2.15 (t, J=11.6 Hz, 2H), 1.80 (d, J=11.2 Hz, 2H).

Example 157: (E)-3-(5-(3-oxomorpholino)-2-((3-(trifluoromethyl)benzoyl)imino)-2,3-dihydro-1H-benzo[d]imidazol-1-yl)propanoic acid (166)

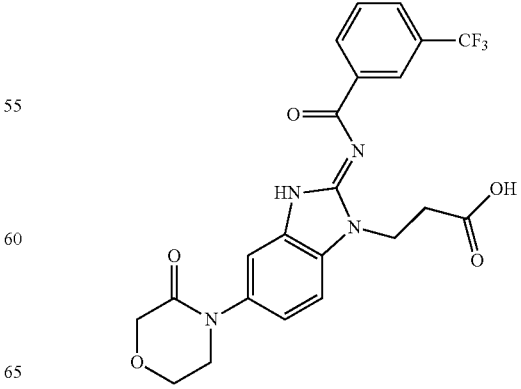

In a glass RBF equipped with a Teflon-coated magnetic stirrer was dissolved Intermediate 44 (1 eq.), 3-trifluoromethyl-benzoic acid (1.1 eq.) and HATU (1.2 eq.) in DMF (0.1 M). To this was then added ethyl-diisopropyl-amine (2.5 eq.) and the resulting yellow solution was allowed to stir at RT for 14 h. The crude reaction mixture was diluted with EtOAc and washed sequentially with water, 10% aq. NaHCO$_3$, 10% aq. NH$_4$Cl, water and brine. The organic extract was then dried over Na$_2$SO$_4$, filtered and the filtrate concentrated in vacuo. Further purification by way of column chromatography (SiO$_2$, gradient elution, 1:1 (v/v) Hex:EtOAc→EtOAc) furnished the intermediate amide. This coupled product was then taken up in methanol (0.15 M), added lithium hydroxide (5 eq.) and the resulting mixture was stirred at RT for 18 h. The reaction mixture was then carefully neutralized with 1 N aq. HCl to a pH of ~4 and the volatiles were removed in vacuo. The resulting residue was subjected to reverse phase column chromatography (C$_{18}$, gradient elution, 10:1 (v/v) H$_2$O:MeCN+0.1% formic acid 4 MeCN+0.1% formic acid) to furnish the title compound as a white solid. ESI$^+$: M+1: 477. $^1$H NMR (300 MHz, DMSO-d$_6$) δ 8.56 (s, 1H), 8.49 (d, J=7.8 Hz, 1H), 7.76 (d, J=7.7 Hz, 1H), 7.60 (t, J=7.8 Hz, 1H), 7.35 (d, J=1.4 Hz, 2H), 7.24 (dd, J=8.6, 1.9 Hz, 1H), 4.56 (t, J=6.9 Hz, 2H), 4.37 (s, 2H), 4.09 (dd, J=6.1, 4.0 Hz, 2H), 3.81 (t, J=5.1 Hz, 2H), 2.98 (t, J=6.9 Hz, 2H).

Example 158: (E)-2-(5-(3-oxomorpholino)-2-((3-(trifluoromethyl)benzoyl)imino)-2,3-dihydro-1H-benzo[d]imidazol-1-yl)acetic acid (167)

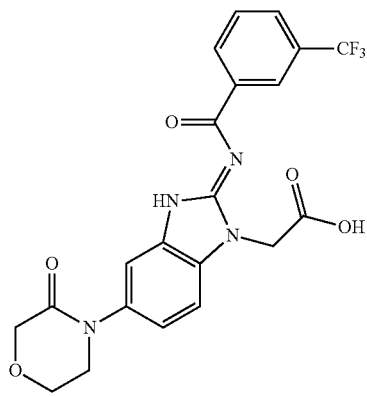 [SMILES: O=C(O)Cn1/c(=N/C(=O)c2cccc(C(F)(F)F)c2)[nH]c2cc(N3CCOCC3=O)ccc21]

In a glass RBF equipped with a Teflon-coated magnetic stirrer was dissolved Intermediate 45 (1 eq.), 3-trifluoromethyl-benzoic acid (1.1 eq.) and HATU (1.2 eq.) in DMF (0.1 M). To this was then added ethyl-diisopropyl-amine (2.5 eq.) and the resulting yellow solution was allowed to stir at RT for 14 h. The crude reaction mixture was diluted with EtOAc and washed sequentially with water, 10% aq. NaHCO$_3$, 10% aq. NH$_4$Cl, water and brine. The organic extract was then dried over Na$_2$SO$_4$, filtered and the filtrate concentrated in vacuo. Further purification by way of column chromatography (SiO$_2$, gradient elution, 1:1 (v/v) Hex:EtOAc→EtOAc) furnished the intermediate amide. This coupled product was then taken up in methanol (0.15 M), added trifluoroacetic acid (25 eq.) and the resulting mixture was stirred at RT for 18 h. The volatiles were removed in vacuo and the resulting residue was subjected to reverse phase column chromatography (C$_{18}$, gradient elution, 10:1 (v/v) H$_2$O:MeCN+0.1% formic acid 4 MeCN+0.1% formic acid) to furnish the title compound as a white solid (47% yield). ESI$^+$: M+1: 463. $^1$H NMR (300 MHz, DMSO-d$_6$) δ 13.30 (s, 1H), 12.93 (s, 1H), 8.49 (d, J=9.0 Hz, 2H), 7.91 (d, J=7.8 Hz, 1H), 7.74 (t, J=7.7 Hz, 1H), 7.64-7.48 (m, 2H), 7.27 (dd, J=8.5, 2.0 Hz, 1H), 5.09 (s, 2H), 4.24 (s, 2H), 4.01 (dd, J=6.0, 4.0 Hz, 2H), 3.75 (dd, J=6.1, 4.1 Hz, 2H).

Example 159: (E)-4-(5-(2-oxo-1,3-oxazinan-3-yl)-2-((3-(trifluoromethyl)benzoyl)imino)-2,3-dihydro-1H-benzo[d]imidazol-1-yl)butanoic acid (168)

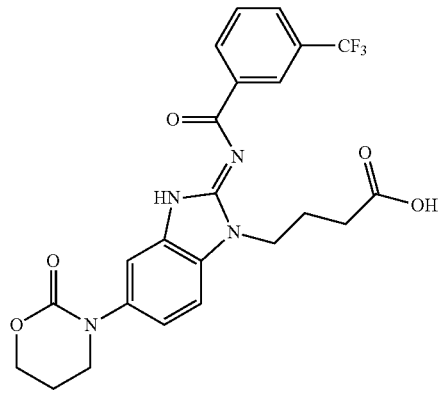 [SMILES: O=C(O)CCCn1/c(=N/C(=O)c2cccc(C(F)(F)F)c2)[nH]c2cc(N3CCCOC3=O)ccc21]

Prepared in an analogous fashion to Example 158, but using Intermediate 46 (1 eq.) in place of Intermediate 45 (48% yield). ESI$^+$: M+1: 491. $^1$H NMR (300 MHz, DMSO-d$_6$) δ 12.92 (s, 1H), 8.61-8.45 (m, 2H), 7.96-7.86 (m, 1H), 7.74 (t, J=7.8 Hz, 1H), 7.62-7.46 (m, 2H), 7.28 (dd, J=8.5, 2.0 Hz, 1H), 4.39-4.30 (m, 4H), 3.69-3.65 (m, 2H), 2.37 (t, J=7.1 Hz, 2H), 2.20-1.96 (m, 4H).

Example 160: (E)-4-(2-((3-(difluoromethyl)benzoyl)imino)-5-(2-oxo-1,3-oxazinan-3-yl)-2,3-dihydro-1H-benzo[d]imidazol-1-yl)butanoic acid (169)

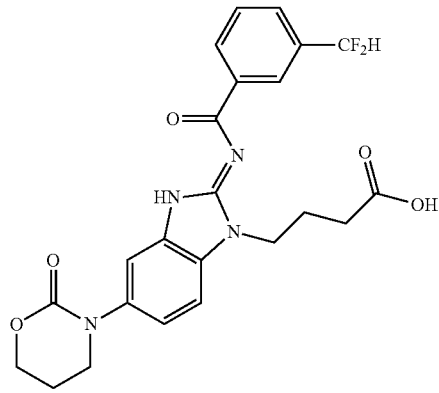

Prepared in an analogous fashion to Example 158, but using Intermediate 46 (1 eq.) in place of Intermediate 45, and 3-difluoro-benzoic acid (1.1 eq.) in place of 3-trifluoromethyl-benzoic acid (34% yield). ESI$^+$: M+1: 473. $^1$H NMR (300 MHz, DMSO-d$_6$) δ 12.84 (s, 1H), 12.21 (s, 1H), 8.50-8.37 (m, 2H), 7.75-7.72 (m, 1H), 7.66-7.54 (m, 2H), 7.48 (d, J=2.0 Hz, 1H), 7.38-6.91 (m, 2H), 4.39-4.30 (m, 4H), 3.67 (t, J=6.0 Hz, 2H), 2.37 (t, J=7.1 Hz, 2H), 2.20-1.96 (m, 4H).

Example 161: (E)-N-(1-cyclobutyl-5-(2-oxo-1,3-oxazinan-3-yl)-1H-benzo[d]imidazol-2(3H)-ylidene)-3-(trifluoromethyl)benzamide (170)

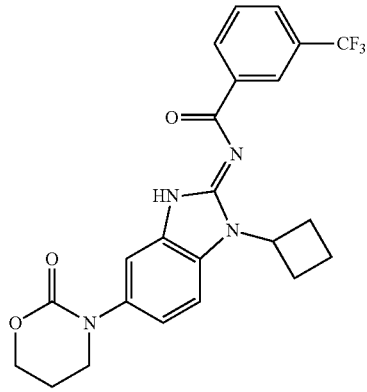 [SMILES: O=C(/N=c1\[nH]c2cc(N3CCCOC3=O)ccc2n1C1CCC1)c1cccc(C(F)(F)F)c1]

Prepared in an analogous fashion to Example 9, but using Intermediate 47 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (68% yield). ESI$^+$: M+1: 459. $^1$H NMR (300 MHz, CDCl$_3$) δ 12.60 (s, 1H), 8.63 (s, 1H), 8.51 (d, J=7.8 Hz, 1H), 7.80-7.70 (m, 1H), 7.65-7.49 (m, 1H), 7.32-7.16 (m, 3H), 5.47-5.27 (m, 1H), 4.50-4.40 (m, 2H), 3.71 (t, J=6.1 Hz, 2H), 3.09-3.02 (m, 2H), 2.59 (dtd, J=12.5, 8.2, 2.8 Hz, 2H), 2.30-2.13 (m, 2H), 2.13-1.96 (m, 2H).

Example 162: (E)-N-(1-cyclopentyl-5-(2-oxo-1,3-oxazinan-3-yl)-1H-benzo[d]imidazol-2(3H)-ylidene)-3-(trifluoromethyl)benzamide (171)

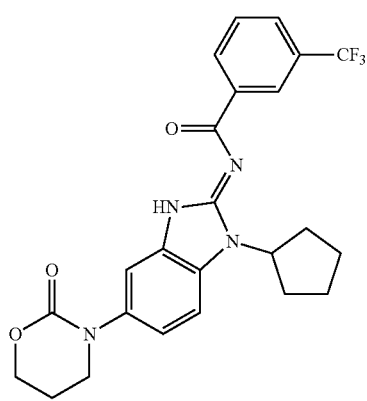 [SMILES: O=C(/N=c1\[nH]c2cc(N3CCCOC3=O)ccc2n1C1CCCC1)c1cccc(C(F)(F)F)c1]

Prepared in an analogous fashion to Example 9, but using Intermediate 48 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (49% yield). ESI$^+$: M+1: 473. $^1$H NMR (300 MHz, CDCl$_3$) δ 12.63 (s, 1H), 8.60 (s, 1H), 8.50 (d, J=7.7 Hz, 1H), 7.79-7.69 (m, 1H), 7.64-7.52 (m, 1H), 7.40-7.28 (m, 3H), 5.43-5.37 (m, 1H), 4.51-4.41 (m, 2H), 3.72 (t, J=6.1 Hz, 2H), 2.31-1.83 (m, 10H).

Example 163: (E)-N-(1-cyclopropyl-5-(2-oxo-1,3-oxazinan-3-yl)-1H-benzo[d]imidazol-2(3H)-ylidene)-3-(trifluoromethyl)benzamide (172)

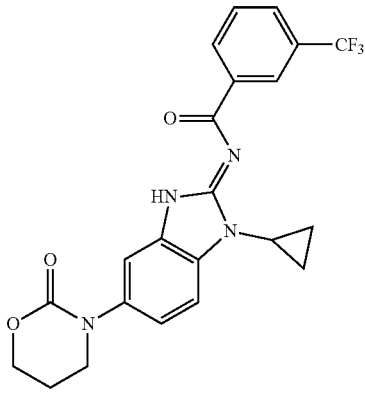 [SMILES: O=C(/N=c1\[nH]c2cc(N3CCCOC3=O)ccc2n1C1CC1)c1cccc(C(F)(F)F)c1]

Prepared in an analogous fashion to Example 9, but using Intermediate 49 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (61% yield). ESI$^+$: M+1: 445. $^1$H NMR (300 MHz, CDCl$_3$) δ 8.64 (s, 1H), 8.51 (d, J=7.7 Hz, 1H), 7.75 (d, J=7.6 Hz, 1H), 7.64-7.51 (m, 1H), 7.31-7.26 (m, 3H), 4.46 (t, J=5.4 Hz, 2H), 3.72 (dd, J=7.0, 5.2 Hz, 2H), 3.20-3.15 (m, 1H), 2.31-2.04 (m, 2H), 1.37-0.85 (m, 4H).

Example 164: (E)-N-(1-neopentyl-5-(2-oxo-1,3-oxazinan-3-yl)-1H-benzo[d]imidazol-2(3H)-ylidene)-3-(trifluoromethyl)benzamide (173)

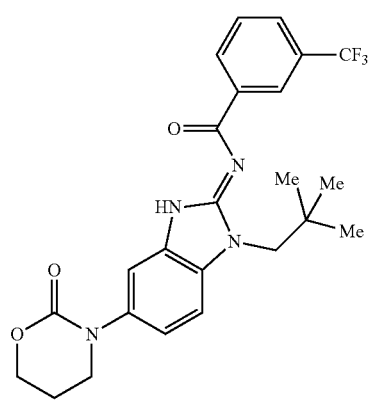 [SMILES: CC(C)(C)Cn1/c(=N/C(=O)c2cccc(C(F)(F)F)c2)[nH]c2cc(N3CCCOC3=O)ccc21]

Prepared in an analogous fashion to Example 9, but using Intermediate 50 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (85% yield). ESI$^+$: M+1: 475. $^1$H NMR (300 MHz, CDCl$_3$) δ 12.53 (s, 1H), 8.63 (s, 1H), 8.49 (d, J=7.8 Hz, 1H), 7.74 (d, J=7.6 Hz, 1H), 7.58 (t, J=7.8 Hz, 1H), 7.37-7.18 (m, 3H), 4.52-4.41 (m, 2H), 4.08 (s, 2H), 3.74 (t, J=6.1 Hz, 2H), 2.25 (p, J=6.0 Hz, 1H), 1.13 (s, 9H).

Example 165: (E)-1-((5-(2-oxo-1,3-oxazinan-3-yl)-2-((3-(trifluoromethyl)benzoyl)imino)-2,3-dihydro-1H-benzo[d]imidazol-1-yl)methyl)cyclopropanecarboxylic acid (174)

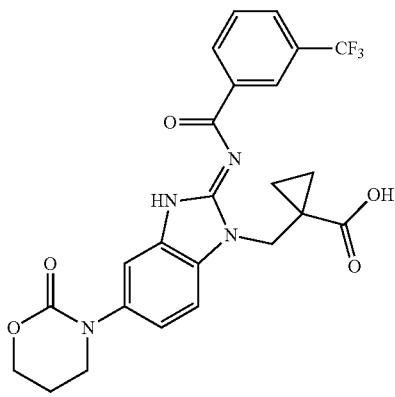 [SMILES: O=C(/N=c1\[nH]c2cc(N3CCCOC3=O)ccc2n1CC1(C(=O)O)CC1)c1cccc(C(F)(F)F)c1]

Prepared in an analogous fashion to Example 157, but using Intermediate 51 (1 eq.) in place of Intermediate 44 (48% yield). ESI⁺: M+1: 503. ¹H NMR (300 MHz, DMSO-$d_6$) δ 8.52 (s, 1H), 8.41 (d, J=7.8 Hz, 1H), 7.74 (t, J=8.6 Hz, 2H), 7.58 (t, J=7.7 Hz, 1H), 7.34 (d, J=2.0 Hz, 1H), 7.19 (dd, J=8.6, 2.0 Hz, 1H), 4.68 (s, 2H), 4.44 (t, J=5.3 Hz, 2H), 3.72-3.65 (m, 2H), 2.25-2.17 (m, 2H), 1.51-1.26 (m, 4H).

Example 166: (E)-N-(5-(2-oxo-1,3-oxazinan-3-yl)-1-(prop-2-yn-1-yl)-1H-benzo[d]imidazol-2(3H)-ylidene)-3-(trifluoromethyl)benzamide (175)

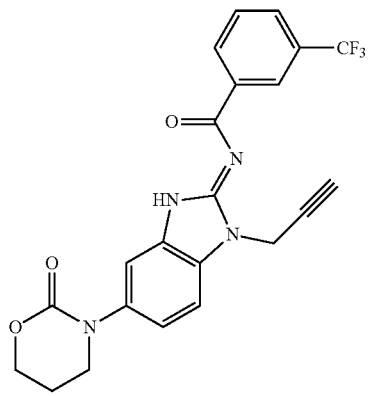 [SMILES: C#CCn1/c(=N/C(=O)c2cccc(C(F)(F)F)c2)[nH]c2cc(N3CCCOC3=O)ccc21]

Prepared in an analogous fashion to Example 9, but using Intermediate 52 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (31% yield). ESI⁺: M+1: 443. ¹H NMR (300 MHz, CDCl₃) δ 8.61-8.46 (m, 2H), 7.77 (d, J=7.6 Hz, 1H), 7.71-7.55 (m, 2H), 7.51 (d, J=8.5 Hz, 1H), 7.43-7.23 (m, 3H), 5.13 (d, J=2.6 Hz, 2H), 4.49 (t, J=5.4 Hz, 2H), 3.77 (t, J=6.1 Hz, 2H), 2.46 (t, J=2.6 Hz, 1H), 2.28 (p, J=5.8 Hz, 2H).

Example 167: (E)-N-(5-(2-oxo-1,3-oxazinan-3-yl)-1-(3,3,3-trifluoropropyl)-1H-benzo[d]imidazol-2(3H)-ylidene)-3-(trifluoromethyl)benzamide (176)

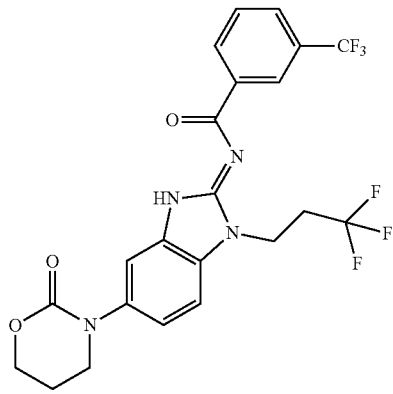 [SMILES: O=C(/N=c1\[nH]c2cc(N3CCCOC3=O)ccc2n1CCC(F)(F)F)c1cccc(C(F)(F)F)c1]

Prepared in an analogous fashion to Example 9, but using Intermediate 53 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (20% yield). ESI⁺: M+1: 501. ¹H NMR (300 MHz, CDCl₃) δ 12.38 (s, 1H), 8.61 (d, J=2.0 Hz, 1H), 8.50 (d, J=7.7 Hz, 1H), 7.77 (d, J=7.7 Hz, 1H), 7.59 (t, J=7.8 Hz, 1H), 7.32-7.20 (m, 3H), 4.54-4.39 (m, 4H), 3.68 (t, J=6.1 Hz, 2H), 2.83-2.65 (m, 2H), 2.28-2.11 (m, 2H).

Example 168: (E)-N-(5-(2-oxo-1,3-oxazinan-3-yl)-1-(2,2,3,3,3-pentafluoropropyl)-1H-benzo[d]imidazol-2(3H)-ylidene)-3-(trifluoromethyl)benzamide (177)

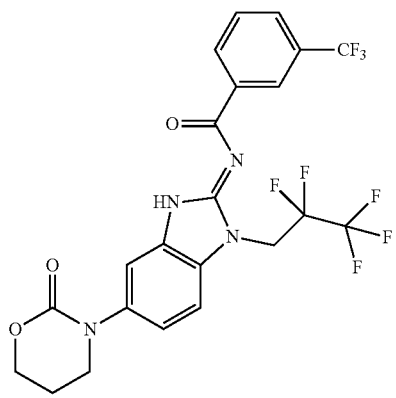 [SMILES: O=C(/N=c1\[nH]c2cc(N3CCCOC3=O)ccc2n1CC(F)(F)C(F)(F)F)c1cccc(C(F)(F)F)c1]

Prepared in an analogous fashion to Example 9, but using Intermediate 54 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (90% yield). ESI⁺: M+1: 537. ¹H NMR (300 MHz, CDCl₃) δ 12.39 (s, 1H), 8.57 (s, 1H), 8.48 (d, J=7.8 Hz, 1H), 7.77 (d, J=7.6 Hz, 1H), 7.59 (t, J=7.8 Hz, 1H), 7.46-7.30 (m, 2H), 7.27 (dd, J=8.6, 2.0 Hz, 1H), 4.63 (t, J=12.1 Hz, 2H), 4.52-4.42 (m, 2H), 3.75 (t, J=6.1 Hz, 2H), 2.29-2.22 (m, 2H).

Example 169: (E)-N-(1-(2-fluoro-2-methylpropyl)-5-(2-oxo-1,3-oxazinan-3-yl)-1H-benzo[d]imidazol-2(3H)-ylidene)-3-(trifluoromethyl)benzamide (178)

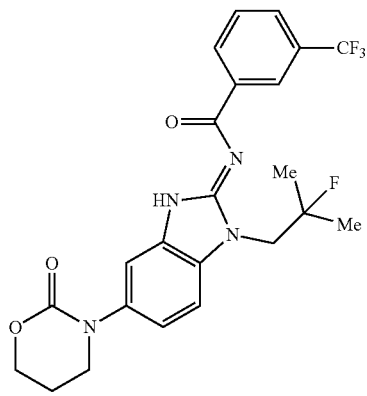 [SMILES: CC(C)(F)Cn1/c(=N/C(=O)c2cccc(C(F)(F)F)c2)[nH]c2cc(N3CCCOC3=O)ccc21]

Prepared in an analogous fashion to Example 9, but using Intermediate 55 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (64% yield). ESI⁺: M+1: 479. ¹H NMR (300 MHz, CDCl₃) δ 12.42 (s, 1H), 8.56 (s, 1H), 8.46 (d, J=7.8 Hz, 1H), 7.75 (d, J=7.8 Hz, 1H), 7.58 (t, J=7.8 Hz, 1H), 7.45 (dd, J=8.6, 2.6 Hz, 1H), 7.36-7.16 (m, 2H), 4.51-4.35 (m, 4H), 3.74 (t, J=6.1 Hz, 2H), 2.32-2.17 (m, 2H), 1.50 (d, J=21.3 Hz, 6H).

Example 170: (E)-N-(1-(2,2-difluoropropyl)-5-(2-oxo-1,3-oxazinan-3-yl)-1H-benzo[d]imidazol-2(3H)-ylidene)-3-(trifluoromethyl)benzamide (179)

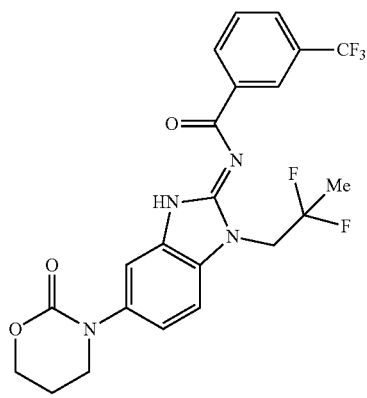 [SMILES: CC(F)(F)Cn1/c(=N/C(=O)c2cccc(C(F)(F)F)c2)[nH]c2cc(N3CCCOC3=O)ccc21]

Prepared in an analogous fashion to Example 9, but using Intermediate 56 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (63% yield). ESI⁺: M+1: 483. ¹H NMR (300 MHz, CDCl₃) δ 12.39 (s, 1H), 8.57 (s, 1H), 8.48 (d, J=7.8 Hz, 1H), 7.77 (d, J=7.6 Hz, 1H), 7.59 (t, J=7.8 Hz, 1H), 7.46-7.30 (m, 2H), 7.27 (dd, J=8.6, 2.0 Hz, 1H), 4.63 (t, J=12.1 Hz, 2H), 4.52-4.42 (m, 2H), 3.75 (t, J=6.1 Hz, 2H), 2.26 (p, J=6.0 Hz, 2H), 1.73 (t, J=18.9 Hz, 3H).

Example 171: (E)-N-(5-(2-oxo-1,3-oxazinan-3-yl)-1-((tetrahydro-2H-pyran-3-yl)methyl)-1H-benzo[d]imidazol-2(3H)-ylidene)-3-(trifluoromethyl)benzamide (180)

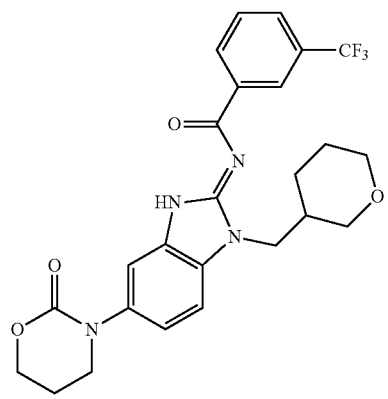 [SMILES: O=C(/N=c1\[nH]c2cc(N3CCCOC3=O)ccc2n1CC1CCCOC1)c1cccc(C(F)(F)F)c1]

Prepared in an analogous fashion to Example 9, but using Intermediate 57 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (44% yield). ESI⁺: M+1: 503. ¹H NMR (300 MHz, CDCl₃) δ 12.42 (s, 1H), 8.63 (s, 1H), 8.50 (d, J=7.8 Hz, 1H), 7.75 (d, J=7.7 Hz, 1H), 7.59 (t, J=7.8 Hz, 1H), 7.37-7.17 (m, 3H), 4.45 (t, J=5.4 Hz, 2H), 4.30-4.10 (m, 2H), 3.90-3.66 (m, 5H), 3.45 (dd, J=11.5, 7.9 Hz, 1H), 2.35-2.27 (m, 1H), 2.26 (p, J=6.0 Hz, 2H), 1.88-1.25 (m, 4H).

Example 172: (E)-N-(1-(cyclohexylmethyl)-5-(2-oxo-1,3-oxazinan-3-yl)-1H-benzo[d]imidazol-2(3H)-ylidene)-3-(trifluoromethyl)benzamide (181)

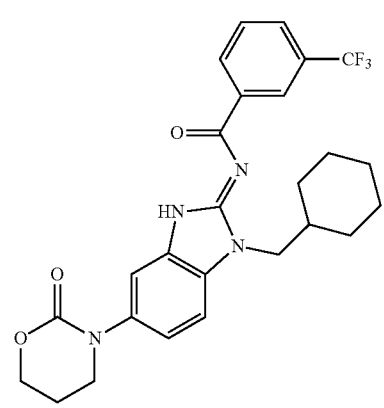 [SMILES: O=C(/N=c1\[nH]c2cc(N3CCCOC3=O)ccc2n1CC1CCCCC1)c1cccc(C(F)(F)F)c1]

Prepared in an analogous fashion to Example 9, but using Intermediate 58 (1 eq.) in place of Intermediate 1-OH, 3-trifluoromethyl-benzoic acid (1.1 eq.) in place of 4-methyl-3-trifluoromethyl-benzoic acid, and EDCI (1.1 eq.) in place of HBTU (70% yield). ESI⁺: M+1: 501. ¹H NMR (300 MHz, CDCl₃) δ 12.46 (s, 1H), 8.63 (s, 1H), 8.51 (d, J=7.8 Hz, 1H), 7.75 (d, J=7.7 Hz, 1H), 7.59 (d, J=7.7 Hz, 1H), 7.32-7.19 (m, 3H), 4.50-4.40 (m, 2H), 4.09 (d, J=7.2 Hz, 2H), 3.70 (t, J=6.1 Hz, 2H), 2.29-2.15 (m, 2H), 1.78-1.63 (m, 5H), 1.21-0.80 (m, 6H).

Example 173: (E)-N-(5-(4-cyclopropyl-2-oxopiperazin-1-yl)-1-(3-hydroxypropyl)-1H-benzo[d]imidazol-2(3H)-ylidene)-3-(difluoromethyl)benzamide (182)

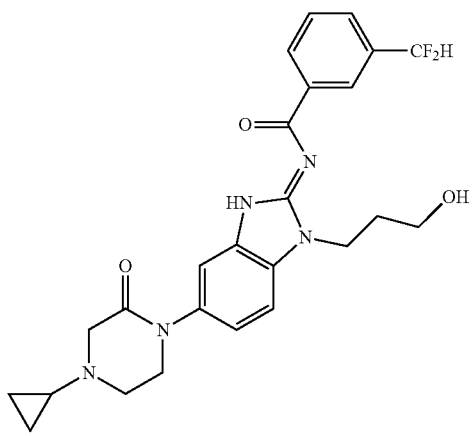 [SMILES: O=C(/N=c1\[nH]c2cc(N3CCN(C4CC4)CC3=O)ccc2n1CCCO)c1cccc(C(F)F)c1]

Prepared in an analogous fashion to Example 47, but using (1-ethoxy-cyclopropoxy)-trimethylsilane (6 eq.) in place of formaldehyde in step 1. ESI+: M+1: 484. $^1$H NMR (300 MHz, CDCl$_3$) δ 12.65 (s, 1H), 8.40-8.31 (m, 2H), 7.70-7.60 (m, 1H), 7.59-7.47 (m, 1H), 7.29-7.14 (m, 3H), 6.71 (t, J=56.4 Hz, 1H), 4.71-4.64 (m, 1H), 4.48-4.38 (m, 2H), 3.59-3.49 (m, 2H), 3.48-3.42 (m, 4H), 3.00-2.90 (m, 2H), 2.08-1.92 (m, 2H), 1.82-1.69 (m, 1H), 0.61-0.42 (m, 4H).

Example 174: (E)-N-(5-(4-cyclopropyl-2-oxopiperazin-1-yl)-1-(3-hydroxypropyl)-1H-benzo[d]imidazol-2(3H)-ylidene)-3-(trifluoromethyl)benzamide (183)

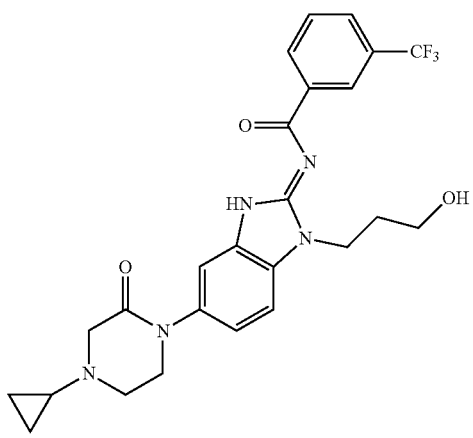 [SMILES: O=C(/N=c1\[nH]c2cc(N3CCN(C4CC4)CC3=O)ccc2n1CCCO)c1cccc(C(F)(F)F)c1]

Prepared in an analogous fashion to Example 47, but using (1-ethoxy-cyclopropoxy)-trimethylsilane (6 eq.) in place of formaldehyde, and Intermediate 3-CF$_3$ (1 eq.) in place of Intermediate 3-CF$_2$H in step 1. ESI+: M+1: 502. $^1$H NMR (300 MHz, CDCl$_3$) δ 12.53 (s, 1H), 8.53-8.37 (m, 2H), 7.74 (d, J=7.2 Hz, 1H), 7.57 (t, J=7.8 Hz, 1H), 7.35-7.16 (m, 3H), 4.50-4.39 (m, 3H), 3.67-3.57 (m, 2H), 3.52-3.42 (m, 4H), 3.05-2.95 (m, 2H), 2.07-1.95 (m, 2H), 1.84-1.70 (m, 1H), 0.63-0.44 (m, 4H).

Example 175: (E)-N-(5-(4-cyclobutyl-2-oxopiperazin-1-yl)-1-(3-hydroxypropyl)-1H-benzo[d]imidazol-2(3H)-ylidene)-3-(difluoromethyl)benzamide (184)

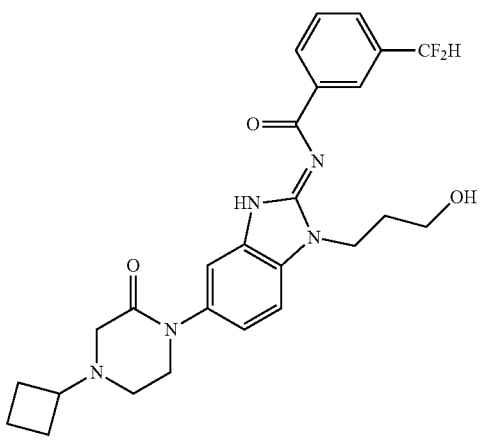 [SMILES: O=C(/N=c1\[nH]c2cc(N3CCN(C4CCC4)CC3=O)ccc2n1CCCO)c1cccc(C(F)F)c1]

Prepared in an analogous fashion to Example 47, but using cyclobutanone (1.1 eq.) in place of formaldehyde, triacetoxyborohydride (1.8 eq.) in place of sodium cyanoborohydride, and dichloroethane (0.03 M) in place of methanol in step 1. ESI+: M+1: 498. $^1$H NMR (300 MHz, CDCl$_3$) δ 12.72 (s, 1H), 8.46-8.37 (m, 2H), 7.70 (d, J=7.6 Hz, 1H), 7.59 (t, J=7.9 Hz, 1H), 7.38-7.23 (m, 3H), 6.76 (t, J=56.4 Hz, 1H), 4.76-4.69 (m, 1H), 4.53-4.43 (m, 2H), 3.67-3.57 (m, 2H), 3.24 (s, 2H), 2.99-2.82 (m, 1H), 2.74-2.63 (m, 2H), 2.18-1.87 (m, 6H), 1.88-1.72 (m, 2H).

Example 176: (E)-3-(difluoromethyl)-N-(1-(3-hydroxypropyl)-5-(4-isopropyl-2-oxopiperazin-1-yl)-1H-benzo[d]imidazol-2(3H)-ylidene)benzamide (185)

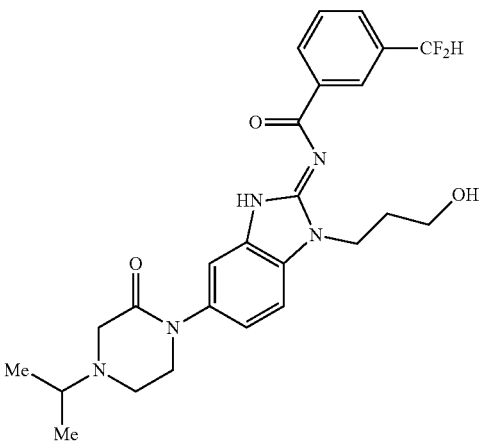 [SMILES: CC(C)N1CCN(c2ccc3c(c2)[nH]/c(=N\C(=O)c2cccc(C(F)F)c2)n3CCCO)C(=O)C1]

Prepared in an analogous fashion to Example 47, but using acetone (5 eq.) in place of formaldehyde, triacetoxyborohydride (2 eq.) in place of sodium cyanoborohydride, and dichloroethane (0.03 M) in place of methanol in step 1. ESI⁺: M+1: 486. ¹H NMR (300 MHz, CDCl₃) δ 12.61 (s, 1H), 8.41-8.32 (m, 2H), 7.67 (d, J=7.7 Hz, 1H), 7.55 (t, J=7.9 Hz, 1H), 7.36-7.19 (m, 3H), 6.73 (t, J=56.4 Hz, 1H), 4.72-4.65 (m, 1H), 4.51-4.41 (m, 2H), 3.69-3.58 (m, 2H), 3.54-3.35 (m, 4H), 2.90-2.74 (m, 3H), 2.12-1.96 (m, 2H), 1.12 (d, J=6.5 Hz, 6H).

Example 177: (E)-N-(1-(3-hydroxypropyl)-5-(3-oxothiomorpholino)-1H-benzo[d]imidazol-2(3H)-ylidene)-3-(trifluoromethyl)benzamide (186)

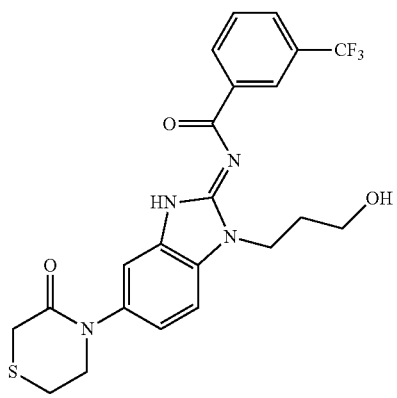 [SMILES: O=C(/N=c1\[nH]c2cc(N3CCSCC3=O)ccc2n1CCCO)c1cccc(C(F)(F)F)c1]

Step 1: (Z)-3-(5-(3-oxothiomorpholino)-2-((3-(trifluoromethyl)benzoyl)imino)-3-((2-(trimethylsilyl)ethoxy)methyl)-2,3-dihydro-1H-benzo[d]imidazol-1-yl)propyl acetate In a glass reaction vessel equipped with a Teflon-coated screw cap was suspended Intermediate 59-CF₃ (1 eq.), thiomorpholin-3-one (1 eq.), copper(I) iodide (0.15 eq.), (1R,2R)—N,N'-dimethylcyclohexane-1,2-diamine (0.3 eq.) and potassium carbonate (1.2 eq.) in DMF (0.6 M). The resulting suspension was then de-oxygenated via sub-surface purging for 5 min before the vessel was tightly sealed and heated at 100° C. for 18 h. The volatiles were removed in vacuo and the resulting residue was partitioned between water and EtOAc. The aqueous layer was separated and back-extracted with EtOAc. The combined organic extracts were washed further with water and brine, dried over Na₂SO₄, filtered and the filtrate concentrated in vacuo. Purification by way of column chromatography (SiO₂, gradient elution, 1:1 (v/v) Hex:EtOAc→EtOAc→10:1 (v/v) EtOAc:MeOH) furnished the desired product compound as a viscous oil (31% yield).

Step 2: (E)-3-(5-(3-oxothiomorpholino)-2-((3-(trifluoromethyl)benzoyl)imino)-2,3-dihydro-1H-benzo[d]imidazol-1-yl)propyl acetate In a glass RBF equipped with a Teflon-coated magnetic stirrer was dissolved (Z)-3-(5-(3-oxothiomorpholino)-2-((3-(trifluoromethyl)benzoyl)imino)-3-((2-(trimethylsilyl)ethoxy)methyl)-2,3-dihydro-1H-benzo[d]imidazol-1-yl)propyl acetate (1 eq.) from the previous step in THF (0.1 M). To this was then added tetrabutylammonium fluoride (1.5 eq., 1 M solution in THF) drop-wise over a period of 1 min. The resulting mixture was allowed to stir at 60° C. for 24 h. The crude reaction mixture was diluted with EtOAc and washed sequentially with water and brine. The organic extract was then dried over Na₂SO₄, filtered and the filtrate concentrated in vacuo. Purification by way of column chromatography (SiO₂, gradient elution, 1:1 (v/v) Hex:EtOAc→EtOAc→10:1 (v/v) EtOAc:MeOH) furnished the desired product compound (40% yield).

Step 3: (E)-N-(1-(3-hydroxypropyl)-5-(3-oxothiomorpholino)-1H-benzo[d]imidazol-2(3H)-ylidene)-3-(trifluoromethyl)benzamide In a glass RBF equipped with a Teflon-coated magnetic stirrer was dissolved (E)-3-(5-(3-oxothiomorpholino)-2-((3-(trifluoromethyl)benzoyl)imino)-2,3-dihydro-1H-benzo[d]imidazol-1-yl)propyl acetate (1 eq.) from the previous step in methanol (0.04 M). To this was then added potassium carbonate (2 eq.) and the resulting suspension was stirred at RT for 2 h. The volatiles were then removed in vacuo and the resulting residue was partitioned between water and dichloromethane. The aqueous layer was separated and back-extracted with dichloromethane. The combined organic extracts were washed further with water and brine, dried over Na₂SO₄, filtered and the filtrate concentrated in vacuo. Purification by way of column chromatography (SiO₂, gradient elution, EtOAc→4:1 (v/v) EtOAc:MeOH) furnished the desired product compound as a dark yellow solid (54% yield). ESI⁺: M+1: 479. ¹H NMR (300 MHz, CDCl₃) δ 12.51 (s, 1H), 8.50 (s, 1H), 8.47-8.37 (m, 1H), 7.80-7.71 (m, 1H), 7.65-7.53 (m, 1H), 7.41-7.29 (m, 2H), 7.25-7.20 (m, 1H), 4.52-4.43 (m, 3H), 4.07-3.97 (m, 2H), 3.55-3.48 (m, 4H), 3.11-3.04 (m, 2H), 2.08-2.01 (m, 2H).

Example 178: (E)-3-(difluoromethyl)-N-(1-(3-hydroxypropyl)-5-(3-oxothiomorpholino)-1H-benzo[d]imidazol-2(3H)-ylidene)benzamide (187)

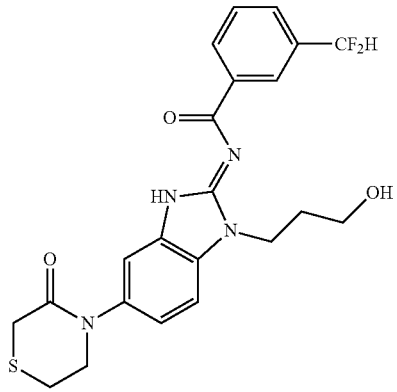 [SMILES: O=C(/N=c1\[nH]c2cc(N3CCSCC3=O)ccc2n1CCCO)c1cccc(C(F)F)c1]

Prepared in an analogous fashion to Example 177, but using Intermediate 59-CF₂H (1 eq.) in place of Intermediate 58-CF₃ in step 1. ESI⁺: M+1: 461. ¹H NMR (300 MHz, CDCl₃) δ 12.54 (s, 1H), 8.40-8.33 (m, 2H), 7.68 (d, J=7.5 Hz, 1H), 7.56 (t, J=7.6 Hz, 1H), 7.39-7.18 (m, 3H), 6.73 (t, J=56.3 Hz, 1H), 4.65-4.54 (m, 1H), 4.52-4.45 (m, 2H), 4.05-3.96 (m, 2H), 3.54-3.44 (m, 4H), 3.12-3.01 (m, 2H), 2.08-2.01 (m, 2H).

Example 179: (E)-N-(1-(3-hydroxypropyl)-5-(4-methyl-5-oxo-4,5-dihydro-1H-1,2,4-triazol-1-yl)-1H-benzo[d]imidazol-2(3H)-ylidene)-3-(trifluoromethyl)benzamide (188)

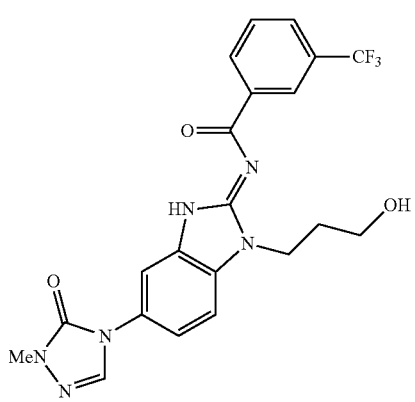 [SMILES: Cn1ncn(-c2ccc3c(c2)[nH]/c(=N\C(=O)c2cccc(C(F)(F)F)c2)n3CCCO)c1=O]

Prepared in an analogous fashion to Example 177, but using 4-methyl-1H-1,2,4-triazol-5(4H)-one (1 eq.) in place of thiomorpholin-3-one in step 1. ESI+: M+1: 461. $^1$H NMR (300 MHz, CDCl$_3$) δ 12.88 (s, 1H), 8.55-8.45 (m, 2H), 8.19 (s, 1H), 8.08 (d, J=2.0 Hz, 1H), 7.92-7.76 (m, 2H), 7.71 (t, J=7.7 Hz, 1H), 7.59 (d, J=8.8 Hz, 1H), 4.71-4.61 (m, 1H), 4.32 (t, J=6.9 Hz, 2H), 3.52-3.40 (m, 2H), 3.26 (s, 3H), 2.00-1.89 (m, 2H).

Example 180: (E)-N-(1-(3-hydroxypropyl)-5-(1-methyl-5-oxo-4,5-dihydro-1H-1,2,4-triazol-4(5H)-yl)-1H-benzo[d]imidazol-2(3H)-ylidene)-3-(trifluoromethyl)benzamide (189)

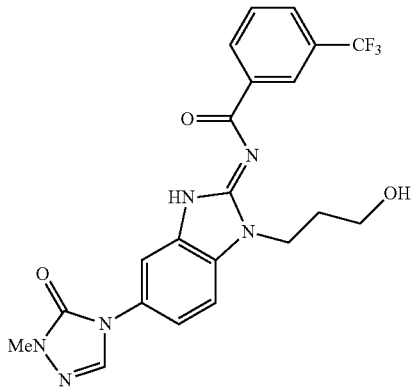 [SMILES: Cn1ncn(-c2ccc3c(c2)[nH]/c(=N\C(=O)c2cccc(C(F)(F)F)c2)n3CCCO)c1=O]

Prepared in an analogous fashion to Example 177, but using 1-methyl-1H-1,2,4-triazol-5(4H)-one (1 eq.) in place of thiomorpholin-3-one in step 1. ESI+: M+1: 461. $^1$H NMR (300 MHz, CDCl$_3$) δ 12.95 (s, 1H), 8.56-8.46 (m, 2H), 8.41 (s, 1H), 7.89 (d, J=8.0 Hz, 1H), 7.83 (d, J=2.1 Hz, 1H), 7.78-7.61 (m, 2H), 7.44 (dd, J=8.6, 2.1 Hz, 1H), 4.69-4.63 (m, 1H), 4.35 (t, J=6.8 Hz, 2H), 3.52-3.43 (m, 2H), 3.40 (s, 3H), 2.01-1.90 (m, 2H).

Example 181: (E)-N-(5-(1,1-dioxido-1,2-thiazinan-2-yl)-1-(3-hydroxypropyl)-1H-benzo[d]imidazol-2(3H)-ylidene)-3-(trifluoromethyl)benzamide (190)

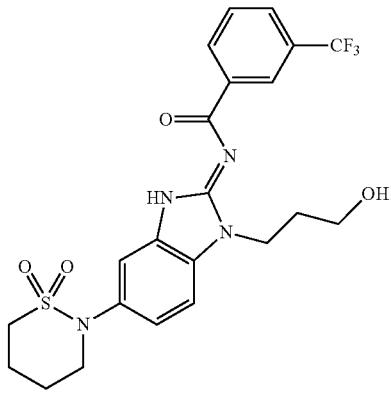 [SMILES: O=C(/N=c1\[nH]c2cc(N3CCCCS3(=O)=O)ccc2n1CCCO)c1cccc(C(F)(F)F)c1]

Prepared in an analogous fashion to Example 177, but using 1,2-thiazinane-1,1-dioxide (1 eq.) in place of thiomorpholin-3-one in step 1. ESI+: M+1: 497. $^1$H NMR (300 MHz, CDCl$_3$) δ 12.57 (s, 1H), 8.55-8.48 (m, 1H), 8.44 (d, J=7.8 Hz, 1H), 7.79-7.70 (m, 1H), 7.58 (d, J=7.8 Hz, 1H), 7.40-7.24 (m, 3H), 4.51-4.41 (m, 3H), 3.71-3.61 (m, 2H), 3.54-3.43 (m, 2H), 3.29-3.18 (m, 2H), 2.41-2.23 (m, 2H), 2.10-1.95 (m, 2H), 1.98-1.83 (m, 2H).

Example 182: (E)-N-(5-(3,3-dimethyl-2-oxopiperazin-1-yl)-1-(3-hydroxypropyl)-1H-benzo[d]imidazol-2(3H)-ylidene)-3-(trifluoromethyl)benzamide hydrochloride (191)

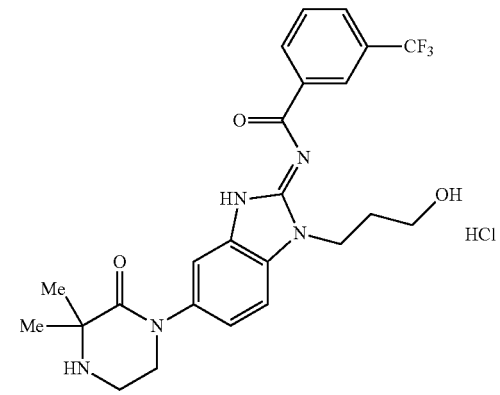 [SMILES: CC1(C)NCCN(c2ccc3c(c2)[nH]/c(=N\C(=O)c2cccc(C(F)(F)F)c2)n3CCCO)C1=O ; Cl]

Prepared in an analogous fashion to Example 177, but using tert-butyl 2,2-dimethyl-3-oxopiperazine-1-carboxylate (1 eq.) in place of thiomorpholin-3-one in step 1, TFA (50 eq.) in place of tetrabutylammonium fluoride in step 2, dichloroethane (0.38 M) in place of THF in step 2, and HCl (1.1 eq., 4 M solution in dioxane) was added to the purified product in step 3. ESI+: M+1: 490. $^1$H NMR (300 MHz, DMSO-d$_6$) δ 10.26 (s, 2H), 8.57-8.47 (m, 2H), 7.91 (d, J=7.7 Hz, 1H), 7.74 (d, J=7.6 Hz, 1H), 7.62 (d, J=8.5 Hz, 1H), 7.45 (s, 1H), 7.20 (d, J=8.3 Hz, 1H), 4.39-4.32 (m, 2H), 4.06-3.72 (m, 3H), 3.67-3.60 (m, 2H), 3.52-3.45 (m, 2H), 2.04-1.91 (m, 2H), 1.64 (s, 6H).

Example 183: (E)-N-(1-(3-hydroxypropyl)-5-(5-oxo-1,4-oxazepan-4-yl)-1H-benzo[d]imidazol-2(3H)-ylidene)-3-(trifluoromethyl)benzamide (192)

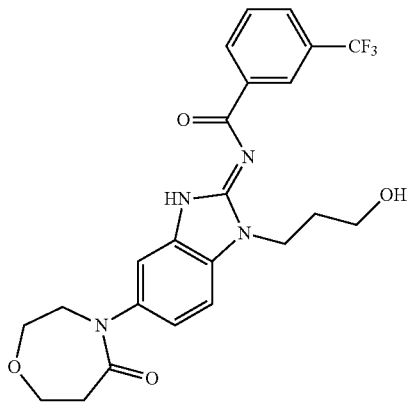 [SMILES: O=C(/N=c1\[nH]c2cc(N3CCOCCC3=O)ccc2n1CCCO)c1cccc(C(F)(F)F)c1]

Prepared in an analogous fashion to Example 177, but using 1,4-oxazepan-5-one (1 eq.) in place of thiomorpholin-3-one in step 1. ESI⁺: M+1: 477. $^1$H NMR (300 MHz, CDCl$_3$) δ 12.58 (s, 1H), 8.52 (s, 1H), 8.44 (d, J=7.7 Hz, 1H), 7.77 (d, J=7.7 Hz, 1H), 7.59 (t, J=7.7 Hz, 1H), 7.35-7.09 (m, 3H), 4.52-4.42 (m, 3H), 4.02-3.80 (m, 6H), 3.51-3.44 (m, 2H), 3.01-2.91 (m, 2H), 2.08-1.98 (m, 2H).

Example 184: (E)-N-(1-(3-hydroxypropyl)-5-(3-oxo-1,4-oxazepan-4-yl)-1H-benzo[d]imidazol-2(3H)-ylidene)-3-(trifluoromethyl)benzamide (193)

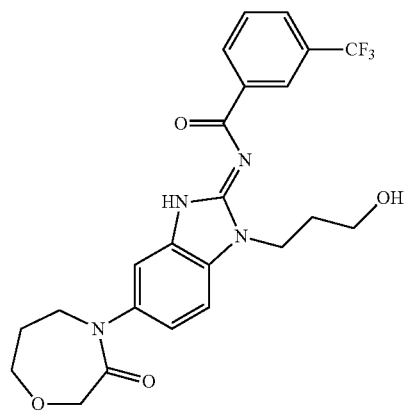 [SMILES: O=C(/N=c1\[nH]c2cc(N3CCCOCC3=O)ccc2n1CCCO)c1cccc(C(F)(F)F)c1]

Prepared in an analogous fashion to Example 177, but using 1,4-oxazepan-3-one (1 eq.) in place of thiomorpholin-3-one in step 1. ESI⁺: M+1: 477. $^1$H NMR (300 MHz, CDCl$_3$) δ 12.56 (s, 1H), 8.52 (s, 1H), 8.44 (d, J=7.8 Hz, 1H), 7.76 (d, J=7.7 Hz, 1H), 7.59 (t, J=7.7 Hz, 1H), 7.38-7.14 (m, 3H), 4.65-4.36 (m, 5H), 4.03-3.93 (m, 2H), 3.93-3.82 (m, 2H), 3.53-3.43 (m, 2H), 2.17-1.96 (m, 4H).

Example 185: (E)-N-(5-(4-cyclopropyl-3,3-dimethyl-2-oxopiperazin-1-yl)-1-(3-hydroxypropyl)-1H-benzo[d]imidazol-2(3H)-ylidene)-3-(trifluoromethyl)benzamide (194)

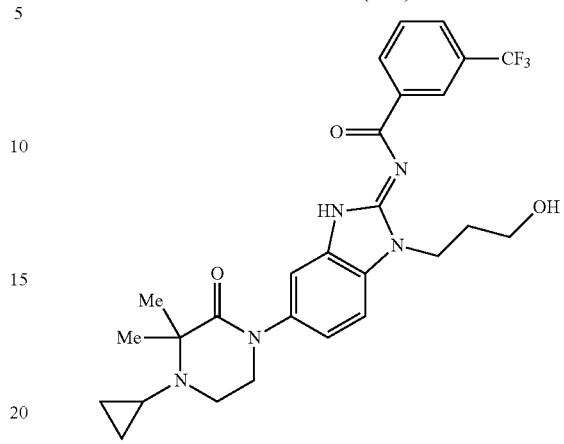

In a glass RBF equipped with a Teflon-coated magnetic stirrer was dissolved Example 182 (1 eq.) in methanol (0.1 M). To this was then added (1-ethoxy-cyclopropoxy)-trimethylsilane (6 eq.) and glacial acetic acid (10 eq.), and the resulting solution was stirred at RT for 30 min. Finally, sodium cyanoborohydride (2 eq.) was added in one rapid portion and the resulting mixture was heated at 80° C. for 1 h. The volatiles were removed in vacuo and the resulting residue was partitioned between 10% aq. NaHCO$_3$ and dichloromethane. The aqueous layer was separated and back-extracted with dichloromethane. The combined organic extracts were washed further with water and brine, dried over Na$_2$SO$_4$, filtered and the filtrate concentrated in vacuo. Purification by way of column chromatography (SiO$_2$, gradient elution, 2:1 (v/v) Hex:EtOAc→EtOAc→9:1 (v/v) EtOAc:MeOH) furnished the desired product compound as a white solid (71% yield). ESI⁺: M+1: 530. $^1$H NMR (300 MHz, CDCl$_3$) δ 12.50 (s, 1H), 8.51 (s, 1H), 8.43 (d, J=7.7 Hz, 1H), 7.75 (d, J=7.7 Hz, 1H), 7.58 (t, J=7.7 Hz, 1H), 7.36-7.18 (m, 3H), 4.59-4.42 (m, 3H), 3.69-3.58 (m, 2H), 3.52-3.43 (m, 2H), 3.21-3.11 (m, 2H), 2.06-2.00 (m, 3H), 1.54 (s, 6H), 0.69-0.60 (m, 2H), 0.58-0.50 (m, 2H).

Example 186: (E)-3-(difluoromethyl)-N-(1-(3-hydroxypropyl)-5-(3-oxo-1,4-oxazepan-4-yl)-1H-benzo[d]imidazol-2(3H)-ylidene)benzamide (195)

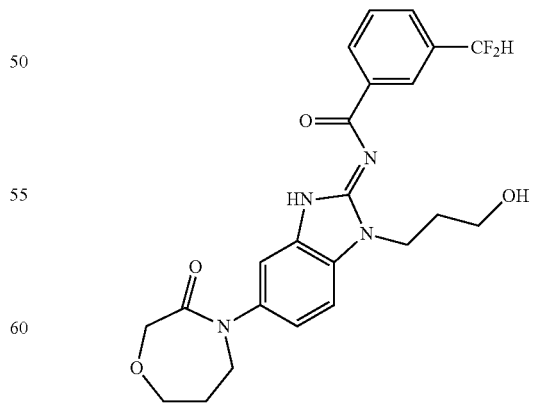

Prepared in an analogous fashion to Example 177, but using Intermediate 59-CF$_2$H (1 eq.) in place of Intermediate 59-CF$_3$, and 1,4-oxazepan-3-one (1 eq.) in place of thiomorpholin-3-one in step 1. ESI⁺: M+1: 459. ¹H NMR (300 MHz, CDCl₃) δ 12.58 (s, 1H), 8.41-8.32 (m, 2H), 7.67 (d, J=7.6 Hz, 1H), 7.56 (t, J=7.8 Hz, 1H), 7.32 (d, J=8.4 Hz, 1H), 7.27-7.13 (m, 2H), 6.73 (t, J=56.4 Hz, 1H), 4.71-4.64 (m, 1H), 4.50-4.38 (m, 4H), 3.97 (t, J=5.7 Hz, 2H), 3.93-3.83 (m, 2H), 3.50-3.44 (m, 2H), 2.17-1.95 (m, 4H).

Example 187: (E)-3-(difluoromethyl)-N-(1-(3-hydroxypropyl)-5-(5-oxo-1,4-oxazepan-4-yl)-1H-benzo[d]imidazol-2(3H)-ylidene)benzamide (196)

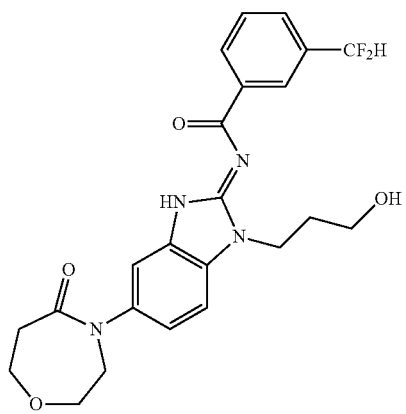 [SMILES: O=C(/N=c1\[nH]c2cc(N3CCOCCC3=O)ccc2n1CCCO)c1cccc(C(F)F)c1]

Prepared in an analogous fashion to Example 177, but using Intermediate 59-CF₂H (1 eq.) in place of Intermediate 59-CF₃, and 1,4-oxazepan-5-one (1 eq.) in place of thiomorpholin-3-one in step 1. ESI⁺: M+1: 459. ¹H NMR (300 MHz, CDCl₃) δ 12.55 (s, 1H), 8.40-8.34 (m, 2H), 7.68 (d, J=7.8 Hz, 1H), 7.57 (t, J=7.9 Hz, 1H), 7.33 (d, J=8.5 Hz, 1H), 7.28-7.11 (m, 2H), 6.74 (t, J=56.3 Hz, 1H), 4.68-4.59 (m, 1H), 4.48 (t, J=6.0 Hz, 2H), 4.01-3.88 (m, 6H), 3.52-3.43 (m, 2H), 3.02-2.92 (m, 2H), 2.06-2.01 (m, 2H).

Example 188: (E)-N-(5-(4-cyclopropyl-3,3-dimethyl-2-oxopiperazin-1-yl)-1-(3-hydroxypropyl)-1H-benzo[d]imidazol-2(3H)-ylidene)-3-(difluoromethyl)benzamide (197)

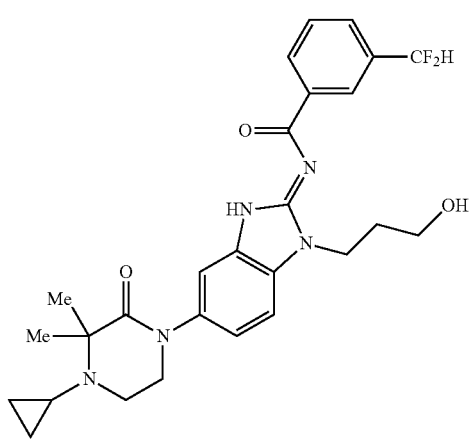

Step 1: (Z)-tert-butyl 4-(1-(3-acetoxypropyl)-2-((3-(difluoromethyl)benzoyl)imino)-3-((2-(trimethylsilyl)ethoxy)methyl)-2,3-dihydro-1H-benzo[d]imidazol-5-yl)-2,2-dimethyl-3-oxopiperazine-1-carboxylate In a glass reaction vessel equipped with a Teflon-coated screw cap was suspended Intermediate 59-CF₂H (1 eq.), tert-butyl 2,2-dimethyl-3-oxopiperazine-1-carboxylate (1 eq.), copper(I) iodide (0.25 eq.), (1R,2R)—N,N'-dimethylcyclohexane-1,2-diamine (0.5 eq.) and potassium carbonate (2.5 eq.) in DMF (0.1 M). The resulting suspension was then de-oxygenated via sub-surface purging for 5 min before the vessel was tightly sealed and heated at 100° C. for 22 h. The now black reaction suspension was allowed to cool to RT and then diluted with EtOAc. The aqueous layer was separated and back-extracted with EtOAc. The combined organic extracts were washed further with sat. aq. NH₄Cl, water and brine, dried over Na₂SO₄, filtered and the filtrate concentrated in vacuo. Purification by way of column chromatography (SiO₂, gradient elution, 1:1 (v/v) Hex:EtOAc→EtOAc→10:1 (v/v) EtOAc:MeOH) furnished the desired product compound as a viscous oil (86% yield).

Step 2: (E)-3-(2-((3-(difluoromethyl)benzoyl)imino)-5-(3,3-dimethyl-2-oxopiperazin-1-yl)-2,3-dihydro-1H-benzo[d]imidazol-1-yl)propyl acetate In a glass RBF equipped with a Teflon-coated magnetic stirrer was dissolved (Z)-tert-butyl 4-(1-(3-acetoxypropyl)-2-((3-(difluoromethyl)benzoyl)imino)-3-((2-(trimethylsilyl)ethoxy)methyl)-2,3-dihydro-1H-benzo[d]imidazol-5-yl)-2,2-dimethyl-3-oxopiperazine-1-carboxylate (1 eq.) from the previous step in dichloroethane (0.07 M). To this was then added TFA (50 eq.) drop-wise over a period of 1 min. The resulting mixture was allowed to stir at RT for 18 h. The crude reaction mixture was then diluted with DCM and washed sequentially with sat. aq. NaHCO₃, water and brine. The organic extract was then dried over Na₂SO₄ and filtered. Concentration of the filtrate in vacuo furnished the desired product compound as an off-white solid (90% yield).

Step 3: (E)-3-(5-(4-cyclopropyl-3,3-dimethyl-2-oxopiperazin-1-yl)-2-O-(difluormethyl)benzoyl)imino)-2,3-dihydro-1H-benzo[d]imidazol-1-yl)propyl acetate In a glass RBF equipped with a Teflon-coated magnetic stirrer was dissolved (E)-3-(2-((3-(difluoromethyl)benzoyl)imino)-5-(3,3-dimethyl-2-oxopiperazin-1-yl)-2,3-dihydro-1H-benzo[d]imidazol-1-yl)propyl acetate (1 eq.) from the previous step in methanol (0.1 M). To this was then added (1-ethoxy-cyclopropoxy)-trimethylsilane (5 eq.) and glacial acetic acid (8 eq.), and the resulting solution was stirred at RT for 30 min. Finally, sodium cyanoborohydride (4 eq.) was added in one rapid portion and the resulting mixture was heated at 70° C. for 90 min. The volatiles were removed in vacuo and the resulting residue was partitioned between 10% aq. NaHCO₃ and dichloromethane. The aqueous layer was separated and back-extracted with dichloromethane. The combined organic extracts were washed further with water and brine, dried over Na₂SO₄, filtered and the filtrate concentrated in vacuo. Purification by way of column chromatography (SiO₂, gradient elution, 2:1 (v/v) Hex:EtOAc→EtOAc→9:1 (v/v) EtOAc:MeOH) furnished the desired product compound as a white solid (71% yield).

Step 4: (E)-N-(5-(4-cyclopropyl-3,3-dimethyl-2-oxopiperazin-1-yl)-1-(3-hydroxypropyl)-1H-benzo[d]imidazol-2(3H)-ylidene)-3-(difluoromethyl)benzamide In a glass RBF equipped with a Teflon-coated magnetic stirrer was dissolved (E)-3-(5-(4-cyclopropyl-3,3-dimethyl-2-oxopiperazin-1-yl)-2-((3-(difluormethyl)benzoyl)imino)-2,3-dihydro-1H-benzo[d]imidazol-1-yl)propyl acetate (1 eq.) from the previous step in methanol (0.035 M). To this was then added potassium carbonate (2 eq.) and the resulting suspension was stirred at RT for 18 h. The volatiles were then removed in vacuo and the resulting residue was partitioned between water and dichloromethane. The aqueous layer was separated and back-extracted with dichloromethane. The combined organic extracts were washed further with water and brine, dried over $Na_2SO_4$, filtered and the filtrate concentrated in vacuo. Purification by way of column chromatography ($SiO_2$, gradient elution, EtOAc→4:1 (v/v) EtOAc:MeOH) furnished the desired product compound as a white solid (81% yield). ESI$^+$: M+1: 512. $^1$H NMR (300 MHz, CDCl$_3$) δ 12.63 (s, 1H), 8.42-8.33 (m, 2H), 7.67 (d, J=7.7 Hz, 1H), 7.55 (t, J=7.9 Hz, 1H), 7.34-7.14 (m, 3H), 6.73 (t, J=56.4 Hz, 1H), 4.75-4.68 (m, 1H), 4.51-4.41 (m, 2H), 3.55 (t, J=5.4 Hz, 2H), 3.49-3.41 (m, 2H), 3.11 (t, J=5.4 Hz, 2H), 2.08-1.94 (m, 3H), 1.51 (s, 6H), 0.70-0.46 (m, 4H).

Example 189: (E)-N-(1-(3-hydroxypropyl)-5-(5-oxo-7-oxa-4-azaspiro[2.5]octan-4-yl)-1H-benzo[d]imidazol-2(3H)-ylidene)-3-(trifluoromethyl)benzamide (198)

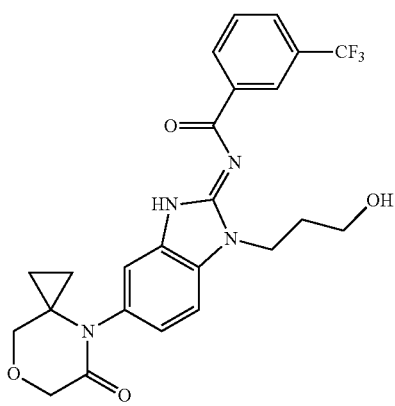

Prepared in an analogous fashion to Example 177, but using 7-oxa-4-azaspiro[2.5]octan-5-one (1 eq.) in place of thiomorpholin-3-one in step 1. ESI$^+$: M+1: 489. $^1$H NMR (300 MHz, CDCl$_3$) δ 12.56 (s, 1H), 8.52 (s, 1H), 8.44 (d, J=7.8 Hz, 1H), 7.77 (d, J=7.7 Hz, 1H), 7.59 (t, J=7.8 Hz, 1H), 7.34 (d, J=8.4 Hz, 1H), 7.16-7.01 (m, 2H), 4.54-4.41 (m, 5H), 3.88 (s, 2H), 3.53-3.47 (m, 2H), 2.08-1.97 (m, 2H), 0.81-0.62 (m, 4H).

Example 190: (E)-3-(difluoromethyl)-N-(1-(3-hydroxypropyl)-5-(5-oxo-7-oxa-4-azaspiro[2.5]octan-4-yl)-1H-benzo[d]imidazol-2(3H)-ylidene)benzamide (199)

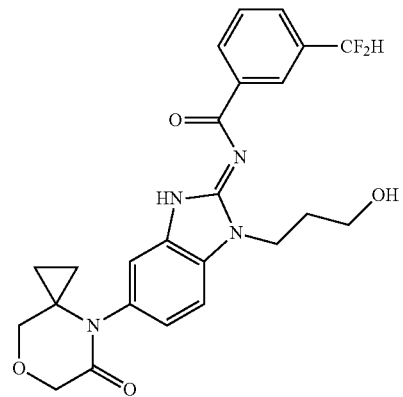

Prepared in an analogous fashion to Example 177, but using Intermediate 59-CF$_2$H (1 eq.) in place of Intermediate 59-CF$_3$, and 7-oxa-4-azaspiro[2.5]octan-5-one (1 eq.) in place of thiomorpholin-3-one in step 1. ESI$^+$: M+1: 471. $^1$H NMR (300 MHz, CDCl$_3$) δ 12.64 (s, 1H), 8.42-8.33 (m, 2H), 7.69 (d, J=7.7 Hz, 1H), 7.57 (t, J=7.7 Hz, 1H), 7.28 (d, J=7.5 Hz, 1H), 7.11-6.98 (m, 2H), 6.74 (t, J=56.3 Hz, 1H), 4.68-4.61 (m, 1H), 4.53-4.40 (m, 4H), 3.84 (s, 2H), 3.49 (t, J=5.4 Hz, 2H), 2.08-1.95 (m, 2H), 0.78-0.59 (m, 4H).

Example 191: (E)-N-(5-(4-cyclopropyl-7-oxo-1,4-diazepan-1-yl)-1-(3-hydroxypropyl)-1H-benzo[d]imidazol-2(3H)-ylidene)-3-(trifluoromethyl)benzamide (200)

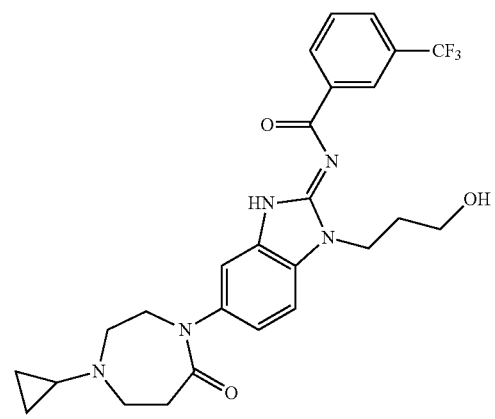 [SMILES: O=C(/N=c1\[nH]c2cc(N3CCN(C4CC4)CCC3=O)ccc2n1CCCO)c1cccc(C(F)(F)F)c1]

Prepared in an analogous fashion to Example 188, but using tert-butyl 5-oxo-1,4-diazepane-1-carboxylate (1 eq.) in place of tert-butyl 2,2-dimethyl-3-oxopiperazine-1-carboxylate, and Intermediate 59-CF$_3$ (1 eq.) in place of Intermediate 59-CF$_2$H in step 1. ESI$^+$: M+1: 516. $^1$H NMR (300 MHz, DMSO-d$_6$) δ 12.82 (s, 1H), 8.57-8.48 (m, 2H), 7.90 (d, J=7.7 Hz, 1H), 7.74 (t, J=7.7 Hz, 1H), 7.53 (d, J=8.5 Hz, 1H), 7.37 (s, 1H), 7.10 (d, J=8.3 Hz, 1H), 4.73-4.66 (m, 1H), 4.37-4.31 (m, 2H), 3.82-3.75 (m, 2H), 3.51-3.44 (m, 2H), 2.89-2.78 (m, 4H), 2.74-2.67 (m, 2H), 1.99-1.81 (m, 3H), 0.50 (d, J=5.9 Hz, 2H), 0.39-0.35 (m, 2H).

Example 192: (E)-N-(5-(4-cyclopropyl-2-oxo-1,4-diazepan-1-yl)-1-(3-hydroxypropyl)-1H-benzo[d]imidazol-2(3H)-ylidene)-3-(trifluoromethyl)benzamide (201)

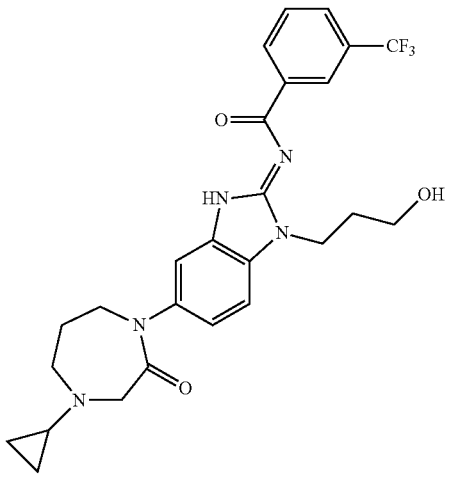 [SMILES: O=C(/N=c1\[nH]c2cc(N3CCCN(C4CC4)CC3=O)ccc2n1CCCO)c1cccc(C(F)(F)F)c1]

Prepared in an analogous fashion to Example 188, but using tert-butyl 3-oxo-1,4-diazepane-1-carboxylate (1 eq.) in place of tert-butyl 2,2-dimethyl-3-oxopiperazine-1-carboxylate, and Intermediate 59-CF$_3$ (1 eq.) in place of Intermediate 59-CF$_2$H in step 1. ESI$^+$: M+1: 516. $^1$H NMR (300 MHz, DMSO-d$_6$) δ 12.81 (s, 1H), 8.57-8.48 (m, 2H), 7.90 (d, J=7.7 Hz, 1H), 7.74 (t, J=7.7 Hz, 1H), 7.53 (d, J=8.5 Hz, 1H), 7.39 (s, 1H), 7.11 (d, J=8.3 Hz, 1H), 4.69 (t, J=5.0 Hz, 1H), 4.37-4.31 (m, 2H), 3.87-3.80 (m, 2H), 3.66 (s, 2H), 3.52-3.44 (m, 2H), 3.06-2.99 (m, 2H), 2.21-2.09 (m, 1H), 2.01-1.91 (m, 2H), 1.91-1.84 (m, 2H), 0.55-0.46 (m, 2H), 0.41-0.34 (m, 2H).

Example 193: (E)-N-(1-(3-hydroxypropyl)-5-(2-oxopyridin-1(2H)-yl)-1H-benzo[d]imidazol-2(3H)-ylidene)-3-(trifluoromethyl)benzamide (202)

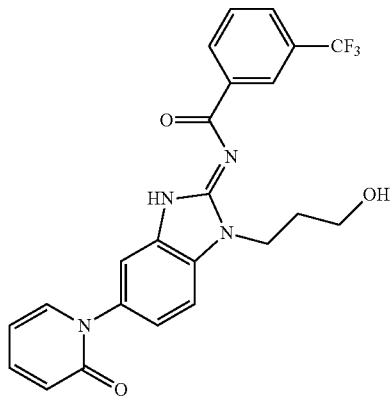

Prepared in an analogous fashion to Example 177, but using pyridine-2(1H)-one (1 eq.) in place of thiomorpholin-3-one in step 1. ESI$^+$: M+1: 457. $^1$H NMR (300 MHz, CDCl$_3$) δ 12.63 (s, 1H), 8.51 (s, 1H), 8.43 (d, J=7.8 Hz, 1H), 7.75 (d, J=7.7 Hz, 1H), 7.58 (t, J=7.8 Hz, 1H), 7.51-7.23 (m, 5H), 6.71 (d, J=9.3 Hz, 1H), 6.34-6.25 (m, 1H), 4.56-4.35 (m, 3H), 3.56-3.44 (m, 2H), 2.12-1.98 (m, 2H).

Example 194: (E)-3-(difluoromethyl)-N-(1-(3-hydroxypropyl)-5-(2-oxopyridin-1(2H)-yl)-1H-benzo[d]imidazol-2(3H)-ylidene)benzamide (203)

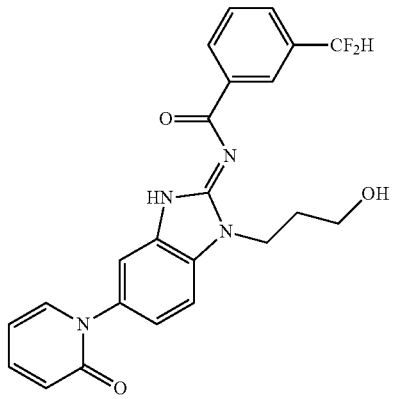 [SMILES: O=C(/N=c1\[nH]c2cc(-n3ccccc3=O)ccc2n1CCCO)c1cccc(C(F)F)c1]

Prepared in an analogous fashion to Example 177, but using pyridine-2(1H)-one (1 eq.) in place of thiomorpholin-3-one, and Intermediate 59-CF$_2$H (1 eq.) in place of Intermediate 59-CF$_3$ in step 1. ESI$^+$: M+1: 439. $^1$H NMR (300 MHz, CDCl$_3$) δ 12.66 (s, 1H), 8.40-8.32 (m, 2H), 7.66 (d, J=7.6 Hz, 1H), 7.55 (t, J=7.8 Hz, 1H), 7.50-7.28 (m, 5H), 6.95-6.51 (m, 2H), 6.33-6.23 (m, 1H), 4.64-4.57 (m, 1H), 4.49 (t, J=5.9 Hz, 2H), 3.54-3.44 (m, 2H), 2.12-1.97 (m, 2H).

Example 195: (E)-3-(difluoromethyl)-N-(5-(4-(2-hydroxyethyl)-3,3-dimethyl-2-oxopiperazin-1-yl)-1-(3-hydroxypropyl)-1H-benzo[d]imidazol-2(3H)-ylidene)benzamide (204)

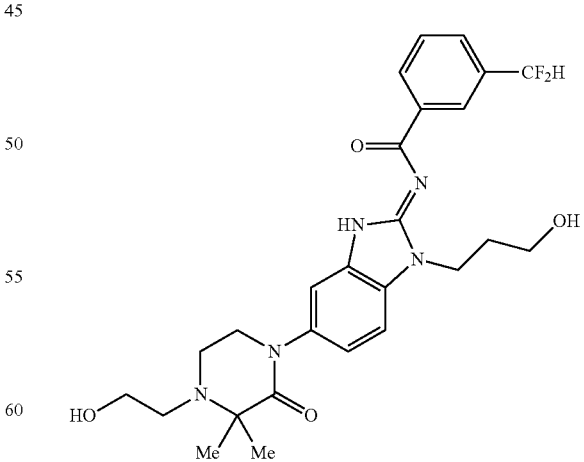

Prepared in an analogous fashion to Example 188, but using ((trimethylsilyl)oxy)acetaldehyde (5 eq.) in place of (1-ethoxy-cyclopropoxy)-trimethylsilane in step 3. ESI$^+$: M+1: 516. $^1$H NMR (300 MHz, CDCl$_3$) δ 12.68 (s, 1H), 8.43-8.35 (m, 2H), 7.68 (d, J=7.6 Hz, 1H), 7.57 (t, J=7.8 Hz, 1H), 7.36-7.17 (m, 3H), 6.74 (t, J=56.4 Hz, 1H), 4.73-4.66 (m, 1H), 4.48 (t, J=5.6 Hz, 2H), 3.65-3.46 (m, 6H), 2.94 (t, J=5.2 Hz, 2H), 2.74-2.64 (m, 3H), 2.08-1.99 (m, 2H), 1.41 (s, 6H).

Example 196: (E)-3-(difluoromethyl)-N-(5-(4,4-dimethyl-2-oxooxazolidin-3-yl)-1-(3-hydroxypropyl)-1H-benzo[d]imidazol-2(3H)-ylidene)benzamide (205)

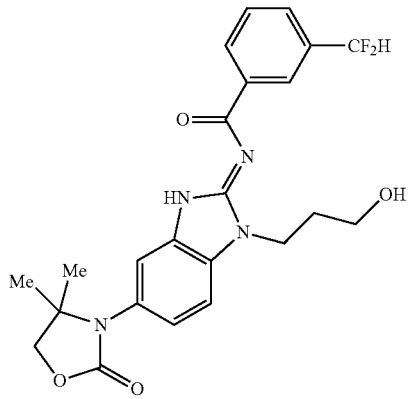 [SMILES: CC1(C)COC(=O)N1c1ccc2c(c1)[nH]/c(=N\C(=O)c1cccc(C(F)F)c1)n2CCCO]

Prepared in an analogous fashion to Example 177, but using Intermediate 59-CF$_2$H (1 eq.) in place of Intermediate 59-CF$_3$, and 4,4-dimethyloxazolidin-2-one (1 eq.) in place of thiomorpholin-3-one in step 1. ESI$^+$: M+1: 459. $^1$H NMR (300 MHz, CDCl$_3$) δ 12.59 (s, 1H), 8.41-8.35 (m, 2H), 7.68 (d, J=7.7 Hz, 1H), 7.57 (t, J=7.4 Hz, 1H), 7.37 (d, J=8.5 Hz, 1H), 7.26-7.13 (m, 2H), 6.74 (t, J=56.2 Hz, 1H), 4.64-4.57 (m, 1H), 4.53-4.46 (m, 2H), 4.24 (s, 2H), 3.53-3.46 (m, 2H), 2.08-2.02 (m, 2H), 1.36 (s, 6H).

Example 197: (E)-N-(5-(7-cyclopropyl-5-oxo-4,7-diazaspiro[2.5]octan-4-yl)-1-(3-hydroxypropyl)-1H-benzo[d]imidazol-2(3H)-ylidene)-3-(trifluoromethyl)benzamide (206)

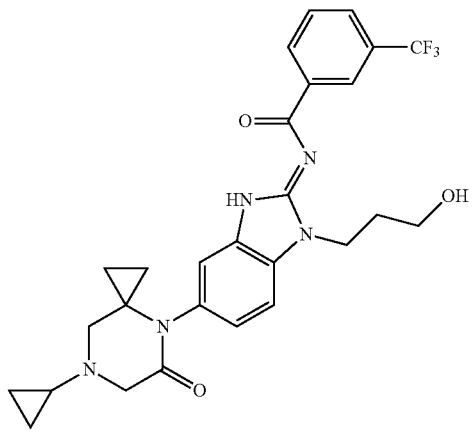 [SMILES: O=C(/N=c1\[nH]c2cc(N3C(=O)CN(C4CC4)CC34CC4)ccc2n1CCCO)c1cccc(C(F)(F)F)c1]

Prepared in an analogous fashion to Example 188, but using tert-butyl 5-oxo-4,7-diazaspiro[2.5]octane-7-carboxylate (1 eq.) in place of tert-butyl 2,2-dimethyl-3-oxopiperazine-1-carboxylate, and Intermediate 59-CF$_3$ (1 eq.) in place of Intermediate 59-CF$_2$H in step 1. ESI$^+$: M+1: 528. $^1$H NMR (300 MHz, CDCl$_3$) δ 12.49 (s, 1H), 8.50 (s, 1H), 8.42 (d, J=7.9 Hz, 1H), 7.76 (d, J=7.9 Hz, 1H), 7.59 (t, J=7.6 Hz, 1H), 7.34 (d, J=8.5 Hz, 1H), 7.13 (s, 1H), 7.06 (d, J=8.1 Hz, 1H), 4.53-4.44 (m, 3H), 3.66 (s, 2H), 3.53-3.46 (m, 2H), 2.97 (s, 2H), 2.08-1.98 (m, 2H), 1.93-1.86 (m, 1H), 0.74-0.41 (m, 8H).

Example 198: (E)-N-(5-(7-cyclopropyl-5-oxo-4,7-diazaspiro[2.5]octan-4-yl)-1-(3-hydroxypropyl)-1H-benzo[d]imidazol-2(3H)-ylidene)-3-(difluoromethyl)benzamide (207)

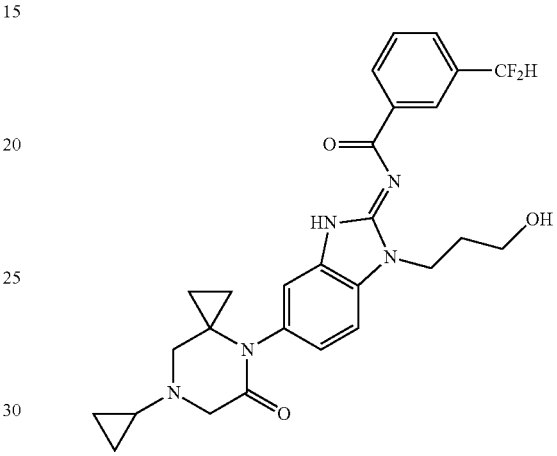

Prepared in an analogous fashion to Example 188, but using tert-butyl 5-oxo-4,7-diazaspiro[2.5]octane-7-carboxylate (1 eq.) in place of tert-butyl 2,2-dimethyl-3-oxopiperazine-1-carboxylate in step 1. ESI$^+$: M+1: 510. $^1$H NMR (300 MHz, CDCl$_3$) δ 12.55 (s, 1H), 8.40-8.31 (m, 2H), 7.68 (d, J=7.7 Hz, 1H), 7.56 (t, J=7.8 Hz, 1H), 7.36-7.23 (m, 1H), 7.10 (s, 1H), 7.04 (d, J=8.4 Hz, 1H), 6.74 (t, J=56.4 Hz, 1H), 4.73-4.66 (m, 1H), 4.46 (t, J=5.6 Hz, 2H), 3.65 (s, 2H), 3.49 (t, J=5.3 Hz, 2H), 2.95 (s, 2H), 2.08-1.99 (m, 2H), 1.96-1.84 (m, 1H), 0.67-0.50 (m, 8H).

Example 199: (E)-N-(5-(5,5-dimethyl-2-oxooxazolidin-3-yl)-1-(3-hydroxypropyl)-1H-benzo[d]imidazol-2(3H)-ylidene)-3-(trifluoromethyl)benzamide (208)

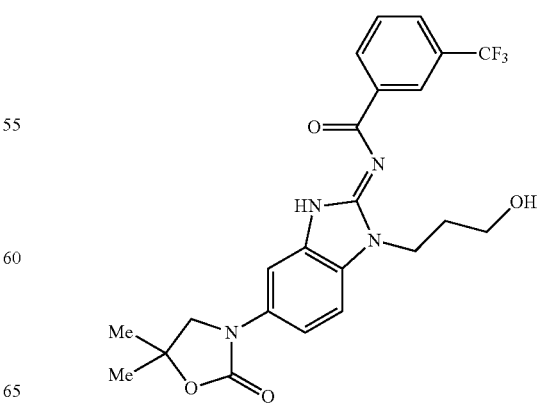

Prepared in an analogous fashion to Example 177, but using 5,5-dimethyloxazolidin-2-one (1 eq.) in place of thiomorpholin-3-one in step 1. ESI⁺: M+1: 477. ¹H NMR (300 MHz, CDCl₃) δ 12.72 (s, 1H), 8.56 (s, 1H), 8.52-8.41 (m, 1H), 7.76 (d, J=7.8 Hz, 1H), 7.68-7.53 (m, 2H), 7.42 (s, 1H), 7.34-7.27 (m, 1H), 4.61-4.55 (m, 1H), 4.48 (t, J=5.8 Hz, 2H), 3.54 (s, 2H), 3.50-3.44 (m, 2H), 2.09-1.97 (m, 2H), 1.51 (s, 6H).

Example 200: (E)-3-(difluoromethyl)-N-(5-(5,5-dimethyl-2-oxooxazolidin-3-yl)-1-(3-hydroxypropyl)-1H-benzo[d]imidazol-2(3H)-ylidene)benzamide (209)

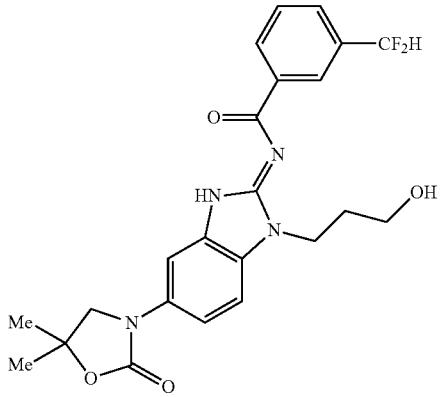 [SMILES: CC1(C)CN(c2ccc3c(c2)[nH]/c(=N\C(=O)c2cccc(C(F)F)c2)n3CCCO)C(=O)O1]

Prepared in an analogous fashion to Example 177, but using Intermediate 59-CF₂H (1 eq.) in place of Intermediate 59-CF₃, and 5,5-dimethyloxazolidin-2-one (1 eq.) in place of thiomorpholin-3-one in step 1. ESI⁺: M+1: 459. ¹H NMR (300 MHz, CDCl₃) δ 12.84 (s, 1H), 8.48-8.39 (m, 2H), 7.74-7.65 (m, 2H), 7.58 (t, J=7.7 Hz, 1H), 7.32-7.24 (m, 2H), 6.74 (t, J=56.4 Hz, 1H), 4.78-4.71 (m, 1H), 4.48 (t, J=5.7 Hz, 2H), 3.49-3.38 (m, 4H), 2.09-1.97 (m, 2H), 1.48 (s, 6H).

Example 201: (E)-N-(1-(3-hydroxypropyl)-5-(6-oxopyridazin-1(6H)-yl)-1H-benzo[d]imidazol-2(3H)-ylidene)-3-(trifluoromethyl)benzamide (210)

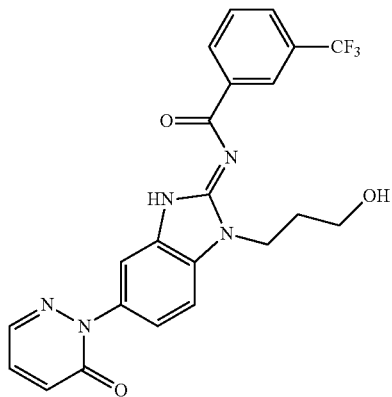 [SMILES: O=C(/N=c1\[nH]c2cc(-n3ncccc3=O)ccc2n1CCCO)c1cccc(C(F)(F)F)c1]

Prepared in an analogous fashion to Example 177, but using pyridazin-3(2H)-one (1.1 eq.) in place of thiomorpholin-3-one in step 1. ESI⁺: M+1: 458. ¹H NMR (300 MHz, DMSO-d₃) δ 12.96 (s, 1H), 8.54 (d, J=9.9 Hz, 1H), 8.09 (dd, J=3.8, 1.6 Hz, 1H), 7.91 (d, J=7.9 Hz, 1H), 7.81-7.60 (m, 3H), 7.53 (dd, J=9.5, 3.8 Hz, 1H), 7.44 (dd, J=8.6, 2.0 Hz, 1H), 7.11 (dd, J=9.5, 1.6 Hz, 1H), 4.70 (t, J=5.1 Hz, 1H), 4.38 (t, J=6.8 Hz, 2H), 3.50 (q, J=5.8 Hz, 2H), 2.05-1.92 (m, 2H).

Example 202: (E)-N-(1-(3-hydroxypropyl)-6-(trideuteromethoxy)-5-(3-oxomorpholino)-1H-benzo[d]imidazol-2(3H)-ylidene)-3-(trifluoromethyl)benzamide (211)

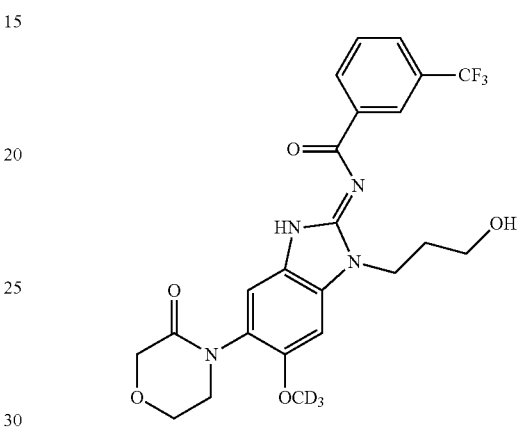

Prepared in an analogous fashion to Example 1, but using Intermediate 60 (1 eq.) in place of Intermediate 1-OTIPS. ESI⁺: M+1: 496. ¹H NMR (300 MHz, DMSO-d₆) δ 12.80 (s, 1H), 8.57-8.48 (m, 2H), 7.90 (d, J=7.8 Hz, 1H), 7.73 (t, J=7.8 Hz, 1H), 7.35 (d, J=3.9 Hz, 2H), 4.71 (t, J=5.0 Hz, 1H), 4.37 (t, J=6.7 Hz, 2H), 4.21 (s, 2H), 3.98 (t, J=5.0 Hz, 2H), 3.65-3.42 (m, 4H), 2.04-1.93 (m, 2H).

Example 203: (E)-3-(difluoromethyl)-N-(1-(3-hydroxypropyl)-6-(trideuteromethoxy)-5-(3-oxomorpholino)-1H-benzo[d]imidazol-2(3H)-ylidene)benzamide (212)

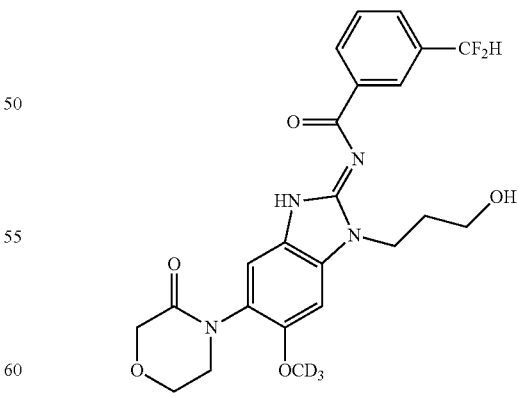

Prepared in an analogous fashion to Example 1, but using Intermediate 60 (1 eq.) in place of Intermediate 1-OTIPS, and 3-difluoromethyl-benzoic acid (1 eq.) in place of 3-trifluoromethyl-benzoic acid in step 1. ESI⁺: M+1: 478. ¹H NMR (300 MHz, DMSO-d₆) δ 12.77 (s, 1H), 8.40 (s, 2H), 7.81-7.68 (m, 1H), 7.68-7.56 (m, 1H), 7.42-6.92 (m, 3H), 4.83-4.63 (m, 1H), 4.40-4.33 (m, 2H), 4.21 (s, 2H), 4.01-3.94 (s, 2H), 3.60-3.45 (m, 4H), 2.02-1.96 (m, 2H).

Example 204: (E)-N-(1-(3-hydroxypropyl)-6-(trideuteromethoxy)-5-(2-oxo-1,3-oxazinan-3-yl)-1H-benzo[d]imidazol-2(3H)-ylidene)-3-(trifluoromethyl)benzamide (213)

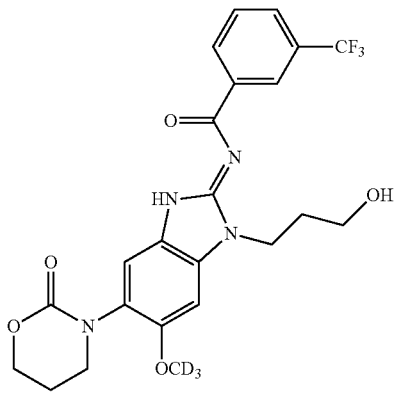

Prepared in an analogous fashion to Example 1, but using Intermediate 61 (1 eq.) in place of Intermediate 1-OTIPS. ESI+: M+1: 496. $^1$H NMR (300 MHz, DMSO-$d_6$) δ 12.78 (s, 1H), 8.56-8.47 (m, 2H), 7.89 (d, J=7.7 Hz, 1H), 7.73 (t, J=7.8 Hz, 1H), 7.37 (s, 1H), 7.33 (s, 1H), 4.71 (t, J=5.0 Hz, 1H), 4.36 (t, J=6.7 Hz, 2H), 3.56-3.43 (m, 4H), 2.21-1.88 (m, 4H).

Example 205: (E)-3-(difluoromethyl)-N-(1-(3-hydroxypropyl)-6-(trideuteromethoxy)-5-(2-oxo-1,3-oxazinan-3-yl)-1H-benzo[d]imidazol-2(3H)-ylidene)benzamide (214)

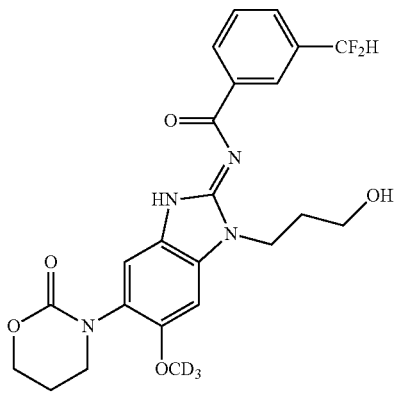

Prepared in an analogous fashion to Example 1, but using Intermediate 61 (1 eq.) in place of Intermediate 1-OTIPS, and 3-difluoromethyl-benzoic acid (1 eq.) in place of 3-trifluoromethyl-benzoic acid in step 1. ESI+: M+1: 478. $^1$H NMR (300 MHz, DMSO-$d_6$) δ 12.76 (s, 1H), 8.43-8.36 (s, 2H), 7.72 (d, J=7.7 Hz, 1H), 7.63 (t, J=7.8 Hz, 1H), 7.42-6.93 (m, 3H), 4.72 (t, J=5.0 Hz, 1H), 4.45-4.24 (m, 4H), 3.54-3.43 (m, 4H), 2.20-1.88 (m, 4H).

Example 206: (E)-N-(1-(3-hydroxypropyl)-6-methoxy-5-(2-oxo-1,3-oxazinan-3-yl)-1H-benzo[d]imidazol-2(3H)-ylidene)-3-(trifluoromethyl)benzamide (215)

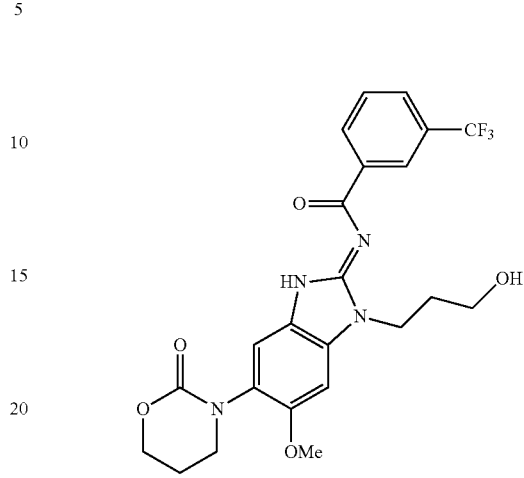

Prepared in an analogous fashion to Example 1, but using Intermediate 62 (1 eq.) in place of Intermediate 1-OTIPS. ESI+: M+1: 493. $^1$H NMR (300 MHz, CDCl$_3$) δ 12.42 (s, 1H), 8.50 (s, 1H), 8.41 (d, J=7.8 Hz, 1H), 7.74 (d, J=7.8 Hz, 1H), 7.58 (t, J=7.8 Hz, 1H), 7.27 (s, 1H), 6.86 (s, 1H), 4.57 (s, 1H), 4.51-4.41 (m, 4H), 3.92 (s, 3H), 3.58 (s, 2H), 3.47 (d, J=5.5 Hz, 2H), 2.21 (p, J=5.8 Hz, 2H), 2.08-1.97 (m, 2H).

Example 207: (E)-3-(difluoromethyl)-N-(1-(3-hydroxypropyl)-6-methoxy-5-(2-oxo-1,3-oxazinan-3-yl)-1H-benzo[d]imidazol-2(3H)-ylidene)benzamide (216)

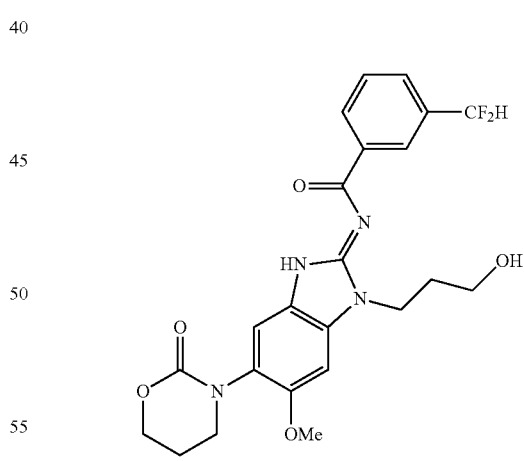

Prepared in an analogous fashion to Example 1, but using Intermediate 62 (1 eq.) in place of Intermediate 1-OTIPS, and 3-difluoromethyl-benzoic acid (1 eq.) in place of 3-trifluoromethyl-benzoic acid in step 1. ESI+: M+1: 475. $^1$H NMR (300 MHz, CDCl$_3$) δ 12.46 (s, 1H), 8.36-8.33 (m, 2H), 7.66 (d, J=7.7 Hz, 1H), 7.56 (t, J=7.9 Hz, 1H), 7.27 (s, 1H), 6.98-6.50 (m, 2H), 4.75 (s, 1H), 4.50-4.40 (m, 4H), 3.92 (s, 3H), 3.71-3.38 (m, 4H), 2.20 (p, J=5.9 Hz, 2H), 2.08-1.96 (m, 2H).

Example 208: (E)-N-(6-cyclopropyl-1-(3-hydroxy-propyl)-5-(3-oxomorpholino)-1H-benzo[d]imidazol-2(3H)-ylidene)-3-(trifluoromethyl)benzamide (217)

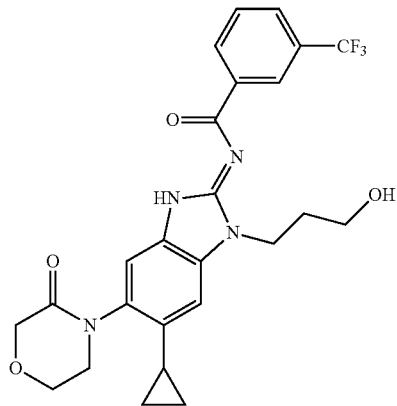

Prepared in an analogous fashion to Example 1, but using Intermediate 63 (1 eq.) in place of Intermediate 1-OTIPS. ESI$^+$: M+1: 503. $^1$H NMR (300 MHz, DMSO-d$_6$) δ 12.83 (s, 1H), 8.53-8.51 (m, 2H), 7.90 (d, J=7.7 Hz, 1H), 7.73 (t, J=7.6 Hz, 1H), 7.33 (s, 1H), 7.22 (s, 1H), 4.67 (t, J=5.0 Hz, 1H), 4.34 (t, J=7.0 Hz, 2H), 4.26 (s, 2H), 4.08-3.98 (m, 2H), 3.73-3.54 (m, 2H), 3.47 (q, J=5.9 Hz, 2H), 2.02-1.85 (m, 3H), 0.93-0.88 (m, 3H), 0.62-0.59 (m, 1H).

Example 209: (E)-N-(6-cyclopropyl-1-(3-hydroxy-propyl)-5-(3-oxomorpholino)-1H-benzo[d]imidazol-2(3H)-ylidene)-3-(difluoromethyl)benzamide (218)

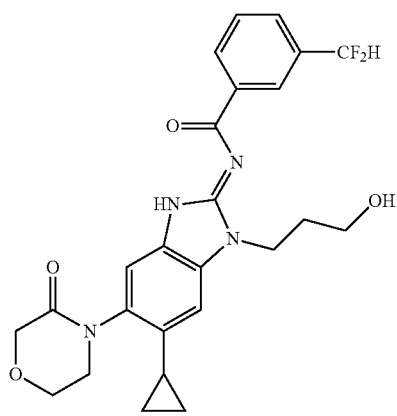

Prepared in an analogous fashion to Example 1, but using Intermediate 63 (1 eq.) in place of Intermediate 1-OTIPS, and 3-difluoromethyl-benzoic acid (1 eq.) in place of 3-trifluoromethyl-benzoic acid in step 1. ESI$^+$: M+1: 485. $^1$H NMR (300 MHz, DMSO-d$_6$) δ 12.80 (s, 1H), 8.45-8.36 (m, 2H), 7.77-7.57 (m, 2H), 7.38-6.92 (m, 3H), 4.68 (t, J=5.1 Hz, 1H), 4.33 (t, J=7.0 Hz, 2H), 4.26 (s, 2H), 4.12-3.97 (m, 2H), 3.75-3.54 (m, 2H), 3.47 (q, J=5.9 Hz, 2H), 2.02-1.85 (m, 3H), 0.93-0.88 (m, 3H), 0.62-0.59 (m, 1H).

Example 210: (E)-N-(7-fluoro-1-(3-hydroxypropyl)-5-(3-oxomorpholino)-1H-benzo[d]imidazol-2(3H)-ylidene)-3-(trifluoromethyl)benzamide (219)

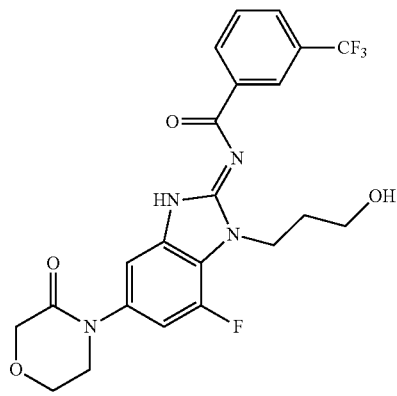 [SMILES: O=C(/N=c1\[nH]c2cc(N3CCOCC3=O)cc(F)c2n1CCCO)c1cccc(C(F)(F)F)c1]

Prepared in an analogous fashion to Example 188, but using 3-oxomorpholine (1 eq.) in place of tert-butyl 2,2-dimethyl-3-oxopiperazine-1-carboxylate, and Intermediate 64-CF$_3$ (1 eq.) in place of Intermediate 58-CF$_2$H in step 1. Furthermore, both step 3 and step 4 were omitted. ESI$^+$: M+1: 481. $^1$H NMR (300 MHz, DMSO-d$_6$) δ 13.06 (s, 1H), 8.58-8.48 (m, 2H), 7.92 (d, J=7.7 Hz, 1H), 7.75 (t, J=7.6 Hz, 1H), 7.41 (d, J=1.8 Hz, 1H), 7.31 (dd, J=12.8, 1.8 Hz, 1H), 4.64 (t, J=5.1 Hz, 1H), 4.42 (t, J=7.1 Hz, 2H), 4.24 (s, 2H), 4.05-3.95 (m, 2H), 3.81-3.71 (m, 2H), 3.53 (q, J=5.9 Hz, 2H), 2.03-1.92 (m, 2H).

Example 211: (E)-N-(6-(difluoromethoxy)-1-(3-hydroxypropyl)-5-(3-oxomorpholino)-1H-benzo[d]imidazol-2(3H)-ylidene)-3-(trifluoromethyl)benzamide (220)

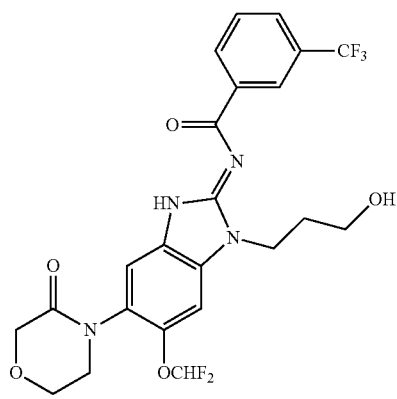 [SMILES: O=C(/N=c1\[nH]c2cc(N3CCOCC3=O)c(OC(F)F)cc2n1CCCO)c1cccc(C(F)(F)F)c1]

Prepared in an analogous fashion to Example 1, but using Intermediate 65 (1 eq.) in place of Intermediate 1-OTIPS. ESI$^+$: M+1: 529. $^1$H NMR (300 MHz, CD$_3$OD) δ 8.55 (d, J=8.0 Hz, 2H), 7.82 (d, J=7.8 Hz, 1H), 7.67 (t, J=7.6 Hz, 1H), 7.54 (s, 2H), 6.82 (t, J=73.7 Hz, 1H), 4.45 (t, J=6.8 Hz, 2H), 4.34 (s, 2H), 4.09-3.98 (m, 2H), 3.76 (s, 2H), 3.68-3.56 (m, 2H), 2.20-2.04 (m, 2H).

Example 212: (E)-3-(difluoromethyl)-N-(1-(3-hydroxypropyl)-5-(3-oxo-1,4-diazabicyclo[3.2.2]nonan-4-yl)-1H-benzo[d]imidazol-2(3H)-ylidene)benzamide (221)

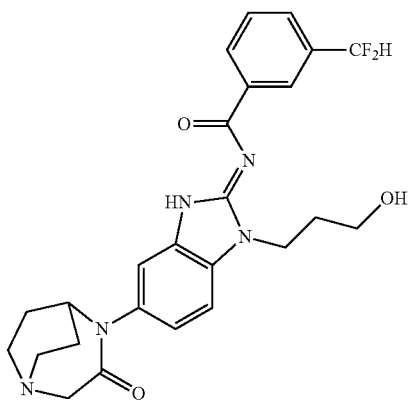 [SMILES: O=C(/N=c1\[nH]c2cc(N3C(=O)CN4CCC3CC4)ccc2n1CCCO)c1cccc(C(F)F)c1]

Prepared in an analogous fashion to Example 177, but using Intermediate 59-CF$_2$H (1 eq.) in place of Intermediate 59-CF$_3$, and 1,4-diazabicyclo[3.2.2]nonan-3-one (1 eq.) in place of thiomorpholin-3-one in step 1. ESI$^+$: M+1: 484. $^1$H NMR (300 MHz, CDCl$_3$) δ 12.56 (s, 1H), 8.41-8.32 (m, 2H), 7.68 (d, J=7.6 Hz, 1H), 7.57 (t, J=7.9 Hz, 1H), 7.33 (d, J=8.4 Hz, 1H), 7.23 (d, J=1.8 Hz, 1H), 7.15 (dd, J=8.5, 1.9 Hz, 1H), 6.74 (t, J=56.4 Hz, 1H), 4.68 (s, 1H), 4.48 (t, J=6.0 Hz, 2H), 3.92 (s, 2H), 3.84-3.78 (m, 1H), 3.51-3.44 (m, 2H), 3.19 (d, J=9.2 Hz, 4H), 2.42-2.31 (m, 2H), 2.11-1.94 (m, 4H).

Example 213: (E)-3-(difluoromethyl)-N-(1-(3-hydroxypropyl)-5-(2-oxo-3,6-diazabicyclo[3.1.1]heptan-3-yl)-1H-benzo[d]imidazol-2(3H)-ylidene)benzamide (222)

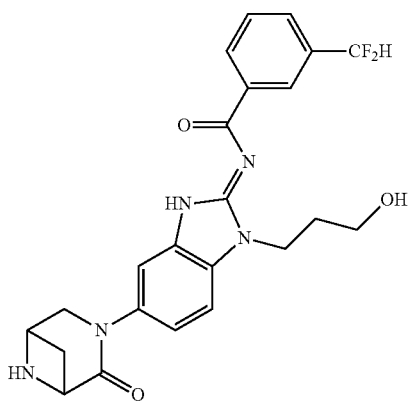 [SMILES: O=C(/N=c1\[nH]c2cc(N3CC4CC(N4)C3=O)ccc2n1CCCO)c1cccc(C(F)F)c1]

Prepared in an analogous fashion to Example 177, but using Intermediate 59-CF$_2$H (1 eq.) in place of Intermediate 59-CF$_3$, and tert-butyl 2-oxo-3,6-diazabicyclo[3.1.1]heptane-6-carboxylate (1 eq.) in place of thiomorpholin-3-one in step 1, and TFA (50 eq.) in place of tetrabutylammonium fluoride in step 2. ESI$^+$: M+1: 456. $^1$H NMR (300 MHz, DMSO-d$_6$) δ 12.75 (s, 1H), 8.45-8.36 (m, 2H), 7.88 (d, J=2.0 Hz, 1H), 7.72 (d, J=7.8 Hz, 1H), 7.63 (d, J=7.8 Hz, 1H), 7.51 (dd, J=8.7, 1.9 Hz, 1H), 7.39 (dd, J=8.8, 2.1 Hz, 1H), 7.15 (t, J=55.8 Hz, 1H), 4.75 (s, 1H), 4.68 (t, J=5.1 Hz, 1H), 4.32 (t, J=6.7 Hz, 2H), 3.61 (s, 1H), 3.51-3.40 (m, 2H), 3.03 (d, J=9.5 Hz, 1H), 2.84 (d, J=9.6 Hz, 1H), 2.01-1.88 (m, 3H), 1.69 (d, J=9.7 Hz, 1H).

Example 214: (E)-N-(5-(8-cyclopropyl-2-oxo-3,8-diazabicyclo[3.2.1]octan-3-yl)-1-(3-hydroxypropyl)-1H-benzo[d]imidazol-2(3H)-ylidene)-3-(difluoromethyl)benzamide (223)

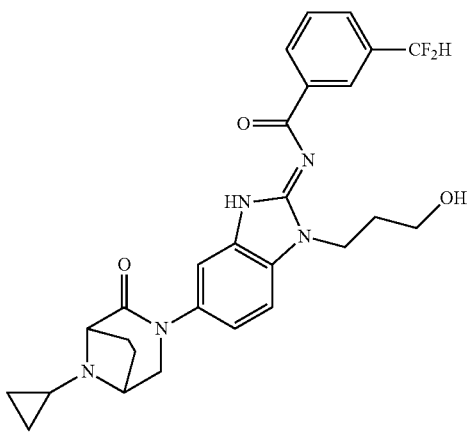

Prepared in an analogous fashion to Example 188, but using tert-butyl 2-oxo-3,8-diazabicyclo[3.2.1]octane-8-carboxylate (1 eq.) in place of tert-butyl 2,2-dimethyl-3-oxopiperazine-1-carboxylate in step 1. ESI$^+$: M+1: 510. $^1$H NMR (300 MHz, DMSO-d$_6$) δ 12.79 (s, 1H), 8.46-8.36 (m, 2H), 7.73 (d, J=7.7 Hz, 1H), 7.63 (t, J=7.8 Hz, 1H), 7.54 (d, J=8.5 Hz, 1H), 7.41 (d, J=1.9 Hz, 1H), 7.37-6.95 (m, 2H), 4.70-4.67 (m, 1H), 4.34 (t, J=6.8 Hz, 2H), 3.92 (dd, J=11.3, 4.0 Hz, 1H), 3.60-3.38 (m, 4H), 3.35-3.28 (m, 1H), 2.19-2.07 (m, 3H), 2.02-1.91 (m, 4H), 0.58-0.49 (m, 2H), 0.46 (s, 2H).

Example 215: (E)-N-(5-(8-cyclopropyl-2-oxo-3,8-diazabicyclo[3.2.1]octan-3-yl)-1-(3-hydroxypropyl)-1H-benzo[d]imidazol-2(3H)-ylidene)-3-(trifluoromethyl)benzamide (224)

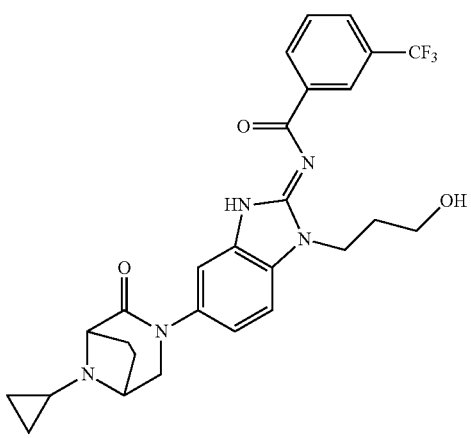 [SMILES: O=C(/N=c1\[nH]c2cc(N3CC4CCC(C3=O)N4C3CC3)ccc2n1CCCO)c1cccc(C(F)(F)F)c1]

Prepared in an analogous fashion to Example 188, but using tert-butyl 2-oxo-3,8-diazabicyclo[3.2.1]octane-8-carboxylate (1 eq.) in place of tert-butyl 2,2-dimethyl-3-oxopiperazine-1-carboxylate, and Intermediate 59-CF$_3$ (1 eq.) in place of Intermediate 59-CF$_2$H in step 1. ESI$^+$: M+1: 528. $^1$H NMR (300 MHz, DMSO-d$_6$) δ 12.82 (s, 1H), 8.65-8.48 (m, 2H), 7.90 (d, J=7.9 Hz, 1H), 7.74 (t, J=7.8 Hz, 1H), 7.55 (d, J=8.5 Hz, 1H), 7.42 (d, J=1.9 Hz, 1H), 7.21 (dd, J=8.6, 2.0 Hz, 1H), 4.68 (t, J=5.0 Hz, 1H), 4.34 (t, J=6.8 Hz, 2H), 3.92 (dd, J=11.2, 3.9 Hz, 1H), 3.60-3.39 (m, 4H), 3.30 (d, J=4.5 Hz, 1H), 2.19-2.07 (m, 3H), 2.02-1.85 (m, 4H), 0.58-0.49 (m, 2H), 0.46 (s, 2H).

Example 216: (E)-N-(1-(3-hydroxypropyl)-5-(2-oxo-3,6-diazabicyclo[3.1.1]heptan-3-yl)-1H-benzo[d]imidazol-2(3H)-ylidene)-3-(trifluoromethyl)benzamide (225)

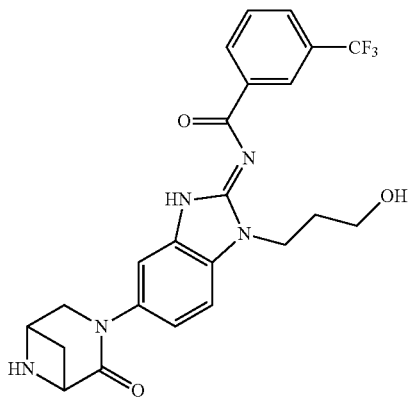 [SMILES: O=C(/N=c1\[nH]c2cc(N3CC4CC(N4)C3=O)ccc2n1CCCO)c1cccc(C(F)(F)F)c1]

Prepared in an analogous fashion to Example 177, but using tert-butyl 2-oxo-3,6-diazabicyclo[3.1.1]heptane-6-carboxylate (1 eq.) in place of thiomorpholin-3-one in step 1, and TFA (50 eq.) in place of tetrabutylammonium fluoride in step 2. ESI$^+$: M+1: 474. $^1$H NMR (300 MHz, DMSO-d$_6$) δ 12.78 (s, 1H), 8.56-8.47 (m, 2H), 7.95-7.85 (m, 2H), 7.73 (t, J=7.7 Hz, 1H), 7.53 (d, J=8.7 Hz, 1H), 7.39 (dd, J=8.8, 2.1 Hz, 1H), 4.75 (s, 1H), 4.68 (t, J=5.1 Hz, 1H), 4.32 (t, J=6.8 Hz, 2H), 3.60 (s, 1H), 3.53-3.36 (m, 2H), 3.03 (d, J=9.4 Hz, 1H), 2.83 (d, J=9.5 Hz, 1H), 2.01-1.88 (m, 3H), 1.68 (d, J=9.7 Hz, 1H).

Example 217: (E)-N-(1-(3-hydroxypropyl)-5-(2-oxo-8-oxa-3-azabicyclo[3.2.1]octan-3-yl)-1H-benzo[d]imidazol-2(3H)-ylidene)-3-(trifluoromethyl)benzamide (226)

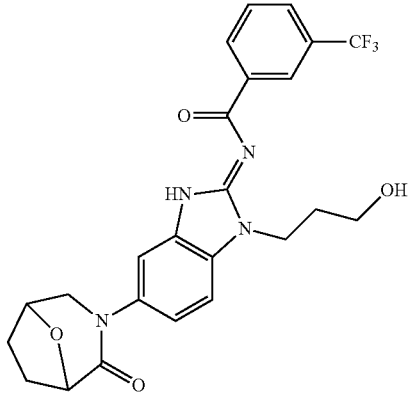 [SMILES: O=C(/N=c1\[nH]c2cc(N3CC4CCC(O4)C3=O)ccc2n1CCCO)c1cccc(C(F)(F)F)c1]

Prepared in an analogous fashion to Example 177, but using 8-oxa-3-azabicyclo[3.2.1]octan-3-one (1 eq.) in place of thiomorpholin-3-one in step 1. ESI$^+$: M+1: 489. $^1$H NMR (300 MHz, DMSO-d$_6$) δ 12.85 (s, 1H), 8.58-8.48 (m, 2H), 7.90 (d, J=7.8 Hz, 1H), 7.74 (t, J=7.8 Hz, 1H), 7.57 (d, J=8.5 Hz, 1H), 7.45 (d, J=2.0 Hz, 1H), 7.24 (dd, J=8.6, 2.0 Hz, 1H), 4.81-4.72 (m, 1H), 4.68 (t, J=5.1 Hz, 2H), 4.51 (d, J=5.3 Hz, 1H), 4.35 (d, J=6.9 Hz, 4H), 3.93 (dd, J=11.4, 4.2 Hz, 1H), 3.54-3.34 (m, 3H), 2.22-2.02 (m, 4H), 2.02-1.89 (m, 2H).

Example 218: (E)-3-(difluoromethyl)-N-(5-(4,4-dimethyl-2-oxo-1,3-oxazinan-3-yl)-1-(3-hydroxypropyl)-1H-benzo[d]imidazol-2(3H)-ylidene)benzamide (227) and Example 219: (E)-3-(difluoromethyl)-N-(6-(6,6-dimethyl-2-oxo-1,3-oxazinan-3-yl)-1-(3-hydroxypropyl)-1H-benzo[d]imidazol-2(3H)-ylidene)benzamide (228)

Example 218

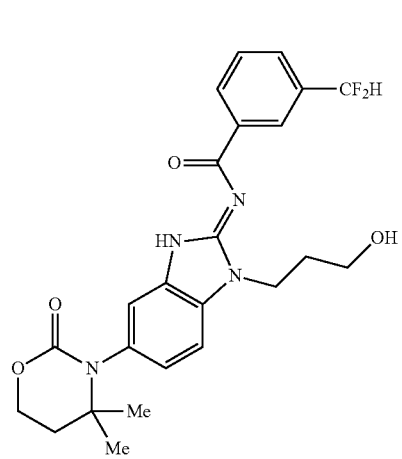

Example 219

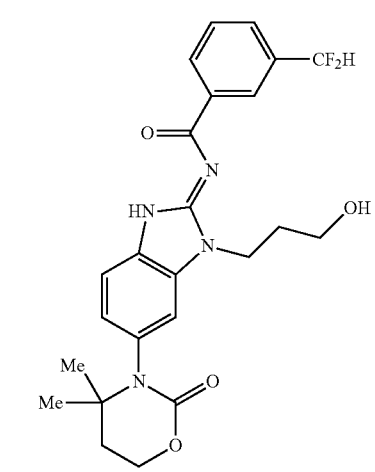

In a glass RBF equipped with a Teflon-coated magnetic stirrer was dissolved 3-difluoromethyl-benzoic acid (1.1 eq.), hydroxybenzotriazole (1.5 eq.), EDCI (1.5 eq.) and Intermediate 66 (1 eq.) in DMF (0.32 M). To the resulting solution was then added ethyl-diisopropyl-amine (2 eq.) and the resulting mixture was stirred at RT for 18 h. The crude reaction mixture was then diluted with EtOAc and washed sequentially with sat. aq. $Na_2CO_3$ and brine. The organic extract was then dried over $MgSO_4$, filtered and the filtrate concentrated in vacuo. Purification of the crude product thus obtained by way of column chromatography ($SiO_2$, gradient elution, 4:1 (v/v) Hex:EtOAc→EtOAc→10:1 (v/v) EtOAc:MeOH) furnished the desired coupled product. This intermediate amide, potassium carbonate (2.05 eq.) and 3-iodo-propan-1-ol (3 eq.) were then taken up in a 5:1 (v/v) DMF:acetone solution (0.1 M). After 3 h of stirring at RT, the reaction mixture was diluted with EtOAc and washed sequentially with water and brine. The organic extract was dried over $MgSO_4$, filtered and the filtrate concentrated in vacuo. Purification by way of high pressure liquid chromatography ($C_{18}$, gradient elution, 3:7 (v/v) $H_2O$:MeCN+0.1% TFA→2:3 (v/v) $H_2O$:MeCN+0.1% TFA) furnished both Example 218 (11% yield) and Example 219 (15% yield) as white solids. Example 218: ESI+: M+1: 473. $^1$H NMR (300 MHz, DMSO-$d_6$) δ 12.85 (s, 1H), 8.44-8.38 (m, 2H), 7.78-7.69 (m, 1H), 7.64 (t, J=7.7 Hz, 1H), 7.53 (d, J=8.3 Hz, 1H), 7.41 (s, 1H), 7.37-6.91 (m, 2H), 4.72-4.66 (m, 1H), 4.38-4.32 (m, 4H), 3.53-3.46 (m, 2H), 2.13-2.06 (m, 2H), 1.97 (d, J=14.2 Hz, 2H), 1.23 (s, 6H). Example 219: ESI+: M+1: 473. $^1$H NMR (300 MHz, DMSO-$d_6$) δ 12.83 (s, 1H), 8.44-8.38 (m, 2H), 7.75-7.69 (m, 1H), 7.67-7.60 (m, 1H), 7.54 (d, J=8.3 Hz, 1H), 7.41-6.92 (m, 3H), 4.74-4.67 (m, 1H), 4.37-4.32 (m, 4H), 3.54-3.47 (m, 2H), 2.13-2.06 (m, 2H), 2.02-1.95 (m, 2H), 1.21 (s, 6H).

Example 220: (E)-3-(trifluoromethyl)-N-(5-(4,4-dimethyl-2-oxo-1,3-oxazinan-3-yl)-1-(3-hydroxypropyl)-1H-benzo[d]imidazol-2(3H)-ylidene)benzamide (229) and Example 221: (E)-3-(trifluoromethyl)-N-(6-(6,6-dimethyl-2-oxo-1,3-oxazinan-3-yl)-1-(3-hydroxypropyl)-1H-benzo[d]imidazol-2(3H)-ylidene)benzamide (230)

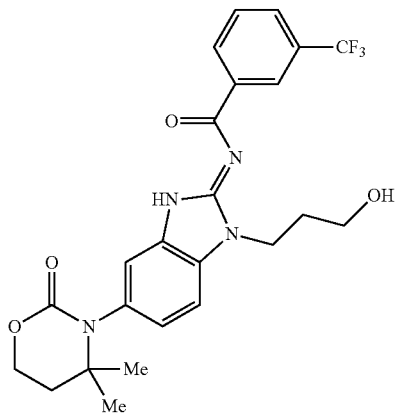

Example 220

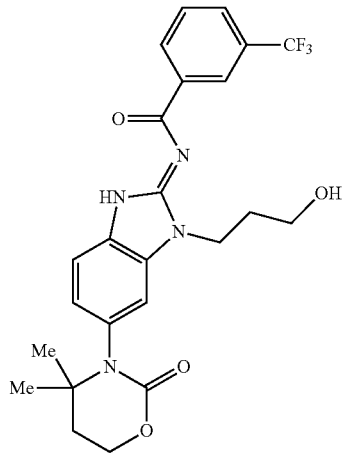

Example 221

Prepared in an analogous fashion to Example 218 and Example 219 but using 3-trifluoromethyl-benzoic acid (1.1 eq.) in place of 3-difluoromethyl-benzoic acid. Example 220: ESI+: M+1: 491. $^1$H NMR (300 MHz, Acetone-$d_6$) δ 12.60 (s, 1H), 8.64-8.55 (m, 2H), 7.86 (d, J=7.8 Hz, 1H), 7.77-7.62 (m, 2H), 7.48 (d, J=1.9 Hz, 1H), 7.15 (dd, J=8.4, 1.9 Hz, 1H), 4.51 (t, J=6.6 Hz, 2H), 4.47-4.37 (m, 2H), 4.10 (t, J=5.7 Hz, 1H), 3.62 (q, J=5.8 Hz, 2H), 2.23-2.05 (m, 4H), 1.35 (s, 6H). Example 221: ESI+: M+1: 491. $^1$H NMR (300 MHz, DMSO-$d_6$) δ 12.86 (s, 1H), 8.58-8.48 (m, 2H), 7.91 (d, J=7.8 Hz, 1H), 7.74 (t, J=7.7 Hz, 1H), 7.55 (d, J=8.5 Hz, 1H), 7.36 (d, J=1.9 Hz, 1H), 7.10 (dd, J=8.5, 2.0 Hz, 1H), 4.70 (s, 1H), 4.43-4.30 (m, 4H), 3.55-3.46 (m, 2H), 2.10 (t, J=5.4 Hz, 2H), 1.99 (q, J=6.4 Hz, 2H), 1.21 (s, 6H).

Example 222: (E)-3-(difluoromethyl)-N-(5-(2,2-dimethyl-3-oxomorpholino)-1-(3-hydroxypropyl)-1H-benzo[d]imidazol-2(3H)-ylidene)benzamide (231)

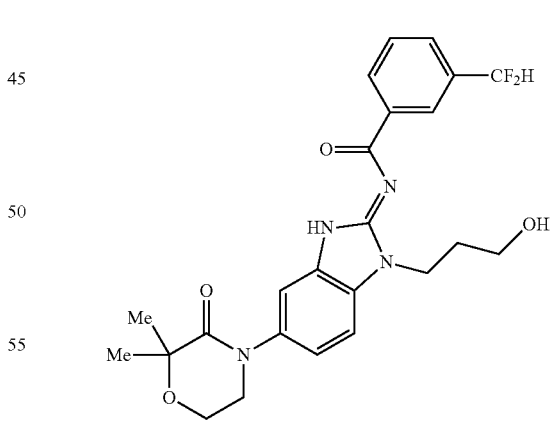

In a glass RBF equipped with a Teflon-coated magnetic stirrer was dissolved 3-difluoromethyl-benzoic acid (1 eq.), hydroxybenzotriazole (1.5 eq.), EDCI (1.5 eq.) and Intermediate 67 (1 eq.) in DMF (0.12 M). To the resulting solution was then added ethyl-diisopropyl-amine (5 eq.) and the resulting mixture was stirred at RT for 18 h. The crude reaction mixture thus obtained was directly subjected to purification by way of high pressure liquid chromatography ($C_{18}$, gradient elution, 2:3 (v/v) $H_2O$:MeCN+0.1% TFA→1:4 (v/v) $H_2O$:MeCN+0.1% TFA). The title compound was isolated as a tan solid (16% yield): ESI+: M+1: 473. $^1$H NMR (300 MHz, DMSO-$d_6$) δ 12.84 (s, 1H), 8.44-8.38 (m, 2H), 7.73 (d, J=7.7 Hz, 1H), 7.63 (t, J=7.7 Hz, 1H), 7.56 (d, J=8.5 Hz, 1H), 7.46 (d, J=2.0 Hz, 1H), 7.39-6.95 (m, 2H), 4.69 (t, J=5.1 Hz, 1H), 4.34 (t, J=6.4 Hz, 2H), 4.02-3.96 (m, 2H), 3.78-3.68 (m, 2H), 3.53-3.44 (m, 2H), 2.02-1.91 (m, 2H), 1.44 (s, 6H).

Example 223: (E)-3-(trifluoromethyl)-N-(5-(2,2-dimethyl-3-oxomorpholino)-1-(3-hydroxypropyl)-1H-benzo[d]imidazol-2(3H)-ylidene)benzamide (232)

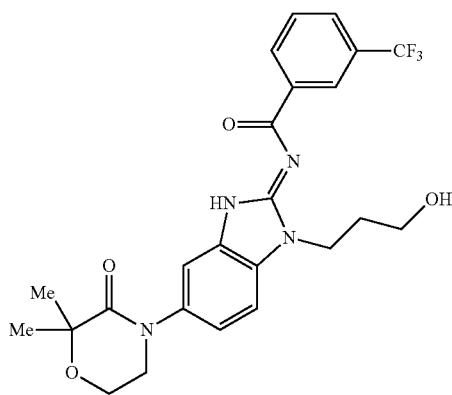

In a glass RBF equipped with a Teflon-coated magnetic stirrer was dissolved 3-trifluoromethyl-benzoic acid (1 eq.), hydroxybenzotriazole (1.5 eq.), EDCI (1.5 eq.) and Intermediate 67 (1 eq.) in DMF (0.12 M). To the resulting solution was then added ethyl-diisopropyl-amine (5 eq.) and the resulting mixture was stirred at RT for 18 h. The crude reaction mixture thus obtained was directly subjected to purification by way of high pressure liquid chromatography ($C_{18}$, gradient elution, 2:3 (v/v) $H_2O$:MeCN+0.1% TFA→1:4 (v/v) $H_2O$:MeCN+0.1% TFA). The title compound was isolated as a white solid (8% yield): ESI+: M+1: 491. $^1$H NMR (300 MHz, acetone-$d_6$) δ12.56 (s, 1H), 8.64-8.54 (m, 2H), 7.86 (d, J=7.8 Hz, 1H), 7.77-7.54 (m, 3H), 7.32 (dd, J=8.5, 2.0 Hz, 1H), 4.51 (t, J=6.6 Hz, 2H), 4.16-4.02 (m, 3H), 3.92-3.82 (m, 2H), 3.62 (q, J=5.7 Hz, 2H), 2.17-2.05 (m, 2H), 1.48 (s, 6H).

Example 224: (E)-N-(1-(3-hydroxypropyl)-5-(3-methyl-2-oxotetrahydropyrimidin-1(2H)-yl)-1H-benzo[d]imidazol-2(3H)-ylidene)-3-(trifluoromethyl)benzamide (233)

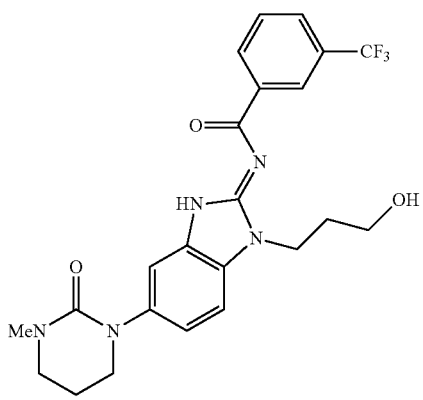 [SMILES: CN1CCCN(c2ccc3c(c2)[nH]/c(=N\C(=O)c2cccc(C(F)(F)F)c2)n3CCCO)C1=O]

Step 1: (E)-3-(5-(2-oxotetrahydropyrimidin-1(2H)-yl)-2-((3-(trifluoromethyl)benzoyl)imino)-2,3-dihydro-1H-benzo[d]imidazol-1-yl)propyl acetate In a glass RBF equipped with a Teflon-coated magnetic stirrer was dissolved Example 42 (1 eq.) in pyridine (1.1 eq.). To this was then added acetic anhydride (3 eq.) and the resulting solution was allowed to stir at RT for 18 h. The volatiles were then removed in vacuo to afford the crude title compound. This was used in the next step without further purification.

Step 2: (Z)-3-(5-(2-oxotetrahydropyrimidin-1(2H)-yl)-2-((3-(trifluoromethyl)benzoyl)imino)-3-((2-(trimethylsilyl)ethoxy)methyl)-2,3-dihydro-1H-benzo[d]imidazol-1-yl)propyl acetate In a glass RBF equipped with a Teflon-coated magnetic stirrer was suspended (E)-3-(5-(2-oxotetrahydropyrimidin-1(2H)-yl)-2-((3-(trifluoromethyl)benzoyl)imino)-2,3-dihydro-1H-benzo[d]imidazol-1-yl)propyl acetate (1 eq.) from the previous step and potassium carbonate (5 eq.) in DMF (0.32 M). To this was then added (2-(chloromethoxy)ethyl)trimethylsilane (3 eq.) and the resulting reaction mixture was allowed to stir at RT for 30 min. The reaction then quenched with the addition of water and extracted with EtOAc. The combined organic extracts were washed further with water and brine, dried over $MgSO_4$, filtered and the filtrate concentrated in vacuo. Further purification by way of column chromatography ($SiO_2$, gradient elution, 4:1 (v/v) Hex:EtOAc→EtOAc→10:1 (v/v) EtOAc:MeOH) furnished the desired product as a colorless oil (69% yield over two steps).

Step 3: (Z)-3-(5-(3-methyl-2-oxotetrahydropyrimidin-1(2H)-yl)-2-((3-(trifluoromethyl)benzoyl)imino)-3-((2-(trimethylsilyl)ethoxy)methyl)-2,3-dihydro-1H-benzo[d]imidazol-1-yl)propyl acetate In a glass RBF equipped with a Teflon-coated magnetic stirrer was dissolved (Z)-3-(5-(2-oxotetrahydropyrimidin-1(2H)-yl)-2-((3-(trifluoromethyl)benzoyl)imino)-3-((2-(trimethylsilyl)ethoxy)methyl)-2,3-dihydro-1H-benzo[d]imidazol-1-yl)propyl acetate (1 eq.) from the previous step in DMF (0.5 M). To this was then added sequentially sodium hydride (2.4 eq., 60% (w/w) dispersion in paraffin oil) and iodomethane (3 eq.). The resulting mixture was allowed to stir at RT for 3 h and then directly subjected to purification by way of column chromatography ($SiO_2$, gradient elution, 4:1 (v/v) Hex:EtOAc→EtOAc→10:1 (v/v) EtOAc:MeOH) to furnish the desired product (73% yield).

Step 4: (E)-N-(1-(3-hydroxypropyl)-5-(3-methyl-2-oxotetrahydropyrimidin-1(2H)-yl)-1H-benzo[d]imidazol-2(3H)-ylidene)-3-(trifluoromethyl)benzamide In a glass RBF equipped with a Teflon-coated magnetic stirrer was dissolved (Z)-3-(5-(3-methyl-2-oxotetrahydropyrimidin-1(2H)-yl)-2-((3-(trifluoromethyl)benzoyl)imino)-3-((2-(trimethylsilyl)ethoxy)methyl)-2,3-dihydro-1H-benzo[d]imidazol-1-yl)propyl acetate (1 eq.) from the previous step in dichloromethane (0.035 M). To this was then TFA (50 eq.) neat and drop-wise over a period of 1 min. The resulting mixture was allowed to stir at RT for 18 h. The volatiles were then removed in vacuo and the resulting residue was taken up in methanol (0.035 M) and added potassium carbonate (5 eq.). The resulting suspension was stirred at RT for 3 h. The insolubles were then removed via filtration and the filtrate thus obtained was directly subjected to high pressure liquid chromatography (C$_{18}$, gradient elution, 2:3 (v/v) H$_2$O: MeCN+0.1% TFA→1:4 (v/v) H$_2$O:MeCN+0.1% TFA). The title compound was isolated as a white solid (67% yield): ESI$^+$: M+1: 476. $^1$H NMR (300 MHz, CDCl$_3$) δ 12.48 (s, 1H), 8.52 (s, 1H), 8.44 (d, J=7.8 Hz, 1H), 7.75 (d, J=7.7 Hz, 1H), 7.58 (t, J=7.8 Hz, 1H), 7.29-7.14 (m, 3H), 4.68 (s, 1H), 4.45 (t, J=6.0 Hz, 2H), 3.65 (t, J=5.7 Hz, 2H), 3.53-3.35 (m, 4H), 3.01 (s, 3H), 2.13 (p, J=6.0 Hz, 2H), 2.07-1.95 (m, 2H).

Example 225: (E)-N-(1-(3-hydroxypropyl)-5-(3-methyl-2-oxotetrahydropyrimidin-1(2H)-yl)-1H-benzo[d]imidazol-2(3H)-ylidene)-3-(difluoromethyl)benzamide (234)

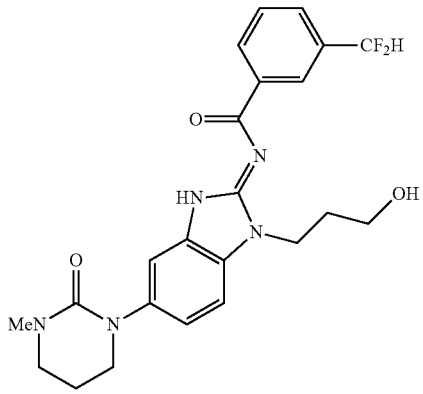 [SMILES: CN1CCCN(c2ccc3c(c2)[nH]/c(=N\C(=O)c2cccc(C(F)F)c2)n3CCCO)C1=O]

Prepared in an analogous fashion to Example 224, but using Example 43 (1 eq.) in place of Example 42 in step 1. ESI$^+$: M+1: 458. $^1$H NMR (300 MHz, CDCl$_3$) δ 12.52 (s, 1H), 8.41-8.34 (m, 2H), 7.67 (d, J=7.7 Hz, 1H), 7.55 (t, J=7.9 Hz, 1H), 7.27-7.17 (m, 3H), 6.73 (t, J=56.4 Hz, 1H), 4.83 (s, 1H), 4.45 (t, J=6.0 Hz, 2H), 3.61 (t, J=5.7 Hz, 2H), 3.50-3.34 (m, 4H), 3.01 (s, 3H), 2.11 (p, J=6.0 Hz, 2H), 2.02-1.90 (m, 2H).

Example 226: (E)-N-(1-(2-fluoro-3-hydroxy-2-methylpropyl)-5-(2-oxo-1,3-oxazinan-3-yl)-1H-benzo[d]imidazol-2(3H)-ylidene)-3-(trifluoromethyl)benzamide (235)

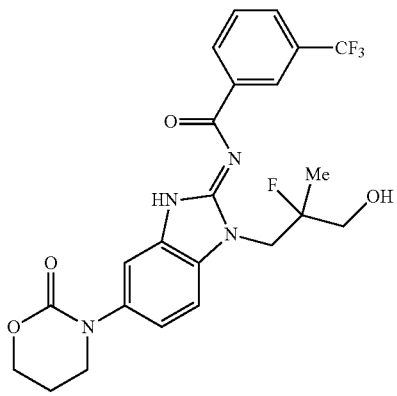 [SMILES: CC(F)(CO)Cn1/c(=N/C(=O)c2cccc(C(F)(F)F)c2)[nH]c2cc(N3CCCOC3=O)ccc21]

Prepared in an analogous fashion to Example 133, but using Intermediate 68-CF$_3$ (1 eq.) in place of Intermediate 32-CF$_3$. ESI$^+$: M+1: 495. $^1$H NMR (300 MHz, DMSO-d$_6$) δ 12.97 (s, 1H), 8.57-8.46 (m, 2H), 7.91 (d, J=7.9 Hz, 1H), 7.74 (t, J=7.7 Hz, 1H), 7.53 (d, J=8.5 Hz, 1H), 7.48 (d, J=2.0 Hz, 1H), 7.26 (dd, J=8.6, 2.0 Hz, 1H), 5.39 (s, 1H), 4.79-4.42 (m, 2H), 4.41-4.33 (m, 2H), 3.75-3.49 (m, 4H), 2.14 (q, J=5.6 Hz, 2H), 1.33 (d, J=22.2 Hz, 3H).

Example 227: (E)-3-(difluoromethyl)-N-(1-((3-fluorooxetan-3-yl)methyl)-5-(2-oxo-1,3-oxazinan-3-yl)-1H-benzo[d]imidazol-2(3H)-ylidene)benzamide (236)

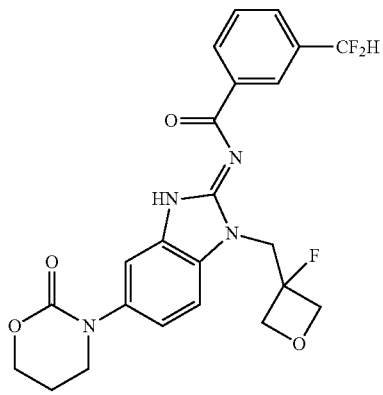

Prepared in an analogous fashion to Example 9, but using Intermediate 69 (1 eq.) in place of Intermediate 1-OH, 3-difluoromethyl-benzoic acid (1.1 eq.) in place of 4-methyl-3-trifluoromethyl-benzoic acid, and HATU (1.2 eq.) in place of HBTU (41% yield). ESI$^+$: M+1: 475. $^1$H NMR (300 MHz, DMSO-d$_6$) δ 12.96 (s, 1H), 8.45 (d, J=7.7 Hz, 1H), 8.40 (s, 1H), 7.74 (d, J=7.7 Hz, 1H), 7.66 (t, J=7.6 Hz, 1H), 7.55-7.43 (m, 2H), 7.40-6.89 (m, 2H), 5.09-4.82 (m, 4H), 4.68 (dd, J=20.5, 8.1 Hz, 2H), 4.37 (t, J=5.2 Hz, 2H), 3.66 (t, J=6.0 Hz, 2H), 2.12-2.07 (m, 2H).

Example 228: (E)-3-(difluoromethyl)-N-(1-((4-fluorotetrahydro-2H-pyran-4-yl)methyl)-5-(2-oxo-1,3-oxazinan-3-yl)-1H-benzo[d]imidazol-2(3H)-ylidene)benzamide (237)

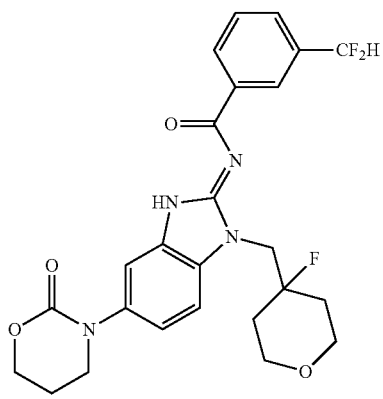 [SMILES: O=C(/N=c1\[nH]c2cc(N3CCCOC3=O)ccc2n1CC1(F)CCOCC1)c1cccc(C(F)F)c1]

Prepared in an analogous fashion to Example 9, but using Intermediate 70 (1 eq.) in place of Intermediate 1-OH, 3-difluoromethyl-benzoic acid (1.1 eq.) in place of 4-methyl-3-trifluoromethyl-benzoic acid, and HATU (1.2 eq.) in place of HBTU (42% yield). ESI+: M+1: 503. $^1$H NMR (300 MHz, DMSO-$d_6$) δ 12.95 (s, 1H), 8.49-8.37 (m, 2H), 7.74 (d, J=7.6 Hz, 1H), 7.65 (t, J=7.6 Hz, 1H), 7.54-7.44 (m, 2H), 7.38-6.91 (m, 2H), 4.58 (d, J=22.4 Hz, 2H), 4.37 (t, J=5.3 Hz, 2H), 3.79 (d, J=11.6 Hz, 2H), 3.66 (t, J=6.0 Hz, 2H), 3.51 (t, J=11.1 Hz, 2H), 2.20-1.84 (m, 4H), 1.73 (t, J=12.2 Hz, 2H).

Example 229: (E)-N-(1-((4-fluorotetrahydro-2H-pyran-4-yl)methyl)-5-(2-oxo-1,3-oxazinan-3-yl)-1H-benzo[d]imidazol-2(3H)-ylidene)-3-(trifluoromethyl)benzamide (238)

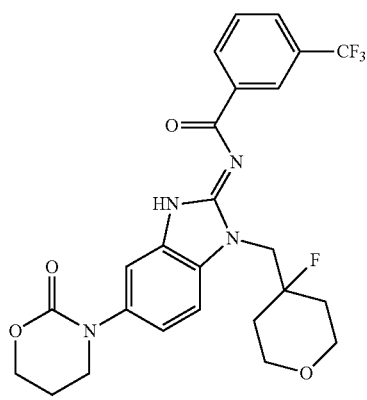

Prepared in an analogous fashion to Example 9, but using Intermediate 70 (1 eq.) in place of Intermediate 1-OH, 3-trifluoromethyl-benzoic acid (1.1 eq.) in place of 4-methyl-3-trifluoromethyl-benzoic acid, and HATU (1.2 eq.) in place of HBTU (23% yield). ESI+: M+1: 521. $^1$H NMR (300 MHz, DMSO-$d_6$) δ 12.98 (s, 1H), 8.57 (d, J=7.7 Hz, 1H), 8.49 (s, 1H), 7.92 (d, J=7.9 Hz, 1H), 7.76 (t, J=7.8 Hz, 1H), 7.57-7.45 (m, 2H), 7.26 (dd, J=8.6, 2.0 Hz, 1H), 4.59 (d, J=22.5 Hz, 2H), 4.37 (t, J=5.3 Hz, 2H), 3.79 (d, J=11.5 Hz, 2H), 3.67 (t, J=6.0 Hz, 2H), 3.52 (t, J=11.1 Hz, 2H), 2.20-1.83 (m, 4H), 1.73 (t, J=12.3 Hz, 2H).

Example 230: (E)-3-cyano-N-(1-((4-fluorotetrahydro-2H-pyran-4-yl)methyl)-5-(2-oxo-1,3-oxazinan-3-yl)-1H-benzo[d]imidazol-2(3H)-ylidene)benzamide (239)

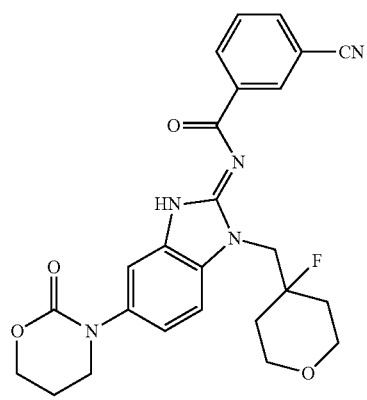

Prepared in an analogous fashion to Example 9, but using Intermediate 70 (1 eq.) in place of Intermediate 1-OH, 3-cyano-benzoic acid (1.1 eq.) in place of 4-methyl-3-trifluoromethyl-benzoic acid, and HATU (1.2 eq.) in place of HBTU (40% yield). ESI+: M+1: 478. $^1$H NMR (300 MHz, DMSO-$d_6$) δ 13.00 (s, 1H), 8.57 (dd, J=7.6, 1.4 Hz, 1H), 8.01 (dt, J=7.7, 1.5 Hz, 1H), 7.72 (td, J=7.6, 1.1 Hz, 1H), 7.57-7.44 (m, 2H), 7.25 (dd, J=8.6, 2.0 Hz, 1H), 4.61 (d, J=22.4 Hz, 2H), 4.37 (t, J=5.3 Hz, 2H), 3.79 (d, J=10.5 Hz, 2H), 3.66 (t, J=6.0 Hz, 2H), 3.50 (t, J=11.0 Hz, 2H), 2.23-1.61 (m, 6H).

Example 231: (E)-3-acetyl-N-(1-(3-hydroxypropyl)-5-(3-oxomorpholino)-1H-benzo[d]imidazol-2(3H)-ylidene)benzamide (240)

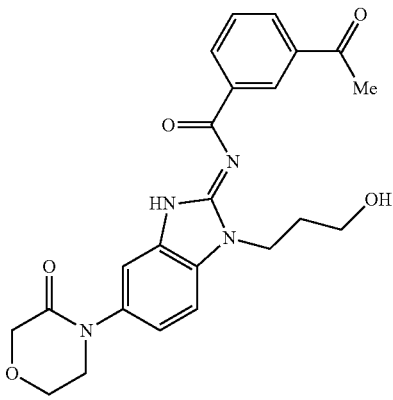

Prepared in an analogous fashion to Example 1, but using 3-acetyl-benzoic acid (1 eq.) in place of 3-trifluoromethyl-benzoic acid in Step 1. ESI+: M+1: 437. $^1$H NMR (300 MHz, DMSO-$d_6$) δ 12.87 (s, 1H), 8.80 (s, 1H), 8.49 (d, J=7.3 Hz, 1H), 8.11 (d, J=7.7 Hz, 1H), 7.70-7.53 (m, 2H), 7.50 (s, 1H), 7.28 (d, J=8.4 Hz, 1H), 4.74-4.67 (m, 1H), 4.39-4.32 (m, 2H), 4.23 (s, 2H), 4.04-3.97 (m, 2H), 3.80-3.69 (m, 2H), 3.54-3.46 (m, 2H), 2.66 (s, 3H), 2.01-1.95 (m, 2H).

Example 232: (E)-N-(1-(3-hydroxypropyl)-5-(3-oxomorpholino)-1H-benzo[d]imidazol-2(3H)-ylidene)benzo[d]thiazole-5-carboxamide (241)

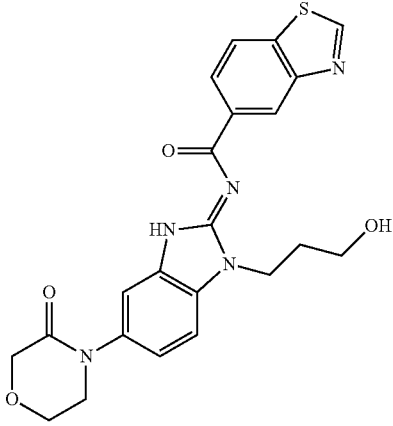

Prepared in an analogous fashion to Example 1, but using benzothiazole-5-carboxylic acid (1 eq.) in place of 3-trifluoromethyl-benzoic acid in Step 1. ESI+: M+1: 452. $^1$H NMR (300 MHz, DMSO-$d_6$) δ 12.91 (s, 1H), 9.48 (s, 1H), 8.90 (d, J=1.3 Hz, 1H), 8.43-8.33 (m, 1H), 8.26 (d, J=8.4 Hz, 1H), 7.58 (d, J=8.6 Hz, 1H), 7.50 (d, J=1.9 Hz, 1H), 7.27 (dd, J=8.5, 2.0 Hz, 1H), 4.73 (t, J=5.2 Hz, 1H), 4.38 (t, J=6.8 Hz, 2H), 4.24 (s, 2H), 4.01 (t, J=5.1 Hz, 2H), 3.75 (t, J=5.1 Hz, 2H), 3.51 (q, J=5.9 Hz, 2H), 2.06-1.96 (m, 2H).

Example 233: Enzymatic Assays

IRAK4 Enzymatic Assay:

IRAK4 is a human purified recombinant enzyme (His-TEV-IRAK4 (1-460)).

In this assay, IRAK4 hydrolyses ATP, autophosphorylates and phosphorylates a Serine/Threonine generic peptidic substrate (STK: 61ST1BLC from CisBio International). Measurement of IRAK-4 inhibition is performed in 384-well format based on a luminescence assay (ADP-Glo™ Kinase Assay from Promega). Purified human recombinant IRAK4 (0.3 µg/ml) and serial diluted compounds in DMSO (range of concentration from 10 µM to 0.5 nM) or controls (1% DMSO) are incubated for 15 minutes at RT in assay buffer containing 50 mM Hepes pH 7.0, Fatty acid-free BSA 0.1%, Dithiothreitol (DTT) 2 mM, MgCl2 10 mM, EGTA 0.5 mM, Triton X-100 0.01%, MnCl2 5 mM. The kinase reaction is then initiated by the addition of ATP (2 µM) and the peptidic substrate STK1-biotin peptide (300 nM). After 2 hours of incubation at RT, the reaction is stopped and the unconsumed ATP depleted by the addition of ADP-Glo™ Reagent according to supplier instructions. After 40 minutes of incubation at RT, the Kinase Detection Reagent is then added to the assay plate according to supplier instructions. After 20 minutes of incubation at RT, the luminescence signal is measured with a plate-reading luminometer (PerkinElmer Envision or equivalent reader).

IRAK1 Enzymatic Assay:

IRAK1 is a human purified recombinant enzyme (His-TEV-IRAK1 (194-712))

In this assay, IRAK1 hydrolyses ATP and autophosphorylates. Measurement of IRAK-1 inhibition is performed in 384-well format based on luminescence assay (ADP-Glo™ Kinase Assay from Promega). Purified human recombinant IRAK1 (0.3 µg/ml) and serial diluted compounds in DMSO (range of concentration from 10 µM to 0.5 nM) or controls (1% DMSO) are incubated for 15 minutes at RT in assay buffer containing 50 mM Hepes pH 7.0, Fatty acid-free BSA 0.1%, Dithiothreitol (DTT) 2 mM, MgCl2 10 mM, EGTA 0.5 mM, Triton X-100 0.01%. The kinase reaction is then initiated by the addition of ATP at a concentration of After 2 hours of incubation at RT, the reaction is stopped and the unconsumed ATP depleted by the addition of ADP-Glo™ Reagent according to supplier instructions. After 40 minutes of incubation at RT, the Kinase Detection Reagent is then added to the assay plate according to supplier instructions. After 20 minutes of incubation at RT, the luminescence signal is measured with a luminometer (PerkinElmer Envision or equivalent reader).

Results are given in the following table.

TABLE 2

$IC_{50}$ +++ ≤100 nM
$IC_{50}$ ++ >100 nM to 1 µM
$IC_{50}$ + >1 µM

| Example | Compound | MS (ESI+) | IRAK1 ADP-Glo* | IRAK4 ADP-Glo* |
|---|---|---|---|---|
| 1 | 86 | 463 | ++ | +++ |
| 2 | 6 | 461 | ++ | +++ |
| 3 | 100 | 474 | +++ | +++ |
| 4 | 81 | 481 | +++ | +++ |
| 5 | 4 | 481 | ++ | +++ |
| 6 | 5 | 481 | +++ | +++ |
| 7 | 7 | 479 | ++ | +++ |
| 8 | 79 | 445 | +++ | +++ |
| 9 | 78 | 477 | + | +++ |
| 10 | 77 | 396 | ++ | +++ |
| 11 | 101 | 502 | ++ | +++ |
| 12 | 21 | 425 | ++ | +++ |
| 13 | 20 | 449 | + | ++ |
| 14 | 22 | 449 | + | + |
| 15 | 23 | 451 | + | +++ |
| 16 | 60 | 449 | + | + |
| 17 | 37 | 475 | ++ | +++ |
| 18 | 34 | 464 | +++ | +++ |
| 19 | 30 | 395 | ++ | ++ |
| 20 | 36 | 508 | ++ | + |
| 21 | 47 | 466 | ++ | ++ |
| 22 | 35 | 413 | ++ | +++ |
| 23 | 38 | 450 | + | + |
| 24 | 102 | 435 | + | + |
| 25 | 103 | 459 | ++ | +++ |
| 26 | 104 | 427 | ++ | +++ |
| 27 | 105 | 409 | ++ | +++ |
| 28 | 106 | 429 | ++ | +++ |
| 29 | 107 | 488 | +++ | +++ |
| 30 | 97 | 488 | +++ | +++ |
| 31 | 82 | 473 | ++ | +++ |
| 32 | 83 | 463 | ++ | +++ |
| 33 | 3 | 420 | ++ | +++ |
| 34 | 2 | 462 | ++ | ++ |
| 35 | 84 | 464 | + | ++ |
| 36 | 85 | 464 | ++ | +++ |
| 37 | 8 | 449 | ++ | +++ |
| 38 | 11 | 406 | ++ | +++ |
| 39 | 33 | 463 | +++ | +++ |
| 40 | 29 | 445 | +++ | +++ |
| 41 | 58 | 420 | +++ | +++ |
| 42 | 1 | 462 | ++ | +++ |
| 43 | 46 | 444 | ++ | +++ |
| 44 | 108 | 462 | +++ | +++ |
| 45 | 109 | 444 | ++ | +++ |
| 46 | 110 | 486 | +++ | +++ |
| 47 | 111 | 458 | ++ | +++ |
| 48 | 112 | 498 | +++ | +++ |
| 49 | 113 | 526 | ++ | +++ |
| 50 | 43 | 477 | ++ | +++ |
| 51 | 44 | 459 | ++ | +++ |
| 52 | 42 | 434 | ++ | +++ |
| 53 | 114 | 531 | + | + |
| 54 | 115 | 513 | + | ++ |
| 55 | 39 | 517 | + | + |
| 56 | 116 | 517 | + | ++ |
| 57 | 117 | 499 | ++ | ++ |
| 58 | 118 | 517 | ++ | +++ |
| 59 | 119 | 499 | ++ | +++ |
| 60 | 120 | 517 | ++ | +++ |
| 61 | 121 | 499 | ++ | +++ |
| 62 | 57 | 503 | +++ | +++ |
| 63 | 56 | 485 | +++ | +++ |
| 64 | 55 | 460 | +++ | +++ |
| 65 | 54 | 513 | +++ | +++ |
| 66 | 32 | 503 | ++ | +++ |
| 67 | 28 | 485 | +++ | +++ |
| 68 | 27 | 460 | +++ | +++ |
| 69 | 31 | 513 | +++ | +++ |
| 70 | 122 | 517 | +++ | +++ |
| 71 | 123 | 499 | +++ | +++ |
| 72 | 15 | 477 | ++ | +++ |
| 73 | 242 | 459 | +++ | +++ |
| 74 | 16 | 459 | ++ | +++ |
| 75 | 10 | 434 | ++ | +++ |
| 76 | 24 | 487 | ++ | +++ |
| 77 | 65 | 475 | +++ | +++ |

TABLE 2-continued

IC$_{50}$ +++ ≤100 nM
IC$_{50}$ ++ >100 nM to 1 μM
IC$_{50}$ + >1 μM

| Example | Compound | MS (ESI⁺) | IRAK1 ADP-Glo* | IRAK4 ADP-Glo* |
|---|---|---|---|---|
| 78 | 124 | 491 | + | ++ |
| 79 | 125 | 473 | + | +++ |
| 80 | 17 | 477 | ++ | +++ |
| 81 | 26 | 459 | +++ | +++ |
| 82 | 18 | 434 | ++ | +++ |
| 83 | 19 | 487 | ++ | +++ |
| 84 | 45 | 487 | + | ++ |
| 85 | 9 | 489 | ++ | +++ |
| 86 | 14 | 471 | +++ | +++ |
| 87 | 12 | 446 | +++ | +++ |
| 88 | 13 | 499 | +++ | +++ |
| 89 | 66 | 487 | ++ | +++ |
| 90 | 25 | 507 | ++ | +++ |
| 91 | 126 | 588 | + | +++ |
| 92 | 127 | 570 | ++ | +++ |
| 93 | 128 | 488 | + | +++ |
| 94 | 129 | 470 | ++ | +++ |
| 95 | 130 | 530 | +++ | +++ |
| 96 | 131 | 512 | ++ | +++ |
| 97 | 132 | 566 | ++ | +++ |
| 98 | 133 | 548 | +++ | +++ |
| 99 | 134 | 559 | ++ | +++ |
| 100 | 135 | 541 | +++ | +++ |
| 101 | 136 | 537 | ++ | +++ |
| 102 | 63 | 461 | ++ | +++ |
| 103 | 92 | 475 | ++ | +++ |
| 104 | 89 | 489 | + | ++ |
| 105 | 94 | 477 | ++ | +++ |
| 106 | 93 | 493 | +++ | +++ |
| 107 | 91 | 491 | ++ | +++ |
| 108 | 90 | 507 | +++ | +++ |
| 109 | 88 | 505 | ++ | +++ |
| 110 | 137 | 503 | +++ | +++ |
| 111 | 76 | 494 | +++ | +++ |
| 112 | 75 | 475 | +++ | +++ |
| 113 | 74 | 450 | +++ | +++ |
| 114 | 73 | 512 | +++ | +++ |
| 115 | 64 | 455 | ++ | +++ |
| 116 | 70 | 477 | ++ | +++ |
| 117 | 69 | 459 | +++ | +++ |
| 118 | 31 | 434 | ++ | +++ |
| 119 | 67 | 495 | +++ | +++ |
| 120 | 50 | 541 | ++ | +++ |
| 121 | 138 | 488 | + | +++ |
| 122 | 49 | 525 | ++ | +++ |
| 123 | 48 | 499 | ++ | +++ |
| 124 | 139 | 481 | ++ | +++ |
| 125 | 140 | 463 | ++ | +++ |
| 126 | 141 | 497 | + | +++ |
| 127 | 142 | 479 | ++ | +++ |
| 128 | 53 | 519 | +++ | +++ |
| 129 | 52 | 501 | +++ | +++ |
| 130 | 51 | 476 | ++ | +++ |
| 131 | 143 | 507 | ++ | +++ |
| 132 | 40 | 489 | +++ | +++ |
| 133 | 144 | 475 | + | +++ |
| 134 | 145 | 481 | +++ | +++ |
| 135 | 146 | 419 | ++ | ++ |
| 136 | 147 | 463 | ++ | +++ |
| 137 | 148 | 475 | ++ | +++ |
| 138 | 149 | 445 | + | + |
| 139 | 72 | 397 | + | + |
| 140 | 80 | 519 | +++ | +++ |
| 141 | 150 | 530 | ++ | +++ |
| 142 | 151 | 495 | +++ | +++ |
| 143 | 152 | 527 | +++ | +++ |
| 144 | 153 | 502 | +++ | +++ |
| 145 | 154 | 488 | + | ++ |
| 146 | 155 | 503 | ++ | +++ |
| 147 | 156 | 495 | ++ | +++ |
| 148 | 157 | 523 | +++ | +++ |
| 149 | 158 | 475 | ++ | +++ |
| 150 | 159 | 457 | ++ | +++ |
| 151 | 160 | 484 | ++ | +++ |
| 152 | 161 | 460 | +++ | +++ |
| 153 | 162 | 503 | +++ | +++ |
| 154 | 163 | 570 | ++ | +++ |
| 155 | 164 | 538 | ++ | +++ |
| 156 | 165 | 484 | ++ | ++ |
| 157 | 166 | 477 | + | +++ |
| 158 | 167 | 463 | + | + |
| 159 | 168 | 491 | + | +++ |
| 160 | 169 | 473 | + | +++ |
| 161 | 170 | 459 | + | +++ |
| 162 | 171 | 473 | + | +++ |
| 163 | 172 | 445 | + | +++ |
| 164 | 173 | 475 | ++ | +++ |
| 165 | 174 | 503 | ++ | +++ |
| 166 | 175 | 443 | ++ | +++ |
| 167 | 176 | 501 | ++ | +++ |
| 168 | 177 | 537 | + | +++ |
| 169 | 178 | 479 | ++ | +++ |
| 170 | 179 | 483 | ++ | +++ |
| 171 | 180 | 503 | ++ | +++ |
| 172 | 181 | 501 | + | +++ |
| 173 | 182 | 484 | +++ | +++ |
| 174 | 183 | 502 | +++ | +++ |
| 175 | 184 | 498 | +++ | +++ |
| 176 | 185 | 486 | +++ | +++ |
| 177 | 186 | 479 | ++ | +++ |
| 178 | 187 | 461 | +++ | +++ |
| 179 | 188 | 461 | ++ | +++ |
| 180 | 189 | 461 | +++ | +++ |
| 181 | 190 | 497 | ++ | +++ |
| 182 | 191 | 490 | ++ | +++ |
| 183 | 192 | 477 | ++ | +++ |
| 184 | 193 | 477 | +++ | +++ |
| 185 | 194 | 530 | ++ | +++ |
| 186 | 195 | 459 | +++ | +++ |
| 187 | 196 | 459 | +++ | +++ |
| 188 | 197 | 512 | +++ | +++ |
| 189 | 198 | 489 | +++ | +++ |
| 190 | 199 | 471 | +++ | +++ |
| 191 | 200 | 516 | ++ | +++ |
| 192 | 201 | 516 | ++ | +++ |
| 193 | 202 | 457 | ++ | +++ |
| 194 | 203 | 439 | ++ | +++ |
| 195 | 204 | 516 | ++ | +++ |
| 196 | 205 | 459 | ++ | +++ |
| 197 | 206 | 528 | +++ | +++ |
| 198 | 207 | 510 | +++ | +++ |
| 199 | 208 | 477 | ++ | +++ |
| 200 | 209 | 459 | ++ | +++ |
| 201 | 210 | 458 | +++ | +++ |
| 202 | 211 | 496 | +++ | +++ |
| 203 | 212 | 478 | +++ | +++ |
| 204 | 213 | 496 | +++ | +++ |
| 205 | 214 | 478 | +++ | +++ |
| 206 | 215 | 493 | +++ | +++ |
| 207 | 216 | 475 | +++ | +++ |
| 208 | 217 | 503 | +++ | +++ |
| 209 | 218 | 485 | +++ | +++ |
| 210 | 219 | 481 | ++ | +++ |
| 211 | 220 | 529 | +++ | +++ |
| 212 | 221 | 484 | ++ | +++ |
| 213 | 222 | 456 | ++ | +++ |
| 214 | 223 | 510 | ++ | +++ |
| 215 | 224 | 528 | + | +++ |
| 216 | 225 | 474 | ++ | +++ |
| 217 | 226 | 489 | ++ | +++ |
| 218 | 227 | 473 | +++ | +++ |
| 219 | 228 | 473 | ++ | +++ |
| 220 | 229 | 491 | +++ | +++ |
| 221 | 230 | 491 | ++ | +++ |
| 222 | 231 | 473 | ++ | +++ |
| 223 | 232 | 491 | +++ | +++ |

TABLE 2-continued

IC$_{50}$ +++ ≤100 nM
IC$_{50}$ ++ >100 nM to 1 μM
IC$_{50}$ + >1 μM

| Example | Compound | MS (ESI$^+$) | IRAK1 ADP-Glo* | IRAK4 ADP-Glo* |
|---|---|---|---|---|
| 224 | 233 | 476 | ++ | +++ |
| 225 | 234 | 458 | ++ | +++ |
| 226 | 235 | 495 | +++ | +++ |
| 227 | 236 | 475 | ++ | +++ |
| 228 | 237 | 503 | ++ | +++ |
| 229 | 238 | 521 | ++ | +++ |
| 230 | 239 | 478 | ++ | +++ |
| 231 | 240 | 437 | ++ | +++ |
| 232 | 241 | 452 | + | +++ |

Example 234: Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I,

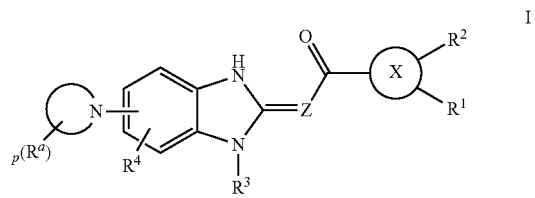

or a pharmaceutically acceptable salt thereof, wherein:

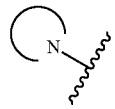

is selected from

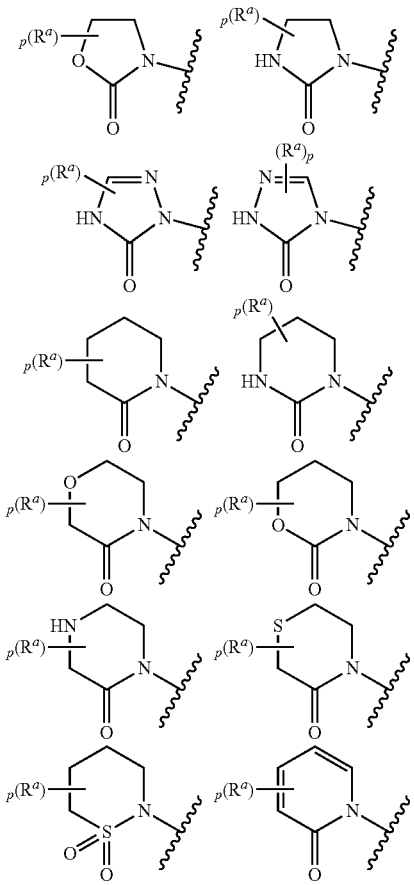

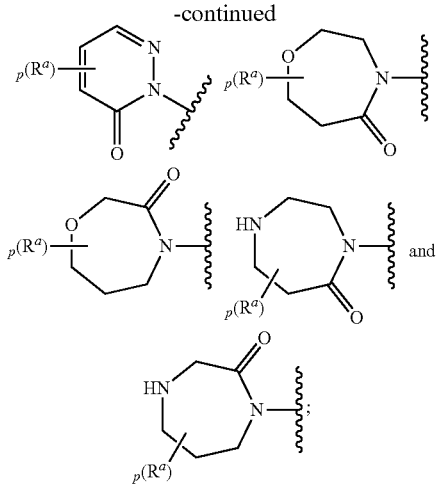

each $R^a$ is independently —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

Ring X is a $C_{3-10}$ aryl; a 5-6 membered monocyclic heteroaryl ring having 1-4 heteroatoms independently selected from nitrogen, oxygen, or sulfur; a fused $C_{3-10}$ aryl, a fused 5-10 membered saturated or partially unsaturated carbocyclic ring, a fused 5-10 membered heterocyclic ring having 1-4 heteroatoms independently selected from nitrogen, oxygen, or sulfur, or a fused 5-10 membered monocyclic heteroaryl ring having 1-4 heteroatoms independently selected from nitrogen, oxygen, or sulfur; each of which is optionally substituted;

$R^1$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^2$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

$R^3$ is $C_{1-6}$ aliphatic, a 3-8 membered saturated or partially unsaturated carbocyclic ring, or a 3-7 membered heterocylic ring having 1-4 heteroatoms independently selected from nitrogen, oxygen, or sulfur; each of which is optionally substituted; or $R^3$ is -haloalkyl;

$R^4$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;

Z is N or CR;

each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

and p is 0, 1, 2, 3, 4, or 5.

2. The compound of claim 1, wherein Ring X is an optionally substituted $C_{3-10}$ aryl; an optionally substituted 5-6 membered monocyclic heteroaryl ring having 1-4 heteroatoms independently selected from nitrogen, oxygen, or sulfur; an optionally substituted fused $C_{3-10}$ aryl; or an optionally substituted fused 5-10 membered monocyclic heteroaryl ring having 1-4 heteroatoms independently selected from nitrogen, oxygen, or sulfur.

3. The compound of claim 2, wherein Ring X is phenyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isoindazolyl, isoindolinyl, isoindolyl, isoquinolinyl, isothiazolyl, isoxazolyl, oxadiazolyl, 1,2,3-oxadiazolyl, 1,2,4-oxadiazolyl;-1,2,5-oxadiazolyl, 1,3,4-oxadiazolyl, oxazolidinyl, oxazolyl, oxazolidinyl, pyrimidinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, tetrazole, triazinyl, 1,2,3-triazolyl, 1,2,4-triazolyl, 1,2,5-triazolyl, or 1,3,4-triazolyl; each of which is optionally substituted.

4. The compound of claim 3, wherein Ring X is phenyl, benzimidazolyl, benzofuranyl, benzothiofuranyl, benzothiophenyl, 1H-indazolyl, isobenzofuranyl, isoxazolyl, pyrazinyl, pyrazolyl, pyridinyl, pyridyl, or tetrazole; each of which is optionally substituted.

5. The compound of claim 2, wherein Ring X is selected from:

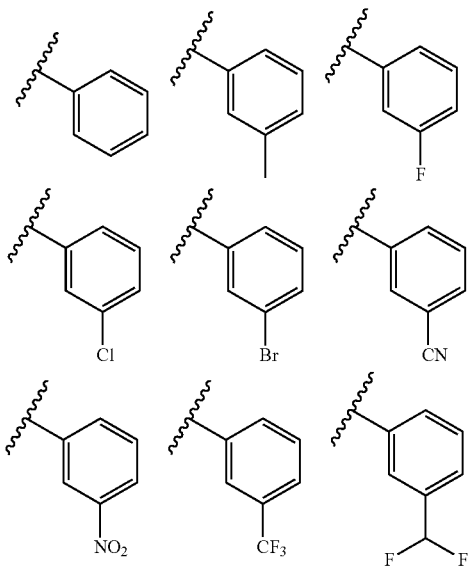

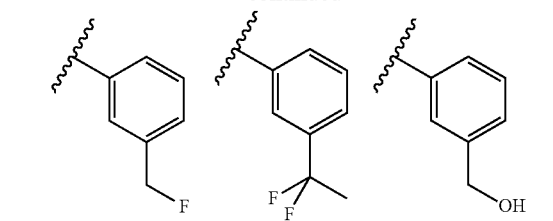
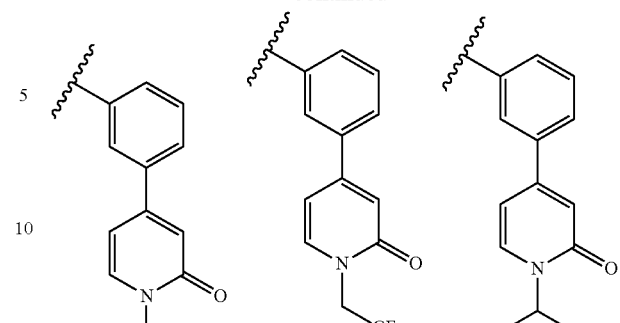
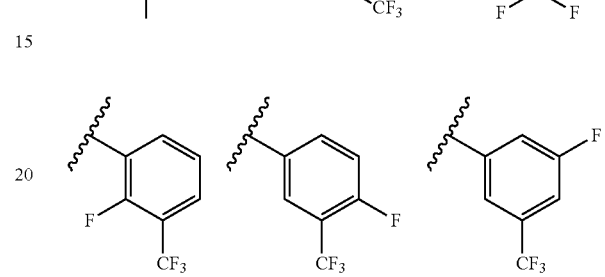
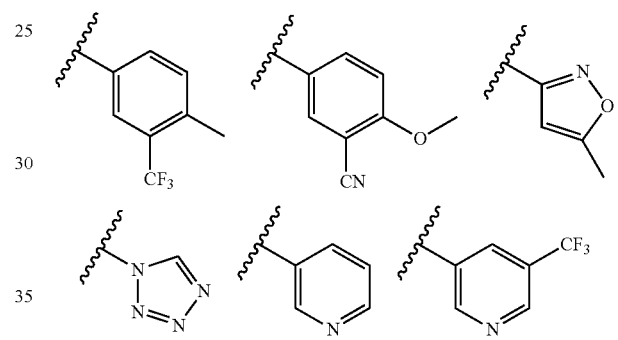
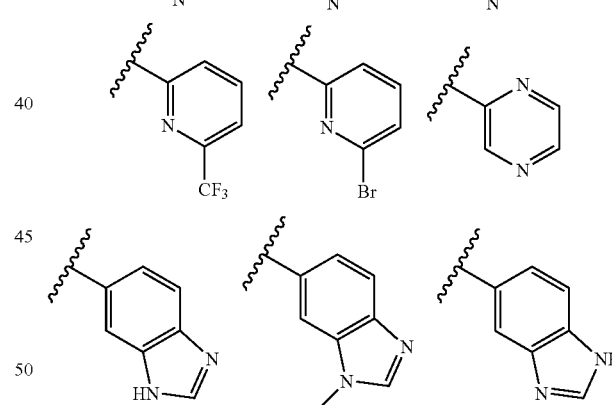
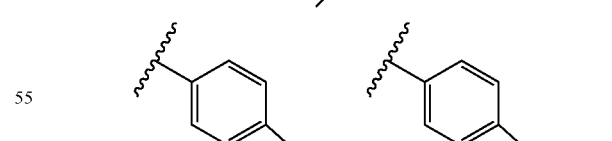
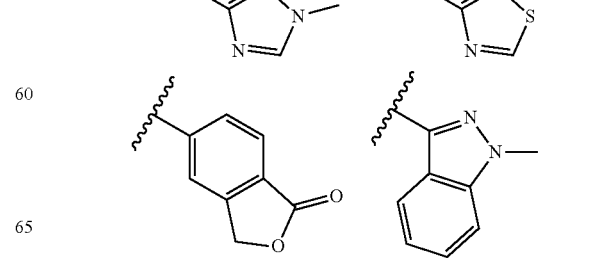

6. The compound of claim 1, wherein $R^3$ is selected from:
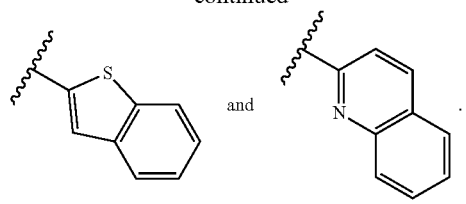
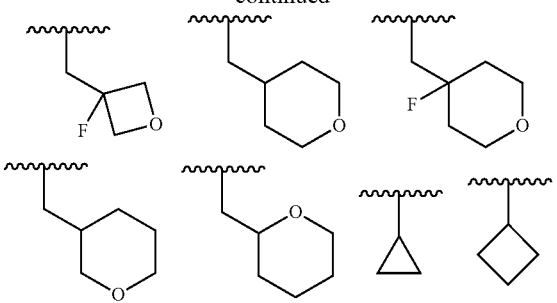
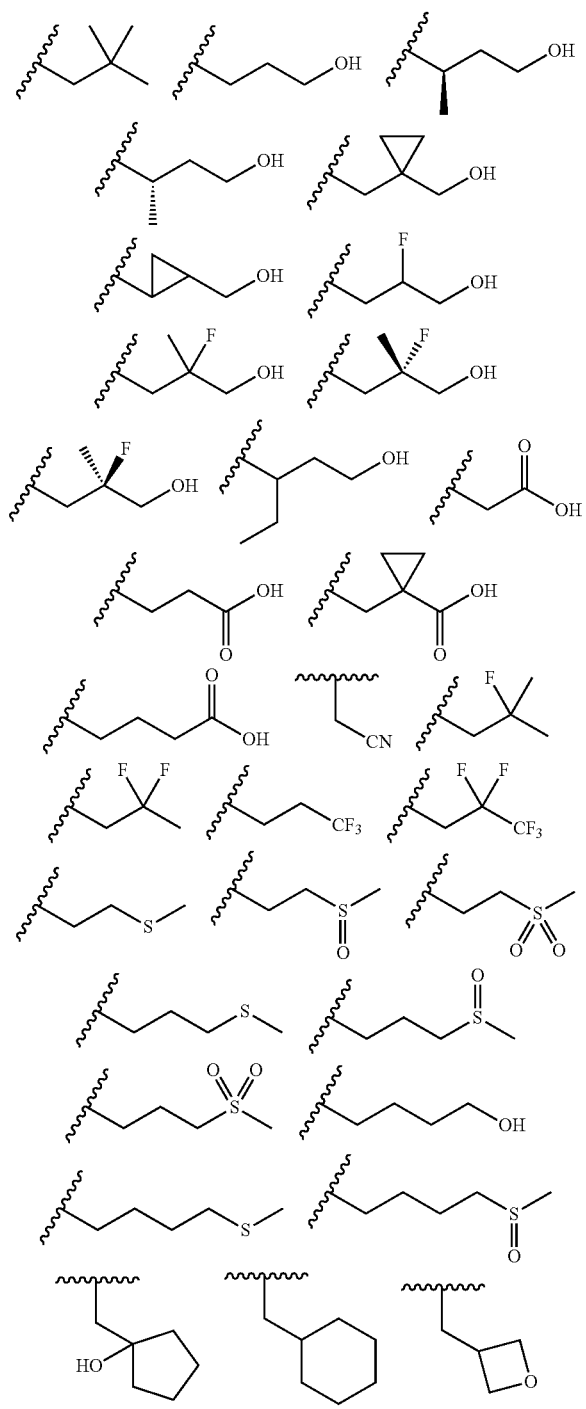
7. The compound of claim 1, wherein $R^4$ is —R, —CN, halogen, or —OR.

8. The compound of claim 1, of formula I-d,
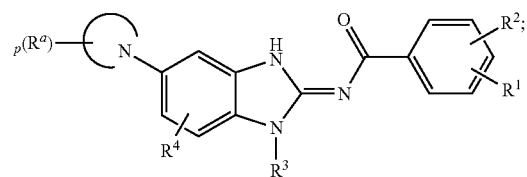
or a pharmaceutically acceptable salt thereof.
9. The compound of claim 1, selected from
1
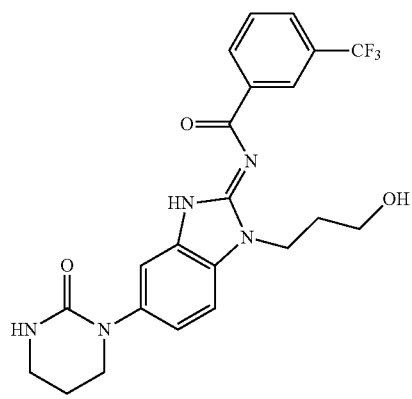
2
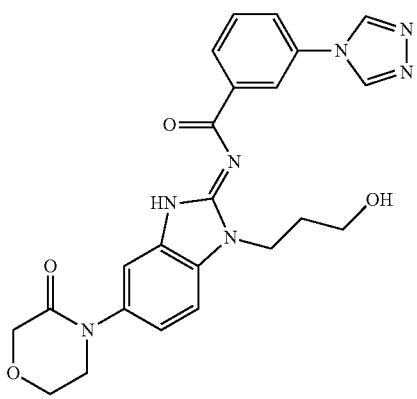
3
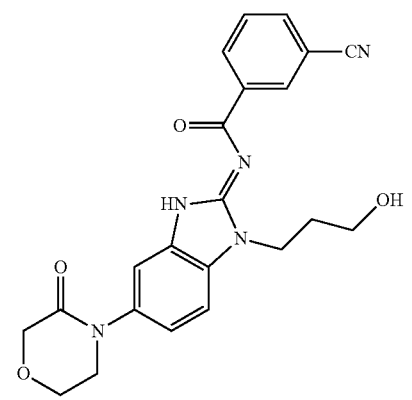
4
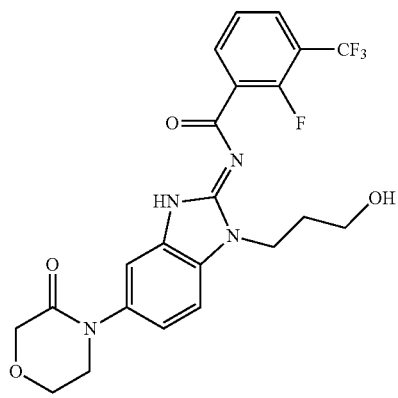
5
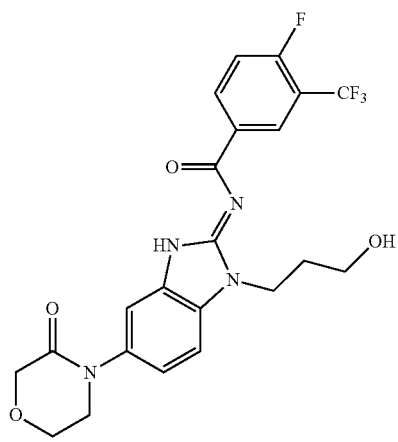
6
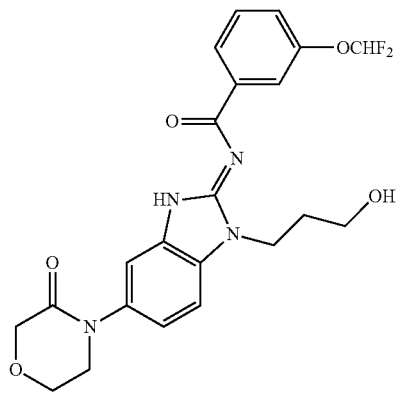
7
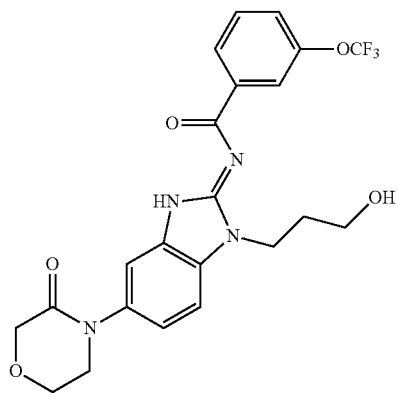

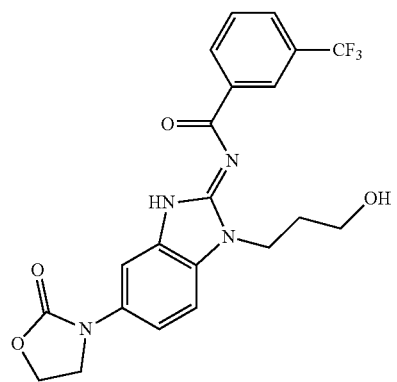
8
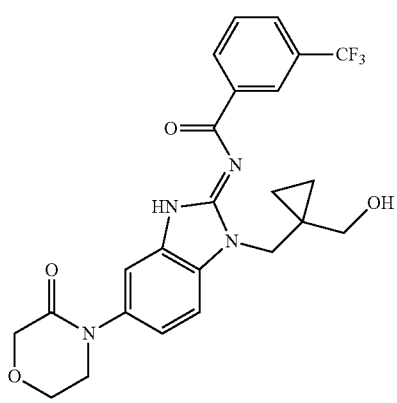
9
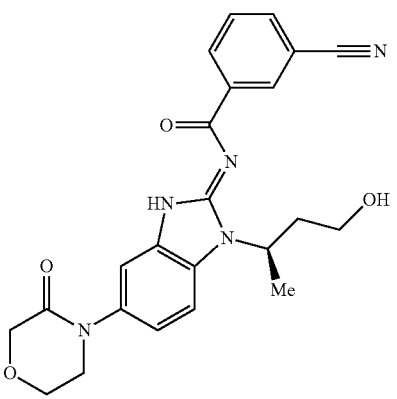
10
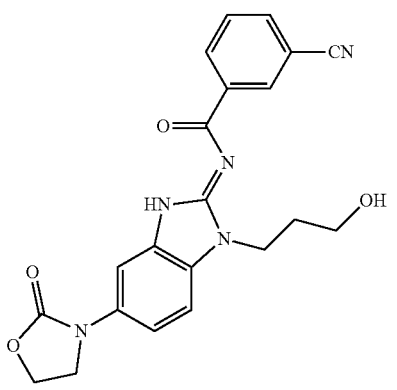
11
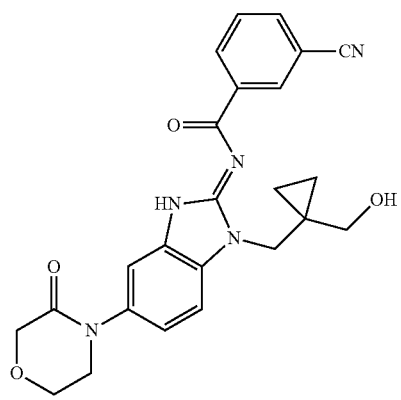
12
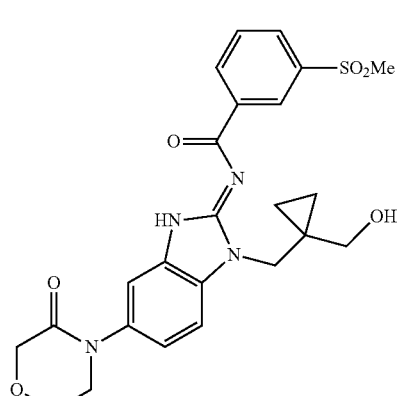
13
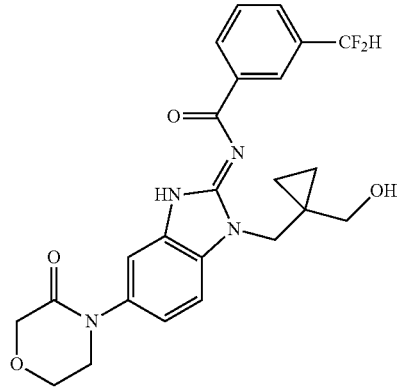
14
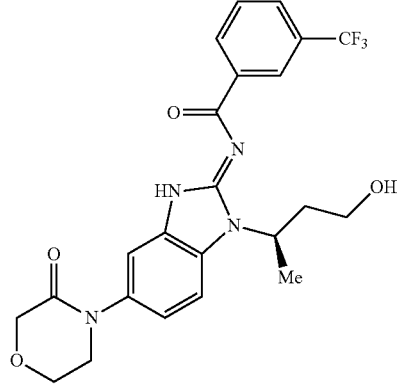
15

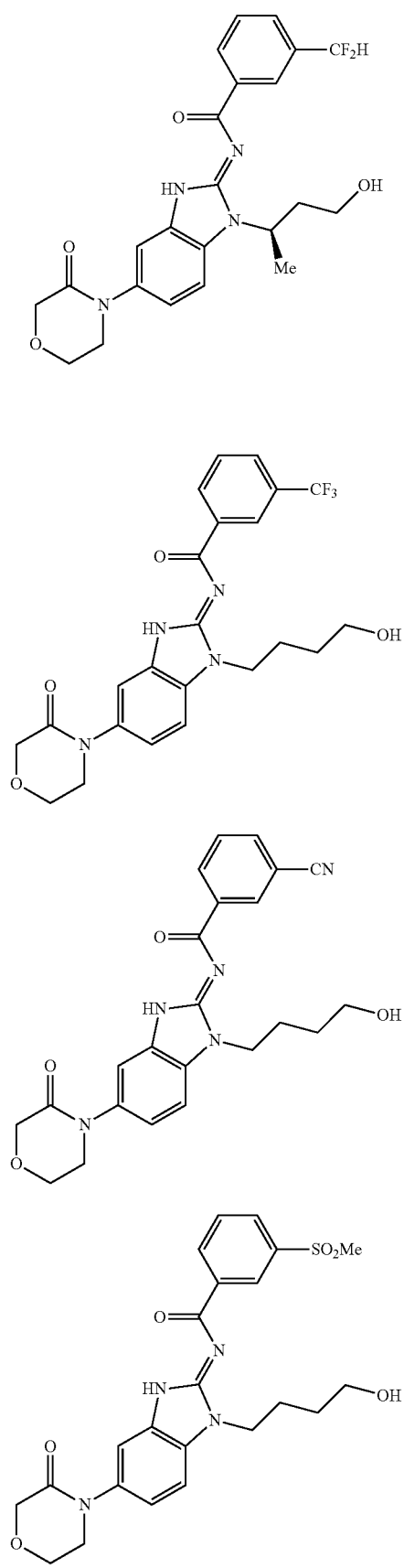
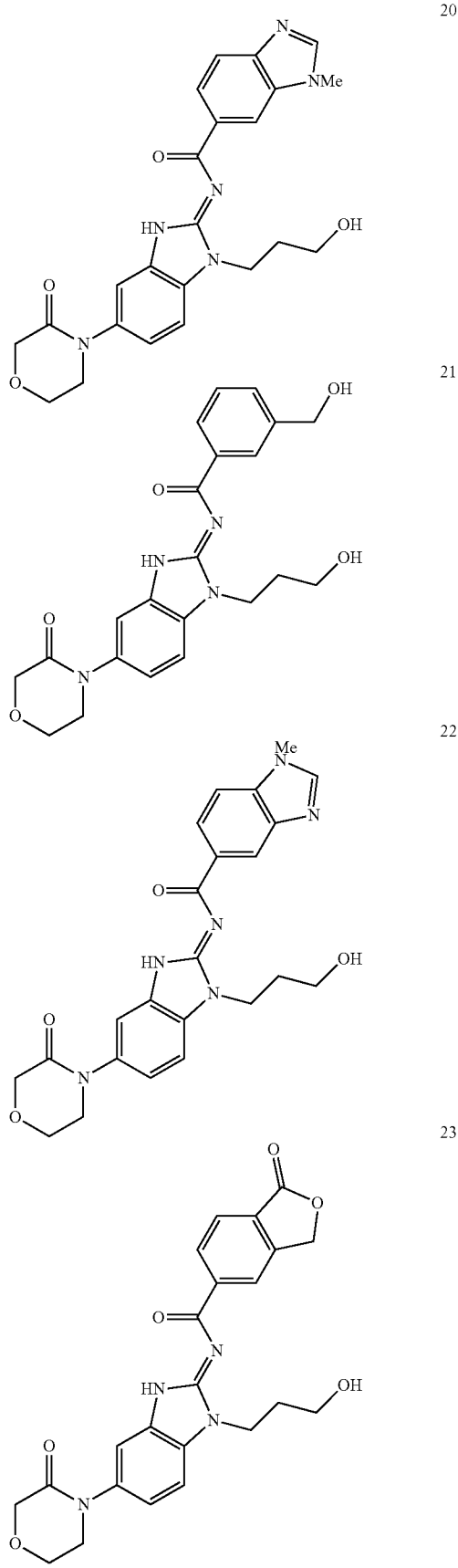

| | |
|---|---|
| 24 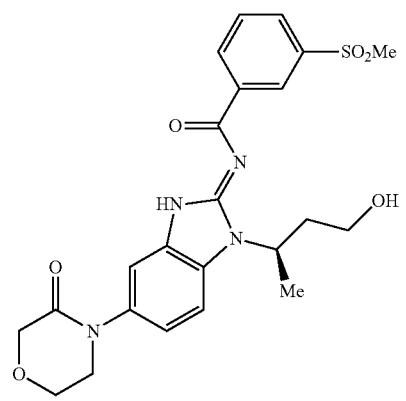 | 28 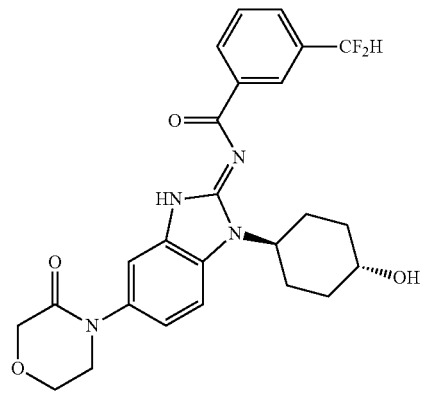 |
| 25 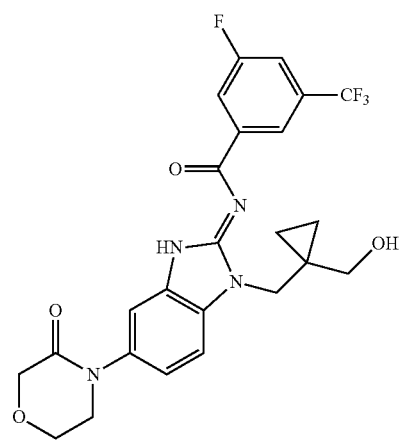 | 29 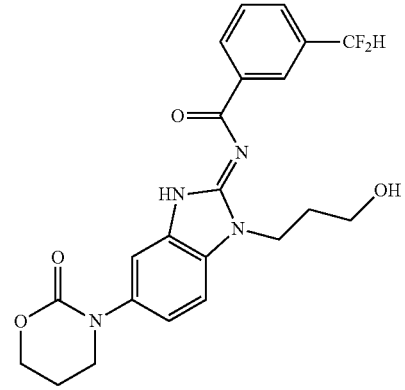 |
| 26 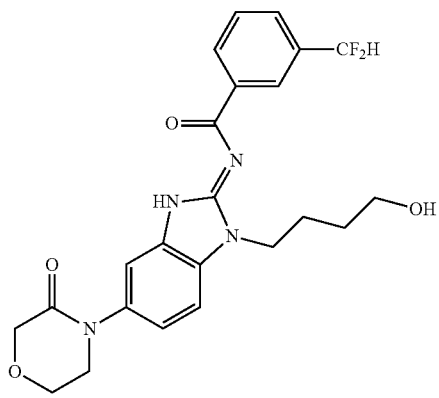 | 30 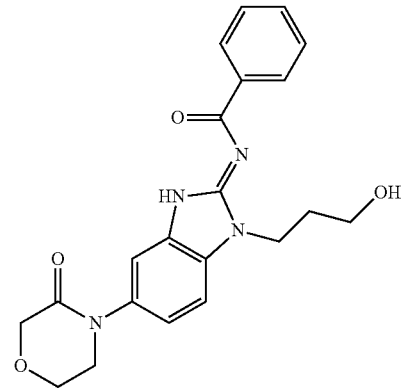 |
| 27 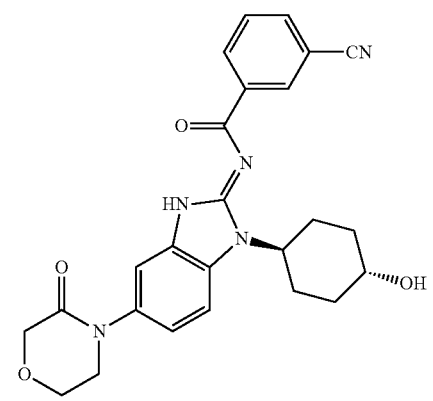 | 31 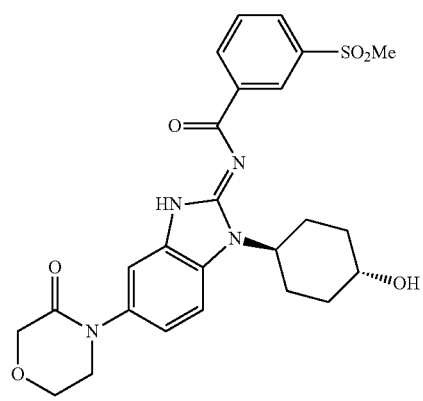 |

-continued
32
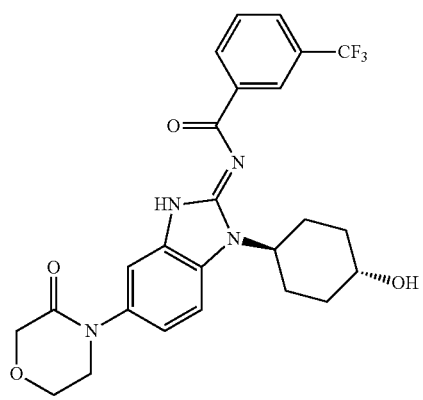
33
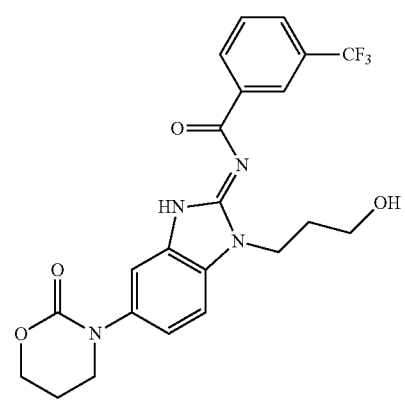
34
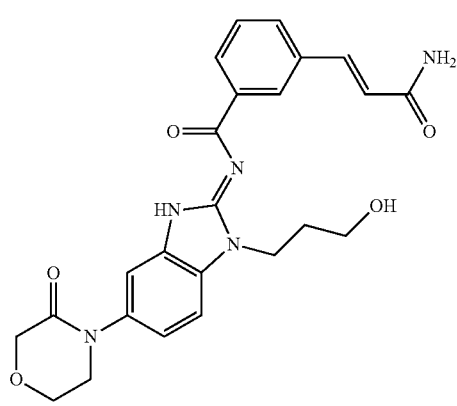
35
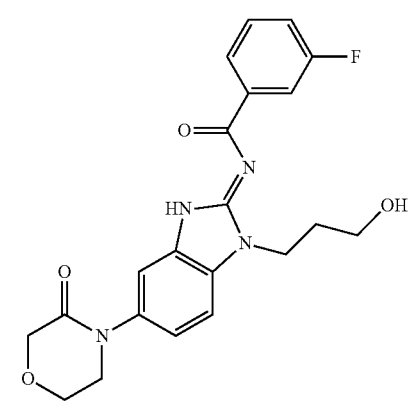
-continued
36
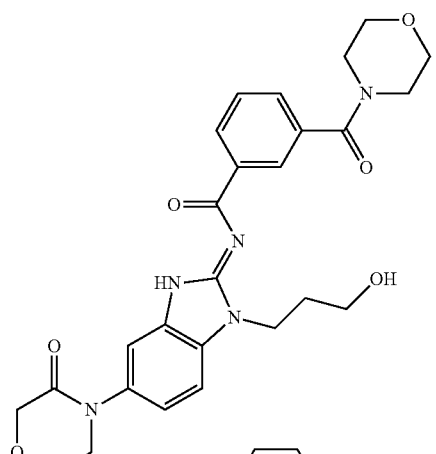
37
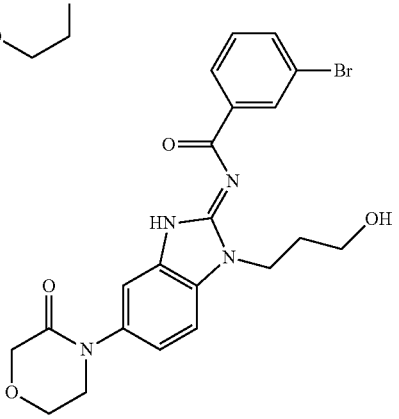
38
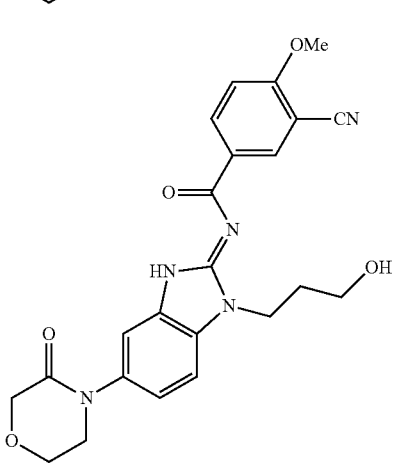
39
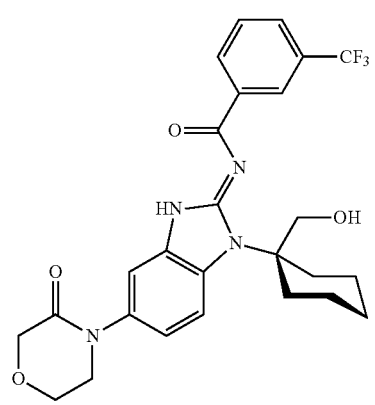

| 40 | 44 |
|---|---|
| 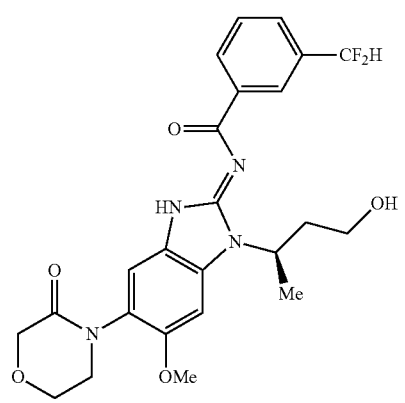 | 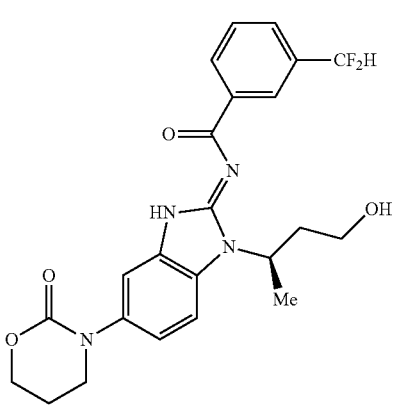 |
| 41 | 45 |
| 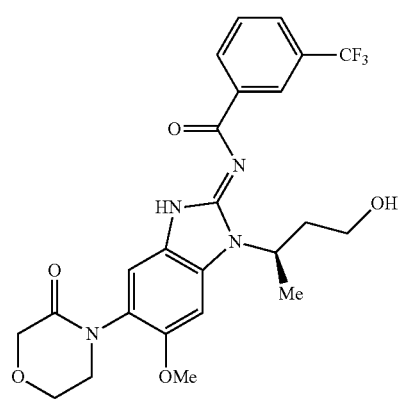 | 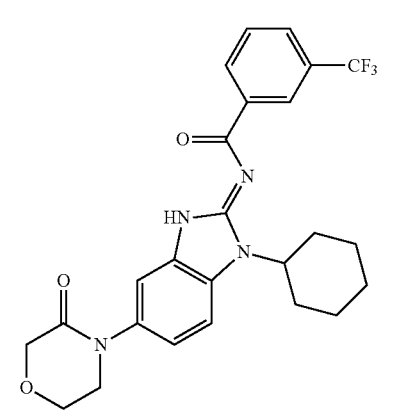 |
| 42 | 46 |
| 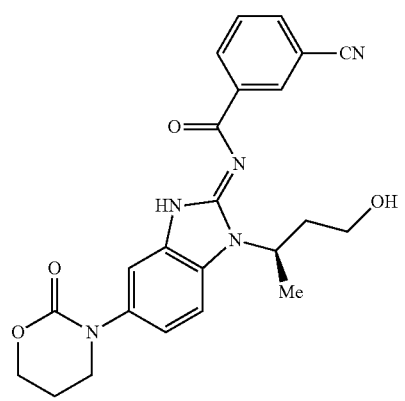 | 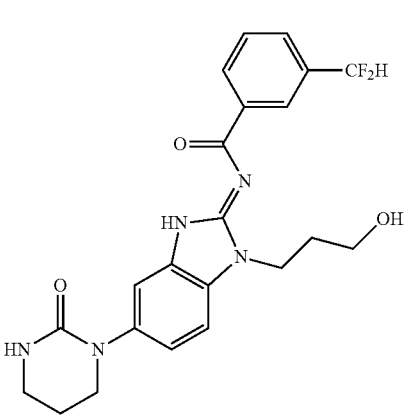 |
| 43 | 47 |
| 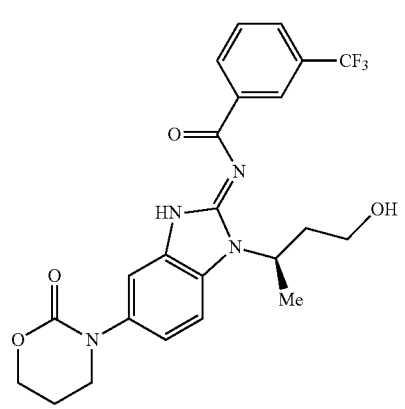 | 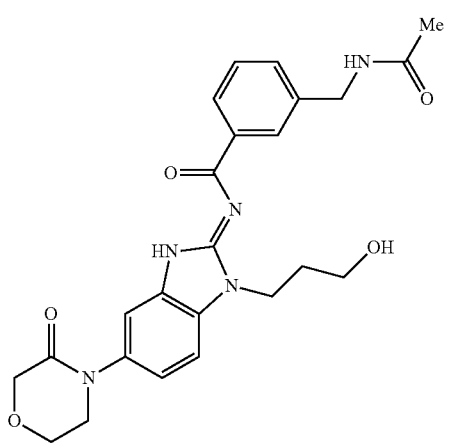 |

48
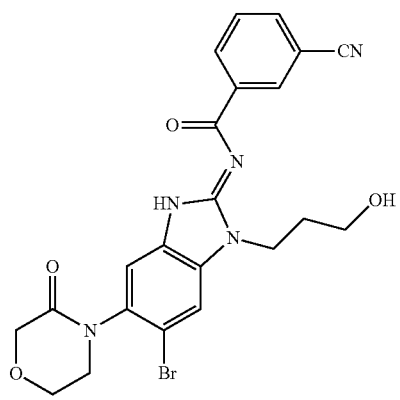
49
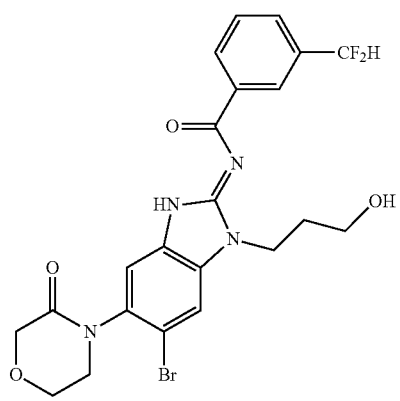
50
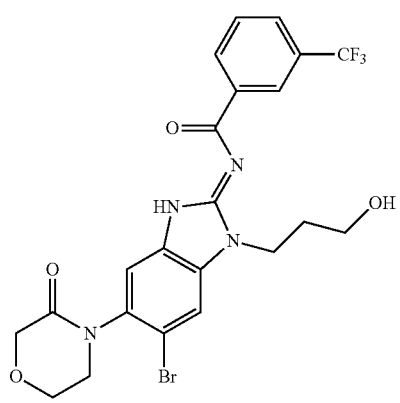
51
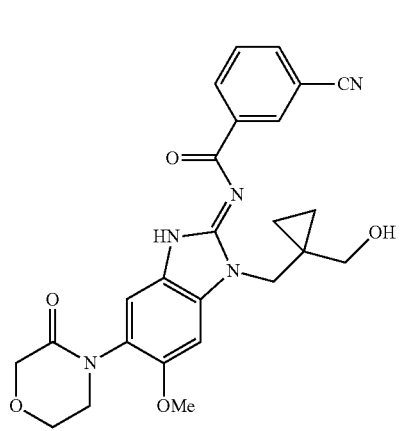
52
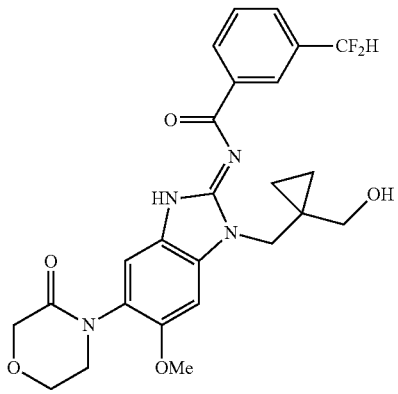
53
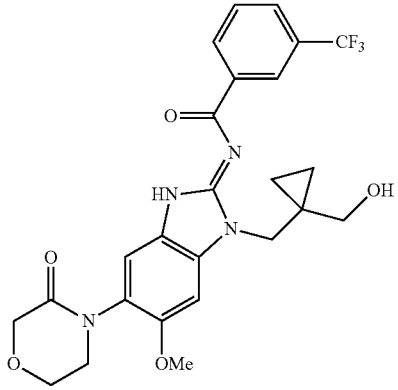
54
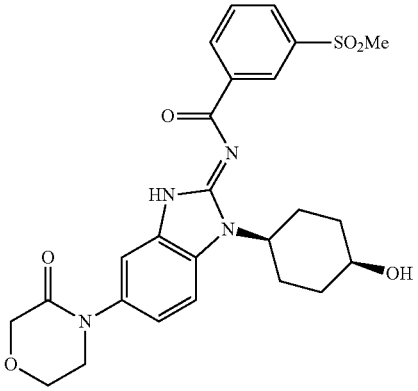
55
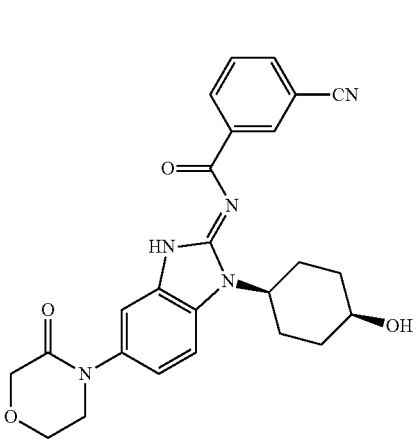

| 56 | 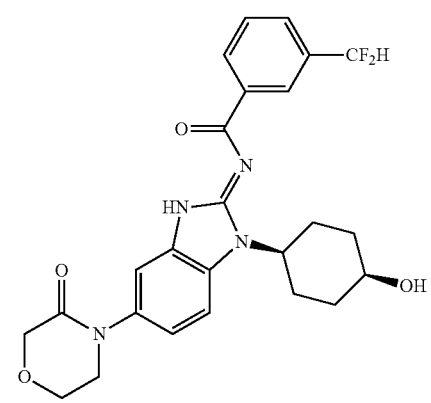 |
| --- | --- |
| 57 | 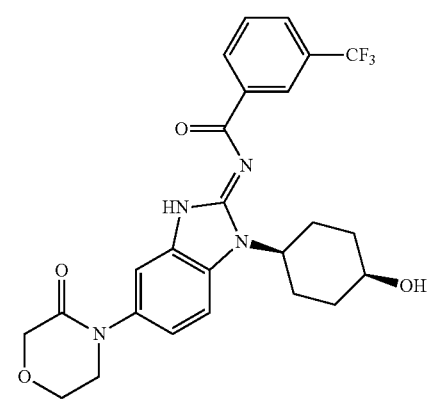 |
| 58 | 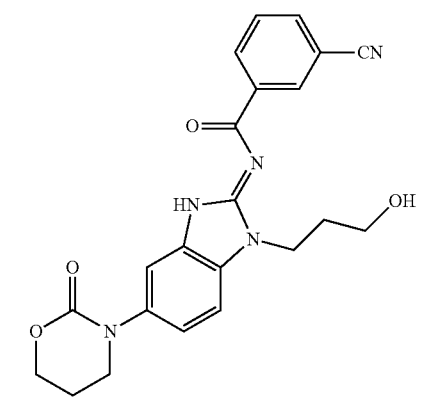 |
| 59 | 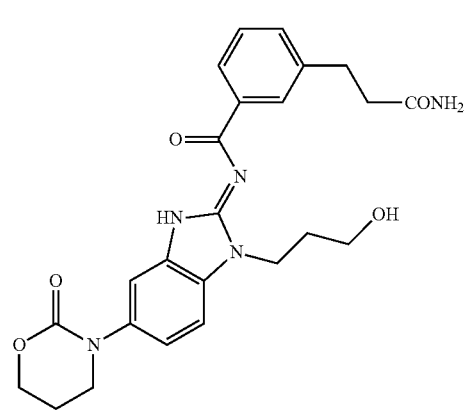 |
| 60 | 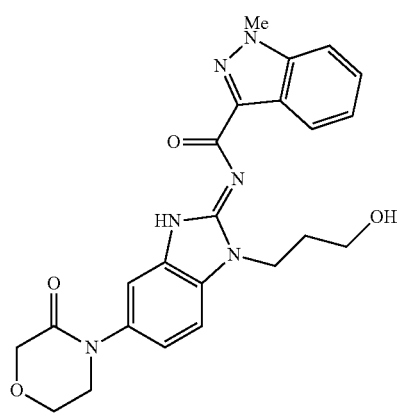 |
| --- | --- |
| 61 | 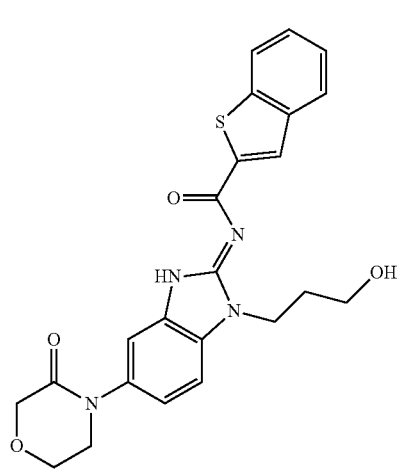 |
| 62 | 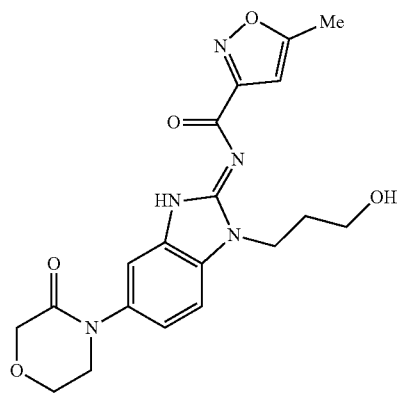 |
| 63 | 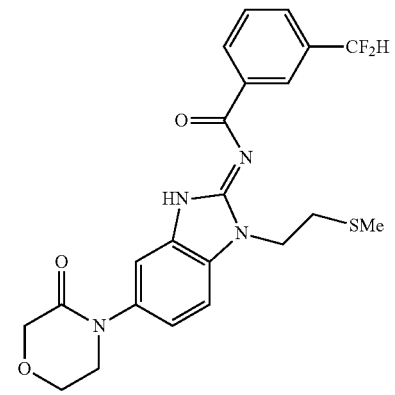 |

| 64 | 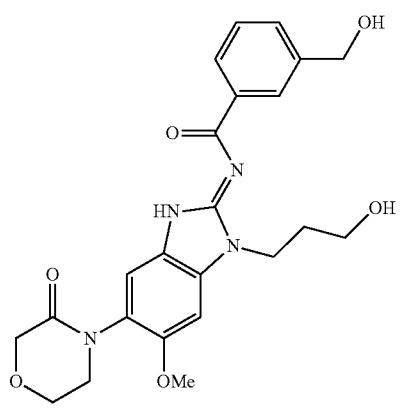 | 68 | 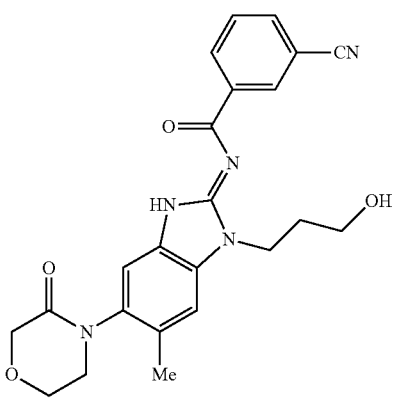 |
| 65 | 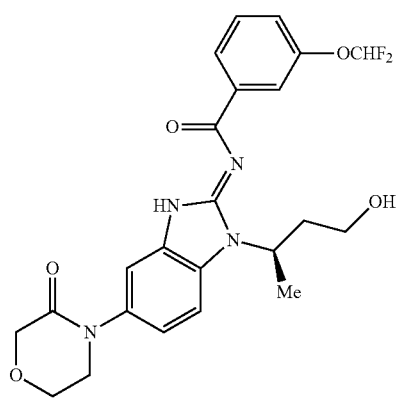 | 69 | 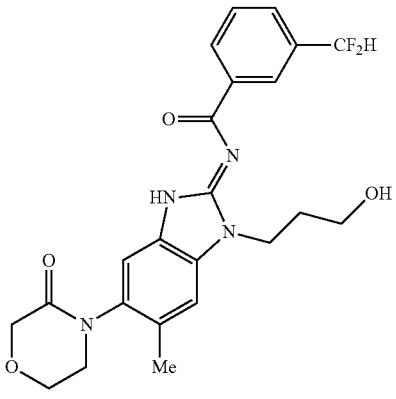 |
| 66 | 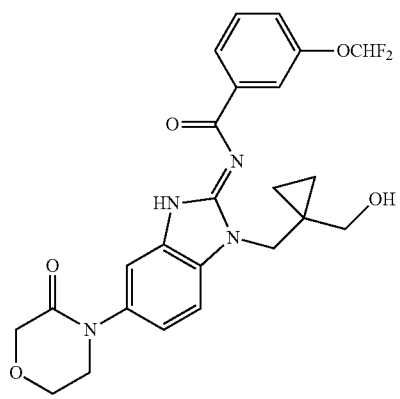 | 70 | 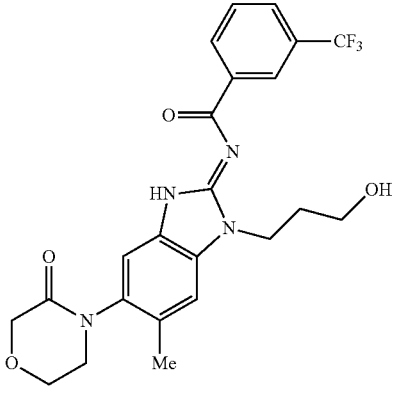 |
| 67 | 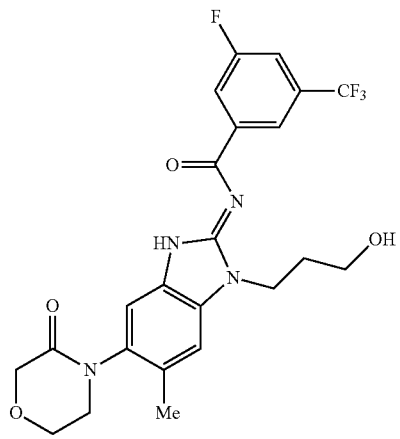 | 71 | 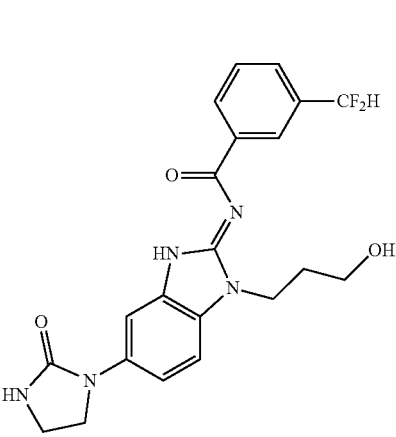 |

72 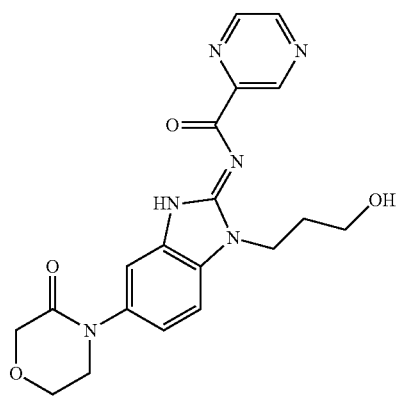
73 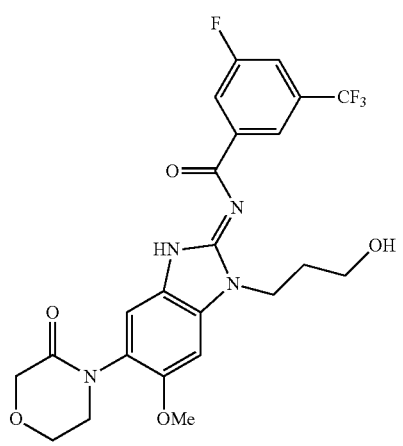
74 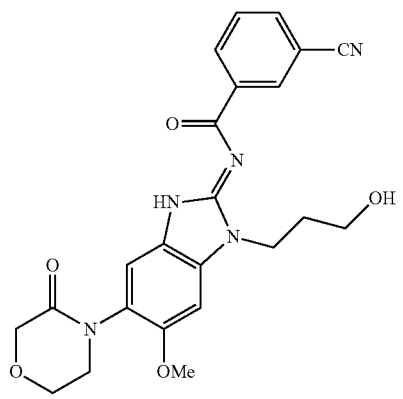
75 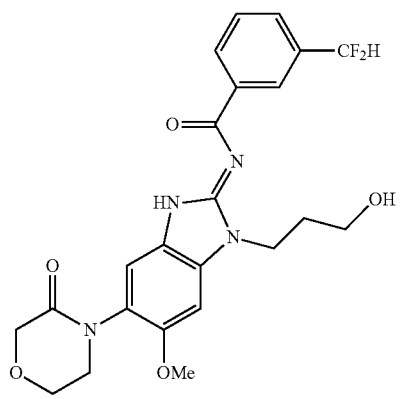
76 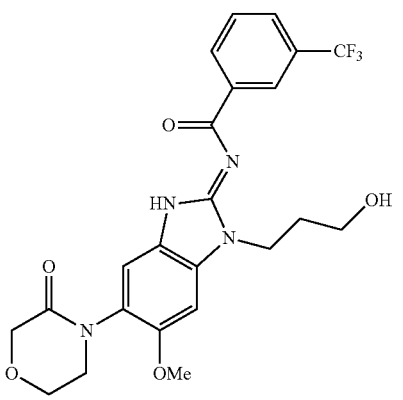
77 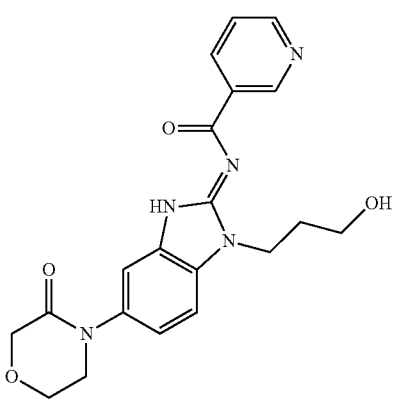
78 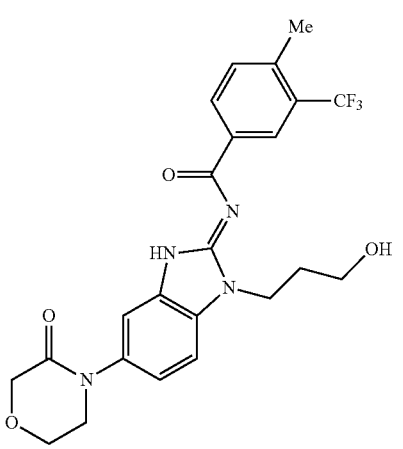
79 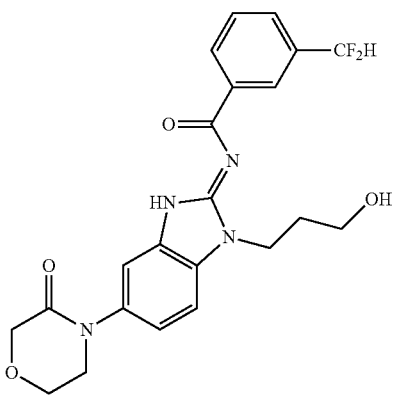

-continued
80 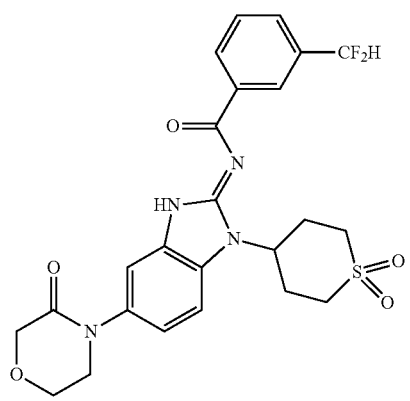
81 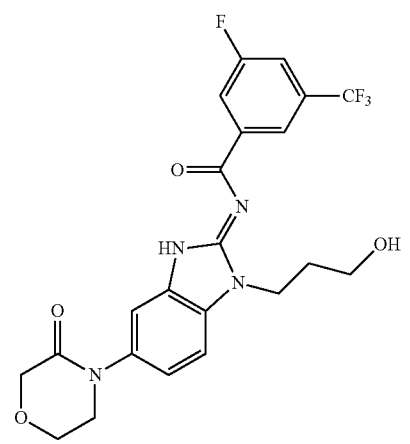
82 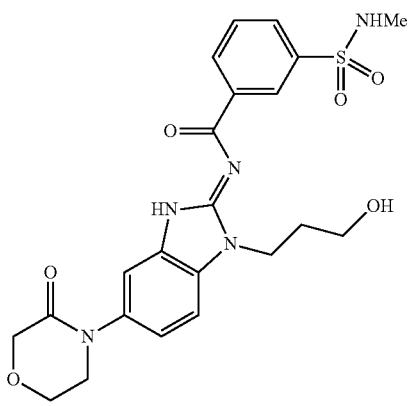
83 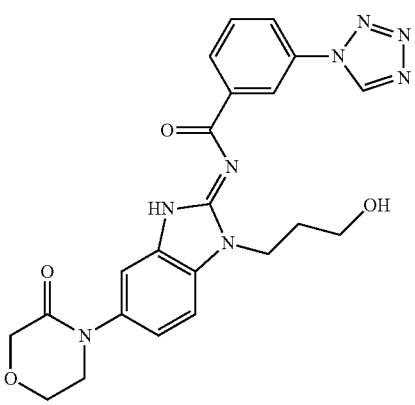
-continued
84 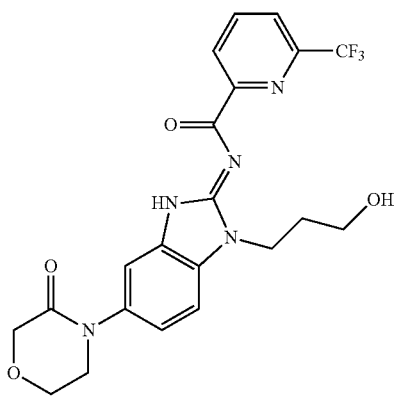
85 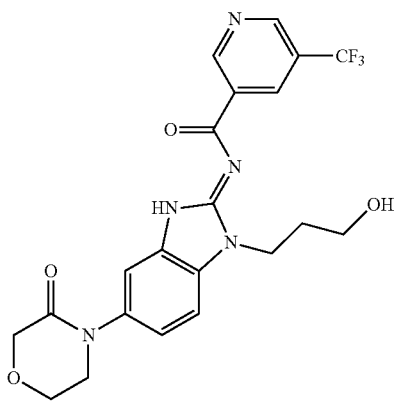
86 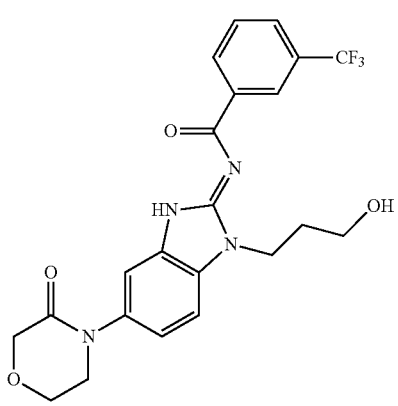
87 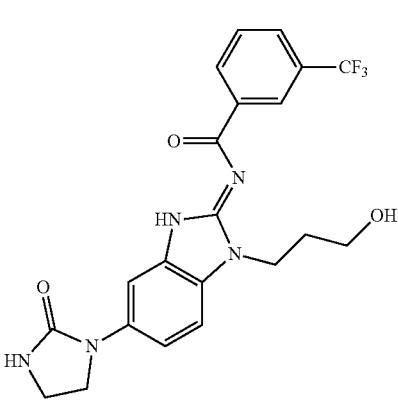

| 88 | 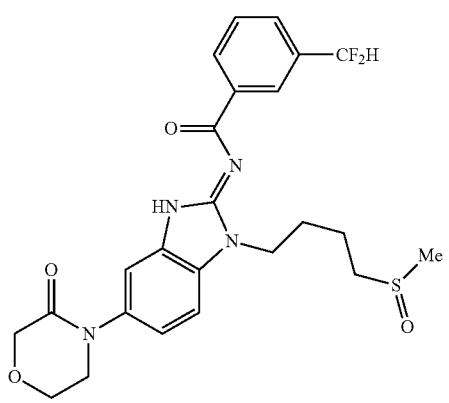 | 92 | 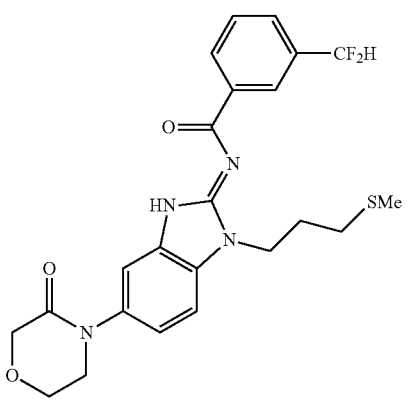 |
| 89 | 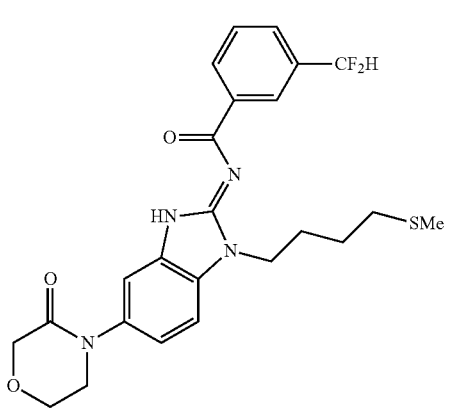 | 93 | 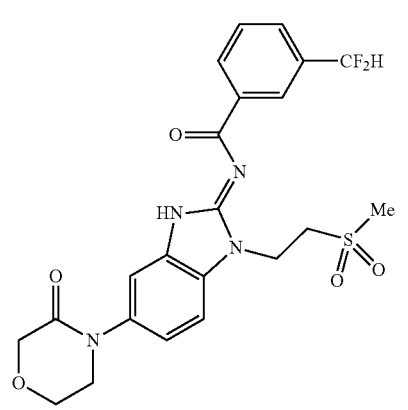 |
| 90 | 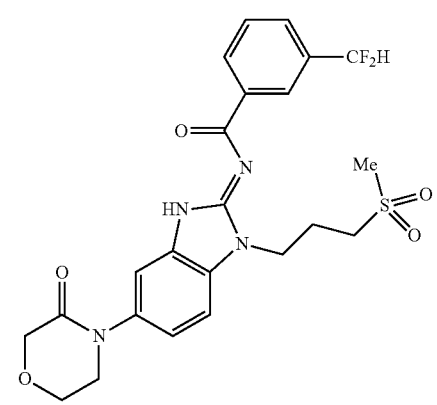 | 94 | 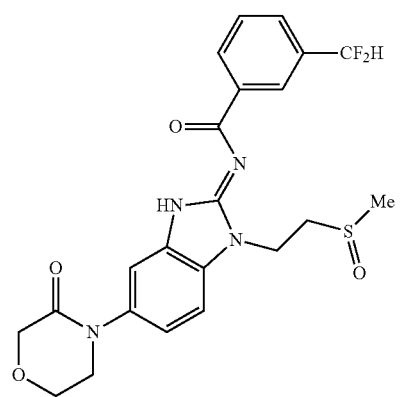 |
| 91 | 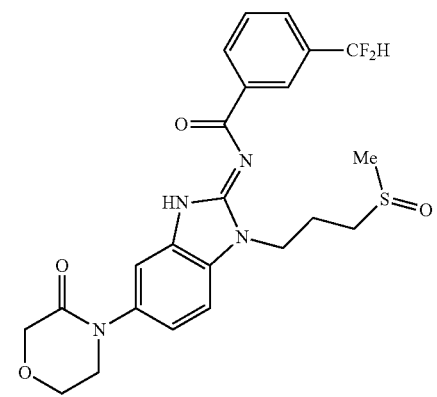 | 97 | 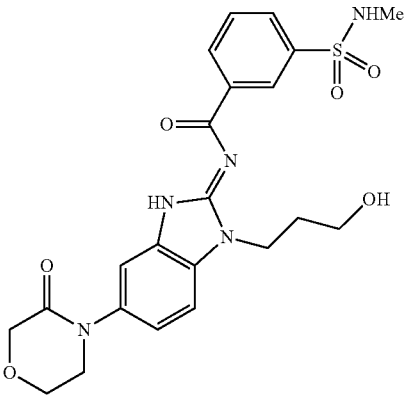 |

98
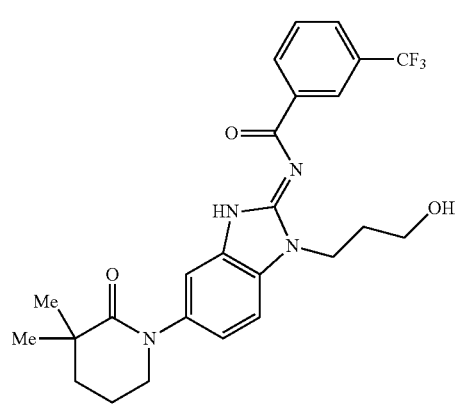
99
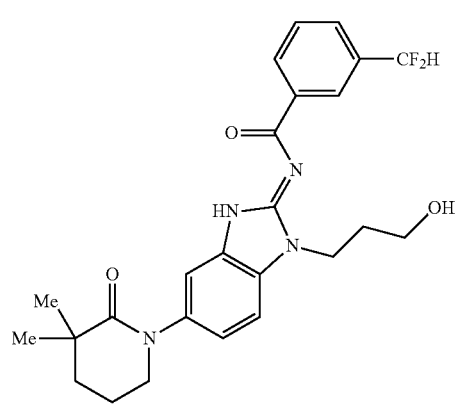
100
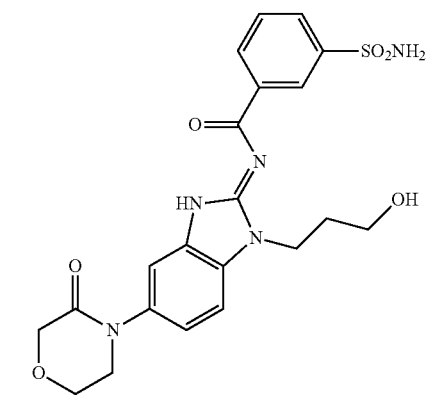
101
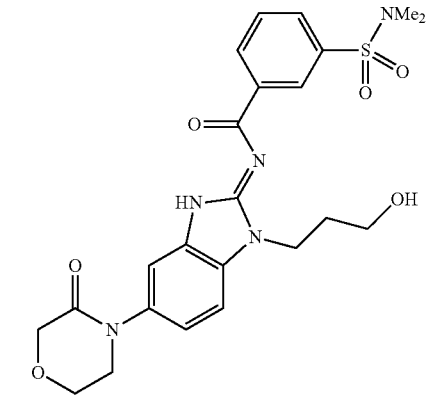
102
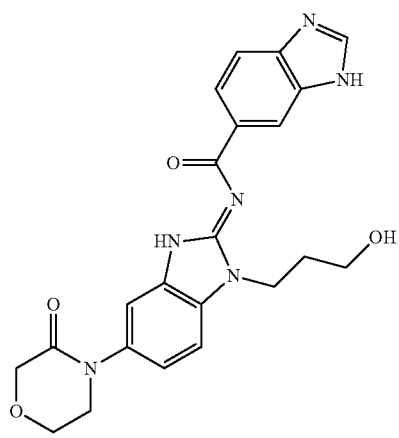
103
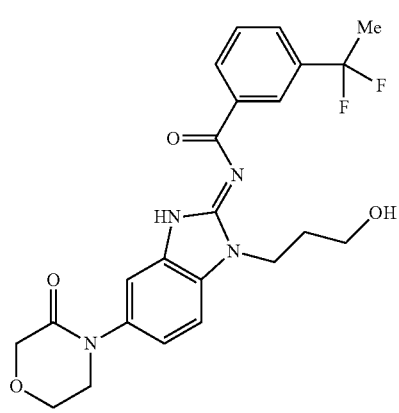
104
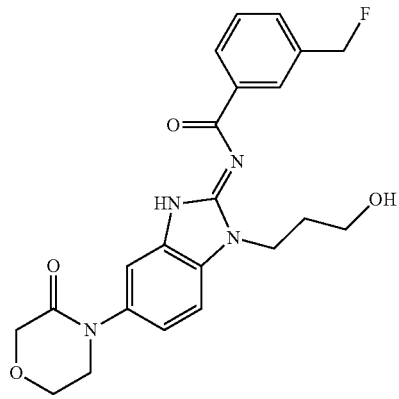
105
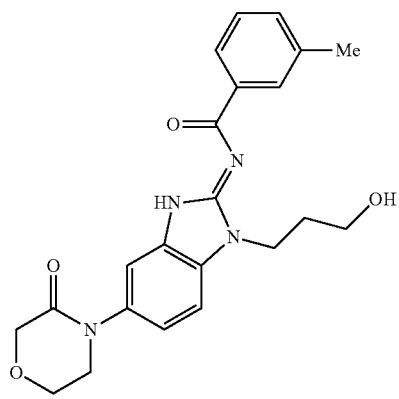

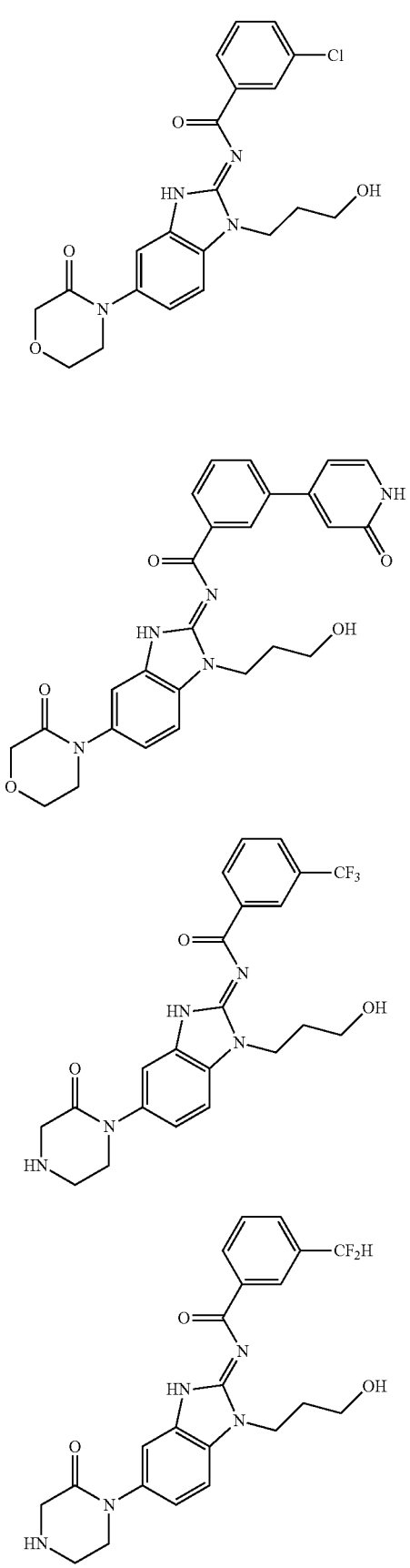

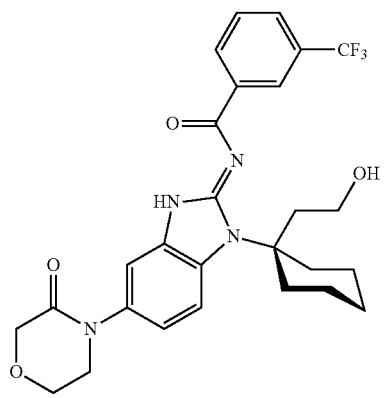
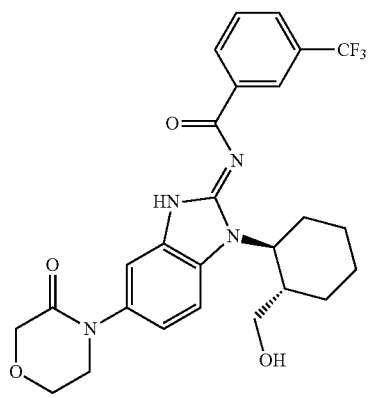

| 122 | 126 |
|---|---|
| 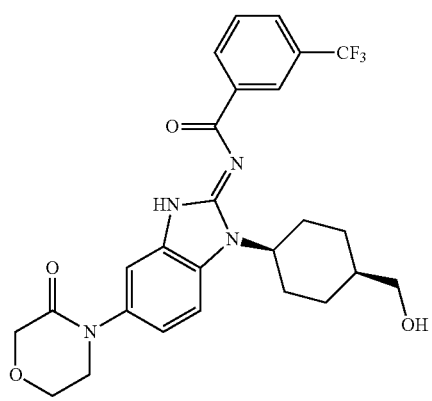 | 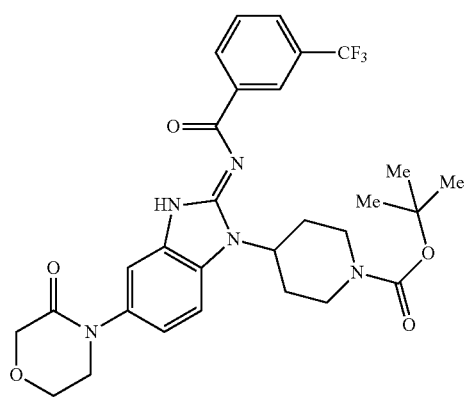 |
| 123 | 127 |
| 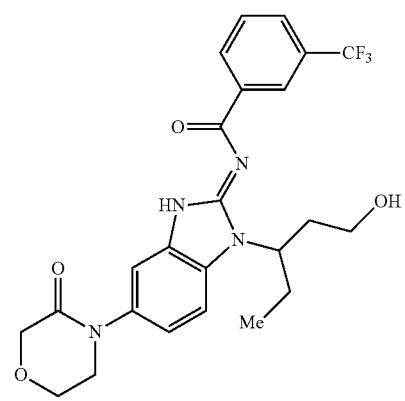 | 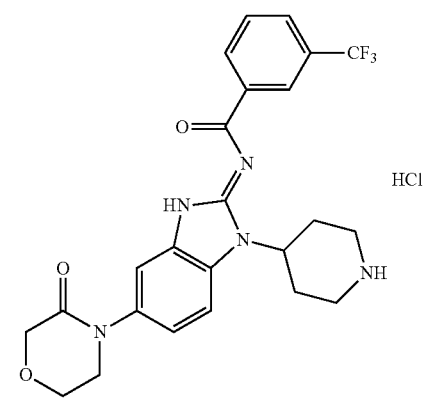 |
| 124 | 128 |
| 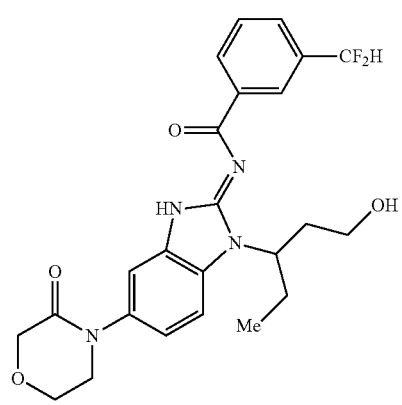 | 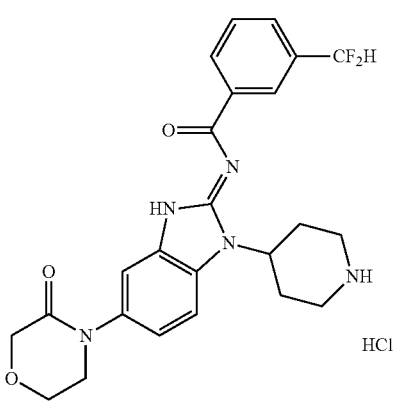 |
| 125 | 129 |

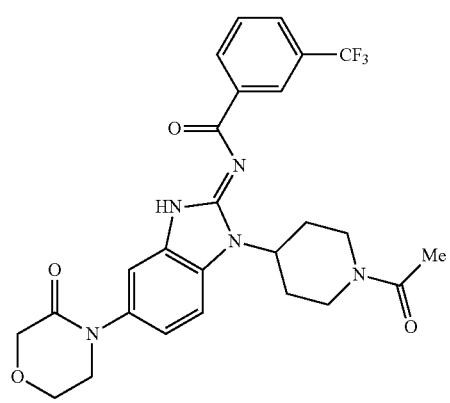
130
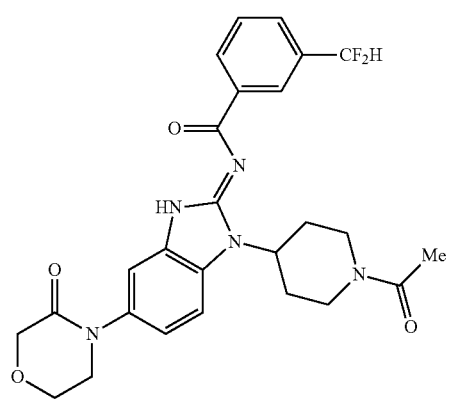
131
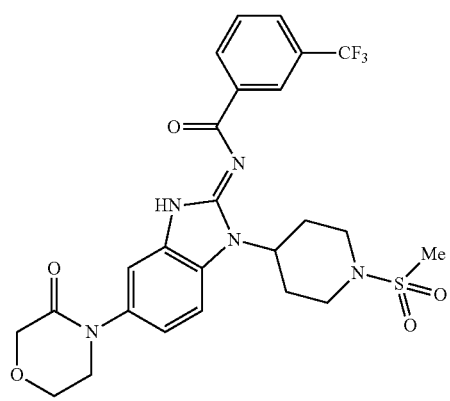
132
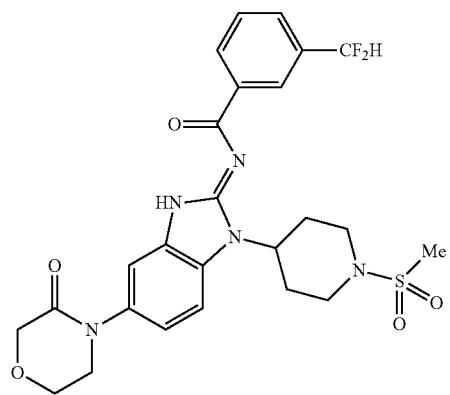
133
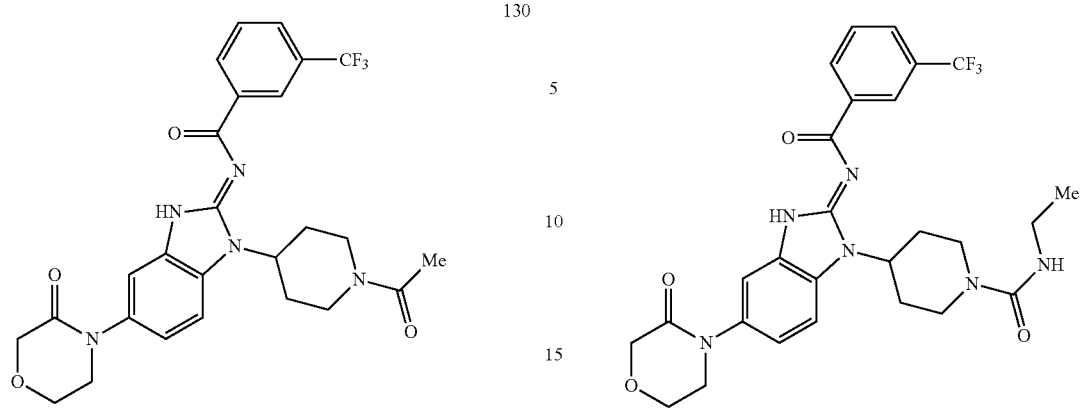
134
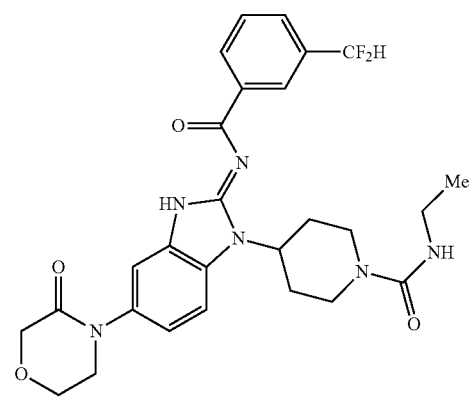
135
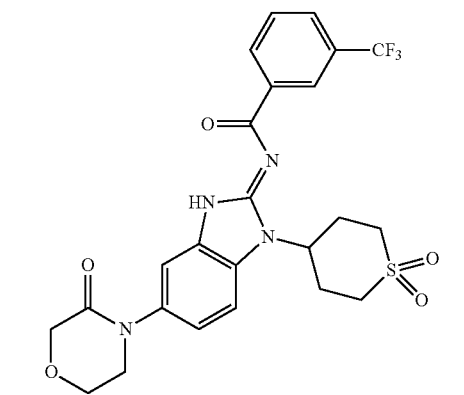
136
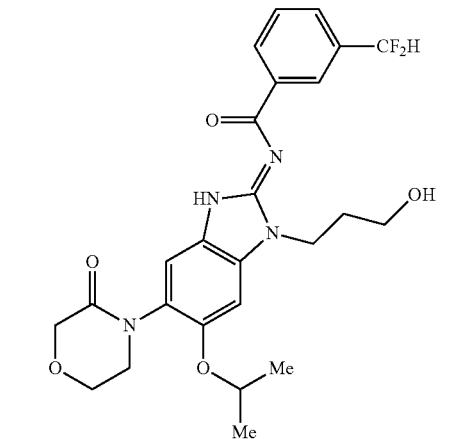
137

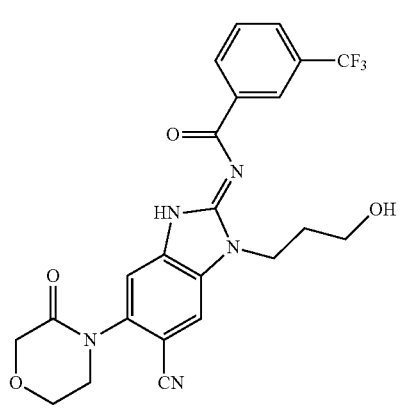
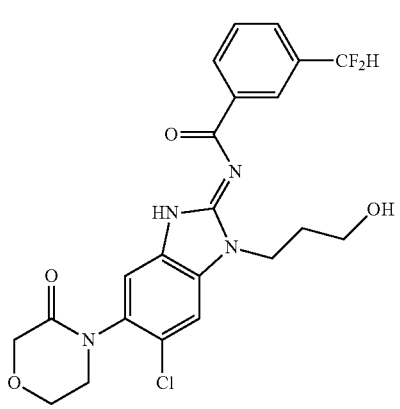

| 146 | 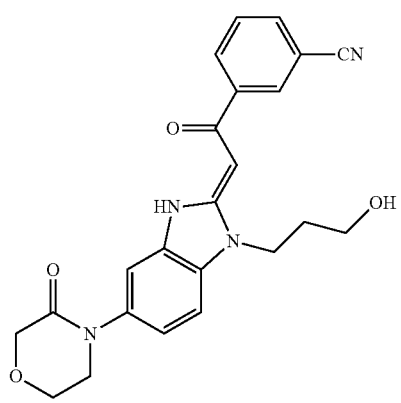 |
|---|---|
| 147 | 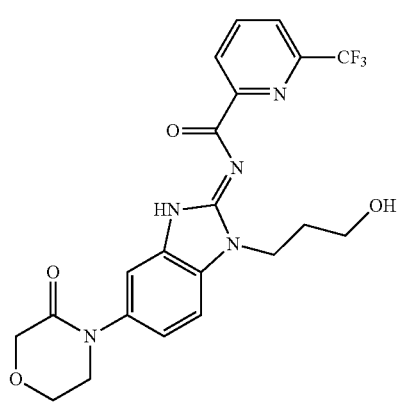 |
| 148 | 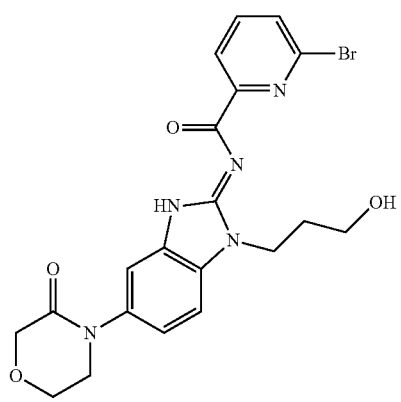 |
| 149 | 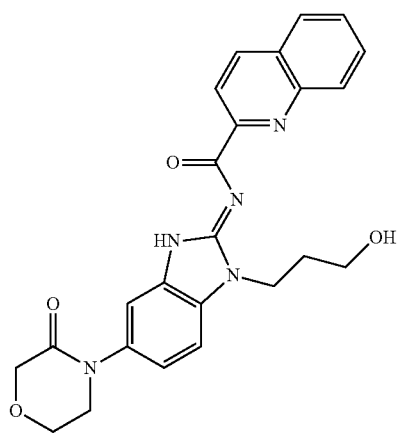 |
| 150 | 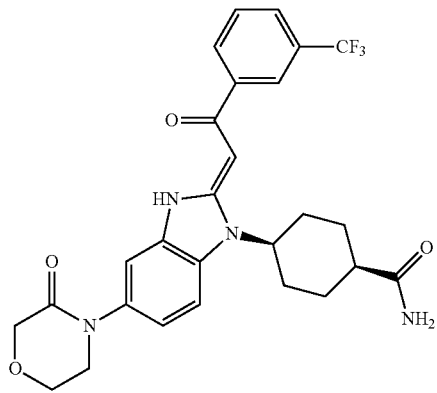 |
|---|---|
| 151 | 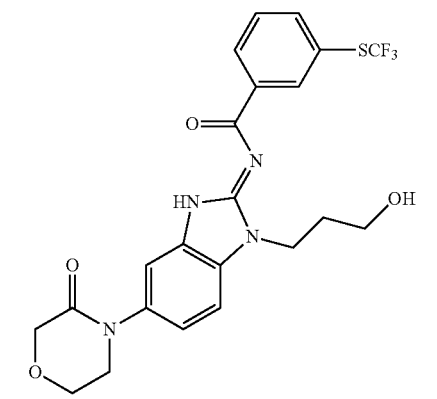 |
| 152 | 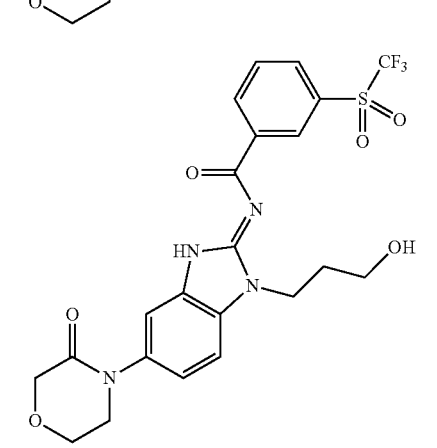 |
| 153 | 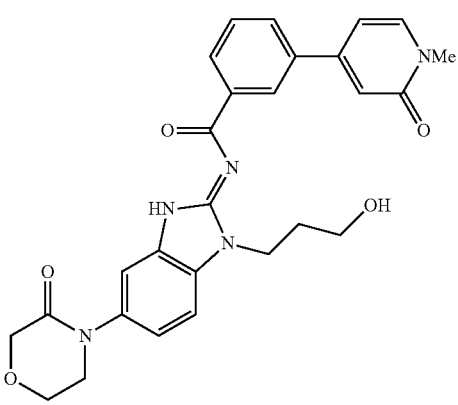 |

| 154 | 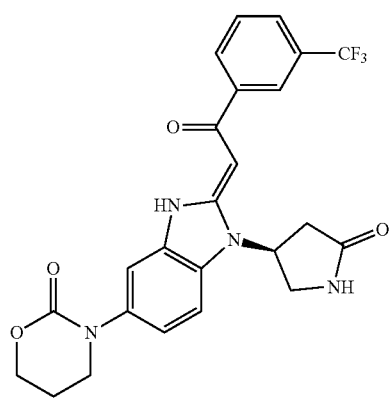 | 158 | 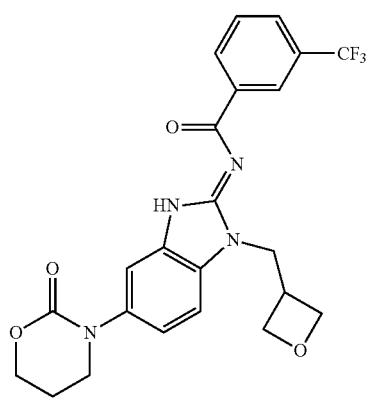 |
| --- | --- | --- | --- |
| 155 | 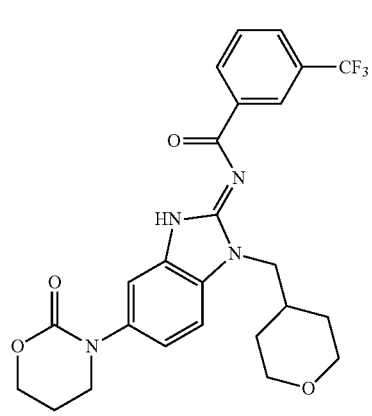 | 159 | 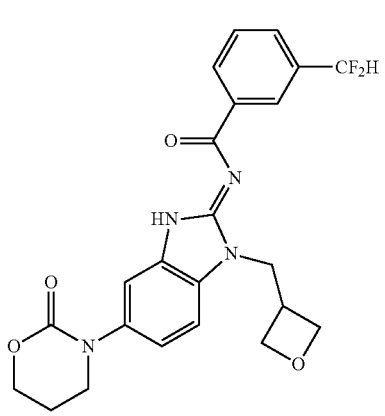 |
| 156 | 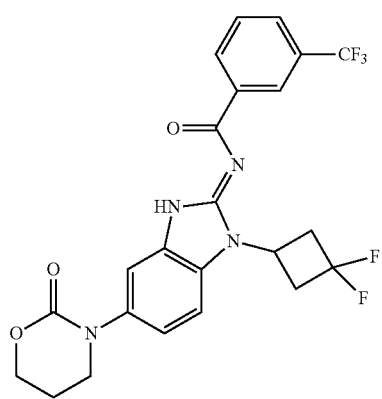 | 160 | 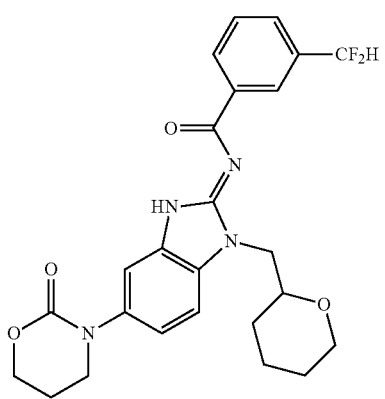 |
| 157 | 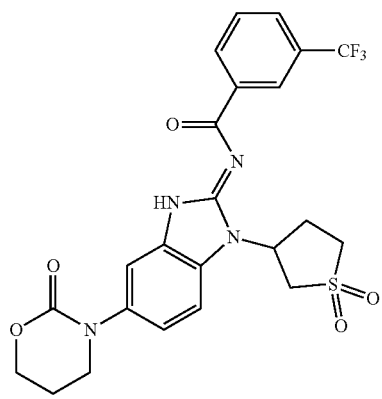 | 161 | 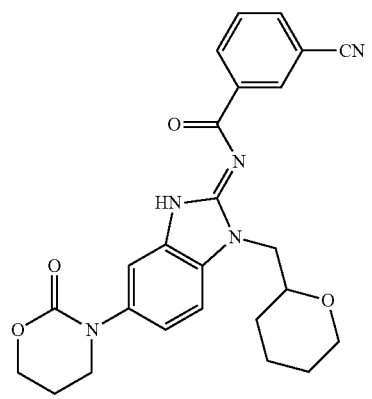 |

| | |
|---|---|
| 162 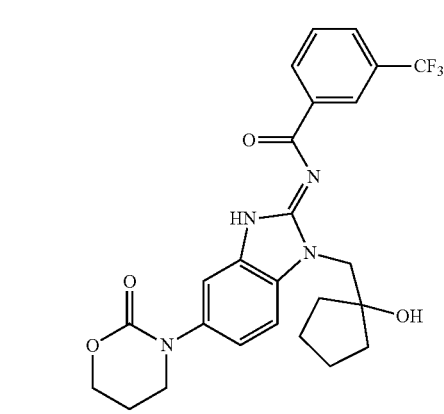 | 166 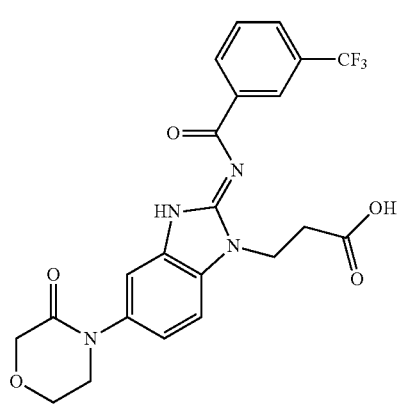 |
| 163 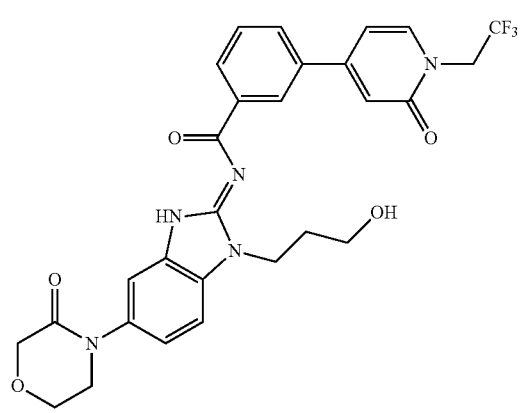 | 167 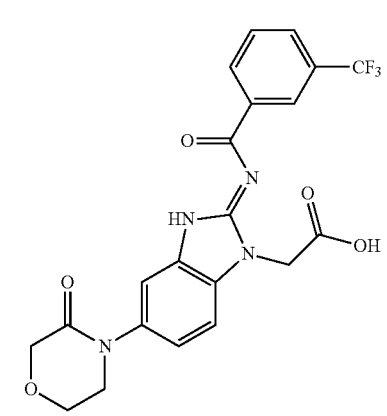 |
| 164 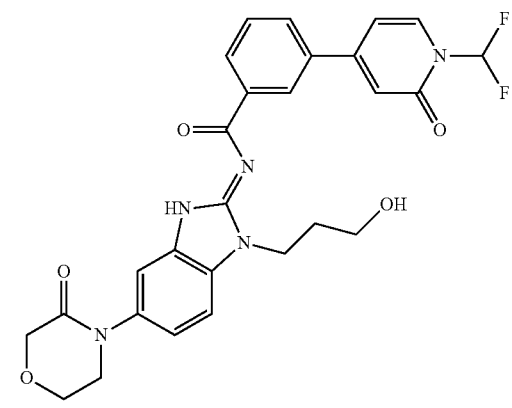 | 168 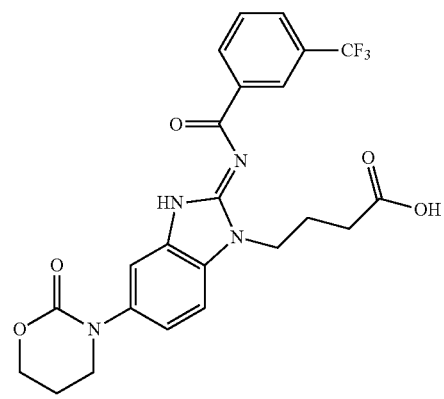 |
| 165 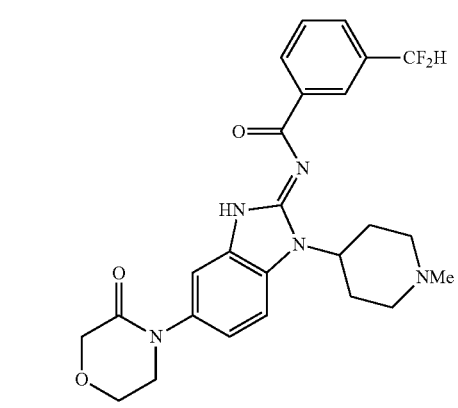 | 169 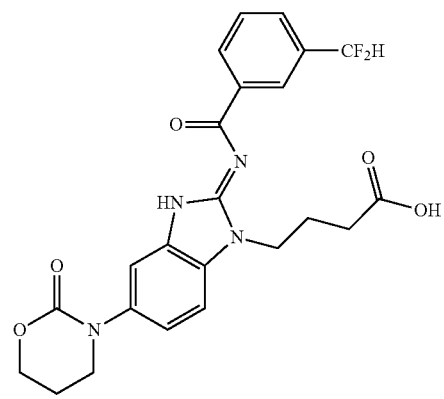 |

170 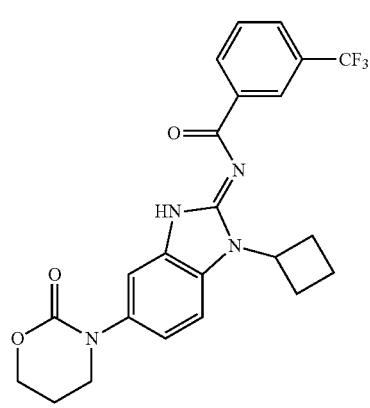
171 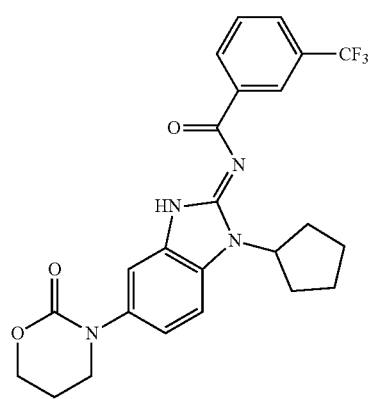
172 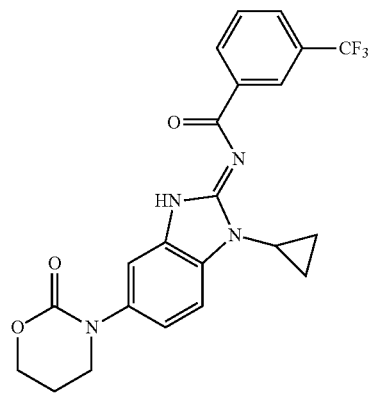
173 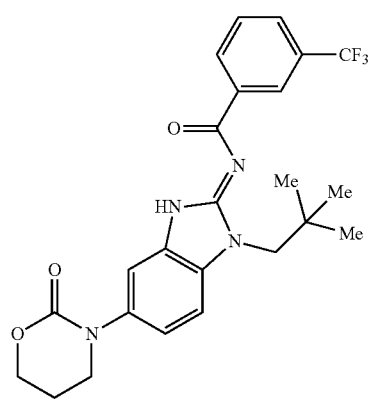
174 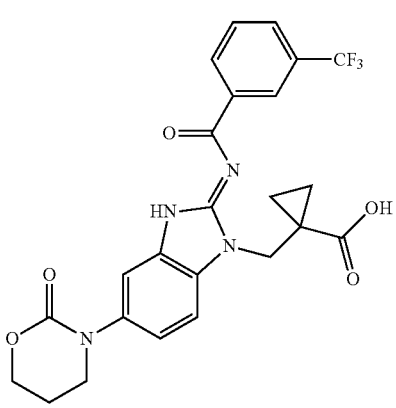
175 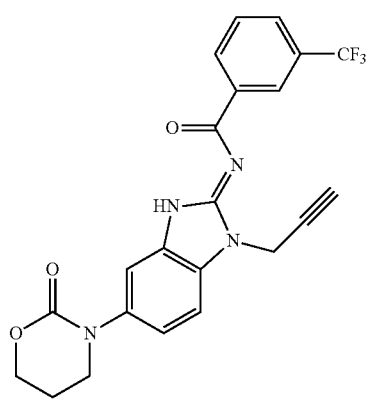
176 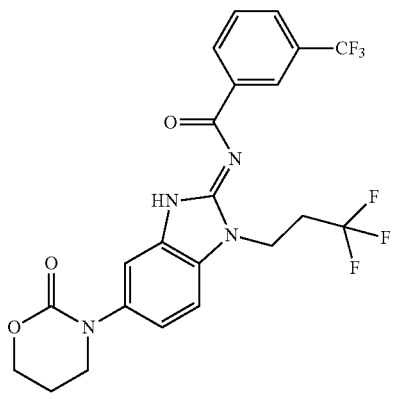
177 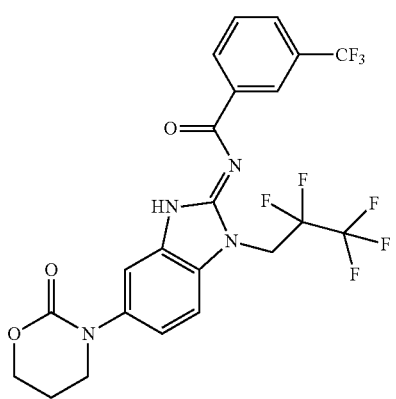

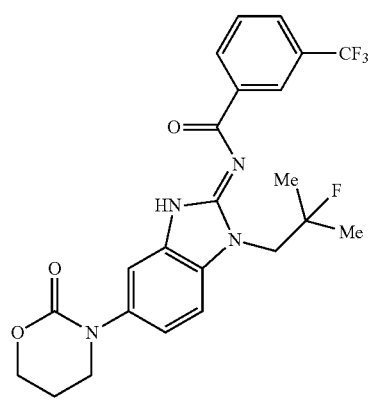
178
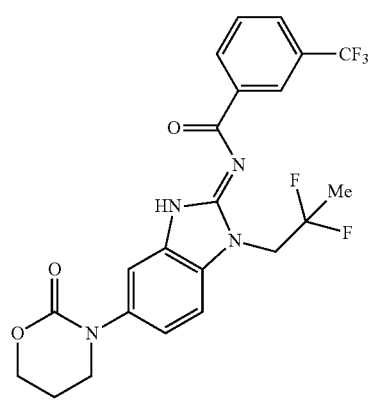
179
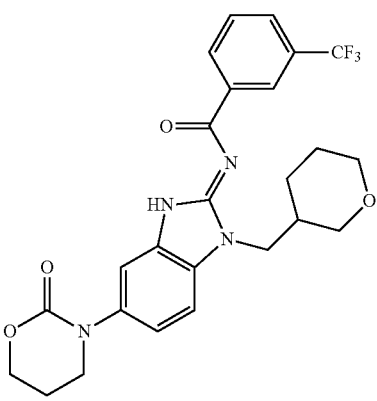
180
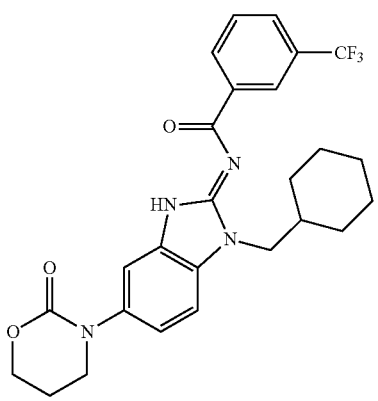
181
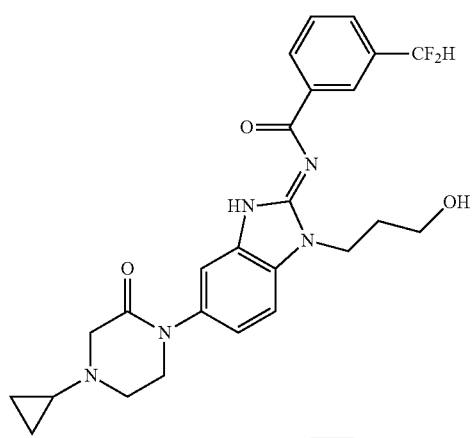
182
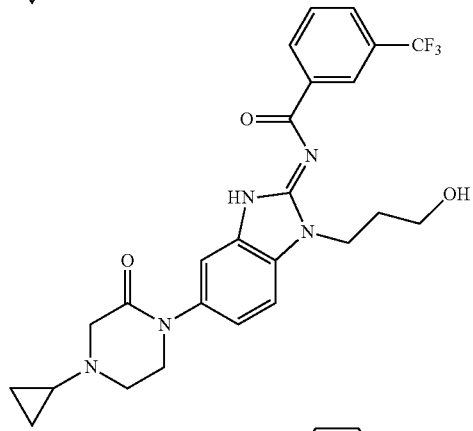
183
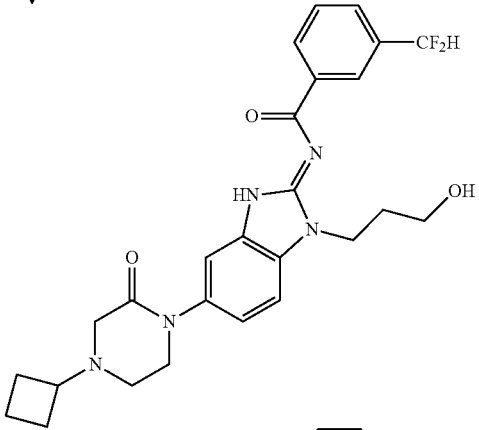
184
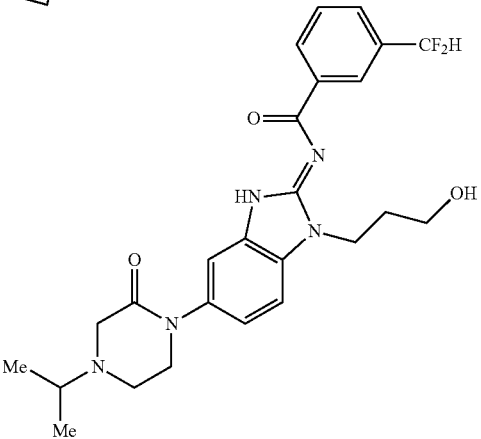
185

186 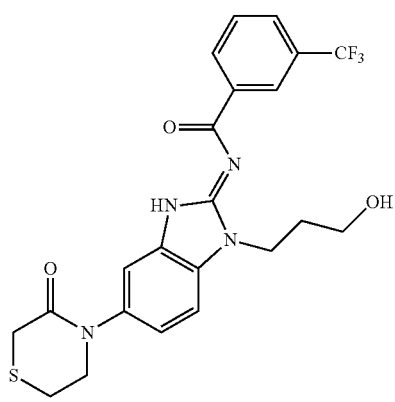
187 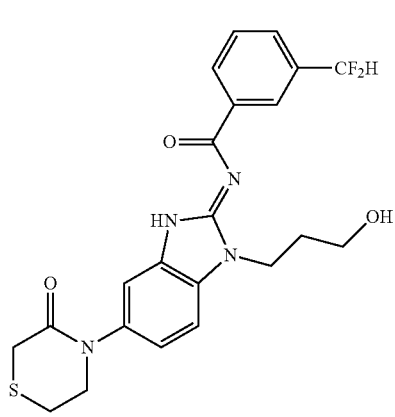
188 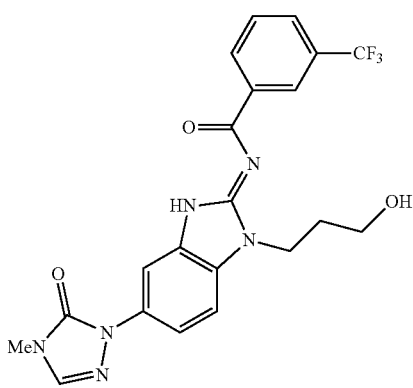
189 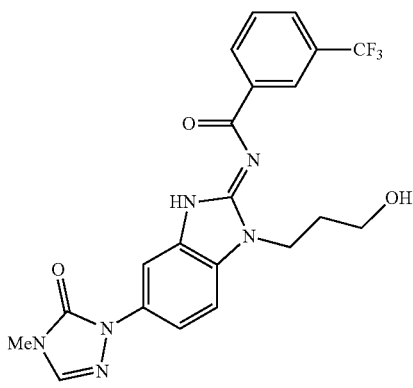
190 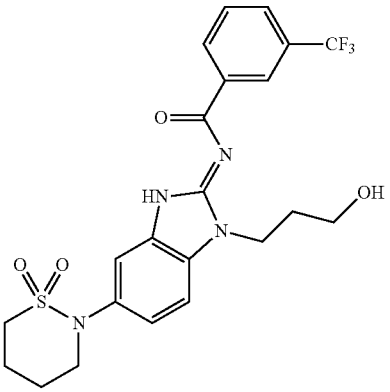
191 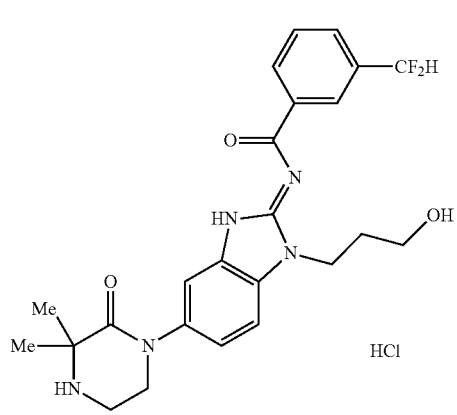
HCl
192 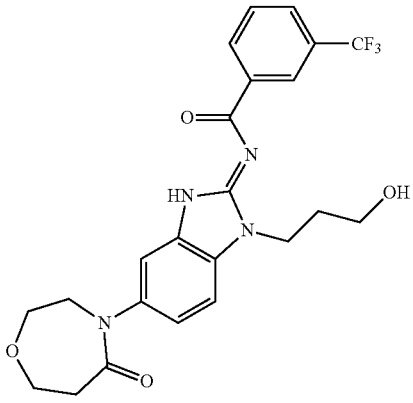
193 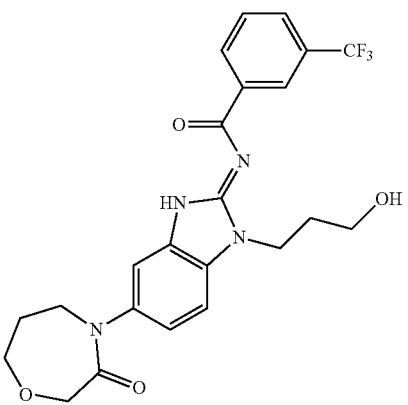

194
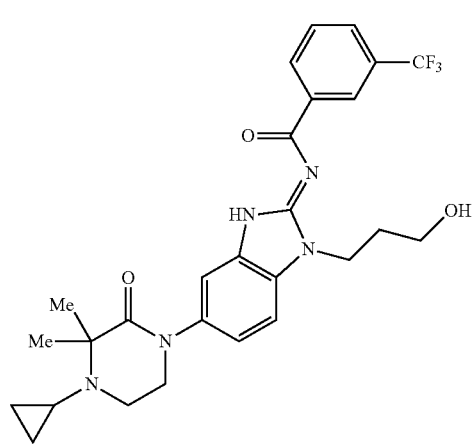
195
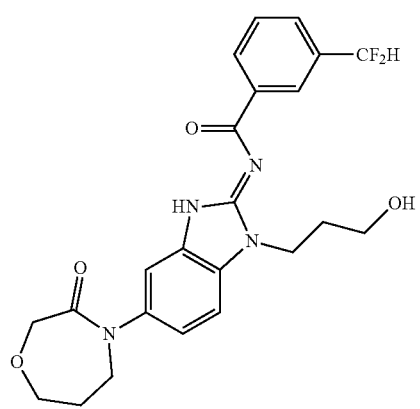
196
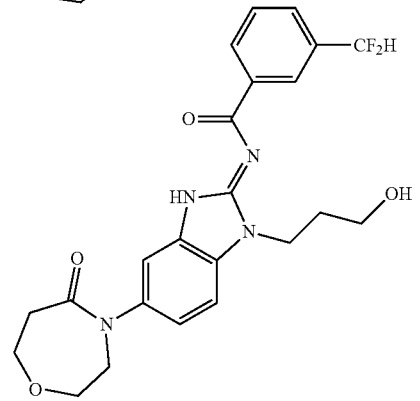
197
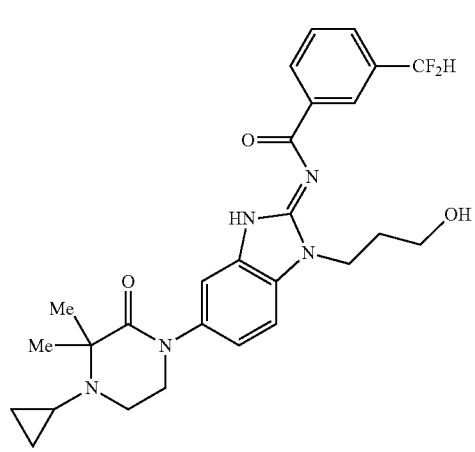
198
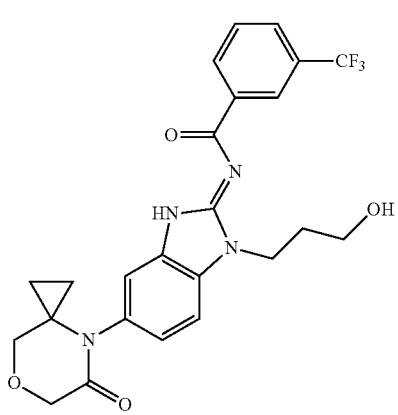
199
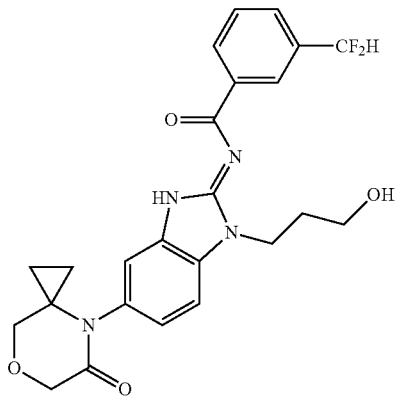
200
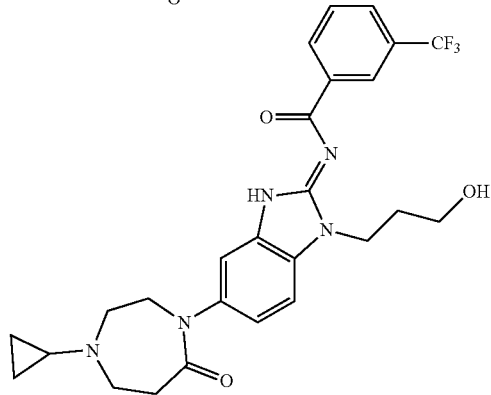
201
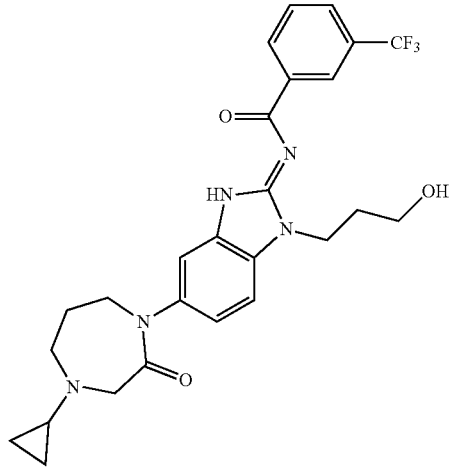

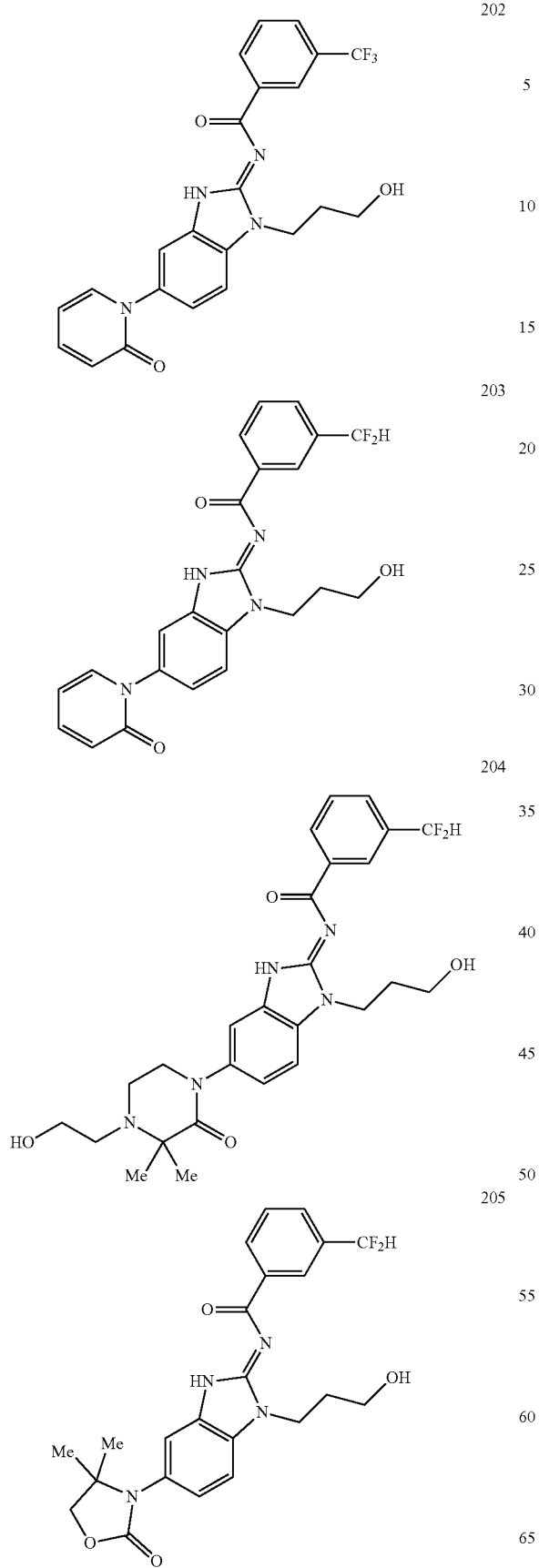
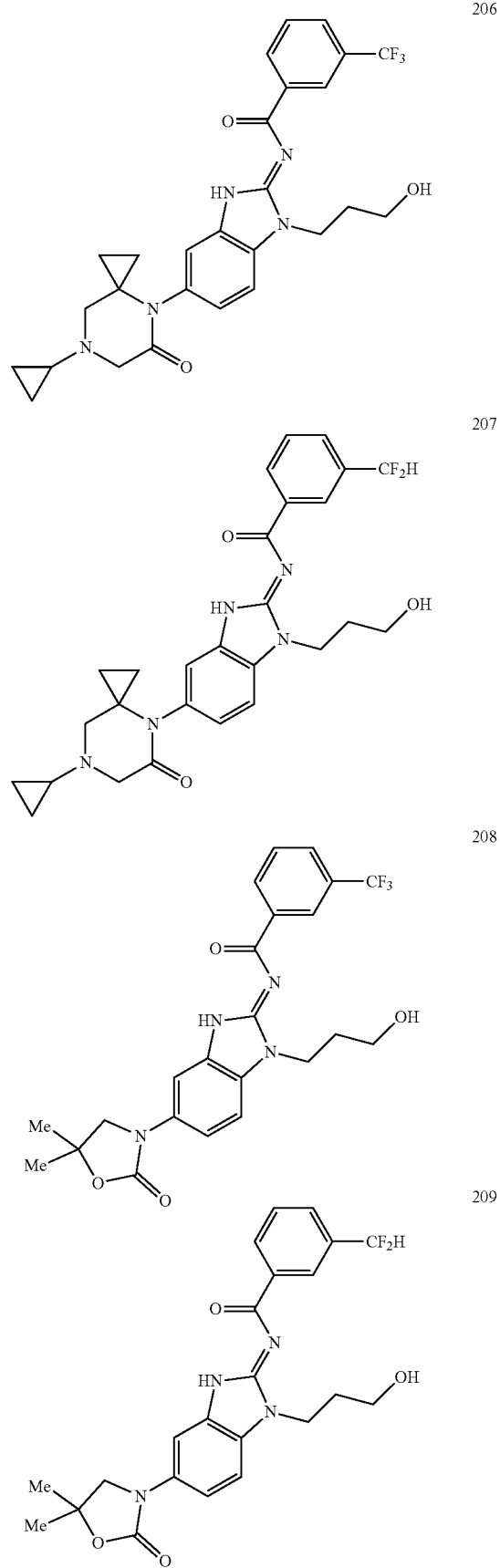

210
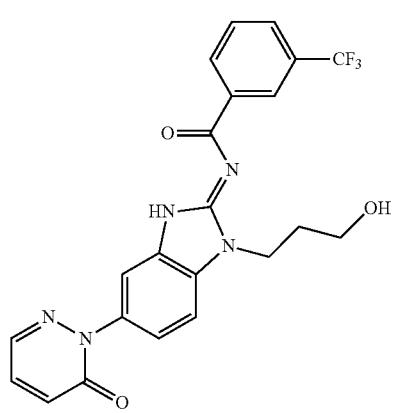
211
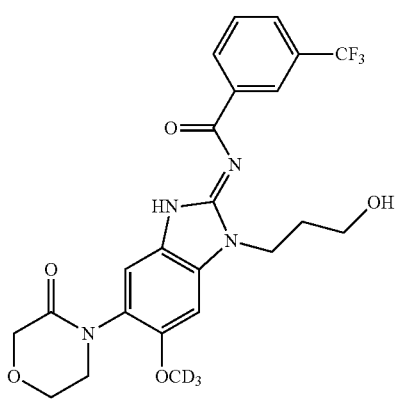
212
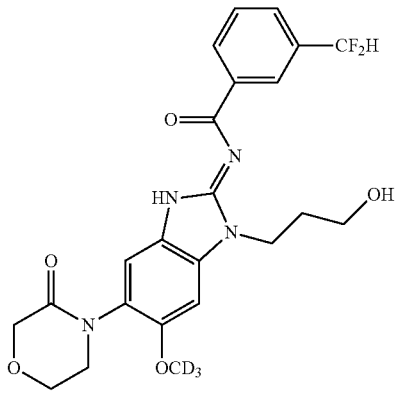
213
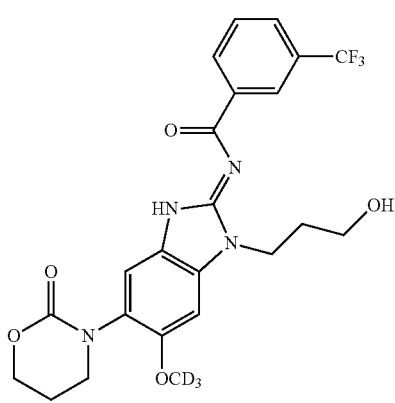
214
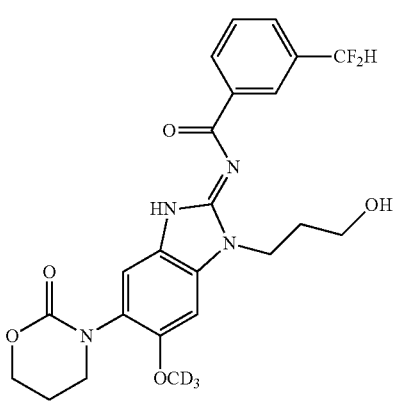
215
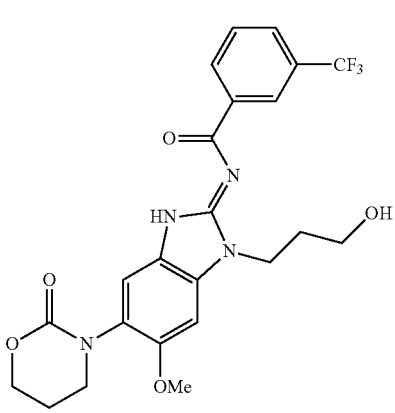
216
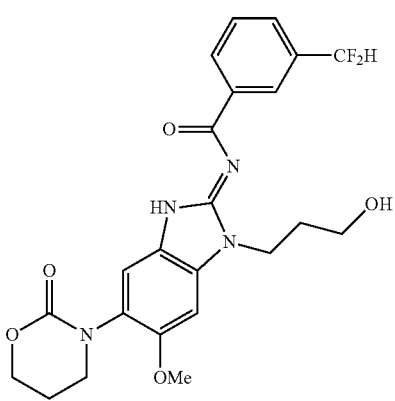
217
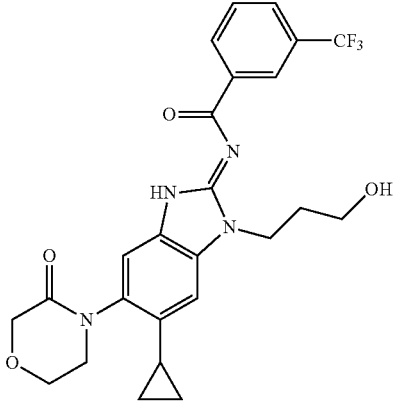

-continued

218

219

220

221

222

223

224

225

226
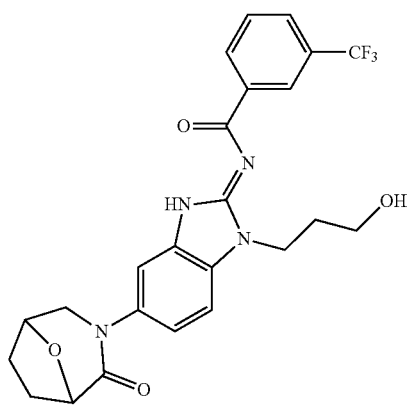
227
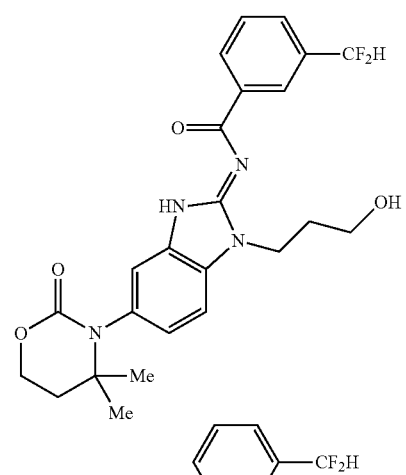
228
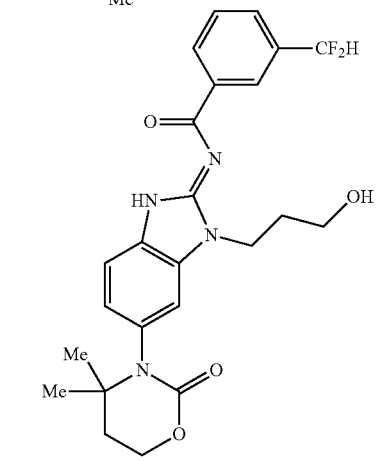
229
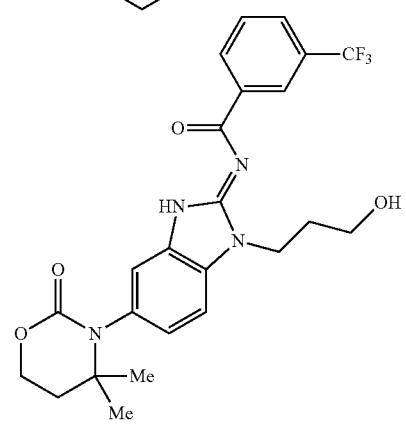
230
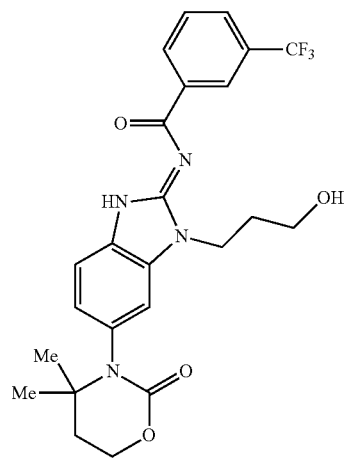
231
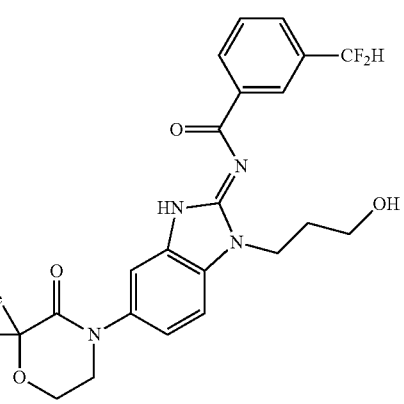
232
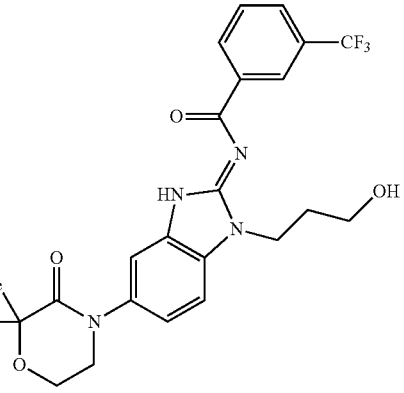
233
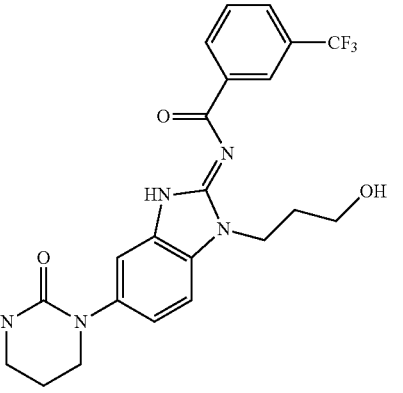

| 234 | 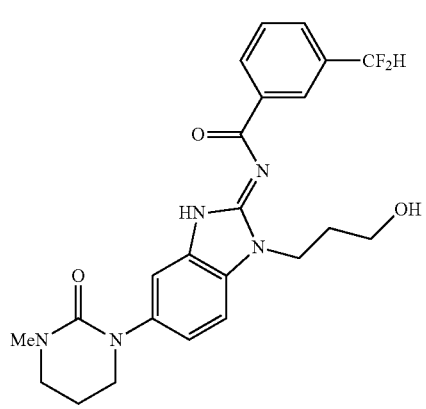 | 238 | 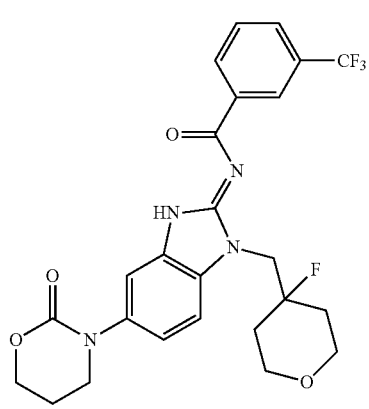 [SMILES: O=C(/N=c1\[nH]c2cc(N3CCCOC3=O)ccc2n1CC1(F)CCOCC1)c1cccc(C(F)(F)F)c1] |
| 235 | 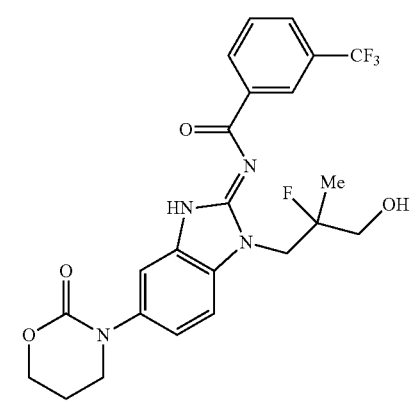 | 239 | 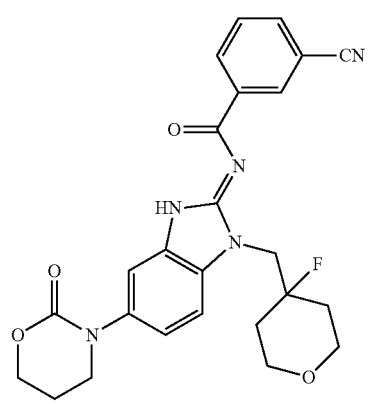 [SMILES: N#Cc1cccc(C(=O)/N=c2\[nH]c3cc(N4CCCOC4=O)ccc3n2CC2(F)CCOCC2)c1] |
| 236 | 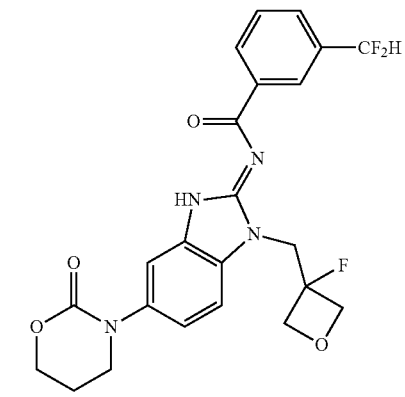 | 240 | 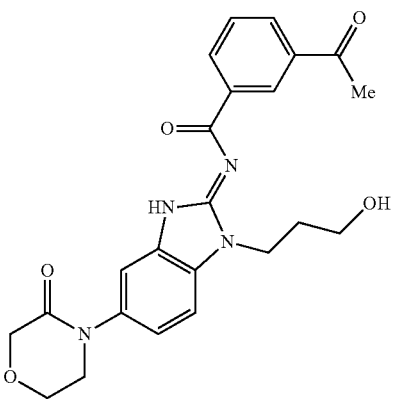 [SMILES: CC(=O)c1cccc(C(=O)/N=c2\[nH]c3cc(N4CCOCC4=O)ccc3n2CCCO)c1] |
| 237 | | 241 | 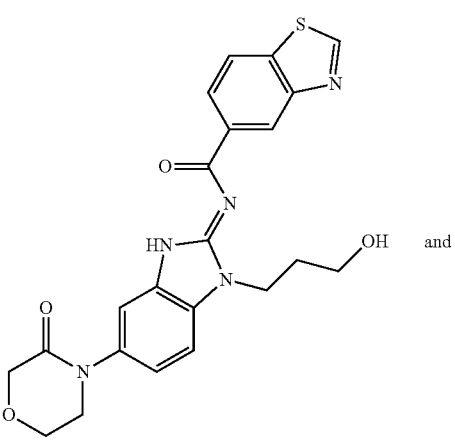 and |

-continued

242

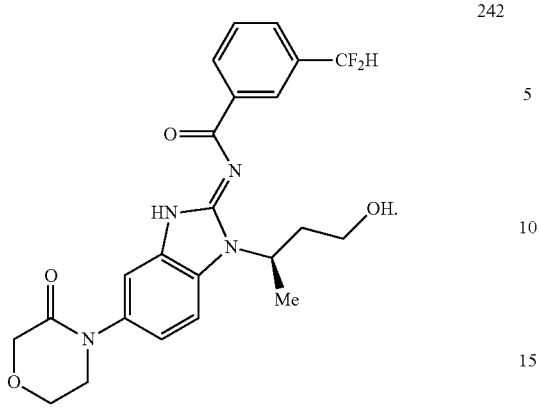

10. A pharmaceutical composition comprising a compound of claim 1, and a pharmaceutically acceptable adjuvant, carrier, or vehicle.

11. A method for inhibiting IRAK, or a mutant thereof, activity in a patient or in a biological sample, comprising the step of administering to said patient or contacting said biological sample with a compound of claim 1 or a physiologically acceptable salt thereof.

* * * * *

UNITED STATES PATENT AND TRADEMARK OFFICE
CERTIFICATE OF CORRECTION

PATENT NO. : 10,059,701 B2
APPLICATION NO. : 15/267565
DATED : August 28, 2018
INVENTOR(S) : Catherine Jorand-Lebrun et al.

It is certified that error appears in the above-identified patent and that said Letters Patent is hereby corrected as shown below:

In the Claims

Column 303 Line 19 - Column 363 Lines 1-15 Claim 9 should be corrected to read:
9. The compound of claim 1, selected from:

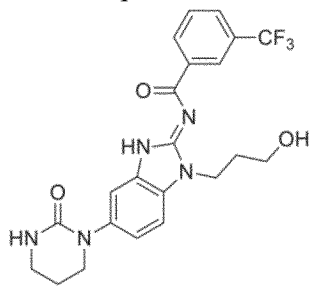 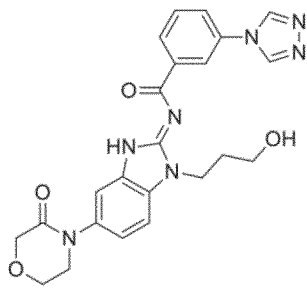 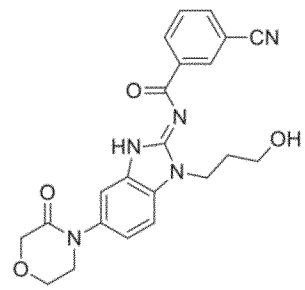

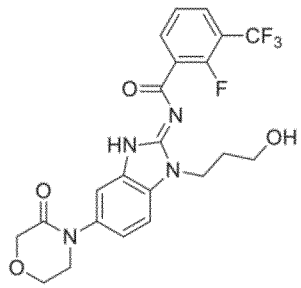 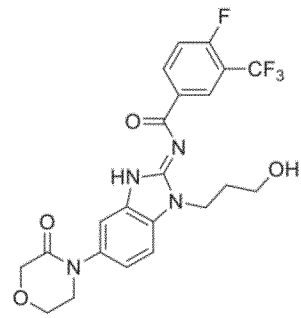 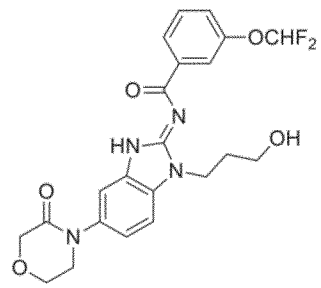

Signed and Sealed this
Fourteenth Day of April, 2020

Andrei Iancu
*Director of the United States Patent and Trademark Office*

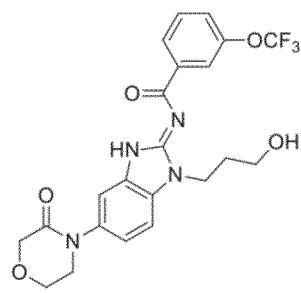
7
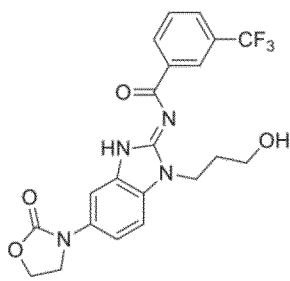
8
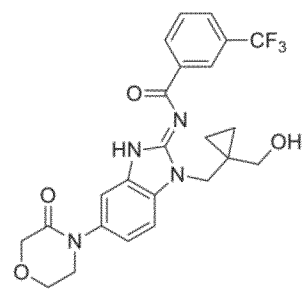
9
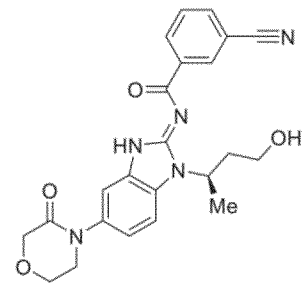
10
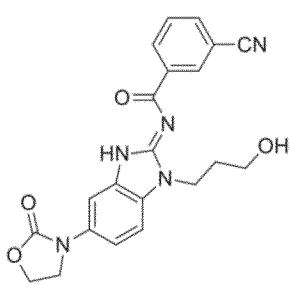
11
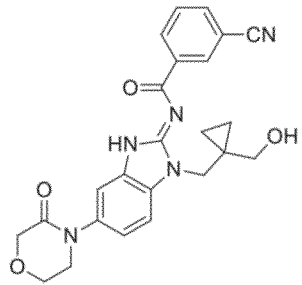
12
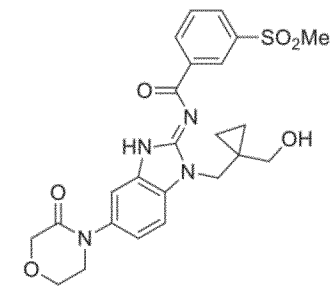
13
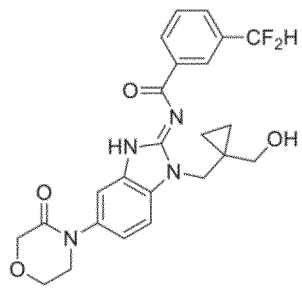
14
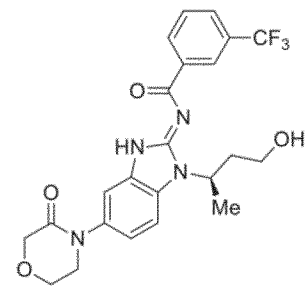
15
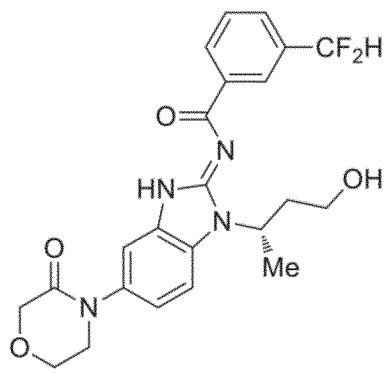
16

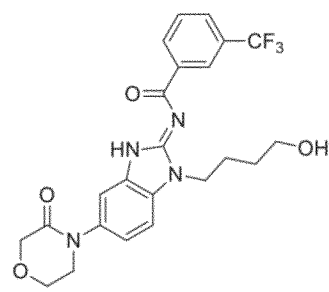
17
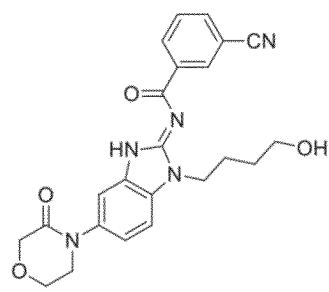
18
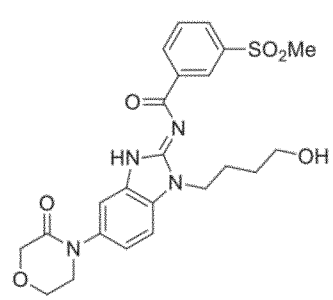
19
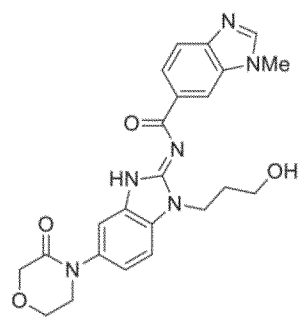
20
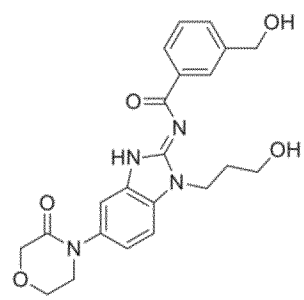
21
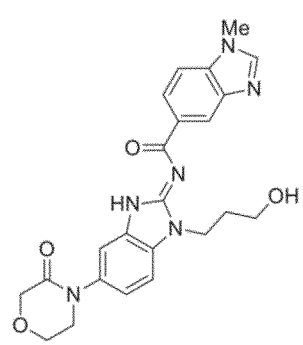
22
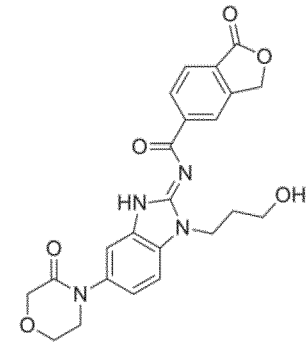
23
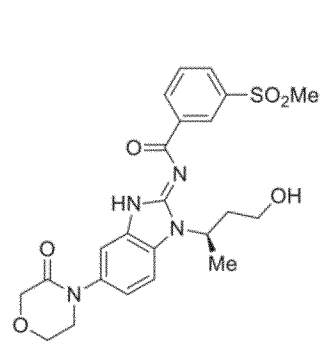
24
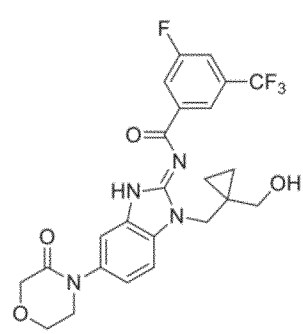
25
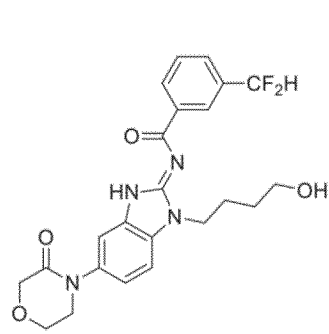
26
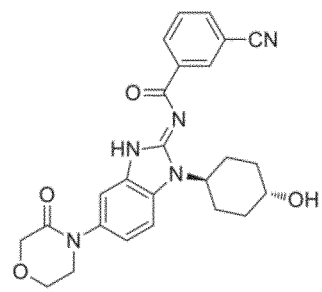
27

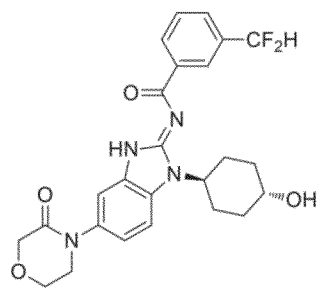
28
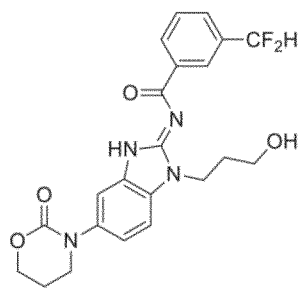
29
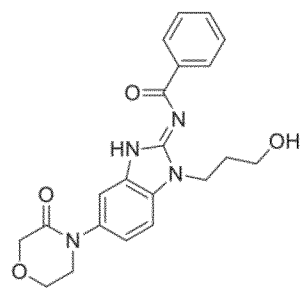
30
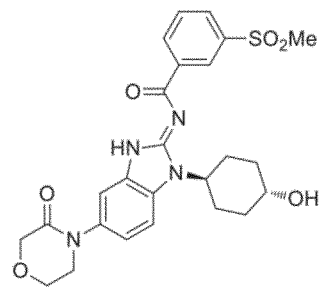
31
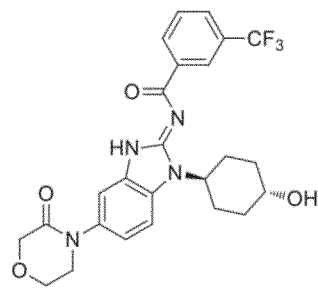
32
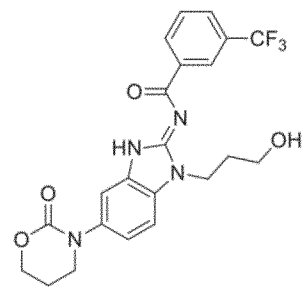
33
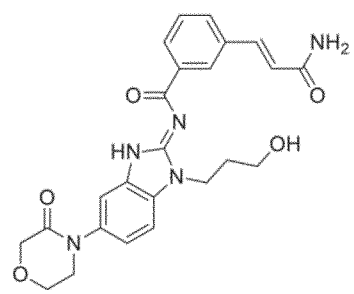
34
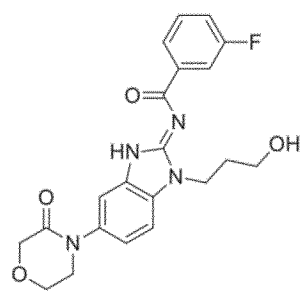
35
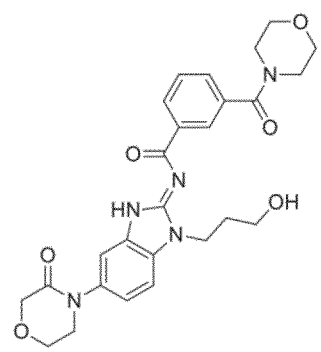
36
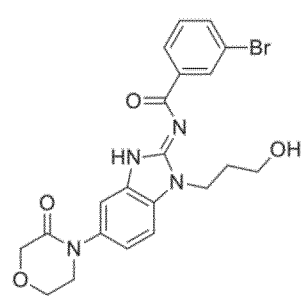
37
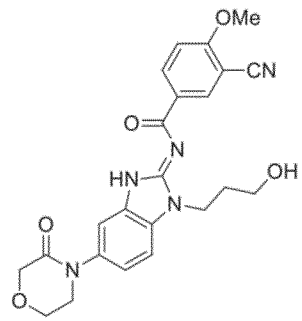
38
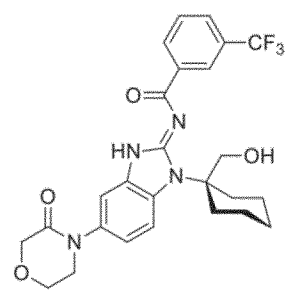
39

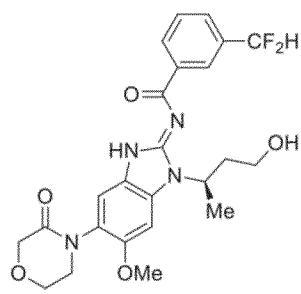
40
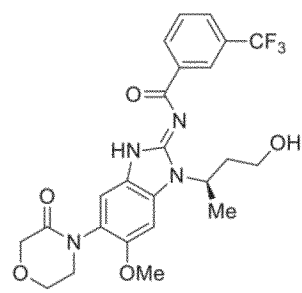
41
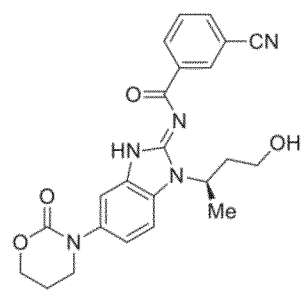
42
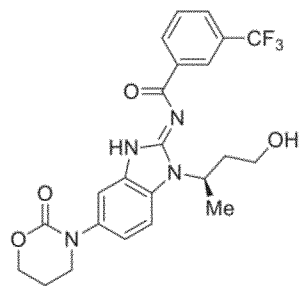
43
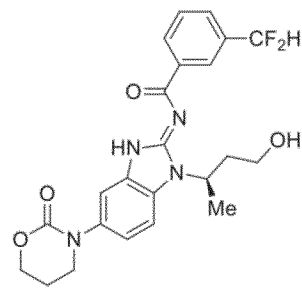
44
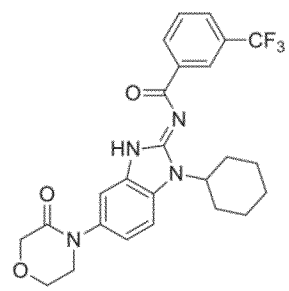
45
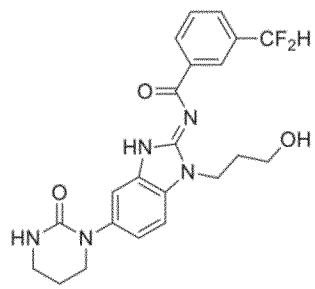
46
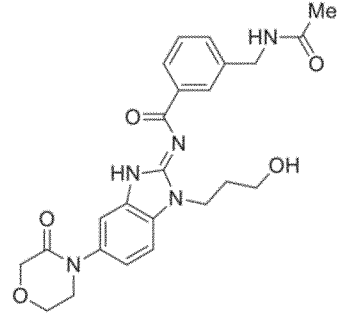
47
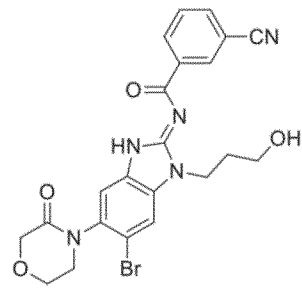
48
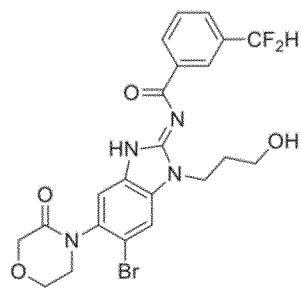
49
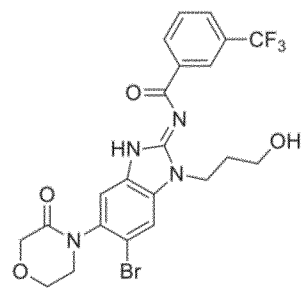
50
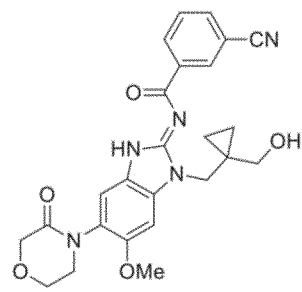
51

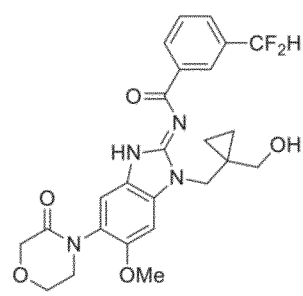
52
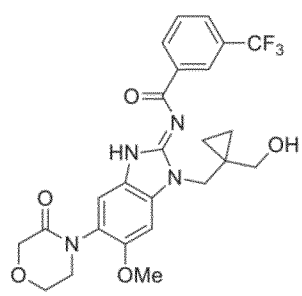
53
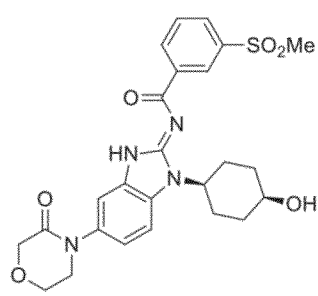
54
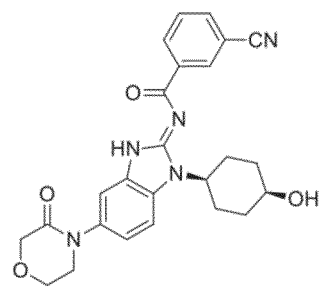
55
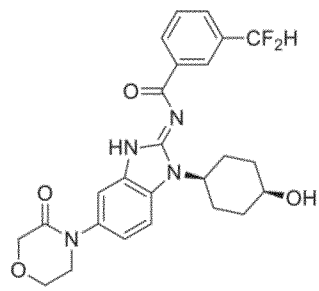
56
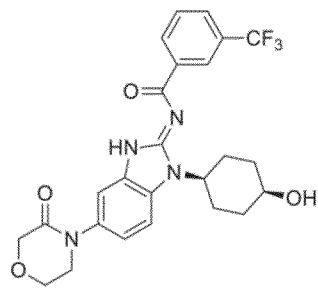
57
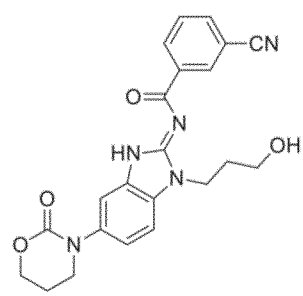
58
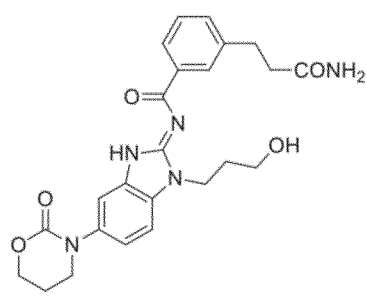
59
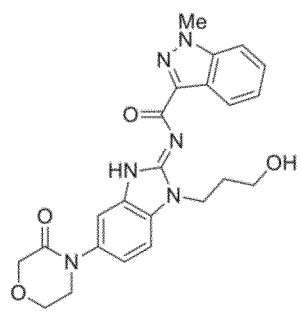
60
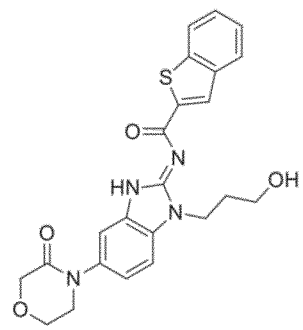
61
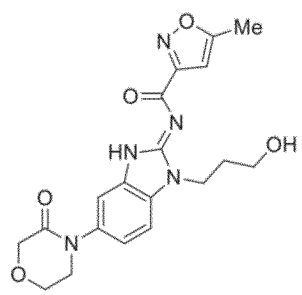
62
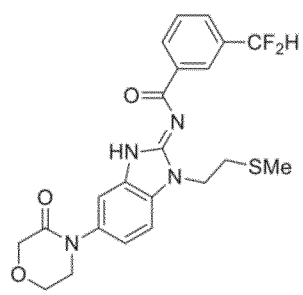
63

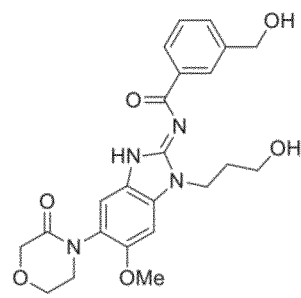
64
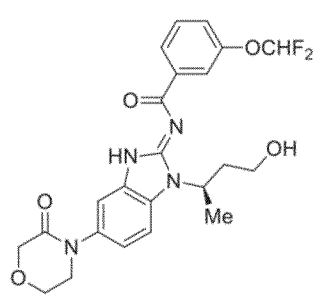
65
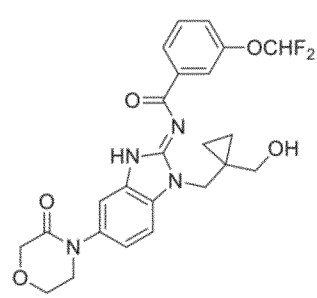
66
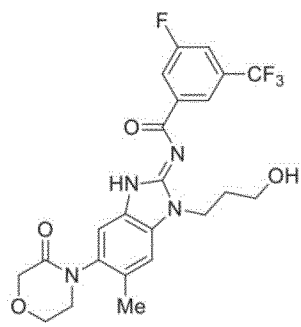
67
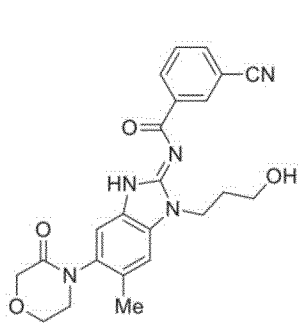
68
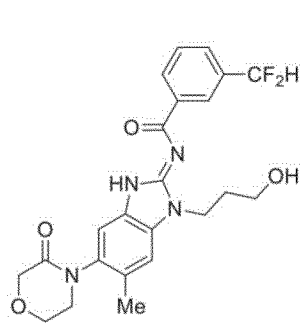
69
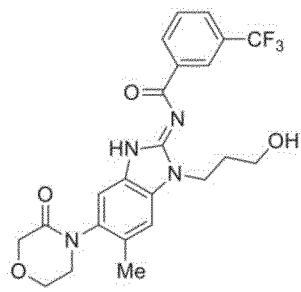
70
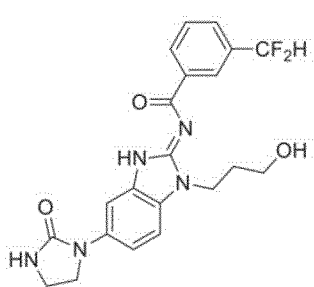
71
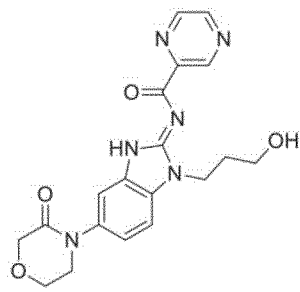
72
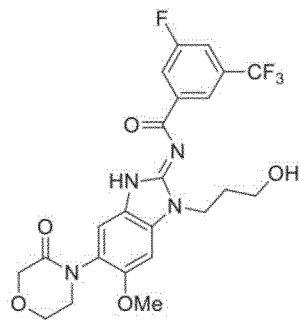
73
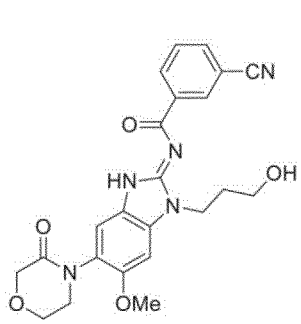
74
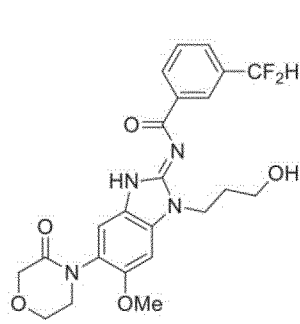
75

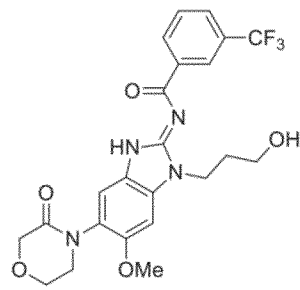
76
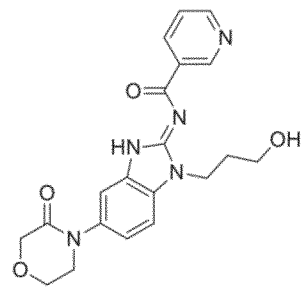
77
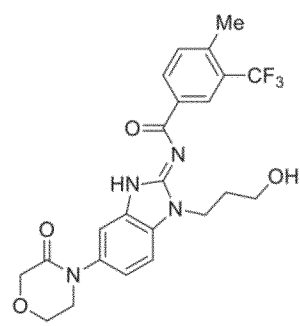
78
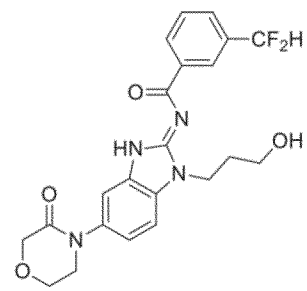
79
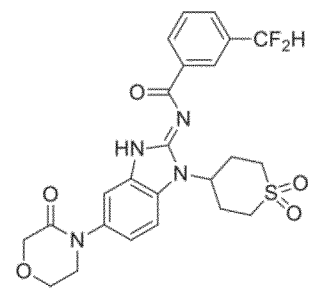
80
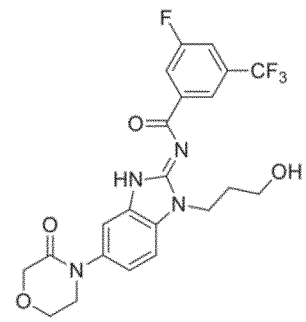
81
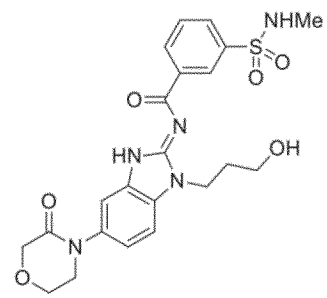
82
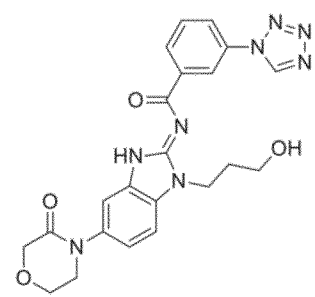
83
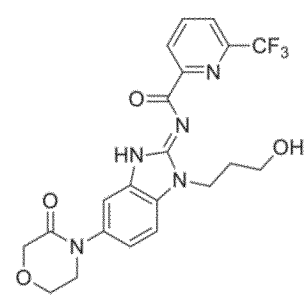
84
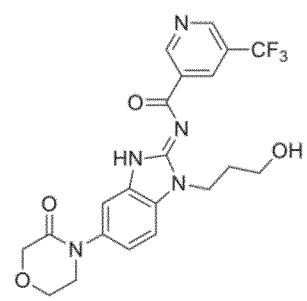
85
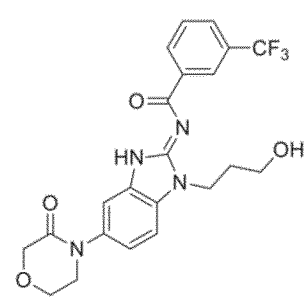
86
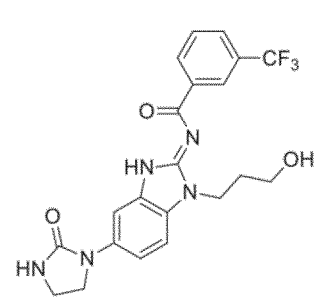
87

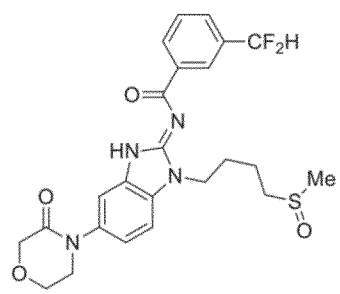
88
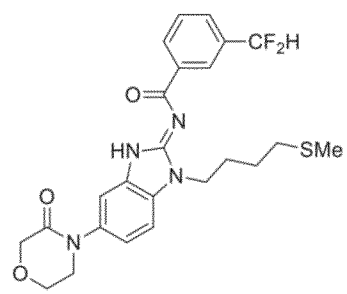
89
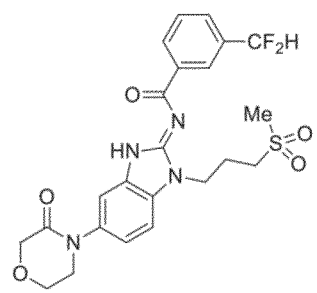
90
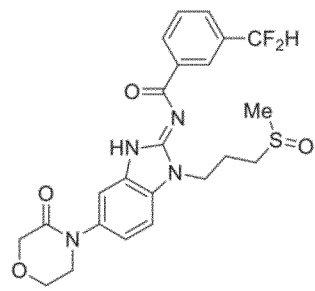
91
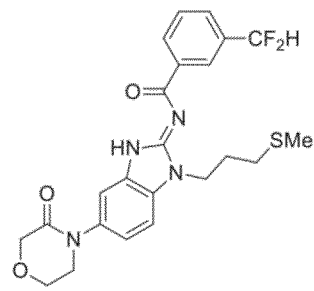
92
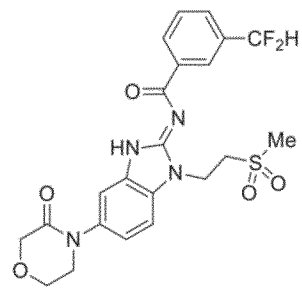
93
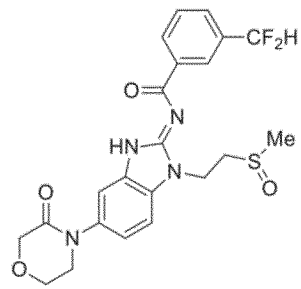
94
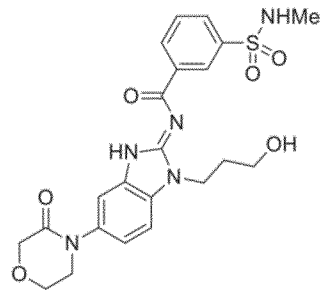
97
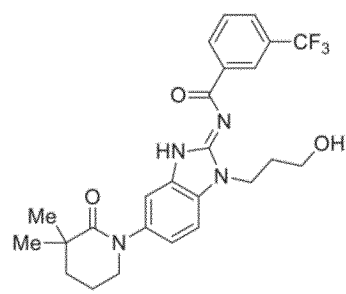
98
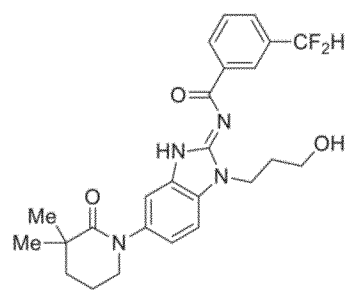
99

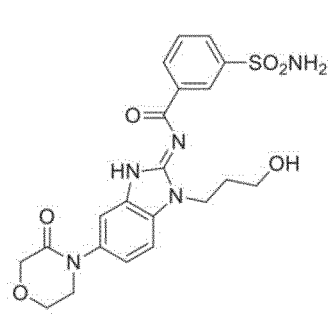 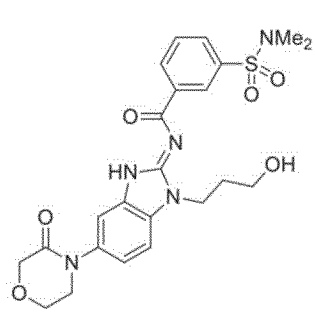 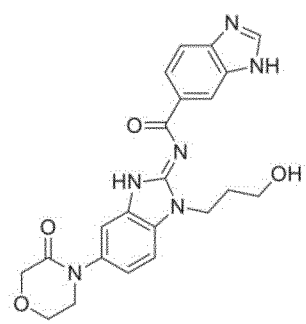
100        101        102
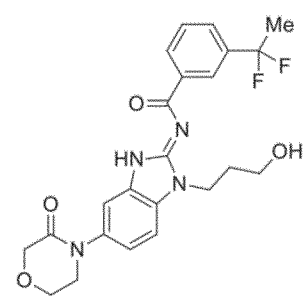 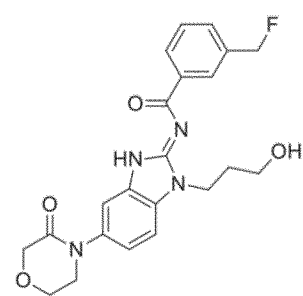 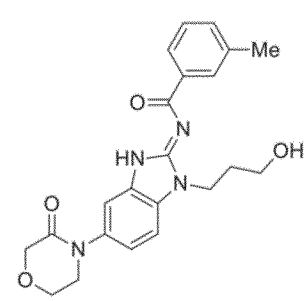
103        104        105
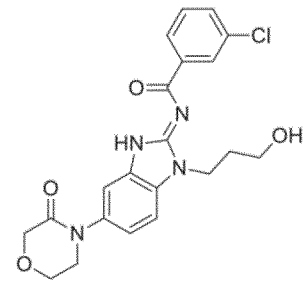 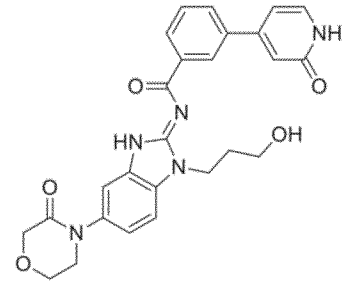 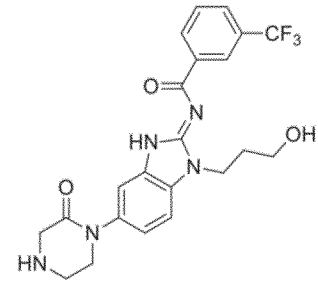
106        107        108
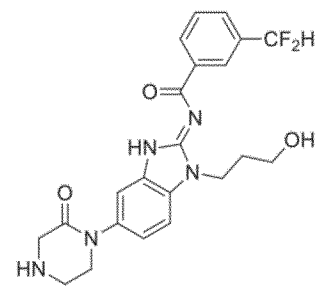 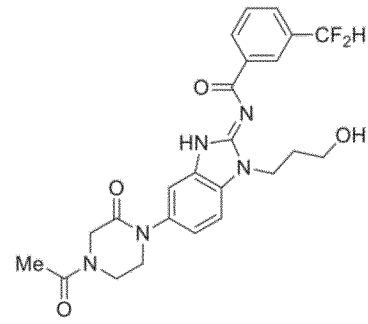 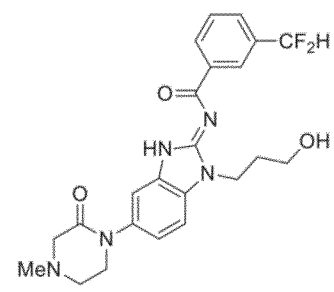
109        110        111

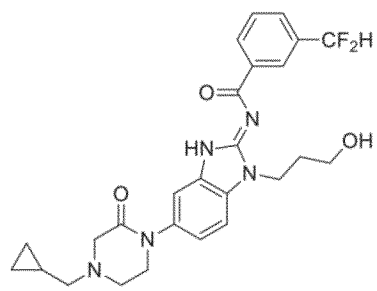
112
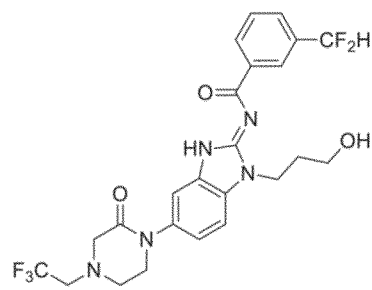
113
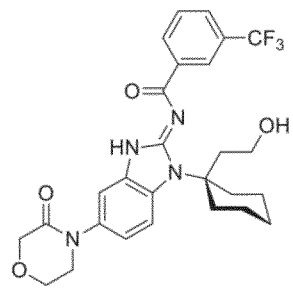
114
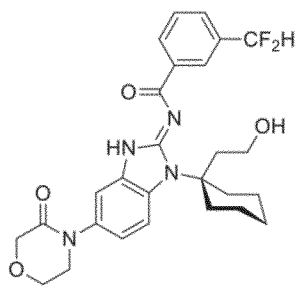
115
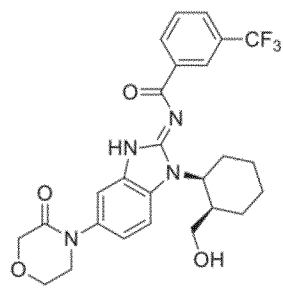
116
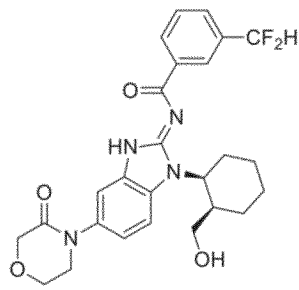
117
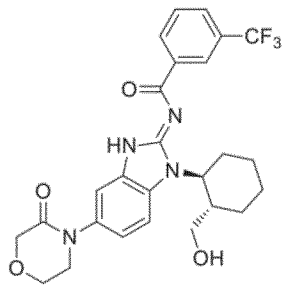
118
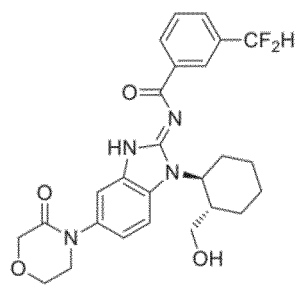
119
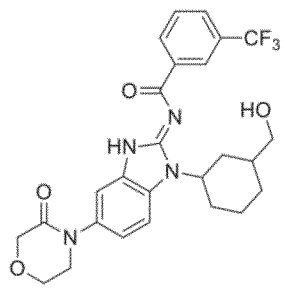
120
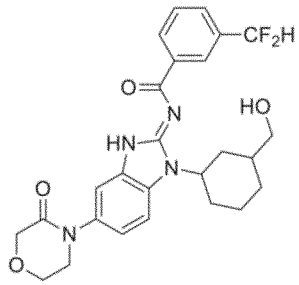
121
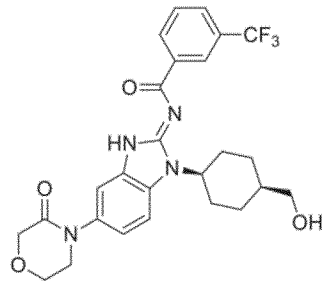
122
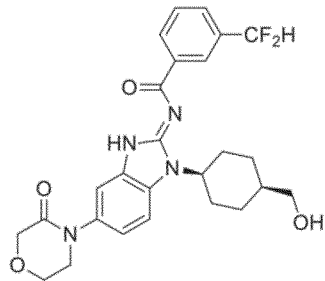
123

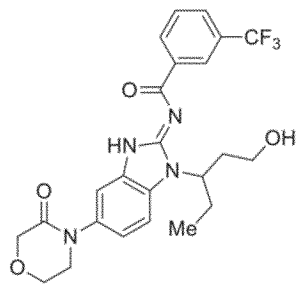
124
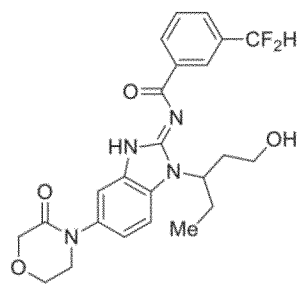
125
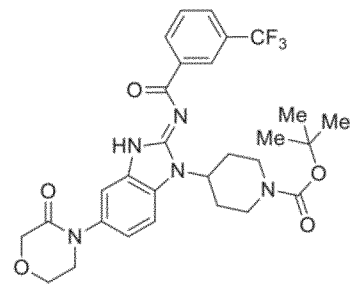
126
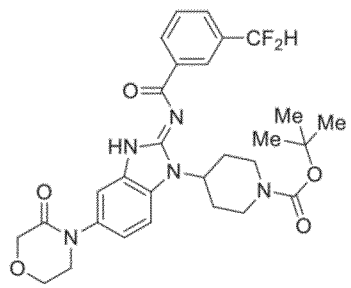
127
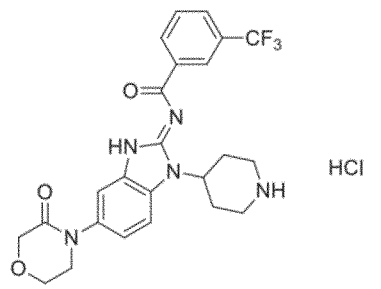
128
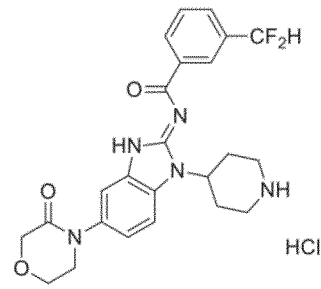
129
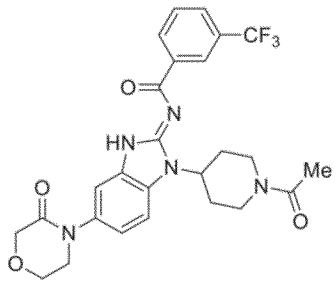
130
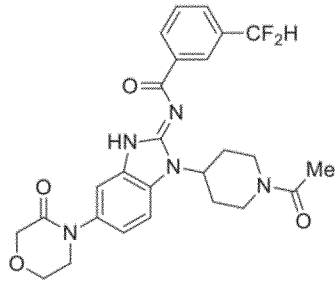
131
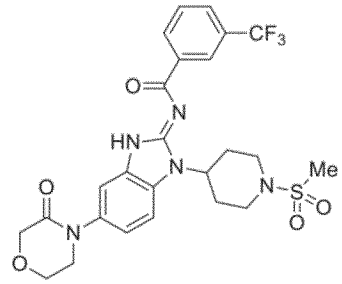
132
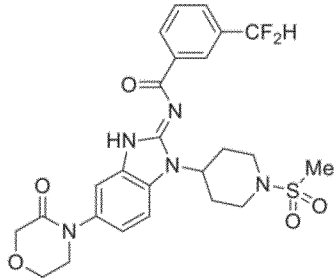
133
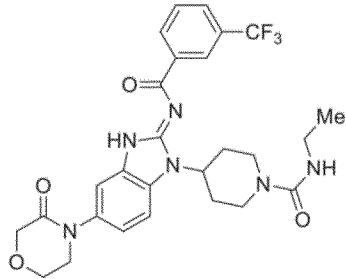
134
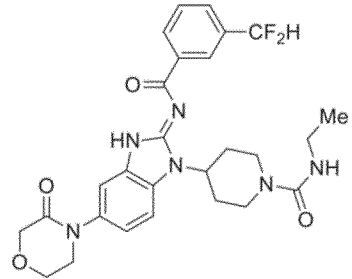
135

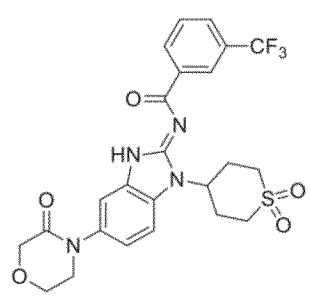
136
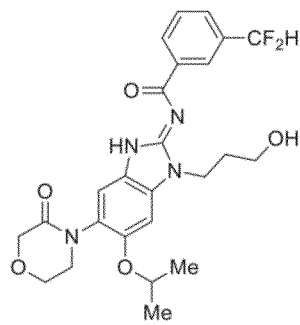
137
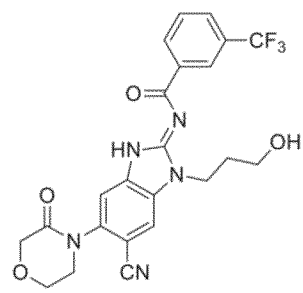
138
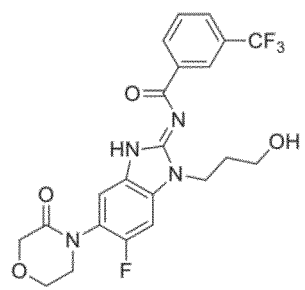
139
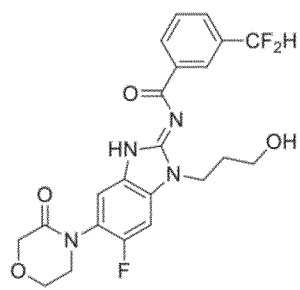
140
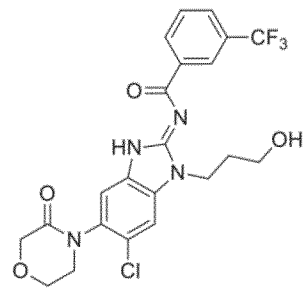
141
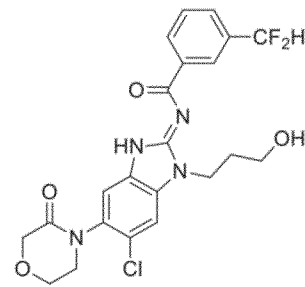
142
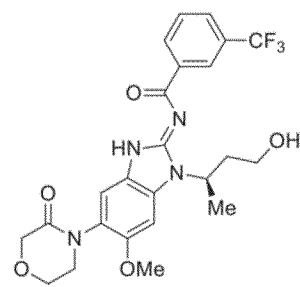
143
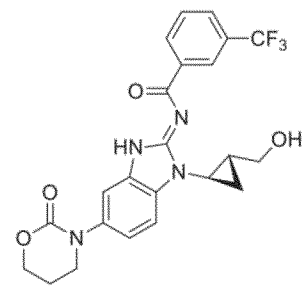
144
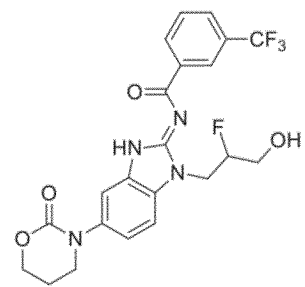
145
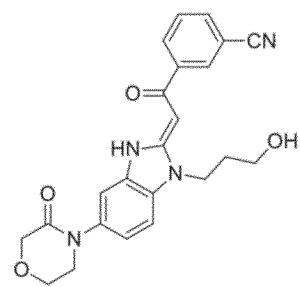
146
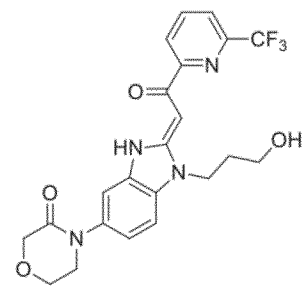
147

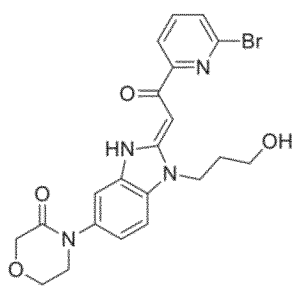
148
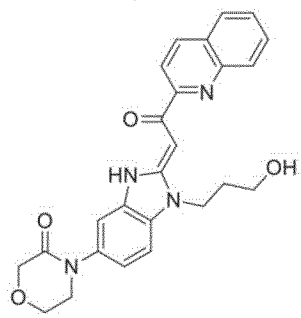
149
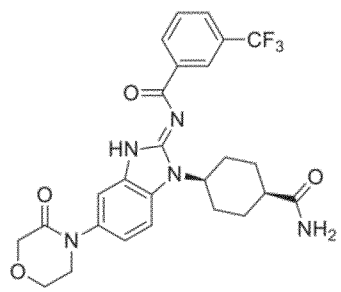
150
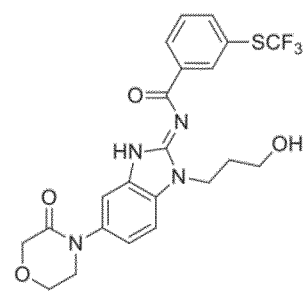
151
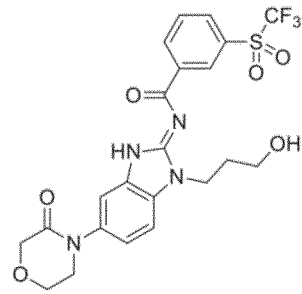
152
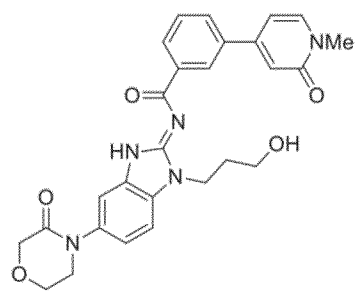
153
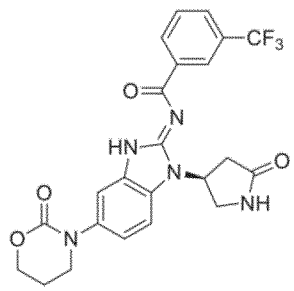
154
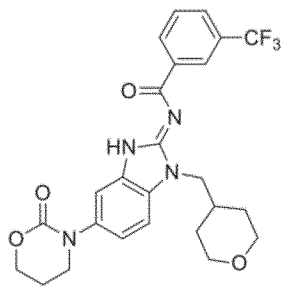
155

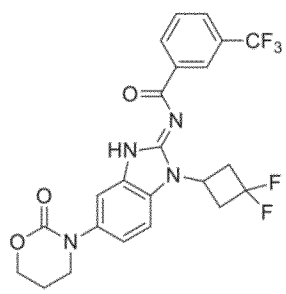
156
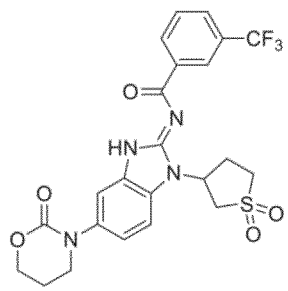
157
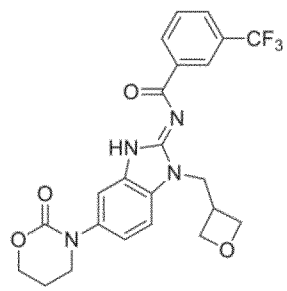
158
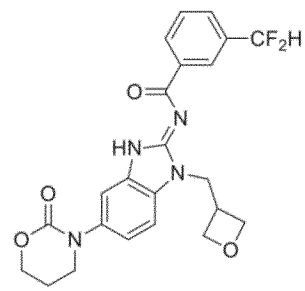
159
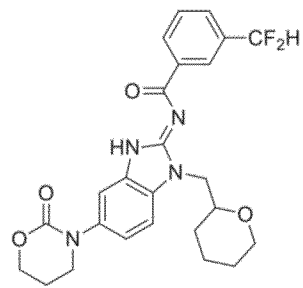
160
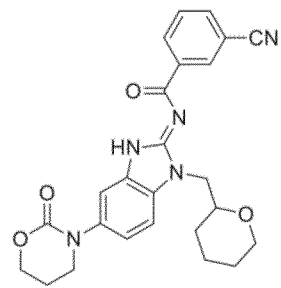
161
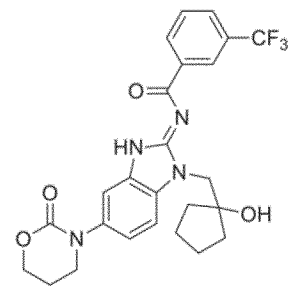
162
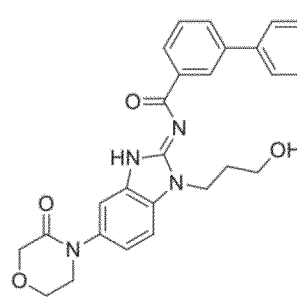
163
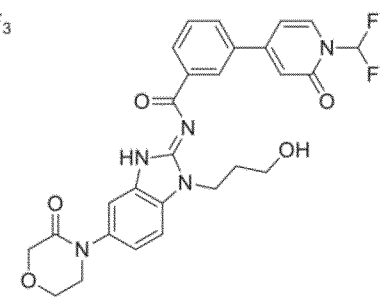
164
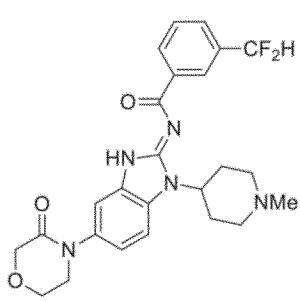
165

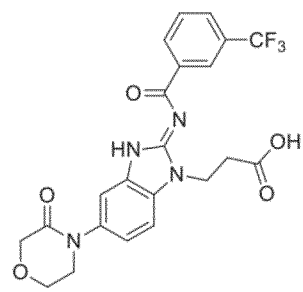
166
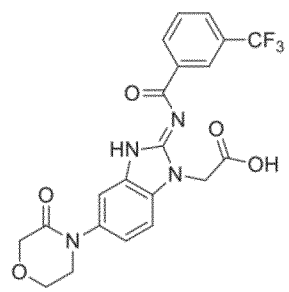
167
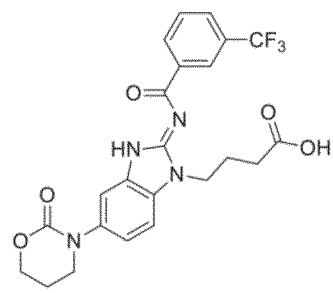
168
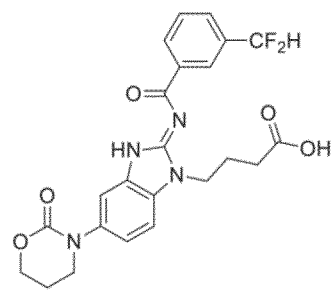
169
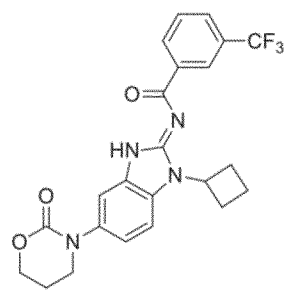
170
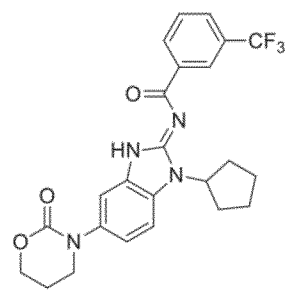
171
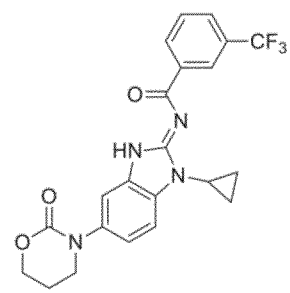
172
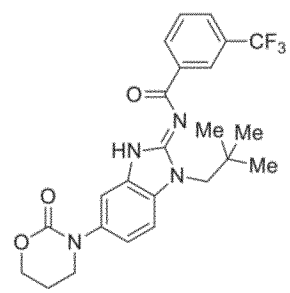
173
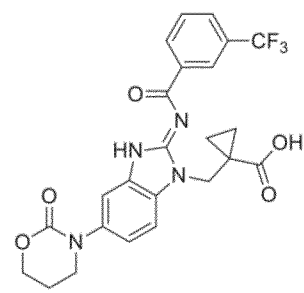
174
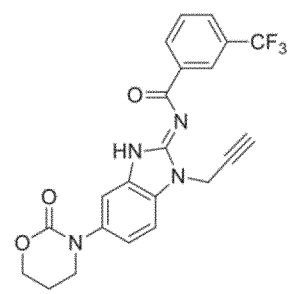
175
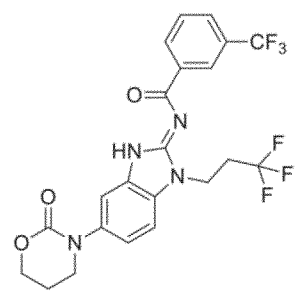
176
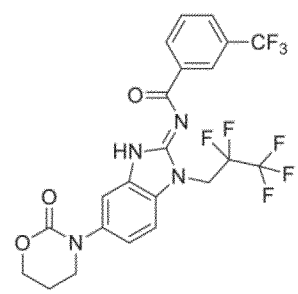
177

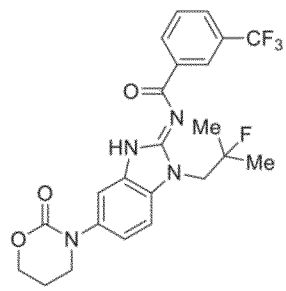
178
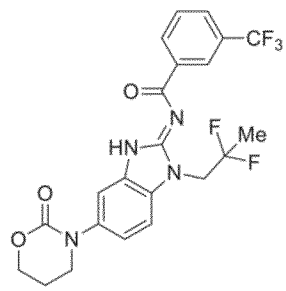
179
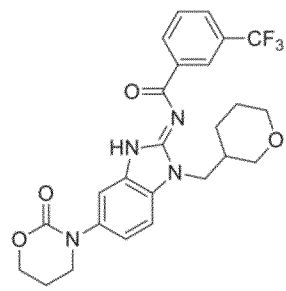
180
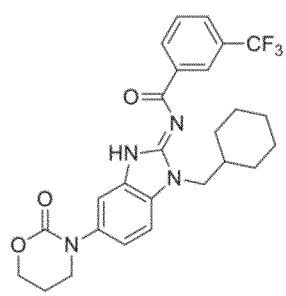
181
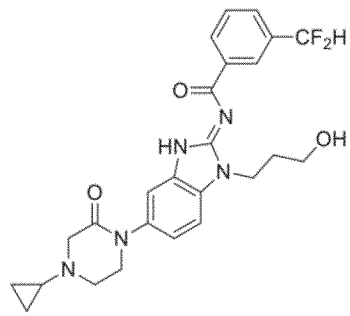
182
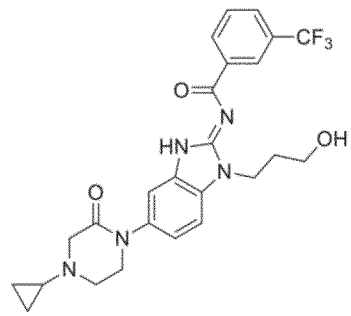
183
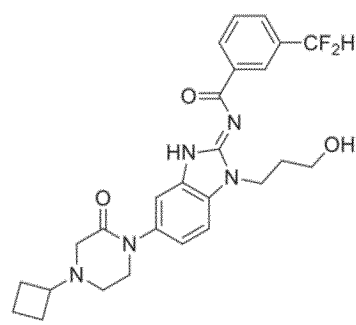
184
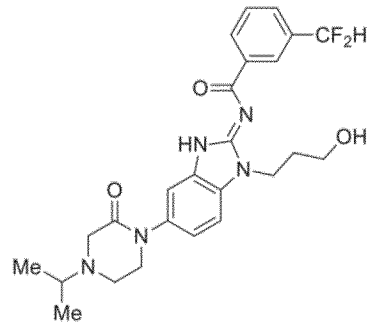
185
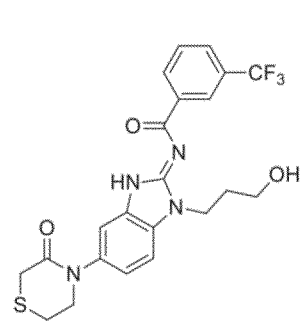
186
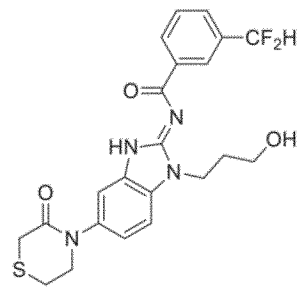
187
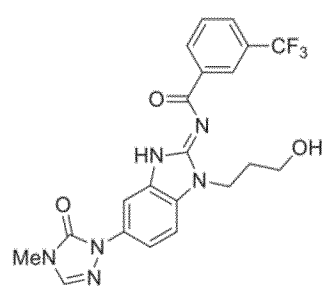
188

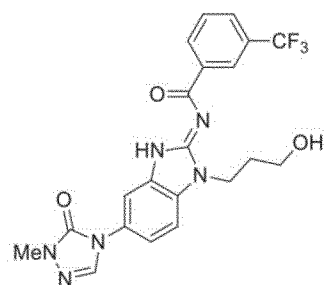
189
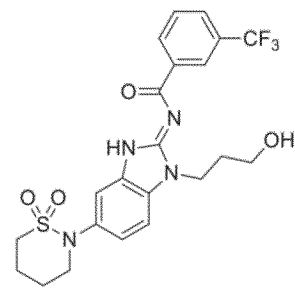
190
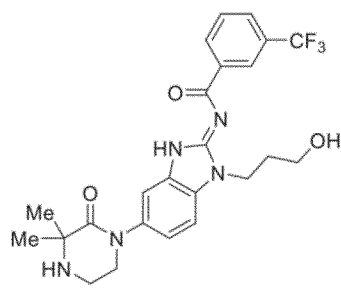
191
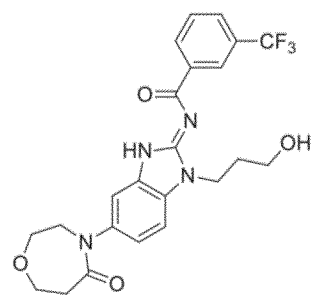
192
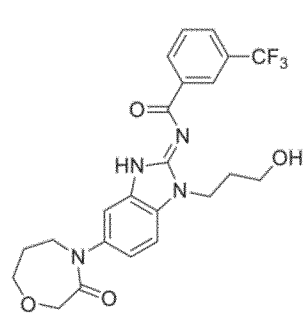
193
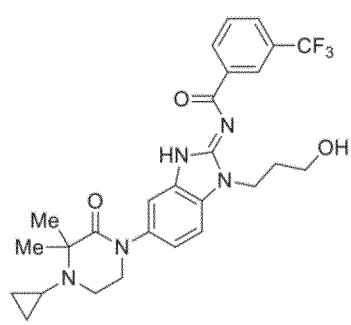
194
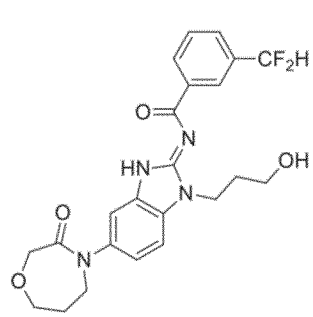
195

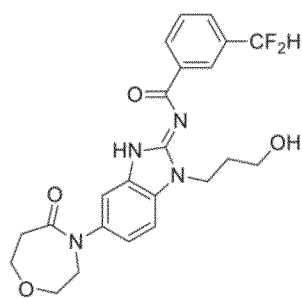
196
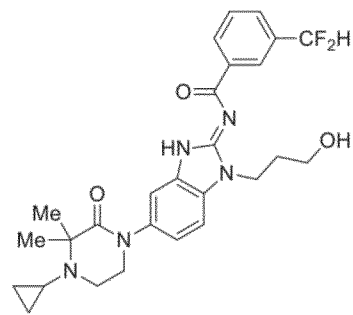
197
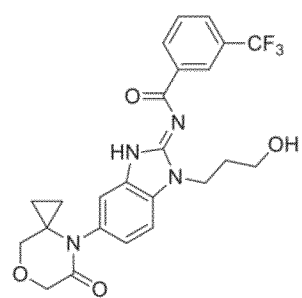
198
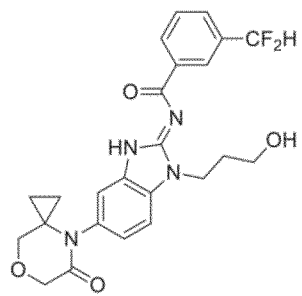
199
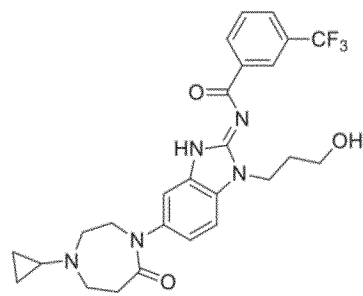
200
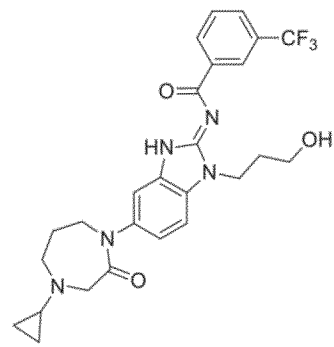
201
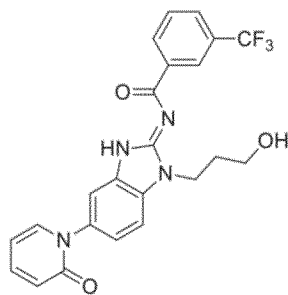
202
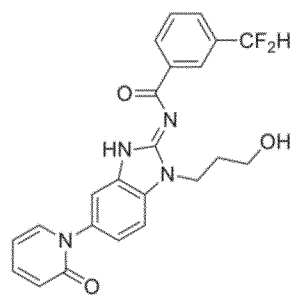
203
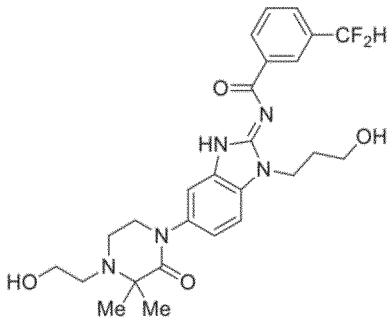
204
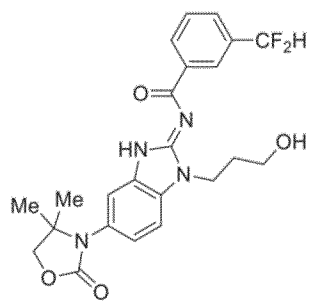
205
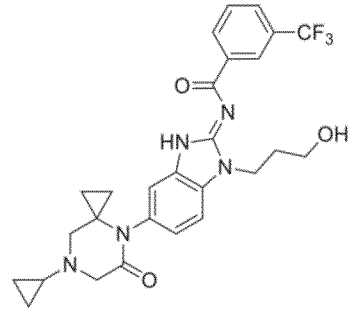
206
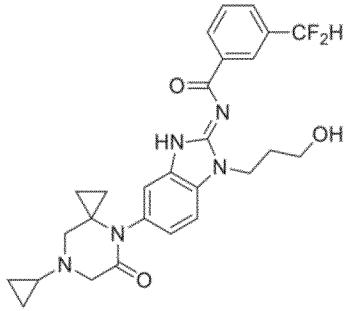
207

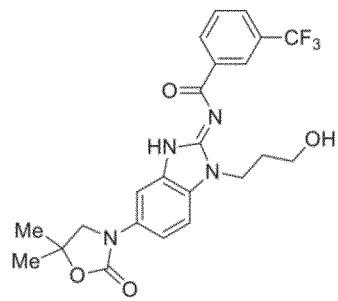
208
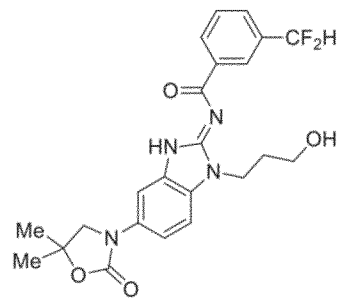
209
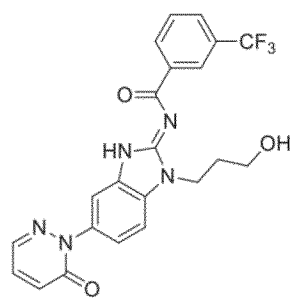
210
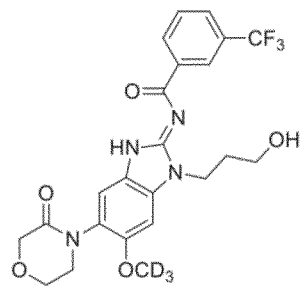
211
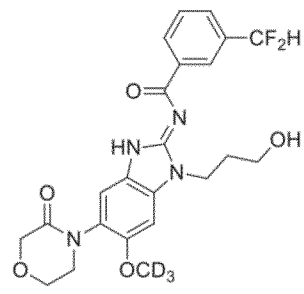
212
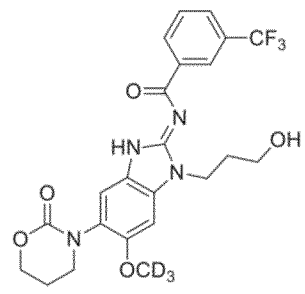
213
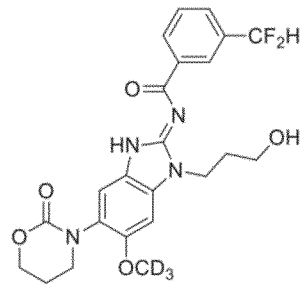
214
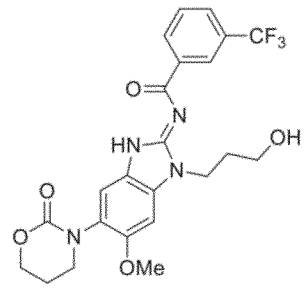
215
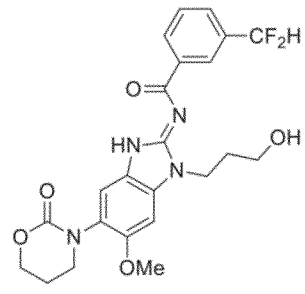
216
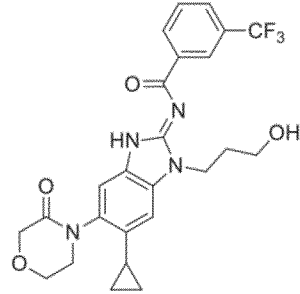
217
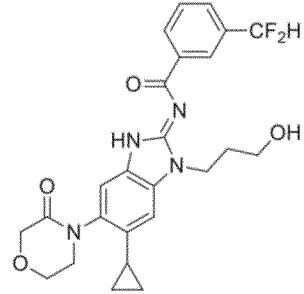
218
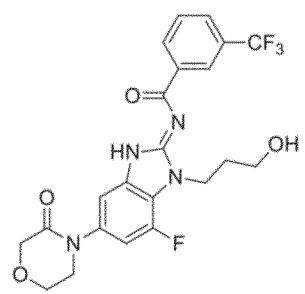
219

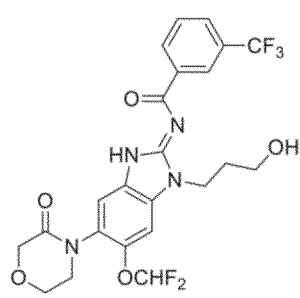
220
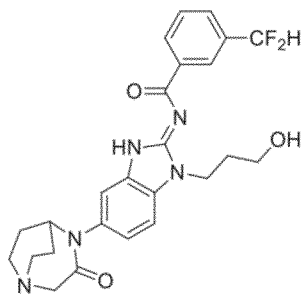
221
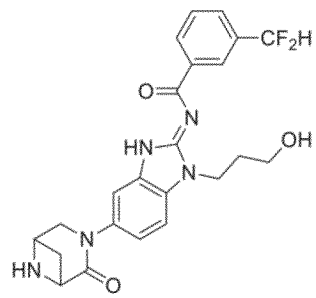
222
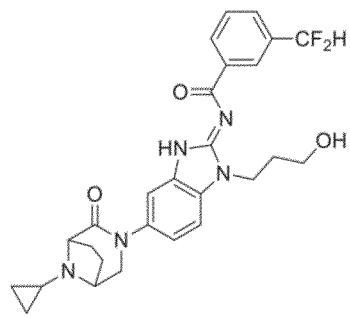
223
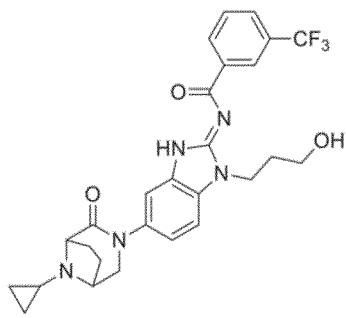
224
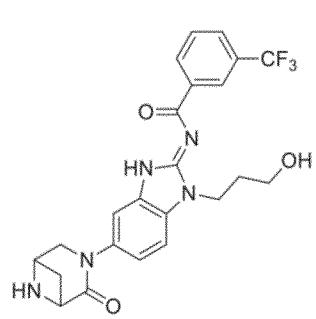
225
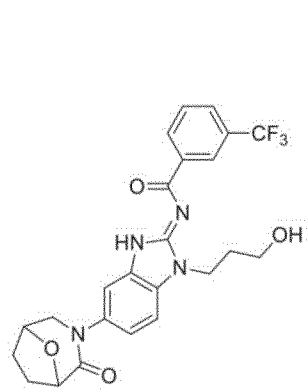
226
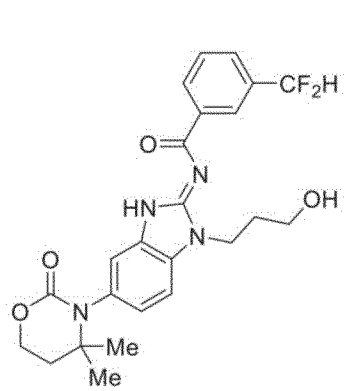
227
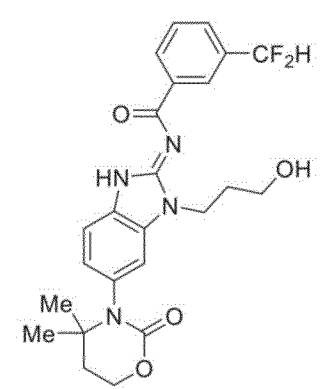
228
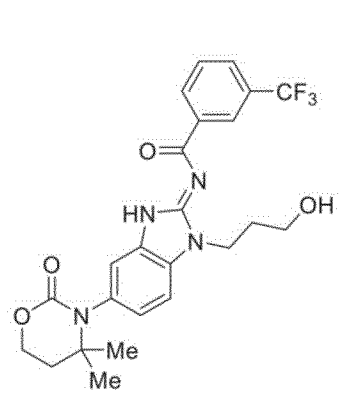
229
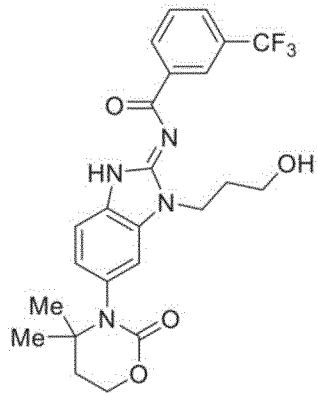
230
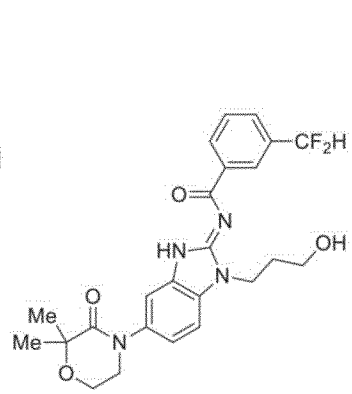
231

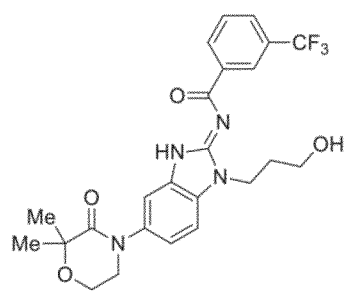 232 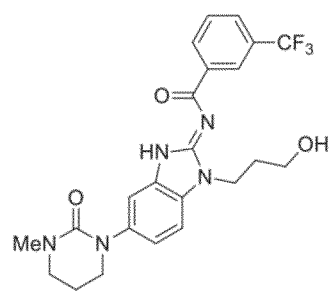 233 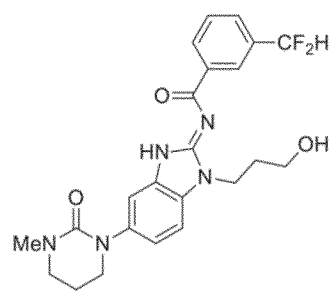 234
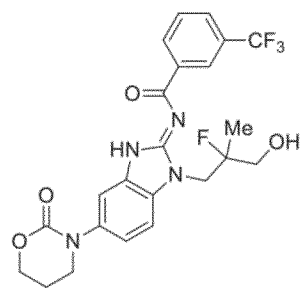 235 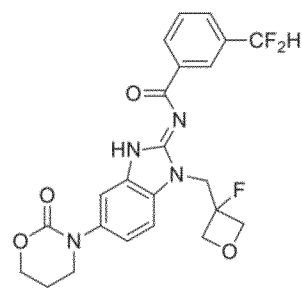 236 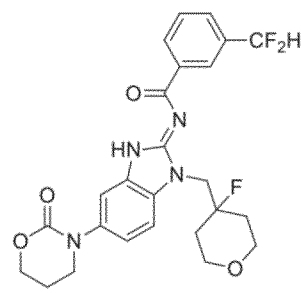 237
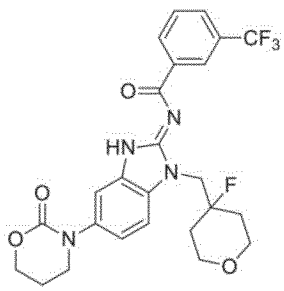 238 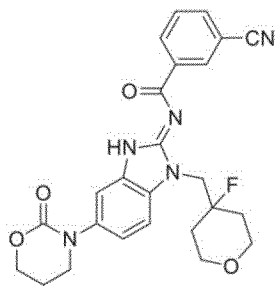 239 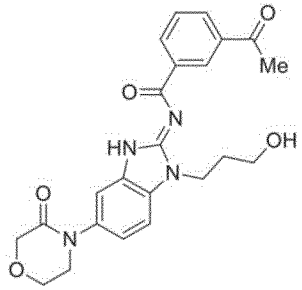 240
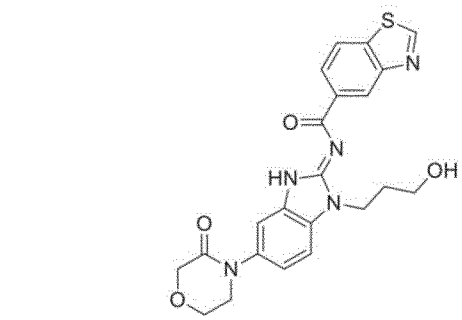 241 and 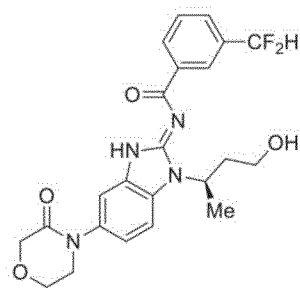 242.